US006376660B1

(12) United States Patent
Daggett et al.

(10) Patent No.: US 6,376,660 B1
(45) Date of Patent: *Apr. 23, 2002

(54) HUMAN N-METHYL-D-ASPARTATE RECEPTOR SUBUNITS, NUCLEIC ACIDS ENCODING SAME AND USES THEREFOR

(75) Inventors: Lorrie P. Daggett; Chin-Chun Lu, both of San Diego, CA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/935,105

(22) Filed: Sep. 29, 1997

Related U.S. Application Data

(60) Division of application No. 08/231,193, filed on Apr. 20, 1994, now Pat. No. 5,849,895, which is a continuation-in-part of application No. 08/052,449, filed on Apr. 20, 1993, now abandoned.

(51) Int. Cl.$^7$ .............................................. C12N 15/12
(52) U.S. Cl. .................. 536/23.5; 435/69.1; 435/252.3; 435/320.1
(58) Field of Search ........................ 435/7.1, 7.2, 69.1, 435/252.3, 320.1; 530/350; 536/23.5

(56) References Cited

U.S. PATENT DOCUMENTS

| | | | |
|---|---|---|---|
| 4,837,148 A | 6/1989 | Cregg | 435/172.3 |
| 4,855,231 A | 8/1989 | Stroman et al. | 435/68 |
| 4,882,279 A | 11/1989 | Cregg | 435/68 |
| 4,929,555 A | 5/1990 | Cregg et al. | 435/172.3 |
| 5,024,939 A | 6/1991 | Gorman | 435/69.1 |
| 5,028,707 A | 7/1991 | Nichols et al. | 546/156 |
| 5,202,257 A | 4/1993 | Heinemann et al. | 435/252.3 |
| 5,401,629 A | 3/1995 | Harpold et al. | 435/6 |
| 5,403,484 A | 4/1995 | Ladner et al. | 435/235.1 |
| 5,436,128 A | 7/1995 | Harpold et al. | 435/6 |
| 5,502,166 A | 3/1996 | Mishina | 530/350 |
| 5,648,259 A | 7/1997 | Mallet | 435/252.3 |

FOREIGN PATENT DOCUMENTS

| | | |
|---|---|---|
| EP | 0600278 A2 | 6/1994 |
| EP | 0606734 | 7/1994 |
| EP | 0674003 | 9/1995 |
| GB | 9223769 | 11/1992 |
| GB | 9307026 | 4/1993 |
| GB | 2291647 | 1/1996 |
| JP | 6014783 | 1/1994 |
| WO | 9106648 | 5/1991 |
| WO | 9313423 | 7/1993 |
| WO | 9323536 | 11/1993 |
| WO | 9324629 | 12/1993 |
| WO | 9325679 | 12/1993 |
| WO | 9401094 | 1/1994 |
| WO | 9404698 | 3/1994 |
| WO | 9406428 | 3/1994 |
| WO | 9411501 | 5/1994 |
| WO | 9526401 | 10/1995 |

OTHER PUBLICATIONS

George et al. Macromolecular Sequencing and Synthesis, Selected Methods and Applications. Alan R. Liss, Inc., Chptr. 12, pp. 127–149, 1988.*
Monyer et al, Science 256:1217–1221, May 22, 1992.*
Puckett et al. P.N.A.S. 88:7557–7561, Sep. 1991.*
Schofield et al. Febs Letters 244(2):361–364, Feb. 1989.*
Grenningloh et al. The Embro J. 9(3):771–776, Mar. 1990.*
Bledsoe et al., Molecular homology and DNA Hybridization, J. Mol. Evol. 30:425–433 (1990).
Gilbert, *Development Biology*, 2nd ed., Sinauer Associates, Sunderland MA, pp. 54–55 (1988).
Hess et al., Cloning and functional characterization of human heteromeric N–methyl–D–aspartate receptors, *J. Pharm. Exp. Ther.*, 278:808–816 (1996).
Hess et al., Functional characterization of human N–methyl–D–aspartate subtype 1A/2D receptors, *J Neurochem* 70(3):1269–79 (1998).
Ikeda et al., Cloning and expression of the espilon4 subunit of the NMDA receptor channel, *FEBS Lett.* 313(1):34–38 (1992).

(List continued on next page.)

Primary Examiner—John Ulm
(74) Attorney, Agent, or Firm—Vineet Kohli; Jack L. Tribble

(57) ABSTRACT

In accordance with the present invention, there are provided nucleic acids encoding human NMDA receptor protein subunits and the proteins encoded thereby. The NMDA receptor subunits of the invention comprise components of NMDA receptors that have cation-selective channels and bind glutamate and NMDA. In one aspect of the invention, the nucleic acids encode NMDAR1 and NMDAR2 subunits of human NMDA receptors. In a preferred embodiment, the invention nucleic acids encode NMDAR1, NMDAR2A, NMDAR2B, NMDAR2C and NMDAR2D subunits of human NMDA receptors. In addition to being useful for the production of NMDA receptor subunit proteins, these nucleic acids are also useful as probes, thus enabling those skilled in the art, without undue experimentation, to identify and isolate related human receptor subunits. Functional glutamate receptors can be assembled, in accordance with the present invention, from a plurality of one type of NMDA receptor subunit protein (homomeric) or from a mixture of two or more types of subunit proteins (heteromeric). In addition to disclosing novel NMDA receptor protein subunits, the present invention also comprises methods for using such receptor subunits to identify and characterize compounds which affect the function of such receptors, e.g., agonists, antagonists, and modulators of glutamate receptor function. The invention also comprises methods for determining whether unknown protein(s) are functional as NMDA receptor subunits.

21 Claims, 7 Drawing Sheets

OTHER PUBLICATIONS

Jansen et al., Acutoradiographic visualisation of [3H]DTG binding to sigma receptors, [3H]TCP binding sites, and I–[3H]glutamate binding to NMDA receptors in the human cerebellum, *Neursci. Lett.* 125:143–146 (1991).

Mori et al., Involvement of the carboxyl–terminal region in modulation by TPA of the NMDA receptor channel, *Neuroreport* 4(5):519–22 (1993).

Nakanishi et al., Alternative splicing generates functionally distinct N–methyl–D–aspartate receptors, *Proc. Natl. Acad. Sci. USA* 89:8552–8556 (1992).

Shepard, *Neurobiology*, 2nd ed., Oxford University Press, New York, pp. 31, 76, 155, 157, 161 (1988).

Williams K, Pharmacological properties of recombinant N–methyl–D–aspartate (NMDA) receptors containing the epsilon 4 (NR2D) subunit, *Neurosci Lett* 184(3):181–4 (1995).

Yamakura et al., Different sensitivites of NMDA receptors channel subtypes to non–competitive antagonists, *Neuroreport* 4(6):687–90 (1993).

Abbott, NMDA receptor cloned, *Trends Pharmacol. Sci.* 12:449 (1991).

Abbott, NMDA receptor subunit cloned, *Trends Pharmacol. Sci.* 12:334 (1991).

Abe et al., Molecular characterization of a novel metabotropic glutamate receptor mGluR5 coupled to inositol phosphate/$Ca^{2+}$signal transduction, *J. Biol. Chem.* 267:13361–13368 (1992).

Albin et al., Abnormalities of striatal projection neurons and N–methyl–D–aspartate receptors in presymptomatic Huntington's Disease, *N. Engl. J. Med.* 322(18):1293–1298 (1990).

Anantharam et al., Combinatorial RNA splicing alters the surface charge on the NMDA receptors, *FEBS Lett.* 305(1):27–30 (1992).

Bhouth et al., Immunological approaches for probing receptor structure and function, *Trends Pharmacol. Sci.* 12:338–343 (1991).

Barnard, Will the real NMDA receptor please stand up? *Trends Pharmacol. Sci.* 13:11–12 (1992).

Beal, Mechanisms of excitotoxicity in neurologic diseases, *FASEB J.* 6:3338–3344 (1992).

Ben–Ari et al., Protein kinase C modulation of NMDA currents: an important link for LTP induction, *Trends Neurosci.* 15:333–339 (1992).

Black et al., N–methyl–D–aspartate–or glutamate–mediated toxicity in cultured rat cortical rat cortical neurons is antagonized by FPL 15896AR, *J. Neurochem.* 65:2170–2177 (1995).

Bottaro et al, Identification of the hepatocyte growth factor receptor as the c–met proto–oncogene product, *Science* 251:802–804 (1991).

Bradford, A rapid and sensitive method of the quantitation of microgram quantities of protein utilizing the principle of protein–dye binding, *Anal. Biochem.* 72:248 (1976).

Bristow et al., The glycine/NMDA recepter antagonist R–(+)–HA–966, blocks actvation of the mesolimbic depaminergic system induced by phencyclidine and dizcilpine (MK–801) in rodents, *Br. J. Pharmacol.* 108:1156–1163 (1993).

Chio, Calcuim–medicated neurotoxicity: Relationship to specific channel types and role in ischemic damage,*Trends Neurosci.* 11(10):465469 (1988).

Chio, Glutamate neurotoxicity and diseases of the nervous system, *Neuron* 1:623–634 (1988).

Chiba–Geigy Unveils Research Agreement with SIBIA of U.S., *The Wall Street Journal* (Sep. 17, 1992).

Coyle et al., Oxidative stress, glutamate, and neurodegenerative disorders, *Science* 262:689–695 (1993).

Daggett et al., Cloning and functional characterization of three splice variants of the human NMDAR1 receptor, *Biophys J.*, 36(2):447 (1994).

Dascal, The use of *Xenopus oocytes* for the study of ion channels, *CRC Critical Reviews in Biochemistry* 22(4):317–387 (1987).

Donnelly and Pallotta, Single–channel currents from diethylpyrocarbonate–modified NMDA receptors in cultured rat brain cortical neurons,*J. Gen. Physol.* 105:837–859 (1995).

Durand et al., Cloning of an apparent splice variant of the rat N–methyl–D–asparate receptor NMDAR1 with altered sensitivity to polyamines and activators of protein kinase C, *Proc. Natl. Acad. Sci. USA* 89:9359–9363 (1992).

Egebjerg et al., Intron sequences directs RNA editing of the glutamate receptor subunit GluR2 coding sequence, *Proc. Natl. Acad. Sci. USA* 91:10270–10274 (1994).

Felder et al., A transfected m1 muscarinic acetylcholine receptor stimulates adenylate cyclase via phosphatidylinisitol hydrolysis, *J. Biol. Chem.* 264:20356–20362 (1989).

Fisher and Aronson, Characterization of the cDNA and genomic sequence of a G protein γ subunit ($γ_5$), *Mol. Cell. Bio.* 12:1585 (1992).

Foldes et al., Cloning and sequence analysis of cDNAs encoding human hippocampus N–methyl–D–aspartate receptor subunits: Evidence of alternative splicing, *Gene* 131:293–298 (1993).

Gautam et al., A G protein gamma subunit shares homology with ras proteins, *Science* 244:971 (1989).

Gautam et al., G protein diversity in increased by associations with a variety of γ subunits, *Proc. Natl. Acad. Sci. USA* 87:7973 (1990).

Gereau and Conn, Multiple presynaptic metabotropic glutamate receptors modulate excitatory in inhibitory synaptic transmission in hippocampai area CA1, *J. Neurosci* 15(10):6879–6889 (1995).

Greenamyre et al., Synaptic localization of striatal NMDA, quisqualate and kainate receptors, *Neurosci. Lett.* 101:133–137 (1989).

Grimwood et al., Interactions between the glutamate and glycine recognition site of the N–methyl–D–aspartate receptor from rat brain, as revealed from radioligand binding studies, *J. Neurochem.* 60:1729–1738 (1993).

Gubler et al., A simple and very efficient method for generating cDNA libraries, *Gene* 25:263–269 (1983).

Gunasekar et al., NMDA receptor activation produces concurrent generation of nitric oxide and reactive oxygen species: Implication for cell death, *J. Neurochem.* 65:2016–2021 (1995).

Gundersen et al., Glutamate and kainate receptors induced by rat brain messenger RNA in Xenopus oocytes, *Proc. R. Soc. London Ser.* 221:127 (1984).

Hess et al., Cloning, functional expression, and pharmacological characterization of human NMDAR1/NMDAR2 heteromeric receptors, *Biophys. J.*, 36(2):446 (1994) (abstract and poster).

Hess et al., Biophysical properties of human NMDA receptors stably expressed in mammalian cells, *Soc. Neurosci. Abstr.* 21:1–3 (1995).

Hoffman, NMDA receptor cloned——twice! *Science* 254:801–802 (1991).

Hollman et al., Zinc potentiates agonist–induced currents at certain splice variants of the NMDA receptor, *Neuron* 10:943–954 (1993).

Hollman et al., Cloned glutamate receptors, *Annu. Rev. Neurosci.* 17:31–108 (1994).

Hurley et al., Isolation and characterization of a cDNA clone for the γ subunit of bovine retinal transducin, *Proc. Natl. Acad. Sci. USA* 81:6948 (1984).

Ishii et al., Molecular characterization of the family of the N–methyl–D–aspartate receptor subunits, *J. Biol. Chem.* 268(4):2836–2843 (1993).

Ito et al., Characterization of prostaglandin $E_2$–induced $Ca^{2+}$ mobilization in single bovine adrenal chromaffin cells by digital image microscopy, *J. Neurochem.* 56:531–540 (1991).

Jones et al., Characterization of the binding of radioligands to the N–methyl–D–asparate, phencyclidine, and glycine receptors in buffy coat membranes, *J. Pharmacol. Meth.* 21:161 (1989).

Kantak et al., Effects of N–methyl–D–aspartate antagonists in rats discriminating different doses of cocaine: Comparisons with direct and indirect dopamine agonists, *J. Pharmacol. Exper. Therap.* 274:657–665 (1995).

Karp et al., Molecular cloning and chromosomal localization of the key subunit of the human N–methyl–D–aspartate receptor, *J. Biol. Chem.* 268:3728–3733 (1993).

Kemp et al., Protein kinase recognition sequence motifs, *Trends Biochem. Sci.* 15:342–346 (1990).

Kishimoto et al. Studies on the phosphorylation of myelin basic protein by protein kinase C and adenosine 3':5'–monophosphate–dependent protein kinase, *J. Biol. Chem.* 260:12492–12499 (1985).

Kisselev et al., Receptor–G protein coupling is established by a conformational switch in the βγ complex, *Proc. Natl. Acad. Sci. USA* 92:9102–9106 (1995).

Kleuss et al., Selectivity in signal transduction determined by γ subunits of heterotrimeric G proteins, *Science* 259:832 (1993).

Köhr et al., NMDA receptor Channels: Subunit–specific potentiation by reducing agents, *Neuron* 12:1031–1040 (1994).

Kozak, Structural features in eukaryotic mRNAs that modulate the initiation of translation, *J. Biol. Chem.* 266:19867–19870 (1991).

Krieg and Melton, Functional messenger RNAs are produced by SP6 in vitro transcription of cloned cDNAs, *Nucleic Acids Research* 12:7057–7070 (1984).

Kumar et al., Cloning of cDNA for the glutamate–binding subunit of an NMDA receptor complex, *Nature* 354:70–73 (1991).

Kutsuwada et al., Molecular diversity of the NMDA receptor channel, *Nature* 358:36–41 (1992).

Kyte and Doolittle, A simple method for displaying the hydropathic chacter of a protein, *J. Mol. Biol.* 157:105 (1982).

Landwehrmeyer et al., NMDA receptor subunit mRNA expression by projection neurons and interneurons in rat straitum, *J. Neurosci.* 15(7):5297–5307 (1995).

Le Bourdellès et al., Cloning, functional coexpression, and pharmacological characterisation of human cDNAs encoding NMDA receptor NR1 and NR2A subunits, *J. Neurochem.* 62:2091–2098 (1994).

Linder and Gilman, G proteins, *Scientific American* 267:56–65 (1992).

Liu et al., Mutational analysis of the relative orientation of transmembrane helices I and VII in G protein–coupled receptors, *J. Biol. Chem.* 270(3):19532–19539 (1995).

Lynch et al., Pharmacological chacterization of heterodimeric NMDA receptors of NR1a and 2B subunits: Differences with receptors formed from NR 1a and 2A, *J. Neurochem.* 64:1462–1468 (1995).

Masayuki, Human mRNA for key subunit of the N–methyl–D–aspartate, DDBJ database (Jul. 20, 1993).

Masu et al., Sequences and expression of a metabotropic glutamate receptor, *Nature* 349:760–765 (1991).

Matsui et al., Functional comparison of D–Serine and glycine in rodents: the effect on cloned NMDA receptors and the extracellular concentration, *J. Neurochemistry* 65:454–458 (1995).

Mayer, NMDA receptors cloned at last, *Nature* 354:16–17 (1991).

Meguro et al., Functional characterization of a heteromeric NMDA receptor channel expressed from cloned cDNAs, *Nature* 357:70–74 (1992).

Meldrum, Possible therapeutic applications of antagonists of excitatory amino acid neurotransmitters, *Clin. Sci.* 68:113–122 (1985).

Meldrum et al., Excitatory amino acid neurotoxicity and neurodegenerative disease, *Trends Pharmacol. Sci.* 11:379–387 (1990).

Minakami et al., The expression of two splice variants of metabotropic glutamate receptor subtype 5 in the rat brain and neuronal cells during development, *J. Neurochem.* 65:1536–1542 (1995).

Monaghan et al., The excitory amino acid receptors: Their classes, pharmacology, and distinct properties in the function of the central nervous system, *Ann. Rev. Pharmacol. Toxicol.* 29:365–402 (1980).

Monyer et al., Heteromeric NMDA receptors: Molecular and functional distinction of subtypes, *Science* 256:1217–1221 (1992).

Monyer et al., Developmental and regional expression in the rat brain and functional properties of four NMDA receptors, *Neuron* 12:529–540 ((1994).

Moriyoshi et al., Molecular cloning and characterization of the rat NMDA receptor, *Nature* 354:31–37 (1991).

Nakajima et al., Direct linkage of three tachykinin receptors to stimulation of both phosphatidylinositol hydrolysis and cyclic AMP cascades in tranfected Chinese hamster ovary cells, *J. Biol. Chem.* 267:2437–2442 (1992).

Nakanishi, Molecular diversity of glutamate receptors and implications for brain function, *Science* 258:597–602 (1992).

Nicoletti et al., The activation of inositol phospholipid metabolism as a signal–transducing system for excitory amino acids in primary cultures of cerebellar granule cells, *J. Neurosci.* 6: 1905 (1986).

SIBIA/Ciba–Geigy agreement, *UCSD Connect* (Sep. 16, 1992).

Ogita et al., A possible role of glutathione as an endogenous agonist at the N–methyl–D–asparate recognition domain in rat brain, *J. Neurochem.* 64:1088–1096 (1995).

Other News to Note, *BioWorld Today*, 6 (Apr. 15, 1994).

O'Connor et al., Tetanically induced LTP involves a similar increase in the AMPA and NMDA receptor components of the excitory postsynaptic current: Investigations of the involvement of mGLU receptors, *J. Neurosci.* 15(3):2013–2020 (1995).

Paoletti and Ascher, Mechansensitivity of NMDA receptors in cultured mouse central neurons, *Neuron* 13:645–655 (1995).

Pin et al., Alternative splicing generates metabotropic glutamate receptors inducing different patterns of calcium release in Xenopus oocytes, *Neurobiology* 89:10331–10335 (1992).

Planells–Cases et al., Molecular cloning, functional expression, and pharmacological characterization of an N–methyl–D–asparate receptor subunit from human brain, *Proc. Natl. Acad. Sci. USA* 90:5057–5061 (1993).

Potter, Sibia to collaborate with Ciba–Geigy, *BioWorld Today* 3:1 (Sep. 17, 1992).

Reeck et al., "Homology" in proteins and nucleic acids: a terminology muddl;e and a way out of it, *Cell* 50: 667 (1987).

Reuter et al., Glutamate receptor RNA editing in vitro by enzymatic conversion of adenosine to inosine, *Science* 267:1491–1494 (1995).

Sakurada et al., Alternation of $Ca^{2+}$ permeability and sensitivity to $Mg^{2+}$ and channel blockers by a single amino acid substitution in the N–methyl–D–aspartate , *J. Biol. Chem.* 268(1):410–415 (1993).

Sambrook et al., *Molecular Cloning. A Laboratory Manual*, 2nd Ed., Cold Spring Harbor Laboratory Press (1989).

Sanes et al., Use of recombinant retrovirus to study post–implantation cell lineage in mouse embryos, *Embo J.* 5(12):3133–3142 (1986).

Sanner et al., NMDA receptor blockade rescues Clarke's and red nucleus neurons after spinal hemisection, *J. Neurosci* 14(11):6472–6480 (1995).

Schoepp et al., 1S,3R–ACPD–sensitive (metabotropic [$^3$H] glutamate receptor binding in membranes, *Neurosci. Lett.* 145:100 (1992).

Sills et al., [$^3$H]CGP 39653: a new N–methyl–D–asparate antagonist radioligand with low nanamolar affinity in rat brain, *Eur. J. Pharmacol.* 192:19 (1991).

Simon et al., Diversity of G proteins in signal transduction, *Science* 252:802 (1991).

Singaram et al., Dopaminergic defect of enteric nervous system in Parkinson's disease patients with chronic constipation, *Lancet* 346:861–864 (1995).

Sladeczek et al., Glutamate stimulates inositol phosphate formation in striatial neurones, *Nature* 317:717 (1985).

Smirnova et al., Cloning a complementary DNA fragment of human brain kainate receptor, *Dokl. Akad. Nauk SSSR* 309(3):745–748 (1989).

Smirnova et al., Characterization of a presynaptic glutamate receptor, *Science* 262:430–433 (1993).

Smirnova et al., Transsynaptic expression of a presynaptic glutamate receptor during hippocampal long–term potentiation, *Science* 262:433–436 (1993).

Sommer et al., Glutamate receptor channels: novel properties and new clones, *Trends Pharmacol. Sci.* 13:291 296 (1992).

Steiner et al., Radioimmunoassay for cyclic nucleotides, *J. Biol. Chem.* 247:1106–1113 (1972).

Stillman et al., Replication and supercoiling of simian virus 40DNA in cell extracts from human cells, *Mol. Cell. Biol.* 5:2051–2060 (1985).

Stühmer, Electrophysiological recording from Xenopus oocytes, *Meth. Enzymol.* 207:319–339 (1992).

Stumpo D. et al., Identification of c–fos sequences involved in induction by insulin and phorbol esters, *J. Biol. Chem.* 263(4):1611 (1988).

Sugihara et al., Structures and properties of seven isoforms of the NMDA receptor generated by alternative splicing, *Biochem. Biophys. Res. Commun.* 185(3):826–832 (1992).

Sugiyama et al., A new type of glutamate receptor linked to inositol phospholipid metabolism, *Nature* 325:531 (1987).

Sullivan et al., Identifiction of two cysteine residues that are required for redox modulation of the NMDA subtype of glutamate receptor, *Neuron* 13:929–936 (1994).

Takano et al., Chromosomal localization of the $\epsilon 1, \epsilon 3$ and $\zeta 1$ subunit genes of the human NMDA receptor channel, *Biochem. Biophys. Res. Commun.* 197(2):922–926 (1993).

Tamir et al., G–protein $\beta\gamma$ forms: identity of $\beta$ and diversity of $\gamma$ subunits, *Biochemistry* 30:3929 (1991).

Tanabe et al., A family of metabotropic glutamate receptors, *Neuron* 8:169–179 (1992).

Tingley et al., Regulation of NMDA receptor phosphorylation of alternative splicing of the C–terminal domain, *Nature* 364:70–73 (1993).

Ulas et al., Selective increase of NMDA–sensitive glutamate binding in the striatum of Parkinson's disease, Alzheimer's disease, and mixed Parkinson's disease/ Alzheimer's disease patients: An autoradiographic study, *J. Neurosci.* 14(11):6317–6324 (1994).

Urlaub et al., Effect of gamma rays at the dihydrofolate reductase locus: Deletions and Inversions, *Somatic Cell and Mol. Genetics* 12(6):555–566 (1986).

Varney et al., Stable expression and characterization of recombinant human dimeric NMDA receptor subtypes 1A/2A and 1A/2B in mammalian cells, *Soc. Neurosci. Abstr.* (1995).

Vornov et al., Enhancement of NMDA receptor–mediated neurotoxicity in the hippocampal slice by depolarization and ischemia, *Brain Res.* 555:99–106 (1991).

Waechter and Baserga, Effect of methylation on expression of microinjected genes, *Proc. Nat. Acad. Sci. USA* 79:1106–1110 (1982).

Wafford et al., Preferential co–assembly of recombinant NMDA receptors composed of three different subunits, *NeuroReport* 4(12):1347–1349 (1993).

Wahlestedt et al., Antisense oligodeoxynucleotides to NMDA–R1 receptor channel protect cortical neurons from excitotoxicity and reduce focal ischaemic infarctions, *Nature* 363:260–263 (1993).

Wenzel et al., Distribution of NMDA receptor subunit proteins NR2A, 2B, 2C, and 2D in rat brain, *NeuroReport* 745–48 (1995).

Wigler et al., DNA–mediated transfer of the adenine phosphoribosyltransferase locus into mammalian cells, *Proc. Natl. Acad. Sci. USA* 76:1373–1376 (1979).

Wong et al., The anticonvulsant MK–801 is a potent N–methyl–D–aspartate antagonist, *Proc. Natl. Acad. Sci. USA* 83:7104 (1986).

Yakel et al., Identification of a $Ca^{2+}$/calmodulin protein kinase II regulatory phosphorylation site in N–methylD–aspartate glutamate receptors, *Proc. Natl. Acad. Sci. USA* 92:1376–1380 (1995).

Yamazaki, M. et al., Cloning, expression and molulation of a mouse NMDA receptor subunit *FEBS Letters 300*(1):39 (1992).

Young et al., NMDA receptor losses in putamen from patients with Huntington's Disease, *Science 241*:981–983 (1988).

Younkin et al., Inducible expression of neuronal glutamate receptor channels in the NT2 human cell line, *Proc. Natl. Acad. Sci. USA 90*:2174–2178 (1993).

Zeevalk et al., Chemically induced hypoglycemia and anoxia: Relationship to glutamate receptor–mediated toxicity in retina, *J. Pharmacol. Exp. Thera. 253*(3):1285–1292 (1990).

Zeevalk et al., Mechanisms underlying initiation of excitotoxicity associated with metabolic inhibition, *J. Pharmacol. Exp. Thera. 257*:870–878 (1991).

Zhang et al., Spermine potentiation of recombinant N–methyl–D–aspartate receptors is affected by subunit composition, *Proc. Natl. Acad. Sci. USA 91*:10883–10887 (1994).

Zipser et al., Mapping function domains in the promoter region of the herpes thymidine kinase gene, *Proc. Natl. Acad. Sci. USA 78*(10):6276–6280 (1981).

* cited by examiner

NUCLEOTIDE SEQUENCE OF THE HUMAN NMDAR1A RECEPTOR

```
   1  ccagccggc gttcggagct gtgccggcc ccgcttcagc accggacca gcgccggcc cgtggggctg agcgccgagc ccccgcgcac gcttcagccc
 101  cccttccctc ggccgacgtc ccggaccgc cgctccgggg gggcgtggc gtccgcagcc cgccgagcc ggcgagcgca ggccggcccg gaagcccgc
 201  gggggatgcg ccgagggccc cgcgttcgcg ccgcgcagag ccaggcccgc ggcccgagcc ATGGCCCTGC TGAGCACC AGCAGAGCGA GATGTTCCGC GAGGCCGTGA
                                                                  — START
 301  TCCTGCTCCG TGGCCGTGC CGCGTCCGAC CCCAAGATCG TCAACATTGG CCCGGTGCTG CGCGTCACGC ACAAGCCCAA CGGCATCCGG ATGCCTCTGT CGGTGTGCGA
 401  ACCAGGCCAA CAAGCGGCAC GGCTCCTGGA AGATTCAGCT CAATGCCACC TCCGTCACGC ATAAGCCCAA AGTGAAGCTC CCCACCCCTG TCTCCTACAC AGCCGGCTTC
 501  GGAACTCATC TCCAGCCAGG TCTAGTTAGC CATCCACCTA CCTCAAGATC CCACTTCACT CCTGCGCAC TCCTGCCGCC CGTGCCGCCC TACTCCCACC
 601  TACGGCATAC CCGTGCTGGG GCTGACCACC CGCATGTCCA CAGAGCATC TCTACTCGGA CAAGAGCATC CACCTGAGCT CACCTGAGCT CCGTGCGCAC TACTCCCACC
 701  AGTCCAGCGT GTGGTTTGAG ATGATGATCGTG TCTACAGCTG GAACCACATC TCAGCGCTGG TCAGGGACGA CCACGAGGGC CGGGGGGCTC AGAAACGCCT
                                    ┌Pvu II┐
                                    ┌—63 bp INSERT
 801  GGAGAGCCTG CTGGAGTCCA GTCAGAGAAG GTGCTGCAGT TTGACCCAGG GACCAAGAAC GTGACGGCCC TGCTGATGGA GGGCAAAGAG
                                                  Bgl II
 901  CTGAGGAGCCC GGGTCATCAT CCTTTCTGCC AGCGGAGACG ATGCGCCAC TGTATACCGC GCAGCCGCGA TGCTGAACAT GACGGCTCC GGGTACGTGT
                                                                                                        ┌— 204 bp
                                                                                                        └ DELETION
1001  GGCTGGTCGG CGAGCGCGAG ATCTCGGGGA ACGCCCTGCG CTACGCCCCA GACGGCCATCC TGGGCTGCA GCTCATCAAC GGCAAGAACG AGTCGCCCCA
1101  CATCAGCGAC GCCGTGGGCG TGGTGCCCA GCCGTGCAC GAGCTCCTCG AGAAGGAGAA CATCACCGAC CCGCCGGGG GCTGCGTGGG CAACACCAAC
1201  ATCTGGAAGA CCGGGCCGCT CTTCAAGAGA GTGCTGATGT CTTCCAAGTA TGCCGATGGC GTGACTGGTC GCGTGGAGTT CAATGAGGAT GGGACCGGA
1301  AGTTCGCCAA CTACAGCATC ATGAACCTGC AGAACCGCAA GCTGGTCCAA GTGGGCATCT ACAATGGCAC CCACGTCATC CCTAATGACA GGAAGATCAT
1401  CTGGCCAGGC GGAGACACAG AGGGTACCAC ATGTCCACCA GACTGAAGAT TGTGACGGAT CACCAGGAGC CCTTCGTGTA CGTCAAGCCC
1501  ACCCTGAGTG ATGGAACATG CAAGGAGGAG TTCACAGTCA ACGGCGACCC AGTCAAGAAG GTGATCTGCA CCGGGCCCAA CGACACGTCG CCGGGCAGCC
1601  CCCGCCACAC GGTGCCTCAG GCTTTTGCAT CGACCTGCTC ATCAAGCTGG CACGGACCAT GAACTTCACC TACGAGGTGC ACCTGGTGGC
1701  AGATGGCAAG TTCGCACAC AGGAGCGGGT GAACAACAGC AACAAGAAGG AGTGAATGG GATGGATGGG CCTGCTCA GCGGCAGGC AGACATGATC
1801  GTGGCGCGC TAACCATAAA CGGCAGTACA TCGAGTTTTC CAAGCCCTTC AAGTACCAGG GCCTGACTAT TCTGGTCAAG AAGGAGATTC
1901  CCCGAGCAC GCTGACTCCG CGTTCCAGAG CACACTGTGG CTGCTGTCGT GACGTGGTG GGCTGTGATGC GCAGTGGTG CAGGAGGCT
2001  GGACGCCTTC AGCCCCTTCG GCCGGTTCAA GGTGAACAGC GAGGAGAGG ACTGACCCTG TCCTCGGCCA TGTGTTCTC CTGGGGGTC
```

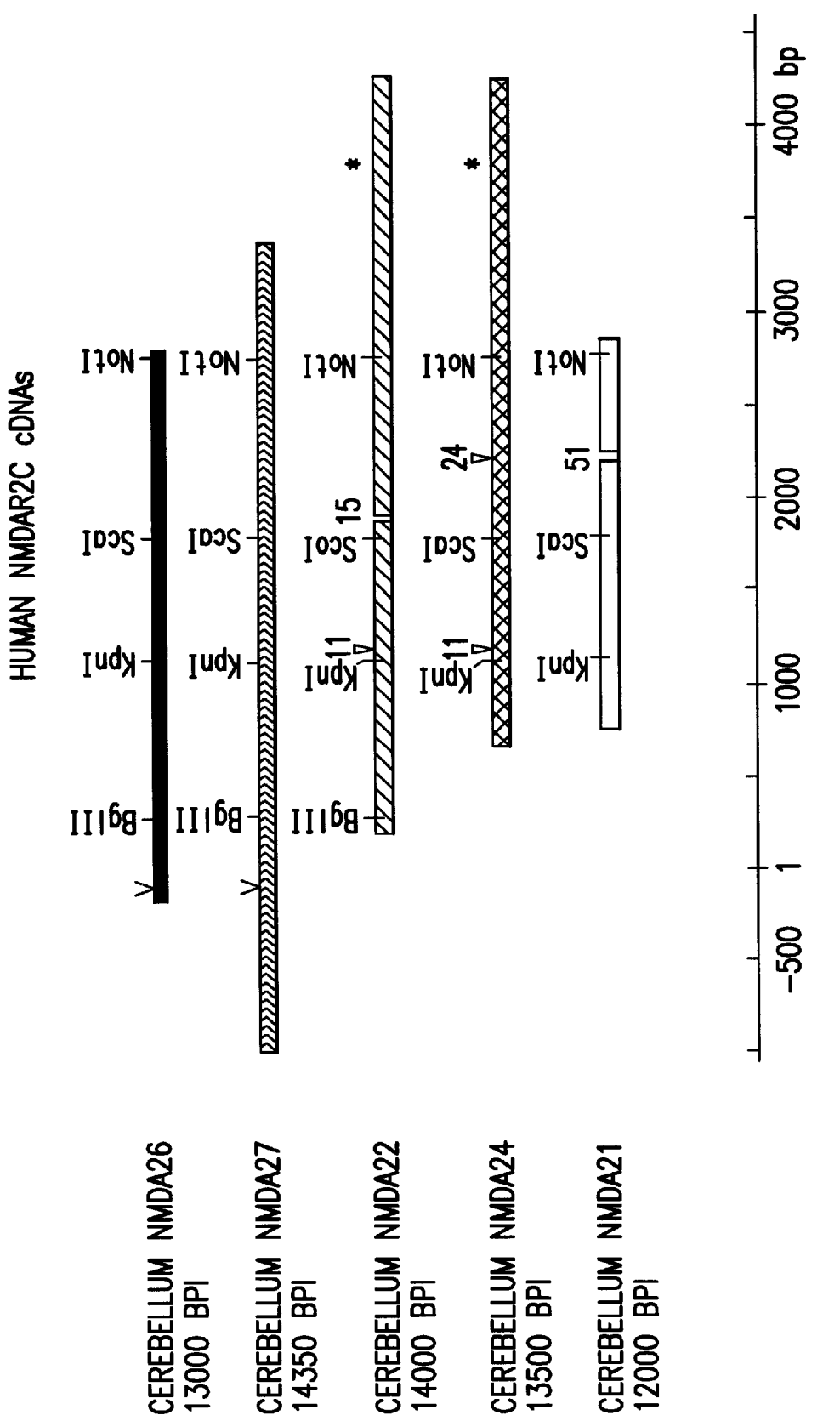

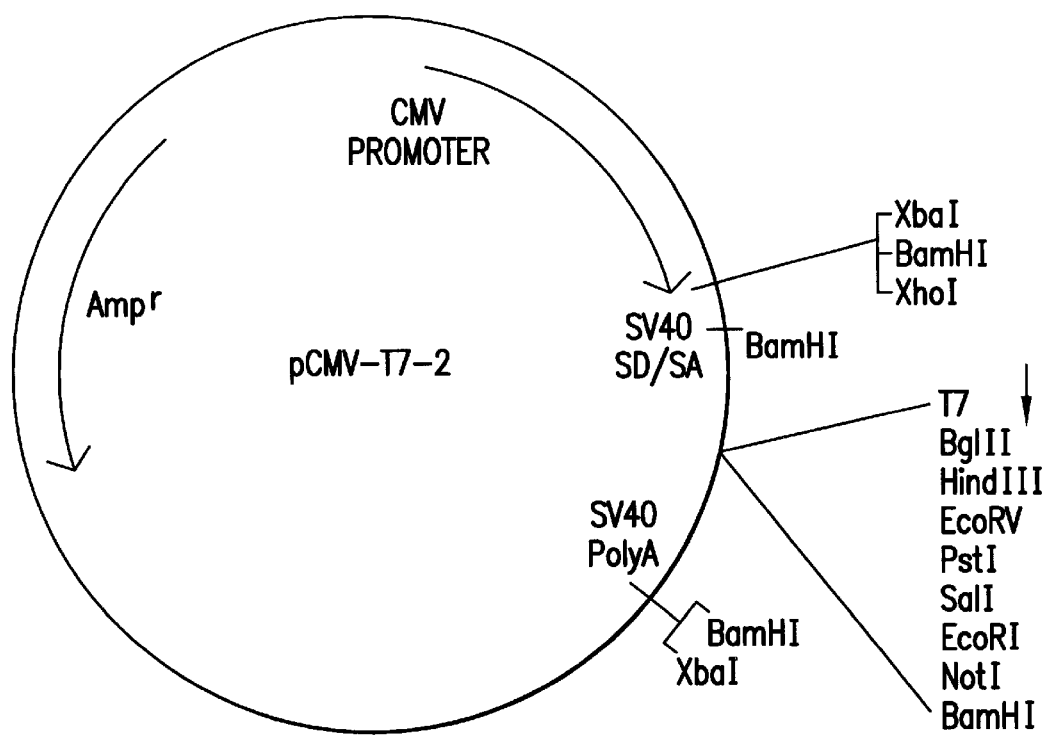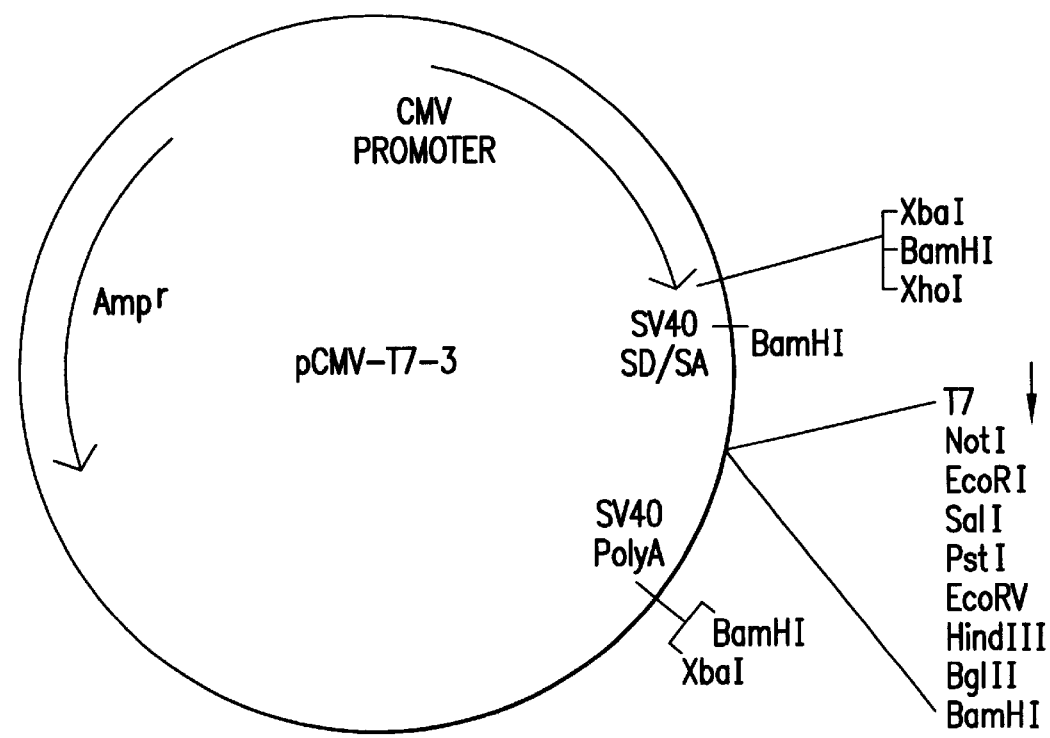
FIG.6

SEQUENCE LISTING (1) GENERAL INFORMATION:

(iii) NUMBER OF SEQUENCES: 63

(2) INFORMATION FOR SEQ ID NO:1:

(i) SEQUENCE CHARACTERISTICS:
       (A) LENGTH: 4298 base pairs
       (B) TYPE: nucleic acid
       (C) STRANDEDNESS: both
       (D) TOPOLOGY: both (ii) MOLECULE TYPE: cDNA (ix) FEATURE:
       (A) NAME/KEY: CDS
       (B) LOCATION: 262..3078

(xi) SEQUENCE DESCRIPTION: SEQ ID NO:1:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                         Met Ser Thr Met Arg Leu Leu Thr Leu Ala
                          1               5                    10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
             15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
                 30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
             45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
         60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                     95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
             110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
         125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
     140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                 175                 180                 185
```

```
CGT GAG TCC AAG GCA GAG AAG GTG CTG CAG TTT GAC CCA GGG ACC AAG      867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC      915
Asn Val Thr Ala Leu Leu Met Glu Ala Lys Glu Leu Glu Ala Arg Val
            205                 210                 215

ATC ATC CTT TCT GCC AGC GAG GAC GAT GCT GCC ACT GTA TAC CGC GCA      963
Ile Ile Leu Ser Ala Ser Glu Asp Asp Ala Ala Thr Val Tyr Arg Ala
            220                 225                 230

GCC GCG ATG CTG AAC ATG ACG GGC TCC GGG TAC GTG TGG CTG GTC GGC     1011
Ala Ala Met Leu Asn Met Thr Gly Ser Gly Tyr Val Trp Leu Val Gly
235                 240                 245                 250

GAG CGC GAG ATC TCG GGG AAC GCC CTG CGC TAC GCC CCA GAC GGC ATC     1059
Glu Arg Glu Ile Ser Gly Asn Ala Leu Arg Tyr Ala Pro Asp Gly Ile
            255                 260                 265

CTC GGG CTG CAG CTC ATC AAC GGC AAG AAC GAG TCG GCC CAC ATC AGC     1107
Leu Gly Leu Gln Leu Ile Asn Gly Lys Asn Glu Ser Ala His Ile Ser
            270                 275                 280

GAC GCC GTG GGC GTG GTG GCC CAG GCC GTG CAC GAG CTC CTC GAG AAG     1155
Asp Ala Val Gly Val Val Ala Gln Ala Val His Glu Leu Leu Glu Lys
            285                 290                 295

GAG AAC ATC ACC GAC CCG CCG CGG GGC TGC GTG GGC AAC ACC AAC ATC     1203
Glu Asn Ile Thr Asp Pro Pro Arg Gly Cys Val Gly Asn Thr Asn Ile
            300                 305                 310

TGG AAG ACC GGG CCG CTC TTC AAG AGA GTG CTG ATG TCT TCC AAG TAT     1251
Trp Lys Thr Gly Pro Leu Phe Lys Arg Val Leu Met Ser Ser Lys Tyr
315                 320                 325                 330

GCG GAT GGG GTG ACT GGT CGC GTG GAG TTC AAT GAG GAT GGG GAC CGG     1299
Ala Asp Gly Val Thr Gly Arg Val Glu Phe Asn Glu Asp Gly Asp Arg
            335                 340                 345

AAG TTC GCC AAC TAC AGC ATC ATG AAC CTG CAG AAC CGC AAG CTG GTG     1347
Lys Phe Ala Asn Tyr Ser Ile Met Asn Leu Gln Asn Arg Lys Leu Val
            350                 355                 360

CAA GTG GGC ATC TAC AAT GGC ACC CAC GTC ATC CCT AAT GAC AGG AAG     1395
Gln Val Gly Ile Tyr Asn Gly Thr His Val Ile Pro Asn Asp Arg Lys
            365                 370                 375

ATC ATC TGG CCA GGC GGA GAG ACA GAG AAG CCT CGA GGG TAC CAG ATG     1443
Ile Ile Trp Pro Gly Gly Glu Thr Glu Lys Pro Arg Gly Tyr Gln Met
380                 385                 390

TCC ACC AGA CTG AAG ATT GTG ACG ATC CAC CAG GAG CCC TTC GTG TAC     1491
Ser Thr Arg Leu Lys Ile Val Thr Ile His Gln Glu Pro Phe Val Tyr
395                 400                 405                 410

GTC AAG CCC ACG CTG AGT GAT GGG ACA TGC AAG GAG GAG TTC ACA GTC     1539
Val Lys Pro Thr Leu Ser Asp Gly Thr Cys Lys Glu Glu Phe Thr Val
            415                 420                 425

AAC GGC GAC CCA GTC AAG AAG GTG ATC TGC ACC GGG CCC AAC GAC ACG     1587
Asn Gly Asp Pro Val Lys Lys Val Ile Cys Thr Gly Pro Asn Asp Thr
            430                 435                 440

TCG CCG GGC AGC CCC CGC CAC ACG GTG CCT CAG TGT TGC TAC GGC TTT     1635
Ser Pro Gly Ser Pro Arg His Thr Val Pro Gln Cys Cys Tyr Gly Phe
            445                 450                 455

TGC ATC GAC CTG CTC ATC AAG CTG GCA CGG ACC ATG AAC TTC ACC TAC     1683
Cys Ile Asp Leu Leu Ile Lys Leu Ala Arg Thr Met Asn Phe Thr Tyr
460                 465                 470

GAG GTG CAC CTG GTG GCA GAT GGC AAG TTC GGC ACA CAG GAG CGG GTG     1731
Glu Val His Leu Val Ala Asp Gly Lys Phe Gly Thr Gln Glu Arg Val
475                 480                 485                 490

AAC AAC AGC AAC AAG AAG GAG TGG AAT GGG ATG ATG GGC GAG CTG CTC     1779
Asn Asn Ser Asn Lys Lys Glu Trp Asn Gly Met Met Gly Glu Leu Leu
```

```
                495                 500                       505
AGC GGG CAG GCA GAC ATG ATC GTG GCG CCG CTA ACC ATA AAC AAC GAG    1827
Ser Gly Gln Ala Asp Met Ile Val Ala Pro Leu Thr Ile Asn Asn Glu
            510             515                 520

CGC GCG CAG TAC ATC GAG TTT TCC AAG CCC TTC AAG TAC CAG GGC CTG    1875
Arg Ala Gln Tyr Ile Glu Phe Ser Lys Pro Phe Lys Tyr Gln Gly Leu
        525                 530                 535

ACT ATT CTG GTC AAG AAG GAG ATT CCC CGG AGC ACG CTG GAC TCG TTC    1923
Thr Ile Leu Val Lys Lys Glu Ile Pro Arg Ser Thr Leu Asp Ser Phe
    540                 545                 550

ATG CAG CCG TTC CAG AGC ACA CTG TGG CTG CTG GTG GGG CTG TCG GTG    1971
Met Gln Pro Phe Gln Ser Thr Leu Trp Leu Leu Val Gly Leu Ser Val
555                 560                 565                 570

CAC GTG GTG GCC GTG ATG CTG TAC CTG CTG GAC CGC TTC AGC CCC TTC    2019
His Val Val Ala Val Met Leu Tyr Leu Leu Asp Arg Phe Ser Pro Phe
                575                 580                 585

GGC CGG TTC AAG GTG AAC AGC GAG GAG GAG GAG GAG GAC GCA CTG ACC    2067
Gly Arg Phe Lys Val Asn Ser Glu Glu Glu Glu Glu Asp Ala Leu Thr
            590                 595                 600

CTG TCC TCG GCC ATG TGG TTC TCC TGG GGC GTC CTG CTC AAC TCC GGC    2115
Leu Ser Ser Ala Met Trp Phe Ser Trp Gly Val Leu Leu Asn Ser Gly
        605                 610                 615

ATC GGG GAA GGC GCC CCC AGA AGC TTC TCA GCG CGC ATC CTG GGC ATG    2163
Ile Gly Glu Gly Ala Pro Arg Ser Phe Ser Ala Arg Ile Leu Gly Met
    620                 625                 630

GTG TGG GCC GGC TTT GCC ATG ATC ATC GTG GCC TCC TAC ACC GCC AAC    2211
Val Trp Ala Gly Phe Ala Met Ile Ile Val Ala Ser Tyr Thr Ala Asn
635                 640                 645                 650

CTG GCG GCC TTC CTG GTG CTG GAC CGG CCG GAG GAG CGC ATC ACG GGC    2259
Leu Ala Ala Phe Leu Val Leu Asp Arg Pro Glu Glu Arg Ile Thr Gly
                655                 660                 665

ATC AAC GAC CCT CGG CTG AGG AAC CCC TCG GAC AAG TTT ATC TAC GCC    2307
Ile Asn Asp Pro Arg Leu Arg Asn Pro Ser Asp Lys Phe Ile Tyr Ala
            670                 675                 680

ACG GTG AAG CAG AGC TCC GTG GAT ATC TAC TTC CGG CGC CAG GTG GAG    2355
Thr Val Lys Gln Ser Ser Val Asp Ile Tyr Phe Arg Arg Gln Val Glu
        685                 690                 695

CTG AGC ACC ATG TAC CGG CAT ATG GAG AAG CAC AAC TAC GAG AGT GCG    2403
Leu Ser Thr Met Tyr Arg His Met Glu Lys His Asn Tyr Glu Ser Ala
    700                 705                 710

GCG GAG GCC ATC CAG GCC GTG AGA GAC AAC AAG CTG CAT GCC TTC ATC    2451
Ala Glu Ala Ile Gln Ala Val Arg Asp Asn Lys Leu His Ala Phe Ile
715                 720                 725                 730

TGG GAC TCG GCG GTG CTG GAG TTC GAG GCC TCG CAG AAG TGC GAC CTG    2499
Trp Asp Ser Ala Val Leu Glu Phe Glu Ala Ser Gln Lys Cys Asp Leu
                735                 740                 745

GTG ACG ACT GGA GAG CTG TTT TTC CGC TCG GGC TTC GGC ATA GGC ATG    2547
Val Thr Thr Gly Glu Leu Phe Phe Arg Ser Gly Phe Gly Ile Gly Met
            750                 755                 760

CGC AAA GAC AGC CCC TGG AAG CAG AAC GTC TCC CTG TCC ATC CTC AAG    2595
Arg Lys Asp Ser Pro Trp Lys Gln Asn Val Ser Leu Ser Ile Leu Lys
        765                 770                 775

TCC CAC GAG AAT GGC TTC ATG GAA GAC CTG GAC AAG ACG TGG GTT CGG    2643
Ser His Glu Asn Gly Phe Met Glu Asp Leu Asp Lys Thr Trp Val Arg
    780                 785                 790

TAT CAG GAA TGT GAC TCG CGC AGC AAC GCC CCT GCG ACC CTT ACT TTT    2691
Tyr Gln Glu Cys Asp Ser Arg Ser Asn Ala Pro Ala Thr Leu Thr Phe
795                 800                 805                 810

GAG AAC ATG GCC GGG GTC TTC ATG CTG GTA GCT GGG GGC ATC GTG GCC    2739
```

```
Glu Asn Met Ala Gly Val Phe Met Leu Val Ala Gly Gly Ile Val Ala
                815                 820                 825

GGG ATC TTC CTG ATT TTC ATC GAG ATT GCC TAC AAG CGG CAC AAG GAT        2787
Gly Ile Phe Leu Ile Phe Ile Glu Ile Ala Tyr Lys Arg His Lys Asp
            830                 835                 840

GCT CGC CGG AAG CAG ATG CAG CTG GCC TTT GCC GCC GTT AAC GTG TGG        2835
Ala Arg Arg Lys Gln Met Gln Leu Ala Phe Ala Ala Val Asn Val Trp
        845                 850                 855

CGG AAG AAC CTG CAG GAT AGA AAG AGT GGT AGA GCA GAG CCT GAC CCT        2883
Arg Lys Asn Leu Gln Asp Arg Lys Ser Gly Arg Ala Glu Pro Asp Pro
    860                 865                 870

AAA AAG AAA GCC ACA TTT AGG GCT ATC ACC TCC ACC CTG GCT TCC AGC        2931
Lys Lys Lys Ala Thr Phe Arg Ala Ile Thr Ser Thr Leu Ala Ser Ser
875                 880                 885                 890

TTC AAG AGG CGT AGG TCC TCC AAA GAC ACG AGC ACC GGG GGT GGA CGC        2979
Phe Lys Arg Arg Arg Ser Ser Lys Asp Thr Ser Thr Gly Gly Gly Arg
                895                 900                 905

GGT GCT TTG CAA AAC CAA AAA GAC ACA GTG CTG CCG CGA CGC GCT ATT        3027
Gly Ala Leu Gln Asn Gln Lys Asp Thr Val Leu Pro Arg Arg Ala Ile
            910                 915                 920

GAG AGG GAG GAG GGC CAG CTG CAG CTG TGT TCC CGT CAT AGG GAG AGC        3075
Glu Arg Glu Glu Gly Gln Leu Gln Leu Cys Ser Arg His Arg Glu Ser
        925                 930                 935

TGAGACTCCC CGCCCGCCCT CCTCTGCCCC CTCCCCCGCA GACAGACAGA CAGACGGACG      3135

GGACAGCGGC CCGGCCCACG CAGAGCCCCG GAGCACCACG GGGTCGGGGG AGGAGCACCC      3195

CCAGCCTCCC CCAGGCTGCG CCTGCCCGCC CGCCGGTTGG CCGGCTGGCC GGTCCACCCC      3255

GTCCCGGCCC CGCGCGTGCC CCCAGCGTGG GGCTAACGGG CGCCTTGTCT GTGTATTTCT      3315

ATTTTGCAGC AGTACCATCC CACTGATATC ACGGGCCCGC TCAACCTCTC AGATCCCTCG      3375

GTCAGCACCG TGGTGTGAGG CCCCCGGAGG CGCCCACCTG CCCAGTTAGC CCGGCCAAGG      3435

ACACTGATGG GTCCTGCTGC TCGGGAAGGC CTGAGGGAAG CCCACCCGCC CCAGAGACTG      3495

CCCACCCTGG GCCTCCCGTC CGTCCGCCCG CCCACCCCGC TGCCTGGCGG GCAGCCCCTG      3555

CTGGACCAAG GTGCGGACCG GAGCGGCTGA GGACGGGGCA GAGCTGAGTC GGCTGGGCAG      3615

GGCCGCAGGG CGCTCCGGCA GAGGCAGGCC CCTGGGGTCT CTGAGCAGTG GGGAGCGGGG      3675

GCTAACTGCC CCCAGGCGGA GGGGCTTGGA GCAGAGACGG CAGCCCCATC CTTCCCGCAG      3735

CACCAGCCTG AGCCACAGTG GGGCCCATGG CCCCAGCTGG CTGGGTCGCC CCTCCTCGGG      3795

CGCCTGCGCT CCTCTGCAGC CTGAGCTCCA CCCTCCCCTC TTCTTGCGGC ACCGCCCACC      3855

AAACACCCCG TCTGCCCCTT GACGCCACAC GCCGGGGCTG GCGCTGCCCT CCCCCACGGC      3915

CGTCCCTGAC TTCCCAGCTG GCAGCGCCTC CCGCCGCCTC GGGCCGCCTC CTCCAGAATC      3975

GAGAGGGCTG AGCCCCTCCT CTCCTCGTCC GGCCTGCAGC ACAGAAGGGG GCCTCCCCGG      4035

GGGTCCCCGG ACGCTGGCTC GGGACTGTCT TCAACCCTGC CCTGCACCTT GGGCACGGGA      4095

GAGCGCCACC CGCCCGCCCC CGCCCTCGCT CCGGGTGCGT GACCGGCCCG CCACCTTGTA      4155

CAGAACCAGC ACTCCCAGGG CCCGAGCGCG TGCCTTCCCC GTGCGCAGCC GCGCTCTGCC      4215

CCTCCGTCCC CAGGGTGCAG GCGCGCACCG CCCAACCCCC ACCTCCCGGT GTATGCAGTG      4275

GTGATGCCTA AAGGAATGTC ACG                                              4298

(2) INFORMATION FOR SEQ ID NO:2:

(i) SEQUENCE CHARACTERISTICS:
        (A) LENGTH: 938 amino acids
        (B) TYPE: amino acid
```

(D) TOPOLOGY: linear (ii) MOLECULE TYPE: protein (xi) SEQUENCE DESCRIPTION: SEQ ID NO:2:

Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
             35                  40                  45

Ala Asn Lys Arg His Gly Ser Trp Lys Ile Gln Leu Asn Ala Thr Ser
         50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
            115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
            195                 200                 205

Met Glu Ala Lys Glu Leu Glu Ala Arg Val Ile Ile Leu Ser Ala Ser
        210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile

-continued

```
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
                420                 425                 430

Lys Val Ile Cys Thr Gly Pro Asn Asp Thr Ser Pro Gly Ser Pro Arg
                435                 440                 445

His Thr Val Pro Gln Cys Cys Tyr Gly Phe Cys Ile Asp Leu Leu Ile
                450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
                500                 505                 510

Ile Val Ala Pro Leu Thr Ile Asn Asn Glu Arg Ala Gln Tyr Ile Glu
                515                 520                 525

Phe Ser Lys Pro Phe Lys Tyr Gln Gly Leu Thr Ile Leu Val Lys Lys
            530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
                580                 585                 590

Ser Glu Glu Glu Glu Asp Ala Leu Thr Leu Ser Ser Ala Met Trp
                595                 600                 605

Phe Ser Trp Gly Val Leu Leu Asn Ser Gly Ile Gly Glu Gly Ala Pro
            610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
                660                 665                 670

Arg Asn Pro Ser Asp Lys Phe Ile Tyr Ala Thr Val Lys Gln Ser Ser
                675                 680                 685

Val Asp Ile Tyr Phe Arg Arg Gln Val Glu Leu Ser Thr Met Tyr Arg
            690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
                740                 745                 750

Phe Phe Arg Ser Gly Phe Gly Ile Gly Met Arg Lys Asp Ser Pro Trp
            755                 760                 765

Lys Gln Asn Val Ser Leu Ser Ile Leu Lys Ser His Glu Asn Gly Phe
        770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815
```

```
Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Asp
            850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Ser Thr Gly Gly Arg Gly Ala Leu Gln Asn Gln
            900                 905                 910

Lys Asp Thr Val Leu Pro Arg Arg Ala Ile Glu Arg Glu Glu Gly Gln
            915                 920                 925

Leu Gln Leu Cys Ser Arg His Arg Glu Ser
            930                 935
```

(2) INFORMATION FOR SEQ ID NO:3:

(i) SEQUENCE CHARACTERISTICS:
        (A) LENGTH: 63 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..63

(xi) SEQUENCE DESCRIPTION: SEQ ID NO:3:

```
AGT AAA AAA AGG AAC TAT GAA AAC CTC GAC CAA CTG TCC TAT GAC AAC     48
Ser Lys Lys Arg Asn Tyr Glu Asn Leu Asp Gln Leu Ser Tyr Asp Asn
 1               5                  10                  15

AAG CGC GGA CCC AAG                                                 63
Lys Arg Gly Pro Lys
            20
```

(2) INFORMATION FOR SEQ ID NO:4:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:4:

```
Ser Lys Lys Arg Asn Tyr Glu Asn Leu Asp Gln Leu Ser Tyr Asp Asn
 1               5                  10                  15

Lys Arg Gly Pro Lys
            20
```

(2) INFORMATION FOR SEQ ID NO:5:

(i) SEQUENCE CHARACTERISTICS:
        (A) LENGTH: 4068 base pairs
        (B) TYPE: nucleic acid
        (C) STRANDEDNESS: both
        (D) TOPOLOGY: both (ii) MOLECULE TYPE: cDNA -continued

```
    (ix) FEATURE:
         (A) NAME/KEY: CDS
         (B) LOCATION: 189..3899

(xi) SEQUENCE DESCRIPTION: SEQ ID NO:5:

CCCTTAATAA GATTTGCTAC GTACACTCGA GCCATCGCGA GTGTCCTTGA GCCGCGGGTG      60

ACGGTGGCTC TCGCTGCTCG CGCCCCCTCC TCCCGCGGGG GGAGCCTGAT GCCACGTTCC     120

CTATGAATTA TTTATCGCCG GCCTAAAAAT ACCCCGAACT TCACAGCCCG AGTGACCCTC     180

CGGTGGAC ATG GGT GGG GCC CTG GGG CCG GCC CTG TTG CTC ACC TCG CTC      230
         Met Gly Gly Ala Leu Gly Pro Ala Leu Leu Leu Thr Ser Leu
         1               5                   10

TTC GGT GCC TGG GCA GGG CTG GGT CCG GGG CAG GGC GAG CAG GGC ATG       278
Phe Gly Ala Trp Ala Gly Leu Gly Pro Gly Gln Gly Glu Gln Gly Met
 15                  20                  25                  30

ACG GTG GCC GTG GTG TTT AGC AGC TCA GGG CCG CCC CAG GCC CAG TTC       326
Thr Val Ala Val Val Phe Ser Ser Ser Gly Pro Pro Gln Ala Gln Phe
                 35                  40                  45

CGT GTC CGC CTC ACC CCC CAG AGC TTC CTG GAC CTA CCC CTG GAG ATC       374
Arg Val Arg Leu Thr Pro Gln Ser Phe Leu Asp Leu Pro Leu Glu Ile
             50                  55                  60

CAG CCG CTC ACA GTT GGG GTC AAC ACC ACC AAC CCC AGC AGC CTC CTC       422
Gln Pro Leu Thr Val Gly Val Asn Thr Thr Asn Pro Ser Ser Leu Leu
         65                  70                  75

ACC CAG ATC TGC GGC CTC CTG GGT GCT GCC CAC GTC CAC GGC ATT GTC       470
Thr Gln Ile Cys Gly Leu Leu Gly Ala Ala His Val His Gly Ile Val
     80                  85                  90

TTT GAG GAC AAC GTG GAC ACC GAG GCG GTG GCC CAG ATC CTT GAC TTC       518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT       566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG       614
Ala Val Val Leu Thr Pro Lys Glu Pro Gly Ser Ala Phe Leu Gln Leu
            130                 135                 140

GGC GTG TCC CTG GAG CAG CAG CTG CAG GTG CTG TTC AAG GTG CTG GAA       662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC       710
Glu Tyr Asp Trp Ser Ala Phe Ala Val Ile Thr Ser Leu His Pro Gly
160                 165                 170

CAC GCG CTC TTC CTG GAG GGC GTG CGC GCC GTC GCC GAC GCC AGC CAC       758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA       806
Val Ser Trp Arg Leu Leu Asp Val Val Thr Leu Glu Leu Asp Pro Gly
                195                 200                 205

GGG CCG CGC GCG CGC ACG CAG CGC CTG CTG CGC CAG CTC GAC GCG CCC       854
Gly Pro Arg Ala Arg Thr Gln Arg Leu Leu Arg Gln Leu Asp Ala Pro
            210                 215                 220

GTG TTT GTG GCC TAC TGC TCG CGC GAG GAG GCC GAG GTG CTC TTC GCC       902
Val Phe Val Ala Tyr Cys Ser Arg Glu Glu Ala Glu Val Leu Phe Ala
        225                 230                 235

GAG GCG GCG CAG GCC GGT CTG GTG GGG CCC GGC CAC GTG TGG CTG GTG       950
Glu Ala Ala Gln Ala Gly Leu Val Gly Pro Gly His Val Trp Leu Val
    240                 245                 250

CCC AAC CTG GCG CTG GGC AGC ACC GAT GCG CCC CCC GCC ACC TTC CCC       998
Pro Asn Leu Ala Leu Gly Ser Thr Asp Ala Pro Pro Ala Thr Phe Pro
255                 260                 265                 270
```

```
GTG GGC CTC ATC AGC GTC GTC ACC GAG AGC TGG CGC CTC AGC CTG CGC    1046
Val Gly Leu Ile Ser Val Val Thr Glu Ser Trp Arg Leu Ser Leu Arg
                275             280             285

CAG AAG GTG CGC GAC GGC GTG GCC ATT CTG GCC CTG GGC GCC CAC AGC    1094
Gln Lys Val Arg Asp Gly Val Ala Ile Leu Ala Leu Gly Ala His Ser
            290             295             300

TAC TGG CGC CAG CAT GGA ACC CTG CCA GCC CCG GCC GGG GAC TGC CGT    1142
Tyr Trp Arg Gln His Gly Thr Leu Pro Ala Pro Ala Gly Asp Cys Arg
        305             310             315

GTT CAC CCT GGG CCC GTC AGC CCT GCC CGG GAG GCC TTC TAC AGG CAC    1190
Val His Pro Gly Pro Val Ser Pro Ala Arg Glu Ala Phe Tyr Arg His
    320             325             330

CTA CTG AAT GTC ACC TGG GAG GGC CGA GAC TTC TCC TTC AGC CCT GGT    1238
Leu Leu Asn Val Thr Trp Glu Gly Arg Asp Phe Ser Phe Ser Pro Gly
335             340             345             350

GGG TAC CTG GTC CAG CCC ACC ATG GTG GTG ATC GCC CTC AAC CGG CAC    1286
Gly Tyr Leu Val Gln Pro Thr Met Val Val Ile Ala Leu Asn Arg His
            355             360             365

CGC CTC TGG GAG ATG GTG GGG CGC TGG GAG CAT GGC GTC CTA TAC ATG    1334
Arg Leu Trp Glu Met Val Gly Arg Trp Glu His Gly Val Leu Tyr Met
        370             375             380

AAG TAC CCC GTG TGG CCT CGC TAC AGT GCC TCT CTG CAG CCT GTG GTG    1382
Lys Tyr Pro Val Trp Pro Arg Tyr Ser Ala Ser Leu Gln Pro Val Val
    385             390             395

GAC AGT CGG CAC CTG ACG GTG GCC ACG CTG GAA GAG CGG CCC TTT GTC    1430
Asp Ser Arg His Leu Thr Val Ala Thr Leu Glu Glu Arg Pro Phe Val
400             405             410

ATC GTG GAG AGC CCT GAC CCT GGC ACA GGA GGC TGT GTC CCC AAC ACC    1478
Ile Val Glu Ser Pro Asp Pro Gly Thr Gly Gly Cys Val Pro Asn Thr
415             420             425             430

GTG CCC TGC CGC AGG CAG AGC AAC CAC ACC TTC AGC AGC GGG GAC GTG    1526
Val Pro Cys Arg Arg Gln Ser Asn His Thr Phe Ser Ser Gly Asp Val
            435             440             445

GCC CCC TAC ACC AAG CTC TGC TGT AAG GGA TTC TGC ATC GAC ATC CTC    1574
Ala Pro Tyr Thr Lys Leu Cys Cys Lys Gly Phe Cys Ile Asp Ile Leu
        450             455             460

AAG AAG CTG GCC AGA GTG GTC AAA TTC TCC TAC GAC CTG TAC CTG GTG    1622
Lys Lys Leu Ala Arg Val Val Lys Phe Ser Tyr Asp Leu Tyr Leu Val
    465             470             475

ACC AAC GGC AAG CAT GGC AAG CGG GTG CGC GGC GTA TGG AAC GGC ATG    1670
Thr Asn Gly Lys His Gly Lys Arg Val Arg Gly Val Trp Asn Gly Met
480             485             490

ATT GGG GAG GTG TAC TAC AAG CGG GCA GAC ATG GCC ATC GGC TCC CTC    1718
Ile Gly Glu Val Tyr Tyr Lys Arg Ala Asp Met Ala Ile Gly Ser Leu
495             500             505             510

ACC ATC AAT GAG GAA CGC TCC GAG ATC GTA GAC TTC TCT GTA CCC TTT    1766
Thr Ile Asn Glu Glu Arg Ser Glu Ile Val Asp Phe Ser Val Pro Phe
            515             520             525

GTG GAG ACG GGC ATC AGT GTG ATG GTG GCT CGC AGC AAT GGC ACC GTC    1814
Val Glu Thr Gly Ile Ser Val Met Val Ala Arg Ser Asn Gly Thr Val
        530             535             540

TCC CCC TCG GCC TTC TTG GAG CCA TAT AGC CCT GCA GTG TGG GTG ATG    1862
Ser Pro Ser Ala Phe Leu Glu Pro Tyr Ser Pro Ala Val Trp Val Met
    545             550             555

ATG TTT GTC ATG TGC CTC ACT GTG GTG GCC ATC ACC GTC TTC ATG TTC    1910
Met Phe Val Met Cys Leu Thr Val Val Ala Ile Thr Val Phe Met Phe
560             565             570

GAG TAC TTC AGC CCT GTC AGC TAC AAC CAG AAC CTC ACC AGA GGC AAG    1958
Glu Tyr Phe Ser Pro Val Ser Tyr Asn Gln Asn Leu Thr Arg Gly Lys
```

```
                575                 580                 585                 590
AAG TCC GGG GGC CCA GCT TTC ACT ATC GGC AAG TCC GTG TGG CTG CTG              2006
Lys Ser Gly Gly Pro Ala Phe Thr Ile Gly Lys Ser Val Trp Leu Leu
                    595                 600                 605

TGG GCG CTG GTC TTC AAC AAC TCA GTG CCC ATC GAG AAC CCG CGG GGC              2054
Trp Ala Leu Val Phe Asn Asn Ser Val Pro Ile Glu Asn Pro Arg Gly
                610                 615                 620

ACC ACC AGC AAG ATC ATG GTT CTG GTC TGG GCC TTC TTT GCT GTC ATC              2102
Thr Thr Ser Lys Ile Met Val Leu Val Trp Ala Phe Phe Ala Val Ile
            625                 630                 635

TTC CTC GCC AGA TAC ACG GCC AAC CTG GCC GCC TTC ATG ATC CAA GAG              2150
Phe Leu Ala Arg Tyr Thr Ala Asn Leu Ala Ala Phe Met Ile Gln Glu
        640                 645                 650

CAA TAC ATC GAC ACT GTG TCG GGC CTC AGT GAC AAG AAG TTT CAG CGG              2198
Gln Tyr Ile Asp Thr Val Ser Gly Leu Ser Asp Lys Lys Phe Gln Arg
655                 660                 665                 670

CCT CAA GAT CAG TAC CCA CCT TTC CGC TTC GGC ACG GTG CCC AAC GGC              2246
Pro Gln Asp Gln Tyr Pro Pro Phe Arg Phe Gly Thr Val Pro Asn Gly
                675                 680                 685

AGC ACG GAG CGG AAC ATC CGC AGT AAC TAC CGT GAC ATG CAC ACC CAC              2294
Ser Thr Glu Arg Asn Ile Arg Ser Asn Tyr Arg Asp Met His Thr His
            690                 695                 700

ATG GTC AAG TTC AAC CAG CGC TCG GTG GAG GAC GCG CTC ACC AGC CTC              2342
Met Val Lys Phe Asn Gln Arg Ser Val Glu Asp Ala Leu Thr Ser Leu
        705                 710                 715

AAG ATG GGG AAG CTG GAT GCC TTC ATC TAT GAT GCT GCT GTC CTC AAC              2390
Lys Met Gly Lys Leu Asp Ala Phe Ile Tyr Asp Ala Ala Val Leu Asn
    720                 725                 730

TAC ATG GCA GGC AAG GAC GAG GGC TGC AAG CTG GTC ACC ATT GGG TCT              2438
Tyr Met Ala Gly Lys Asp Glu Gly Cys Lys Leu Val Thr Ile Gly Ser
735                 740                 745                 750

GGC AAG GTC TTT GCT ACC ACT GGC TAC GGC ATC GCC ATG CAG AAG GAC              2486
Gly Lys Val Phe Ala Thr Thr Gly Tyr Gly Ile Ala Met Gln Lys Asp
                755                 760                 765

TCC CAC TGG AAG CGG GCC ATA GAC CTG GCG CTC TTG CAG TTC CTG GGG              2534
Ser His Trp Lys Arg Ala Ile Asp Leu Ala Leu Leu Gln Phe Leu Gly
            770                 775                 780

GAC GGA GAG ACA CAG AAA CTG GAG ACA GTG TGG CTC TCA GGG ATC TGC              2582
Asp Gly Glu Thr Gln Lys Leu Glu Thr Val Trp Leu Ser Gly Ile Cys
        785                 790                 795

CAG AAT GAG AAG AAC GAG GTG ATG AGC AGC AAG CTG GAC ATC GAC AAC              2630
Gln Asn Glu Lys Asn Glu Val Met Ser Ser Lys Leu Asp Ile Asp Asn
    800                 805                 810

ATG GGA GGC GTC TTC TAC ATG CTG CTG GTG GCC ATG GGG CTG GCC CTG              2678
Met Gly Gly Val Phe Tyr Met Leu Leu Val Ala Met Gly Leu Ala Leu
815                 820                 825                 830

CTG GTC TTC GCC TGG GAG CAC CTG GTC TAC TGG AAG CTG CGC CAC TCG              2726
Leu Val Phe Ala Trp Glu His Leu Val Tyr Trp Lys Leu Arg His Ser
                835                 840                 845

GTG CCC AAC TCA TCC CAG CTG GAC TTC CTG CTG GCT TTC AGC AGG GGC              2774
Val Pro Asn Ser Ser Gln Leu Asp Phe Leu Leu Ala Phe Ser Arg Gly
            850                 855                 860

ATC TAC AGC TGC TTC AGC GGG GTG CAG AGC CTC GCC AGC CCA CCG CGG              2822
Ile Tyr Ser Cys Phe Ser Gly Val Gln Ser Leu Ala Ser Pro Pro Arg
        865                 870                 875

CAG GCC AGC CCG GAC CTC ACG GCC AGC TCG GCC CAG GCC AGC GTG CTC              2870
Gln Ala Ser Pro Asp Leu Thr Ala Ser Ser Ala Gln Ala Ser Val Leu
    880                 885                 890

AAG ATT CTG CAG GCA GCC CGC GAC ATG GTG ACC ACG GCG GGC GTA AGC              2918
```

```
                 Lys Ile Leu Gln Ala Ala Arg Asp Met Val Thr Thr Ala Gly Val Ser
                 895                 900                 905                 910

AAC TCC CTG GAC CGC GCC ACT CGC ACC ATC GAG AAT TGG GGT GGC GGC         2966
Asn Ser Leu Asp Arg Ala Thr Arg Thr Ile Glu Asn Trp Gly Gly Gly
                915                 920                 925

CGC CGT GCG CCC CCA CCG TCC CCC TGC CCG ACC CCG CGG TCT GGC CCC         3014
Arg Arg Ala Pro Pro Pro Ser Pro Cys Pro Thr Pro Arg Ser Gly Pro
                930                 935                 940

AGC CCA TGC CTG CCC ACC CCC GAC CCG CCC CCA GAG CCG AGC CCC ACG         3062
Ser Pro Cys Leu Pro Thr Pro Asp Pro Pro Pro Glu Pro Ser Pro Thr
                945                 950                 955

GGC TGG GGA CCG CCA GAC GGG GGT CGC GCG GCG CTT GTG CGC AGG GCT         3110
Gly Trp Gly Pro Pro Asp Gly Gly Arg Ala Ala Leu Val Arg Arg Ala
        960                 965                 970

CCG CAG CCC CCG GGC CGC CCC CCG ACG CCG GGG CCG CCC CTG TCC GAC         3158
Pro Gln Pro Pro Gly Arg Pro Pro Thr Pro Gly Pro Pro Leu Ser Asp
975                 980                 985                 990

GTC TCC CGA GTG TCG CGC CGC CCA GCC TGG GAG GCG CGG TGG CCG GTG         3206
Val Ser Arg Val Ser Arg Arg Pro Ala Trp Glu Ala Arg Trp Pro Val
                995                 1000                1005

CGG ACC GGG CAC TGC GGG AGG CAC CTC TCG GCC TCC GAG CGG CCC CTG         3254
Arg Thr Gly His Cys Gly Arg His Leu Ser Ala Ser Glu Arg Pro Leu
        1010                1015                1020

TCG CCC GCG CGC TGT CAC TAC AGC TCC TTT CCT CGA GCC GAC CGA TCC         3302
Ser Pro Ala Arg Cys His Tyr Ser Ser Phe Pro Arg Ala Asp Arg Ser
        1025                1030                1035

GGC CGC CCC TTC CTC CCG CTC TTC CCG GAG CCC CCG GAG CTG GAG GAC         3350
Gly Arg Pro Phe Leu Pro Leu Phe Pro Glu Pro Pro Glu Leu Glu Asp
        1040                1045                1050

CTG CCG CTG CTC GGT CCG GAG CAG CTG GCC CGG CGG GAG GCC CTG CTG         3398
Leu Pro Leu Leu Gly Pro Glu Gln Leu Ala Arg Arg Glu Ala Leu Leu
1055                1060                1065                1070

AAC GCG GCC TGG GCC CGG GGC TCG CGC CCG AGT CAC GCT TCC CTG CCC         3446
Asn Ala Ala Trp Ala Arg Gly Ser Arg Pro Ser His Ala Ser Leu Pro
                1075                1080                1085

AGC TCC GTG GCC GAG GCC TTC GCT CGG CCC AGC TCG CTG CCC GCT GGG         3494
Ser Ser Val Ala Glu Ala Phe Ala Arg Pro Ser Ser Leu Pro Ala Gly
                1090                1095                1100

TGC ACC GGC CCC GCC TGC GCC CGC CCC GAC GGC CAC TCG GCC TGC AGG         3542
Cys Thr Gly Pro Ala Cys Ala Arg Pro Asp Gly His Ser Ala Cys Arg
        1105                1110                1115

CGC TTG GCG CAG GCG CAG TCG ATG TGC TTG CCG ATC TAC CGG GAG GCC         3590
Arg Leu Ala Gln Ala Gln Ser Met Cys Leu Pro Ile Tyr Arg Glu Ala
        1120                1125                1130

TGC CAG GAG GGC GAG CAG GCA GGG GCC CCC GCC TGG CAG CAC AGA CAG         3638
Cys Gln Glu Gly Glu Gln Ala Gly Ala Pro Ala Trp Gln His Arg Gln
1135                1140                1145                1150

CAC GTC TGC CTG CAC GCC CAC GCC CAC CTG CCA TTG TGC TGG GGG GCT         3686
His Val Cys Leu His Ala His Ala His Leu Pro Leu Cys Trp Gly Ala
                1155                1160                1165

GTC TGT CCT CAC CTT CCA CCC TGT GAC AGC CAC GGC TCC TGG CTC TCC         3734
Val Cys Pro His Leu Pro Pro Cys Asp Ser His Gly Ser Trp Leu Ser
                1170                1175                1180

GGC GCC TGG GGG CCT CTG GGG CAC AGC GGC AGG ACT CTG GGG CTG GGC         3782
Gly Ala Trp Gly Pro Leu Gly His Ser Gly Arg Thr Leu Gly Leu Gly
        1185                1190                1195

ACA GGC TAC AGA GAC AGT GGG GGA CTG GAC GAG ATC AGC AGT GTA GCC         3830
Thr Gly Tyr Arg Asp Ser Gly Gly Leu Asp Glu Ile Ser Ser Val Ala
        1200                1205                1210
```

```
CGT GGG ACG CAA GGC TTC CCG GGA CCC TGC ACC TGG AGA CGG ATC TCC    3878
Arg Gly Thr Gln Gly Phe Pro Gly Pro Cys Thr Trp Arg Arg Ile Ser
1215                1220                1225                1230

AGT CTG GAG TCA GAA GTG TGAGTTATCA GCCACTCAGG CTCCGAGCCA           3926
Ser Leu Glu Ser Glu Val
                1235

GCTGGATTCT CTGCCTGCCA CTGTCAGGGT TAAGCGGCAG GCAGGATTGG CCCTTCTCTG  3986

GCTTCTACCA TGAAATCCTG GCCATGGCAC CCCAGTGACA GATGATGTCT TCCATGGTCA  4046

TCAGTGACCT CAGCTAGCCT CA                                           4068

(2) INFORMATION FOR SEQ ID NO:6:

(i) SEQUENCE CHARACTERISTICS:
        (A) LENGTH: 1236 amino acids
        (B) TYPE: amino acid
        (D) TOPOLOGY: linear (ii) MOLECULE TYPE: protein (xi) SEQUENCE DESCRIPTION: SEQ ID NO:6:

Met Gly Gly Ala Leu Gly Pro Ala Leu Leu Thr Ser Leu Phe Gly
 1               5                  10                  15

Ala Trp Ala Gly Leu Gly Pro Gly Gln Gly Glu Gln Gly Met Thr Val
                20                  25                  30

Ala Val Val Phe Ser Ser Gly Pro Pro Gln Ala Gln Phe Arg Val
         35                  40                  45

Arg Leu Thr Pro Gln Ser Phe Leu Asp Leu Pro Leu Glu Ile Gln Pro
     50                  55                  60

Leu Thr Val Gly Val Asn Thr Thr Asn Pro Ser Ser Leu Leu Thr Gln
 65                  70                  75                  80

Ile Cys Gly Leu Leu Gly Ala Ala His Val His Gly Ile Val Phe Glu
                 85                  90                  95

Asp Asn Val Asp Thr Glu Ala Val Ala Gln Ile Leu Asp Phe Ile Ser
                100                 105                 110

Ser Gln Thr His Val Pro Ile Leu Ser Ile Ser Gly Gly Ser Ala Val
            115                 120                 125

Val Leu Thr Pro Lys Glu Pro Gly Ser Ala Phe Leu Gln Leu Gly Val
        130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
        195                 200                 205

Arg Ala Arg Thr Gln Arg Leu Leu Arg Gln Leu Asp Ala Pro Val Phe
    210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
        275                 280                 285
```

```
Val Arg Asp Gly Val Ala Ile Leu Ala Leu Gly Ala His Ser Tyr Trp
    290                 295                 300
Arg Gln His Gly Thr Leu Pro Ala Pro Ala Gly Asp Cys Arg Val His
305                 310                 315                 320
Pro Gly Pro Val Ser Pro Ala Arg Glu Ala Phe Tyr Arg His Leu Leu
                325                 330                 335
Asn Val Thr Trp Glu Gly Arg Asp Phe Ser Phe Ser Pro Gly Gly Tyr
                340                 345                 350
Leu Val Gln Pro Thr Met Val Val Ile Ala Leu Asn Arg His Arg Leu
            355                 360                 365
Trp Glu Met Val Gly Arg Trp Glu His Gly Val Leu Tyr Met Lys Tyr
370                 375                 380
Pro Val Trp Pro Arg Tyr Ser Ala Ser Leu Gln Pro Val Val Asp Ser
385                 390                 395                 400
Arg His Leu Thr Val Ala Thr Leu Glu Glu Arg Pro Phe Val Ile Val
                405                 410                 415
Glu Ser Pro Asp Pro Gly Thr Gly Gly Cys Val Pro Asn Thr Val Pro
            420                 425                 430
Cys Arg Arg Gln Ser Asn His Thr Phe Ser Ser Gly Asp Val Ala Pro
        435                 440                 445
Tyr Thr Lys Leu Cys Cys Lys Gly Phe Cys Ile Asp Ile Leu Lys Lys
    450                 455                 460
Leu Ala Arg Val Val Lys Phe Ser Tyr Asp Leu Tyr Leu Val Thr Asn
465                 470                 475                 480
Gly Lys His Gly Lys Arg Val Arg Gly Val Trp Asn Gly Met Ile Gly
                485                 490                 495
Glu Val Tyr Tyr Lys Arg Ala Asp Met Ala Ile Gly Ser Leu Thr Ile
                500                 505                 510
Asn Glu Glu Arg Ser Glu Ile Val Asp Phe Ser Val Pro Phe Val Glu
            515                 520                 525
Thr Gly Ile Ser Val Met Val Ala Arg Ser Asn Gly Thr Val Ser Pro
        530                 535                 540
Ser Ala Phe Leu Glu Pro Tyr Ser Pro Ala Val Trp Val Met Met Phe
545                 550                 555                 560
Val Met Cys Leu Thr Val Val Ala Ile Thr Val Phe Met Phe Glu Tyr
                565                 570                 575
Phe Ser Pro Val Ser Tyr Asn Gln Asn Leu Thr Arg Gly Lys Lys Ser
                580                 585                 590
Gly Gly Pro Ala Phe Thr Ile Gly Lys Ser Val Trp Leu Leu Trp Ala
            595                 600                 605
Leu Val Phe Asn Asn Ser Val Pro Ile Glu Asn Pro Arg Gly Thr Thr
        610                 615                 620
Ser Lys Ile Met Val Leu Val Trp Ala Phe Phe Ala Val Ile Phe Leu
625                 630                 635                 640
Ala Arg Tyr Thr Ala Asn Leu Ala Ala Phe Met Ile Gln Glu Gln Tyr
                645                 650                 655
Ile Asp Thr Val Ser Gly Leu Ser Asp Lys Lys Phe Gln Arg Pro Gln
                660                 665                 670
Asp Gln Tyr Pro Pro Phe Arg Phe Gly Thr Val Pro Asn Gly Ser Thr
            675                 680                 685
Glu Arg Asn Ile Arg Ser Asn Tyr Arg Asp Met His Thr His Met Val
        690                 695                 700
```

-continued

```
Lys Phe Asn Gln Arg Ser Val Glu Asp Ala Leu Thr Ser Leu Lys Met
705                 710                 715                 720

Gly Lys Leu Asp Ala Phe Ile Tyr Asp Ala Val Leu Asn Tyr Met
            725                 730                 735

Ala Gly Lys Asp Glu Gly Cys Lys Leu Val Thr Ile Gly Ser Gly Lys
            740                 745                 750

Val Phe Ala Thr Thr Gly Tyr Gly Ile Ala Met Gln Lys Asp Ser His
            755                 760                 765

Trp Lys Arg Ala Ile Asp Leu Ala Leu Leu Gln Phe Leu Gly Asp Gly
            770                 775                 780

Glu Thr Gln Lys Leu Glu Thr Val Trp Leu Ser Gly Ile Cys Gln Asn
785                 790                 795                 800

Glu Lys Asn Glu Val Met Ser Ser Lys Leu Asp Ile Asp Asn Met Gly
            805                 810                 815

Gly Val Phe Tyr Met Leu Leu Val Ala Met Gly Leu Ala Leu Leu Val
            820                 825                 830

Phe Ala Trp Glu His Leu Val Tyr Trp Lys Leu Arg His Ser Val Pro
            835                 840                 845

Asn Ser Ser Gln Leu Asp Phe Leu Leu Ala Phe Ser Arg Gly Ile Tyr
850                 855                 860

Ser Cys Phe Ser Gly Val Gln Ser Leu Ala Ser Pro Pro Arg Gln Ala
865                 870                 875                 880

Ser Pro Asp Leu Thr Ala Ser Ser Ala Gln Ala Ser Val Leu Lys Ile
            885                 890                 895

Leu Gln Ala Ala Arg Asp Met Val Thr Thr Ala Gly Val Ser Asn Ser
            900                 905                 910

Leu Asp Arg Ala Thr Arg Thr Ile Glu Asn Trp Gly Gly Arg Arg
            915                 920                 925

Ala Pro Pro Ser Pro Cys Pro Thr Pro Arg Ser Gly Pro Ser Pro
            930                 935                 940

Cys Leu Pro Thr Pro Asp Pro Pro Glu Pro Ser Pro Thr Gly Trp
945                 950                 955                 960

Gly Pro Pro Asp Gly Gly Arg Ala Ala Leu Val Arg Arg Ala Pro Gln
            965                 970                 975

Pro Pro Gly Arg Pro Pro Thr Pro Gly Pro Pro Leu Ser Asp Val Ser
            980                 985                 990

Arg Val Ser Arg Arg Pro Ala Trp Glu Ala Arg Trp Pro Val Arg Thr
            995                 1000                1005

Gly His Cys Gly Arg His Leu Ser Ala Ser Glu Arg Pro Leu Ser Pro
    1010                1015                1020

Ala Arg Cys His Tyr Ser Ser Phe Pro Arg Ala Asp Arg Ser Gly Arg
1025                1030                1035                1040

Pro Phe Leu Pro Leu Phe Pro Gly Pro Pro Glu Leu Glu Asp Leu Pro
            1045                1050                1055

Leu Leu Gly Pro Glu Gln Leu Ala Arg Arg Glu Ala Leu Leu Asn Ala
            1060                1065                1070

Ala Trp Ala Arg Gly Ser Arg Pro Ser His Ala Ser Leu Pro Ser Ser
            1075                1080                1085

Val Ala Glu Ala Phe Ala Arg Pro Ser Ser Leu Pro Ala Gly Cys Thr
            1090                1095                1100

Gly Pro Ala Cys Ala Arg Pro Asp Gly His Ser Ala Cys Arg Arg Leu
1105                1110                1115                1120

Ala Gln Ala Gln Ser Met Cys Leu Pro Ile Tyr Arg Glu Ala Cys Gln
```

1125                1130              1135

Glu Gly Glu Gln Ala Gly Ala Pro Ala Trp Gln His Arg Gln His Val
            1140            1145              1150

Cys Leu His Ala His Ala His Leu Pro Leu Cys Trp Gly Ala Val Cys
        1155            1160              1165

Pro His Leu Pro Pro Cys Asp Ser His Gly Ser Trp Leu Ser Gly Ala
    1170            1175              1180

Trp Gly Pro Leu Gly His Ser Gly Arg Thr Leu Gly Leu Gly Thr Gly
1185            1190            1195                1200

Tyr Arg Asp Ser Gly Gly Leu Asp Glu Ile Ser Ser Val Ala Arg Gly
            1205            1210              1215

Thr Gln Gly Phe Pro Gly Pro Cys Thr Trp Arg Arg Ile Ser Ser Leu
        1220            1225              1230

Glu Ser Glu Val
    1235

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 2..22

(xi) SEQUENCE DESCRIPTION: SEQ ID NO:7:

C TCT GAG GCT CAG CCT GTC CCC AG                                      24
  Ser Glu Ala Gln Pro Val Pro
  1           5

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:8:

Ser Glu Ala Gln Pro Val Pro
1           5

(2) INFORMATION FOR SEQ ID NO:9:

(i) SEQUENCE CHARACTERISTICS:
        (A) LENGTH: 11 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:9:

AGAAGGGGGT G                                                          11

(2) INFORMATION FOR SEQ ID NO:10:

(i) SEQUENCE CHARACTERISTICS:
        (A) LENGTH: 4808 base pairs (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 311..4705

(xi) SEQUENCE DESCRIPTION: SEQ ID NO:10:

```
ATCATGGGAC CGGGTGAGCG CTGAGAATCG CGGCCGCAGC CATCAGCCCT GGAGATGACC        60

AGGAGCGGCC ACTGCTGAGA ACTATGTGGA GAGAGGCTGC GAGCCCTGCT GCAGAGCCTC       120

CGGCTGGGAT AGCCGCCCCC CGTGGGGGCG ATGCGGACAG CGCGGGACAG CCAGGGGAGC       180

GCGCTGGGGC CGCAGCATGC GGGAACCCGC TAAACCCGGT GGCTGCTGAG GCGGCCGAGA       240

TGCTCGTGCG CGCAGCGCGC CCCACTGCAT CCTCGACCTT CTCGGGCTAC AGGGACCGTC       300

AGTGGCGACT ATG GGC AGA GTG GGC TAT TGG ACC CTG CTG GTG CTG CCG         349
            Met Gly Arg Val Gly Tyr Trp Thr Leu Leu Val Leu Pro
              1               5                  10

GCC CTT CTG GTC TGG CGC GGT CCG GCG CCG AGC GCG GCG GCG GAG AAG        397
Ala Leu Leu Val Trp Arg Gly Pro Ala Pro Ser Ala Ala Ala Glu Lys
         15                  20                  25

GGT CCC CCC GCG CTA AAT ATT GCG GTG ATG CTG GGT CAC AGC CAC GAC        445
Gly Pro Pro Ala Leu Asn Ile Ala Val Met Leu Gly His Ser His Asp
 30                  35                  40                  45

GTG ACA GAG CGC GAA CTT CGA ACA CTG TGG GGC CCC GAG CAG GCG GCG        493
Val Thr Glu Arg Glu Leu Arg Thr Leu Trp Gly Pro Glu Gln Ala Ala
                 50                  55                  60

GGG CTG CCC CTG GAC GTG AAC GTG GTA GCT CTG CTG ATG AAC CGC ACC        541
Gly Leu Pro Leu Asp Val Asn Val Val Ala Leu Leu Met Asn Arg Thr
             65                  70                  75

GAC CCC AAG AGC CTC ATC ACG CAC GTG TGC GAC CTC ATG TCC GGG GCA        589
Asp Pro Lys Ser Leu Ile Thr His Val Cys Asp Leu Met Ser Gly Ala
         80                  85                  90

CGC ATC CAC GGC CTC GTG TTT GGG GAC GAC ACG GAC CAG GAG GCC GTA        637
Arg Ile His Gly Leu Val Phe Gly Asp Asp Thr Asp Gln Glu Ala Val
     95                  100                 105

GCC CAG ATG CTG GAT TTT ATC TCC TCC CAC ACC TTC GTC CCC ATC TTG        685
Ala Gln Met Leu Asp Phe Ile Ser Ser His Thr Phe Val Pro Ile Leu
110                 115                 120                 125

GGC ATT CAT GGG GGC GCA TCT ATG ATC ATG GCT GAC AAG GAT CCG ACG        733
Gly Ile His Gly Gly Ala Ser Met Ile Met Ala Asp Lys Asp Pro Thr
                130                 135                 140

TCT ACC TTC TTC CAG TTT GGA GCG TCC ATC CAG CAG CAA GCC ACG GTC        781
Ser Thr Phe Phe Gln Phe Gly Ala Ser Ile Gln Gln Gln Ala Thr Val
            145                 150                 155

ATG CTG AAG ATC ATG CAG GAT TAT GAC TGG CAT GTC TTC TCC CTG GTG        829
Met Leu Lys Ile Met Gln Asp Tyr Asp Trp His Val Phe Ser Leu Val
        160                 165                 170

ACC ACT ATC TTC CCT GGC TAC AGG GAA TTC ATC AGC TTC GTC AAG ACC        877
Thr Thr Ile Phe Pro Gly Tyr Arg Glu Phe Ile Ser Phe Val Lys Thr
    175                 180                 185

ACA GTG GAC AAC AGC TTT GTG GGC TGG GAC ATG CAG AAT GTG ATC ACA        925
Thr Val Asp Asn Ser Phe Val Gly Trp Asp Met Gln Asn Val Ile Thr
190                 195                 200                 205

CTG GAC ACT TCC TTT GAG GAT GCA AAG ACA CAA GTC CAG CTG AAG AAG        973
Leu Asp Thr Ser Phe Glu Asp Ala Lys Thr Gln Val Gln Leu Lys Lys
                210                 215                 220

ATC CAC TCT TCT GTC ATC TTG CTC TAC TGT TCC AAA GAC GAG GCT GTT       1021
```

```
Ile His Ser Ser Val Ile Leu Leu Tyr Cys Ser Lys Asp Glu Ala Val
            225                 230                 235

CTC ATT CTG AGT GAG GCC CGC TCC CTT GGC CTC ACC GGG TAT GAT TTC         1069
Leu Ile Leu Ser Glu Ala Arg Ser Leu Gly Leu Thr Gly Tyr Asp Phe
        240                 245                 250

TTC TGG ATT GTC CCC AGC TTG GTC TCT GGG AAC ACG GAG CTC ATC CCA         1117
Phe Trp Ile Val Pro Ser Leu Val Ser Gly Asn Thr Glu Leu Ile Pro
    255                 260                 265

AAA GAG TTT CCA TCG GGA CTC ATT TCT GTC TCC TAC GAT GAC TGG GAC         1165
Lys Glu Phe Pro Ser Gly Leu Ile Ser Val Ser Tyr Asp Asp Trp Asp
270                 275                 280                 285

TAC AGC CTG GAG GCG AGA GTG AGG GAC GGC ATT GGC ATC CTA ACC ACC         1213
Tyr Ser Leu Glu Ala Arg Val Arg Asp Gly Ile Gly Ile Leu Thr Thr
                290                 295                 300

GCT GCA TCT TCT ATG CTG GAG AAG TTC TCC TAC ATC CCC GAG GCC AAG         1261
Ala Ala Ser Ser Met Leu Glu Lys Phe Ser Tyr Ile Pro Glu Ala Lys
            305                 310                 315

GCC AGC TGC TAC GGG CAG ATG GAG AGG CCA GAG GTC CCG ATG CAC ACC         1309
Ala Ser Cys Tyr Gly Gln Met Glu Arg Pro Glu Val Pro Met His Thr
        320                 325                 330

TTG CAC CCA TTT ATG GTC AAT GTT ACA TGG GAT GGC AAA GAC TTA TCC         1357
Leu His Pro Phe Met Val Asn Val Thr Trp Asp Gly Lys Asp Leu Ser
    335                 340                 345

TTC ACT GAG GAA GGC TAC CAG GTG CAC CCC AGG CTG GTG GTG ATT GTG         1405
Phe Thr Glu Glu Gly Tyr Gln Val His Pro Arg Leu Val Val Ile Val
350                 355                 360                 365

CTG AAC AAA GAC CGG GAA TGG GAA AAG GTG GGC AAG TGG GAG AAC CAT         1453
Leu Asn Lys Asp Arg Glu Trp Glu Lys Val Gly Lys Trp Glu Asn His
                370                 375                 380

ACG CTG AGC CTG AGG CAC GCC GTG TGG CCC AGG TAC AAG TCC TTC TCC         1501
Thr Leu Ser Leu Arg His Ala Val Trp Pro Arg Tyr Lys Ser Phe Ser
            385                 390                 395

GAC TGT GAG CCG GAT GAC AAC CAT CTC AGC ATC GTC ACC CTG GAG GAG         1549
Asp Cys Glu Pro Asp Asp Asn His Leu Ser Ile Val Thr Leu Glu Glu
        400                 405                 410

GCC CCA TTC GTC ATC GTG GAA GAC ATA GAC CCC CTG ACC GAG ACG TGT         1597
Ala Pro Phe Val Ile Val Glu Asp Ile Asp Pro Leu Thr Glu Thr Cys
    415                 420                 425

GTG AGG AAC ACC GTG CCA TGT CGG AAG TTC GTC AAA ATC AAC AAT TCA         1645
Val Arg Asn Thr Val Pro Cys Arg Lys Phe Val Lys Ile Asn Asn Ser
430                 435                 440                 445

ACC AAT GAG GGG ATG AAT GTG AAG AAA TGC TGC AAG GGG TTC TGC ATT         1693
Thr Asn Glu Gly Met Asn Val Lys Lys Cys Cys Lys Gly Phe Cys Ile
                450                 455                 460

GAT ATT CTG AAG AAG CTT TCC AGA ACT GTG AAG TTT ACT TAC GAC CTC         1741
Asp Ile Leu Lys Lys Leu Ser Arg Thr Val Lys Phe Thr Tyr Asp Leu
            465                 470                 475

TAT CTG GTG ACC AAT GGG AAG CAT GGC AAG AAA GTT AAC AAT GTG TGG         1789
Tyr Leu Val Thr Asn Gly Lys His Gly Lys Lys Val Asn Asn Val Trp
        480                 485                 490

AAT GGA ATG ATC GGT GAA GTG GTC TAT CAA CGG GCA GTC ATG GCA GTT         1837
Asn Gly Met Ile Gly Glu Val Val Tyr Gln Arg Ala Val Met Ala Val
    495                 500                 505

GGC TCG CTC ACC ATC AAT GAG GAA CGT TCT GAA GTG GTG GAC TTC TCT         1885
Gly Ser Leu Thr Ile Asn Glu Glu Arg Ser Glu Val Val Asp Phe Ser
510                 515                 520                 525

GTG CCC TTT GTG GAA ACG GGA ATC AGT GTC ATG GTT TCA AGA AGT AAT         1933
Val Pro Phe Val Glu Thr Gly Ile Ser Val Met Val Ser Arg Ser Asn
                530                 535                 540
```

```
                                           -continued

GGC ACC GTC TCA CCT TCT GCT TTT CTA GAA CCA TTC AGC GCC TCT GTC    1981
Gly Thr Val Ser Pro Ser Ala Phe Leu Glu Pro Phe Ser Ala Ser Val
            545                 550                 555

TGG GTG ATG ATG TTT GTG ATG CTG CTC ATT GTT TCT GCC ATA GCT GTT    2029
Trp Val Met Met Phe Val Met Leu Leu Ile Val Ser Ala Ile Ala Val
            560                 565                 570

TGG GTC TTG GAT TAC TCC AGC CCT GTT GGA TAC AAC AGA AAC TTA GCC    2077
Trp Val Leu Asp Tyr Ser Ser Pro Val Gly Tyr Asn Arg Asn Leu Ala
575                 580                 585

AAA GGG AAA GCA CCC CAT GGG CCT TCT TTT ACA ATT GGA AAA GCT ATA    2125
Lys Gly Lys Ala Pro His Gly Pro Ser Phe Thr Ile Gly Lys Ala Ile
590                 595                 600                 605

TGG CTT CTT TGG GGC CTG GTG TTC AAT AAC TCC GTG CCT GTC CAG AAT    2173
Trp Leu Leu Trp Gly Leu Val Phe Asn Asn Ser Val Pro Val Gln Asn
                610                 615                 620

CCT AAA GGG ACC ACC AGC AAG ATC ATG GTA TCT GTA TGG GCC TTC TTC    2221
Pro Lys Gly Thr Thr Ser Lys Ile Met Val Ser Val Trp Ala Phe Phe
            625                 630                 635

GCT GTC ATA TTC CTG GCT AGC TAC ACA GCC AAT CTG GCT GCC TTC ATG    2269
Ala Val Ile Phe Leu Ala Ser Tyr Thr Ala Asn Leu Ala Ala Phe Met
            640                 645                 650

ATC CAA GAG GAA TTT GTG GAC CAA GTG ACC GGC CTC AGT GAC AAA AAG    2317
Ile Gln Glu Glu Phe Val Asp Gln Val Thr Gly Leu Ser Asp Lys Lys
            655                 660                 665

TTT CAG AGA CCT CAT GAC TAT TCC CCA CCT TTT CGA TTT GGG ACA GTG    2365
Phe Gln Arg Pro His Asp Tyr Ser Pro Pro Phe Arg Phe Gly Thr Val
670                 675                 680                 685

CCT AAT GGA AGC ACG GAG AGA AAC ATT CGG AAT AAC TAT CCC TAC ATG    2413
Pro Asn Gly Ser Thr Glu Arg Asn Ile Arg Asn Asn Tyr Pro Tyr Met
                690                 695                 700

CAT CAG TAC ATG ACC AAA TTT AAT CAG AAA GGA GTA GAG GAC GCC TTG    2461
His Gln Tyr Met Thr Lys Phe Asn Gln Lys Gly Val Glu Asp Ala Leu
            705                 710                 715

GTC AGC CTG AAA ACG GGG AAG CTG GAC GCT TTC ATC TAC GAT GCC GCA    2509
Val Ser Leu Lys Thr Gly Lys Leu Asp Ala Phe Ile Tyr Asp Ala Ala
            720                 725                 730

GTC TTG AAT TAC AAG GCT GGG AGG GAT GAA GGC TGC AAG CTG GTG ACC    2557
Val Leu Asn Tyr Lys Ala Gly Arg Asp Glu Gly Cys Lys Leu Val Thr
            735                 740                 745

ATC GGG AGT GGG TAC ATC TTT GCC ACC ACC GGT TAT GGA ATT GCC CTT    2605
Ile Gly Ser Gly Tyr Ile Phe Ala Thr Thr Gly Tyr Gly Ile Ala Leu
750                 755                 760                 765

CAG AAA GGC TCT CCT TGG AAG AGG CAG ATC GAC CTG GCC TTG CTT CAG    2653
Gln Lys Gly Ser Pro Trp Lys Arg Gln Ile Asp Leu Ala Leu Leu Gln
                770                 775                 780

TTT GTG GGT GAT GGT GAG ATG GAG GAG CTG GAG ACC CTG TGG CTC ACT    2701
Phe Val Gly Asp Gly Glu Met Glu Glu Leu Glu Thr Leu Trp Leu Thr
            785                 790                 795

GGG ATC TGC CAC AAC GAG AAG AAC GAG GTG ATG AGC AGC CAG CTG GAC    2749
Gly Ile Cys His Asn Glu Lys Asn Glu Val Met Ser Ser Gln Leu Asp
            800                 805                 810

ATT GAC AAC ATG GCG GGC GTA TTC TAC ATG CTG GCT GCC GCC ATG GCC    2797
Ile Asp Asn Met Ala Gly Val Phe Tyr Met Leu Ala Ala Ala Met Ala
            815                 820                 825

CTT AGC CTC ATC ACC TTC ATC TGG GAG CAC CTC TTC TAC TGG AAG CTG    2845
Leu Ser Leu Ile Thr Phe Ile Trp Glu His Leu Phe Tyr Trp Lys Leu
830                 835                 840                 845

CGC TTC TGT TTC ACG GGC GTG TGC TCC GAC CGG CCT GGG TTG CTC TTC    2893
Arg Phe Cys Phe Thr Gly Val Cys Ser Asp Arg Pro Gly Leu Leu Phe
                850                 855                 860
```

```
TCC ATC AGC AGG GGC ATC TAC AGC TGC ATT CAT GGA GTG CAC ATT GAA       2941
Ser Ile Ser Arg Gly Ile Tyr Ser Cys Ile His Gly Val His Ile Glu
            865                 870                 875

GAA AAG AAG AAG TCT CCA GAC TTC AAT CTG ACG GGA TCC CAG AGC AAC       2989
Glu Lys Lys Lys Ser Pro Asp Phe Asn Leu Thr Gly Ser Gln Ser Asn
        880                 885                 890

ATG TTA AAA CTC CTC CGG TCA GCC AAA AAC ATT TCC AGC ATG TCC AAC       3037
Met Leu Lys Leu Leu Arg Ser Ala Lys Asn Ile Ser Ser Met Ser Asn
    895                 900                 905

ATG AAC TCC TCA AGA ATG GAC TCA CCC AAA AGA GCT GCT GAC TTC ATC       3085
Met Asn Ser Ser Arg Met Asp Ser Pro Lys Arg Ala Ala Asp Phe Ile
910                 915                 920                 925

CAA AGA GGT TCC CTC ATC ATG GAC ATG GTT TCA GAT AAG GGG AAT TTG       3133
Gln Arg Gly Ser Leu Ile Met Asp Met Val Ser Asp Lys Gly Asn Leu
            930                 935                 940

ATG TAC TCA GAC AAC AGG TCC TTT CAG GGG AAA GAG AGC ATT TTT GGA       3181
Met Tyr Ser Asp Asn Arg Ser Phe Gln Gly Lys Glu Ser Ile Phe Gly
        945                 950                 955

GAC AAC ATG AAC GAA CTC CAA ACA TTT GTG GCC AAC CGG CAG AAG GAT       3229
Asp Asn Met Asn Glu Leu Gln Thr Phe Val Ala Asn Arg Gln Lys Asp
    960                 965                 970

AAC CTC AAT AAC TAT GTA TTC CAG GGA CAA CAT CCT CTT ACT CTC AAT       3277
Asn Leu Asn Asn Tyr Val Phe Gln Gly Gln His Pro Leu Thr Leu Asn
975                 980                 985

GAG TCC AAC CCT AAC ACG GTG GAG GTG GCC GTG AGC ACA GAA TCC AAA       3325
Glu Ser Asn Pro Asn Thr Val Glu Val Ala Val Ser Thr Glu Ser Lys
            990                 995                1000                1005

GCG AAC TCT AGA CCC CGG CAG CTG TGG AAG AAA TCC GTG GAT TCC ATA       3373
Ala Asn Ser Arg Pro Arg Gln Leu Trp Lys Lys Ser Val Asp Ser Ile
        1010                1015                1020

CGC CAG GAT TCA CTA TCC CAG AAT CCA GTC TCC CAG AGG GAT GAG GCA       3421
Arg Gln Asp Ser Leu Ser Gln Asn Pro Val Ser Gln Arg Asp Glu Ala
    1025                1030                1035

ACA GCA GAG AAT AGG ACC CAC TCC CTA AAG AGC CCT AGG TAT CTT CCA       3469
Thr Ala Glu Asn Arg Thr His Ser Leu Lys Ser Pro Arg Tyr Leu Pro
        1040                1045                1050

GAA GAG ATG GCC CAC TCT GAC ATT TCA GAA ACG TCA AAT CGG GCC ACG       3517
Glu Glu Met Ala His Ser Asp Ile Ser Glu Thr Ser Asn Arg Ala Thr
    1055                1060                1065

TGC CAC AGG GAA CCT GAC AAC AGT AAG AAC CAC AAA ACC AAG GAC AAC       3565
Cys His Arg Glu Pro Asp Asn Ser Lys Asn His Lys Thr Lys Asp Asn
1070                1075                1080                1085

TTT AAA AGG TCA GTG GCC TCC AAA TAC CCC AAG GAC TGT AGT GAG GTC       3613
Phe Lys Arg Ser Val Ala Ser Lys Tyr Pro Lys Asp Cys Ser Glu Val
            1090                1095                1100

GAG CGC ACC TAC CTG AAA ACC AAA TCA AGC TCC CCT AGA GAC AAG ATC       3661
Glu Arg Thr Tyr Leu Lys Thr Lys Ser Ser Ser Pro Arg Asp Lys Ile
        1105                1110                1115

TAC ACT ATA GAT GGT GAG AAG GAG CCT GGT TTC CAC TTA GAT CCA CCC       3709
Tyr Thr Ile Asp Gly Glu Lys Glu Pro Gly Phe His Leu Asp Pro Pro
    1120                1125                1130

CAG TTT GTT GAA AAT GTG ACC CTG CCC GAG AAC GTG GAC TTC CCG GAC       3757
Gln Phe Val Glu Asn Val Thr Leu Pro Glu Asn Val Asp Phe Pro Asp
    1135                1140                1145

CCC TAC CAG GAT CCC AGT GAA AAC TTC CGC AAG GGG GAC TCC ACG CTG       3805
Pro Tyr Gln Asp Pro Ser Glu Asn Phe Arg Lys Gly Asp Ser Thr Leu
1150                1155                1160                1165

CCA ATG AAC CGG AAC CCC TTG CAT AAT GAA GAG GGG CTT TCC AAC AAC       3853
Pro Met Asn Arg Asn Pro Leu His Asn Glu Glu Gly Leu Ser Asn Asn
```

```
                 1170              1175              1180
GAC CAG TAT AAA CTC TAC TCC AAG CAC TTC ACC TTG AAA GAC AAG GGT        3901
Asp Gln Tyr Lys Leu Tyr Ser Lys His Phe Thr Leu Lys Asp Lys Gly
             1185              1190              1195

TCC CCG CAC AGT GAG ACC AGC GAG CGA TAC CGG CAG AAC TCC ACG CAC        3949
Ser Pro His Ser Glu Thr Ser Glu Arg Tyr Arg Gln Asn Ser Thr His
         1200              1205              1210

TGC AGA AGC TGC CTT TCC AAC ATG CCC ACC TAT TCA GGC CAC TTC ACC        3997
Cys Arg Ser Cys Leu Ser Asn Met Pro Thr Tyr Ser Gly His Phe Thr
         1215              1220              1225

ATG AGG TCC CCC TTC AAG TGC GAT GCC TGC CTG CGG ATG GGG AAC CTC        4045
Met Arg Ser Pro Phe Lys Cys Asp Ala Cys Leu Arg Met Gly Asn Leu
1230              1235              1240              1245

TAT GAC ATC GAT GAA GAC CAG ATG CTT CAG GAG ACA GGT AAC CCA GCC        4093
Tyr Asp Ile Asp Glu Asp Gln Met Leu Gln Glu Thr Gly Asn Pro Ala
             1250              1255              1260

ACC GGG GAG CAG GTC TAC CAG CAG GAC TGG GCA CAG AAC AAT GCC CTT        4141
Thr Gly Glu Gln Val Tyr Gln Gln Asp Trp Ala Gln Asn Asn Ala Leu
         1265              1270              1275

CAA TTA CAA AAG AAC AAG CTA AGG ATT AGC CGT CAG CAT TCC TAC GAT        4189
Gln Leu Gln Lys Asn Lys Leu Arg Ile Ser Arg Gln His Ser Tyr Asp
         1280              1285              1290

AAC ATT GTC GAC AAA CCT AGG GAG CTA GAC CTT AGC AGG CCC TCC CGG        4237
Asn Ile Val Asp Lys Pro Arg Glu Leu Asp Leu Ser Arg Pro Ser Arg
     1295              1300              1305

AGC ATA AGC CTC AAG GAC AGG GAA CGG CTT CTG GAG GGA AAT TTT TAC        4285
Ser Ile Ser Leu Lys Asp Arg Glu Arg Leu Leu Glu Gly Asn Phe Tyr
1310              1315              1320              1325

GGC AGC CTG TTT AGT GTC CCC TCA AGC AAA CTC TCG GGG AAA AAA AGC        4333
Gly Ser Leu Phe Ser Val Pro Ser Ser Lys Leu Ser Gly Lys Lys Ser
             1330              1335              1340

TCC CTT TTC CCC CAA GGT CTG GAG GAC AGC AAG AGG AGC AAG TCT CTC        4381
Ser Leu Phe Pro Gln Gly Leu Glu Asp Ser Lys Arg Ser Lys Ser Leu
         1345              1350              1355

TTG CCA GAC CAC ACC TCC GAT AAC CCT TTC CTC CAC TCC CAC AGG GAT        4429
Leu Pro Asp His Thr Ser Asp Asn Pro Phe Leu His Ser His Arg Asp
         1360              1365              1370

GAC CAA CGC TTG GTT ATT GGG AGA TGC CCC TCG GAC CCT TAC AAA CAC        4477
Asp Gln Arg Leu Val Ile Gly Arg Cys Pro Ser Asp Pro Tyr Lys His
     1375              1380              1385

TCG TTG CCA TCC CAG GCG GTG AAT GAC AGC TAT CTT CGG TCG TCC TTG        4525
Ser Leu Pro Ser Gln Ala Val Asn Asp Ser Tyr Leu Arg Ser Ser Leu
1390              1395              1400              1405

AGG TCA ACG GCA TCG TAC TGT TCC AGG GAC AGT CGG GGC CAC AAT GAT        4573
Arg Ser Thr Ala Ser Tyr Cys Ser Arg Asp Ser Arg Gly His Asn Asp
             1410              1415              1420

GTG TAT ATT TCG GAG CAT GTT ATG CCT TAT GCT GCA AAT AAG AAT AAT        4621
Val Tyr Ile Ser Glu His Val Met Pro Tyr Ala Ala Asn Lys Asn Asn
         1425              1430              1435

ATG TAC TCT ACC CCC AGG GTT TTA AAT TCC TGC AGC AAT AGA CGC GTG        4669
Met Tyr Ser Thr Pro Arg Val Leu Asn Ser Cys Ser Asn Arg Arg Val
         1440              1445              1450

TAC AAG GAA ATG CCT AGT ATC GAA TCT GAT GTT TAAAAATCTT CCATTAATGT      4722
Tyr Lys Glu Met Pro Ser Ile Glu Ser Asp Val
     1455              1460              146

TTTATCTATA GGGAAATACA CGTAATGGCC AATGTTCTGG AGGGTAAATG TTGGATGTCC      4782

AATAGTGCCC TGCTAAGAGG AAGGAG                                          4808
```

(2) INFORMATION FOR SEQ ID NO:11:

(i) SEQUENCE CHARACTERISTICS:
        (A) LENGTH: 1464 amino acids
        (B) TYPE: amino acid
        (D) TOPOLOGY: linear (ii) MOLECULE TYPE: protein (xi) SEQUENCE DESCRIPTION: SEQ ID NO:11:

```
Met Gly Arg Val Gly Tyr Trp Thr Leu Leu Val Leu Pro Ala Leu Leu
 1               5                  10                  15

Val Trp Arg Gly Pro Ala Pro Ser Ala Ala Glu Lys Gly Pro Pro
             20                  25                  30

Ala Leu Asn Ile Ala Val Met Leu Gly His Ser His Asp Val Thr Glu
             35                  40                  45

Arg Glu Leu Arg Thr Leu Trp Gly Pro Glu Gln Ala Ala Gly Leu Pro
         50                  55                  60

Leu Asp Val Asn Val Val Ala Leu Leu Met Asn Arg Thr Asp Pro Lys
 65                  70                  75                  80

Ser Leu Ile Thr His Val Cys Asp Leu Met Ser Gly Ala Arg Ile His
                 85                  90                  95

Gly Leu Val Phe Gly Asp Asp Thr Asp Gln Glu Ala Val Ala Gln Met
                100                 105                 110

Leu Asp Phe Ile Ser Ser His Thr Phe Val Pro Ile Leu Gly Ile His
            115                 120                 125

Gly Gly Ala Ser Met Ile Met Ala Asp Lys Asp Pro Thr Ser Thr Phe
        130                 135                 140

Phe Gln Phe Gly Ala Ser Ile Gln Gln Gln Ala Thr Val Met Leu Lys
145                 150                 155                 160

Ile Met Gln Asp Tyr Asp Trp His Val Phe Ser Leu Val Thr Thr Ile
                165                 170                 175

Phe Pro Gly Tyr Arg Glu Phe Ile Ser Phe Val Lys Thr Thr Val Asp
            180                 185                 190

Asn Ser Phe Val Gly Trp Asp Met Gln Asn Val Ile Thr Leu Asp Thr
        195                 200                 205

Ser Phe Glu Asp Ala Lys Thr Gln Val Gln Leu Lys Lys Ile His Ser
210                 215                 220

Ser Val Ile Leu Leu Tyr Cys Ser Lys Asp Glu Ala Val Leu Ile Leu
225                 230                 235                 240

Ser Glu Ala Arg Ser Leu Gly Leu Thr Gly Tyr Asp Phe Phe Trp Ile
                245                 250                 255

Val Pro Ser Leu Val Ser Gly Asn Thr Glu Leu Ile Pro Lys Glu Phe
            260                 265                 270

Pro Ser Gly Leu Ile Ser Val Ser Tyr Asp Asp Trp Asp Tyr Ser Leu
        275                 280                 285

Glu Ala Arg Val Arg Asp Gly Ile Gly Ile Leu Thr Thr Ala Ala Ser
290                 295                 300

Ser Met Leu Glu Lys Phe Ser Tyr Ile Pro Glu Ala Lys Ala Ser Cys
305                 310                 315                 320

Tyr Gly Gln Met Glu Arg Pro Glu Val Pro Met His Thr Leu His Pro
                325                 330                 335

Phe Met Val Asn Val Thr Trp Asp Gly Lys Asp Leu Ser Phe Thr Glu
            340                 345                 350

Glu Gly Tyr Gln Val His Pro Arg Leu Val Val Ile Val Leu Asn Lys
        355                 360                 365
```

```
Asp Arg Glu Trp Glu Lys Val Gly Lys Trp Glu Asn His Thr Leu Ser
    370                 375                 380

Leu Arg His Ala Val Trp Pro Arg Tyr Lys Ser Phe Ser Asp Cys Glu
385                 390                 395                 400

Pro Asp Asn His Leu Ser Ile Val Thr Leu Glu Glu Ala Pro Phe
                405                 410                 415

Val Ile Val Glu Asp Ile Asp Pro Leu Thr Glu Thr Cys Val Arg Asn
                420                 425                 430

Thr Val Pro Cys Arg Lys Phe Val Lys Ile Asn Asn Ser Thr Asn Glu
            435                 440                 445

Gly Met Asn Val Lys Lys Cys Cys Lys Gly Phe Cys Ile Asp Ile Leu
        450                 455                 460

Lys Lys Leu Ser Arg Thr Val Lys Phe Thr Tyr Asp Leu Tyr Leu Val
465                 470                 475                 480

Thr Asn Gly Lys His Gly Lys Lys Val Asn Asn Val Trp Asn Gly Met
                485                 490                 495

Ile Gly Glu Val Val Tyr Gln Arg Ala Val Met Ala Val Gly Ser Leu
                500                 505                 510

Thr Ile Asn Glu Glu Arg Ser Glu Val Val Asp Phe Ser Val Pro Phe
            515                 520                 525

Val Glu Thr Gly Ile Ser Val Met Val Ser Arg Ser Asn Gly Thr Val
        530                 535                 540

Ser Pro Ser Ala Phe Leu Glu Pro Phe Ser Ala Ser Val Trp Val Met
545                 550                 555                 560

Met Phe Val Met Leu Leu Ile Val Ser Ala Ile Ala Val Trp Val Leu
                565                 570                 575

Asp Tyr Ser Ser Pro Val Gly Tyr Asn Arg Asn Leu Ala Lys Gly Lys
                580                 585                 590

Ala Pro His Gly Pro Ser Phe Thr Ile Gly Lys Ala Ile Trp Leu Leu
            595                 600                 605

Trp Gly Leu Val Phe Asn Asn Ser Val Pro Val Gln Asn Pro Lys Gly
        610                 615                 620

Thr Thr Ser Lys Ile Met Val Ser Val Trp Ala Phe Phe Ala Val Ile
625                 630                 635                 640

Phe Leu Ala Ser Tyr Thr Ala Asn Leu Ala Ala Phe Met Ile Gln Glu
                645                 650                 655

Glu Phe Val Asp Gln Val Thr Gly Leu Ser Asp Lys Lys Phe Gln Arg
                660                 665                 670

Pro His Asp Tyr Ser Pro Pro Phe Arg Phe Gly Thr Val Pro Asn Gly
            675                 680                 685

Ser Thr Glu Arg Asn Ile Arg Asn Asn Tyr Pro Tyr Met His Gln Tyr
        690                 695                 700

Met Thr Lys Phe Asn Gln Lys Gly Val Glu Asp Ala Leu Val Ser Leu
705                 710                 715                 720

Lys Thr Gly Lys Leu Asp Ala Phe Ile Tyr Asp Ala Ala Val Leu Asn
                725                 730                 735

Tyr Lys Ala Gly Arg Asp Glu Gly Cys Lys Leu Val Thr Ile Gly Ser
                740                 745                 750

Gly Tyr Ile Phe Ala Thr Thr Gly Tyr Gly Ile Ala Leu Gln Lys Gly
            755                 760                 765

Ser Pro Trp Lys Arg Gln Ile Asp Leu Ala Leu Leu Gln Phe Val Gly
        770                 775                 780
```

```
Asp Gly Glu Met Glu Glu Leu Glu Thr Leu Trp Leu Thr Gly Ile Cys
785                 790                 795                 800

His Asn Glu Lys Asn Glu Val Met Ser Ser Gln Leu Asp Ile Asp Asn
                805                 810                 815

Met Ala Gly Val Phe Tyr Met Leu Ala Ala Met Ala Leu Ser Leu
                820                 825                 830

Ile Thr Phe Ile Trp Glu His Leu Phe Tyr Trp Lys Leu Arg Phe Cys
        835                 840                 845

Phe Thr Gly Val Cys Ser Asp Arg Pro Gly Leu Leu Phe Ser Ile Ser
850                 855                 860

Arg Gly Ile Tyr Ser Cys Ile His Gly Val His Ile Glu Glu Lys Lys
865                 870                 875                 880

Lys Ser Pro Asp Phe Asn Leu Thr Gly Ser Gln Ser Asn Met Leu Lys
                885                 890                 895

Leu Leu Arg Ser Ala Lys Asn Ile Ser Ser Met Ser Asn Met Asn Ser
                900                 905                 910

Ser Arg Met Asp Ser Pro Lys Arg Ala Ala Asp Phe Ile Gln Arg Gly
                915                 920                 925

Ser Leu Ile Met Asp Met Val Ser Asp Lys Gly Asn Leu Met Tyr Ser
                930                 935                 940

Asp Asn Arg Ser Phe Gln Gly Lys Glu Ser Ile Phe Gly Asp Asn Met
945                 950                 955                 960

Asn Glu Leu Gln Thr Phe Val Ala Asn Arg Gln Lys Asp Asn Leu Asn
                965                 970                 975

Asn Tyr Val Phe Gln Gly Gln His Pro Leu Thr Leu Asn Glu Ser Asn
                980                 985                 990

Pro Asn Thr Val Glu Val Ala Val Ser Thr Glu Ser Lys Ala Asn Ser
                995                 1000                1005

Arg Pro Arg Gln Leu Trp Lys Lys Ser Val Asp Ser Ile Arg Gln Asp
        1010                1015                1020

Ser Leu Ser Gln Asn Pro Val Ser Gln Arg Asp Glu Ala Thr Ala Glu
1025                1030                1035                1040

Asn Arg Thr His Ser Leu Lys Ser Pro Arg Tyr Leu Pro Glu Glu Met
                1045                1050                1055

Ala His Ser Asp Ile Ser Glu Thr Ser Asn Arg Ala Thr Cys His Arg
                1060                1065                1070

Glu Pro Asp Asn Ser Lys Asn His Lys Thr Lys Asp Asn Phe Lys Arg
                1075                1080                1085

Ser Val Ala Ser Lys Tyr Pro Lys Asp Cys Ser Glu Val Glu Arg Thr
                1090                1095                1100

Tyr Leu Lys Thr Lys Ser Ser Pro Arg Asp Lys Ile Tyr Thr Ile
1105                1110                1115                1120

Asp Gly Glu Lys Glu Pro Gly Phe His Leu Asp Pro Pro Gln Phe Val
                1125                1130                1135

Glu Asn Val Thr Leu Pro Glu Asn Val Asp Phe Pro Asp Pro Tyr Gln
                1140                1145                1150

Asp Pro Ser Glu Asn Phe Arg Lys Gly Asp Ser Thr Leu Pro Met Asn
                1155                1160                1165

Arg Asn Pro Leu His Asn Glu Glu Gly Leu Ser Asn Asn Asp Gln Tyr
        1170                1175                1180

Lys Leu Tyr Ser Lys His Phe Thr Leu Lys Asp Lys Gly Ser Pro His
1185                1190                1195                1200

Ser Glu Thr Ser Glu Arg Tyr Arg Gln Asn Ser Thr His Cys Arg Ser
```

```
                    1205                1210                1215
Cys Leu Ser Asn Met Pro Thr Tyr Ser Gly His Phe Thr Met Arg Ser
            1220                1225                1230

Pro Phe Lys Cys Asp Ala Cys Leu Arg Met Gly Asn Leu Tyr Asp Ile
        1235                1240                1245

Asp Glu Asp Gln Met Leu Gln Glu Thr Gly Asn Pro Ala Thr Gly Glu
    1250                1255                1260

Gln Val Tyr Gln Gln Asp Trp Ala Gln Asn Asn Ala Leu Gln Leu Gln
1265                1270                1275                1280

Lys Asn Lys Leu Arg Ile Ser Arg Gln His Ser Tyr Asp Asn Ile Val
            1285                1290                1295

Asp Lys Pro Arg Glu Leu Asp Leu Ser Arg Pro Ser Arg Ser Ile Ser
        1300                1305                1310

Leu Lys Asp Arg Glu Arg Leu Leu Glu Gly Asn Phe Tyr Gly Ser Leu
    1315                1320                1325

Phe Ser Val Pro Ser Ser Lys Leu Ser Gly Lys Lys Ser Ser Leu Phe
1330                1335                1340

Pro Gln Gly Leu Glu Asp Ser Lys Arg Ser Lys Ser Leu Leu Pro Asp
1345                1350                1355                1360

His Thr Ser Asp Asn Pro Phe Leu His Ser His Arg Asp Asp Gln Arg
            1365                1370                1375

Leu Val Ile Gly Arg Cys Pro Ser Asp Pro Tyr Lys His Ser Leu Pro
        1380                1385                1390

Ser Gln Ala Val Asn Asp Ser Tyr Leu Arg Ser Ser Leu Arg Ser Thr
    1395                1400                1405

Ala Ser Tyr Cys Ser Arg Asp Ser Arg Gly His Asn Asp Val Tyr Ile
    1410                1415                1420

Ser Glu His Val Met Pro Tyr Ala Ala Asn Lys Asn Asn Met Tyr Ser
1425                1430                1435                1440

Thr Pro Arg Val Leu Asn Ser Cys Ser Asn Arg Arg Val Tyr Lys Glu
            1445                1450                1455

Met Pro Ser Ile Glu Ser Asp Val
            1460

(2) INFORMATION FOR SEQ ID NO:12:

(i) SEQUENCE CHARACTERISTICS:
        (A) LENGTH: 74 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:12:

CGAGGGAGGC GGCCGGCGCG GACTCTCTTC GCGGGCGCAG CGCCCCTTCC CCCTCGGACC    60

CTCCGGTGGA CATG                                                     74

(2) INFORMATION FOR SEQ ID NO:13:

(i) SEQUENCE CHARACTERISTICS:
        (A) LENGTH: 3155 base pairs
        (B) TYPE: nucleic acid
        (C) STRANDEDNESS: both
        (D) TOPOLOGY: both (ii) MOLECULE TYPE: cDNA (ix) FEATURE:
```

-continued (A) NAME/KEY: CDS
        (B) LOCATION: 262..3030

(xi) SEQUENCE DESCRIPTION: SEQ ID NO:13:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC       291
                        Met Ser Thr Met Arg Leu Leu Thr Leu Ala
                         1               5                   10

CTG CTG TTC TCC TGC TCC GTC GCC CGT GCC GCG TGC GAC CCC AAG ATC       339
Leu Leu Phe Ser Cys Ser Val Ala Arg Ala Ala Cys Asp Pro Lys Ile
             15                  20                  25

GTC AAC ATT GGC GCG GTG CTG AGC ACG CGG AAG CAC GAG CAG ATG TTC       387
Val Asn Ile Gly Ala Val Leu Ser Thr Arg Lys His Glu Gln Met Phe
         30                  35                  40

CGC GAG GCC GTG AAC CAG GCC AAC AAG CGG CAC GGC TCC TGG AAG ATT       435
Arg Glu Ala Val Asn Gln Ala Asn Lys Arg His Gly Ser Trp Lys Ile
     45                  50                  55

CAG CTC AAT GCC ACC TCC GTC ACG CAC AAG CCC AAC GCC ATC CAG ATG       483
Gln Leu Asn Ala Thr Ser Val Thr His Lys Pro Asn Ala Ile Gln Met
 60                  65                  70

GCT CTG TCG GTG TGC GAG GAC CTC ATC TCC AGC CAG GTC TAC GCC ATC       531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT       579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC       627
Val Ser Tyr Thr Ala Gly Phe Tyr Arg Ile Pro Val Leu Gly Leu Thr
             110                 115                 120

ACC CGC ATG TCC ATC TAC TCG GAC AAG AGC ATC CAC CTG AGC TTC CTG       675
Thr Arg Met Ser Ile Tyr Ser Asp Lys Ser Ile His Leu Ser Phe Leu
         125                 130                 135

CGC ACC GTG CCG CCC TAC TCC CAC CAG TCC AGC GTG TGG TTT GAG ATG       723
Arg Thr Val Pro Pro Tyr Ser His Gln Ser Ser Val Trp Phe Glu Met
 140                 145                 150

ATG CGT GTC TAC AGC TGG AAC CAC ATC ATC CTG CTG GTC AGC GAC GAC       771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG       819
His Glu Gly Arg Ala Ala Gln Lys Arg Leu Glu Thr Leu Leu Glu Glu
                 175                 180                 185

CGT GAG TCC AAG GCA GAG AAG GTG CTG CAG TTT GAC CCA GGG ACC AAG       867
Arg Glu Ser Lys Ala Glu Lys Val Leu Gln Phe Asp Pro Gly Thr Lys
             190                 195                 200

AAC GTG ACG GCC CTG CTG ATG GAG GCG AAA GAG CTG GAG GCC CGG GTC       915
Asn Val Thr Ala Leu Leu Met Glu Ala Lys Glu Leu Glu Ala Arg Val
         205                 210                 215

ATC ATC CTT TCT GCC AGC GAG GAC GAT GCT GCC ACT GTA TAC CGC GCA       963
Ile Ile Leu Ser Ala Ser Glu Asp Asp Ala Ala Thr Val Tyr Arg Ala
 220                 225                 230

GCC GCG ATG CTG AAC ATG ACG GGC TCC GGG TAC GTG TGG CTG GTC GGC      1011
Ala Ala Met Leu Asn Met Thr Gly Ser Gly Tyr Val Trp Leu Val Gly
235                 240                 245                 250

GAG CGC GAG ATC TCG GGG AAC GCC CTG CGC TAC GCC CCA GAC GGC ATC      1059
Glu Arg Glu Ile Ser Gly Asn Ala Leu Arg Tyr Ala Pro Asp Gly Ile
```

-continued

```
                      255                 260                 265
CTC GGG CTG CAG CTC ATC AAC GGC AAG AAC GAG TCG GCC CAC ATC AGC    1107
Leu Gly Leu Gln Leu Ile Asn Gly Lys Asn Glu Ser Ala His Ile Ser
                      270                 275                 280

GAC GCC GTG GGC GTG GTG GCC CAG GCC GTG CAC GAG CTC CTC GAG AAG    1155
Asp Ala Val Gly Val Val Ala Gln Ala Val His Glu Leu Leu Glu Lys
            285                 290                 295

GAG AAC ATC ACC GAC CCG CCG CGG GGC TGC GTG GGC AAC ACC AAC ATC    1203
Glu Asn Ile Thr Asp Pro Pro Arg Gly Cys Val Gly Asn Thr Asn Ile
        300                 305                 310

TGG AAG ACC GGG CCG CTC TTC AAG AGA GTG CTG ATG TCT TCC AAG TAT    1251
Trp Lys Thr Gly Pro Leu Phe Lys Arg Val Leu Met Ser Ser Lys Tyr
315                 320                 325                 330

GCG GAT GGG GTG ACT GGT CGC GTG GAG TTC AAT GAG GAT GGG GAC CGG    1299
Ala Asp Gly Val Thr Gly Arg Val Glu Phe Asn Glu Asp Gly Asp Arg
                335                 340                 345

AAG TTC GCC AAC TAC AGC ATC ATG AAC CTG CAG AAC CGC AAG CTG GTG    1347
Lys Phe Ala Asn Tyr Ser Ile Met Asn Leu Gln Asn Arg Lys Leu Val
            350                 355                 360

CAA GTG GGC ATC TAC AAT GGC ACC CAC GTC ATC CCT AAT GAC AGG AAG    1395
Gln Val Gly Ile Tyr Asn Gly Thr His Val Ile Pro Asn Asp Arg Lys
        365                 370                 375

ATC ATC TGG CCA GGC GGA GAG ACA GAG AAG CCT CGA GGG TAC CAG ATG    1443
Ile Ile Trp Pro Gly Gly Glu Thr Glu Lys Pro Arg Gly Tyr Gln Met
380                 385                 390

TCC ACC AGA CTG AAG ATT GTG ACG ATC CAC CAG GAG CCC TTC GTG TAC    1491
Ser Thr Arg Leu Lys Ile Val Thr Ile His Gln Glu Pro Phe Val Tyr
395                 400                 405                 410

GTC AAG CCC ACG CTG AGT GAT GGG ACA TGC AAG GAG GAG TTC ACA GTC    1539
Val Lys Pro Thr Leu Ser Asp Gly Thr Cys Lys Glu Glu Phe Thr Val
                415                 420                 425

AAC GGC GAC CCA GTC AAG AAG GTG ATC TGC ACC GGG CCC AAC GAC ACG    1587
Asn Gly Asp Pro Val Lys Lys Val Ile Cys Thr Gly Pro Asn Asp Thr
            430                 435                 440

TCG CCG GGC AGC CCC CGC CAC ACG GTG CCT CAG TGT TGC TAC GGC TTT    1635
Ser Pro Gly Ser Pro Arg His Thr Val Pro Gln Cys Cys Tyr Gly Phe
        445                 450                 455

TGC ATC GAC CTG CTC ATC AAG CTG GCA CGG ACC ATG AAC TTC ACC TAC    1683
Cys Ile Asp Leu Leu Ile Lys Leu Ala Arg Thr Met Asn Phe Thr Tyr
460                 465                 470

GAG GTG CAC CTG GTG GCA GAT GGC AAG TTC GGC ACA CAG GAG CGG GTG    1731
Glu Val His Leu Val Ala Asp Gly Lys Phe Gly Thr Gln Glu Arg Val
475                 480                 485                 490

AAC AAC AGC AAC AAG AAG GAG TGG AAT GGG ATG ATG GGC GAG CTG CTC    1779
Asn Asn Ser Asn Lys Lys Glu Trp Asn Gly Met Met Gly Glu Leu Leu
                495                 500                 505

AGC GGG CAG GCA GAC ATG ATC GTG GCG CCG CTA ACC ATA AAC AAC GAG    1827
Ser Gly Gln Ala Asp Met Ile Val Ala Pro Leu Thr Ile Asn Asn Glu
            510                 515                 520

CGC GCG CAG TAC ATC GAG TTT TCC AAG CCC TTC AAG TAC CAG GGC CTG    1875
Arg Ala Gln Tyr Ile Glu Phe Ser Lys Pro Phe Lys Tyr Gln Gly Leu
        525                 530                 535

ACT ATT CTG GTC AAG AAG GAG ATT CCC CGG AGC ACG CTG GAC TCG TTC    1923
Thr Ile Leu Val Lys Lys Glu Ile Pro Arg Ser Thr Leu Asp Ser Phe
    540                 545                 550

ATG CAG CCG TTC CAG AGC ACA CTG TGG CTG CTG GTG GGG CTG TCG GTG    1971
Met Gln Pro Phe Gln Ser Thr Leu Trp Leu Leu Val Gly Leu Ser Val
555                 560                 565                 570

CAC GTG GTG GCC GTG ATG CTG TAC CTG CTG GAC CGC TTC AGC CCC TTC    2019
```

-continued

| | | | | | | | | | | | | |
|---|---|---|---|---|---|---|---|---|---|---|---|---|
|His|Val|Val|Ala|Val|Met|Leu|Tyr|Leu|Leu|Asp|Arg|Phe|Ser|Pro|Phe|
| | | |575| | | |580| | | | |585|

GGC CGG TTC AAG GTG AAC AGC GAG GAG GAG GAG GAC GCA CTG ACC  2067
Gly Arg Phe Lys Val Asn Ser Glu Glu Glu Glu Asp Ala Leu Thr
            590                 595                 600

CTG TCC TCG GCC ATG TGG TTC TCC TGG GGC GTC CTG CTC AAC TCC GGC  2115
Leu Ser Ser Ala Met Trp Phe Ser Trp Gly Val Leu Leu Asn Ser Gly
605                 610                 615

ATC GGG GAA GGC GCC CCC AGA AGC TTC TCA GCG CGC ATC CTG GGC ATG  2163
Ile Gly Glu Gly Ala Pro Arg Ser Phe Ser Ala Arg Ile Leu Gly Met
            620                 625                 630

GTG TGG GCC GGC TTT GCC ATG ATC ATC GTG GCC TCC TAC ACC GCC AAC  2211
Val Trp Ala Gly Phe Ala Met Ile Ile Val Ala Ser Tyr Thr Ala Asn
635                 640                 645                 650

CTG GCG GCC TTC CTG GTG CTG GAC CGG CCG GAG GAG CGC ATC ACG GGC  2259
Leu Ala Ala Phe Leu Val Leu Asp Arg Pro Glu Glu Arg Ile Thr Gly
                655                 660                 665

ATC AAC GAC CCT CGG CTG AGG AAC CCC TCG GAC AAG TTT ATC TAC GCC  2307
Ile Asn Asp Pro Arg Leu Arg Asn Pro Ser Asp Lys Phe Ile Tyr Ala
            670                 675                 680

ACG GTG AAG CAG AGC TCC GTG GAT ATC TAC TTC CGG CGC CAG GTG GAG  2355
Thr Val Lys Gln Ser Ser Val Asp Ile Tyr Phe Arg Arg Gln Val Glu
            685                 690                 695

CTG AGC ACC ATG TAC CGG CAT ATG GAG AAG CAC AAC TAC GAG AGT GCG  2403
Leu Ser Thr Met Tyr Arg His Met Glu Lys His Asn Tyr Glu Ser Ala
700                 705                 710

GCG GAG GCC ATC CAG GCC GTG AGA GAC AAC AAG CTG CAT GCC TTC ATC  2451
Ala Glu Ala Ile Gln Ala Val Arg Asp Asn Lys Leu His Ala Phe Ile
715                 720                 725                 730

TGG GAC TCG GCG GTG CTG GAG TTC GAG GCC TCG CAG AAG TGC GAC CTG  2499
Trp Asp Ser Ala Val Leu Glu Phe Glu Ala Ser Gln Lys Cys Asp Leu
                735                 740                 745

GTG ACG ACT GGA GAG CTG TTT TTC CGC TCG GGC TTC GGC ATA GGC ATG  2547
Val Thr Thr Gly Glu Leu Phe Phe Arg Ser Gly Phe Gly Ile Gly Met
            750                 755                 760

CGC AAA GAC AGC CCC TGG AAG CAG AAC GTC TCC CTG TCC ATC CTC AAG  2595
Arg Lys Asp Ser Pro Trp Lys Gln Asn Val Ser Leu Ser Ile Leu Lys
            765                 770                 775

TCC CAC GAG AAT GGC TTC ATG GAA GAC CTG GAC AAG ACG TGG GTT CGG  2643
Ser His Glu Asn Gly Phe Met Glu Asp Leu Asp Lys Thr Trp Val Arg
780                 785                 790

TAT CAG GAA TGT GAC TCG CGC AGC AAC GCC CCT GCG ACC CTT ACT TTT  2691
Tyr Gln Glu Cys Asp Ser Arg Ser Asn Ala Pro Ala Thr Leu Thr Phe
795                 800                 805                 810

GAG AAC ATG GCC GGG GTC TTC ATG CTG GTA GCT GGG GGC ATC GTG GCC  2739
Glu Asn Met Ala Gly Val Phe Met Leu Val Ala Gly Gly Ile Val Ala
                815                 820                 825

GGG ATC TTC CTG ATT TTC ATC GAG ATT GCC TAC AAG CGG CAC AAG GAT  2787
Gly Ile Phe Leu Ile Phe Ile Glu Ile Ala Tyr Lys Arg His Lys Asp
            830                 835                 840

GCT CGC CGG AAG CAG ATG CAG CTG GCC TTT GCC GCC GTT AAC GTG TGG  2835
Ala Arg Arg Lys Gln Met Gln Leu Ala Phe Ala Ala Val Asn Val Trp
            845                 850                 855

CGG AAG AAC CTG CAG GAT AGA AAG AGT GGT AGA GCA GAG CCT GAC CCT  2883
Arg Lys Asn Leu Gln Asp Arg Lys Ser Gly Arg Ala Glu Pro Asp Pro
            860                 865                 870

AAA AAG AAA GCC ACA TTT AGG GCT ATC ACC TCC ACC CTG GCT TCC AGC  2931
Lys Lys Lys Ala Thr Phe Arg Ala Ile Thr Ser Thr Leu Ala Ser Ser
875                 880                 885                 890

-continued

```
TTC AAG AGG CGT AGG TCC TCC AAA GAC ACG CAG TAC CAT CCC ACT GAT    2979
Phe Lys Arg Arg Arg Ser Ser Lys Asp Thr Gln Tyr His Pro Thr Asp
            895                 900                 905

ATC ACG GGC CCG CTC AAC CTC TCA GAT CCC TCG GTC AGC ACC GTG GTG    3027
Ile Thr Gly Pro Leu Asn Leu Ser Asp Pro Ser Val Ser Thr Val Val
        910                 915                 920

TGAGGCCCCC GGAGGCGCCC ACCTGCCCAG TTAGCCCGGC CAAGGACACT GATGGGTCCT   3087

GCTGCTCGGG AAGGCCTGAG GGAAGCCCAC CCGCCCCAGA GACTGCCCAC CCTGGGCCTC   3147

CCGTCCGT                                                            3155
```

(2) INFORMATION FOR SEQ ID NO:14:

(i) SEQUENCE CHARACTERISTICS:
        (A) LENGTH: 922 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
 65                 70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
                100                 105                 110

Phe Tyr Arg Ile Pro Val Leu Gly Leu Thr Thr Arg Met Ser Ile Tyr
            115                 120                 125

Ser Asp Lys Ser Ile His Leu Ser Phe Leu Arg Thr Val Pro Pro Tyr
        130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285
```

-continued

```
Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
                340                 345                 350

Ile Met Asn Leu Gln Asn Arg Lys Leu Val Gln Val Gly Ile Tyr Asn
                355                 360                 365

Gly Thr His Val Ile Pro Asn Asp Arg Lys Ile Trp Pro Gly Gly
370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
                420                 425                 430

Lys Val Ile Cys Thr Gly Pro Asn Asp Thr Ser Pro Gly Ser Pro Arg
                435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
                500                 505                 510

Ile Val Ala Pro Leu Thr Ile Asn Asn Glu Arg Ala Gln Tyr Ile Glu
                515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Ala Val Met
                565                 570                 575

Leu Tyr Leu Leu Asp Arg Phe Ser Pro Phe Gly Arg Phe Lys Val Asn
                580                 585                 590

Ser Glu Glu Glu Glu Asp Ala Leu Thr Leu Ser Ser Ala Met Trp
    595                 600                 605

Phe Ser Trp Gly Val Leu Leu Asn Ser Gly Ile Gly Glu Gly Ala Pro
610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
                660                 665                 670

Arg Asn Pro Ser Asp Lys Phe Ile Tyr Ala Thr Val Lys Gln Ser Ser
    675                 680                 685

Val Asp Ile Tyr Phe Arg Arg Gln Val Glu Leu Ser Thr Met Tyr Arg
    690                 695                 700
```

```
His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
                740                 745                 750

Phe Phe Arg Ser Gly Phe Gly Ile Gly Met Arg Lys Asp Ser Pro Trp
            755                 760                 765

Lys Gln Asn Val Ser Leu Ser Ile Leu Lys Ser His Glu Asn Gly Phe
        770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
                835                 840                 845

Gln Leu Ala Phe Ala Ala Val Asn Val Trp Arg Lys Asn Leu Gln Asp
        850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Gln Tyr His Pro Thr Asp Ile Thr Gly Pro Leu Asn
                900                 905                 910

Leu Ser Asp Pro Ser Val Ser Thr Val Val
        915                 920

(2) INFORMATION FOR SEQ ID NO:15:

(i) SEQUENCE CHARACTERISTICS:
        (A) LENGTH: 2540 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..2334

(xi) SEQUENCE DESCRIPTION: SEQ ID NO:15:

AAC GAC CAC TTC ACT CCC ACC CCT GTC TCC TAC ACA GCC GGC TTC TAC        48
Asn Asp His Phe Thr Pro Thr Pro Val Ser Tyr Thr Ala Gly Phe Tyr
 1               5                  10                  15

CGC ATA CCC GTG CTG GGG CTG ACC ACC CGC ATG TCC ATC TAC TCG GAC        96
Arg Ile Pro Val Leu Gly Leu Thr Thr Arg Met Ser Ile Tyr Ser Asp
             20                  25                  30

AAG AGC ATC CAC CTG AGC TTC CTG CGC ACC GTG CCG CCC TAC TCC CAC       144
Lys Ser Ile His Leu Ser Phe Leu Arg Thr Val Pro Pro Tyr Ser His
         35                  40                  45

CAG TCC AGC GTG TGG TTT GAG ATG ATG CGT GTC TAC AGC TGG AAC CAC       192
Gln Ser Ser Val Trp Phe Glu Met Met Arg Val Tyr Ser Trp Asn His
     50                  55                  60

ATC ATC CTG CTG GTC AGC GAC GAC CAC GAG GGC CGG GCG GCT CAG AAA       240
Ile Ile Leu Leu Val Ser Asp Asp His Glu Gly Arg Ala Ala Gln Lys
 65                  70                  75                  80
```

```
CGC CTG GAG ACG CTG CTG GAG GAG CGT GAG TCC AAG AGT AAA AAA AGG      288
Arg Leu Glu Thr Leu Leu Glu Glu Arg Glu Ser Lys Ser Lys Lys Arg
             85                  90                  95

AAC TAT GAA AAC CTC GAC CAA CTG TCC TAT GAC AAC AAG CGC GGA CCC      336
Asn Tyr Glu Asn Leu Asp Gln Leu Ser Tyr Asp Asn Lys Arg Gly Pro
            100                 105                 110

AAG GCA GAG AAG GTG CTG CAG TTT GAC CCA GGG ACC AAG AAC GTG ACG      384
Lys Ala Glu Lys Val Leu Gln Phe Asp Pro Gly Thr Lys Asn Val Thr
            115                 120                 125

GCC CTG CTG ATG GAG GCG AAA GAG CTG GAG GCC CGG GTC ATC ATC CTT      432
Ala Leu Leu Met Glu Ala Lys Glu Leu Glu Ala Arg Val Ile Ile Leu
            130                 135                 140

TCT GCC AGC GAG GAC GAT GCT GCC ACT GTA TAC CGC GCA GCC GCG ATG      480
Ser Ala Ser Glu Asp Asp Ala Ala Thr Val Tyr Arg Ala Ala Ala Met
145                 150                 155                 160

CTG AAC ATG ACG GGC AAC ACC AAC ATC TGG AAG ACC GGG CCG CTC TTC      528
Leu Asn Met Thr Gly Asn Thr Asn Ile Trp Lys Thr Gly Pro Leu Phe
            165                 170                 175

AAG AGA GTG CTG ATG TCT TCC AAG TAT GCG GAT GGG GTG ACT GGT CGC      576
Lys Arg Val Leu Met Ser Ser Lys Tyr Ala Asp Gly Val Thr Gly Arg
            180                 185                 190

GTG GAG TTC AAT GAG GAT GGG GAC CGG AAG TTC GCC AAC TAC AGC ATC      624
Val Glu Phe Asn Glu Asp Gly Asp Arg Lys Phe Ala Asn Tyr Ser Ile
            195                 200                 205

ATG AAC CTG CAG AAC CGC AAG CTG GTG CAA GTG GGC ATC TAC AAT GGC      672
Met Asn Leu Gln Asn Arg Lys Leu Val Gln Val Gly Ile Tyr Asn Gly
            210                 215                 220

ACC CAC GTC ATC CCT AAT GAC AGG AAG ATC ATC TGG CCA GGC GGA GAG      720
Thr His Val Ile Pro Asn Asp Arg Lys Ile Ile Trp Pro Gly Gly Glu
225                 230                 235                 240

ACA GAG AAG CCT CGA GGG TAC CAG ATG TCC ACC AGA CTG AAG ATT GTG      768
Thr Glu Lys Pro Arg Gly Tyr Gln Met Ser Thr Arg Leu Lys Ile Val
            245                 250                 255

ACG ATC CAC CAG GAG CCC TTC GTG TAC GTC AAG CCC ACG CTG AGT GAT      816
Thr Ile His Gln Glu Pro Phe Val Tyr Val Lys Pro Thr Leu Ser Asp
            260                 265                 270

GGG ACA TGC AAG GAG GAG TTC ACA GTC AAC GGC GAC CCA GTC AAG AAG      864
Gly Thr Cys Lys Glu Glu Phe Thr Val Asn Gly Asp Pro Val Lys Lys
            275                 280                 285

GTG ATC TGC ACC GGG CCC AAC GAC ACG TCG CCG GGC AGC CCC CGC CAC      912
Val Ile Cys Thr Gly Pro Asn Asp Thr Ser Pro Gly Ser Pro Arg His
            290                 295                 300

ACG GTG CCT CAG TGT TGC TAC GGC TTT TGC ATC GAC CTG CTC ATC AAG      960
Thr Val Pro Gln Cys Cys Tyr Gly Phe Cys Ile Asp Leu Leu Ile Lys
305                 310                 315                 320

CTG GCA CGG ACC ATG AAC TTC ACC TAC GAG GTG CAC CTG GTG GCA GAT     1008
Leu Ala Arg Thr Met Asn Phe Thr Tyr Glu Val His Leu Val Ala Asp
            325                 330                 335

GGC AAG TTC GGC ACA CAG GAG CGG GTG AAC AAC AGC AAC AAG AAG GAG     1056
Gly Lys Phe Gly Thr Gln Glu Arg Val Asn Asn Ser Asn Lys Lys Glu
            340                 345                 350

TGG AAT GGG ATG ATG GGC GAG CTG CTC AGC GGG CAG GCA GAC ATG ATC     1104
Trp Asn Gly Met Met Gly Glu Leu Leu Ser Gly Gln Ala Asp Met Ile
            355                 360                 365

GTG GCG CCG CTA ACC ATA AAC AAC GAG CGC GCG CAG TAC ATC GAG TTT     1152
Val Ala Pro Leu Thr Ile Asn Asn Glu Arg Ala Gln Tyr Ile Glu Phe
            370                 375                 380

TCC AAG CCC TTC AAG TAC CAG GGC CTG ACT ATT CTG GTC AAG AAG GAG     1200
Ser Lys Pro Phe Lys Tyr Gln Gly Leu Thr Ile Leu Val Lys Lys Glu
385                 390                 395                 400
```

```
ATT CCC CGG AGC ACG CTG GAC TCG TTC ATG CAG CCG TTC CAG AGC ACA      1248
Ile Pro Arg Ser Thr Leu Asp Ser Phe Met Gln Pro Phe Gln Ser Thr
            405                 410                 415

CTG TGG CTG CTG GTG GGG CTG TCG GTG CAC GTG GTG GCC GTG ATG CTG      1296
Leu Trp Leu Leu Val Gly Leu Ser Val His Val Val Ala Val Met Leu
            420                 425                 430

TAC CTG CTG GAC CGC TTC AGC CCC TTC GGC CGG TTC AAG GTG AAC AGC      1344
Tyr Leu Leu Asp Arg Phe Ser Pro Phe Gly Arg Phe Lys Val Asn Ser
            435                 440                 445

GAG GAG GAG GAG GAG GAC GCA CTG ACC CTG TCC TCG GCC ATG TGG TTC      1392
Glu Glu Glu Glu Glu Asp Ala Leu Thr Leu Ser Ser Ala Met Trp Phe
        450                 455                 460

TCC TGG GGC GTC CTG CTC AAC TCC GGC ATC GGG GAA GGC GCC CCC AGA      1440
Ser Trp Gly Val Leu Leu Asn Ser Gly Ile Gly Glu Gly Ala Pro Arg
465                 470                 475                 480

AGC TTC TCA GCG CGC ATC CTG GGC ATG GTG TGG GCC GGC TTT GCC ATG      1488
Ser Phe Ser Ala Arg Ile Leu Gly Met Val Trp Ala Gly Phe Ala Met
                485                 490                 495

ATC ATC GTG GCC TCC TAC ACC GCC AAC CTG GCG GCC TTC CTG GTG CTG      1536
Ile Ile Val Ala Ser Tyr Thr Ala Asn Leu Ala Ala Phe Leu Val Leu
            500                 505                 510

GAC CGG CCG GAG GAG CGC ATC ACG GGC ATC AAC GAC CCT CGG CTG AGG      1584
Asp Arg Pro Glu Glu Arg Ile Thr Gly Ile Asn Asp Pro Arg Leu Arg
            515                 520                 525

AAC CCC TCG GAC AAG TTT ATC TAC GCC ACG GTG AAG CAG AGC TCC GTG      1632
Asn Pro Ser Asp Lys Phe Ile Tyr Ala Thr Val Lys Gln Ser Ser Val
        530                 535                 540

GAT ATC TAC TTC CGG CGC CAG GTG GAG CTG AGC ACC ATG TAC CGG CAT      1680
Asp Ile Tyr Phe Arg Arg Gln Val Glu Leu Ser Thr Met Tyr Arg His
545                 550                 555                 560

ATG GAG AAG CAC AAC TAC GAG AGT GCG GCG GAG GCC ATC CAG GCC GTG      1728
Met Glu Lys His Asn Tyr Glu Ser Ala Ala Glu Ala Ile Gln Ala Val
                565                 570                 575

AGA GAC AAC AAG CTG CAT GCC TTC ATC TGG GAC TCG GCG GTG CTG GAG      1776
Arg Asp Asn Lys Leu His Ala Phe Ile Trp Asp Ser Ala Val Leu Glu
            580                 585                 590

TTC GAG GCC TCG CAG AAG TGC GAC CTG GTG ACG ACT GGA GAG CTG TTT      1824
Phe Glu Ala Ser Gln Lys Cys Asp Leu Val Thr Thr Gly Glu Leu Phe
            595                 600                 605

TTC CGC TCG GGC TTC GGC ATA GGC ATG CGC AAA GAC AGC CCC TGG AAG      1872
Phe Arg Ser Gly Phe Gly Ile Gly Met Arg Lys Asp Ser Pro Trp Lys
            610                 615                 620

CAG AAC GTC TCC CTG TCC ATC CTC AAG TCC CAC GAG AAT GGC TTC ATG      1920
Gln Asn Val Ser Leu Ser Ile Leu Lys Ser His Glu Asn Gly Phe Met
625                 630                 635                 640

GAA GAC CTG GAC AAG ACG TGG GTT CGG TAT CAG GAA TGT GAC TCG CGC      1968
Glu Asp Leu Asp Lys Thr Trp Val Arg Tyr Gln Glu Cys Asp Ser Arg
                645                 650                 655

AGC AAC GCC CCT GCG ACC CTT ACT TTT GAG AAC ATG GCC GGG GTC TTC      2016
Ser Asn Ala Pro Ala Thr Leu Thr Phe Glu Asn Met Ala Gly Val Phe
            660                 665                 670

ATG CTG GTA GCT GGG GGC ATC GTG GCC GGG ATC TTC CTG ATT TTC ATC      2064
Met Leu Val Ala Gly Gly Ile Val Ala Gly Ile Phe Leu Ile Phe Ile
            675                 680                 685

GAG ATT GCC TAC AAG CGG CAC AAG GAT GCT CGC CGG AAG CAG ATG CAG      2112
Glu Ile Ala Tyr Lys Arg His Lys Asp Ala Arg Arg Lys Gln Met Gln
            690                 695                 700

CTG GCC TTT GCC GCC GTT AAC GTG TGG CGG AAG AAC CTG CAG GAT AGA      2160
Leu Ala Phe Ala Ala Val Asn Val Trp Arg Lys Asn Leu Gln Asp Arg
```

```
705                 710                 715                 720
AAG AGT GGT AGA GCA GAG CCT GAC CCT AAA AAG AAA GCC ACA TTT AGG         2208
Lys Ser Gly Arg Ala Glu Pro Asp Pro Lys Lys Lys Ala Thr Phe Arg
                725                 730                 735

GCT ATC ACC TCC ACC CTG GCT TCC AGC TTC AAG AGG CGT AGG TCC TCC         2256
Ala Ile Thr Ser Thr Leu Ala Ser Ser Phe Lys Arg Arg Arg Ser Ser
                740                 745                 750

AAA GAC ACG CAG TAC CAT CCC ACT GAT ATC ACG GGC CCG CTC AAC CTC         2304
Lys Asp Thr Gln Tyr His Pro Thr Asp Ile Thr Gly Pro Leu Asn Leu
                755                 760                 765

TCA GAT CCC TCG GTC AGC ACC GTG GTG TGAGGCCCCC GGAGGCGCCC               2351
Ser Asp Pro Ser Val Ser Thr Val Val
                770                 775

ACCTGCCCAG TTAGCCCGGC CAAGGACACT GATGGGTCCT GCTGCTCGGG AAGGCCTGAG       2411

GGAAGCCCAC CCGCCCCAGA GACTGCCCAC CCTGGGCCTC CCGTCCGTCC GCCCGCCCAC       2471

CCCGCTGCCT GGCGGGCAGC CCCTGCTGGA CCAAGGTGCG GACCGGAGCG GCTGAGGACG       2531

GGGCAGAGC                                                               2540

(2) INFORMATION FOR SEQ ID NO:16:

(i) SEQUENCE CHARACTERISTICS:
        (A) LENGTH: 777 amino acids
        (B) TYPE: amino acid
        (D) TOPOLOGY: linear (ii) MOLECULE TYPE: protein (xi) SEQUENCE DESCRIPTION: SEQ ID NO:16:

Asn Asp His Phe Thr Pro Thr Pro Val Ser Tyr Thr Ala Gly Phe Tyr
  1               5                  10                  15

Arg Ile Pro Val Leu Gly Leu Thr Thr Arg Met Ser Ile Tyr Ser Asp
                 20                  25                  30

Lys Ser Ile His Leu Ser Phe Leu Arg Thr Val Pro Pro Tyr Ser His
                 35                  40                  45

Gln Ser Ser Val Trp Phe Glu Met Met Arg Val Tyr Ser Trp Asn His
     50                  55                  60

Ile Ile Leu Leu Val Ser Asp Asp His Glu Gly Arg Ala Ala Gln Lys
 65                  70                  75                  80

Arg Leu Glu Thr Leu Leu Glu Glu Arg Glu Ser Lys Ser Lys Lys Arg
                 85                  90                  95

Asn Tyr Glu Asn Leu Asp Gln Leu Ser Tyr Asp Asn Lys Arg Gly Pro
                100                 105                 110

Lys Ala Glu Lys Val Leu Gln Phe Asp Pro Gly Thr Lys Asn Val Thr
                115                 120                 125

Ala Leu Leu Met Glu Ala Lys Glu Leu Glu Ala Arg Val Ile Ile Leu
                130                 135                 140

Ser Ala Ser Glu Asp Asp Ala Ala Thr Val Tyr Arg Ala Ala Ala Met
145                 150                 155                 160

Leu Asn Met Thr Gly Asn Thr Asn Ile Trp Lys Thr Gly Pro Leu Phe
                165                 170                 175

Lys Arg Val Leu Met Ser Ser Lys Tyr Ala Asp Gly Val Thr Gly Arg
                180                 185                 190

Val Glu Phe Asn Glu Asp Gly Asp Arg Lys Phe Ala Asn Tyr Ser Ile
                195                 200                 205

Met Asn Leu Gln Asn Arg Lys Leu Val Gln Val Gly Ile Tyr Asn Gly
                210                 215                 220
```

-continued

```
Thr His Val Ile Pro Asn Asp Arg Lys Ile Ile Trp Pro Gly Gly Glu
225                 230                 235                 240

Thr Glu Lys Pro Arg Gly Tyr Gln Met Ser Thr Arg Leu Lys Ile Val
            245                 250                 255

Thr Ile His Gln Glu Pro Phe Val Tyr Val Lys Pro Thr Leu Ser Asp
            260                 265                 270

Gly Thr Cys Lys Glu Glu Phe Thr Val Asn Gly Asp Pro Val Lys Lys
        275                 280                 285

Val Ile Cys Thr Gly Pro Asn Asp Thr Ser Pro Gly Ser Pro Arg His
    290                 295                 300

Thr Val Pro Gln Cys Cys Tyr Gly Phe Cys Ile Asp Leu Leu Ile Lys
305                 310                 315                 320

Leu Ala Arg Thr Met Asn Phe Thr Tyr Glu Val His Leu Val Ala Asp
                325                 330                 335

Gly Lys Phe Gly Thr Gln Glu Arg Val Asn Asn Ser Asn Lys Lys Glu
            340                 345                 350

Trp Asn Gly Met Met Gly Glu Leu Leu Ser Gly Gln Ala Asp Met Ile
        355                 360                 365

Val Ala Pro Leu Thr Ile Asn Asn Glu Arg Ala Gln Tyr Ile Glu Phe
    370                 375                 380

Ser Lys Pro Phe Lys Tyr Gln Gly Leu Thr Ile Leu Val Lys Lys Glu
385                 390                 395                 400

Ile Pro Arg Ser Thr Leu Asp Ser Phe Met Gln Pro Phe Gln Ser Thr
                405                 410                 415

Leu Trp Leu Leu Val Gly Leu Ser Val His Val Ala Val Met Leu
            420                 425                 430

Tyr Leu Leu Asp Arg Phe Ser Pro Phe Gly Arg Phe Lys Val Asn Ser
            435                 440                 445

Glu Glu Glu Glu Asp Ala Leu Thr Leu Ser Ser Ala Met Trp Phe
450                 455                 460

Ser Trp Gly Val Leu Leu Asn Ser Gly Ile Gly Glu Gly Ala Pro Arg
465                 470                 475                 480

Ser Phe Ser Ala Arg Ile Leu Gly Met Val Trp Ala Gly Phe Ala Met
            485                 490                 495

Ile Ile Val Ala Ser Tyr Thr Ala Asn Leu Ala Ala Phe Leu Val Leu
            500                 505                 510

Asp Arg Pro Glu Glu Arg Ile Thr Gly Ile Asn Asp Pro Arg Leu Arg
            515                 520                 525

Asn Pro Ser Asp Lys Phe Ile Tyr Ala Thr Val Lys Gln Ser Ser Val
530                 535                 540

Asp Ile Tyr Phe Arg Arg Gln Val Glu Leu Ser Thr Met Tyr Arg His
545                 550                 555                 560

Met Glu Lys His Asn Tyr Glu Ser Ala Ala Glu Ala Ile Gln Ala Val
                565                 570                 575

Arg Asp Asn Lys Leu His Ala Phe Ile Trp Asp Ser Ala Val Leu Glu
            580                 585                 590

Phe Glu Ala Ser Gln Lys Cys Asp Leu Val Thr Thr Gly Glu Leu Phe
            595                 600                 605

Phe Arg Ser Gly Phe Gly Ile Gly Met Arg Lys Asp Ser Pro Trp Lys
        610                 615                 620

Gln Asn Val Ser Leu Ser Ile Leu Lys Ser His Glu Asn Gly Phe Met
625                 630                 635                 640
```

```
Glu Asp Leu Asp Lys Thr Trp Val Arg Tyr Gln Glu Cys Asp Ser Arg
            645                 650                 655

Ser Asn Ala Pro Ala Thr Leu Thr Phe Glu Asn Met Ala Gly Val Phe
            660                 665                 670

Met Leu Val Ala Gly Gly Ile Val Ala Gly Ile Phe Leu Ile Phe Ile
            675                 680                 685

Glu Ile Ala Tyr Lys Arg His Lys Asp Ala Arg Arg Lys Gln Met Gln
            690                 695                 700

Leu Ala Phe Ala Ala Val Asn Val Trp Arg Lys Asn Leu Gln Asp Arg
705                 710                 715                 720

Lys Ser Gly Arg Ala Glu Pro Asp Pro Lys Lys Lys Ala Thr Phe Arg
            725                 730                 735

Ala Ile Thr Ser Thr Leu Ala Ser Ser Phe Lys Arg Arg Arg Ser Ser
            740                 745                 750

Lys Asp Thr Gln Tyr His Pro Thr Asp Ile Thr Gly Pro Leu Asn Leu
            755                 760                 765

Ser Asp Pro Ser Val Ser Thr Val Val
            770                 775

(2) INFORMATION FOR SEQ ID NO:17:

(i) SEQUENCE CHARACTERISTICS:
        (A) LENGTH: 595 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..576

(xi) SEQUENCE DESCRIPTION: SEQ ID NO:17:

GAA GAC CTG GAC AAG ACG TGG GTT CGG TAT CAG GAA TGT GAC TCG CGC        48
Glu Asp Leu Asp Lys Thr Trp Val Arg Tyr Gln Glu Cys Asp Ser Arg
 1               5                  10                  15

AGC AAC GCC CCT GCG ACC CTT ACT TTT GAG AAC ATG GCC GGG GTC TTC        96
Ser Asn Ala Pro Ala Thr Leu Thr Phe Glu Asn Met Ala Gly Val Phe
                20                  25                  30

ATG CTG GTA GCT GGG GGC ATC GTG GCC GGG ATC TTC CTG ATT TTC ATC       144
Met Leu Val Ala Gly Gly Ile Val Ala Gly Ile Phe Leu Ile Phe Ile
            35                  40                  45

GAG ATT GCC TAC AAG CGG CAC AAG GAT GCT CGC CGG AAG CAG ATG CAG       192
Glu Ile Ala Tyr Lys Arg His Lys Asp Ala Arg Arg Lys Gln Met Gln
    50                  55                  60

CTG GCC TTT GCC GCC GTT AAC GTG TGG CGG AAG AAC CTG CAG GAT AGA       240
Leu Ala Phe Ala Ala Val Asn Val Trp Arg Lys Asn Leu Gln Asp Arg
65                  70                  75                  80

AAG AGT GGT AGA GCA GAG CCT GAC CCT AAA AAG AAA GCC ACA TTT AGG       288
Lys Ser Gly Arg Ala Glu Pro Asp Pro Lys Lys Lys Ala Thr Phe Arg
                85                  90                  95

GCT ATC ACC TCC ACC CTG GCT TCC AGC TTC AAG AGG CGT AGG TCC TCC       336
Ala Ile Thr Ser Thr Leu Ala Ser Ser Phe Lys Arg Arg Arg Ser Ser
            100                 105                 110

AAA GAC ACG CTG GCT CGG GAC TGT CTT CAA CCC TGC CCT GCA CCT TGG       384
Lys Asp Thr Leu Ala Arg Asp Cys Leu Gln Pro Cys Pro Ala Pro Trp
    115                 120                 125

GCA CGG GAG AGC GCC ACC CGC CCG CCC CCG CCC TCG CTC CGG GTG CGT       432
Ala Arg Glu Ser Ala Thr Arg Pro Pro Pro Ser Leu Arg Val Arg
130                 135                 140
```

```
GAC CGG CCC GCC ACC TTG TAC AGA ACC AGC ACT CCC AGG GCC CGA GCG    480
Asp Arg Pro Ala Thr Leu Tyr Arg Thr Ser Thr Pro Arg Ala Arg Ala
145                 150                 155                 160

CGT GCC TTC CCC GTG CGC AGC CGC GCT CTG CCC CTC CGT CCC CAG GGT    528
Arg Ala Phe Pro Val Arg Ser Arg Ala Leu Pro Leu Arg Pro Gln Gly
                165                 170                 175

GCA GGC GCG CAC CGC CCA ACC CCC ACC TCC CGG TGT ATG CAG TGG        573
Ala Gly Ala His Arg Pro Thr Pro Thr Ser Arg Cys Met Gln Trp
            180                 185                 190

TGATGCCTAA AGGAATGTCA CG                                           595
```

(2) INFORMATION FOR SEQ ID NO:18:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO:18:

```
Glu Asp Leu Asp Lys Thr Trp Val Arg Tyr Gln Glu Cys Asp Ser Arg
1               5                   10                  15

Ser Asn Ala Pro Ala Thr Leu Thr Phe Glu Asn Met Ala Gly Val Phe
            20                  25                  30

Met Leu Val Ala Gly Gly Ile Val Ala Gly Ile Phe Leu Ile Phe Ile
        35                  40                  45

Glu Ile Ala Tyr Lys Arg His Lys Asp Ala Arg Arg Lys Gln Met Gln
    50                  55                  60

Leu Ala Phe Ala Ala Val Asn Val Trp Arg Lys Asn Leu Gln Asp Arg
65                  70                  75                  80

Lys Ser Gly Arg Ala Glu Pro Asp Pro Lys Lys Lys Ala Thr Phe Arg
                85                  90                  95

Ala Ile Thr Ser Thr Leu Ala Ser Ser Phe Lys Arg Arg Arg Ser Ser
            100                 105                 110

Lys Asp Thr Leu Ala Arg Asp Cys Leu Gln Pro Cys Pro Ala Pro Trp
        115                 120                 125

Ala Arg Glu Ser Ala Thr Arg Pro Pro Pro Ser Leu Arg Val Arg
    130                 135                 140

Asp Arg Pro Ala Thr Leu Tyr Arg Thr Ser Thr Pro Arg Ala Arg Ala
145                 150                 155                 160

Arg Ala Phe Pro Val Arg Ser Arg Ala Leu Pro Leu Arg Pro Gln Gly
                165                 170                 175

Ala Gly Ala His Arg Pro Thr Pro Thr Ser Arg Cys Met Gln Trp
            180                 185                 190
```

(2) INFORMATION FOR SEQ ID NO:19:

(i) SEQUENCE CHARACTERISTICS:
        (A) LENGTH: 3935 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..3030

(xi) SEQUENCE DESCRIPTION: SEQ ID NO:19:

-continued

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                         Met Ser Thr Met Arg Leu Leu Thr Leu Ala
                          1               5                    10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
            30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                95                  100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG      867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC      915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA      963
Ile Ile Leu Ser Ala Ser Glu Asp Asp Ala Ala Thr Val Tyr Arg Ala
    220                 225                 230

GCC GCG ATG CTG AAC ATG ACG GGC TCC GGG TAC GTG TGG CTG GTC GGC     1011
Ala Ala Met Leu Asn Met Thr Gly Ser Gly Tyr Val Trp Leu Val Gly
235                 240                 245                 250

GAG CGC GAG ATC TCG GGG AAC GCC CTG CGC TAC GCC CCA GAC GGC ATC     1059
Glu Arg Glu Ile Ser Gly Asn Ala Leu Arg Tyr Ala Pro Asp Gly Ile
                255                 260                 265

CTC GGG CTG CAG CTC ATC AAC GGC AAG AAC GAG TCG GCC CAC ATC AGC     1107
Leu Gly Leu Gln Leu Ile Asn Gly Lys Asn Glu Ser Ala His Ile Ser
```

```
                    270                 275                 280
GAC GCC GTG GGC GTG GTG GCC CAG GCC GTG CAC GAG CTC CTC GAG AAG    1155
Asp Ala Val Gly Val Val Ala Gln Ala Val His Glu Leu Leu Glu Lys
        285                 290                 295

GAG AAC ATC ACC GAC CCG CCG CGG GGC TGC GTG GGC AAC ACC AAC ATC    1203
Glu Asn Ile Thr Asp Pro Pro Arg Gly Cys Val Gly Asn Thr Asn Ile
    300                 305                 310

TGG AAG ACC GGG CCG CTC TTC AAG AGA GTG CTG ATG TCT TCC AAG TAT    1251
Trp Lys Thr Gly Pro Leu Phe Lys Arg Val Leu Met Ser Ser Lys Tyr
315                 320                 325                 330

GCG GAT GGG GTG ACT GGT CGC GTG GAG TTC AAT GAG GAT GGG GAC CGG    1299
Ala Asp Gly Val Thr Gly Arg Val Glu Phe Asn Glu Asp Gly Asp Arg
                335                 340                 345

AAG TTC GCC AAC TAC AGC ATC ATG AAC CTG CAG AAC CGC AAG CTG GTG    1347
Lys Phe Ala Asn Tyr Ser Ile Met Asn Leu Gln Asn Arg Lys Leu Val
            350                 355                 360

CAA GTG GGC ATC TAC AAT GGC ACC CAC GTC ATC CCT AAT GAC AGG AAG    1395
Gln Val Gly Ile Tyr Asn Gly Thr His Val Ile Pro Asn Asp Arg Lys
        365                 370                 375

ATC ATC TGG CCA GGC GGA GAG ACA GAG AAG CCT CGA GGG TAC CAG ATG    1443
Ile Ile Trp Pro Gly Gly Glu Thr Glu Lys Pro Arg Gly Tyr Gln Met
    380                 385                 390

TCC ACC AGA CTG AAG ATT GTG ACG ATC CAC CAG GAG CCC TTC GTG TAC    1491
Ser Thr Arg Leu Lys Ile Val Thr Ile His Gln Glu Pro Phe Val Tyr
395                 400                 405                 410

GTC AAG CCC ACG CTG AGT GAT GGG ACA TGC AAG GAG GAG TTC ACA GTC    1539
Val Lys Pro Thr Leu Ser Asp Gly Thr Cys Lys Glu Glu Phe Thr Val
                415                 420                 425

AAC GGC GAC CCA GTC AAG AAG GTG ATC TGC ACC GGG CCC AAC GAC ACG    1587
Asn Gly Asp Pro Val Lys Lys Val Ile Cys Thr Gly Pro Asn Asp Thr
            430                 435                 440

TCG CCG GGC AGC CCC CGC CAC ACG GTG CCT CAG TGT TGC TAC GGC TTT    1635
Ser Pro Gly Ser Pro Arg His Thr Val Pro Gln Cys Cys Tyr Gly Phe
        445                 450                 455

TGC ATC GAC CTC CTC ATC AAG CTG GCA CGG ACC ATG AAC TTC ACC TAC    1683
Cys Ile Asp Leu Leu Ile Lys Leu Ala Arg Thr Met Asn Phe Thr Tyr
    460                 465                 470

GAG GTG CAC CTG GTG GCA GAT GGC AAG TTC GGC ACA CAG GAG CGG GTG    1731
Glu Val His Leu Val Ala Asp Gly Lys Phe Gly Thr Gln Glu Arg Val
475                 480                 485                 490

AAC AAC AGC AAC AAG AAG GAG TGG AAT GGG ATG ATG GGC GAG CTG CTC    1779
Asn Asn Ser Asn Lys Lys Glu Trp Asn Gly Met Met Gly Glu Leu Leu
                495                 500                 505

AGC GGG CAG GCA GAC ATG ATC GTG GCG CCG CTA ACC ATA AAC AAC GAG    1827
Ser Gly Gln Ala Asp Met Ile Val Ala Pro Leu Thr Ile Asn Asn Glu
            510                 515                 520

CGC GCG CAG TAC ATC GAG TTT TCC AAG CCC TTC AAG TAC CAG GGC CTG    1875
Arg Ala Gln Tyr Ile Glu Phe Ser Lys Pro Phe Lys Tyr Gln Gly Leu
        525                 530                 535

ACT ATT CTG GTC AAG AAG GAG ATT CCC CGG AGC ACG CTG GAC TCG TTC    1923
Thr Ile Leu Val Lys Lys Glu Ile Pro Arg Ser Thr Leu Asp Ser Phe
    540                 545                 550

ATG CAG CCG TTC CAG AGC ACA CTG TGG CTG CTG GTG GGG CTG TCG GTG    1971
Met Gln Pro Phe Gln Ser Thr Leu Trp Leu Leu Val Gly Leu Ser Val
555                 560                 565                 570

CAC GTG GTG GCC GTG ATG CTG TAC CTG CTG GAC CGC TTC AGC CCC TTC    2019
His Val Val Ala Val Met Leu Tyr Leu Leu Asp Arg Phe Ser Pro Phe
                575                 580                 585

GGC CGG TTC AAG GTG AAC AGC GAG GAG GAG GAG GAG GAC GCA CTG ACC    2067
```

```
                                                          -continued

Gly Arg Phe Lys Val Asn Ser Glu Glu Glu Glu Asp Ala Leu Thr
            590                 595                 600

CTG TCC TCG GCC ATG TGG TTC TCC TGG GGC GTC CTG CTC AAC TCC GGC    2115
Leu Ser Ser Ala Met Trp Phe Ser Trp Gly Val Leu Leu Asn Ser Gly
            605                 610                 615

ATC GGG GAA GGC GCC CCC AGA AGC TTC TCA GCG CGC ATC CTG GGC ATG    2163
Ile Gly Glu Gly Ala Pro Arg Ser Phe Ser Ala Arg Ile Leu Gly Met
620                 625                 630

GTG TGG GCC GGC TTT GCC ATG ATC ATC GTG GCC TCC TAC ACC GCC AAC    2211
Val Trp Ala Gly Phe Ala Met Ile Ile Val Ala Ser Tyr Thr Ala Asn
635                 640                 645                 650

CTG GCG GCC TTC CTG GTG CTG GAC CGG CCG GAG GAG CGC ATC ACG GGC    2259
Leu Ala Ala Phe Leu Val Leu Asp Arg Pro Glu Glu Arg Ile Thr Gly
                655                 660                 665

ATC AAC GAC CCT CGG CTG AGG AAC CCC TCG GAC AAG TTT ATC TAC GCC    2307
Ile Asn Asp Pro Arg Leu Arg Asn Pro Ser Asp Lys Phe Ile Tyr Ala
                670                 675                 680

ACG GTG AAG CAG AGC TCC GTG GAT ATC TAC TTC CGG CGC CAG GTG GAG    2355
Thr Val Lys Gln Ser Ser Val Asp Ile Tyr Phe Arg Arg Gln Val Glu
            685                 690                 695

CTG AGC ACC ATG TAC CGG CAT ATG GAG AAG CAC AAC TAC GAG AGT GCG    2403
Leu Ser Thr Met Tyr Arg His Met Glu Lys His Asn Tyr Glu Ser Ala
            700                 705                 710

GCG GAG GCC ATC CAG GCC GTG AGA GAC AAC AAG CTG CAT GCC TTC ATC    2451
Ala Glu Ala Ile Gln Ala Val Arg Asp Asn Lys Leu His Ala Phe Ile
715                 720                 725                 730

TGG GAC TCG GCG GTG CTG GAG TTC GAG GCC TCG CAG AAG TGC GAC CTG    2499
Trp Asp Ser Ala Val Leu Glu Phe Glu Ala Ser Gln Lys Cys Asp Leu
                735                 740                 745

GTG ACG ACT GGA GAG CTG TTT TTC CGC TCG GGC TTC GGC ATA GGC ATG    2547
Val Thr Thr Gly Glu Leu Phe Phe Arg Ser Gly Phe Gly Ile Gly Met
                750                 755                 760

CGC AAA GAC AGC CCC TGG AAG CAG AAC GTC TCC CTG TCC ATC CTC AAG    2595
Arg Lys Asp Ser Pro Trp Lys Gln Asn Val Ser Leu Ser Ile Leu Lys
            765                 770                 775

TCC CAC GAG AAT GGC TTC ATG GAA GAC CTG GAC AAG ACG TGG GTT CGG    2643
Ser His Glu Asn Gly Phe Met Glu Asp Leu Asp Lys Thr Trp Val Arg
            780                 785                 790

TAT CAG GAA TGT GAC TCG CGC AGC AAC GCC CCT GCG ACC CTT ACT TTT    2691
Tyr Gln Glu Cys Asp Ser Arg Ser Asn Ala Pro Ala Thr Leu Thr Phe
795                 800                 805                 810

GAG AAC ATG GCC GGG GTC TTC ATG CTG GTA GCT GGG GGC ATC GTG GCC    2739
Glu Asn Met Ala Gly Val Phe Met Leu Val Ala Gly Gly Ile Val Ala
                815                 820                 825

GGG ATC TTC CTG ATT TTC ATC GAG ATT GCC TAC AAG CGG CAC AAG GAT    2787
Gly Ile Phe Leu Ile Phe Ile Glu Ile Ala Tyr Lys Arg His Lys Asp
                830                 835                 840

GCT CGC CGG AAG CAG ATG CAG CTG GCC TTT GCC GCC GTT AAC GTG TGG    2835
Ala Arg Arg Lys Gln Met Gln Leu Ala Phe Ala Ala Val Asn Val Trp
            845                 850                 855

CGG AAG AAC CTG CAG GAT AGA AAG AGT GGT AGA GCA GAG CCT GAC CCT    2883
Arg Lys Asn Leu Gln Asp Arg Lys Ser Gly Arg Ala Glu Pro Asp Pro
            860                 865                 870

AAA AAG AAA GCC ACA TTT AGG GCT ATC ACC TCC ACC CTG GCT TCC AGC    2931
Lys Lys Lys Ala Thr Phe Arg Ala Ile Thr Ser Thr Leu Ala Ser Ser
875                 880                 885                 890

TTC AAG AGG CGT AGG TCC TCC AAA GAC ACG CAG TAC CAT CCC ACT GAT    2979
Phe Lys Arg Arg Arg Ser Ser Lys Asp Thr Gln Tyr His Pro Thr Asp
                895                 900                 905
```

```
ATC ACG GGC CCG CTC AAC CTC TCA GAT CCC TCG GTC AGC ACC GTG GTG    3027
Ile Thr Gly Pro Leu Asn Leu Ser Asp Pro Ser Val Ser Thr Val Val
            910                 915                 920

TGAGGCCCCC GGAGGCGCCC ACCTGCCCAG TTAGCCCGGC CAAGGACACT GATGGGTCCT   3087

GCTGCTCGGG AAGGCCTGAG GGAAGCCCAC CCGCCCCAGA GACTGCCCAC CCTGGGCCTC   3147

CCGTCCGTCC GCCCGCCCAC CCCGCTGCCT GGCGGGCAGC CCCTGCTGGA CCAAGGTGCG   3207

GACCGGAGCG GCTGAGGACG GGCAGAGCT GAGTCGGCTG GGCAGGGCCG CAGGGCGCTC    3267

CGGCAGAGGC AGGCCCCTGG GGTCTCTGAG CAGTGGGGAG CGGGGGCTAA CTGCCCCCAG   3327

GCGGAGGGGC TTGGAGCAGA GACGGCAGCC CCATCCTTCC CGCAGCACCA GCCTGAGCCA   3387

CAGTGGGGCC CATGGCCCCA GCTGGCTGGG TCGCCCCTCC TCGGGCGCCT GCGCTCCTCT   3447

GCAGCCTGAG CTCCACCCTC CCCTCTTCTT GCGGCACCGC CCACCAAACA CCCCGTCTGC   3507

CCCTTGACGC CACACGCCGG GGCTGGCGCT GCCCTCCCCC ACGGCCGTCC CTGACTTCCC   3567

AGCTGGCAGC GCCTCCCGCC GCCTCGGGCC GCCTCCTCCA GAATCGAGAG GGCTGAGCCC   3627

CTCCTCTCCT CGTCCGGCCT GCAGCACAGA AGGGGCCTC CCCGGGGGTC CCCGGACGCT    3687

GGCTCGGGAC TGTCTTCAAC CCTGCCCTGC ACCTTGGGCA CGGGAGAGCG CCACCCGCCC   3747

GCCCCCGCCC TCGCTCCGGG TGCGTGACCG GCCCGCCACC TTGTACAGAA CCAGCACTCC   3807

CAGGGCCCGA GCGCGTGCCT TCCCCGTGCG CAGCCGCGCT CTGCCCCTCC GTCCCCAGGG   3867

TGCAGGCGCG CACCGCCCAA CCCCCACCTC CCGGTGTATG CAGTGGTGAT GCCTAAAGGA   3927

ATGTCACG                                                            3935
```

(2) INFORMATION FOR SEQ ID NO:20:

(i) SEQUENCE CHARACTERISTICS:
        (A) LENGTH: 922 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
 65                 70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
```

-continued

```
                    165                 170                 175
Gln Lys Arg Leu Glu Thr Leu Leu Glu Glu Arg Ser Lys Ala Glu
                180                 185                 190

Lys Val Leu Gln Phe Asp Pro Gly Thr Lys Asn Val Thr Ala Leu Leu
            195                 200                 205

Met Glu Ala Lys Glu Leu Glu Ala Arg Val Ile Ile Leu Ser Ala Ser
210                 215                 220

Glu Asp Ala Ala Thr Val Tyr Arg Ala Ala Met Leu Asn Met
225                 230                 235                 240

Thr Gly Ser Gly Tyr Val Trp Leu Val Gly Arg Glu Ile Ser Gly
                245                 250                 255

Asn Ala Leu Arg Tyr Ala Pro Asp Gly Ile Leu Gly Leu Gln Leu Ile
                260                 265                 270

Asn Gly Lys Asn Glu Ser Ala His Ile Ser Asp Ala Val Gly Val Val
            275                 280                 285

Ala Gln Ala Val His Glu Leu Leu Glu Lys Glu Asn Ile Thr Asp Pro
290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
                340                 345                 350

Ile Met Asn Leu Gln Asn Arg Lys Leu Val Gln Val Gly Ile Tyr Asn
                355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
            435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
            515                 520                 525

Phe Ser Lys Pro Phe Lys Tyr Gln Gly Leu Thr Ile Leu Val Lys Lys
            530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
                580                 585                 590
```

```
Ser Glu Glu Glu Glu Asp Ala Leu Thr Leu Ser Ser Ala Met Trp
    595                 600                 605

Phe Ser Trp Gly Val Leu Leu Asn Ser Ile Gly Glu Gly Ala Pro
610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
                660                 665                 670

Arg Asn Pro Ser Asp Lys Phe Ile Tyr Ala Thr Val Lys Gln Ser Ser
                675                 680                 685

Val Asp Ile Tyr Phe Arg Arg Gln Val Glu Leu Ser Thr Met Tyr Arg
690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
                740                 745                 750

Phe Phe Arg Ser Gly Phe Gly Ile Gly Met Arg Lys Asp Ser Pro Trp
                755                 760                 765

Lys Gln Asn Val Ser Leu Ser Ile Leu Lys Ser His Glu Asn Gly Phe
770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
                835                 840                 845

Gln Leu Ala Phe Ala Ala Val Asn Val Trp Arg Lys Asn Leu Gln Asp
850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Gln Tyr His Pro Thr Asp Ile Thr Gly Pro Leu Asn
                900                 905                 910

Leu Ser Asp Pro Ser Val Ser Thr Val Val
                915                 920
```

(2) INFORMATION FOR SEQ ID NO:21:

(i) SEQUENCE CHARACTERISTICS:
        (A) LENGTH: 3211 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..3192

(xi) SEQUENCE DESCRIPTION: SEQ ID NO:21:

```
CAAGCCGGGC GTTCGGAGCT GTGCCCGGCC CCGCTTCAGC ACCGCGGACA GCGCCGGCCG        60

CGTGGGGCTG AGCGCCGAGC CCCCGCGCAC GCTTCAGCCC CCCTTCCCTC GGCCGACGTC       120

CCGGGACCGC CGCTCCGGGG GAGACGTGGC GTCCGCAGCC CGCGGGGCCG GGCGAGCGCA       180

GGACGGCCCG GAAGCCCCGC GGGGGATGCG CCGAGGGCCC CGCGTTCGCG CCGCGCAGAG       240

CCAGGCCCGC GGCCCGAGCC C ATG AGC ACC ATG CGC CTG CTG ACG CTC GCC        291
                         Met Ser Thr Met Arg Leu Leu Thr Leu Ala
                           1               5                  10

CTG CTG TTC TCC TGC TCC GTC GCC CGT GCC GCG TGC GAC CCC AAG ATC        339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC        387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT        435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG        483
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC        531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT        579
Leu Val Ser His Pro Pro Thr Pro Asn Asp His Phe Thr Pro Thr Pro
                     95                 100                 105

GTC TCC TAC ACA GCC GGC TTC TAC CGC ATA CCC GTG CTG GGG CTG ACC        627
Val Ser Tyr Thr Ala Gly Phe Tyr Arg Ile Pro Val Leu Gly Leu Thr
                110                 115                 120

ACC CGC ATG TCC ATC TAC TCG GAC AAG AGC ATC CAC CTG AGC TTC CTG        675
Thr Arg Met Ser Ile Tyr Ser Asp Lys Ser Ile His Leu Ser Phe Leu
            125                 130                 135

CGC ACC GTG CCG CCC TAC TCC CAC CAG TCC AGC GTG TGG TTT GAG ATG        723
Arg Thr Val Pro Pro Tyr Ser His Gln Ser Ser Val Trp Phe Glu Met
        140                 145                 150

ATG CGT GTC TAC AGC TGG AAC CAC ATC ATC CTG CTG GTC AGC GAC GAC        771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG        819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG        867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC        915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA        963
Ile Ile Leu Ser Ala Ser Glu Asp Asp Ala Ala Thr Val Tyr Arg Ala
    220                 225                 230

GCC GCG ATG CTG AAC ATG ACG GGC TCC GGG TAC GTG TGG CTG GTC GGC       1011
Ala Ala Met Leu Asn Met Thr Gly Ser Gly Tyr Val Trp Leu Val Gly
235                 240                 245                 250

GAG CGC GAG ATC TCG GGG AAC GCC CTG CGC TAC GCC CCA GAC GGC ATC       1059
Glu Arg Glu Ile Ser Gly Asn Ala Leu Arg Tyr Ala Pro Asp Gly Ile
                255                 260                 265

CTC GGG CTG CAG CTC ATC AAC GGC AAG AAC GAG TCG GCC CAC ATC AGC       1107
```

```
                                                                    -continued Leu Gly Leu Gln Leu Ile Asn Gly Lys Asn Glu Ser Ala His Ile Ser
            270                 275                 280

GAC GCC GTG GGC GTG GTG GCC CAG GCC GTG CAC GAG CTC CTC GAG AAG       1155
Asp Ala Val Gly Val Val Ala Gln Ala Val His Glu Leu Leu Glu Lys
            285                 290                 295

GAG AAC ATC ACC GAC CCG CCG CGG GGC TGC GTG GGC AAC ACC AAC ATC       1203
Glu Asn Ile Thr Asp Pro Pro Arg Gly Cys Val Gly Asn Thr Asn Ile
300                 305                 310

TGG AAG ACC GGG CCG CTC TTC AAG AGA GTG CTG ATG TCT TCC AAG TAT       1251
Trp Lys Thr Gly Pro Leu Phe Lys Arg Val Leu Met Ser Ser Lys Tyr
315                 320                 325                 330

GCG GAT GGG GTG ACT GGT CGC GTG GAG TTC AAT GAG GAT GGG GAC CGG       1299
Ala Asp Gly Val Thr Gly Arg Val Glu Phe Asn Glu Asp Gly Asp Arg
            335                 340                 345

AAG TTC GCC AAC TAC AGC ATC ATG AAC CTG CAG AAC CGC AAG CTG GTG       1347
Lys Phe Ala Asn Tyr Ser Ile Met Asn Leu Gln Asn Arg Lys Leu Val
            350                 355                 360

CAA GTG GGC ATC TAC AAT GGC ACC CAC GTC ATC CCT AAT GAC AGG AAG       1395
Gln Val Gly Ile Tyr Asn Gly Thr His Val Ile Pro Asn Asp Arg Lys
            365                 370                 375

ATC ATC TGG CCA GGC GGA GAG ACA GAG AAG CCT CGA GGG TAC CAG ATG       1443
Ile Ile Trp Pro Gly Gly Glu Thr Glu Lys Pro Arg Gly Tyr Gln Met
            380                 385                 390

TCC ACC AGA CTG AAG ATT GTG ACG ATC CAC CAG GAG CCC TTC GTG TAC       1491
Ser Thr Arg Leu Lys Ile Val Thr Ile His Gln Glu Pro Phe Val Tyr
395                 400                 405                 410

GTC AAG CCC ACG CTG AGT GAT GGG ACA TGC AAG GAG GAG TTC ACA GTC       1539
Val Lys Pro Thr Leu Ser Asp Gly Thr Cys Lys Glu Glu Phe Thr Val
            415                 420                 425

AAC GGC GAC CCA GTC AAG AAG GTG ATC TGC ACC GGG CCC AAC GAC ACG       1587
Asn Gly Asp Pro Val Lys Lys Val Ile Cys Thr Gly Pro Asn Asp Thr
            430                 435                 440

TCG CCG GGC AGC CCC CGC CAC ACG GTG CCT CAG TGT TGC TAC GGC TTT       1635
Ser Pro Gly Ser Pro Arg His Thr Val Pro Gln Cys Cys Tyr Gly Phe
            445                 450                 455

TGC ATC GAC CTG CTC ATC AAG CTG GCA CGG ACC ATG AAC TTC ACC TAC       1683
Cys Ile Asp Leu Leu Ile Lys Leu Ala Arg Thr Met Asn Phe Thr Tyr
            460                 465                 470

GAG GTG CAC CTG GTG GCA GAT GGC AAG TTC GGC ACA CAG GAG CGG GTG       1731
Glu Val His Leu Val Ala Asp Gly Lys Phe Gly Thr Gln Glu Arg Val
475                 480                 485                 490

AAC AAC AGC AAC AAG AAG GAG TGG AAT GGG ATG ATG GGC GAG CTG CTC       1779
Asn Asn Ser Asn Lys Lys Glu Trp Asn Gly Met Met Gly Glu Leu Leu
            495                 500                 505

AGC GGG CAG GCA GAC ATG ATC GTG GCG CCG CTA ACC ATA AAC AAC GAG       1827
Ser Gly Gln Ala Asp Met Ile Val Ala Pro Leu Thr Ile Asn Asn Glu
            510                 515                 520

CGC GCG CAG TAC ATC GAG TTT TCC AAG CCC TTC AAG TAC CAG GGC CTG       1875
Arg Ala Gln Tyr Ile Glu Phe Ser Lys Pro Phe Lys Tyr Gln Gly Leu
            525                 530                 535

ACT ATT CTG GTC AAG AAG GAG ATT CCC CGG AGC ACG CTG GAC TCG TTC       1923
Thr Ile Leu Val Lys Lys Glu Ile Pro Arg Ser Thr Leu Asp Ser Phe
            540                 545                 550

ATG CAG CCG TTC CAG AGC ACA CTG TGG CTG CTG GTG GGG CTG TCG GTG       1971
Met Gln Pro Phe Gln Ser Thr Leu Trp Leu Leu Val Gly Leu Ser Val
555                 560                 565                 570

CAC GTG GTG GCC GTG ATG CTG TAC CTG CTG GAC CGC TTC AGC CCC TTC       2019
His Val Val Ala Val Met Leu Tyr Leu Leu Asp Arg Phe Ser Pro Phe
            575                 580                 585
```

```
GGC CGG TTC AAG GTG AAC AGC GAG GAG GAG GAG GAG GAC GCA CTG ACC    2067
Gly Arg Phe Lys Val Asn Ser Glu Glu Glu Glu Glu Asp Ala Leu Thr
            590             595             600

CTG TCC TCG GCC ATG TGG TTC TCC TGG GGC GTC CTG CTC AAC TCC GGC    2115
Leu Ser Ser Ala Met Trp Phe Ser Trp Gly Val Leu Leu Asn Ser Gly
605             610             615

ATC GGG GAA GGC GCC CCC AGA AGC TTC TCA GCG CGC ATC CTG GGC ATG    2163
Ile Gly Glu Gly Ala Pro Arg Ser Phe Ser Ala Arg Ile Leu Gly Met
    620             625             630

GTG TGG GCC GGC TTT GCC ATG ATC ATC GTG GCC TCC TAC ACC GCC AAC    2211
Val Trp Ala Gly Phe Ala Met Ile Ile Val Ala Ser Tyr Thr Ala Asn
635             640             645             650

CTG GCG GCC TTC CTG GTG CTG GAC CGG CCG GAG GAG CGC ATC ACG GGC    2259
Leu Ala Ala Phe Leu Val Leu Asp Arg Pro Glu Glu Arg Ile Thr Gly
                655             660             665

ATC AAC GAC CCT CGG CTG AGG AAC CCC TCG GAC AAG TTT ATC TAC GCC    2307
Ile Asn Asp Pro Arg Leu Arg Asn Pro Ser Asp Lys Phe Ile Tyr Ala
            670             675             680

ACG GTG AAG CAG AGC TCC GTG GAT ATC TAC TTC CGG CGC CAG GTG GAG    2355
Thr Val Lys Gln Ser Ser Val Asp Ile Tyr Phe Arg Arg Gln Val Glu
                685             690             695

CTG AGC ACC ATG TAC CGG CAT ATG GAG AAG CAC AAC TAC GAG AGT GCG    2403
Leu Ser Thr Met Tyr Arg His Met Glu Lys His Asn Tyr Glu Ser Ala
700             705             710

GCG GAG GCC ATC CAG GCC GTG AGA GAC AAC AAG CTG CAT GCC TTC ATC    2451
Ala Glu Ala Ile Gln Ala Val Arg Asp Asn Lys Leu His Ala Phe Ile
715             720             725             730

TGG GAC TCG GCG GTG CTG GAG TTC GAG GCC TCG CAG AAG TGC GAC CTG    2499
Trp Asp Ser Ala Val Leu Glu Phe Glu Ala Ser Gln Lys Cys Asp Leu
                735             740             745

GTG ACG ACT GGA GAG CTG TTT TTC CGC TCG GGC TTC GGC ATA GGC ATG    2547
Val Thr Thr Gly Glu Leu Phe Phe Arg Ser Gly Phe Gly Ile Gly Met
            750             755             760

CGC AAA GAC AGC CCC TGG AAG CAG AAC GTC TCC CTG TCC ATC CTC AAG    2595
Arg Lys Asp Ser Pro Trp Lys Gln Asn Val Ser Leu Ser Ile Leu Lys
            765             770             775

TCC CAC GAG AAT GGC TTC ATG GAA GAC CTG GAC AAG ACG TGG GTT CGG    2643
Ser His Glu Asn Gly Phe Met Glu Asp Leu Asp Lys Thr Trp Val Arg
780             785             790

TAT CAG GAA TGT GAC TCG CGC AGC AAC GCC CCT GCG ACC CTT ACT TTT    2691
Tyr Gln Glu Cys Asp Ser Arg Ser Asn Ala Pro Ala Thr Leu Thr Phe
795             800             805             810

GAG AAC ATG GCC GGG GTC TTC ATG CTG GTA GCT GGG GGC ATC GTG GCC    2739
Glu Asn Met Ala Gly Val Phe Met Leu Val Ala Gly Gly Ile Val Ala
                815             820             825

GGG ATC TTC CTG ATT TTC ATC GAG ATT GCC TAC AAG CGG CAC AAG GAT    2787
Gly Ile Phe Leu Ile Phe Ile Glu Ile Ala Tyr Lys Arg His Lys Asp
            830             835             840

GCT CGC CGG AAG CAG ATG CAG CTG GCC TTT GCC GCC GTT AAC GTG TGG    2835
Ala Arg Arg Lys Gln Met Gln Leu Ala Phe Ala Ala Val Asn Val Trp
        845             850             855

CGG AAG AAC CTG CAG GAT AGA AAG AGT GGT AGA GCA GAG CCT GAC CCT    2883
Arg Lys Asn Leu Gln Asp Arg Lys Ser Gly Arg Ala Glu Pro Asp Pro
860             865             870

AAA AAG AAA GCC ACA TTT AGG GCT ATC ACC TCC ACC CTG GCT TCC AGC    2931
Lys Lys Lys Ala Thr Phe Arg Ala Ile Thr Ser Thr Leu Ala Ser Ser
875             880             885             890

TTC AAG AGG CGT AGG TCC TCC AAA GAC ACG CTG GCT CGG GAC TGT CTT    2979
Phe Lys Arg Arg Arg Ser Ser Lys Asp Thr Leu Ala Arg Asp Cys Leu
                895             900             905
```

```
CAA CCC TGC CCT GCA CCT TGG GCA CGG GAG AGC GCC ACC CGC CCG CCC    3027
Gln Pro Cys Pro Ala Pro Trp Ala Arg Glu Ser Ala Thr Arg Pro Pro
        910                 915                 920

CCG CCC TCG CTC CGG GTG CGT GAC CGG CCC GCC ACC TTG TAC AGA ACC    3075
Pro Pro Ser Leu Arg Val Arg Asp Arg Pro Ala Thr Leu Tyr Arg Thr
            925                 930                 935

AGC ACT CCC AGG GCC CGA GCG CGT GCC TTC CCC GTG CGC AGC CGC GCT    3123
Ser Thr Pro Arg Ala Arg Ala Arg Ala Phe Pro Val Arg Ser Arg Ala
        940                 945                 950

CTG CCC CTC CGT CCC CAG GGT GCA GGC GCG CAC CGC CCA ACC CCC ACC    3171
Leu Pro Leu Arg Pro Gln Gly Ala Gly Ala His Arg Pro Thr Pro Thr
955                 960                 965                 970

TCC CGG TGT ATG CAG TGG TGATGCCTAA AGGAATGTCA CG                   3211
Ser Arg Cys Met Gln Trp
                975
```

(2) INFORMATION FOR SEQ ID NO:22:

(i) SEQUENCE CHARACTERISTICS:
        (A) LENGTH: 976 amino acids
        (B) TYPE: amino acid
        (D) TOPOLOGY: linear (ii) MOLECULE TYPE: protein (xi) SEQUENCE DESCRIPTION: SEQ ID NO:22:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
 65                 70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
        210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
```

-continued

```
                245                 250                 255
Asn Ala Leu Arg Tyr Ala Pro Asp Gly Ile Leu Gly Leu Gln Leu Ile
                260                 265                 270
Asn Gly Lys Asn Glu Ser Ala His Ile Ser Asp Ala Val Gly Val Val
                275                 280                 285
Ala Gln Ala Val His Glu Leu Leu Glu Lys Glu Asn Ile Thr Asp Pro
                290                 295                 300
Pro Arg Gly Cys Val Gly Asn Thr Asn Ile Trp Lys Thr Gly Pro Leu
305                 310                 315                 320
Phe Lys Arg Val Leu Met Ser Ser Lys Tyr Ala Asp Gly Val Thr Gly
                    325                 330                 335
Arg Val Glu Phe Asn Glu Asp Gly Asp Arg Lys Phe Ala Asn Tyr Ser
                340                 345                 350
Ile Met Asn Leu Gln Asn Arg Lys Leu Val Gln Val Gly Ile Tyr Asn
                355                 360                 365
Gly Thr His Val Ile Pro Asn Asp Arg Lys Ile Ile Trp Pro Gly Gly
    370                 375                 380
Glu Thr Glu Lys Pro Arg Gly Tyr Gln Met Ser Thr Arg Leu Lys Ile
385                 390                 395                 400
Val Thr Ile His Gln Glu Pro Phe Val Tyr Val Lys Pro Thr Leu Ser
                405                 410                 415
Asp Gly Thr Cys Lys Glu Glu Phe Thr Val Asn Gly Asp Pro Val Lys
                420                 425                 430
Lys Val Ile Cys Thr Gly Pro Asn Asp Thr Ser Pro Gly Ser Pro Arg
                435                 440                 445
His Thr Val Pro Gln Cys Cys Tyr Gly Phe Cys Ile Asp Leu Leu Ile
    450                 455                 460
Lys Leu Ala Arg Thr Met Asn Phe Thr Tyr Glu Val His Leu Val Ala
465                 470                 475                 480
Asp Gly Lys Phe Gly Thr Gln Glu Arg Val Asn Asn Ser Asn Lys Lys
                485                 490                 495
Glu Trp Asn Gly Met Met Gly Glu Leu Leu Ser Gly Gln Ala Asp Met
                500                 505                 510
Ile Val Ala Pro Leu Thr Ile Asn Asn Glu Arg Ala Gln Tyr Ile Glu
                515                 520                 525
Phe Ser Lys Pro Phe Lys Tyr Gln Gly Leu Thr Ile Leu Val Lys Lys
                530                 535                 540
Glu Ile Pro Arg Ser Thr Leu Asp Ser Phe Met Gln Pro Phe Gln Ser
545                 550                 555                 560
Thr Leu Trp Leu Leu Val Gly Leu Ser Val His Val Val Ala Val Met
                    565                 570                 575
Leu Tyr Leu Leu Asp Arg Phe Ser Pro Phe Gly Arg Phe Lys Val Asn
                580                 585                 590
Ser Glu Glu Glu Glu Asp Ala Leu Thr Leu Ser Ser Ala Met Trp
                595                 600                 605
Phe Ser Trp Gly Val Leu Leu Asn Ser Gly Ile Gly Glu Gly Ala Pro
    610                 615                 620
Arg Ser Phe Ser Ala Arg Ile Leu Gly Met Val Trp Ala Gly Phe Ala
625                 630                 635                 640
Met Ile Ile Val Ala Ser Tyr Thr Ala Asn Leu Ala Ala Phe Leu Val
                    645                 650                 655
Leu Asp Arg Pro Glu Glu Arg Ile Thr Gly Ile Asn Asp Pro Arg Leu
                660                 665                 670
```

```
Arg Asn Pro Ser Asp Lys Phe Ile Tyr Ala Thr Val Lys Gln Ser Ser
            675                 680                 685

Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Leu Ala Arg Asp Cys Leu Gln Pro Cys Pro Ala Pro
            900                 905                 910

Trp Ala Arg Glu Ser Ala Thr Arg Pro Pro Pro Ser Leu Arg Val
        915                 920                 925

Arg Asp Arg Pro Ala Thr Leu Tyr Arg Thr Ser Thr Pro Arg Ala Arg
930                 935                 940

Ala Arg Ala Phe Pro Val Arg Ser Arg Ala Leu Pro Leu Arg Pro Gln
945                 950                 955                 960

Gly Ala Gly Ala His Arg Pro Thr Pro Thr Ser Arg Cys Met Gln Trp
                965                 970                 975

(2) INFORMATION FOR SEQ ID NO:23:

(i) SEQUENCE CHARACTERISTICS:
        (A) LENGTH: 4361 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..3141

(xi) SEQUENCE DESCRIPTION: SEQ ID NO:23:

CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120
```

```
CCGGGACCGC CGCTCCGGGG GAGACGTGGC GTCCGCAGCC CGCGGGGCCG GGCGAGCGCA      180

GGACGGCCCG GAAGCCCCGC GGGGGATGCG CCGAGGGCCC CGCGTTCGCG CCGCGCAGAG      240

CCAGGCCCGC GGCCCGAGCC C ATG AGC ACC ATG CGC CTG CTG ACG CTC GCC       291
                         Met Ser Thr Met Arg Leu Leu Thr Leu Ala
                          1               5                    10

CTG CTG TTC TCC TGC TCC GTC GCC CGT GCC GCG TGC GAC CCC AAG ATC       339
Leu Leu Phe Ser Cys Ser Val Ala Arg Ala Ala Cys Asp Pro Lys Ile
             15                  20                  25

GTC AAC ATT GGC GCG GTG CTG AGC ACG CGG AAG CAC GAG CAG ATG TTC       387
Val Asn Ile Gly Ala Val Leu Ser Thr Arg Lys His Glu Gln Met Phe
         30                  35                  40

CGC GAG GCC GTG AAC CAG GCC AAC AAG CGG CAC GGC TCC TGG AAG ATT       435
Arg Glu Ala Val Asn Gln Ala Asn Lys Arg His Gly Ser Trp Lys Ile
     45                  50                  55

CAG CTC AAT GCC ACC TCC GTC ACG CAC AAG CCC AAC GCC ATC CAG ATG       483
Gln Leu Asn Ala Thr Ser Val Thr His Lys Pro Asn Ala Ile Gln Met
 60                  65                  70

GCT CTG TCG GTG TGC GAG GAC CTC ATC TCC AGC CAG GTC TAC GCC ATC       531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT       579
Leu Val Ser His Pro Pro Thr Pro Asn Asp His Phe Thr Pro Thr Pro
                 95                  100                 105

GTC TCC TAC ACA GCC GGC TTC TAC CGC ATA CCC GTG CTG GGG CTG ACC       627
Val Ser Tyr Thr Ala Gly Phe Tyr Arg Ile Pro Val Leu Gly Leu Thr
             110                 115                 120

ACC CGC ATG TCC ATC TAC TCG GAC AAG AGC ATC CAC CTG AGC TTC CTG       675
Thr Arg Met Ser Ile Tyr Ser Asp Lys Ser Ile His Leu Ser Phe Leu
         125                 130                 135

CGC ACC GTG CCG CCC TAC TCC CAC CAG TCC AGC GTG TGG TTT GAG ATG       723
Arg Thr Val Pro Pro Tyr Ser His Gln Ser Ser Val Trp Phe Glu Met
     140                 145                 150

ATG CGT GTC TAC AGC TGG AAC CAC ATC ATC CTG CTG GTC AGC GAC GAC       771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG       819
His Glu Gly Arg Ala Ala Gln Lys Arg Leu Glu Thr Leu Leu Glu Glu
                 175                 180                 185

CGT GAG TCC AAG AGT AAA AAA AGG AAC TAT GAA AAC CTC GAC CAA CTG       867
Arg Glu Ser Lys Ser Lys Lys Arg Asn Tyr Glu Asn Leu Asp Gln Leu
             190                 195                 200

TCC TAT GAC AAC AAG CGC GGA CCC AAG GCA GAG AAG GTG CTG CAG TTT       915
Ser Tyr Asp Asn Lys Arg Gly Pro Lys Ala Glu Lys Val Leu Gln Phe
         205                 210                 215

GAC CCA GGG ACC AAG AAC GTG ACG GCC CTG CTG ATG GAG GCG AAA GAG       963
Asp Pro Gly Thr Lys Asn Val Thr Ala Leu Leu Met Glu Ala Lys Glu
     220                 225                 230

CTG GAG GCC CGG GTC ATC ATC CTT TCT GCC AGC GAG GAC GAT GCT GCC      1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC TCC GGG TAC      1059
Thr Val Tyr Arg Ala Ala Ala Met Leu Asn Met Thr Gly Ser Gly Tyr
                 255                 260                 265

GTG TGG CTG GTC GGC GAG CGC GAG ATC TCG GGG AAC GCC CTG CGC TAC      1107
Val Trp Leu Val Gly Glu Arg Glu Ile Ser Gly Asn Ala Leu Arg Tyr
             270                 275                 280

GCC CCA GAC GGC ATC CTC GGG CTG CAG CTC ATC AAC GGC AAG AAC GAG      1155
Ala Pro Asp Gly Ile Leu Gly Leu Gln Leu Ile Asn Gly Lys Asn Glu
         285                 290                 295
```

```
TCG GCC CAC ATC AGC GAC GCC GTG GGC GTG GTG GCC CAG GCC GTG CAC      1203
Ser Ala His Ile Ser Asp Ala Val Gly Val Val Ala Gln Ala Val His
    300                 305                 310

GAG CTC CTC GAG AAG GAG AAC ATC ACC GAC CCG CCG CGG GGC TGC GTG      1251
Glu Leu Leu Glu Lys Glu Asn Ile Thr Asp Pro Pro Arg Gly Cys Val
315                 320                 325                 330

GGC AAC ACC AAC ATC TGG AAG ACC GGG CCG CTC TTC AAG AGA GTG CTG      1299
Gly Asn Thr Asn Ile Trp Lys Thr Gly Pro Leu Phe Lys Arg Val Leu
                335                 340                 345

ATG TCT TCC AAG TAT GCG GAT GGG GTG ACT GGT CGC GTG GAG TTC AAT      1347
Met Ser Ser Lys Tyr Ala Asp Gly Val Thr Gly Arg Val Glu Phe Asn
        350                 355                 360

GAG GAT GGG GAC CGG AAG TTC GCC AAC TAC AGC ATC ATG AAC CTG CAG      1395
Glu Asp Gly Asp Arg Lys Phe Ala Asn Tyr Ser Ile Met Asn Leu Gln
            365                 370                 375

AAC CGC AAG CTG GTG CAA GTG GGC ATC TAC AAT GGC ACC CAC GTC ATC      1443
Asn Arg Lys Leu Val Gln Val Gly Ile Tyr Asn Gly Thr His Val Ile
        380                 385                 390

CCT AAT GAC AGG AAG ATC ATC TGG CCA GGC GGA GAG ACA GAG AAG CCT      1491
Pro Asn Asp Arg Lys Ile Ile Trp Pro Gly Gly Glu Thr Glu Lys Pro
395                 400                 405                 410

CGA GGG TAC CAG ATG TCC ACC AGA CTG AAG ATT GTG ACG ATC CAC CAG      1539
Arg Gly Tyr Gln Met Ser Thr Arg Leu Lys Ile Val Thr Ile His Gln
                415                 420                 425

GAG CCC TTC GTG TAC GTC AAG CCC ACG CTG AGT GAT GGG ACA TGC AAG      1587
Glu Pro Phe Val Tyr Val Lys Pro Thr Leu Ser Asp Gly Thr Cys Lys
            430                 435                 440

GAG GAG TTC ACA GTC AAC GGC GAC CCA GTC AAG AAG GTG ATC TGC ACC      1635
Glu Glu Phe Thr Val Asn Gly Asp Pro Val Lys Lys Val Ile Cys Thr
        445                 450                 455

GGG CCC AAC GAC ACG TCG CCG GGC AGC CCC CGC CAC ACG GTG CCT CAG      1683
Gly Pro Asn Asp Thr Ser Pro Gly Ser Pro Arg His Thr Val Pro Gln
460                 465                 470

TGT TGC TAC GGC TTT TGC ATC GAC CTG CTC ATC AAG CTG GCA CGG ACC      1731
Cys Cys Tyr Gly Phe Cys Ile Asp Leu Leu Ile Lys Leu Ala Arg Thr
475                 480                 485                 490

ATG AAC TTC ACC TAC GAG GTG CAC CTG GTG GCA GAT GGC AAG TTC GGC      1779
Met Asn Phe Thr Tyr Glu Val His Leu Val Ala Asp Gly Lys Phe Gly
                495                 500                 505

ACA CAG GAG CGG GTG AAC AAC AGC AAC AAG AAG GAG TGG AAT GGG ATG      1827
Thr Gln Glu Arg Val Asn Asn Ser Asn Lys Lys Glu Trp Asn Gly Met
            510                 515                 520

ATG GGC GAG CTG CTC AGC GGG CAG GCA GAC ATG ATC GTG GCG CCG CTA      1875
Met Gly Glu Leu Leu Ser Gly Gln Ala Asp Met Ile Val Ala Pro Leu
        525                 530                 535

ACC ATA AAC AAC GAG CGC GCG CAG TAC ATC GAG TTT TCC AAG CCC TTC      1923
Thr Ile Asn Asn Glu Arg Ala Gln Tyr Ile Glu Phe Ser Lys Pro Phe
540                 545                 550

AAG TAC CAG GGC CTG ACT ATT CTG GTC AAG AAG GAG ATT CCC CGG AGC      1971
Lys Tyr Gln Gly Leu Thr Ile Leu Val Lys Lys Glu Ile Pro Arg Ser
555                 560                 565                 570

ACG CTG GAC TCG TTC ATG CAG CCG TTC CAG AGC ACA CTG TGG CTG CTG      2019
Thr Leu Asp Ser Phe Met Gln Pro Phe Gln Ser Thr Leu Trp Leu Leu
        575                 580                 585

GTG GGG CTG TCG GTG CAC GTG GTG GCC GTG ATG CTG TAC CTG CTG GAC      2067
Val Gly Leu Ser Val His Val Val Ala Val Met Leu Tyr Leu Leu Asp
            590                 595                 600

CGC TTC AGC CCC TTC GGC CGG TTC AAG GTG AAC AGC GAG GAG GAG GAG      2115
Arg Phe Ser Pro Phe Gly Arg Phe Lys Val Asn Ser Glu Glu Glu Glu
```

-continued

```
           605                 610                 615
GAG GAC GCA CTG ACC CTG TCC TCG GCC ATG TGG TTC TCC TGG GGC GTC    2163
Glu Asp Ala Leu Thr Leu Ser Ser Ala Met Trp Phe Ser Trp Gly Val
        620                 625                 630

CTG CTC AAC TCC GGC ATC GGG GAA GGC GCC CCC AGA AGC TTC TCA GCG    2211
Leu Leu Asn Ser Gly Ile Gly Glu Gly Ala Pro Arg Ser Phe Ser Ala
635                 640                 645                 650

CGC ATC CTG GGC ATG GTG TGG GCC GGC TTT GCC ATG ATC ATC GTG GCC    2259
Arg Ile Leu Gly Met Val Trp Ala Gly Phe Ala Met Ile Ile Val Ala
                655                 660                 665

TCC TAC ACC GCC AAC CTG GCG GCC TTC CTG GTG CTG GAC CGG CCG GAG    2307
Ser Tyr Thr Ala Asn Leu Ala Ala Phe Leu Val Leu Asp Arg Pro Glu
        670                 675                 680

GAG CGC ATC ACG GGC ATC AAC GAC CCT CGG CTG AGG AAC CCC TCG GAC    2355
Glu Arg Ile Thr Gly Ile Asn Asp Pro Arg Leu Arg Asn Pro Ser Asp
                685                 690                 695

AAG TTT ATC TAC GCC ACG GTG AAG CAG AGC TCC GTG GAT ATC TAC TTC    2403
Lys Phe Ile Tyr Ala Thr Val Lys Gln Ser Ser Val Asp Ile Tyr Phe
        700                 705                 710

CGG CGC CAG GTG GAG CTG AGC ACC ATG TAC CGG CAT ATG GAG AAG CAC    2451
Arg Arg Gln Val Glu Leu Ser Thr Met Tyr Arg His Met Glu Lys His
715                 720                 725                 730

AAC TAC GAG AGT GCG GCG GAG GCC ATC CAG GCC GTG AGA GAC AAC AAG    2499
Asn Tyr Glu Ser Ala Ala Glu Ala Ile Gln Ala Val Arg Asp Asn Lys
                735                 740                 745

CTG CAT GCC TTC ATC TGG GAC TCG GCG GTG CTG GAG TTC GAG GCC TCG    2547
Leu His Ala Phe Ile Trp Asp Ser Ala Val Leu Glu Phe Glu Ala Ser
        750                 755                 760

CAG AAG TGC GAC CTG GTG ACG ACT GGA GAG CTG TTT TTC CGC TCG GGC    2595
Gln Lys Cys Asp Leu Val Thr Thr Gly Glu Leu Phe Phe Arg Ser Gly
                765                 770                 775

TTC GGC ATA GGC ATG CGC AAA GAC AGC CCC TGG AAG CAG AAC GTC TCC    2643
Phe Gly Ile Gly Met Arg Lys Asp Ser Pro Trp Lys Gln Asn Val Ser
780                 785                 790

CTG TCC ATC CTC AAG TCC CAC GAG AAT GGC TTC ATG GAA GAC CTG GAC    2691
Leu Ser Ile Leu Lys Ser His Glu Asn Gly Phe Met Glu Asp Leu Asp
795                 800                 805                 810

AAG ACG TGG GTT CGG TAT CAG GAA TGT GAC TCG CGC AGC AAC GCC CCT    2739
Lys Thr Trp Val Arg Tyr Gln Glu Cys Asp Ser Arg Ser Asn Ala Pro
                815                 820                 825

GCG ACC CTT ACT TTT GAG AAC ATG GCC GGG GTC TTC ATG CTG GTA GCT    2787
Ala Thr Leu Thr Phe Glu Asn Met Ala Gly Val Phe Met Leu Val Ala
        830                 835                 840

GGG GGC ATC GTG GCC GGG ATC TTC CTG ATT TTC ATC GAG ATT GCC TAC    2835
Gly Gly Ile Val Ala Gly Ile Phe Leu Ile Phe Ile Glu Ile Ala Tyr
        845                 850                 855

AAG CGG CAC AAG GAT GCT CGC CGG AAG CAG ATG CAG CTG GCC TTT GCC    2883
Lys Arg His Lys Asp Ala Arg Arg Lys Gln Met Gln Leu Ala Phe Ala
860                 865                 870

GCC GTT AAC GTG TGG CGG AAG AAC CTG CAG GAT AGA AAG AGT GGT AGA    2931
Ala Val Asn Val Trp Arg Lys Asn Leu Gln Asp Arg Lys Ser Gly Arg
875                 880                 885                 890

GCA GAG CCT GAC CCT AAA AAG AAA GCC ACA TTT AGG GCT ATC ACC TCC    2979
Ala Glu Pro Asp Pro Lys Lys Lys Ala Thr Phe Arg Ala Ile Thr Ser
                895                 900                 905

ACC CTG GCT TCC AGC TTC AAG AGG CGT AGG TCC TCC AAA GAC ACG AGC    3027
Thr Leu Ala Ser Ser Phe Lys Arg Arg Arg Ser Ser Lys Asp Thr Ser
        910                 915                 920

ACC GGG GGT GGA CGC GGT GCT TTG CAA AAC CAA AAA GAC ACA GTG CTG    3075
```

```
Thr Gly Gly Gly Arg Gly Ala Leu Gln Asn Gln Lys Asp Thr Val Leu
    925                 930                 935

CCG CGA CGC GCT ATT GAG AGG GAG GAG GGC CAG CTG CAG CTG TGT TCC   3123
Pro Arg Arg Ala Ile Glu Arg Glu Glu Gly Gln Leu Gln Leu Cys Ser
    940                 945                 950

CGT CAT AGG GAG AGC TGAGACTCCC CGCCCGCCCT CCTCTGCCCC CTCCCCCGCA   3178
Arg His Arg Glu Ser
955                 960

GACAGACAGA CAGACGGACG GGACAGCGGC CCGGCCCACG CAGAGCCCCG GAGCACCACG   3238

GGGTCGGGGG AGGAGCACCC CCAGCCTCCC CCAGGCTGCG CCTGCCCGCC CGCCGGTTGG   3298

CCGGCTGGCC GGTCCACCCC GTCCCGGCCC CGCGCGTGCC CCCAGCGTGG GGCTAACGGG   3358

CGCCTTGTCT GTGTATTTCT ATTTTGCAGC AGTACCATCC CACTGATATC ACGGGCCCGC   3418

TCAACCTCTC AGATCCCTCG GTCAGCACCG TGGTGTGAGG CCCCCGGAGG CGCCCACCTG   3478

CCCAGTTAGC CCGGCCAAGG ACACTGATGG GTCCTGCTGC TCGGGAAGGC CTGAGGGAAG   3538

CCCACCCGCC CCAGAGACTG CCCACCCTGG GCCTCCCGTC CGTCCGCCCG CCCACCCCGC   3598

TGCCTGGCGG GCAGCCCCTG CTGGACCAAG GTGCGGACCG GAGCGGCTGA GGACGGGGCA   3658

GAGCTGAGTC GGCTGGGCAG GGCCGCAGGG CGCTCCGGCA GAGGCAGGCC CCTGGGGTCT   3718

CTGAGCAGTG GGGAGCGGGG GCTAACTGCC CCCAGGCGGA GGGGCTTGGA GCAGAGACGG   3778

CAGCCCCATC CTTCCCGCAG CACCAGCCTG AGCCACAGTG GGGCCCATGG CCCCAGCTGG   3838

CTGGGTCGCC CCTCCTCGGG CGCCTGCGCT CCTCTGCAGC CTGAGCTCCA CCCTCCCCTC   3898

TTCTTGCGGC ACCGCCCACC AAACACCCCG TCTGCCCCTT GACGCCACAC GCCGGGGCTG   3958

GCGCTGCCCT CCCCCACGGC CGTCCCTGAC TTCCCAGCTG GCAGCGCCTC CCGCCGCCTC   4018

GGGCCGCCTC CTCCAGAATC GAGAGGGCTG AGCCCCTCCT CTCCTCGTCC GGCCTGCAGC   4078

ACAGAAGGGG GCCTCCCCGG GGGTCCCCGG ACGCTGGCTC GGGACTGTCT TCAACCCTGC   4138

CCTGCACCTT GGGCACGGGA GAGCGCCACC CGCCCGCCCC CGCCCTCGCT CCGGGTGCGT   4198

GACCGGCCCG CCACCTTGTA CAGAACCAGC ACTCCCAGGG CCCGAGCGCG TGCCTTCCCC   4258

GTGCGCAGCC GCGCTCTGCC CCTCCGTCCC CAGGGTGCAG GCGCGCACCG CCCAACCCCC   4318

ACCTCCCGGT GTATGCAGTG GTGATGCCTA AAGGAATGTC ACG                    4361

(2) INFORMATION FOR SEQ ID NO:24:

(i) SEQUENCE CHARACTERISTICS:
        (A) LENGTH: 959 amino acids
        (B) TYPE: amino acid
        (D) TOPOLOGY: linear (ii) MOLECULE TYPE: protein (xi) SEQUENCE DESCRIPTION: SEQ ID NO:24:

Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
```

```
                    85                  90                  95
Thr Pro Asn Asp His Phe Thr Pro Thr Pro Val Ser Tyr Thr Ala Gly
                100                 105                 110
Phe Tyr Arg Ile Pro Val Leu Gly Leu Thr Thr Arg Met Ser Ile Tyr
            115                 120                 125
Ser Asp Lys Ser Ile His Leu Ser Phe Leu Arg Thr Val Pro Pro Tyr
        130                 135                 140
Ser His Gln Ser Ser Val Trp Phe Glu Met Met Arg Val Tyr Ser Trp
145                 150                 155                 160
Asn His Ile Ile Leu Leu Val Ser Asp Asp His Glu Gly Arg Ala Ala
                165                 170                 175
Gln Lys Arg Leu Glu Thr Leu Leu Glu Glu Arg Glu Ser Lys Ser Lys
            180                 185                 190
Lys Arg Asn Tyr Glu Asn Leu Asp Gln Leu Ser Tyr Asp Asn Lys Arg
        195                 200                 205
Gly Pro Lys Ala Glu Lys Val Leu Gln Phe Asp Pro Gly Thr Lys Asn
        210                 215                 220
Val Thr Ala Leu Leu Met Glu Ala Lys Glu Leu Glu Ala Arg Val Ile
225                 230                 235                 240
Ile Leu Ser Ala Ser Glu Asp Asp Ala Ala Thr Val Tyr Arg Ala Ala
                245                 250                 255
Ala Met Leu Asn Met Thr Gly Ser Gly Tyr Val Trp Leu Val Gly Glu
            260                 265                 270
Arg Glu Ile Ser Gly Asn Ala Leu Arg Tyr Ala Pro Asp Gly Ile Leu
        275                 280                 285
Gly Leu Gln Leu Ile Asn Gly Lys Asn Glu Ser Ala His Ile Ser Asp
        290                 295                 300
Ala Val Gly Val Val Ala Gln Ala Val His Glu Leu Leu Glu Lys Glu
305                 310                 315                 320
Asn Ile Thr Asp Pro Pro Arg Gly Cys Val Gly Asn Thr Asn Ile Trp
                325                 330                 335
Lys Thr Gly Pro Leu Phe Lys Arg Val Leu Met Ser Ser Lys Tyr Ala
            340                 345                 350
Asp Gly Val Thr Gly Arg Val Glu Phe Asn Glu Asp Gly Asp Arg Lys
        355                 360                 365
Phe Ala Asn Tyr Ser Ile Met Asn Leu Gln Asn Arg Lys Leu Val Gln
        370                 375                 380
Val Gly Ile Tyr Asn Gly Thr His Val Ile Pro Asn Asp Arg Lys Ile
385                 390                 395                 400
Ile Trp Pro Gly Gly Glu Thr Glu Lys Pro Arg Gly Tyr Gln Met Ser
                405                 410                 415
Thr Arg Leu Lys Ile Val Thr Ile His Gln Glu Pro Phe Val Tyr Val
            420                 425                 430
Lys Pro Thr Leu Ser Asp Gly Thr Cys Lys Glu Glu Phe Thr Val Asn
        435                 440                 445
Gly Asp Pro Val Lys Lys Val Ile Cys Thr Gly Pro Asn Asp Thr Ser
        450                 455                 460
Pro Gly Ser Pro Arg His Thr Val Pro Gln Cys Cys Tyr Gly Phe Cys
465                 470                 475                 480
Ile Asp Leu Leu Ile Lys Leu Ala Arg Thr Met Asn Phe Thr Tyr Glu
                485                 490                 495
Val His Leu Val Ala Asp Gly Lys Phe Gly Thr Gln Glu Arg Val Asn
            500                 505                 510
```

```
Asn Ser Asn Lys Lys Glu Trp Asn Gly Met Met Gly Glu Leu Leu Ser
        515                 520                 525
Gly Gln Ala Asp Met Ile Val Ala Pro Leu Thr Ile Asn Asn Glu Arg
    530                 535                 540
Ala Gln Tyr Ile Glu Phe Ser Lys Pro Phe Lys Tyr Gln Gly Leu Thr
545                 550                 555                 560
Ile Leu Val Lys Lys Glu Ile Pro Arg Ser Thr Leu Asp Ser Phe Met
                565                 570                 575
Gln Pro Phe Gln Ser Thr Leu Trp Leu Leu Val Gly Leu Ser Val His
            580                 585                 590
Val Val Ala Val Met Leu Tyr Leu Leu Asp Arg Phe Ser Pro Phe Gly
        595                 600                 605
Arg Phe Lys Val Asn Ser Glu Glu Glu Glu Asp Ala Leu Thr Leu
    610                 615                 620
Ser Ser Ala Met Trp Phe Ser Trp Gly Val Leu Leu Asn Ser Gly Ile
625                 630                 635                 640
Gly Glu Gly Ala Pro Arg Ser Phe Ser Ala Arg Ile Leu Gly Met Val
                645                 650                 655
Trp Ala Gly Phe Ala Met Ile Ile Val Ala Ser Tyr Thr Ala Asn Leu
            660                 665                 670
Ala Ala Phe Leu Val Leu Asp Arg Pro Glu Glu Arg Ile Thr Gly Ile
        675                 680                 685
Asn Asp Pro Arg Leu Arg Asn Pro Ser Asp Lys Phe Ile Tyr Ala Thr
    690                 695                 700
Val Lys Gln Ser Ser Val Asp Ile Tyr Phe Arg Arg Gln Val Glu Leu
705                 710                 715                 720
Ser Thr Met Tyr Arg His Met Glu Lys His Asn Tyr Glu Ser Ala Ala
                725                 730                 735
Glu Ala Ile Gln Ala Val Arg Asp Asn Lys Leu His Ala Phe Ile Trp
            740                 745                 750
Asp Ser Ala Val Leu Glu Phe Glu Ala Ser Gln Lys Cys Asp Leu Val
        755                 760                 765
Thr Thr Gly Glu Leu Phe Phe Arg Ser Gly Phe Gly Ile Gly Met Arg
770                 775                 780
Lys Asp Ser Pro Trp Lys Gln Asn Val Ser Leu Ser Ile Leu Lys Ser
785                 790                 795                 800
His Glu Asn Gly Phe Met Glu Asp Leu Asp Lys Thr Trp Val Arg Tyr
                805                 810                 815
Gln Glu Cys Asp Ser Arg Ser Asn Ala Pro Ala Thr Leu Thr Phe Glu
            820                 825                 830
Asn Met Ala Gly Val Phe Met Leu Val Ala Gly Gly Ile Val Ala Gly
        835                 840                 845
Ile Phe Leu Ile Phe Ile Glu Ile Ala Tyr Lys Arg His Lys Asp Ala
850                 855                 860
Arg Arg Lys Gln Met Gln Leu Ala Phe Ala Ala Val Asn Val Trp Arg
865                 870                 875                 880
Lys Asn Leu Gln Asp Arg Lys Ser Gly Arg Ala Glu Pro Asp Pro Lys
                885                 890                 895
Lys Lys Ala Thr Phe Arg Ala Ile Thr Ser Thr Leu Ala Ser Ser Phe
            900                 905                 910
Lys Arg Arg Arg Ser Ser Lys Asp Thr Ser Thr Gly Gly Gly Arg Gly
        915                 920                 925
```

```
Ala Leu Gln Asn Gln Lys Asp Thr Val Leu Pro Arg Arg Ala Ile Glu
    930             935             940
Arg Glu Glu Gly Gln Leu Gln Leu Cys Ser Arg His Arg Glu Ser
945             950             955
```

(2) INFORMATION FOR SEQ ID NO:25:

(i) SEQUENCE CHARACTERISTICS:
        (A) LENGTH: 4157 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..2937

(xi) SEQUENCE DESCRIPTION: SEQ ID NO:25:

```
CAAGCCGGGC GTTCGGAGCT GTGCCCGGCC CCGCTTCAGC ACCGCGGACA GCGCCGGCCG    60

CGTGGGGCTG AGCGCCGAGC CCCCGCGCAC GCTTCAGCCC CCCTTCCCTC GGCCGACGTC   120

CCGGGACCGC CGCTCCGGGG GAGACGTGGC GTCCGCAGCC CGCGGGGCCG GGCGAGCGCA   180

GGACGGCCCG GAAGCCCCGC GGGGGATGCG CCGAGGGCCC CGCGTTCGCG CCGCGCAGAG   240

CCAGGCCCGC GGCCCGAGCC C ATG AGC ACC ATG CGC CTG CTG ACG CTC GCC    291
                         Met Ser Thr Met Arg Leu Leu Thr Leu Ala
                          1               5                    10

CTG CTG TTC TCC TGC TCC GTC GCC CGT GCC GCG TGC GAC CCC AAG ATC    339
Leu Leu Phe Ser Cys Ser Val Ala Arg Ala Ala Cys Asp Pro Lys Ile
        15                  20                  25

GTC AAC ATT GGC GCG GTG CTG AGC ACG CGG AAG CAC GAG CAG ATG TTC    387
Val Asn Ile Gly Ala Val Leu Ser Thr Arg Lys His Glu Gln Met Phe
                30                  35                  40

CGC GAG GCC GTG AAC CAG GCC AAC AAG CGG CAC GGC TCC TGG AAG ATT    435
Arg Glu Ala Val Asn Gln Ala Asn Lys Arg His Gly Ser Trp Lys Ile
            45                  50                  55

CAG CTC AAT GCC ACC TCC GTC ACG CAC AAG CCC AAC GCC ATC CAG ATG    483
Gln Leu Asn Ala Thr Ser Val Thr His Lys Pro Asn Ala Ile Gln Met
        60                  65                  70

GCT CTG TCG GTG TGC GAG GAC CTC ATC TCC AGC CAG GTC TAC GCC ATC    531
Ala Leu Ser Val Cys Glu Asp Leu Ile Ser Ser Gln Val Tyr Ala Ile
 75                 80                  85                  90

CTA GTT AGC CAT CCA CCT ACC CCC AAC GAC CAC TTC ACT CCC ACC CCT    579
Leu Val Ser His Pro Pro Thr Pro Asn Asp His Phe Thr Pro Thr Pro
                95                  100                 105

GTC TCC TAC ACA GCC GGC TTC TAC CGC ATA CCC GTG CTG GGG CTG ACC    627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG    675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG    723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC    771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG    819
His Glu Gly Arg Ala Ala Gln Lys Arg Leu Glu Thr Leu Leu Glu Glu
                175                 180                 185
```

```
CGT GAG TCC AAG AGT AAA AAA AGG AAC TAT GAA AAC CTC GAC CAA CTG        867
Arg Glu Ser Lys Ser Lys Lys Arg Asn Tyr Glu Asn Leu Asp Gln Leu
            190                 195                 200

TCC TAT GAC AAC AAG CGC GGA CCC AAG GCA GAG AAG GTG CTG CAG TTT        915
Ser Tyr Asp Asn Lys Arg Gly Pro Lys Ala Glu Lys Val Leu Gln Phe
            205                 210                 215

GAC CCA GGG ACC AAG AAC GTG ACG GCC CTG CTG ATG GAG GCG AAA GAG        963
Asp Pro Gly Thr Lys Asn Val Thr Ala Leu Leu Met Glu Ala Lys Glu
        220                 225                 230

CTG GAG GCC CGG GTC ATC ATC CTT TCT GCC AGC GAG GAC GAT GCT GCC       1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC AAC ACC AAC       1059
Thr Val Tyr Arg Ala Ala Ala Met Leu Asn Met Thr Gly Asn Thr Asn
                255                 260                 265

ATC TGG AAG ACC GGG CCG CTC TTC AAG AGA GTG CTG ATG TCT TCC AAG       1107
Ile Trp Lys Thr Gly Pro Leu Phe Lys Arg Val Leu Met Ser Ser Lys
            270                 275                 280

TAT GCG GAT GGG GTG ACT GGT CGC GTG GAG TTC AAT GAG GAT GGG GAC       1155
Tyr Ala Asp Gly Val Thr Gly Arg Val Glu Phe Asn Glu Asp Gly Asp
            285                 290                 295

CGG AAG TTC GCC AAC TAC AGC ATC ATG AAC CTG CAG AAC CGC AAG CTG       1203
Arg Lys Phe Ala Asn Tyr Ser Ile Met Asn Leu Gln Asn Arg Lys Leu
300                 305                 310

GTG CAA GTG GGC ATC TAC AAT GGC ACC CAC GTC ATC CCT AAT GAC AGG       1251
Val Gln Val Gly Ile Tyr Asn Gly Thr His Val Ile Pro Asn Asp Arg
315                 320                 325                 330

AAG ATC ATC TGG CCA GGC GGA GAG ACA GAG AAG CCT CGA GGG TAC CAG       1299
Lys Ile Ile Trp Pro Gly Gly Glu Thr Glu Lys Pro Arg Gly Tyr Gln
                335                 340                 345

ATG TCC ACC AGA CTG AAG ATT GTG ACG ATC CAC CAG GAG CCC TTC GTG       1347
Met Ser Thr Arg Leu Lys Ile Val Thr Ile His Gln Glu Pro Phe Val
            350                 355                 360

TAC GTC AAG CCC ACG CTG AGT GAT GGG ACA TGC AAG GAG GAG TTC ACA       1395
Tyr Val Lys Pro Thr Leu Ser Asp Gly Thr Cys Lys Glu Glu Phe Thr
            365                 370                 375

GTC AAC GGC GAC CCA GTC AAG AAG GTG ATC TGC ACC GGG CCC AAC GAC       1443
Val Asn Gly Asp Pro Val Lys Lys Val Ile Cys Thr Gly Pro Asn Asp
380                 385                 390

ACG TCG CCG GGC AGC CCC CGC CAC ACG GTG CCT CAG TGT TGC TAC GGC       1491
Thr Ser Pro Gly Ser Pro Arg His Thr Val Pro Gln Cys Cys Tyr Gly
395                 400                 405                 410

TTT TGC ATC GAC CTG CTC ATC AAG CTG GCA CGG ACC ATG AAC TTC ACC       1539
Phe Cys Ile Asp Leu Leu Ile Lys Leu Ala Arg Thr Met Asn Phe Thr
                415                 420                 425

TAC GAG GTG CAC CTG GTG GCA GAT GGC AAG TTC GGC ACA CAG GAG CGG       1587
Tyr Glu Val His Leu Val Ala Asp Gly Lys Phe Gly Thr Gln Glu Arg
            430                 435                 440

GTG AAC AAC AGC AAC AAG AAG GAG TGG AAT GGG ATG ATG GGC GAG CTG       1635
Val Asn Asn Ser Asn Lys Lys Glu Trp Asn Gly Met Met Gly Glu Leu
            445                 450                 455

CTC AGC GGG CAG GCA GAC ATG ATC GTG GCG CCG CTA ACC ATA AAC AAC       1683
Leu Ser Gly Gln Ala Asp Met Ile Val Ala Pro Leu Thr Ile Asn Asn
            460                 465                 470

GAG CGC GCG CAG TAC ATC GAG TTT TCC AAG CCC TTC AAG TAC CAG GGC       1731
Glu Arg Ala Gln Tyr Ile Glu Phe Ser Lys Pro Phe Lys Tyr Gln Gly
475                 480                 485                 490

CTG ACT ATT CTG GTC AAG AAG GAG ATT CCC CGG AGC ACG CTG GAC TCG       1779
Leu Thr Ile Leu Val Lys Lys Glu Ile Pro Arg Ser Thr Leu Asp Ser
                495                 500                 505
```

```
TTC ATG CAG CCG TTC CAG AGC ACA CTG TGG CTG CTG GTG GGG CTG TCG      1827
Phe Met Gln Pro Phe Gln Ser Thr Leu Trp Leu Leu Val Gly Leu Ser
        510                 515                 520

GTG CAC GTG GTG GCC GTG ATG CTG TAC CTG CTG GAC CGC TTC AGC CCC      1875
Val His Val Val Ala Val Met Leu Tyr Leu Leu Asp Arg Phe Ser Pro
            525                 530                 535

TTC GGC CGG TTC AAG GTG AAC AGC GAG GAG GAG GAG GAG GAC GCA CTG      1923
Phe Gly Arg Phe Lys Val Asn Ser Glu Glu Glu Glu Glu Asp Ala Leu
        540                 545                 550

ACC CTG TCC TCG GCC ATG TGG TTC TCC TGG GGC GTC CTG CTC AAC TCC      1971
Thr Leu Ser Ser Ala Met Trp Phe Ser Trp Gly Val Leu Leu Asn Ser
555                 560                 565                 570

GGC ATC GGG GAA GGC GCC CCC AGA AGC TTC TCA GCG CGC ATC CTG GGC      2019
Gly Ile Gly Glu Gly Ala Pro Arg Ser Phe Ser Ala Arg Ile Leu Gly
        575                 580                 585

ATG GTG TGG GCC GGC TTT GCC ATG ATC ATC GTG GCC TCC TAC ACC GCC      2067
Met Val Trp Ala Gly Phe Ala Met Ile Ile Val Ala Ser Tyr Thr Ala
            590                 595                 600

AAC CTG GCG GCC TTC CTG GTG CTG GAC CGG CCG GAG GAG CGC ATC ACG      2115
Asn Leu Ala Ala Phe Leu Val Leu Asp Arg Pro Glu Glu Arg Ile Thr
        605                 610                 615

GGC ATC AAC GAC CCT CGG CTG AGG AAC CCC TCG GAC AAG TTT ATC TAC      2163
Gly Ile Asn Asp Pro Arg Leu Arg Asn Pro Ser Asp Lys Phe Ile Tyr
        620                 625                 630

GCC ACG GTG AAG CAG AGC TCC GTG GAT ATC TAC TTC CGG CGC CAG GTG      2211
Ala Thr Val Lys Gln Ser Ser Val Asp Ile Tyr Phe Arg Arg Gln Val
635                 640                 645                 650

GAG CTG AGC ACC ATG TAC CGG CAT ATG GAG AAG CAC AAC TAC GAG AGT      2259
Glu Leu Ser Thr Met Tyr Arg His Met Glu Lys His Asn Tyr Glu Ser
                655                 660                 665

GCG GCG GAG GCC ATC CAG GCC GTG AGA GAC AAC AAG CTG CAT GCC TTC      2307
Ala Ala Glu Ala Ile Gln Ala Val Arg Asp Asn Lys Leu His Ala Phe
        670                 675                 680

ATC TGG GAC TCG GCG GTG CTG GAG TTC GAG GCC TCG CAG AAG TGC GAC      2355
Ile Trp Asp Ser Ala Val Leu Glu Phe Glu Ala Ser Gln Lys Cys Asp
            685                 690                 695

CTG GTG ACG ACT GGA GAG CTG TTT TTC CGC TCG GGC TTC GGC ATA GGC      2403
Leu Val Thr Thr Gly Glu Leu Phe Phe Arg Ser Gly Phe Gly Ile Gly
700                 705                 710

ATG CGC AAA GAC AGC CCC TGG AAG CAG AAC GTC TCC CTG TCC ATC CTC      2451
Met Arg Lys Asp Ser Pro Trp Lys Gln Asn Val Ser Leu Ser Ile Leu
715                 720                 725                 730

AAG TCC CAC GAG AAT GGC TTC ATG GAA GAC CTG GAC AAG ACG TGG GTT      2499
Lys Ser His Glu Asn Gly Phe Met Glu Asp Leu Asp Lys Thr Trp Val
                735                 740                 745

CGG TAT CAG GAA TGT GAC TCG CGC AGC AAC GCC CCT GCG ACC CTT ACT      2547
Arg Tyr Gln Glu Cys Asp Ser Arg Ser Asn Ala Pro Ala Thr Leu Thr
        750                 755                 760

TTT GAG AAC ATG GCC GGG GTC TTC ATG CTG GTA GCT GGG GGC ATC GTG      2595
Phe Glu Asn Met Ala Gly Val Phe Met Leu Val Ala Gly Gly Ile Val
            765                 770                 775

GCC GGG ATC TTC CTG ATT TTC ATC GAG ATT GCC TAC AAG CGG CAC AAG      2643
Ala Gly Ile Phe Leu Ile Phe Ile Glu Ile Ala Tyr Lys Arg His Lys
        780                 785                 790

GAT GCT CGC CGG AAG CAG ATG CAG CTG GCC TTT GCC GCC GTT AAC GTG      2691
Asp Ala Arg Arg Lys Gln Met Gln Leu Ala Phe Ala Ala Val Asn Val
795                 800                 805                 810

TGG CGG AAG AAC CTG CAG GAT AGA AAG AGT GGT AGA GCA GAG CCT GAC      2739
Trp Arg Lys Asn Leu Gln Asp Arg Lys Ser Gly Arg Ala Glu Pro Asp
```

```
                   815                 820                 825
CCT AAA AAG AAA GCC ACA TTT AGG GCT ATC ACC TCC ACC CTG GCT TCC    2787
Pro Lys Lys Lys Ala Thr Phe Arg Ala Ile Thr Ser Thr Leu Ala Ser
            830                 835                 840

AGC TTC AAG AGG CGT AGG TCC TCC AAA GAC ACG AGC ACC GGG GGT GGA    2835
Ser Phe Lys Arg Arg Arg Ser Ser Lys Asp Thr Ser Thr Gly Gly Gly
            845                 850                 855

CGC GGT GCT TTG CAA AAC CAA AAA GAC ACA GTG CTG CCG CGA CGC GCT    2883
Arg Gly Ala Leu Gln Asn Gln Lys Asp Thr Val Leu Pro Arg Arg Ala
            860                 865                 870

ATT GAG AGG GAG GAG GGC CAG CTG CAG CTG TGT TCC CGT CAT AGG GAG    2931
Ile Glu Arg Glu Glu Gly Gln Leu Gln Leu Cys Ser Arg His Arg Glu
875                 880                 885                 890

AGC TGAGACTCCC CGCCCGCCCT CCTCTGCCCC CTCCCCCGCA GACAGACAGA        2984
Ser

CAGACGGACG GGACAGCGGC CCGGCCCACG CAGAGCCCCG GAGCACCACG GGGTCGGGGG   3044

AGGAGCACCC CCAGCCTCCC CCAGGCTGCG CCTGCCCGCC CGCCGGTTGG CCGGCTGGCC   3104

GGTCCACCCC GTCCCGGCCC CGCGCGTGCC CCCAGCGTGG GGCTAACGGG CGCCTTGTCT   3164

GTGTATTTCT ATTTTGCAGC AGTACCATCC CACTGATATC ACGGGCCCGC TCAACCTCTC   3224

AGATCCCTCG GTCAGCACCG TGGTGTGAGG CCCCCGGAGG CGCCCACCTG CCCAGTTAGC   3284

CCGGCCAAGG ACACTGATGG GTCCTGCTGC TCGGGAAGGC CTGAGGGAAG CCCACCCGCC   3344

CCAGAGACTG CCCACCCTGG GCCTCCCGTC CGTCCGCCCG CCCACCCCGC TGCCTGGCGG   3404

GCAGCCCCTG CTGGACCAAG GTGCGGACCG GAGCGGCTGA GGACGGGCA GAGCTGAGTC    3464

GGCTGGGCAG GGCCGCAGGG CGCTCCGGCA GAGGCAGGCC CCTGGGGTCT CTGAGCAGTG   3524

GGGAGCGGGG GCTAACTGCC CCCAGGCGGA GGGGCTTGGA GCAGAGACGG CAGCCCCATC   3584

CTTCCCGCAG CACCAGCCTG AGCCACAGTG GGGCCCATGG CCCCAGCTGG CTGGGTCGCC   3644

CCTCCTCGGG CGCCTGCGCT CCTCTGCAGC CTGAGCTCCA CCCTCCCCTC TTCTTGCGGC   3704

ACCGCCCACC AAACACCCCG TCTGCCCCTT GACGCCACAC GCCGGGGCTG GCGCTGCCCT   3764

CCCCCACGGC CGTCCCTGAC TTCCCAGCTG GCAGCGCCTC CCGCCGCCTC GGGCCGCCTC   3824

CTCCAGAATC GAGAGGGCTG AGCCCCTCCT CTCCTCGTCC GGCCTGCAGC ACAGAAGGGG   3884

GCCTCCCCGG GGGTCCCCGG ACGCTGGCTC GGGACTGTCT TCAACCCTGC CCTGCACCTT   3944

GGGCACGGGA GAGCGCCACC CGCCCGCCCC CGCCCTCGCT CCGGGTGCGT GACCGGCCCG   4004

CCACCTTGTA CAGAACCAGC ACTCCCAGGG CCCGAGCGCG TGCCTTCCCC GTGCGCAGCC   4064

GCGCTCTGCC CCTCCGTCCC CAGGGTGCAG GCGCGCACCG CCCAACCCCC ACCTCCCGGT   4124

GTATGCAGTG GTGATGCCTA AAGGAATGTC ACG                              4157

(2) INFORMATION FOR SEQ ID NO:26:

(i) SEQUENCE CHARACTERISTICS:
        (A) LENGTH: 891 amino acids
        (B) TYPE: amino acid
        (D) TOPOLOGY: linear (ii) MOLECULE TYPE: protein (xi) SEQUENCE DESCRIPTION: SEQ ID NO:26:

Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
            20                  25                  30
```

```
Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65              70                  75                      80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
             100                 105                 110

Phe Tyr Arg Ile Pro Val Leu Gly Leu Thr Thr Arg Met Ser Ile Tyr
         115                 120                 125

Ser Asp Lys Ser Ile His Leu Ser Phe Leu Arg Thr Val Pro Pro Tyr
     130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                 165                 170                 175

Gln Lys Arg Leu Glu Thr Leu Leu Glu Arg Glu Ser Lys Ser Lys
             180                 185                 190

Lys Arg Asn Tyr Glu Asn Leu Asp Gln Leu Ser Tyr Asp Asn Lys Arg
         195                 200                 205

Gly Pro Lys Ala Glu Lys Val Leu Gln Phe Asp Pro Gly Thr Lys Asn
     210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                 245                 250                 255

Ala Met Leu Asn Met Thr Gly Asn Thr Asn Ile Trp Lys Thr Gly Pro
             260                 265                 270

Leu Phe Lys Arg Val Leu Met Ser Ser Lys Tyr Ala Asp Gly Val Thr
         275                 280                 285

Gly Arg Val Glu Phe Asn Glu Asp Gly Asp Arg Lys Phe Ala Asn Tyr
     290                 295                 300

Ser Ile Met Asn Leu Gln Asn Arg Lys Leu Val Gln Val Gly Ile Tyr
305                 310                 315                 320

Asn Gly Thr His Val Ile Pro Asn Asp Arg Lys Ile Ile Trp Pro Gly
                 325                 330                 335

Gly Glu Thr Glu Lys Pro Arg Gly Tyr Gln Met Ser Thr Arg Leu Lys
             340                 345                 350

Ile Val Thr Ile His Gln Glu Pro Phe Val Tyr Val Lys Pro Thr Leu
         355                 360                 365

Ser Asp Gly Thr Cys Lys Glu Glu Phe Thr Val Asn Gly Asp Pro Val
     370                 375                 380

Lys Lys Val Ile Cys Thr Gly Pro Asn Asp Thr Ser Pro Gly Ser Pro
385                 390                 395                 400

Arg His Thr Val Pro Gln Cys Cys Tyr Gly Phe Cys Ile Asp Leu Leu
                 405                 410                 415

Ile Lys Leu Ala Arg Thr Met Asn Phe Thr Tyr Glu Val His Leu Val
             420                 425                 430

Ala Asp Gly Lys Phe Gly Thr Gln Glu Arg Val Asn Asn Ser Asn Lys
         435                 440                 445

Lys Glu Trp Asn Gly Met Met Gly Glu Leu Leu Ser Gly Gln Ala Asp
```

-continued

```
            450                 455                 460
Met Ile Val Ala Pro Leu Thr Ile Asn Asn Glu Arg Ala Gln Tyr Ile
465                 470                 475                 480
Glu Phe Ser Lys Pro Phe Lys Tyr Gln Gly Leu Thr Ile Leu Val Lys
                485                 490                 495
Lys Glu Ile Pro Arg Ser Thr Leu Asp Ser Phe Met Gln Pro Phe Gln
                500                 505                 510
Ser Thr Leu Trp Leu Leu Val Gly Leu Ser Val His Val Val Ala Val
                515                 520                 525
Met Leu Tyr Leu Leu Asp Arg Phe Ser Pro Phe Gly Arg Phe Lys Val
530                 535                 540
Asn Ser Glu Glu Glu Glu Asp Ala Leu Thr Leu Ser Ser Ala Met
545                 550                 555                 560
Trp Phe Ser Trp Gly Val Leu Leu Asn Ser Gly Ile Gly Glu Gly Ala
                565                 570                 575
Pro Arg Ser Phe Ser Ala Arg Ile Leu Gly Met Val Trp Ala Gly Phe
                580                 585                 590
Ala Met Ile Ile Val Ala Ser Tyr Thr Ala Asn Leu Ala Ala Phe Leu
                595                 600                 605
Val Leu Asp Arg Pro Glu Glu Arg Ile Thr Gly Ile Asn Asp Pro Arg
610                 615                 620
Leu Arg Asn Pro Ser Asp Lys Phe Ile Tyr Ala Thr Val Lys Gln Ser
625                 630                 635                 640
Ser Val Asp Ile Tyr Phe Arg Arg Gln Val Glu Leu Ser Thr Met Tyr
                645                 650                 655
Arg His Met Glu Lys His Asn Tyr Glu Ser Ala Ala Glu Ala Ile Gln
                660                 665                 670
Ala Val Arg Asp Asn Lys Leu His Ala Phe Ile Trp Asp Ser Ala Val
                675                 680                 685
Leu Glu Phe Glu Ala Ser Gln Lys Cys Asp Leu Val Thr Thr Gly Glu
                690                 695                 700
Leu Phe Phe Arg Ser Gly Phe Gly Ile Gly Met Arg Lys Asp Ser Pro
705                 710                 715                 720
Trp Lys Gln Asn Val Ser Leu Ser Ile Leu Lys Ser His Glu Asn Gly
                725                 730                 735
Phe Met Glu Asp Leu Asp Lys Thr Trp Val Arg Tyr Gln Glu Cys Asp
                740                 745                 750
Ser Arg Ser Asn Ala Pro Ala Thr Leu Thr Phe Glu Asn Met Ala Gly
                755                 760                 765
Val Phe Met Leu Val Ala Gly Gly Ile Val Ala Gly Ile Phe Leu Ile
                770                 775                 780
Phe Ile Glu Ile Ala Tyr Lys Arg His Lys Asp Ala Arg Arg Lys Gln
785                 790                 795                 800
Met Gln Leu Ala Phe Ala Ala Val Asn Val Trp Arg Lys Asn Leu Gln
                805                 810                 815
Asp Arg Lys Ser Gly Arg Ala Glu Pro Asp Pro Lys Lys Lys Ala Thr
                820                 825                 830
Phe Arg Ala Ile Thr Ser Thr Leu Ala Ser Ser Phe Lys Arg Arg Arg
                835                 840                 845
Ser Ser Lys Asp Thr Ser Thr Gly Gly Gly Arg Gly Ala Leu Gln Asn
                850                 855                 860
Gln Lys Asp Thr Val Leu Pro Arg Arg Ala Ile Glu Arg Glu Glu Gly
865                 870                 875                 880
```

Gln Leu Gln Leu Cys Ser Arg His Arg Glu Ser
            885                 890

(2) INFORMATION FOR SEQ ID NO:27:

(i) SEQUENCE CHARACTERISTICS:
        (A) LENGTH: 3794 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..2889

(xi) SEQUENCE DESCRIPTION: SEQ ID NO:27:

```
CAAGCCGGGC GTTCGGAGCT GTGCCCGGCC CCGCTTCAGC ACCGCGGACA GCGCCGGCCG         60

CGTGGGGCTG AGCGCCGAGC CCCCGCGCAC GCTTCAGCCC CCCTTCCCTC GGCCGACGTC        120

CCGGGACCGC CGCTCCGGGG GAGACGTGGC GTCCGCAGCC CGCGGGGCCG GGCGAGCGCA        180

GGACGGCCCG GAAGCCCCGC GGGGGATGCG CCGAGGGCCC CGCGTTCGCG CCGCGCAGAG        240

CCAGGCCCGC GGCCCGAGCC C ATG AGC ACC ATG CGC CTG CTG ACG CTC GCC         291
                        Met Ser Thr Met Arg Leu Leu Thr Leu Ala
                         1               5                   10
```

```
CTG CTG TTC TCC TGC TCC GTC GCC CGT GCC GCG TGC GAC CCC AAG ATC         339
Leu Leu Phe Ser Cys Ser Val Ala Arg Ala Ala Cys Asp Pro Lys Ile
            15                  20                  25
```

```
GTC AAC ATT GGC GCG GTG CTG AGC ACG CGG AAG CAC GAG CAG ATG TTC         387
Val Asn Ile Gly Ala Val Leu Ser Thr Arg Lys His Glu Gln Met Phe
        30                  35                  40
```

```
CGC GAG GCC GTG AAC CAG GCC AAC AAG CGG CAC GGC TCC TGG AAG ATT         435
Arg Glu Ala Val Asn Gln Ala Asn Lys Arg His Gly Ser Trp Lys Ile
    45                  50                  55
```

```
CAG CTC AAT GCC ACC TCC GTC ACG CAC AAG CCC AAC GCC ATC CAG ATG         483
Gln Leu Asn Ala Thr Ser Val Thr His Lys Pro Asn Ala Ile Gln Met
60                  65                  70
```

```
GCT CTG TCG GTG TGC GAG GAC CTC ATC TCC AGC CAG GTC TAC GCC ATC         531
Ala Leu Ser Val Cys Glu Asp Leu Ile Ser Ser Gln Val Tyr Ala Ile
75                  80                  85                  90
```

```
CTA GTT AGC CAT CCA CCT ACC CCC AAC GAC CAC TTC ACT CCC ACC CCT         579
Leu Val Ser His Pro Pro Thr Pro Asn Asp His Phe Thr Pro Thr Pro
                95                  100                 105
```

```
GTC TCC TAC ACA GCC GGC TTC TAC CGC ATA CCC GTG CTG GGG CTG ACC         627
Val Ser Tyr Thr Ala Gly Phe Tyr Arg Ile Pro Val Leu Gly Leu Thr
            110                 115                 120
```

```
ACC CGC ATG TCC ATC TAC TCG GAC AAG AGC ATC CAC CTG AGC TTC CTG         675
Thr Arg Met Ser Ile Tyr Ser Asp Lys Ser Ile His Leu Ser Phe Leu
        125                 130                 135
```

```
CGC ACC GTG CCG CCC TAC TCC CAC CAG TCC AGC GTG TGG TTT GAG ATG         723
Arg Thr Val Pro Pro Tyr Ser His Gln Ser Ser Val Trp Phe Glu Met
    140                 145                 150
```

```
ATG CGT GTC TAC AGC TGG AAC CAC ATC ATC CTG CTG GTC AGC GAC GAC         771
Met Arg Val Tyr Ser Trp Asn His Ile Ile Leu Leu Val Ser Asp Asp
155                 160                 165                 170
```

```
CAC GAG GGC CGG GCG GCT CAG AAA CGC CTG GAG ACG CTG CTG GAG GAG         819
His Glu Gly Arg Ala Ala Gln Lys Arg Leu Glu Thr Leu Leu Glu Glu
                175                 180                 185
```

```
CGT GAG TCC AAG AGT AAA AAA AGG AAC TAT GAA AAC CTC GAC CAA CTG         867
Arg Glu Ser Lys Ser Lys Lys Arg Asn Tyr Glu Asn Leu Asp Gln Leu
```

-continued

```
               190               195                200
TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
        205                 210                 215

GAC CCA GGG ACC AAG AAC GTG ACG GCC CTG CTG ATG GAG GCG AAA GAG      963
Asp Pro Gly Thr Lys Asn Val Thr Ala Leu Leu Met Glu Ala Lys Glu
    220                 225                 230

CTG GAG GCC CGG GTC ATC ATC CTT TCT GCC AGC GAG GAC GAT GCT GCC     1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC AAC ACC AAC     1059
Thr Val Tyr Arg Ala Ala Ala Met Leu Asn Met Thr Gly Asn Thr Asn
                    255                 260                 265

ATC TGG AAG ACC GGG CCG CTC TTC AAG AGA GTG CTG ATG TCT TCC AAG     1107
Ile Trp Lys Thr Gly Pro Leu Phe Lys Arg Val Leu Met Ser Ser Lys
                270                 275                 280

TAT GCG GAT GGG GTG ACT GGT CGC GTG GAG TTC AAT GAG GAT GGG GAC     1155
Tyr Ala Asp Gly Val Thr Gly Arg Val Glu Phe Asn Glu Asp Gly Asp
            285                 290                 295

CGG AAG TTC GCC AAC TAC AGC ATC ATG AAC CTG CAG AAC CGC AAG CTG     1203
Arg Lys Phe Ala Asn Tyr Ser Ile Met Asn Leu Gln Asn Arg Lys Leu
        300                 305                 310

GTG CAA GTG GGC ATC TAC AAT GGC ACC CAC GTC ATC CCT AAT GAC AGG     1251
Val Gln Val Gly Ile Tyr Asn Gly Thr His Val Ile Pro Asn Asp Arg
315                 320                 325                 330

AAG ATC ATC TGG CCA GGC GGA GAG ACA GAG AAG CCT CGA GGG TAC CAG     1299
Lys Ile Ile Trp Pro Gly Gly Glu Thr Glu Lys Pro Arg Gly Tyr Gln
                    335                 340                 345

ATG TCC ACC AGA CTG AAG ATT GTG ACG ATC CAC CAG GAG CCC TTC GTG     1347
Met Ser Thr Arg Leu Lys Ile Val Thr Ile His Gln Glu Pro Phe Val
                350                 355                 360

TAC GTC AAG CCC ACG CTG AGT GAT GGG ACA TGC AAG GAG GAG TTC ACA     1395
Tyr Val Lys Pro Thr Leu Ser Asp Gly Thr Cys Lys Glu Glu Phe Thr
            365                 370                 375

GTC AAC GGC GAC CCA GTC AAG AAG GTG ATC TGC ACC GGG CCC AAC GAC     1443
Val Asn Gly Asp Pro Val Lys Lys Val Ile Cys Thr Gly Pro Asn Asp
        380                 385                 390

ACG TCG CCG GGC AGC CCC CGC CAC ACG GTG CCT CAG TGT TGC TAC GGC     1491
Thr Ser Pro Gly Ser Pro Arg His Thr Val Pro Gln Cys Cys Tyr Gly
395                 400                 405                 410

TTT TGC ATC GAC CTG CTC ATC AAG CTG GCA CGG ACC ATG AAC TTC ACC     1539
Phe Cys Ile Asp Leu Leu Ile Lys Leu Ala Arg Thr Met Asn Phe Thr
                    415                 420                 425

TAC GAG GTG CAC CTG GTG GCA GAT GGC AAG TTC GGC ACA CAG GAG CGG     1587
Tyr Glu Val His Leu Val Ala Asp Gly Lys Phe Gly Thr Gln Glu Arg
                430                 435                 440

GTG AAC AAC AGC AAC AAG AAG GAG TGG AAT GGG ATG ATG GGC GAG CTG     1635
Val Asn Asn Ser Asn Lys Lys Glu Trp Asn Gly Met Met Gly Glu Leu
            445                 450                 455

CTC AGC GGG CAG GCA GAC ATG ATC GTG GCG CCG CTA ACC ATA AAC AAC     1683
Leu Ser Gly Gln Ala Asp Met Ile Val Ala Pro Leu Thr Ile Asn Asn
        460                 465                 470

GAG CGC GCG CAG TAC ATC GAG TTT TCC AAG CCC TTC AAG TAC CAG GGC     1731
Glu Arg Ala Gln Tyr Ile Glu Phe Ser Lys Pro Phe Lys Tyr Gln Gly
475                 480                 485                 490

CTG ACT ATT CTG GTC AAG AAG GAG ATT CCC CGG AGC ACG CTG GAC TCG     1779
Leu Thr Ile Leu Val Lys Lys Glu Ile Pro Arg Ser Thr Leu Asp Ser
                    495                 500                 505

TTC ATG CAG CCG TTC CAG AGC ACA CTG TGG CTG CTG GTG GGG CTG TCG     1827
```

```
                                         -continued

Phe Met Gln Pro Phe Gln Ser Thr Leu Trp Leu Leu Val Gly Leu Ser
        510                 515                 520

GTG CAC GTG GTG GCC GTG ATG CTG TAC CTG CTG GAC CGC TTC AGC CCC        1875
Val His Val Val Ala Val Met Leu Tyr Leu Leu Asp Arg Phe Ser Pro
        525                 530                 535

TTC GGC CGG TTC AAG GTG AAC AGC GAG GAG GAG GAG GAC GCA CTG            1923
Phe Gly Arg Phe Lys Val Asn Ser Glu Glu Glu Glu Asp Ala Leu
540                 545                 550

ACC CTG TCC TCG GCC ATG TGG TTC TCC TGG GGC GTC CTG CTC AAC TCC        1971
Thr Leu Ser Ser Ala Met Trp Phe Ser Trp Gly Val Leu Leu Asn Ser
555                 560                 565                 570

GGC ATC GGG GAA GGC GCC CCC AGA AGC TTC TCA GCG CGC ATC CTG GGC        2019
Gly Ile Gly Glu Gly Ala Pro Arg Ser Phe Ser Ala Arg Ile Leu Gly
                575                 580                 585

ATG GTG TGG GCC GGC TTT GCC ATG ATC ATC GTG GCC TCC TAC ACC GCC        2067
Met Val Trp Ala Gly Phe Ala Met Ile Ile Val Ala Ser Tyr Thr Ala
            590                 595                 600

AAC CTG GCG GCC TTC CTG GTG CTG GAC CGG CCG GAG GAG CGC ATC ACG        2115
Asn Leu Ala Ala Phe Leu Val Leu Asp Arg Pro Glu Glu Arg Ile Thr
                605                 610                 615

GGC ATC AAC GAC CCT CGG CTG AGG AAC CCC TCG GAC AAG TTT ATC TAC        2163
Gly Ile Asn Asp Pro Arg Leu Arg Asn Pro Ser Asp Lys Phe Ile Tyr
620                 625                 630

GCC ACG GTG AAG CAG AGC TCC GTG GAT ATC TAC TTC CGG CGC CAG GTG        2211
Ala Thr Val Lys Gln Ser Ser Val Asp Ile Tyr Phe Arg Arg Gln Val
635                 640                 645                 650

GAG CTG AGC ACC ATG TAC CGG CAT ATG GAG AAG CAC AAC TAC GAG AGT        2259
Glu Leu Ser Thr Met Tyr Arg His Met Glu Lys His Asn Tyr Glu Ser
                655                 660                 665

GCG GCG GAG GCC ATC CAG GCC GTG AGA GAC AAC AAG CTG CAT GCC TTC        2307
Ala Ala Glu Ala Ile Gln Ala Val Arg Asp Asn Lys Leu His Ala Phe
            670                 675                 680

ATC TGG GAC TCG GCG GTG CTG GAG TTC GAG GCC TCG CAG AAG TGC GAC        2355
Ile Trp Asp Ser Ala Val Leu Glu Phe Glu Ala Ser Gln Lys Cys Asp
                685                 690                 695

CTG GTG ACG ACT GGA GAG CTG TTT TTC CGC TCG GGC TTC GGC ATA GGC        2403
Leu Val Thr Thr Gly Glu Leu Phe Phe Arg Ser Gly Phe Gly Ile Gly
            700                 705                 710

ATG CGC AAA GAC AGC CCC TGG AAG CAG AAC GTC TCC CTG TCC ATC CTC        2451
Met Arg Lys Asp Ser Pro Trp Lys Gln Asn Val Ser Leu Ser Ile Leu
715                 720                 725                 730

AAG TCC CAC GAG AAT GGC TTC ATG GAA GAC CTG GAC AAG ACG TGG GTT        2499
Lys Ser His Glu Asn Gly Phe Met Glu Asp Leu Asp Lys Thr Trp Val
                735                 740                 745

CGG TAT CAG GAA TGT GAC TCG CGC AGC AAC GCC CCT GCG ACC CTT ACT        2547
Arg Tyr Gln Glu Cys Asp Ser Arg Ser Asn Ala Pro Ala Thr Leu Thr
            750                 755                 760

TTT GAG AAC ATG GCC GGG GTC TTC ATG CTG GTA GCT GGG GGC ATC GTG        2595
Phe Glu Asn Met Ala Gly Val Phe Met Leu Val Ala Gly Gly Ile Val
                765                 770                 775

GCC GGG ATC TTC CTG ATT TTC ATC GAG ATT GCC TAC AAG CGG CAC AAG        2643
Ala Gly Ile Phe Leu Ile Phe Ile Glu Ile Ala Tyr Lys Arg His Lys
            780                 785                 790

GAT GCT CGC CGG AAG CAG ATG CAG CTG GCC TTT GCC GCC GTT AAC GTG        2691
Asp Ala Arg Arg Lys Gln Met Gln Leu Ala Phe Ala Ala Val Asn Val
795                 800                 805                 810

TGG CGG AAG AAC CTG CAG GAT AGA AAG AGT GGT AGA GCA GAG CCT GAC        2739
Trp Arg Lys Asn Leu Gln Asp Arg Lys Ser Gly Arg Ala Glu Pro Asp
                815                 820                 825
```

```
CCT AAA AAG AAA GCC ACA TTT AGG GCT ATC ACC TCC ACC CTG GCT TCC     2787
Pro Lys Lys Lys Ala Thr Phe Arg Ala Ile Thr Ser Thr Leu Ala Ser
        830                 835                 840

AGC TTC AAG AGG CGT AGG TCC TCC AAA GAC ACG CAG TAC CAT CCC ACT     2835
Ser Phe Lys Arg Arg Arg Ser Ser Lys Asp Thr Gln Tyr His Pro Thr
            845                 850                 855

GAT ATC ACG GGC CCG CTC AAC CTC TCA GAT CCC TCG GTC AGC ACC GTG     2883
Asp Ile Thr Gly Pro Leu Asn Leu Ser Asp Pro Ser Val Ser Thr Val
        860                 865                 870

GTG TGAGGCCCCC GGAGGCGCCC ACCTGCCCAG TTAGCCCGGC CAAGGACACT          2936
Val
875

GATGGGTCCT GCTGCTCGGG AAGGCCTGAG GGAAGCCCAC CCGCCCCAGA GACTGCCCAC   2996

CCTGGGCCTC CCGTCCGTCC GCCCGCCCAC CCCGCTGCCT GGCGGGCAGC CCCTGCTGGA   3056

CCAAGGTGCG GACCGGAGCG GCTGAGGACG GGGCAGAGCT GAGTCGGCTG GCAGGGCCG    3116

CAGGGCGCTC CGGCAGAGGC AGGCCCCTGG GGTCTCTGAG CAGTGGGGAG CGGGGGCTAA   3176

CTGCCCCCAG GCGGAGGGGC TTGGAGCAGA GACGGCAGCC CCATCCTTCC CGCAGCACCA   3236

GCCTGAGCCA CAGTGGGGCC CATGGCCCCA GCTGGCTGGG TCGCCCCTCC TCGGGCGCCT   3296

GCGCTCCTCT GCAGCCTGAG CTCCACCCTC CCCTCTTCTT GCGGCACCGC CCACCAAACA   3356

CCCCGTCTGC CCCTTGACGC CACACGCCGG GGCTGGCGCT GCCCTCCCCC ACGGCCGTCC   3416

CTGACTTCCC AGCTGGCAGC GCCTCCCGCC GCCTCGGGCC GCCTCCTCCA GAATCGAGAG   3476

GGCTGAGCCC CTCCTCTCCT CGTCCGGCCT GCAGCACAGA AGGGGCCTC CCCGGGGGTC    3536

CCCGGACGCT GGCTCGGGAC TGTCTTCAAC CCTGCCCTGC ACCTTGGGCA CGGGAGAGCG   3596

CCACCCGCCC GCCCCCGCCC TCGCTCCGGG TGCGTGACCG GCCCGCCACC TTGTACAGAA   3656

CCAGCACTCC CAGGGCCCGA GCGCGTGCCT TCCCCGTGCG CAGCCGCGCT CTGCCCCTCC   3716

GTCCCCAGGG TGCAGGCGCG CACCGCCCAA CCCCCACCTC CCGGTGTATG CAGTGGTGAT   3776

GCCTAAAGGA ATGTCACG                                                 3794
```

(2) INFORMATION FOR SEQ ID NO:28:

(i) SEQUENCE CHARACTERISTICS:
        (A) LENGTH: 875 amino acids
        (B) TYPE: amino acid
        (D) TOPOLOGY: linear (ii) MOLECULE TYPE: protein (xi) SEQUENCE DESCRIPTION: SEQ ID NO:28:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
                100                 105                 110
```

-continued

```
Phe Tyr Arg Ile Pro Val Leu Gly Leu Thr Thr Arg Met Ser Ile Tyr
        115                 120                 125
Ser Asp Lys Ser Ile His Leu Ser Phe Leu Arg Thr Val Pro Pro Tyr
130                 135                 140
Ser His Gln Ser Ser Val Trp Phe Glu Met Met Arg Val Tyr Ser Trp
145                 150                 155                 160
Asn His Ile Ile Leu Leu Val Ser Asp Asp His Glu Gly Arg Ala Ala
                165                 170                 175
Gln Lys Arg Leu Glu Thr Leu Leu Glu Glu Arg Glu Ser Lys Ser Lys
                180                 185                 190
Lys Arg Asn Tyr Glu Asn Leu Asp Gln Leu Ser Tyr Asp Asn Lys Arg
                195                 200                 205
Gly Pro Lys Ala Glu Lys Val Leu Gln Phe Asp Pro Gly Thr Lys Asn
        210                 215                 220
Val Thr Ala Leu Leu Met Glu Ala Lys Glu Leu Glu Ala Arg Val Ile
225                 230                 235                 240
Ile Leu Ser Ala Ser Glu Asp Ala Ala Thr Val Tyr Arg Ala Ala
                245                 250                 255
Ala Met Leu Asn Met Thr Gly Asn Thr Asn Ile Trp Lys Thr Gly Pro
                260                 265                 270
Leu Phe Lys Arg Val Leu Met Ser Ser Lys Tyr Ala Asp Gly Val Thr
        275                 280                 285
Gly Arg Val Glu Phe Asn Glu Asp Gly Asp Arg Lys Phe Ala Asn Tyr
        290                 295                 300
Ser Ile Met Asn Leu Gln Asn Arg Lys Leu Val Gln Val Gly Ile Tyr
305                 310                 315                 320
Asn Gly Thr His Val Ile Pro Asn Asp Arg Lys Ile Ile Trp Pro Gly
                325                 330                 335
Gly Glu Thr Glu Lys Pro Arg Gly Tyr Gln Met Ser Thr Arg Leu Lys
                340                 345                 350
Ile Val Thr Ile His Gln Glu Pro Phe Val Tyr Val Lys Pro Thr Leu
        355                 360                 365
Ser Asp Gly Thr Cys Lys Glu Glu Phe Thr Val Asn Gly Asp Pro Val
        370                 375                 380
Lys Lys Val Ile Cys Thr Gly Pro Asn Asp Thr Ser Pro Gly Ser Pro
385                 390                 395                 400
Arg His Thr Val Pro Gln Cys Cys Tyr Gly Phe Cys Ile Asp Leu Leu
                405                 410                 415
Ile Lys Leu Ala Arg Thr Met Asn Phe Thr Tyr Glu Val His Leu Val
                420                 425                 430
Ala Asp Gly Lys Phe Gly Thr Gln Glu Arg Val Asn Asn Ser Asn Lys
        435                 440                 445
Lys Glu Trp Asn Gly Met Met Gly Glu Leu Leu Ser Gly Gln Ala Asp
        450                 455                 460
Met Ile Val Ala Pro Leu Thr Ile Asn Asn Glu Arg Ala Gln Tyr Ile
465                 470                 475                 480
Glu Phe Ser Lys Pro Phe Lys Tyr Gln Gly Leu Thr Ile Leu Val Lys
                485                 490                 495
Lys Glu Ile Pro Arg Ser Thr Leu Asp Ser Phe Met Gln Pro Phe Gln
                500                 505                 510
Ser Thr Leu Trp Leu Leu Val Gly Leu Ser Val His Val Val Ala Val
        515                 520                 525
Met Leu Tyr Leu Leu Asp Arg Phe Ser Pro Phe Gly Arg Phe Lys Val
```

```
                530                 535                 540
Asn Ser Glu Glu Glu Glu Asp Ala Leu Thr Leu Ser Ser Ala Met
545                 550                 555                 560

Trp Phe Ser Trp Gly Val Leu Leu Asn Ser Gly Ile Gly Glu Gly Ala
                565                 570                 575

Pro Arg Ser Phe Ser Ala Arg Ile Leu Gly Met Val Trp Ala Gly Phe
                580                 585                 590

Ala Met Ile Ile Val Ala Ser Tyr Thr Ala Asn Leu Ala Ala Phe Leu
                595                 600                 605

Val Leu Asp Arg Pro Glu Glu Arg Ile Thr Gly Ile Asn Asp Pro Arg
                610                 615                 620

Leu Arg Asn Pro Ser Asp Lys Phe Ile Tyr Ala Thr Val Lys Gln Ser
625                 630                 635                 640

Ser Val Asp Ile Tyr Phe Arg Arg Gln Val Glu Leu Ser Thr Met Tyr
                645                 650                 655

Arg His Met Glu Lys His Asn Tyr Glu Ser Ala Ala Glu Ala Ile Gln
                660                 665                 670

Ala Val Arg Asp Asn Lys Leu His Ala Phe Ile Trp Asp Ser Ala Val
                675                 680                 685

Leu Glu Phe Glu Ala Ser Gln Lys Cys Asp Leu Val Thr Thr Gly Glu
                690                 695                 700

Leu Phe Phe Arg Ser Gly Phe Gly Ile Gly Met Arg Lys Asp Ser Pro
705                 710                 715                 720

Trp Lys Gln Asn Val Ser Leu Ser Ile Leu Lys Ser His Glu Asn Gly
                725                 730                 735

Phe Met Glu Asp Leu Asp Lys Thr Trp Val Arg Tyr Gln Glu Cys Asp
                740                 745                 750

Ser Arg Ser Asn Ala Pro Ala Thr Leu Thr Phe Glu Asn Met Ala Gly
                755                 760                 765

Val Phe Met Leu Val Ala Gly Gly Ile Val Ala Gly Ile Phe Leu Ile
                770                 775                 780

Phe Ile Glu Ile Ala Tyr Lys Arg His Lys Asp Ala Arg Arg Lys Gln
785                 790                 795                 800

Met Gln Leu Ala Phe Ala Ala Val Asn Val Trp Arg Lys Asn Leu Gln
                805                 810                 815

Asp Arg Lys Ser Gly Arg Ala Glu Pro Asp Pro Lys Lys Lys Ala Thr
                820                 825                 830

Phe Arg Ala Ile Thr Ser Thr Leu Ala Ser Ser Phe Lys Arg Arg Arg
                835                 840                 845

Ser Ser Lys Asp Thr Gln Tyr His Pro Thr Asp Ile Thr Gly Pro Leu
850                 855                 860

Asn Leu Ser Asp Pro Ser Val Ser Thr Val Val
865                 870                 875

(2) INFORMATION FOR SEQ ID NO:29:

(i) SEQUENCE CHARACTERISTICS:
        (A) LENGTH: 4094 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..2874
```

(xi) SEQUENCE DESCRIPTION: SEQ ID NO:29:

```
CAAGCCGGGC GTTCGGAGCT GTGCCCGGCC CCGCTTCAGC ACCGCGGACA GCGCCGGCCG          60

CGTGGGGCTG AGCGCCGAGC CCCCGCGCAC GCTTCAGCCC CCCTTCCCTC GGCCGACGTC         120

CCGGGACCGC CGCTCCGGGG GAGACGTGGC GTCCGCAGCC CGCGGGGCCG GGCGAGCGCA         180

GGACGGCCCG GAAGCCCCGC GGGGGATGCG CCGAGGGCCC CGCGTTCGCG CCGCGCAGAG         240

CCAGGCCCGC GGCCCGAGCC C ATG AGC ACC ATG CGC CTG CTG ACG CTC GCC          291
                        Met Ser Thr Met Arg Leu Leu Thr Leu Ala
                         1               5                  10

CTG CTG TTC TCC TGC TCC GTC GCC CGT GCC GCG TGC GAC CCC AAG ATC          339
Leu Leu Phe Ser Cys Ser Val Ala Arg Ala Ala Cys Asp Pro Lys Ile
             15                  20                  25

GTC AAC ATT GGC GCG GTG CTG AGC ACG CGG AAG CAC GAG CAG ATG TTC          387
Val Asn Ile Gly Ala Val Leu Ser Thr Arg Lys His Glu Gln Met Phe
         30                  35                  40

CGC GAG GCC GTG AAC CAG GCC AAC AAG CGG CAC GGC TCC TGG AAG ATT          435
Arg Glu Ala Val Asn Gln Ala Asn Lys Arg His Gly Ser Trp Lys Ile
     45                  50                  55

CAG CTC AAT GCC ACC TCC GTC ACG CAC AAG CCC AAC GCC ATC CAG ATG          483
Gln Leu Asn Ala Thr Ser Val Thr His Lys Pro Asn Ala Ile Gln Met
 60                  65                  70

GCT CTG TCG GTG TGC GAG GAC CTC ATC TCC AGC CAG GTC TAC GCC ATC          531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT          579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC          627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG          675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG          723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC          771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG          819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG          867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC          915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA          963
Ile Ile Leu Ser Ala Ser Glu Asp Asp Ala Ala Thr Val Tyr Arg Ala
    220                 225                 230

GCC GCG ATG CTG AAC ATG ACG GGC AAC ACC AAC ATC TGG AAG ACC GGG         1011
Ala Ala Met Leu Asn Met Thr Gly Asn Thr Asn Ile Trp Lys Thr Gly
235                 240                 245                 250

CCG CTC TTC AAG AGA GTG CTG ATG TCT TCC AAG TAT GCG GAT GGG GTG         1059
Pro Leu Phe Lys Arg Val Leu Met Ser Ser Lys Tyr Ala Asp Gly Val
                255                 260                 265
```

```
ACT GGT CGC GTG GAG TTC AAT GAG GAT GGG GAC CGG AAG TTC GCC AAC      1107
Thr Gly Arg Val Glu Phe Asn Glu Asp Gly Asp Arg Lys Phe Ala Asn
            270                 275                 280

TAC AGC ATC ATG AAC CTG CAG AAC CGC AAG CTG GTG CAA GTG GGC ATC      1155
Tyr Ser Ile Met Asn Leu Gln Asn Arg Lys Leu Val Gln Val Gly Ile
        285                 290                 295

TAC AAT GGC ACC CAC GTC ATC CCT AAT GAC AGG AAG ATC ATC TGG CCA      1203
Tyr Asn Gly Thr His Val Ile Pro Asn Asp Arg Lys Ile Ile Trp Pro
    300                 305                 310

GGC GGA GAG ACA GAG AAG CCT CGA GGG TAC CAG ATG TCC ACC AGA CTG      1251
Gly Gly Glu Thr Glu Lys Pro Arg Gly Tyr Gln Met Ser Thr Arg Leu
315                 320                 325                 330

AAG ATT GTG ACG ATC CAC CAG GAG CCC TTC GTG TAC GTC AAG CCC ACG      1299
Lys Ile Val Thr Ile His Gln Glu Pro Phe Val Tyr Val Lys Pro Thr
                335                 340                 345

CTG AGT GAT GGG ACA TGC AAG GAG GAG TTC ACA GTC AAC GGC GAC CCA      1347
Leu Ser Asp Gly Thr Cys Lys Glu Glu Phe Thr Val Asn Gly Asp Pro
            350                 355                 360

GTC AAG AAG GTG ATC TGC ACC GGG CCC AAC GAC ACG TCG CCG GGC AGC      1395
Val Lys Lys Val Ile Cys Thr Gly Pro Asn Asp Thr Ser Pro Gly Ser
        365                 370                 375

CCC CGC CAC ACG GTG CCT CAG TGT TGC TAC GGC TTT TGC ATC GAC CTG      1443
Pro Arg His Thr Val Pro Gln Cys Cys Tyr Gly Phe Cys Ile Asp Leu
    380                 385                 390

CTC ATC AAG CTG GCA CGG ACC ATG AAC TTC ACC TAC GAG GTG CAC CTG      1491
Leu Ile Lys Leu Ala Arg Thr Met Asn Phe Thr Tyr Glu Val His Leu
395                 400                 405                 410

GTG GCA GAT GGC AAG TTC GGC ACA CAG GAG CGG GTG AAC AAC AGC AAC      1539
Val Ala Asp Gly Lys Phe Gly Thr Gln Glu Arg Val Asn Asn Ser Asn
                415                 420                 425

AAG AAG GAG TGG AAT GGG ATG ATG GGC GAG CTG CTC AGC GGG CAG GCA      1587
Lys Lys Glu Trp Asn Gly Met Met Gly Glu Leu Leu Ser Gly Gln Ala
            430                 435                 440

GAC ATG ATC GTG GCG CCG CTA ACC ATA AAC AAC GAG CGC GCG CAG TAC      1635
Asp Met Ile Val Ala Pro Leu Thr Ile Asn Asn Glu Arg Ala Gln Tyr
        445                 450                 455

ATC GAG TTT TCC AAG CCC TTC AAG TAC CAG GGC CTG ACT ATT CTG GTC      1683
Ile Glu Phe Ser Lys Pro Phe Lys Tyr Gln Gly Leu Thr Ile Leu Val
    460                 465                 470

AAG AAG GAG ATT CCC CGG AGC ACG CTG GAC TCG TTC ATG CAG CCG TTC      1731
Lys Lys Glu Ile Pro Arg Ser Thr Leu Asp Ser Phe Met Gln Pro Phe
475                 480                 485                 490

CAG AGC ACA CTG TGG CTG CTG GTG GGG CTG TCG GTG CAC GTG GTG GCC      1779
Gln Ser Thr Leu Trp Leu Leu Val Gly Leu Ser Val His Val Val Ala
                495                 500                 505

GTG ATG CTG TAC CTG CTG GAC CGC TTC AGC CCC TTC GGC CGG TTC AAG      1827
Val Met Leu Tyr Leu Leu Asp Arg Phe Ser Pro Phe Gly Arg Phe Lys
            510                 515                 520

GTG AAC AGC GAG GAG GAG GAG GAG GAC GCA CTG ACC CTG TCC TCG GCC      1875
Val Asn Ser Glu Glu Glu Glu Glu Asp Ala Leu Thr Leu Ser Ser Ala
        525                 530                 535

ATG TGG TTC TCC TGG GGC GTC CTG CTC AAC TCC GGC ATC GGG GAA GGC      1923
Met Trp Phe Ser Trp Gly Val Leu Leu Asn Ser Gly Ile Gly Glu Gly
    540                 545                 550

GCC CCC AGA AGC TTC TCA GCG CGC ATC CTG GGC ATG GTG TGG GCC GGC      1971
Ala Pro Arg Ser Phe Ser Ala Arg Ile Leu Gly Met Val Trp Ala Gly
555                 560                 565                 570

TTT GCC ATG ATC ATC GTG GCC TCC TAC ACC GCC AAC CTG GCG GCC TTC      2019
Phe Ala Met Ile Ile Val Ala Ser Tyr Thr Ala Asn Leu Ala Ala Phe
                575                 580                 585
```

-continued

```
CTG GTG CTG GAC CGG CCG GAG GAG CGC ATC ACG GGC ATC AAC GAC CCT        2067
Leu Val Leu Asp Arg Pro Glu Glu Arg Ile Thr Gly Ile Asn Asp Pro
            590                 595                 600

CGG CTG AGG AAC CCC TCG GAC AAG TTT ATC TAC GCC ACG GTG AAG CAG        2115
Arg Leu Arg Asn Pro Ser Asp Lys Phe Ile Tyr Ala Thr Val Lys Gln
            605                 610                 615

AGC TCC GTG GAT ATC TAC TTC CGG CGC CAG GTG GAG CTG AGC ACC ATG        2163
Ser Ser Val Asp Ile Tyr Phe Arg Arg Gln Val Glu Leu Ser Thr Met
            620                 625                 630

TAC CGG CAT ATG GAG AAG CAC AAC TAC GAG AGT GCG GCG GAG GCC ATC        2211
Tyr Arg His Met Glu Lys His Asn Tyr Glu Ser Ala Ala Glu Ala Ile
635                 640                 645                 650

CAG GCC GTG AGA GAC AAC AAG CTG CAT GCC TTC ATC TGG GAC TCG GCG        2259
Gln Ala Val Arg Asp Asn Lys Leu His Ala Phe Ile Trp Asp Ser Ala
            655                 660                 665

GTG CTG GAG TTC GAG GCC TCG CAG AAG TGC GAC CTG GTG ACG ACT GGA        2307
Val Leu Glu Phe Glu Ala Ser Gln Lys Cys Asp Leu Val Thr Thr Gly
            670                 675                 680

GAG CTG TTT TTC CGC TCG GGC TTC GGC ATA GGC ATG CGC AAA GAC AGC        2355
Glu Leu Phe Phe Arg Ser Gly Phe Gly Ile Gly Met Arg Lys Asp Ser
            685                 690                 695

CCC TGG AAG CAG AAC GTC TCC CTG TCC ATC CTC AAG TCC CAC GAG AAT        2403
Pro Trp Lys Gln Asn Val Ser Leu Ser Ile Leu Lys Ser His Glu Asn
    700                 705                 710

GGC TTC ATG GAA GAC CTG GAC AAG ACG TGG GTT CGG TAT CAG GAA TGT        2451
Gly Phe Met Glu Asp Leu Asp Lys Thr Trp Val Arg Tyr Gln Glu Cys
715                 720                 725                 730

GAC TCG CGC AGC AAC GCC CCT GCG ACC CTT ACT TTT GAG AAC ATG GCC        2499
Asp Ser Arg Ser Asn Ala Pro Ala Thr Leu Thr Phe Glu Asn Met Ala
            735                 740                 745

GGG GTC TTC ATG CTG GTA GCT GGG GGC ATC GTG GCC GGG ATC TTC CTG        2547
Gly Val Phe Met Leu Val Ala Gly Gly Ile Val Ala Gly Ile Phe Leu
            750                 755                 760

ATT TTC ATC GAG ATT GCC TAC AAG CGG CAC AAG GAT GCT CGC CGG AAG        2595
Ile Phe Ile Glu Ile Ala Tyr Lys Arg His Lys Asp Ala Arg Arg Lys
            765                 770                 775

CAG ATG CAG CTG GCC TTT GCC GCC GTT AAC GTG TGG CGG AAG AAC CTG        2643
Gln Met Gln Leu Ala Phe Ala Ala Val Asn Val Trp Arg Lys Asn Leu
    780                 785                 790

CAG GAT AGA AAG AGT GGT AGA GCA GAG CCT GAC CCT AAA AAG AAA GCC        2691
Gln Asp Arg Lys Ser Gly Arg Ala Glu Pro Asp Pro Lys Lys Lys Ala
795                 800                 805                 810

ACA TTT AGG GCT ATC ACC TCC ACC CTG GCT TCC AGC TTC AAG AGG CGT        2739
Thr Phe Arg Ala Ile Thr Ser Thr Leu Ala Ser Ser Phe Lys Arg Arg
            815                 820                 825

AGG TCC TCC AAA GAC ACG AGC ACC GGG GGT GGA CGC GGT GCT TTG CAA        2787
Arg Ser Ser Lys Asp Thr Ser Thr Gly Gly Gly Arg Gly Ala Leu Gln
            830                 835                 840

AAC CAA AAA GAC ACA GTG CTG CCG CGA CGC GCT ATT GAG AGG GAG GAG        2835
Asn Gln Lys Asp Thr Val Leu Pro Arg Arg Ala Ile Glu Arg Glu Glu
            845                 850                 855

GGC CAG CTG CAG CTG TGT TCC CGT CAT AGG GAG AGC TGAGACTCCC             2881
Gly Gln Leu Gln Leu Cys Ser Arg His Arg Glu Ser
860                 865                 870

CGCCCGCCCT CCTCTGCCCC CTCCCCCGCA GACAGACAGA CAGACGGACG GGACAGCGGC      2941

CCGGCCCACG CAGAGCCCCG GAGCACCACG GGGTCGGGGG AGGAGCACCC CCAGCCTCCC      3001

CCAGGCTGCG CCTGCCCGCC CGCCGGTTGG CCGGCTGGCC GGTCCACCCC GTCCCGGCCC      3061
```

```
CGCGCGTGCC CCCAGCGTGG GGCTAACGGG CGCCTTGTCT GTGTATTTCT ATTTTGCAGC    3121

AGTACCATCC CACTGATATC ACGGGCCCGC TCAACCTCTC AGATCCCTCG GTCAGCACCG    3181

TGGTGTGAGG CCCCCGGAGG CGCCCACCTG CCCAGTTAGC CCGGCCAAGG ACACTGATGG    3241

GTCCTGCTGC TCGGGAAGGC CTGAGGGAAG CCCACCCGCC CCAGAGACTG CCCACCCTGG    3301

GCCTCCCGTC CGTCCGCCCG CCCACCCCGC TGCCTGGCGG GCAGCCCCTG CTGGACCAAG    3361

GTGCGGACCG GAGCGGCTGA GGACGGGGCA GAGCTGAGTC GGCTGGGCAG GGCCGCAGGG    3421

CGCTCCGGCA GAGGCAGGCC CCTGGGGTCT CTGAGCAGTG GGGAGCGGGG GCTAACTGCC    3481

CCCAGGCGGA GGGGCTTGGA GCAGAGACGG CAGCCCCATC CTTCCCGCAG CACCAGCCTG    3541

AGCCACAGTG GGGCCCATGG CCCCAGCTGG CTGGGTCGCC CCTCCTCGGG CGCCTGCGCT    3601

CCTCTGCAGC CTGAGCTCCA CCCTCCCCTC TTCTTGCGGC ACCGCCCACC AAACACCCCG    3661

TCTGCCCCTT GACGCCACAC GCCGGGGCTG GCGCTGCCCT CCCCCACGGC CGTCCCTGAC    3721

TTCCCAGCTG GCAGCGCCTC CCGCCGCCTC GGGCCGCCTC CTCCAGAATC GAGAGGGCTG    3781

AGCCCCTCCT CTCCTCGTCC GGCCTGCAGC ACAGAAGGGG GCCTCCCCGG GGGTCCCCGG    3841

ACGCTGGCTC GGGACTGTCT TCAACCCTGC CCTGCACCTT GGGCACGGGA GAGCGCCACC    3901

CGCCCGCCCC CGCCCTCGCT CCGGGTGCGT GACCGGCCCG CCACCTTGTA CAGAACCAGC    3961

ACTCCCAGGG CCCGAGCGCG TGCCTTCCCC GTGCGCAGCC GCGCTCTGCC CCTCCGTCCC    4021

CAGGGTGCAG GCGCGCACCG CCCAACCCCC ACCTCCCGGT GTATGCAGTG GTGATGCCTA    4081

AAGGAATGTC ACG                                                      4094
```

(2) INFORMATION FOR SEQ ID NO:30:

(i) SEQUENCE CHARACTERISTICS:
        (A) LENGTH: 870 amino acids
        (B) TYPE: amino acid
        (D) TOPOLOGY: linear (ii) MOLECULE TYPE: protein (xi) SEQUENCE DESCRIPTION: SEQ ID NO:30:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
 65                 70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
                100                 105                 110

Phe Tyr Arg Ile Pro Val Leu Gly Leu Thr Thr Arg Met Ser Ile Tyr
            115                 120                 125

Ser Asp Lys Ser Ile His Leu Ser Phe Leu Arg Thr Val Pro Pro Tyr
        130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
```

-continued

```
                165                 170                 175
Gln Lys Arg Leu Glu Thr Leu Leu Glu Glu Arg Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
210                 215                 220

Glu Asp Ala Ala Thr Val Tyr Arg Ala Ala Met Leu Asn Met
225                 230                 235                 240

Thr Gly Asn Thr Asn Ile Trp Lys Thr Gly Pro Leu Phe Lys Arg Val
                245                 250                 255

Leu Met Ser Ser Lys Tyr Ala Asp Gly Val Thr Gly Arg Val Glu Phe
            260                 265                 270

Asn Glu Asp Gly Asp Arg Lys Phe Ala Asn Tyr Ser Ile Met Asn Leu
        275                 280                 285

Gln Asn Arg Lys Leu Val Gln Val Gly Ile Tyr Asn Gly Thr His Val
290                 295                 300

Ile Pro Asn Asp Arg Lys Ile Ile Trp Pro Gly Gly Glu Thr Glu Lys
305                 310                 315                 320

Pro Arg Gly Tyr Gln Met Ser Thr Arg Leu Lys Ile Val Thr Ile His
                325                 330                 335

Gln Glu Pro Phe Val Tyr Val Lys Pro Thr Leu Ser Asp Gly Thr Cys
            340                 345                 350

Lys Glu Glu Phe Thr Val Asn Gly Asp Pro Val Lys Val Ile Cys
        355                 360                 365

Thr Gly Pro Asn Asp Thr Ser Pro Gly Ser Pro Arg His Thr Val Pro
370                 375                 380

Gln Cys Cys Tyr Gly Phe Cys Ile Asp Leu Leu Ile Lys Leu Ala Arg
385                 390                 395                 400

Thr Met Asn Phe Thr Tyr Glu Val His Leu Val Ala Asp Gly Lys Phe
                405                 410                 415

Gly Thr Gln Glu Arg Val Asn Asn Ser Asn Lys Lys Glu Trp Asn Gly
            420                 425                 430

Met Met Gly Glu Leu Leu Ser Gly Gln Ala Asp Met Ile Val Ala Pro
        435                 440                 445

Leu Thr Ile Asn Asn Glu Arg Ala Gln Tyr Ile Glu Phe Ser Lys Pro
450                 455                 460

Phe Lys Tyr Gln Gly Leu Thr Ile Leu Val Lys Lys Glu Ile Pro Arg
465                 470                 475                 480

Ser Thr Leu Asp Ser Phe Met Gln Pro Phe Gln Ser Thr Leu Trp Leu
                485                 490                 495

Leu Val Gly Leu Ser Val His Val Val Ala Val Met Leu Tyr Leu Leu
            500                 505                 510

Asp Arg Phe Ser Pro Phe Gly Arg Phe Lys Val Asn Ser Glu Glu Glu
        515                 520                 525

Glu Glu Asp Ala Leu Thr Leu Ser Ser Ala Met Trp Phe Ser Trp Gly
530                 535                 540

Val Leu Leu Asn Ser Gly Ile Gly Glu Gly Ala Pro Arg Ser Phe Ser
545                 550                 555                 560

Ala Arg Ile Leu Gly Met Val Trp Ala Gly Phe Ala Met Ile Ile Val
                565                 570                 575

Ala Ser Tyr Thr Ala Asn Leu Ala Ala Phe Leu Val Leu Asp Arg Pro
            580                 585                 590
```

```
Glu Glu Arg Ile Thr Gly Ile Asn Asp Pro Arg Leu Arg Asn Pro Ser
        595                 600                 605

Asp Lys Phe Ile Tyr Ala Thr Val Lys Gln Ser Ser Val Asp Ile Tyr
610                 615                 620

Phe Arg Arg Gln Val Glu Leu Ser Thr Met Tyr Arg His Met Glu Lys
625                 630                 635                 640

His Asn Tyr Glu Ser Ala Ala Glu Ala Ile Gln Ala Val Arg Asp Asn
                645                 650                 655

Lys Leu His Ala Phe Ile Trp Asp Ser Ala Val Leu Glu Phe Glu Ala
            660                 665                 670

Ser Gln Lys Cys Asp Leu Val Thr Thr Gly Glu Leu Phe Phe Arg Ser
        675                 680                 685

Gly Phe Gly Ile Gly Met Arg Lys Asp Ser Pro Trp Lys Gln Asn Val
690                 695                 700

Ser Leu Ser Ile Leu Lys Ser His Glu Asn Gly Phe Met Glu Asp Leu
705                 710                 715                 720

Asp Lys Thr Trp Val Arg Tyr Gln Glu Cys Asp Ser Arg Ser Asn Ala
                725                 730                 735

Pro Ala Thr Leu Thr Phe Glu Asn Met Ala Gly Val Phe Met Leu Val
            740                 745                 750

Ala Gly Gly Ile Val Ala Gly Ile Phe Leu Ile Phe Ile Glu Ile Ala
        755                 760                 765

Tyr Lys Arg His Lys Asp Ala Arg Arg Lys Gln Met Gln Leu Ala Phe
        770                 775                 780

Ala Ala Val Asn Val Trp Arg Lys Asn Leu Gln Asp Arg Lys Ser Gly
785                 790                 795                 800

Arg Ala Glu Pro Asp Pro Lys Lys Ala Thr Phe Arg Ala Ile Thr
                805                 810                 815

Ser Thr Leu Ala Ser Ser Phe Lys Arg Arg Arg Ser Ser Lys Asp Thr
            820                 825                 830

Ser Thr Gly Gly Gly Arg Gly Ala Leu Gln Asn Gln Lys Asp Thr Val
        835                 840                 845

Leu Pro Arg Arg Ala Ile Glu Arg Glu Glu Gly Gln Leu Gln Leu Cys
850                 855                 860

Ser Arg His Arg Glu Ser
865                 870

(2) INFORMATION FOR SEQ ID NO:31:

(i) SEQUENCE CHARACTERISTICS:
        (A) LENGTH: 3731 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..2826

(xi) SEQUENCE DESCRIPTION: SEQ ID NO:31:

CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240
```

```
CCAGGCCCGC GGCCCGAGCC C ATG AGC ACC ATG CGC CTG CTG ACG CTC GCC      291
                        Met Ser Thr Met Arg Leu Leu Thr Leu Ala
                         1               5                   10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
            30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                95                  100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG      867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC      915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA      963
Ile Ile Leu Ser Ala Ser Glu Asp Asp Ala Ala Thr Val Tyr Arg Ala
    220                 225                 230

GCC GCG ATG CTG AAC ATG ACG GGC AAC ACC AAC ATC TGG AAG ACC GGG     1011
Ala Ala Met Leu Asn Met Thr Gly Asn Thr Asn Ile Trp Lys Thr Gly
235                 240                 245                 250

CCG CTC TTC AAG AGA GTG CTG ATG TCT TCC AAG TAT GCG GAT GGG GTG     1059
Pro Leu Phe Lys Arg Val Leu Met Ser Ser Lys Tyr Ala Asp Gly Val
                255                 260                 265

ACT GGT CGC GTG GAG TTC AAT GAG GAT GGG GAC CGG AAG TTC GCC AAC     1107
Thr Gly Arg Val Glu Phe Asn Glu Asp Gly Asp Arg Lys Phe Ala Asn
            270                 275                 280

TAC AGC ATC ATG AAC CTG CAG AAC CGC AAG CTG GTG CAA GTG GGC ATC     1155
Tyr Ser Ile Met Asn Leu Gln Asn Arg Lys Leu Val Gln Val Gly Ile
        285                 290                 295

TAC AAT GGC ACC CAC GTC ATC CCT AAT GAC AGG AAG ATC ATC TGG CCA     1203
Tyr Asn Gly Thr His Val Ile Pro Asn Asp Arg Lys Ile Ile Trp Pro
```

```
                300              305              310
GGC GGA GAG ACA GAG AAG CCT CGA GGG TAC CAG ATG TCC ACC AGA CTG    1251
Gly Gly Glu Thr Glu Lys Pro Arg Gly Tyr Gln Met Ser Thr Arg Leu
315                 320                 325                 330

AAG ATT GTG ACG ATC CAC CAG GAG CCC TTC GTG TAC GTC AAG CCC ACG    1299
Lys Ile Val Thr Ile His Gln Glu Pro Phe Val Tyr Val Lys Pro Thr
                335                 340                 345

CTG AGT GAT GGG ACA TGC AAG GAG GAG TTC ACA GTC AAC GGC GAC CCA    1347
Leu Ser Asp Gly Thr Cys Lys Glu Glu Phe Thr Val Asn Gly Asp Pro
                350                 355                 360

GTC AAG AAG GTG ATC TGC ACC GGG CCC AAC GAC ACG TCG CCG GGC AGC    1395
Val Lys Lys Val Ile Cys Thr Gly Pro Asn Asp Thr Ser Pro Gly Ser
            365                 370                 375

CCC CGC CAC ACG GTG CCT CAG TGT TGC TAC GGC TTT TGC ATC GAC CTG    1443
Pro Arg His Thr Val Pro Gln Cys Cys Tyr Gly Phe Cys Ile Asp Leu
        380                 385                 390

CTC ATC AAG CTG GCA CGG ACC ATG AAC TTC ACC TAC GAG GTG CAC CTG    1491
Leu Ile Lys Leu Ala Arg Thr Met Asn Phe Thr Tyr Glu Val His Leu
395                 400                 405                 410

GTG GCA GAT GGC AAG TTC GGC ACA CAG GAG CGG GTG AAC AAC AGC AAC    1539
Val Ala Asp Gly Lys Phe Gly Thr Gln Glu Arg Val Asn Asn Ser Asn
                415                 420                 425

AAG AAG GAG TGG AAT GGG ATG ATG GGC GAG CTC CTC AGC GGG CAG GCA    1587
Lys Lys Glu Trp Asn Gly Met Met Gly Glu Leu Leu Ser Gly Gln Ala
            430                 435                 440

GAC ATG ATC GTG GCG CCG CTA ACC ATA AAC AAC GAG CGC GCG CAG TAC    1635
Asp Met Ile Val Ala Pro Leu Thr Ile Asn Asn Glu Arg Ala Gln Tyr
        445                 450                 455

ATC GAG TTT TCC AAG CCC TTC AAG TAC CAG GGC CTG ACT ATT CTG GTC    1683
Ile Glu Phe Ser Lys Pro Phe Lys Tyr Gln Gly Leu Thr Ile Leu Val
460                 465                 470

AAG AAG GAG ATT CCC CGG AGC ACG CTG GAC TCG TTC ATG CAG CCG TTC    1731
Lys Lys Glu Ile Pro Arg Ser Thr Leu Asp Ser Phe Met Gln Pro Phe
475                 480                 485                 490

CAG AGC ACA CTG TGG CTG CTG GTG GGG CTG TCG GTG CAC GTG GTG GCC    1779
Gln Ser Thr Leu Trp Leu Leu Val Gly Leu Ser Val His Val Val Ala
                495                 500                 505

GTG ATG CTG TAC CTG CTG GAC CGC TTC AGC CCC TTC GGC CGG TTC AAG    1827
Val Met Leu Tyr Leu Leu Asp Arg Phe Ser Pro Phe Gly Arg Phe Lys
            510                 515                 520

GTG AAC AGC GAG GAG GAG GAG GAG GAC GCA CTG ACC CTG TCC TCG GCC    1875
Val Asn Ser Glu Glu Glu Glu Glu Asp Ala Leu Thr Leu Ser Ser Ala
        525                 530                 535

ATG TGG TTC TCC TGG GGC GTC CTG CTC AAC TCC GGC ATC GGG GAA GGC    1923
Met Trp Phe Ser Trp Gly Val Leu Leu Asn Ser Gly Ile Gly Glu Gly
540                 545                 550

GCC CCC AGA AGC TTC TCA GCG CGC ATC CTG GGC ATG GTG TGG GCC GGC    1971
Ala Pro Arg Ser Phe Ser Ala Arg Ile Leu Gly Met Val Trp Ala Gly
555                 560                 565                 570

TTT GCC ATG ATC ATC GTG GCC TCC TAC ACC GCC AAC CTG GCG GCC TTC    2019
Phe Ala Met Ile Ile Val Ala Ser Tyr Thr Ala Asn Leu Ala Ala Phe
                575                 580                 585

CTG GTG CTG GAC CGG CCG GAG GAG CGC ATC ACG GGC ATC AAC GAC CCT    2067
Leu Val Leu Asp Arg Pro Glu Glu Arg Ile Thr Gly Ile Asn Asp Pro
            590                 595                 600

CGG CTG AGG AAC CCC TCG GAC AAG TTT ATC TAC GCC ACG GTG AAG CAG    2115
Arg Leu Arg Asn Pro Ser Asp Lys Phe Ile Tyr Ala Thr Val Lys Gln
        605                 610                 615

AGC TCC GTG GAT ATC TAC TTC CGG CGC CAG GTG GAG CTG AGC ACC ATG    2163
```

```
Ser Ser Val Asp Ile Tyr Phe Arg Arg Gln Val Glu Leu Ser Thr Met
        620                 625                 630

TAC CGG CAT ATG GAG AAG CAC AAC TAC GAG AGT GCG GCG GAG GCC ATC          2211
Tyr Arg His Met Glu Lys His Asn Tyr Glu Ser Ala Ala Glu Ala Ile
635                 640                 645                 650

CAG GCC GTG AGA GAC AAC AAG CTG CAT GCC TTC ATC TGG GAC TCG GCG          2259
Gln Ala Val Arg Asp Asn Lys Leu His Ala Phe Ile Trp Asp Ser Ala
                655                 660                 665

GTG CTG GAG TTC GAG GCC TCG CAG AAG TGC GAC CTG GTG ACG ACT GGA          2307
Val Leu Glu Phe Glu Ala Ser Gln Lys Cys Asp Leu Val Thr Thr Gly
            670                 675                 680

GAG CTG TTT TTC CGC TCG GGC TTC GGC ATA GGC ATG CGC AAA GAC AGC          2355
Glu Leu Phe Phe Arg Ser Gly Phe Gly Ile Gly Met Arg Lys Asp Ser
        685                 690                 695

CCC TGG AAG CAG AAC GTC TCC CTG TCC ATC CTC AAG TCC CAC GAG AAT          2403
Pro Trp Lys Gln Asn Val Ser Leu Ser Ile Leu Lys Ser His Glu Asn
700                 705                 710

GGC TTC ATG GAA GAC CTG GAC AAG ACG TGG GTT CGG TAT CAG GAA TGT          2451
Gly Phe Met Glu Asp Leu Asp Lys Thr Trp Val Arg Tyr Gln Glu Cys
715                 720                 725                 730

GAC TCG CGC AGC AAC GCC CCT GCG ACC CTT ACT TTT GAG AAC ATG GCC          2499
Asp Ser Arg Ser Asn Ala Pro Ala Thr Leu Thr Phe Glu Asn Met Ala
                735                 740                 745

GGG GTC TTC ATG CTG GTA GCT GGG GGC ATC GTG GCC GGG ATC TTC CTG          2547
Gly Val Phe Met Leu Val Ala Gly Gly Ile Val Ala Gly Ile Phe Leu
            750                 755                 760

ATT TTC ATC GAG ATT GCC TAC AAG CGG CAC AAG GAT GCT CGC CGG AAG          2595
Ile Phe Ile Glu Ile Ala Tyr Lys Arg His Lys Asp Ala Arg Arg Lys
        765                 770                 775

CAG ATG CAG CTG GCC TTT GCC GCC GTT AAC GTG TGG CGG AAG AAC CTG          2643
Gln Met Gln Leu Ala Phe Ala Ala Val Asn Val Trp Arg Lys Asn Leu
780                 785                 790

CAG GAT AGA AAG AGT GGT AGA GCA GAG CCT GAC CCT AAA AAG AAA GCC          2691
Gln Asp Arg Lys Ser Gly Arg Ala Glu Pro Asp Pro Lys Lys Lys Ala
795                 800                 805                 810

ACA TTT AGG GCT ATC ACC TCC ACC CTG GCT TCC AGC TTC AAG AGG CGT          2739
Thr Phe Arg Ala Ile Thr Ser Thr Leu Ala Ser Ser Phe Lys Arg Arg
                815                 820                 825

AGG TCC TCC AAA GAC ACG CAG TAC CAT CCC ACT GAT ATC ACG GGC CCG          2787
Arg Ser Ser Lys Asp Thr Gln Tyr His Pro Thr Asp Ile Thr Gly Pro
            830                 835                 840

CTC AAC CTC TCA GAT CCC TCG GTC AGC ACC GTG GTG TGAGGCCCCC               2833
Leu Asn Leu Ser Asp Pro Ser Val Ser Thr Val Val
        845                 850                 855

GGAGGCGCCC ACCTGCCCAG TTAGCCCGGC CAAGGACACT GATGGGTCCT GCTGCTCGGG        2893

AAGGCCTGAG GGAAGCCCAC CCGCCCCAGA GACTGCCCAC CCTGGGCCTC CCGTCCGTCC        2953

GCCCGCCCAC CCCGCTGCCT GGCGGGCAGC CCCTGCTGGA CCAAGGTGCG GACCGGAGCG        3013

GCTGAGGACG GGGCAGAGCT GAGTCGGCTG GGCAGGGCCG CAGGGCGCTC CGGCAGAGGC        3073

AGGCCCCTGG GGTCTCTGAG CAGTGGGGAG CGGGGGCTAA CTGCCCCCAG GCGGAGGGGC        3133

TTGGAGCAGA GACGGCAGCC CCATCCTTCC CGCAGCACCA GCCTGAGCCA CAGTGGGGCC        3193

CATGGCCCCA GCTGGCTGGG TCGCCCCTCC TCGGGCGCCT GCGCTCCTCT GCAGCCTGAG        3253

CTCCACCCTC CCCTCTTCTT GCGGCACCGC CCACCAAACA CCCCGTCTGC CCCTTGACGC        3313

CACACGCCGG GGCTGGCGCT GCCCTCCCCC ACGGCCGTCC CTGACTTCCC AGCTGGCAGC        3373

GCCTCCCGCC GCCTCGGGCC GCCTCCTCCA GAATCGAGAG GGCTGAGCCC CTCCTCTCCT        3433
```

```
CGTCCGGCCT GCAGCACAGA AGGGGGCCTC CCCGGGGGTC CCCGGACGCT GGCTCGGGAC    3493

TGTCTTCAAC CCTGCCCTGC ACCTTGGGCA CGGGAGAGCG CCACCCGCCC GCCCCCGCCC    3553

TCGCTCCGGG TGCGTGACCG GCCCGCCACC TTGTACAGAA CCAGCACTCC CAGGGCCCGA    3613

GCGCGTGCCT TCCCCGTGCG CAGCCGCGCT CTGCCCCTCC GTCCCAGGG TGCAGGCGCG    3673

CACCGCCCAA CCCCCACCTC CCGGTGTATG CAGTGGTGAT GCCTAAAGGA ATGTCACG     3731
```

(2) INFORMATION FOR SEQ ID NO:32:

(i) SEQUENCE CHARACTERISTICS:
        (A) LENGTH: 854 amino acids
        (B) TYPE: amino acid
        (D) TOPOLOGY: linear (ii) MOLECULE TYPE: protein (xi) SEQUENCE DESCRIPTION: SEQ ID NO:32:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Asn Thr Asn Ile Trp Lys Thr Gly Pro Leu Phe Lys Arg Val
                245                 250                 255

Leu Met Ser Ser Lys Tyr Ala Asp Gly Val Thr Gly Arg Val Glu Phe
            260                 265                 270

Asn Glu Asp Gly Asp Arg Lys Phe Ala Asn Tyr Ser Ile Met Asn Leu
        275                 280                 285

Gln Asn Arg Lys Leu Val Gln Val Gly Ile Tyr Asn Gly Thr His Val
    290                 295                 300
```

-continued

```
Ile Pro Asn Asp Arg Lys Ile Ile Trp Pro Gly Gly Glu Thr Glu Lys
305                 310                 315                 320

Pro Arg Gly Tyr Gln Met Ser Thr Arg Leu Lys Ile Val Thr Ile His
            325                 330                 335

Gln Glu Pro Phe Val Tyr Val Lys Pro Thr Leu Ser Asp Gly Thr Cys
            340                 345                 350

Lys Glu Glu Phe Thr Val Asn Gly Asp Pro Val Lys Lys Val Ile Cys
            355                 360                 365

Thr Gly Pro Asn Asp Thr Ser Pro Gly Ser Pro Arg His Thr Val Pro
370                 375                 380

Gln Cys Cys Tyr Gly Phe Cys Ile Asp Leu Leu Ile Lys Leu Ala Arg
385                 390                 395                 400

Thr Met Asn Phe Thr Tyr Glu Val His Leu Val Ala Asp Gly Lys Phe
                405                 410                 415

Gly Thr Gln Glu Arg Val Asn Asn Ser Asn Lys Lys Glu Trp Asn Gly
            420                 425                 430

Met Met Gly Glu Leu Leu Ser Gly Gln Ala Asp Met Ile Val Ala Pro
            435                 440                 445

Leu Thr Ile Asn Asn Glu Arg Ala Gln Tyr Ile Glu Phe Ser Lys Pro
    450                 455                 460

Phe Lys Tyr Gln Gly Leu Thr Ile Leu Val Lys Lys Glu Ile Pro Arg
465                 470                 475                 480

Ser Thr Leu Asp Ser Phe Met Gln Pro Phe Gln Ser Thr Leu Trp Leu
                485                 490                 495

Leu Val Gly Leu Ser Val His Val Val Ala Val Met Leu Tyr Leu Leu
            500                 505                 510

Asp Arg Phe Ser Pro Phe Gly Arg Phe Lys Val Asn Ser Glu Glu Glu
            515                 520                 525

Glu Glu Asp Ala Leu Thr Leu Ser Ser Ala Met Trp Phe Ser Trp Gly
            530                 535                 540

Val Leu Leu Asn Ser Gly Ile Gly Glu Gly Ala Pro Arg Ser Phe Ser
545                 550                 555                 560

Ala Arg Ile Leu Gly Met Val Trp Ala Gly Phe Ala Met Ile Ile Val
                565                 570                 575

Ala Ser Tyr Thr Ala Asn Leu Ala Ala Phe Leu Val Leu Asp Arg Pro
            580                 585                 590

Glu Glu Arg Ile Thr Gly Ile Asn Asp Pro Arg Leu Arg Asn Pro Ser
            595                 600                 605

Asp Lys Phe Ile Tyr Ala Thr Val Lys Gln Ser Ser Val Asp Ile Tyr
    610                 615                 620

Phe Arg Arg Gln Val Glu Leu Ser Thr Met Tyr Arg His Met Glu Lys
625                 630                 635                 640

His Asn Tyr Glu Ser Ala Ala Glu Ala Ile Gln Ala Val Arg Asp Asn
                645                 650                 655

Lys Leu His Ala Phe Ile Trp Asp Ser Ala Val Leu Glu Phe Glu Ala
            660                 665                 670

Ser Gln Lys Cys Asp Leu Val Thr Thr Gly Glu Leu Phe Phe Arg Ser
            675                 680                 685

Gly Phe Gly Ile Gly Met Arg Lys Asp Ser Pro Trp Lys Gln Asn Val
            690                 695                 700

Ser Leu Ser Ile Leu Lys Ser His Glu Asn Gly Phe Met Glu Asp Leu
705                 710                 715                 720

Asp Lys Thr Trp Val Arg Tyr Gln Glu Cys Asp Ser Arg Ser Asn Ala
```

```
                    725                 730                 735
Pro Ala Thr Leu Thr Phe Glu Asn Met Ala Gly Val Phe Met Leu Val
            740                 745                 750

Ala Gly Gly Ile Val Ala Gly Ile Phe Leu Ile Phe Ile Glu Ile Ala
            755                 760                 765

Tyr Lys Arg His Lys Asp Ala Arg Arg Lys Gln Met Gln Leu Ala Phe
            770                 775                 780

Ala Ala Val Asn Val Trp Arg Lys Asn Leu Gln Asp Arg Lys Ser Gly
785                 790                 795                 800

Arg Ala Glu Pro Asp Pro Lys Lys Ala Thr Phe Arg Ala Ile Thr
                805                 810                 815

Ser Thr Leu Ala Ser Ser Phe Lys Arg Arg Ser Ser Lys Asp Thr
            820                 825                 830

Gln Tyr His Pro Thr Asp Ile Thr Gly Pro Leu Asn Leu Ser Asp Pro
            835                 840                 845

Ser Val Ser Thr Val Val
    850
```

(2) INFORMATION FOR SEQ ID NO:33:

(i) SEQUENCE CHARACTERISTICS:
        (A) LENGTH: 3007 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..2988

(xi) SEQUENCE DESCRIPTION: SEQ ID NO:33:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                       Met Ser Thr Met Arg Leu Leu Thr Leu Ala
                        1               5                   10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
            30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                95                  100                 105
```

| | | |
|---|---|---|
| GTC TCC TAC ACA GCC GGC TTC TAC CGC ATA CCC GTG CTG GGG CTG ACC<br>Val Ser Tyr Thr Ala Gly Phe Tyr Arg Ile Pro Val Leu Gly Leu Thr<br>110                                  115                        120 | 627 |
| ACC CGC ATG TCC ATC TAC TCG GAC AAG AGC ATC CAC CTG AGC TTC CTG<br>Thr Arg Met Ser Ile Tyr Ser Asp Lys Ser Ile His Leu Ser Phe Leu<br>            125                            130                            135 | 675 |
| CGC ACC GTG CCG CCC TAC TCC CAC CAG TCC AGC GTG TGG TTT GAG ATG<br>Arg Thr Val Pro Pro Tyr Ser His Gln Ser Ser Val Trp Phe Glu Met<br>    140                              145                            150 | 723 |
| ATG CGT GTC TAC AGC TGG AAC CAC ATC ATC CTG CTG GTC AGC GAC GAC<br>Met Arg Val Tyr Ser Trp Asn His Ile Ile Leu Leu Val Ser Asp Asp<br>155                                160                        165                        170 | 771 |
| CAC GAG GGC CGG GCG GCT CAG AAA CGC CTG GAG ACG CTG CTG GAG GAG<br>His Glu Gly Arg Ala Ala Gln Lys Arg Leu Glu Thr Leu Leu Glu Glu<br>                    175                            180                          185 | 819 |
| CGT GAG TCC AAG GCA GAG AAG GTG CTG CAG TTT GAC CCA GGG ACC AAG<br>Arg Glu Ser Lys Ala Glu Lys Val Leu Gln Phe Asp Pro Gly Thr Lys<br>            190                            195                            200 | 867 |
| AAC GTG ACG GCC CTG CTG ATG GAG GCG AAA GAG CTG GAG GCC CGG GTC<br>Asn Val Thr Ala Leu Leu Met Glu Ala Lys Glu Leu Glu Ala Arg Val<br>              205                          210                        215 | 915 |
| ATC ATC CTT TCT GCC AGC GAG GAC GAT GCT GCC ACT GTA TAC CGC GCA<br>Ile Ile Leu Ser Ala Ser Glu Asp Asp Ala Ala Thr Val Tyr Arg Ala<br>220                                225                              230 | 963 |
| GCC GCG ATG CTG AAC ATG ACG GGC AAC ACC AAC ATC TGG AAG ACC GGG<br>Ala Ala Met Leu Asn Met Thr Gly Asn Thr Asn Ile Trp Lys Thr Gly<br>235                                240                        245                        250 | 1011 |
| CCG CTC TTC AAG AGA GTG CTG ATG TCT TCC AAG TAT GCG GAT GGG GTG<br>Pro Leu Phe Lys Arg Val Leu Met Ser Ser Lys Tyr Ala Asp Gly Val<br>                    255                            260                          265 | 1059 |
| ACT GGT CGC GTG GAG TTC AAT GAG GAT GGG GAC CGG AAG TTC GCC AAC<br>Thr Gly Arg Val Glu Phe Asn Glu Asp Gly Asp Arg Lys Phe Ala Asn<br>            270                            275                            280 | 1107 |
| TAC AGC ATC ATG AAC CTG CAG AAC CGC AAG CTG GTG CAA GTG GGC ATC<br>Tyr Ser Ile Met Asn Leu Gln Asn Arg Lys Leu Val Gln Val Gly Ile<br>              285                          290                        295 | 1155 |
| TAC AAT GGC ACC CAC GTC ATC CCT AAT GAC AGG AAG ATC ATC TGG CCA<br>Tyr Asn Gly Thr His Val Ile Pro Asn Asp Arg Lys Ile Ile Trp Pro<br>300                                305                            310 | 1203 |
| GGC GGA GAG ACA GAG AAG CCT CGA GGG TAC CAG ATG TCC ACC AGA CTG<br>Gly Gly Glu Thr Glu Lys Pro Arg Gly Tyr Gln Met Ser Thr Arg Leu<br>315                                320                        325                        330 | 1251 |
| AAG ATT GTG ACG ATC CAC CAG GAG CCC TTC GTG TAC GTC AAG CCC ACG<br>Lys Ile Val Thr Ile His Gln Glu Pro Phe Val Tyr Val Lys Pro Thr<br>                    335                            340                          345 | 1299 |
| CTG AGT GAT GGG ACA TGC AAG GAG GAG TTC ACA GTC AAC GGC GAC CCA<br>Leu Ser Asp Gly Thr Cys Lys Glu Glu Phe Thr Val Asn Gly Asp Pro<br>                      350                            355                          360 | 1347 |
| GTC AAG AAG GTG ATC TGC ACC GGG CCC AAC GAC ACG TCG CCG GGC AGC<br>Val Lys Lys Val Ile Cys Thr Gly Pro Asn Asp Thr Ser Pro Gly Ser<br>                        365                            370                        375 | 1395 |
| CCC CGC CAC ACG GTG CCT CAG TGT TGC TAC GGC TTT TGC ATC GAC CTG<br>Pro Arg His Thr Val Pro Gln Cys Cys Tyr Gly Phe Cys Ile Asp Leu<br>380                                385                            390 | 1443 |
| CTC ATC AAG CTG GCA CGG ACC ATG AAC TTC ACC TAC GAG GTG CAC CTG<br>Leu Ile Lys Leu Ala Arg Thr Met Asn Phe Thr Tyr Glu Val His Leu<br>395                                400                        405                        410 | 1491 |
| GTG GCA GAT GGC AAG TTC GGC ACA CAG GAG CGG GTG AAC AAC AGC AAC<br>Val Ala Asp Gly Lys Phe Gly Thr Gln Glu Arg Val Asn Asn Ser Asn<br>                    415                            420                          425 | 1539 |

```
AAG AAG GAG TGG AAT GGG ATG ATG GGC GAG CTG CTC AGC GGG CAG GCA    1587
Lys Lys Glu Trp Asn Gly Met Met Gly Glu Leu Leu Ser Gly Gln Ala
            430                 435                 440

GAC ATG ATC GTG GCG CCG CTA ACC ATA AAC AAC GAG CGC GCG CAG TAC    1635
Asp Met Ile Val Ala Pro Leu Thr Ile Asn Asn Glu Arg Ala Gln Tyr
            445                 450                 455

ATC GAG TTT TCC AAG CCC TTC AAG TAC CAG GGC CTG ACT ATT CTG GTC    1683
Ile Glu Phe Ser Lys Pro Phe Lys Tyr Gln Gly Leu Thr Ile Leu Val
            460                 465                 470

AAG AAG GAG ATT CCC CGG AGC ACG CTG GAC TCG TTC ATG CAG CCG TTC    1731
Lys Lys Glu Ile Pro Arg Ser Thr Leu Asp Ser Phe Met Gln Pro Phe
475                 480                 485                 490

CAG AGC ACA CTG TGG CTG CTG GTG GGG CTG TCG GTG CAC GTG GTG GCC    1779
Gln Ser Thr Leu Trp Leu Leu Val Gly Leu Ser Val His Val Val Ala
            495                 500                 505

GTG ATG CTG TAC CTG CTG GAC CGC TTC AGC CCC TTC GGC CGG TTC AAG    1827
Val Met Leu Tyr Leu Leu Asp Arg Phe Ser Pro Phe Gly Arg Phe Lys
            510                 515                 520

GTG AAC AGC GAG GAG GAG GAG GAG GAC GCA CTG ACC CTG TCC TCG GCC    1875
Val Asn Ser Glu Glu Glu Glu Glu Asp Ala Leu Thr Leu Ser Ser Ala
            525                 530                 535

ATG TGG TTC TCC TGG GGC GTC CTG CTC AAC TCC GGC ATC GGG GAA GGC    1923
Met Trp Phe Ser Trp Gly Val Leu Leu Asn Ser Gly Ile Gly Glu Gly
            540                 545                 550

GCC CCC AGA AGC TTC TCA GCG CGC ATC CTG GGC ATG GTG TGG GCC GGC    1971
Ala Pro Arg Ser Phe Ser Ala Arg Ile Leu Gly Met Val Trp Ala Gly
555                 560                 565                 570

TTT GCC ATG ATC ATC GTG GCC TCC TAC ACC GCC AAC CTG GCG GCC TTC    2019
Phe Ala Met Ile Ile Val Ala Ser Tyr Thr Ala Asn Leu Ala Ala Phe
            575                 580                 585

CTG GTG CTG GAC CGG CCG GAG GAG CGC ATC ACG GGC ATC AAC GAC CCT    2067
Leu Val Leu Asp Arg Pro Glu Glu Arg Ile Thr Gly Ile Asn Asp Pro
            590                 595                 600

CGG CTG AGG AAC CCC TCG GAC AAG TTT ATC TAC GCC ACG GTG AAG CAG    2115
Arg Leu Arg Asn Pro Ser Asp Lys Phe Ile Tyr Ala Thr Val Lys Gln
            605                 610                 615

AGC TCC GTG GAT ATC TAC TTC CGG CGC CAG GTG GAG CTG AGC ACC ATG    2163
Ser Ser Val Asp Ile Tyr Phe Arg Arg Gln Val Glu Leu Ser Thr Met
620                 625                 630

TAC CGG CAT ATG GAG AAG CAC AAC TAC GAG AGT GCG GCG GAG GCC ATC    2211
Tyr Arg His Met Glu Lys His Asn Tyr Glu Ser Ala Ala Glu Ala Ile
635                 640                 645                 650

CAG GCC GTG AGA GAC AAC AAG CTG CAT GCC TTC ATC TGG GAC TCG GCG    2259
Gln Ala Val Arg Asp Asn Lys Leu His Ala Phe Ile Trp Asp Ser Ala
            655                 660                 665

GTG CTG GAG TTC GAG GCC TCG CAG AAG TGC GAC CTG GTG ACG ACT GGA    2307
Val Leu Glu Phe Glu Ala Ser Gln Lys Cys Asp Leu Val Thr Thr Gly
            670                 675                 680

GAG CTG TTT TTC CGC TCG GGC TTC GGC ATA GGC ATG CGC AAA GAC AGC    2355
Glu Leu Phe Phe Arg Ser Gly Phe Gly Ile Gly Met Arg Lys Asp Ser
            685                 690                 695

CCC TGG AAG CAG AAC GTC TCC CTG TCC ATC CTC AAG TCC CAC GAG AAT    2403
Pro Trp Lys Gln Asn Val Ser Leu Ser Ile Leu Lys Ser His Glu Asn
700                 705                 710

GGC TTC ATG GAA GAC CTG GAC AAG ACG TGG GTT CGG TAT CAG GAA TGT    2451
Gly Phe Met Glu Asp Leu Asp Lys Thr Trp Val Arg Tyr Gln Glu Cys
715                 720                 725                 730

GAC TCG CGC AGC AAC GCC CCT GCG ACC CTT ACT TTT GAG AAC ATG GCC    2499
Asp Ser Arg Ser Asn Ala Pro Ala Thr Leu Thr Phe Glu Asn Met Ala
```

-continued

```
                     735                  740                   745
GGG GTC TTC ATG CTG GTA GCT GGG GGC ATC GTG GCC GGG ATC TTC CTG       2547
Gly Val Phe Met Leu Val Ala Gly Gly Ile Val Ala Gly Ile Phe Leu
                750                 755                 760

ATT TTC ATC GAG ATT GCC TAC AAG CGG CAC AAG GAT GCT CGC CGG AAG       2595
Ile Phe Ile Glu Ile Ala Tyr Lys Arg His Lys Asp Ala Arg Arg Lys
            765                 770                 775

CAG ATG CAG CTG GCC TTT GCC GCC GTT AAC GTG TGG CGG AAG AAC CTG       2643
Gln Met Gln Leu Ala Phe Ala Ala Val Asn Val Trp Arg Lys Asn Leu
        780                 785                 790

CAG GAT AGA AAG AGT GGT AGA GCA GAG CCT GAC CCT AAA AAG AAA GCC       2691
Gln Asp Arg Lys Ser Gly Arg Ala Glu Pro Asp Pro Lys Lys Lys Ala
795                 800                 805                 810

ACA TTT AGG GCT ATC ACC TCC ACC CTG GCT TCC AGC TTC AAG AGG CGT       2739
Thr Phe Arg Ala Ile Thr Ser Thr Leu Ala Ser Ser Phe Lys Arg Arg
                815                 820                 825

AGG TCC TCC AAA GAC ACG CTG GCT CGG GAC TGT CTT CAA CCC TGC CCT       2787
Arg Ser Ser Lys Asp Thr Leu Ala Arg Asp Cys Leu Gln Pro Cys Pro
            830                 835                 840

GCA CCT TGG GCA CGG GAG AGC GCC ACC CGC CCG CCG CCC TCG CTC           2835
Ala Pro Trp Ala Arg Glu Ser Ala Thr Arg Pro Pro Pro Ser Leu
        845                 850                 855

CGG GTG CGT GAC CGG CCC GCC ACC TTG TAC AGA ACC AGC ACT CCC AGG       2883
Arg Val Arg Asp Arg Pro Ala Thr Leu Tyr Arg Thr Ser Thr Pro Arg
    860                 865                 870

GCC CGA GCG CGT GCC TTC CCC GTG CGC AGC CGC GCT CTG CCC CTC CGT       2931
Ala Arg Ala Arg Ala Phe Pro Val Arg Ser Arg Ala Leu Pro Leu Arg
875                 880                 885                 890

CCC CAG GGT GCA GGC GCG CAC CGC CCA ACC CCC ACC TCC CGG TGT ATG       2979
Pro Gln Gly Ala Gly Ala His Arg Pro Thr Pro Thr Ser Arg Cys Met
                895                 900                 905

CAG TGG TGATGCCTAA AGGAATGTCA CG                                      3007
Gln Trp
```

(2) INFORMATION FOR SEQ ID NO:34:

(i) SEQUENCE CHARACTERISTICS:
        (A) LENGTH: 908 amino acids
        (B) TYPE: amino acid
        (D) TOPOLOGY: linear (ii) MOLECULE TYPE: protein (xi) SEQUENCE DESCRIPTION: SEQ ID NO:34:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
```

-continued

```
            115                 120                 125
Ser Asp Lys Ser Ile His Leu Ser Phe Leu Arg Thr Val Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp His Glu Gly Arg Ala Ala
                    165                 170                 175

Gln Lys Arg Leu Glu Thr Leu Leu Glu Glu Arg Glu Ser Lys Ala Glu
                180                 185                 190

Lys Val Leu Gln Phe Asp Pro Gly Thr Lys Asn Val Thr Ala Leu Leu
            195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Met Leu Asn Met
225                 230                 235                 240

Thr Gly Asn Thr Asn Ile Trp Lys Thr Gly Pro Leu Phe Lys Arg Val
                    245                 250                 255

Leu Met Ser Ser Lys Tyr Ala Asp Gly Val Thr Gly Arg Val Glu Phe
                260                 265                 270

Asn Glu Asp Gly Asp Arg Lys Phe Ala Asn Tyr Ser Ile Met Asn Leu
            275                 280                 285

Gln Asn Arg Lys Leu Val Gln Val Gly Ile Tyr Asn Gly Thr His Val
    290                 295                 300

Ile Pro Asn Asp Arg Lys Ile Ile Trp Pro Gly Gly Glu Thr Glu Lys
305                 310                 315                 320

Pro Arg Gly Tyr Gln Met Ser Thr Arg Leu Lys Ile Val Thr Ile His
                    325                 330                 335

Gln Glu Pro Phe Val Tyr Val Lys Pro Thr Leu Ser Asp Gly Thr Cys
                340                 345                 350

Lys Glu Glu Phe Thr Val Asn Gly Asp Pro Val Lys Lys Val Ile Cys
            355                 360                 365

Thr Gly Pro Asn Asp Thr Ser Pro Gly Ser Pro Arg His Thr Val Pro
    370                 375                 380

Gln Cys Cys Tyr Gly Phe Cys Ile Asp Leu Leu Ile Lys Leu Ala Arg
385                 390                 395                 400

Thr Met Asn Phe Thr Tyr Glu Val His Leu Val Ala Asp Gly Lys Phe
                    405                 410                 415

Gly Thr Gln Glu Arg Val Asn Asn Ser Asn Lys Lys Glu Trp Asn Gly
                420                 425                 430

Met Met Gly Glu Leu Leu Ser Gly Gln Ala Asp Met Ile Val Ala Pro
            435                 440                 445

Leu Thr Ile Asn Asn Glu Arg Ala Gln Tyr Ile Glu Phe Ser Lys Pro
    450                 455                 460

Phe Lys Tyr Gln Gly Leu Thr Ile Leu Val Lys Lys Glu Ile Pro Arg
465                 470                 475                 480

Ser Thr Leu Asp Ser Phe Met Gln Pro Phe Gln Ser Thr Leu Trp Leu
                    485                 490                 495

Leu Val Gly Leu Ser Val His Val Val Ala Val Met Leu Tyr Leu Leu
                500                 505                 510

Asp Arg Phe Ser Pro Phe Gly Arg Phe Lys Val Asn Ser Glu Glu Glu
            515                 520                 525

Glu Glu Asp Ala Leu Thr Leu Ser Ser Ala Met Trp Phe Ser Trp Gly
    530                 535                 540
```

```
Val Leu Leu Asn Ser Gly Ile Gly Glu Gly Ala Pro Arg Ser Phe Ser
545                 550                 555                 560

Ala Arg Ile Leu Gly Met Val Trp Ala Gly Phe Ala Met Ile Ile Val
                565                 570                 575

Ala Ser Tyr Thr Ala Asn Leu Ala Ala Phe Leu Val Leu Asp Arg Pro
            580                 585                 590

Glu Glu Arg Ile Thr Gly Ile Asn Asp Pro Arg Leu Arg Asn Pro Ser
            595                 600                 605

Asp Lys Phe Ile Tyr Ala Thr Val Lys Gln Ser Ser Val Asp Ile Tyr
610                 615                 620

Phe Arg Arg Gln Val Glu Leu Ser Thr Met Tyr Arg His Met Glu Lys
625                 630                 635                 640

His Asn Tyr Glu Ser Ala Ala Glu Ala Ile Gln Ala Val Arg Asp Asn
                645                 650                 655

Lys Leu His Ala Phe Ile Trp Asp Ser Ala Val Leu Glu Phe Glu Ala
                660                 665                 670

Ser Gln Lys Cys Asp Leu Val Thr Thr Gly Glu Leu Phe Phe Arg Ser
            675                 680                 685

Gly Phe Gly Ile Gly Met Arg Lys Asp Ser Pro Trp Lys Gln Asn Val
690                 695                 700

Ser Leu Ser Ile Leu Lys Ser His Glu Asn Gly Phe Met Glu Asp Leu
705                 710                 715                 720

Asp Lys Thr Trp Val Arg Tyr Gln Glu Cys Asp Ser Arg Ser Asn Ala
                725                 730                 735

Pro Ala Thr Leu Thr Phe Glu Asn Met Ala Gly Val Phe Met Leu Val
            740                 745                 750

Ala Gly Gly Ile Val Ala Gly Ile Phe Leu Ile Phe Ile Glu Ile Ala
            755                 760                 765

Tyr Lys Arg His Lys Asp Ala Arg Arg Lys Gln Met Gln Leu Ala Phe
770                 775                 780

Ala Ala Val Asn Val Trp Arg Lys Asn Leu Gln Asp Arg Lys Ser Gly
785                 790                 795                 800

Arg Ala Glu Pro Asp Pro Lys Lys Lys Ala Thr Phe Arg Ala Ile Thr
                805                 810                 815

Ser Thr Leu Ala Ser Ser Phe Lys Arg Arg Arg Ser Ser Lys Asp Thr
            820                 825                 830

Leu Ala Arg Asp Cys Leu Gln Pro Cys Pro Ala Pro Trp Ala Arg Glu
            835                 840                 845

Ser Ala Thr Arg Pro Pro Pro Ser Leu Arg Val Arg Asp Arg Pro
850                 855                 860

Ala Thr Leu Tyr Arg Thr Ser Thr Pro Arg Ala Arg Ala Arg Ala Phe
865                 870                 875                 880

Pro Val Arg Ser Arg Ala Leu Pro Leu Arg Pro Gln Gly Ala Gly Ala
                885                 890                 895

His Arg Pro Thr Pro Thr Ser Arg Cys Met Gln Trp
                900                 905
```

(2) INFORMATION FOR SEQ ID NO:35:

(i) SEQUENCE CHARACTERISTICS:
    (A) LENGTH: 3998 base pairs
    (B) TYPE: nucleic acid
    (C) STRANDEDNESS: both
    (D) TOPOLOGY: both -continued (ii) MOLECULE TYPE: cDNA (ix) FEATURE:
    (A) NAME/KEY: CDS
    (B) LOCATION: 262..3093

(xi) SEQUENCE DESCRIPTION: SEQ ID NO:35:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC       291
                        Met Ser Thr Met Arg Leu Leu Thr Leu Ala
                         1               5                  10

CTG CTG TTC TCC TGC TCC GTC GCC CGT GCC GCG TGC GAC CCC AAG ATC       339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC       387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT       435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG       483
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC       531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT       579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC       627
Val Ser Tyr Thr Ala Gly Phe Tyr Arg Ile Pro Val Leu Gly Leu Thr
             110                 115                 120

ACC CGC ATG TCC ATC TAC TCG GAC AAG AGC ATC CAC CTG AGC TTC CTG       675
Thr Arg Met Ser Ile Tyr Ser Asp Lys Ser Ile His Leu Ser Phe Leu
         125                 130                 135

CGC ACC GTG CCG CCC TAC TCC CAC CAG TCC AGC GTG TGG TTT GAG ATG       723
Arg Thr Val Pro Pro Tyr Ser His Gln Ser Ser Val Trp Phe Glu Met
     140                 145                 150

ATG CGT GTC TAC AGC TGG AAC CAC ATC ATC CTG CTG GTC AGC GAC GAC       771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG       819
His Glu Gly Arg Ala Ala Gln Lys Arg Leu Glu Thr Leu Leu Glu Glu
                 175                 180                 185

CGT GAG TCC AAG AGT AAA AAA AGG AAC TAT GAA AAC CTC GAC CAA CTG       867
Arg Glu Ser Lys Ser Lys Lys Arg Asn Tyr Glu Asn Leu Asp Gln Leu
             190                 195                 200

TCC TAT GAC AAC AAG CGC GGA CCC AAG GCA GAG AAG GTG CTG CAG TTT       915
Ser Tyr Asp Asn Lys Arg Gly Pro Lys Ala Glu Lys Val Leu Gln Phe
         205                 210                 215

GAC CCA GGG ACC AAG AAC GTG ACG GCC CTG CTG ATG GAG GCG AAA GAG       963
Asp Pro Gly Thr Lys Asn Val Thr Ala Leu Leu Met Glu Ala Lys Glu
     220                 225                 230

CTG GAG GCC CGG GTC ATC ATC CTT TCT GCC AGC GAG GAC GAT GCT GCC      1011
Leu Glu Ala Arg Val Ile Ile Leu Ser Ala Ser Glu Asp Asp Ala Ala
235                 240                 245                 250
```

```
ACT GTA TAC CGC GCA GCC GCG ATG CTG AAC ATG ACG GGC TCC GGG TAC   1059
Thr Val Tyr Arg Ala Ala Ala Met Leu Asn Met Thr Gly Ser Gly Tyr
            255                 260                 265

GTG TGG CTG GTC GGC GAG CGC GAG ATC TCG GGG AAC GCC CTG CGC TAC   1107
Val Trp Leu Val Gly Glu Arg Glu Ile Ser Gly Asn Ala Leu Arg Tyr
        270                 275                 280

GCC CCA GAC GGC ATC CTC GGG CTG CAG CTC ATC AAC GGC AAG AAC GAG   1155
Ala Pro Asp Gly Ile Leu Gly Leu Gln Leu Ile Asn Gly Lys Asn Glu
            285                 290                 295

TCG GCC CAC ATC AGC GAC GCC GTG GGC GTG GTG GCC CAG GCC GTG CAC   1203
Ser Ala His Ile Ser Asp Ala Val Gly Val Val Ala Gln Ala Val His
        300                 305                 310

GAG CTC CTC GAG AAG GAG AAC ATC ACC GAC CCG CCG CGG GGC TGC GTG   1251
Glu Leu Leu Glu Lys Glu Asn Ile Thr Asp Pro Pro Arg Gly Cys Val
315                 320                 325                 330

GGC AAC ACC AAC ATC TGG AAG ACC GGG CCG CTC TTC AAG AGA GTG CTG   1299
Gly Asn Thr Asn Ile Trp Lys Thr Gly Pro Leu Phe Lys Arg Val Leu
                335                 340                 345

ATG TCT TCC AAG TAT GCG GAT GGG GTG ACT GGT CGC GTG GAG TTC AAT   1347
Met Ser Ser Lys Tyr Ala Asp Gly Val Thr Gly Arg Val Glu Phe Asn
            350                 355                 360

GAG GAT GGG GAC CGG AAG TTC GCC AAC TAC AGC ATC ATG AAC CTG CAG   1395
Glu Asp Gly Asp Arg Lys Phe Ala Asn Tyr Ser Ile Met Asn Leu Gln
        365                 370                 375

AAC CGC AAG CTG GTG CAA GTG GGC ATC TAC AAT GGC ACC CAC GTC ATC   1443
Asn Arg Lys Leu Val Gln Val Gly Ile Tyr Asn Gly Thr His Val Ile
        380                 385                 390

CCT AAT GAC AGG AAG ATC ATC TGG CCA GGC GGA GAG ACA GAG AAG CCT   1491
Pro Asn Asp Arg Lys Ile Ile Trp Pro Gly Gly Glu Thr Glu Lys Pro
395                 400                 405                 410

CGA GGG TAC CAG ATG TCC ACC AGA CTG AAG ATT GTG ACG ATC CAC CAG   1539
Arg Gly Tyr Gln Met Ser Thr Arg Leu Lys Ile Val Thr Ile His Gln
                415                 420                 425

GAG CCC TTC GTG TAC GTC AAG CCC ACG CTG AGT GAT GGG ACA TGC AAG   1587
Glu Pro Phe Val Tyr Val Lys Pro Thr Leu Ser Asp Gly Thr Cys Lys
            430                 435                 440

GAG GAG TTC ACA GTC AAC GGC GAC CCA GTC AAG AAG GTG ATC TGC ACC   1635
Glu Glu Phe Thr Val Asn Gly Asp Pro Val Lys Lys Val Ile Cys Thr
        445                 450                 455

GGG CCC AAC GAC ACG TCG CCG GGC AGC CCC CGC CAC ACG GTG CCT CAG   1683
Gly Pro Asn Asp Thr Ser Pro Gly Ser Pro Arg His Thr Val Pro Gln
        460                 465                 470

TGT TGC TAC GGC TTT TGC ATC GAC CTG CTC ATC AAG CTG GCA CGG ACC   1731
Cys Cys Tyr Gly Phe Cys Ile Asp Leu Leu Ile Lys Leu Ala Arg Thr
475                 480                 485                 490

ATG AAC TTC ACC TAC GAG GTG CAC CTG GTG GCA GAT GGC AAG TTC GGC   1779
Met Asn Phe Thr Tyr Glu Val His Leu Val Ala Asp Gly Lys Phe Gly
                495                 500                 505

ACA CAG GAG CGG GTG AAC AAC AGC AAC AAG AAG GAG TGG AAT GGG ATG   1827
Thr Gln Glu Arg Val Asn Asn Ser Asn Lys Lys Glu Trp Asn Gly Met
            510                 515                 520

ATG GGC GAG CTG CTC AGC GGG CAG GCA GAC ATG ATC GTG GCG CCG CTA   1875
Met Gly Glu Leu Leu Ser Gly Gln Ala Asp Met Ile Val Ala Pro Leu
        525                 530                 535

ACC ATA AAC AAC GAG CGC GCG CAG TAC ATC GAG TTT TCC AAG CCC TTC   1923
Thr Ile Asn Asn Glu Arg Ala Gln Tyr Ile Glu Phe Ser Lys Pro Phe
        540                 545                 550

AAG TAC CAG GGC CTG ACT ATT CTG GTC AAG AAG GAG ATT CCC CGG AGC   1971
Lys Tyr Gln Gly Leu Thr Ile Leu Val Lys Lys Glu Ile Pro Arg Ser
```

```
                555                   560                   565                    570
ACG CTG GAC TCG TTC ATG CAG CCG TTC CAG AGC ACA CTG TGG CTG CTG                    2019
Thr Leu Asp Ser Phe Met Gln Pro Phe Gln Ser Thr Leu Trp Leu Leu
                575                   580                   585

GTG GGG CTG TCG GTG CAC GTG GTG GCC GTG ATG CTG TAC CTG CTG GAC                    2067
Val Gly Leu Ser Val His Val Val Ala Val Met Leu Tyr Leu Leu Asp
            590                   595                   600

CGC TTC AGC CCC TTC GGC CGG TTC AAG GTG AAC AGC GAG GAG GAG GAG                    2115
Arg Phe Ser Pro Phe Gly Arg Phe Lys Val Asn Ser Glu Glu Glu Glu
            605                   610                   615

GAG GAC GCA CTG ACC CTG TCC TCG GCC ATG TGG TTC TCC TGG GGC GTC                    2163
Glu Asp Ala Leu Thr Leu Ser Ser Ala Met Trp Phe Ser Trp Gly Val
        620                   625                   630

CTG CTC AAC TCC GGC ATC GGG GAA GGC GCC CCC AGA AGC TTC TCA GCG                    2211
Leu Leu Asn Ser Gly Ile Gly Glu Gly Ala Pro Arg Ser Phe Ser Ala
635                   640                   645                   650

CGC ATC CTG GGC ATG GTG TGG GCC GGC TTT GCC ATG ATC ATC GTG GCC                    2259
Arg Ile Leu Gly Met Val Trp Ala Gly Phe Ala Met Ile Ile Val Ala
                655                   660                   665

TCC TAC ACC GCC AAC CTG GCG GCC TTC CTG GTG CTG GAC CGG CCG GAG                    2307
Ser Tyr Thr Ala Asn Leu Ala Ala Phe Leu Val Leu Asp Arg Pro Glu
            670                   675                   680

GAG CGC ATC ACG GGC ATC AAC GAC CCT CGG CTG AGG AAC CCC TCG GAC                    2355
Glu Arg Ile Thr Gly Ile Asn Asp Pro Arg Leu Arg Asn Pro Ser Asp
            685                   690                   695

AAG TTT ATC TAC GCC ACG GTG AAG CAG AGC TCC GTG GAT ATC TAC TTC                    2403
Lys Phe Ile Tyr Ala Thr Val Lys Gln Ser Ser Val Asp Ile Tyr Phe
        700                   705                   710

CGG CGC CAG GTG GAG CTG AGC ACC ATG TAC CGG CAT ATG GAG AAG CAC                    2451
Arg Arg Gln Val Glu Leu Ser Thr Met Tyr Arg His Met Glu Lys His
715                   720                   725                   730

AAC TAC GAG AGT GCG GCG GAG GCC ATC CAG GCC GTG AGA GAC AAC AAG                    2499
Asn Tyr Glu Ser Ala Ala Glu Ala Ile Gln Ala Val Arg Asp Asn Lys
                735                   740                   745

CTG CAT GCC TTC ATC TGG GAC TCG GCG GTG CTG GAG TTC GAG GCC TCG                    2547
Leu His Ala Phe Ile Trp Asp Ser Ala Val Leu Glu Phe Glu Ala Ser
            750                   755                   760

CAG AAG TGC GAC CTG GTG ACG ACT GGA GAG CTG TTT TTC CGC TCG GGC                    2595
Gln Lys Cys Asp Leu Val Thr Thr Gly Glu Leu Phe Phe Arg Ser Gly
            765                   770                   775

TTC GGC ATA GGC ATG CGC AAA GAC AGC CCC TGG AAG CAG AAC GTC TCC                    2643
Phe Gly Ile Gly Met Arg Lys Asp Ser Pro Trp Lys Gln Asn Val Ser
        780                   785                   790

CTG TCC ATC CTC AAG TCC CAC GAG AAT GGC TTC ATG GAA GAC CTG GAC                    2691
Leu Ser Ile Leu Lys Ser His Glu Asn Gly Phe Met Glu Asp Leu Asp
795                   800                   805                   810

AAG ACG TGG GTT CGG TAT CAG GAA TGT GAC TCG CGC AGC AAC GCC CCT                    2739
Lys Thr Trp Val Arg Tyr Gln Glu Cys Asp Ser Arg Ser Asn Ala Pro
                815                   820                   825

GCG ACC CTT ACT TTT GAG AAC ATG GCC GGG GTC TTC ATG CTG GTA GCT                    2787
Ala Thr Leu Thr Phe Glu Asn Met Ala Gly Val Phe Met Leu Val Ala
            830                   835                   840

GGG GGC ATC GTG GCC GGG ATC TTC CTG ATT TTC ATC GAG ATT GCC TAC                    2835
Gly Gly Ile Val Ala Gly Ile Phe Leu Ile Phe Ile Glu Ile Ala Tyr
            845                   850                   855

AAG CGG CAC AAG GAT GCT CGC CGG AAG CAG ATG CAG CTG GCC TTT GCC                    2883
Lys Arg His Lys Asp Ala Arg Arg Lys Gln Met Gln Leu Ala Phe Ala
        860                   865                   870

GCC GTT AAC GTG TGG CGG AAG AAC CTG CAG GAT AGA AAG AGT GGT AGA                    2931
```

```
Ala Val Asn Val Trp Arg Lys Asn Leu Gln Asp Arg Lys Ser Gly Arg
875                 880                 885                 890

GCA GAG CCT GAC CCT AAA AAG AAA GCC ACA TTT AGG GCT ATC ACC TCC    2979
Ala Glu Pro Asp Pro Lys Lys Lys Ala Thr Phe Arg Ala Ile Thr Ser
                    895                 900                 905

ACC CTG GCT TCC AGC TTC AAG AGG CGT AGG TCC TCC AAA GAC ACG CAG    3027
Thr Leu Ala Ser Ser Phe Lys Arg Arg Arg Ser Ser Lys Asp Thr Gln
                910                 915                 920

TAC CAT CCC ACT GAT ATC ACG GGC CCG CTC AAC CTC TCA GAT CCC TCG    3075
Tyr His Pro Thr Asp Ile Thr Gly Pro Leu Asn Leu Ser Asp Pro Ser
            925                 930                 935

GTC AGC ACC GTG GTG TGAGGCCCCC GGAGGCGCCC ACCTGCCCAG TTAGCCCGGC    3130
Val Ser Thr Val Val
        940
```

CAAGGACACT GATGGGTCCT GCTGCTCGGG AAGGCCTGAG GGAAGCCCAC CCGCCCCAGA  3190

GACTGCCCAC CCTGGGCCTC CCGTCCGTCC GCCCGCCCAC CCCGCTGCCT GGCGGGCAGC  3250

CCCTGCTGGA CCAAGGTGCG GACCGGAGCG GCTGAGGACG GGCAGAGCT GAGTCGGCTG   3310

GGCAGGGCCG CAGGGCGCTC CGGCAGAGGC AGGCCCCTGG GGTCTCTGAG CAGTGGGGAG  3370

CGGGGGCTAA CTGCCCCCAG GCGGAGGGGC TTGGAGCAGA GACGGCAGCC CCATCCTTCC  3430

CGCAGCACCA GCCTGAGCCA CAGTGGGCC CATGGCCCCA GCTGGCTGGG TCGCCCCTCC   3490

TCGGGCGCCT GCGCTCCTCT GCAGCCTGAG CTCCACCCTC CCCTCTTCTT GCGGCACCGC  3550

CCACCAAACA CCCCGTCTGC CCCTTGACGC CACACGCCGG GGCTGGCGCT GCCCTCCCCC  3610

ACGGCCGTCC CTGACTTCCC AGCTGGCAGC GCCTCCCGCC GCCTCGGGCC GCCTCCTCCA  3670

GAATCGAGAG GGCTGAGCCC CTCCTCTCCT CGTCCGGCCT GCAGCACAGA AGGGGGCCTC  3730

CCCGGGGGTC CCCGGACGCT GGCTCGGGAC TGTCTTCAAC CCTGCCCTGC ACCTTGGGCA  3790

CGGGAGAGCG CCACCCGCCC GCCCCCGCCC TCGCTCCGGG TGCGTGACCG GCCCGCCACC  3850

TTGTACAGAA CCAGCACTCC CAGGGCCCGA GCGCGTGCCT TCCCCGTGCG CAGCCGCGCT  3910

CTGCCCCTCC GTCCCCAGGG TGCAGGCGCG CACCGCCCAA CCCCCACCTC CCGGTGTATG  3970

CAGTGGTGAT GCCTAAAGGA ATGTCACG                                     3998

(2) INFORMATION FOR SEQ ID NO:36:

(i) SEQUENCE CHARACTERISTICS:
        (A) LENGTH: 943 amino acids
        (B) TYPE: amino acid
        (D) TOPOLOGY: linear (ii) MOLECULE TYPE: protein (xi) SEQUENCE DESCRIPTION: SEQ ID NO:36:

```
Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
                35                  40                  45

Ala Asn Lys Arg His Gly Ser Trp Lys Ile Gln Leu Asn Ala Thr Ser
            50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95
```

```
Thr Pro Asn Asp His Phe Thr Pro Thr Pro Val Ser Tyr Thr Ala Gly
                100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
        275                 280                 285

Gly Leu Gln Leu Ile Asn Gly Lys Asn Glu Ser Ala His Ile Ser Asp
    290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
        355                 360                 365

Phe Ala Asn Tyr Ser Ile Met Asn Leu Gln Asn Arg Lys Leu Val Gln
    370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
    450                 455                 460

Pro Gly Ser Pro Arg His Thr Val Pro Gln Cys Cys Tyr Gly Phe Cys
465                 470                 475                 480

Ile Asp Leu Leu Ile Lys Leu Ala Arg Thr Met Asn Phe Thr Tyr Glu
                485                 490                 495

Val His Leu Val Ala Asp Gly Lys Phe Gly Thr Gln Glu Arg Val Asn
            500                 505                 510

Asn Ser Asn Lys Lys Glu Trp Asn Gly Met Met Gly Glu Leu Leu Ser
```

```
              515                 520                 525
Gly Gln Ala Asp Met Ile Val Ala Pro Leu Thr Ile Asn Asn Glu Arg
        530                 535                 540

Ala Gln Tyr Ile Glu Phe Ser Lys Pro Phe Lys Tyr Gln Gly Leu Thr
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
            580                 585                 590

Val Val Ala Val Met Leu Tyr Leu Leu Asp Arg Phe Ser Pro Phe Gly
        595                 600                 605

Arg Phe Lys Val Asn Ser Glu Glu Glu Glu Asp Ala Leu Thr Leu
    610                 615                 620

Ser Ser Ala Met Trp Phe Ser Trp Gly Val Leu Leu Asn Ser Gly Ile
625                 630                 635                 640

Gly Glu Gly Ala Pro Arg Ser Phe Ser Ala Arg Ile Leu Gly Met Val
                645                 650                 655

Trp Ala Gly Phe Ala Met Ile Ile Val Ala Ser Tyr Thr Ala Asn Leu
            660                 665                 670

Ala Ala Phe Leu Val Leu Asp Arg Pro Glu Glu Arg Ile Thr Gly Ile
        675                 680                 685

Asn Asp Pro Arg Leu Arg Asn Pro Ser Asp Lys Phe Ile Tyr Ala Thr
690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
        755                 760                 765

Thr Thr Gly Glu Leu Phe Phe Arg Ser Gly Phe Gly Ile Gly Met Arg
770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
            820                 825                 830

Asn Met Ala Gly Val Phe Met Leu Val Ala Gly Gly Ile Val Ala Gly
        835                 840                 845

Ile Phe Leu Ile Phe Ile Glu Ile Ala Tyr Lys Arg His Lys Asp Ala
850                 855                 860

Arg Arg Lys Gln Met Gln Leu Ala Phe Ala Ala Val Asn Val Trp Arg
865                 870                 875                 880

Lys Asn Leu Gln Asp Arg Lys Ser Gly Arg Ala Glu Pro Asp Pro Lys
                885                 890                 895

Lys Lys Ala Thr Phe Arg Ala Ile Thr Ser Thr Leu Ala Ser Ser Phe
            900                 905                 910

Lys Arg Arg Arg Ser Ser Lys Asp Thr Gln Tyr His Pro Thr Asp Ile
        915                 920                 925

Thr Gly Pro Leu Asn Leu Ser Asp Pro Ser Val Ser Thr Val Val
930                 935                 940
```

(2) INFORMATION FOR SEQ ID NO:37:

(i) SEQUENCE CHARACTERISTICS:
        (A) LENGTH: 3274 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..3255

(xi) SEQUENCE DESCRIPTION: SEQ ID NO:37:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                         Met Ser Thr Met Arg Leu Leu Thr Leu Ala
                           1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
             15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
         30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
     45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
 60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
         110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
     125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
 140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                 175                 180                 185

CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
         190                 195                 200

TCC TAT GAC AAC AAG CGC GGA CCC AAG GCA GAG AAG GTG CTG CAG TTT      915
```

-continued

```
Ser Tyr Asp Asn Lys Arg Gly Pro Lys Ala Glu Lys Val Leu Gln Phe
            205                 210                 215

GAC CCA GGG ACC AAG AAC GTG ACG GCC CTG CTG ATG GAG GCG AAA GAG        963
Asp Pro Gly Thr Lys Asn Val Thr Ala Leu Leu Met Glu Ala Lys Glu
220                 225                 230

CTG GAG GCC CGG GTC ATC ATC CTT TCT GCC AGC GAG GAC GAT GCT GCC       1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC TCC GGG TAC       1059
Thr Val Tyr Arg Ala Ala Ala Met Leu Asn Met Thr Gly Ser Gly Tyr
                255                 260                 265

GTG TGG CTG GTC GGC GAG CGC GAG ATC TCG GGG AAC GCC CTG CGC TAC       1107
Val Trp Leu Val Gly Glu Arg Glu Ile Ser Gly Asn Ala Leu Arg Tyr
                270                 275                 280

GCC CCA GAC GGC ATC CTC GGG CTG CAG CTC ATC AAC GGC AAG AAC GAG       1155
Ala Pro Asp Gly Ile Leu Gly Leu Gln Leu Ile Asn Gly Lys Asn Glu
                285                 290                 295

TCG GCC CAC ATC AGC GAC GCC GTG GGC GTG GTG GCC CAG GCC GTG CAC       1203
Ser Ala His Ile Ser Asp Ala Val Gly Val Val Ala Gln Ala Val His
300                 305                 310

GAG CTC CTC GAG AAG GAG AAC ATC ACC GAC CCG CCG CGG GGC TGC GTG       1251
Glu Leu Leu Glu Lys Glu Asn Ile Thr Asp Pro Pro Arg Gly Cys Val
315                 320                 325                 330

GGC AAC ACC AAC ATC TGG AAG ACC GGG CCG CTC TTC AAG AGA GTG CTG       1299
Gly Asn Thr Asn Ile Trp Lys Thr Gly Pro Leu Phe Lys Arg Val Leu
                335                 340                 345

ATG TCT TCC AAG TAT GCG GAT GGG GTG ACT GGT CGC GTG GAG TTC AAT       1347
Met Ser Ser Lys Tyr Ala Asp Gly Val Thr Gly Arg Val Glu Phe Asn
                350                 355                 360

GAG GAT GGG GAC CGG AAG TTC GCC AAC TAC AGC ATC ATG AAC CTG CAG       1395
Glu Asp Gly Asp Arg Lys Phe Ala Asn Tyr Ser Ile Met Asn Leu Gln
                365                 370                 375

AAC CGC AAG CTG GTG CAA GTG GGC ATC TAC AAT GGC ACC CAC GTC ATC       1443
Asn Arg Lys Leu Val Gln Val Gly Ile Tyr Asn Gly Thr His Val Ile
380                 385                 390

CCT AAT GAC AGG AAG ATC ATC TGG CCA GGC GGA GAG ACA GAG AAG CCT       1491
Pro Asn Asp Arg Lys Ile Ile Trp Pro Gly Gly Glu Thr Glu Lys Pro
395                 400                 405                 410

CGA GGG TAC CAG ATG TCC ACC AGA CTG AAG ATT GTG ACG ATC CAC CAG       1539
Arg Gly Tyr Gln Met Ser Thr Arg Leu Lys Ile Val Thr Ile His Gln
                415                 420                 425

GAG CCC TTC GTG TAC GTC AAG CCC ACG CTG AGT GAT GGG ACA TGC AAG       1587
Glu Pro Phe Val Tyr Val Lys Pro Thr Leu Ser Asp Gly Thr Cys Lys
                430                 435                 440

GAG GAG TTC ACA GTC AAC GGC GAC CCA GTC AAG AAG GTG ATC TGC ACC       1635
Glu Glu Phe Thr Val Asn Gly Asp Pro Val Lys Lys Val Ile Cys Thr
                445                 450                 455

GGG CCC AAC GAC ACG TCG CCG GGC AGC CCC CGC CAC ACG GTG CCT CAG       1683
Gly Pro Asn Asp Thr Ser Pro Gly Ser Pro Arg His Thr Val Pro Gln
460                 465                 470

TGT TGC TAC GGC TTT TGC ATC GAC CTG CTC ATC AAG CTG GCA CGG ACC       1731
Cys Cys Tyr Gly Phe Cys Ile Asp Leu Leu Ile Lys Leu Ala Arg Thr
475                 480                 485                 490

ATG AAC TTC ACC TAC GAG GTG CAC CTG GTG GCA GAT GGC AAG TTC GGC       1779
Met Asn Phe Thr Tyr Glu Val His Leu Val Ala Asp Gly Lys Phe Gly
                495                 500                 505

ACA CAG GAG CGG GTG AAC AAC AGC AAC AAG AAG GAG TGG AAT GGG ATG       1827
Thr Gln Glu Arg Val Asn Asn Ser Asn Lys Lys Glu Trp Asn Gly Met
                510                 515                 520
```

```
ATG GGC GAG CTG CTC AGC GGG CAG GCA GAC ATG ATC GTG GCG CCG CTA       1875
Met Gly Glu Leu Leu Ser Gly Gln Ala Asp Met Ile Val Ala Pro Leu
            525                 530                 535

ACC ATA AAC AAC GAG CGC GCG CAG TAC ATC GAG TTT TCC AAG CCC TTC       1923
Thr Ile Asn Asn Glu Arg Ala Gln Tyr Ile Glu Phe Ser Lys Pro Phe
540                 545                 550

AAG TAC CAG GGC CTG ACT ATT CTG GTC AAG AAG GAG ATT CCC CGG AGC       1971
Lys Tyr Gln Gly Leu Thr Ile Leu Val Lys Lys Glu Ile Pro Arg Ser
555                 560                 565                 570

ACG CTG GAC TCG TTC ATG CAG CCG TTC CAG AGC ACA CTG TGG CTG CTG       2019
Thr Leu Asp Ser Phe Met Gln Pro Phe Gln Ser Thr Leu Trp Leu Leu
            575                 580                 585

GTG GGG CTG TCG GTG CAC GTG GTG GCC GTG ATG CTG TAC CTG CTG GAC       2067
Val Gly Leu Ser Val His Val Val Ala Val Met Leu Tyr Leu Leu Asp
                590                 595                 600

CGC TTC AGC CCC TTC GGC CGG TTC AAG GTG AAC AGC GAG GAG GAG GAG       2115
Arg Phe Ser Pro Phe Gly Arg Phe Lys Val Asn Ser Glu Glu Glu Glu
                605                 610                 615

GAG GAC GCA CTG ACC CTG TCC TCG GCC ATG TGG TTC TCC TGG GGC GTC       2163
Glu Asp Ala Leu Thr Leu Ser Ser Ala Met Trp Phe Ser Trp Gly Val
620                 625                 630

CTG CTC AAC TCC GGC ATC GGG GAA GGC GCC CCC AGA AGC TTC TCA GCG       2211
Leu Leu Asn Ser Gly Ile Gly Glu Gly Ala Pro Arg Ser Phe Ser Ala
635                 640                 645                 650

CGC ATC CTG GGC ATG GTG TGG GCC GGC TTT GCC ATG ATC ATC GTG GCC       2259
Arg Ile Leu Gly Met Val Trp Ala Gly Phe Ala Met Ile Ile Val Ala
            655                 660                 665

TCC TAC ACC GCC AAC CTG GCG GCC TTC CTG GTG CTG GAC CGG CCG GAG       2307
Ser Tyr Thr Ala Asn Leu Ala Ala Phe Leu Val Leu Asp Arg Pro Glu
                670                 675                 680

GAG CGC ATC ACG GGC ATC AAC GAC CCT CGG CTG AGG AAC CCC TCG GAC       2355
Glu Arg Ile Thr Gly Ile Asn Asp Pro Arg Leu Arg Asn Pro Ser Asp
                685                 690                 695

AAG TTT ATC TAC GCC ACG GTG AAG CAG AGC TCC GTG GAT ATC TAC TTC       2403
Lys Phe Ile Tyr Ala Thr Val Lys Gln Ser Ser Val Asp Ile Tyr Phe
700                 705                 710

CGG CGC CAG GTG GAG CTG AGC ACC ATG TAC CGG CAT ATG GAG AAG CAC       2451
Arg Arg Gln Val Glu Leu Ser Thr Met Tyr Arg His Met Glu Lys His
715                 720                 725                 730

AAC TAC GAG AGT GCG GCG GAG GCC ATC CAG GCC GTG AGA GAC AAC AAG       2499
Asn Tyr Glu Ser Ala Ala Glu Ala Ile Gln Ala Val Arg Asp Asn Lys
            735                 740                 745

CTG CAT GCC TTC ATC TGG GAC TCG GCG GTG CTG GAG TTC GAG GCC TCG       2547
Leu His Ala Phe Ile Trp Asp Ser Ala Val Leu Glu Phe Glu Ala Ser
                750                 755                 760

CAG AAG TGC GAC CTG GTG ACG ACT GGA GAG CTG TTT TTC CGC TCG GGC       2595
Gln Lys Cys Asp Leu Val Thr Thr Gly Glu Leu Phe Phe Arg Ser Gly
            765                 770                 775

TTC GGC ATA GGC ATG CGC AAA GAC AGC CCC TGG AAG CAG AAC GTC TCC       2643
Phe Gly Ile Gly Met Arg Lys Asp Ser Pro Trp Lys Gln Asn Val Ser
780                 785                 790

CTG TCC ATC CTC AAG TCC CAC GAG AAT GGC TTC ATG GAA GAC CTG GAC       2691
Leu Ser Ile Leu Lys Ser His Glu Asn Gly Phe Met Glu Asp Leu Asp
795                 800                 805                 810

AAG ACG TGG GTT CGG TAT CAG GAA TGT GAC TCG CGC AGC AAC GCC CCT       2739
Lys Thr Trp Val Arg Tyr Gln Glu Cys Asp Ser Arg Ser Asn Ala Pro
            815                 820                 825

GCG ACC CTT ACT TTT GAG AAC ATG GCC GGG GTC TTC ATG CTG GTA GCT       2787
Ala Thr Leu Thr Phe Glu Asn Met Ala Gly Val Phe Met Leu Val Ala
                830                 835                 840
```

```
GGG GGC ATC GTG GCC GGG ATC TTC CTG ATT TTC ATC GAG ATT GCC TAC    2835
Gly Gly Ile Val Ala Gly Ile Phe Leu Ile Phe Ile Glu Ile Ala Tyr
        845                 850                 855

AAG CGG CAC AAG GAT GCT CGC CGG AAG CAG ATG CAG CTG GCC TTT GCC    2883
Lys Arg His Lys Asp Ala Arg Arg Lys Gln Met Gln Leu Ala Phe Ala
        860                 865                 870

GCC GTT AAC GTG TGG CGG AAG AAC CTG CAG GAT AGA AAG AGT GGT AGA    2931
Ala Val Asn Val Trp Arg Lys Asn Leu Gln Asp Arg Lys Ser Gly Arg
875                 880                 885                 890

GCA GAG CCT GAC CCT AAA AAG AAA GCC ACA TTT AGG GCT ATC ACC TCC    2979
Ala Glu Pro Asp Pro Lys Lys Lys Ala Thr Phe Arg Ala Ile Thr Ser
                895                 900                 905

ACC CTG GCT TCC AGC TTC AAG AGG CGT AGG TCC TCC AAA GAC ACG CTG    3027
Thr Leu Ala Ser Ser Phe Lys Arg Arg Arg Ser Ser Lys Asp Thr Leu
        910                 915                 920

GCT CGG GAC TGT CTT CAA CCC TGC CCT GCA CCT TGG GCA CGG GAG AGC    3075
Ala Arg Asp Cys Leu Gln Pro Cys Pro Ala Pro Trp Ala Arg Glu Ser
        925                 930                 935

GCC ACC CGC CCG CCC CCG CCC TCG CTC CGG GTG CGT GAC CGG CCC GCC    3123
Ala Thr Arg Pro Pro Pro Pro Ser Leu Arg Val Arg Asp Arg Pro Ala
940                 945                 950

ACC TTG TAC AGA ACC AGC ACT CCC AGG GCC CGA GCG CGT GCC TTC CCC    3171
Thr Leu Tyr Arg Thr Ser Thr Pro Arg Ala Arg Ala Arg Ala Phe Pro
955                 960                 965                 970

GTG CGC AGC CGC GCT CTG CCC CTC CGT CCC CAG GGT GCA GGC GCG CAC    3219
Val Arg Ser Arg Ala Leu Pro Leu Arg Pro Gln Gly Ala Gly Ala His
                975                 980                 985

CGC CCA ACC CCC ACC TCC CGG TGT ATG CAG TGG TGATGCCTAA AGGAATGTCA  3272
Arg Pro Thr Pro Thr Ser Arg Cys Met Gln Trp
                990                 995

CG                                                                 3274
```

(2) INFORMATION FOR SEQ ID NO:38:

(i) SEQUENCE CHARACTERISTICS:
        (A) LENGTH: 997 amino acids
        (B) TYPE: amino acid
        (D) TOPOLOGY: linear (ii) MOLECULE TYPE: protein (xi) SEQUENCE DESCRIPTION: SEQ ID NO:38:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125
```

-continued

```
Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
        275                 280                 285

Gly Leu Gln Leu Ile Asn Gly Lys Asn Glu Ser Ala His Ile Ser Asp
    290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
        355                 360                 365

Phe Ala Asn Tyr Ser Ile Met Asn Leu Gln Asn Arg Lys Leu Val Gln
    370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
    450                 455                 460

Pro Gly Ser Pro Arg His Thr Val Pro Gln Cys Cys Tyr Gly Phe Cys
465                 470                 475                 480

Ile Asp Leu Leu Ile Lys Leu Ala Arg Thr Met Asn Phe Thr Tyr Glu
                485                 490                 495

Val His Leu Val Ala Asp Gly Lys Phe Gly Thr Gln Glu Arg Val Asn
            500                 505                 510

Asn Ser Asn Lys Lys Glu Trp Asn Gly Met Met Gly Glu Leu Leu Ser
        515                 520                 525

Gly Gln Ala Asp Met Ile Val Ala Pro Leu Thr Ile Asn Asn Glu Arg
    530                 535                 540

Ala Gln Tyr Ile Glu Phe Ser Lys Pro Phe Lys Tyr Gln Gly Leu Thr
```

-continued

```
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
                580                 585                 590

Val Val Ala Val Met Leu Tyr Leu Leu Asp Arg Phe Ser Pro Phe Gly
                595                 600                 605

Arg Phe Lys Val Asn Ser Glu Glu Glu Glu Asp Ala Leu Thr Leu
        610                 615                 620

Ser Ser Ala Met Trp Phe Ser Trp Gly Val Leu Leu Asn Ser Gly Ile
625                 630                 635                 640

Gly Glu Gly Ala Pro Arg Ser Phe Ser Ala Arg Ile Leu Gly Met Val
                645                 650                 655

Trp Ala Gly Phe Ala Met Ile Ile Val Ala Ser Tyr Thr Ala Asn Leu
                660                 665                 670

Ala Ala Phe Leu Val Leu Asp Arg Pro Glu Glu Arg Ile Thr Gly Ile
                675                 680                 685

Asn Asp Pro Arg Leu Arg Asn Pro Ser Asp Lys Phe Ile Tyr Ala Thr
                690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
                740                 745                 750

Asp Ser Ala Val Leu Glu Phe Glu Ala Ser Gln Lys Cys Asp Leu Val
                755                 760                 765

Thr Thr Gly Glu Leu Phe Phe Arg Ser Gly Phe Gly Ile Gly Met Arg
770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
                820                 825                 830

Asn Met Ala Gly Val Phe Met Leu Val Ala Gly Gly Ile Val Ala Gly
                835                 840                 845

Ile Phe Leu Ile Phe Ile Glu Ile Ala Tyr Lys Arg His Lys Asp Ala
850                 855                 860

Arg Arg Lys Gln Met Gln Leu Ala Phe Ala Ala Val Asn Val Trp Arg
865                 870                 875                 880

Lys Asn Leu Gln Asp Arg Lys Ser Gly Arg Ala Glu Pro Asp Pro Lys
                885                 890                 895

Lys Lys Ala Thr Phe Arg Ala Ile Thr Ser Thr Leu Ala Ser Ser Phe
                900                 905                 910

Lys Arg Arg Arg Ser Ser Lys Asp Thr Leu Ala Arg Asp Cys Leu Gln
                915                 920                 925

Pro Cys Pro Ala Pro Trp Ala Arg Glu Ser Ala Thr Arg Pro Pro
                930                 935                 940

Pro Ser Leu Arg Val Arg Asp Arg Pro Ala Thr Leu Tyr Arg Thr Ser
945                 950                 955                 960

Thr Pro Arg Ala Arg Ala Arg Ala Phe Pro Val Arg Ser Arg Ala Leu
                965                 970                 975
```

```
Pro Leu Arg Pro Gln Gly Ala Gly Ala His Arg Pro Thr Pro Thr Ser
        980                 985                 990

Arg Cys Met Gln Trp
        995
```

(2) INFORMATION FOR SEQ ID NO:39:

(i) SEQUENCE CHARACTERISTICS:
        (A) LENGTH: 3070 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..3051

(xi) SEQUENCE DESCRIPTION: SEQ ID NO:39:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                         Met Ser Thr Met Arg Leu Leu Thr Leu Ala
                          1               5                    10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
            30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                95                  100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185
```

```
CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
            190                 195                 200

TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
            205                 210                 215

GAC CCA GGG ACC AAG AAC GTG ACG GCC CTG CTG ATG GAG GCG AAA GAG      963
Asp Pro Gly Thr Lys Asn Val Thr Ala Leu Leu Met Glu Ala Lys Glu
    220                 225                 230

CTG GAG GCC CGG GTC ATC ATC CTT TCT GCC AGC GAG GAC GAT GCT GCC     1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC AAC ACC AAC     1059
Thr Val Tyr Arg Ala Ala Ala Met Leu Asn Met Thr Gly Asn Thr Asn
            255                 260                 265

ATC TGG AAG ACC GGG CCG CTC TTC AAG AGA GTG CTG ATG TCT TCC AAG     1107
Ile Trp Lys Thr Gly Pro Leu Phe Lys Arg Val Leu Met Ser Ser Lys
            270                 275                 280

TAT GCG GAT GGG GTG ACT GGT CGC GTG GAG TTC AAT GAG GAT GGG GAC     1155
Tyr Ala Asp Gly Val Thr Gly Arg Val Glu Phe Asn Glu Asp Gly Asp
            285                 290                 295

CGG AAG TTC GCC AAC TAC AGC ATC ATG AAC CTG CAG AAC CGC AAG CTG     1203
Arg Lys Phe Ala Asn Tyr Ser Ile Met Asn Leu Gln Asn Arg Lys Leu
    300                 305                 310

GTG CAA GTG GGC ATC TAC AAT GGC ACC CAC GTC ATC CCT AAT GAC AGG     1251
Val Gln Val Gly Ile Tyr Asn Gly Thr His Val Ile Pro Asn Asp Arg
315                 320                 325                 330

AAG ATC ATC TGG CCA GGC GGA GAG ACA GAG AAG CCT CGA GGG TAC CAG     1299
Lys Ile Ile Trp Pro Gly Gly Glu Thr Glu Lys Pro Arg Gly Tyr Gln
            335                 340                 345

ATG TCC ACC AGA CTG AAG ATT GTG ACG ATC CAC CAG GAG CCC TTC GTG     1347
Met Ser Thr Arg Leu Lys Ile Val Thr Ile His Gln Glu Pro Phe Val
            350                 355                 360

TAC GTC AAG CCC ACG CTG AGT GAT GGG ACA TGC AAG GAG GAG TTC ACA     1395
Tyr Val Lys Pro Thr Leu Ser Asp Gly Thr Cys Lys Glu Glu Phe Thr
            365                 370                 375

GTC AAC GGC GAC CCA GTC AAG AAG GTG ATC TGC ACC GGG CCC AAC GAC     1443
Val Asn Gly Asp Pro Val Lys Lys Val Ile Cys Thr Gly Pro Asn Asp
380                 385                 390

ACG TCG CCG GGC AGC CCC CGC CAC ACG GTG CCT CAG TGT TGC TAC GGC     1491
Thr Ser Pro Gly Ser Pro Arg His Thr Val Pro Gln Cys Cys Tyr Gly
395                 400                 405                 410

TTT TGC ATC GAC CTG CTC ATC AAG CTG GCA CGG ACC ATG AAC TTC ACC     1539
Phe Cys Ile Asp Leu Leu Ile Lys Leu Ala Arg Thr Met Asn Phe Thr
            415                 420                 425

TAC GAG GTG CAC CTG GTG GCA GAT GGC AAG TTC GGC ACA CAG GAG CGG     1587
Tyr Glu Val His Leu Val Ala Asp Gly Lys Phe Gly Thr Gln Glu Arg
            430                 435                 440

GTG AAC AAC AGC AAC AAG AAG GAG TGG AAT GGG ATG ATG GGC GAG CTG     1635
Val Asn Asn Ser Asn Lys Lys Glu Trp Asn Gly Met Met Gly Glu Leu
            445                 450                 455

CTC AGC GGG CAG GCA GAC ATG ATC GTG GCG CCG CTA ACC ATA AAC AAC     1683
Leu Ser Gly Gln Ala Asp Met Ile Val Ala Pro Leu Thr Ile Asn Asn
    460                 465                 470

GAG CGC GCG CAG TAC ATC GAG TTT TCC AAG CCC TTC AAG TAC CAG GGC     1731
Glu Arg Ala Gln Tyr Ile Glu Phe Ser Lys Pro Phe Lys Tyr Gln Gly
475                 480                 485                 490

CTG ACT ATT CTG GTC AAG AAG GAG ATT CCC CGG AGC ACG CTG GAC TCG     1779
Leu Thr Ile Leu Val Lys Lys Glu Ile Pro Arg Ser Thr Leu Asp Ser
```

```
                        495                 500                      505
TTC ATG CAG CCG TTC CAG AGC ACA CTG TGG CTG CTG GTG GGG CTG TCG         1827
Phe Met Gln Pro Phe Gln Ser Thr Leu Trp Leu Leu Val Gly Leu Ser
                510                 515                 520

GTG CAC GTG GTG GCC GTG ATG CTG TAC CTG CTG GAC CGC TTC AGC CCC         1875
Val His Val Val Ala Val Met Leu Tyr Leu Leu Asp Arg Phe Ser Pro
            525                 530                 535

TTC GGC CGG TTC AAG GTG AAC AGC GAG GAG GAG GAG GAG GAC GCA CTG         1923
Phe Gly Arg Phe Lys Val Asn Ser Glu Glu Glu Glu Glu Asp Ala Leu
        540                 545                 550

ACC CTG TCC TCG GCC ATG TGG TTC TCC TGG GGC GTC CTG CTC AAC TCC         1971
Thr Leu Ser Ser Ala Met Trp Phe Ser Trp Gly Val Leu Leu Asn Ser
555                 560                 565                 570

GGC ATC GGG GAA GGC GCC CCC AGA AGC TTC TCA GCG CGC ATC CTG GGC         2019
Gly Ile Gly Glu Gly Ala Pro Arg Ser Phe Ser Ala Arg Ile Leu Gly
                575                 580                 585

ATG GTG TGG GCC GGC TTT GCC ATG ATC ATC GTG GCC TCC TAC ACC GCC         2067
Met Val Trp Ala Gly Phe Ala Met Ile Ile Val Ala Ser Tyr Thr Ala
            590                 595                 600

AAC CTG GCG GCC TTC CTG GTG CTG GAC CGG CCG GAG GAG CGC ATC ACG         2115
Asn Leu Ala Ala Phe Leu Val Leu Asp Arg Pro Glu Glu Arg Ile Thr
        605                 610                 615

GGC ATC AAC GAC CCT CGG CTG AGG AAC CCC TCG GAC AAG TTT ATC TAC         2163
Gly Ile Asn Asp Pro Arg Leu Arg Asn Pro Ser Asp Lys Phe Ile Tyr
    620                 625                 630

GCC ACG GTG AAG CAG AGC TCC GTG GAT ATC TAC TTC CGG CGC CAG GTG         2211
Ala Thr Val Lys Gln Ser Ser Val Asp Ile Tyr Phe Arg Arg Gln Val
635                 640                 645                 650

GAG CTG AGC ACC ATG TAC CGG CAT ATG GAG AAG CAC AAC TAC GAG AGT         2259
Glu Leu Ser Thr Met Tyr Arg His Met Glu Lys His Asn Tyr Glu Ser
                655                 660                 665

GCG GCG GAG GCC ATC CAG GCC GTG AGA GAC AAC AAG CTG CAT GCC TTC         2307
Ala Ala Glu Ala Ile Gln Ala Val Arg Asp Asn Lys Leu His Ala Phe
            670                 675                 680

ATC TGG GAC TCG GCG GTG CTG GAG TTC GAG GCC TCG CAG AAG TGC GAC         2355
Ile Trp Asp Ser Ala Val Leu Glu Phe Glu Ala Ser Gln Lys Cys Asp
        685                 690                 695

CTG GTG ACG ACT GGA GAG CTG TTT TTC CGC TCG GGC TTC GGC ATA GGC         2403
Leu Val Thr Thr Gly Glu Leu Phe Phe Arg Ser Gly Phe Gly Ile Gly
    700                 705                 710

ATG CGC AAA GAC AGC CCC TGG AAG CAG AAC GTC TCC CTG TCC ATC CTC         2451
Met Arg Lys Asp Ser Pro Trp Lys Gln Asn Val Ser Leu Ser Ile Leu
715                 720                 725                 730

AAG TCC CAC GAG AAT GGC TTC ATG GAA GAC CTG GAC AAG ACG TGG GTT         2499
Lys Ser His Glu Asn Gly Phe Met Glu Asp Leu Asp Lys Thr Trp Val
                735                 740                 745

CGG TAT CAG GAA TGT GAC TCG CGC AGC AAC GCC CCT GCG ACC CTT ACT         2547
Arg Tyr Gln Glu Cys Asp Ser Arg Ser Asn Ala Pro Ala Thr Leu Thr
            750                 755                 760

TTT GAG AAC ATG GCC GGG GTC TTC ATG CTG GTA GCT GGG GGC ATC GTG         2595
Phe Glu Asn Met Ala Gly Val Phe Met Leu Val Ala Gly Gly Ile Val
        765                 770                 775

GCC GGG ATC TTC CTG ATT TTC ATC GAG ATT GCC TAC AAG CGG CAC AAG         2643
Ala Gly Ile Phe Leu Ile Phe Ile Glu Ile Ala Tyr Lys Arg His Lys
    780                 785                 790

GAT GCT CGC CGG AAG CAG ATG CAG CTG GCC TTT GCC GCC GTT AAC GTG         2691
Asp Ala Arg Arg Lys Gln Met Gln Leu Ala Phe Ala Ala Val Asn Val
795                 800                 805                 810

TGG CGG AAG AAC CTG CAG GAT AGA AAG AGT GGT AGA GCA GAG CCT GAC         2739
```

-continued

```
Trp Arg Lys Asn Leu Gln Asp Arg Lys Ser Gly Arg Ala Glu Pro Asp
                815                 820                 825

CCT AAA AAG AAA GCC ACA TTT AGG GCT ATC ACC TCC ACC CTG GCT TCC    2787
Pro Lys Lys Lys Ala Thr Phe Arg Ala Ile Thr Ser Thr Leu Ala Ser
        830                 835                 840

AGC TTC AAG AGG CGT AGG TCC TCC AAA GAC ACG CTG GCT CGG GAC TGT    2835
Ser Phe Lys Arg Arg Arg Ser Ser Lys Asp Thr Leu Ala Arg Asp Cys
            845                 850                 855

CTT CAA CCC TGC CCT GCA CCT TGG GCA CGG GAG AGC GCC ACC CGC CCG    2883
Leu Gln Pro Cys Pro Ala Pro Trp Ala Arg Glu Ser Ala Thr Arg Pro
        860                 865                 870

CCC CCG CCC TCG CTC CGG GTG CGT GAC CGG CCC GCC ACC TTG TAC AGA    2931
Pro Pro Pro Ser Leu Arg Val Arg Asp Arg Pro Ala Thr Leu Tyr Arg
875                 880                 885                 890

ACC AGC ACT CCC AGG GCC CGA GCG CGT GCC TTC CCC GTG CGC AGC CGC    2979
Thr Ser Thr Pro Arg Ala Arg Ala Arg Ala Phe Pro Val Arg Ser Arg
                895                 900                 905

GCT CTG CCC CTC CGT CCC CAG GGT GCA GGC GCG CAC CGC CCA ACC CCC    3027
Ala Leu Pro Leu Arg Pro Gln Gly Ala Gly Ala His Arg Pro Thr Pro
            910                 915                 920

ACC TCC CGG TGT ATG CAG TGG TGATGCCTAA AGGAATGTCA CG               3070
Thr Ser Arg Cys Met Gln Trp
        925                 930
```

(2) INFORMATION FOR SEQ ID NO:40:

(i) SEQUENCE CHARACTERISTICS:
        (A) LENGTH: 929 amino acids
        (B) TYPE: amino acid
        (D) TOPOLOGY: linear (ii) MOLECULE TYPE: protein (xi) SEQUENCE DESCRIPTION: SEQ ID NO:40:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
 65                 70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190
```

```
Lys Arg Asn Tyr Glu Asn Leu Asp Gln Leu Ser Tyr Asp Asn Lys Arg
            195                 200                 205

Gly Pro Lys Ala Glu Lys Val Leu Gln Phe Asp Pro Gly Thr Lys Asn
        210                 215                 220

Val Thr Ala Leu Leu Met Glu Ala Lys Glu Leu Glu Ala Arg Val Ile
225                 230                 235                 240

Ile Leu Ser Ala Ser Glu Asp Ala Ala Thr Val Tyr Arg Ala Ala
                245                 250                 255

Ala Met Leu Asn Met Thr Gly Asn Thr Asn Ile Trp Lys Thr Gly Pro
            260                 265                 270

Leu Phe Lys Arg Val Leu Met Ser Ser Lys Tyr Ala Asp Gly Val Thr
            275                 280                 285

Gly Arg Val Glu Phe Asn Glu Asp Gly Asp Arg Lys Phe Ala Asn Tyr
        290                 295                 300

Ser Ile Met Asn Leu Gln Asn Arg Lys Leu Val Gln Val Gly Ile Tyr
305                 310                 315                 320

Asn Gly Thr His Val Ile Pro Asn Asp Arg Lys Ile Ile Trp Pro Gly
                325                 330                 335

Gly Glu Thr Glu Lys Pro Arg Gly Tyr Gln Met Ser Thr Arg Leu Lys
            340                 345                 350

Ile Val Thr Ile His Gln Glu Pro Phe Val Tyr Val Lys Pro Thr Leu
            355                 360                 365

Ser Asp Gly Thr Cys Lys Glu Glu Phe Thr Val Asn Gly Asp Pro Val
        370                 375                 380

Lys Lys Val Ile Cys Thr Gly Pro Asn Asp Thr Ser Pro Gly Ser Pro
385                 390                 395                 400

Arg His Thr Val Pro Gln Cys Cys Tyr Gly Phe Cys Ile Asp Leu Leu
                405                 410                 415

Ile Lys Leu Ala Arg Thr Met Asn Phe Thr Tyr Glu Val His Leu Val
            420                 425                 430

Ala Asp Gly Lys Phe Gly Thr Gln Glu Arg Val Asn Asn Ser Asn Lys
        435                 440                 445

Lys Glu Trp Asn Gly Met Met Gly Glu Leu Leu Ser Gly Gln Ala Asp
            450                 455                 460

Met Ile Val Ala Pro Leu Thr Ile Asn Asn Glu Arg Ala Gln Tyr Ile
465                 470                 475                 480

Glu Phe Ser Lys Pro Phe Lys Tyr Gln Gly Leu Thr Ile Leu Val Lys
                485                 490                 495

Lys Glu Ile Pro Arg Ser Thr Leu Asp Ser Phe Met Gln Pro Phe Gln
            500                 505                 510

Ser Thr Leu Trp Leu Leu Val Gly Leu Ser Val His Val Val Ala Val
            515                 520                 525

Met Leu Tyr Leu Leu Asp Arg Phe Ser Pro Phe Gly Arg Phe Lys Val
530                 535                 540

Asn Ser Glu Glu Glu Glu Asp Ala Leu Thr Leu Ser Ser Ala Met
545                 550                 555                 560

Trp Phe Ser Trp Gly Val Leu Leu Asn Ser Gly Ile Gly Glu Gly Ala
                565                 570                 575

Pro Arg Ser Phe Ser Ala Arg Ile Leu Gly Met Val Trp Ala Gly Phe
            580                 585                 590

Ala Met Ile Ile Val Ala Ser Tyr Thr Ala Asn Leu Ala Ala Phe Leu
            595                 600                 605

Val Leu Asp Arg Pro Glu Glu Arg Ile Thr Gly Ile Asn Asp Pro Arg
```

```
                   610                 615                 620
Leu Arg Asn Pro Ser Asp Lys Phe Ile Tyr Ala Thr Val Lys Gln Ser
625                 630                 635                 640

Ser Val Asp Ile Tyr Phe Arg Arg Gln Val Glu Leu Ser Thr Met Tyr
                645                 650                 655

Arg His Met Glu Lys His Asn Tyr Glu Ser Ala Ala Glu Ala Ile Gln
                660                 665                 670

Ala Val Arg Asp Asn Lys Leu His Ala Phe Ile Trp Asp Ser Ala Val
                675                 680                 685

Leu Glu Phe Glu Ala Ser Gln Lys Cys Asp Leu Val Thr Thr Gly Glu
690                 695                 700

Leu Phe Phe Arg Ser Gly Phe Gly Ile Gly Met Arg Lys Asp Ser Pro
705                 710                 715                 720

Trp Lys Gln Asn Val Ser Leu Ser Ile Leu Lys Ser His Glu Asn Gly
                725                 730                 735

Phe Met Glu Asp Leu Asp Lys Thr Trp Val Arg Tyr Gln Glu Cys Asp
                740                 745                 750

Ser Arg Ser Asn Ala Pro Ala Thr Leu Thr Phe Glu Asn Met Ala Gly
                755                 760                 765

Val Phe Met Leu Val Ala Gly Gly Ile Val Ala Gly Ile Phe Leu Ile
770                 775                 780

Phe Ile Glu Ile Ala Tyr Lys Arg His Lys Asp Ala Arg Arg Lys Gln
785                 790                 795                 800

Met Gln Leu Ala Phe Ala Ala Val Asn Val Trp Arg Lys Asn Leu Gln
                805                 810                 815

Asp Arg Lys Ser Gly Arg Ala Glu Pro Asp Pro Lys Lys Lys Ala Thr
                820                 825                 830

Phe Arg Ala Ile Thr Ser Thr Leu Ala Ser Ser Phe Lys Arg Arg Arg
                835                 840                 845

Ser Ser Lys Asp Thr Leu Ala Arg Asp Cys Leu Gln Pro Cys Pro Ala
850                 855                 860

Pro Trp Ala Arg Glu Ser Ala Thr Arg Pro Pro Pro Ser Leu Arg
865                 870                 875                 880

Val Arg Asp Arg Pro Ala Thr Leu Tyr Arg Thr Ser Thr Pro Arg Ala
                885                 890                 895

Arg Ala Arg Ala Phe Pro Val Arg Ser Arg Ala Leu Pro Leu Arg Pro
                900                 905                 910

Gln Gly Ala Gly Ala His Arg Pro Thr Pro Thr Ser Arg Cys Met Gln
                915                 920                 925

Trp (2) INFORMATION FOR SEQ ID NO:41:

(i) SEQUENCE CHARACTERISTICS:
        (A) LENGTH: 2326 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 3..2324

(xi) SEQUENCE DESCRIPTION: SEQ ID NO:41:

CC GGC CAC GTG TGG CTG GTG CCC AAC CTG GCG CTG GGC AGC ACC GAT      47
```

```
        Gly His Val Trp Leu Val Pro Asn Leu Ala Leu Gly Ser Thr Asp
         1               5                  10                  15

GCG CCC CCC GCC ACC TTC CCC GTG GGC CTC ATC AGC GTC GTC ACC GAG        95
Ala Pro Pro Ala Thr Phe Pro Val Gly Leu Ile Ser Val Val Thr Glu
             20                  25                  30

AGC TGG CGC CTC AGC CTG CGC CAG AAG GTG CGC GAC GGC GTG GCC ATT       143
Ser Trp Arg Leu Ser Leu Arg Gln Lys Val Arg Asp Gly Val Ala Ile
             35                  40                  45

CTG GCC CTG GGC GCC CAC AGC TAC TGG CGC CAG CAT GGA ACC CTG CCA       191
Leu Ala Leu Gly Ala His Ser Tyr Trp Arg Gln His Gly Thr Leu Pro
             50                  55                  60

GCC CCG GCC GGG GAC TGC CGT GTT CAC CCT GGG CCC GTC AGC CCT GCC       239
Ala Pro Ala Gly Asp Cys Arg Val His Pro Gly Pro Val Ser Pro Ala
 65                  70                  75

CGG GAG GCC TTC TAC AGG CAC CTA CTG AAT GTC ACC TGG GAG GGC CGA       287
Arg Glu Ala Phe Tyr Arg His Leu Leu Asn Val Thr Trp Glu Gly Arg
 80                  85                  90                  95

GAC TTC TCC TTC AGC CCT GGT GGG TAC CTG GTC CAG CCC ACC ATG GTG       335
Asp Phe Ser Phe Ser Pro Gly Gly Tyr Leu Val Gln Pro Thr Met Val
                100                 105                 110

GTG ATC GCC CTC AAC CGG CAC CGC CTC TGG GAG ATG GTG GGG CGC TGG       383
Val Ile Ala Leu Asn Arg His Arg Leu Trp Glu Met Val Gly Arg Trp
                115                 120                 125

GAG CAT GGC GTC CTA TAC ATG AAG TAC CCC GTG TGG CCT CGC TAC AGT       431
Glu His Gly Val Leu Tyr Met Lys Tyr Pro Val Trp Pro Arg Tyr Ser
            130                 135                 140

GCC TCT CTG CAG CCT GTG GTG GAC AGT CGG CAC CTG ACG GTG GCC ACG       479
Ala Ser Leu Gln Pro Val Val Asp Ser Arg His Leu Thr Val Ala Thr
145                 150                 155

CTG GAA GAG CGG CCC TTT GTC ATC GTG GAG AGC CCT GAC CCT GGC ACA       527
Leu Glu Glu Arg Pro Phe Val Ile Val Glu Ser Pro Asp Pro Gly Thr
160                 165                 170                 175

GGA GGC TGT GTC CCC AAC ACC GTG CCC TGC CGC AGG CAG AGC AAC CAC       575
Gly Gly Cys Val Pro Asn Thr Val Pro Cys Arg Arg Gln Ser Asn His
                180                 185                 190

ACC TTC AGC AGC GGG GAC GTG GCC CCC TAC ACC AAG CTC TGC TGT AAG       623
Thr Phe Ser Ser Gly Asp Val Ala Pro Tyr Thr Lys Leu Cys Cys Lys
                195                 200                 205

GGA TTC TGC ATC GAC ATC CTC AAG AAG CTG GCC AGA GTG GTC AAA TTC       671
Gly Phe Cys Ile Asp Ile Leu Lys Lys Leu Ala Arg Val Val Lys Phe
            210                 215                 220

TCC TAC GAC CTG TAC CTG GTG ACC AAC GGC AAG CAT GGC AAG CGG GTG       719
Ser Tyr Asp Leu Tyr Leu Val Thr Asn Gly Lys His Gly Lys Arg Val
225                 230                 235

CGC GGC GTA TGG AAC GGC ATG ATT GGG GAG GTG TAC TAC AAG CGG GCA       767
Arg Gly Val Trp Asn Gly Met Ile Gly Glu Val Tyr Tyr Lys Arg Ala
240                 245                 250                 255

GAC ATG GCC ATC GGC TCC CTC ACC ATC AAT GAG GAA CGC TCC GAG ATC       815
Asp Met Ala Ile Gly Ser Leu Thr Ile Asn Glu Glu Arg Ser Glu Ile
                260                 265                 270

GTA GAC TTC TCT GTA CCC TTT GTG GAG ACG GGC ATC AGT GTG ATG GTG       863
Val Asp Phe Ser Val Pro Phe Val Glu Thr Gly Ile Ser Val Met Val
            275                 280                 285

GCT CGC AGC AAT GGC ACC GTC TCC CCC TCG GCC TTC TTG GAG CCA TAT       911
Ala Arg Ser Asn Gly Thr Val Ser Pro Ser Ala Phe Leu Glu Pro Tyr
            290                 295                 300

AGC CCT GCA GTG TGG GTG ATG ATG TTT GTC ATG TGC CTC ACT GTG GTG       959
Ser Pro Ala Val Trp Val Met Met Phe Val Met Cys Leu Thr Val Val
305                 310                 315
```

```
GCC ATC ACC GTC TTC ATG TTC GAG TAC TTC AGC CCT GTC AGC TAC AAC    1007
Ala Ile Thr Val Phe Met Phe Glu Tyr Phe Ser Pro Val Ser Tyr Asn
320                 325                 330                 335

CAG AAC CTC ACC AGA GGC AAG AAG TCC GGG GGC CCA GCT TTC ACT ATC    1055
Gln Asn Leu Thr Arg Gly Lys Lys Ser Gly Gly Pro Ala Phe Thr Ile
                340                 345                 350

GGC AAG TCC GTG TGG CTG CTG TGG GCG CTG GTC TTC AAC AAC TCA GTG    1103
Gly Lys Ser Val Trp Leu Leu Trp Ala Leu Val Phe Asn Asn Ser Val
            355                 360                 365

CCC ATC GAG AAC CCG CGG GGC ACC ACC AGC AAG ATC ATG GTT CTG GTC    1151
Pro Ile Glu Asn Pro Arg Gly Thr Thr Ser Lys Ile Met Val Leu Val
        370                 375                 380

TGG GCC TTC TTT GCT GTC ATC TTC CTC GCC AGA TAC ACG GCC AAC CTG    1199
Trp Ala Phe Phe Ala Val Ile Phe Leu Ala Arg Tyr Thr Ala Asn Leu
385                 390                 395

GCC GCC TTC ATG ATC CAA GAG CAA TAC ATC GAC ACT GTG TCG GGC CTC    1247
Ala Ala Phe Met Ile Gln Glu Gln Tyr Ile Asp Thr Val Ser Gly Leu
400                 405                 410                 415

AGT GAC AAG AAG TTT CAG CGG CCT CAA GAT CAG TAC CCA CCT TTC CGC    1295
Ser Asp Lys Lys Phe Gln Arg Pro Gln Asp Gln Tyr Pro Pro Phe Arg
                420                 425                 430

TTC GGC ACG GTG CCC AAC GGC AGC ACG GAG CGG AAC ATC CGC AGT AAC    1343
Phe Gly Thr Val Pro Asn Gly Ser Thr Glu Arg Asn Ile Arg Ser Asn
            435                 440                 445

TAC CGT GAC ATG CAC ACC CAC ATG GTC AAG TTC AAC CAG CGC TCG GTG    1391
Tyr Arg Asp Met His Thr His Met Val Lys Phe Asn Gln Arg Ser Val
        450                 455                 460

GAG GAC GCG CTC ACC AGC CTC AAG ATG GGC AAG GAC GAG GGC TGC AAG    1439
Glu Asp Ala Leu Thr Ser Leu Lys Met Gly Lys Asp Glu Gly Cys Lys
465                 470                 475

CTG GTC ACC ATT GGG TCT GGC AAG GTC TTT GCT ACC ACT GGC TAC GGC    1487
Leu Val Thr Ile Gly Ser Gly Lys Val Phe Ala Thr Thr Gly Tyr Gly
480                 485                 490                 495

ATC GCC ATG CAG AAG GAC TCC CAC TGG AAG CGG GCC ATA GAC CTG GCG    1535
Ile Ala Met Gln Lys Asp Ser His Trp Lys Arg Ala Ile Asp Leu Ala
                500                 505                 510

CTC TTG CAG TTC CTG GGG GAC GGA GAG ACA CAG AAA CTG GAG ACA GTG    1583
Leu Leu Gln Phe Leu Gly Asp Gly Glu Thr Gln Lys Leu Glu Thr Val
            515                 520                 525

TGG CTC TCA GGG ATC TGC CAG AAT GAG AAG AAC GAG GTG ATG AGC AGC    1631
Trp Leu Ser Gly Ile Cys Gln Asn Glu Lys Asn Glu Val Met Ser Ser
        530                 535                 540

AAG CTG GAC ATC GAC AAC ATG GGA GGC GTC TTC TAC ATG CTG CTG GTG    1679
Lys Leu Asp Ile Asp Asn Met Gly Gly Val Phe Tyr Met Leu Leu Val
545                 550                 555

GCC ATG GGG CTG GCC CTG CTG GTC TTC GCC TGG GAG CAC CTG GTC TAC    1727
Ala Met Gly Leu Ala Leu Leu Val Phe Ala Trp Glu His Leu Val Tyr
560                 565                 570                 575

TGG AAG CTG CGC CAC TCG GTG CCC AAC TCA TCC CAG CTG GAC TTC CTG    1775
Trp Lys Leu Arg His Ser Val Pro Asn Ser Ser Gln Leu Asp Phe Leu
                580                 585                 590

CTG GCT TTC AGC AGG GGC ATC TAC AGC TGC TTC AGC GGG GTG CAG AGC    1823
Leu Ala Phe Ser Arg Gly Ile Tyr Ser Cys Phe Ser Gly Val Gln Ser
            595                 600                 605

CTC GCC AGC CCA CCG CGG CAG GCC AGC CCG GAC CTC ACG GCC AGC TCG    1871
Leu Ala Ser Pro Pro Arg Gln Ala Ser Pro Asp Leu Thr Ala Ser Ser
        610                 615                 620

GCC CAG GCC AGC GTG CTC AAG ATT CTG CAG GCA GCC CGC GAC ATG GTG    1919
Ala Gln Ala Ser Val Leu Lys Ile Leu Gln Ala Ala Arg Asp Met Val
625                 630                 635
```

```
ACC ACG GCG GGC GTA AGC AAC TCC CTG GAC CGC GCC ACT CGC ACC ATC    1967
Thr Thr Ala Gly Val Ser Asn Ser Leu Asp Arg Ala Thr Arg Thr Ile
640                 645                 650                 655

GAG AAT TGG GGT GGC GGC CGT GCG CCC CCA CCG TCC CCC TGC CCG        2015
Glu Asn Trp Gly Gly Gly Arg Arg Ala Pro Pro Pro Ser Pro Cys Pro
            660                 665                 670

ACC CCG CGG TCT GGC CCC AGC CCA TGC CTG CCC ACC CCC GAC CCG CCC    2063
Thr Pro Arg Ser Gly Pro Ser Pro Cys Leu Pro Thr Pro Asp Pro Pro
                675                 680                 685

CCA GAG CCG AGC CCC ACG GGC TGG GGA CCG CCA GAC GGG GGT CGC GCG    2111
Pro Glu Pro Ser Pro Thr Gly Trp Gly Pro Pro Asp Gly Gly Arg Ala
        690                 695                 700

GCG CTT GTG CGC AGG GCT CCG CAG CCC CCG GGC CGC CCC CCG ACG CCG    2159
Ala Leu Val Arg Arg Ala Pro Gln Pro Pro Gly Arg Pro Pro Thr Pro
705                 710                 715

GGG CCG CCC CTG TCC GAC GTC TCC CGA GTG TCG CGC CGC CCA GCC TGG    2207
Gly Pro Pro Leu Ser Asp Val Ser Arg Val Ser Arg Arg Pro Ala Trp
720                 725                 730                 735

GAG GCG CGG TGG CCG GTG CGG ACC GGG CAC TGC GGG AGG CAC CTC TCG    2255
Glu Ala Arg Trp Pro Val Arg Thr Gly His Cys Gly Arg His Leu Ser
            740                 745                 750

GCC TCC GAG CGG CCC CTG TCG CCC GCG CGC TGT CAC TAC AGC TCC TTT    2303
Ala Ser Glu Arg Pro Leu Ser Pro Ala Arg Cys His Tyr Ser Ser Phe
                755                 760                 765

CCT CGA GCC GAC CGA TCC GGC CG                                     2326
Pro Arg Ala Asp Arg Ser Gly
        770

(2) INFORMATION FOR SEQ ID NO:42:

(i) SEQUENCE CHARACTERISTICS:
        (A) LENGTH: 774 amino acids
        (B) TYPE: amino acid
        (D) TOPOLOGY: linear (ii) MOLECULE TYPE: protein (xi) SEQUENCE DESCRIPTION: SEQ ID NO:42:

Gly His Val Trp Leu Val Pro Asn Leu Ala Leu Gly Ser Thr Asp Ala
1               5                   10                  15

Pro Pro Ala Thr Phe Pro Val Gly Leu Ile Ser Val Val Thr Glu Ser
                20                  25                  30

Trp Arg Leu Ser Leu Arg Gln Lys Val Arg Asp Gly Val Ala Ile Leu
            35                  40                  45

Ala Leu Gly Ala His Ser Tyr Trp Arg Gln His Gly Thr Leu Pro Ala
        50                  55                  60

Pro Ala Gly Asp Cys Arg Val His Pro Gly Pro Val Ser Pro Ala Arg
65                  70                  75                  80

Glu Ala Phe Tyr Arg His Leu Leu Asn Val Thr Trp Glu Gly Arg Asp
                85                  90                  95

Phe Ser Phe Ser Pro Gly Gly Tyr Leu Val Gln Pro Thr Met Val Val
            100                 105                 110

Ile Ala Leu Asn Arg His Arg Leu Trp Glu Met Val Gly Arg Trp Glu
        115                 120                 125

His Gly Val Leu Tyr Met Lys Tyr Pro Val Trp Pro Arg Tyr Ser Ala
    130                 135                 140

Ser Leu Gln Pro Val Val Asp Ser Arg His Leu Thr Val Ala Thr Leu
145                 150                 155                 160
```

-continued

```
Glu Glu Arg Pro Phe Val Ile Val Glu Ser Pro Asp Pro Gly Thr Gly
                165                 170                 175

Gly Cys Val Pro Asn Thr Val Pro Cys Arg Arg Gln Ser Asn His Thr
            180                 185                 190

Phe Ser Ser Gly Asp Val Ala Pro Tyr Thr Lys Leu Cys Cys Lys Gly
        195                 200                 205

Phe Cys Ile Asp Ile Leu Lys Lys Leu Ala Arg Val Lys Phe Ser
    210                 215                 220

Tyr Asp Leu Tyr Leu Val Thr Asn Gly Lys His Gly Lys Arg Val Arg
225                 230                 235                 240

Gly Val Trp Asn Gly Met Ile Gly Glu Val Tyr Tyr Lys Arg Ala Asp
                245                 250                 255

Met Ala Ile Gly Ser Leu Thr Ile Asn Glu Glu Arg Ser Glu Ile Val
            260                 265                 270

Asp Phe Ser Val Pro Phe Val Glu Thr Gly Ile Ser Val Met Val Ala
        275                 280                 285

Arg Ser Asn Gly Thr Val Ser Pro Ser Ala Phe Leu Glu Pro Tyr Ser
    290                 295                 300

Pro Ala Val Trp Val Met Met Phe Val Met Cys Leu Thr Val Val Ala
305                 310                 315                 320

Ile Thr Val Phe Met Phe Glu Tyr Phe Ser Pro Val Ser Tyr Asn Gln
                325                 330                 335

Asn Leu Thr Arg Gly Lys Lys Ser Gly Gly Pro Ala Phe Thr Ile Gly
            340                 345                 350

Lys Ser Val Trp Leu Leu Trp Ala Leu Val Phe Asn Asn Ser Val Pro
        355                 360                 365

Ile Glu Asn Pro Arg Gly Thr Thr Ser Lys Ile Met Val Leu Val Trp
    370                 375                 380

Ala Phe Phe Ala Val Ile Phe Leu Ala Arg Tyr Thr Ala Asn Leu Ala
385                 390                 395                 400

Ala Phe Met Ile Gln Glu Gln Tyr Ile Asp Thr Val Ser Gly Leu Ser
                405                 410                 415

Asp Lys Lys Phe Gln Arg Pro Gln Asp Gln Tyr Pro Pro Phe Arg Phe
            420                 425                 430

Gly Thr Val Pro Asn Gly Ser Thr Glu Arg Asn Ile Arg Ser Asn Tyr
        435                 440                 445

Arg Asp Met His Thr His Met Val Lys Phe Asn Gln Arg Ser Val Glu
450                 455                 460

Asp Ala Leu Thr Ser Leu Lys Met Gly Lys Asp Glu Gly Cys Lys Leu
465                 470                 475                 480

Val Thr Ile Gly Ser Gly Lys Val Phe Ala Thr Thr Gly Tyr Gly Ile
                485                 490                 495

Ala Met Gln Lys Asp Ser His Trp Lys Arg Ala Ile Asp Leu Ala Leu
            500                 505                 510

Leu Gln Phe Leu Gly Asp Gly Glu Thr Gln Lys Leu Glu Thr Val Trp
        515                 520                 525

Leu Ser Gly Ile Cys Gln Asn Glu Lys Asn Glu Val Met Ser Ser Lys
    530                 535                 540

Leu Asp Ile Asp Asn Met Gly Gly Val Phe Tyr Met Leu Leu Val Ala
545                 550                 555                 560

Met Gly Leu Ala Leu Leu Val Phe Ala Trp Glu His Leu Val Tyr Trp
                565                 570                 575

Lys Leu Arg His Ser Val Pro Asn Ser Ser Gln Leu Asp Phe Leu Leu
```

```
                580                    585                    590
Ala Phe Ser Arg Gly Ile Tyr Ser Cys Phe Ser Gly Val Gln Ser Leu
            595                    600                    605

Ala Ser Pro Pro Arg Gln Ala Ser Pro Asp Leu Thr Ala Ser Ser Ala
    610                    615                    620

Gln Ala Ser Val Leu Lys Ile Leu Gln Ala Ala Arg Asp Met Val Thr
625                    630                    635                    640

Thr Ala Gly Val Ser Asn Ser Leu Asp Arg Ala Thr Arg Thr Ile Glu
                645                    650                    655

Asn Trp Gly Gly Gly Arg Arg Ala Pro Pro Ser Pro Cys Pro Thr
            660                    665                    670

Pro Arg Ser Gly Pro Ser Pro Cys Leu Pro Thr Pro Asp Pro Pro Pro
            675                    680                    685

Glu Pro Ser Pro Thr Gly Trp Gly Pro Pro Asp Gly Gly Arg Ala Ala
    690                    695                    700

Leu Val Arg Arg Ala Pro Gln Pro Pro Gly Arg Pro Pro Thr Pro Gly
705                    710                    715                    720

Pro Pro Leu Ser Asp Val Ser Arg Val Ser Arg Pro Ala Trp Glu
                725                    730                    735

Ala Arg Trp Pro Val Arg Thr Gly His Cys Gly Arg His Leu Ser Ala
            740                    745                    750

Ser Glu Arg Pro Leu Ser Pro Ala Arg Cys His Tyr Ser Ser Phe Pro
            755                    760                    765

Arg Ala Asp Arg Ser Gly
    770
```

(2) INFORMATION FOR SEQ ID NO:43:

(i) SEQUENCE CHARACTERISTICS:
        (A) LENGTH: 3698 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 3...3698

(xi) SEQUENCE DESCRIPTION: SEQ ID NO:43:

```
TG GAG ATC CAG CCG CTC ACA GTT GGG GTC AAC ACC ACC AAC CCC AGC         47
   Glu Ile Gln Pro Leu Thr Val Gly Val Asn Thr Thr Asn Pro Ser
    1               5                  10                  15

AGC CTC CTC ACC CAG ATC TGC GGC CTC CTG GGT GCT GCC CAC GTC CAC        95
Ser Leu Leu Thr Gln Ile Cys Gly Leu Leu Gly Ala Ala His Val His
            20                  25                  30

GGC ATT GTC TTT GAG GAC AAC GTG GAC ACC GAG GCG GTG GCC CAG ATC       143
Gly Ile Val Phe Glu Asp Asn Val Asp Thr Glu Ala Val Ala Gln Ile
                35                  40                  45

CTT GAC TTC ATC TCC TCC CAG ACC CAT GTG CCC ATC CTC AGC ATC AGC       191
Leu Asp Phe Ile Ser Ser Gln Thr His Val Pro Ile Leu Ser Ile Ser
            50                  55                  60

GGA GGC TCT GCT GTG GTC CTC ACC CCC AAG GAG CCG GGC TCC GCC TTC       239
Gly Gly Ser Ala Val Val Leu Thr Pro Lys Glu Pro Gly Ser Ala Phe
65                  70                  75

CTG CAG CTG GGC GTG TCC CTG GAG CAG CAG CTG CAG GTG CTG TTC AAG       287
Leu Gln Leu Gly Val Ser Leu Glu Gln Gln Leu Gln Val Leu Phe Lys
80                  85                  90                  95
```

```
GTG CTG GAA GAG TAC GAC TGG AGC GCC TTC GCC GTC ATC ACC AGC CTG        335
Val Leu Glu Glu Tyr Asp Trp Ser Ala Phe Ala Val Ile Thr Ser Leu
            100                 105                 110

CAC CCG GGC CAC GCG CTC TTC CTG GAG GGC GTG CGC GCC GTC GCC GAC        383
His Pro Gly His Ala Leu Phe Leu Glu Gly Val Arg Ala Val Ala Asp
            115                 120                 125

GCC AGC CAC GTG AGT TGG CGG CTG CTG GAC GTG GTC ACG CTG GAA CTG        431
Ala Ser His Val Ser Trp Arg Leu Leu Asp Val Val Thr Leu Glu Leu
            130                 135                 140

GAC CCG GGA GGG CCG CGC GCG CGC ACG CAG CGC CTG CTG CGC CAG CTC        479
Asp Pro Gly Gly Pro Arg Ala Arg Thr Gln Arg Leu Leu Arg Gln Leu
145                 150                 155

GAC GCG CCC GTG TTT GTG GCC TAC TGC TCG CGC GAG GAG GCC GAG GTG        527
Asp Ala Pro Val Phe Val Ala Tyr Cys Ser Arg Glu Glu Ala Glu Val
160                 165                 170                 175

CTC TTC GCC GAG GCG GCG CAG GCC GGT CTG GTG GGG CCC GGC CAC GTG        575
Leu Phe Ala Glu Ala Ala Gln Ala Gly Leu Val Gly Pro Gly His Val
            180                 185                 190

TGG CTG GTG CCC AAC CTG GCG CTG GGC AGC ACC GAT GCG CCC CCC GCC        623
Trp Leu Val Pro Asn Leu Ala Leu Gly Ser Thr Asp Ala Pro Pro Ala
            195                 200                 205

ACC TTC CCC GTG GGC CTC ATC AGC GTC GTC ACC GAG AGC TGG CGC CTC        671
Thr Phe Pro Val Gly Leu Ile Ser Val Val Thr Glu Ser Trp Arg Leu
            210                 215                 220

AGC CTG CGC CAG AAG GTG CGC GAC GGC GTG GCC ATT CTG GCC CTG GGC        719
Ser Leu Arg Gln Lys Val Arg Asp Gly Val Ala Ile Leu Ala Leu Gly
225                 230                 235

GCC CAC AGC TAC TGG CGC CAG CAT GGA ACC CAG AAG GGG GTG TGC CAG        767
Ala His Ser Tyr Trp Arg Gln His Gly Thr Gln Lys Gly Val Cys Gln
240                 245                 250                 255

CCC CGG CCG GGG ACT GCC GTG TTC ACC CTG GGC CCG TCA GCC CTG CCC        815
Pro Arg Pro Gly Thr Ala Val Phe Thr Leu Gly Pro Ser Ala Leu Pro
            260                 265                 270

GGG AGG CCT TCT ACA GGC ACC TAC TGA ATG TCA CCT GGG AGG GCC GAG        863
Gly Arg Pro Ser Thr Gly Thr Tyr  *  Met Ser Pro Gly Arg Ala Glu
            275                 280                 285

ACT TCT CCT TCA GCC CTG GTG GGT ACC TGG TCC AGC CCA CCA TGG TGG        911
Thr Ser Pro Ser Ala Leu Val Gly Thr Trp Ser Ser Pro Pro Trp Trp
            290                 295                 300

TGA TCG CCC TCA ACC GGC ACC GCC TCT GGG AGA TGG TGG GGC GCT GGG        959
 *  Ser Pro Ser Thr Gly Thr Ala Ser Gly Arg Trp Trp Gly Ala Gly
    305                 310                 315

AGC ATG GCG TCC TAT ACA TGA AGT ACC CCG TGT GGC CTC GCT ACA GTG       1007
Ser Met Ala Ser Tyr Thr  *  Ser Thr Pro Cys Gly Leu Ala Thr Val
320                 325                 330                 335

CCT CTC TGC AGC CTG TGG TGG ACA GTC GGC ACC TGA CGG TGG CCA CGC       1055
Pro Leu Cys Ser Leu Trp Trp Thr Val Gly Thr  *  Arg Trp Pro Arg
            340                 345                 350

TGG AAG AGC GGC CCT TTG TCA TCG TGG AGA GCC CTG ACC CTG GCA CAG       1103
Trp Lys Ser Gly Pro Leu Ser Ser Trp Arg Ala Leu Thr Leu Ala Gln
            355                 360                 365

GAG GCT GTG TCC CCA ACA CCG TGC CCT GCC GCA GGC AGA GCA ACC ACA       1151
Glu Ala Val Ser Pro Thr Pro Cys Pro Ala Ala Gly Arg Ala Thr Thr
            370                 375                 380

CCT TCA GCA GCG GGA CGT GGC CCC CT ACA CCA AGC TCT GCT GTA AGG       1199
Pro Ser Ala Ala Gly Thr Trp Pro Pro Thr Pro Ser Ser Ala Val Arg
385                 390                 395

GAT TCT GCA TCG ACA TCC TCA AGA AGC TGG CCA GAG TGG TCA AAT TCT       1247
Asp Ser Ala Ser Thr Ser Ser Arg Ser Trp Pro Glu Trp Ser Asn Ser
400                 405                 410                 415
```

```
CCT ACG ACC TGT ACC TGG TGA CCA ACG GCA AGC ATG GCA AGC GGG TGC       1295
Pro Thr Thr Cys Thr Trp  *  Pro Thr Ala Ser Met Ala Ser Gly Cys
                420                 425                 430

GCG GCG TAT GGA ACG GCA TGA TTG GGG AGG TGT ACT ACA AGC GGG CAG       1343
Ala Ala Tyr Gly Thr Ala  *  Leu Gly Arg Cys Thr Thr Ser Gly Gln
                435                 440                 445

ACA TGG CCA TCG GCT CCC TCA CCA TCA ATG AGG AAC GCT CCG AGA TCG       1391
Thr Trp Pro Ser Ala Pro Ser Pro Ser Met Arg Asn Ala Pro Arg Ser
                450                 455                 460

TAG ACT TCT CTG TAC CCT TTG TGG AGA CGG GCA TCA GTG TGA TGG TGG       1439
 *  Thr Ser Leu Tyr Pro Leu Trp Arg Arg Ala Ser Val  *  Trp Trp
    465                 470                 475

CTC GCA GCA ATG GCA CCG TCT CCC CCT CGG CCT TCT TGG AGC CAT ATA       1487
Leu Ala Ala Met Ala Pro Ser Pro Pro Arg Pro Ser Trp Ser His Ile
480                 485                 490                 495

GCC CTG CAG TGT GGG TGA TGA TGT TTG TCA TGT GCC TCA CTG TGG TGG       1535
Ala Leu Gln Cys Gly  *   *  Cys Leu Ser Cys Ala Ser Leu Trp Trp
                500                 505                 510

CCA TCA CCG TCT TCA TGT TCG AGT ACT TCA GCC CTG TCA GCT ACA ACC       1583
Pro Ser Pro Ser Ser Cys Ser Ser Thr Ser Ala Leu Ser Ala Thr Thr
                515                 520                 525

AGA ACC TCA CCA GAG GCA AGA CTT TCA CTA TCG GCA AGT CCG TGT GGC       1631
Arg Thr Ser Pro Glu Ala Arg Leu Ser Leu Ser Ala Ser Pro Cys Gly
                530                 535                 540

TGC TGT GGG CGC TGG TCT TCA ACA ACT CAG TGC CCA TCG AGA ACC CGC       1679
Cys Cys Gly Arg Trp Ser Ser Thr Thr Gln Cys Pro Ser Arg Thr Arg
                545                 550                 555

GGG GCA CCA CCA GCA AGA TCA TGG TTC TGG TCT GGG CCT TCT TTG CTG       1727
Gly Ala Pro Pro Ala Arg Ser Trp Phe Trp Ser Gly Pro Ser Leu Leu
560                 565                 570                 575

TCA TCT TCC TCG CCA GAT ACA CGG CCA ACC TGG CCG CCT TCA TGA TCC       1775
Ser Ser Ser Ser Pro Asp Thr Arg Pro Thr Trp Pro Pro Ser  *  Ser
                580                 585                 590

AAG AGC AAT ACA TCG ACA CTG TGT CGG GCC TCA GTG ACA AGA AGT TTC       1823
Lys Ser Asn Thr Ser Thr Leu Cys Arg Ala Ser Val Thr Arg Ser Phe
                595                 600                 605

AGC GGC CTC AAG ATC AGT ACC CAC CTT TCC GCT TCG GCA CGG TGC CCA       1871
Ser Gly Leu Lys Ile Ser Thr His Leu Ser Ala Ser Ala Arg Cys Pro
                610                 615                 620

ACG GCA GCA CGG AGC GGA ACA TCC GCA GTA ACT ACC GTG ACA TGC ACA       1919
Thr Ala Ala Arg Ser Gly Thr Ser Ala Val Thr Thr Val Thr Cys Thr
625                 630                 635

CCC ACA TGG TCA AGT TCA ACC AGC GCT CGG TGG AGG ACG CGC TCA CCA       1967
Pro Thr Trp Ser Ser Ser Thr Ser Ala Arg Trp Arg Thr Arg Ser Pro
640                 645                 650                 655

GCC TCA AGA TGG GGA AGC TGG ATG CCT TCA TCT ATG ATG CTG CTG TCC       2015
Ala Ser Arg Trp Gly Ser Trp Met Pro Ser Ser Met Met Leu Leu Ser
                660                 665                 670

TCA ACT ACA TGG CAG GCA AGG ACG AGG GCT GCA AGC TGG TCA CCA TTG       2063
Ser Thr Thr Trp Gln Ala Arg Thr Arg Ala Ala Ser Trp Ser Pro Leu
                675                 680                 685

GGT CTG GCA AGG TCT TTG CTA CCA CTG GCT ACG GCA TCG CCA TGC AGA       2111
Gly Leu Ala Arg Ser Leu Leu Pro Leu Ala Thr Ala Ser Pro Cys Arg
                690                 695                 700

AGG ACT CCC ACT GGA AGC GGG CCA TAG ACC TGG CGC TCT TGC AGT TCC       2159
Arg Thr Pro Thr Gly Ser Gly Pro  *  Thr Trp Arg Ser Cys Ser Ser
                705                 710                 715

TGG GGG ACG GAG AGA CAC AGA AAC TGG AGA CAG TGT GGC TCT CAG GGA       2207
Trp Gly Thr Glu Arg His Arg Asn Trp Arg Gln Cys Gly Ser Gln Gly
```

```
                                                                    -continued
720                       725                       730                       735

TCT GCC AGA ATG AGA AGA ACG AGG TGA TGA GCA GCA AGC TGG ACA TCG                2255
Ser Ala Arg Met Arg Arg Thr Arg  *   *  Ala Ala Ser Trp Thr Ser
                    740                   745                   750

ACA ACA TGG GAG GCG TCT TCT ACA TGC TGC TGG TGG CCA TGG GGC TGG                2303
Thr Thr Trp Glu Ala Ser Ser Thr Cys Cys Trp Trp Pro Trp Gly Trp
                755                   760                   765

CCC TGC TGG TCT TCG CCT GGG AGC ACC TGG TCT ACT GGA AGC TGC GCC                2351
Pro Cys Trp Ser Ser Pro Gly Ser Thr Trp Ser Thr Gly Ser Cys Ala
            770                   775                   780

ACT CGG TGC CCA ACT CAT CCC AGC TGG ACT TCC TGC TGG CTT TCA GCA                2399
Thr Arg Cys Pro Thr His Pro Ser Trp Thr Ser Cys Trp Leu Ser Ala
        785                   790                   795

GGG GCA TCT ACA GCT GCT TCA GCG GGG TGC AGA GCC TCG CCA GCC CAC                2447
Gly Ala Ser Thr Ala Ala Ser Ala Gly Cys Arg Ala Ser Pro Ala His
800                   805                   810                   815

CGC GGC AGG CCA GCC CGG ACC TCA CGG CCA GCT CGG CCC AGG CCA GCG                2495
Arg Gly Arg Pro Ala Arg Thr Ser Arg Pro Ala Arg Pro Arg Pro Ala
                820                   825                   830

TGC TCA AGA TTC TGC AGG CAG CCC GCG ACA TGG TGA CCA CGG CGG GCG                2543
Cys Ser Arg Phe Cys Arg Gln Pro Ala Thr Trp  *  Pro Arg Arg Ala
                835                   840                   845

TAA GCA ACT CCC TGG ACC GCG CCA CTC GCA CCA TCG AGA ATT GGG GTG                2591
 *  Ala Thr Pro Trp Thr Ala Pro Leu Ala Pro Ser Arg Ile Gly Val
        850                   855                   860

GCG GCC GCC GTG CGC CCC CAC CGT CCC CCT GCC CGA CCC CGC GGT CTG                2639
Ala Ala Ala Val Arg Pro His Arg Pro Pro Ala Arg Pro Arg Gly Leu
    865                   870                   875

GCC CCA GCC CAT GCC TGC CCA CCC CCG ACC CGC CCC CAG AGC CGA GCC                2687
Ala Pro Ala His Ala Cys Pro Pro Thr Arg Pro Gln Ser Arg Ala
880                   885                   890                   895

CCA CGG GCT GGG GAC CGC CAG ACG GGG GTC GCG CGG CGC TTG TGC GCA                2735
Pro Arg Ala Gly Asp Arg Gln Thr Gly Val Ala Arg Arg Leu Cys Ala
                900                   905                   910

GGG CTC CGC AGC CCC CGG GCC GCC CCC CGA CGC CGG GGC CGC CCC TGT                2783
Gly Leu Arg Ser Pro Arg Ala Ala Pro Arg Arg Gly Arg Pro Cys
                915                   920                   925

CCG ACG TCT CCC GAG TGT CGC GCC GCC CAG CCT GGG AGG CGC GGT GGC                2831
Pro Thr Ser Pro Glu Cys Arg Ala Ala Gln Pro Gly Arg Arg Gly Gly
            930                   935                   940

CGG TGC GGA CCG GGC ACT GCG GGA GGC ACC TCT CGG CCT CCG AGC GGC                2879
Arg Cys Gly Pro Gly Thr Ala Gly Gly Thr Ser Arg Pro Pro Ser Gly
    945                   950                   955

CCC TGT CGC CCG CGC GCT GTC ACT ACA GCT CCT TTC CTC GAG CCG ACC                2927
Pro Cys Arg Pro Arg Ala Val Thr Thr Ala Pro Phe Leu Glu Pro Thr
960                   965                   970                   975

GAT CCG GCC GCC CCT TCC TCC CGC TCT TCC CGG AGC CCC CGG AGC TGG                2975
Asp Pro Ala Ala Pro Ser Ser Arg Ser Ser Arg Ser Pro Arg Ser Trp
                980                   985                   990

AGG ACC TGC CGC TGC TCG GTC CGG AGC AGC TGG CCC GGC GGG AGG CCC                3023
Arg Thr Cys Arg Cys Ser Val Arg Ser Ser Trp Pro Gly Gly Arg Pro
                995                  1000                  1005

TGC TGA ACG CGG CCT GGG CCC GGG GCT CGC GCC CGA GTC ACG CTT CCC                3071
Cys  *  Thr Arg Pro Gly Pro Gly Ala Arg Ala Arg Val Thr Leu Pro
        1010                  1015                  1020

TGC CCA GCT CCG TGG CCG AGG CCT TCG CTC GGC CCA GCT CGC TGC CCG                3119
Cys Pro Ala Pro Trp Pro Arg Pro Ser Leu Gly Pro Ala Arg Cys Pro
    1025                  1030                  1035

CTG GGT GCA CCG GCC CCG CCT GCG CCC GCC CCG ACG GCC ACT CGG CCT                3167
```

-continued

```
Leu Gly Ala Pro Ala Pro Pro Ala Pro Ala Pro Thr Ala Thr Arg Pro
1040                1045                1050                1055

GCA GGC GCT TGG CGC AGG CGC AGT CGA TGT GCT TGC CGA TCT ACC GGG      3215
Ala Gly Ala Trp Arg Arg Arg Ser Arg Cys Ala Cys Arg Ser Thr Gly
            1060                1065                1070

AGG CCT GCC AGG AGG GCG AGC AGG CAG GGG CCC CCG CCT GGC AGC ACA      3263
Arg Pro Ala Arg Arg Ala Ser Arg Gln Gly Pro Pro Pro Gly Ser Thr
    1075                1080                1085

GAC AGC ACG TCT GCC TGC ACG CCC ACG CCC ACC TGC CAT TGT GCT GGG      3311
Asp Ser Thr Ser Ala Cys Thr Pro Thr Pro Thr Cys His Cys Ala Gly
1090                1095                1100

GGG CTG TCT GTC CTC ACC TTC CAC CCT GTG ACA GCC ACG GCT CCT GGC      3359
Gly Leu Ser Val Leu Thr Phe His Pro Val Thr Ala Thr Ala Pro Gly
        1105                1110                1115

TCT CCG GCG CCT GGG GGC CTC TGG GGC ACA GCG GCA GGA CTC TGG GGC      3407
Ser Pro Ala Pro Gly Gly Leu Trp Gly Thr Ala Ala Gly Leu Trp Gly
1120                1125                1130                1135

TGG GCA CAG GCT ACA GAG ACA GTG GGG GAC TGG ACG AGA TCA GCA GTG      3455
Trp Ala Gln Ala Thr Glu Thr Val Gly Asp Trp Thr Arg Ser Ala Val
            1140                1145                1150

TAG CCC GTG GGA CGC AAG GCT TCC CGG GAC CCT GCA CCT GGA GAC GGA      3503
 *  Pro Val Gly Arg Lys Ala Ser Arg Asp Pro Ala Pro Gly Asp Gly
                1155                1160                1165

TCT CCA GTC TGG AGT CAG AAG TGT GAG TTA TCA GCC ACT CAG GCT CCG      3551
Ser Pro Val Trp Ser Gln Lys Cys Glu Leu Ser Ala Thr Gln Ala Pro
    1170                1175                1180

AGC CAG CTG GAT TCT CTG CCT GCC ACT GTC AGG GTT AAG CGG CAG GCA      3599
Ser Gln Leu Asp Ser Leu Pro Ala Thr Val Arg Val Lys Arg Gln Ala
1185                1190                1195

GGA TTG GCC CTT CTC TGG CTT CTA CCA TGA AAT CCT GGC CAT GGC ACC      3647
Gly Leu Ala Leu Leu Trp Leu Leu Pro  *  Asn Pro Gly His Gly Thr
1200                1205                1210                1215

CCA GTG ACA GAT GAT GTC TTC CAT GGT CAT CAG TGA CCT CAG CTA GCC      3695
Pro Val Thr Asp Asp Val Phe His Gly His Gln  *  Pro Gln Leu Ala
            1220                1225                1230

TCA                                                                   3698
Ser
```

(2) INFORMATION FOR SEQ ID NO:44:

(i) SEQUENCE CHARACTERISTICS:
        (A) LENGTH: 3243 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: Coding Sequence
        (B) LOCATION: 1...3243

(xi) SEQUENCE DESCRIPTION: SEQ ID NO:44:

```
GTG GCC TAC TGC TCG CGC GAG GAG GCC GAG GTG CTC TTC GCC GAG GCG       48
Val Ala Tyr Cys Ser Arg Glu Glu Ala Glu Val Leu Phe Ala Glu Ala
1               5                   10                  15

GCG CAG GCC GGT CTG GTG GGG CCC GGC CAC GTG TGG CTG GTG CCC AAC       96
Ala Gln Ala Gly Leu Val Gly Pro Gly His Val Trp Leu Val Pro Asn
            20                  25                  30

CTG GCG CTG GGC AGC ACC GAT GCG CCC CCC GCC ACC TTC CCC GTG GGC      144
Leu Ala Leu Gly Ser Thr Asp Ala Pro Pro Ala Thr Phe Pro Val Gly
        35                  40                  45
```

```
CTC ATC AGC GTC GTC ACC GAG AGC TGG CGC CTC AGC CTG CGC CAG AAG     192
Leu Ile Ser Val Val Thr Glu Ser Trp Arg Leu Ser Leu Arg Gln Lys
        50                  55                  60

GTG CGC GAC GGC GTG GCC ATT CTG GCC CTG GGC GCC CAC AGC TAC TGG     240
Val Arg Asp Gly Val Ala Ile Leu Ala Leu Gly Ala His Ser Tyr Trp
65                  70                  75                  80

CGC CAG CAT GGA ACC CAG AAG GGG GTG TGC CAG CCC CGG CCG GGG ACT     288
Arg Gln His Gly Thr Gln Lys Gly Val Cys Gln Pro Arg Pro Gly Thr
                85                  90                  95

GCC GTG TTC ACC CTG GGC CCG TCA GCC CTG CCC GGG AGG CCT TCT ACA     336
Ala Val Phe Thr Leu Gly Pro Ser Ala Leu Pro Gly Arg Pro Ser Thr
            100                 105                 110

GGC ACC TAC TGA ATG TCA CCT GGG AGG GCC GAG ACT TCT CCT TCA GCC     384
Gly Thr Tyr  *  Met Ser Pro Gly Arg Ala Glu Thr Ser Pro Ser Ala
            115                 120                 125

CTG GTG GGT ACC TGG TCC AGC CCA CCA TGG TGG TGA TCG CCC TCA ACC     432
Leu Val Gly Thr Trp Ser Ser Pro Pro Trp Trp  *  Ser Pro Ser Thr
130                 135                 140

GGC ACC GCC TCT GGG AGA TGG TGG GGC GCT GGG AGC ATG GCG TCC TAT     480
Gly Thr Ala Ser Gly Arg Trp Trp Gly Ala Gly Ser Met Ala Ser Tyr
145                 150                 155                 160

ACA TGA AGT ACC CCG TGT GGC CTC GCT ACA GTG CCT CTC TGC AGC CTG     528
Thr  *  Ser Thr Pro Cys Gly Leu Ala Thr Val Pro Leu Cys Ser Leu
                165                 170                 175

TGG TGG ACA GTC GGC ACC TGA CGG TGG CCA CGC TGG AAG AGC GGC CCT     576
Trp Trp Thr Val Gly Thr  *  Arg Trp Pro Arg Trp Lys Ser Gly Pro
            180                 185                 190

TTG TCA TCG TGG AGA GCC CTG ACC CTG GCA CAG GAG GCT GTG TCC CCA     624
Leu Ser Ser Trp Arg Ala Leu Thr Leu Ala Gln Glu Ala Val Ser Pro
            195                 200                 205

ACA CCG TGC CCT GCC GCA GGC AGA GCA ACC ACA CCT TCA GCA GCG GGG     672
Thr Pro Cys Pro Ala Ala Gly Arg Ala Thr Thr Pro Ser Ala Ala Gly
        210                 215                 220

ACG TGG CCC CCT ACA CCA AGC TCT GCT GTA AGG GAT TCT GCA TCG ACA     720
Thr Trp Pro Pro Thr Pro Ser Ser Ala Val Arg Asp Ser Ala Ser Thr
225                 230                 235                 240

TCC TCA AGA AGC TGG CCA GAG TGG TCA AAT TCT CCT ACG ACC TGT ACC     768
Ser Ser Arg Ser Trp Pro Glu Trp Ser Asn Ser Pro Thr Thr Cys Thr
                245                 250                 255

TGG TGA CCA ACG GCA AGC ATG GCA AGC GGG TGC GCG GCG TAT GGA ACG     816
Trp  *  Pro Thr Ala Ser Met Ala Ser Gly Cys Ala Ala Tyr Gly Thr
            260                 265                 270

GCA TGA TTG GGG AGG TGT ACT ACA AGC GGG CAG ACA TGG CCA TCG GCT     864
Ala  *  Leu Gly Arg Cys Thr Thr Ser Gly Gln Thr Trp Pro Ser Ala
        275                 280                 285

CCC TCA CCA TCA ATG AGG AAC GCT CCG AGA TCG TAG ACT TCT CTG TAC     912
Pro Ser Pro Ser Met Arg Asn Ala Pro Arg Ser  *  Thr Ser Leu Tyr
            290                 295                 300

CCT TTG TGG AGA CGG GCA TCA GTG TGA TGG TGG CTC GCA GCA ATG GCA     960
Pro Leu Trp Arg Arg Ala Ser Val  *  Trp Trp Leu Ala Ala Met Ala
305                 310                 315                 320

CCG TCT CCC CCT CGG CCT TCT TGG AGC CAT ATA GCC CTG CAG TGT GGG    1008
Pro Ser Pro Pro Arg Pro Ser Trp Ser His Ile Ala Leu Gln Cys Gly
                325                 330                 335

TGA TGA TGT TTG TCA TGT GCC TCA CTG TGG TGG CCA TCA CCG TCT TCA    1056
 *   *  Cys Leu Ser Cys Ala Ser Leu Trp Trp Pro Ser Pro Ser Ser
        340                 345                 350

TGT TCG AGT ACT TCA GCC CTG TCA GCT ACA ACC AGA ACC TCA CCA GAG    1104
Cys Ser Ser Thr Ser Ala Leu Ser Ala Thr Thr Arg Thr Ser Pro Glu
```

```
                    355                 360                 365
GCA AGA AGT CCG GGG GCC CAG CTT TCA CTA TCG GCA AGT CCG TGT GGC    1152
Ala Arg Ser Pro Gly Ala Gln Leu Ser Leu Ser Ala Ser Pro Cys Gly
    370                 375                 380

TGC TGT GGG CGC TGG TCT TCA ACA ACT CAG TGC CCA TCG AGA ACC CGC    1200
Cys Cys Gly Arg Trp Ser Ser Thr Thr Gln Cys Pro Ser Arg Thr Arg
385                 390                 395                 400

GGG GCA CCA CCA GCA AGA TCA TGG TTC TGG TCT GGG CCT TCT TTG CTG    1248
Gly Ala Pro Pro Ala Arg Ser Trp Phe Trp Ser Gly Pro Ser Leu Leu
                405                 410                 415

TCA TCT TCC TCG CCA GAT ACA CGG CCA ACC TGG CCG CCT TCA TGA TCC    1296
Ser Ser Ser Ser Pro Asp Thr Arg Pro Thr Trp Pro Pro Ser  *  Ser
            420                 425                 430

AAG AGC AAT ACA TCG ACA CTG TGT CGG GCC TCA GTG ACA AGA AGT TTC    1344
Lys Ser Asn Thr Ser Thr Leu Cys Arg Ala Ser Val Thr Arg Ser Phe
            435                 440                 445

AGC GGC CTC AAG ATC AGT ACC CAC CTT TCC GCT TCG GCA CGG TGC CCA    1392
Ser Gly Leu Lys Ile Ser Thr His Leu Ser Ala Ser Ala Arg Cys Pro
    450                 455                 460

ACG GCA GCA CGG AGC GGA ACA TCC GCA GTA ACT ACC GTG ACA TGC ACA    1440
Thr Ala Ala Arg Ser Gly Thr Ser Ala Val Thr Thr Val Thr Cys Thr
465                 470                 475                 480

CCC ACA TGG TCA AGT TCA ACC AGC GCT CGG TGG AGG ACG CGC TCA CCA    1488
Pro Thr Trp Ser Ser Thr Ser Ala Arg Trp Arg Thr Arg Ser Pro
                485                 490                 495

GCC TCA AGA TGG GCT CTG AGG CTC AGC CTG TCC CCA GGA AGC TGG ATG    1536
Ala Ser Arg Trp Ala Leu Arg Leu Ser Leu Ser Pro Gly Ser Trp Met
            500                 505                 510

CCT TCA TCT ATG ATG CTG CTG TCC TCA ACT ACA TGG CAG GCA AGG ACG    1584
Pro Ser Ser Met Met Leu Leu Ser Ser Thr Thr Trp Gln Ala Arg Thr
            515                 520                 525

AGG GCT GCA AGC TGG TCA CCA TTG GGT CTG GCA AGG TCT TTG CTA CCA    1632
Arg Ala Ala Ser Trp Ser Pro Leu Gly Leu Ala Arg Ser Leu Leu Pro
    530                 535                 540

CTG GCT ACG GCA TCG CCA TGC AGA AGG ACT CCC ACT GGA AGC GGG CCA    1680
Leu Ala Thr Ala Ser Pro Cys Arg Arg Thr Pro Thr Gly Ser Gly Pro
545                 550                 555                 560

TAG ACC TGG CGC TCT TGC AGT TCC TGG GGG ACG GAG AGA CAC AGA AAC    1728
 *  Thr Trp Arg Ser Cys Ser Ser Trp Gly Thr Glu Arg His Arg Asn
                565                 570                 575

TGG AGA CAG TGT GGC TCT CAG GGA TCT GCC AGA ATG AGA AGA ACG AGG    1776
Trp Arg Gln Cys Gly Ser Gln Gly Ser Ala Arg Met Arg Arg Thr Arg
                580                 585                 590

TGA TGA GCA GCA AGC TGG ACA TCG ACA ACA TGG GAG GCG TCT TCT ACA    1824
 *   *  Ala Ala Ser Trp Thr Ser Thr Thr Trp Glu Ala Ser Ser Thr
            595                 600                 605

TGC TGC TGG TGG CCA TGG GGC TGG CCC TGC TGG TCT TCG CCT GGG AGC    1872
Cys Cys Trp Trp Pro Trp Gly Trp Pro Cys Trp Ser Ser Pro Gly Ser
    610                 615                 620

ACC TGG TCT ACT GGA AGC TGC GCC ACT CGG TGC CAA CTC ATC CCA GC    1920
Thr Trp Ser Thr Gly Ser Cys Ala Thr Arg Cys Pro Thr His Pro Ser
625                 630                 635                 640

TGG ACT TCC TGC TGG CTT TCA GCA GGG GCA TCT ACA GCT GCT TCA GCG    1968
Trp Thr Ser Cys Trp Leu Ser Ala Gly Ala Ser Thr Ala Ala Ser Ala
                645                 650                 655

GGG TGC AGA GCC TCG CCA GCC CAC CGC GGC AGG CCA GCC GGA CCT CA    2016
Gly Cys Arg Ala Ser Pro Ala His Arg Gly Arg Pro Ala Arg Thr Ser
    660                 665                 670

CGG CCA GCT CGG CCC AGG CCA GCG TGC TCA AGA TTC TGC AGG CAG CCC    2064
```

```
                Arg Pro Ala Arg Pro Arg Pro Ala Cys Ser Arg Phe Cys Arg Gln Pro
                                675                 680                 685

GCG ACA TGG TGA CCA CGG CGG GCG TAA GCA ACT CCC TGG ACC GCG CCA                 2112
Ala Thr Trp  *  Pro Arg Arg Ala  *  Ala Thr Pro Trp Thr Ala Pro
690                 695                 700

CTC GCA CCA TCG AGA ATT GGG GTG GCG GCC GCC GTG CGC CCC CAC CGT                 2160
Leu Ala Pro Ser Arg Ile Gly Val Ala Ala Ala Val Arg Pro His Arg
705                 710                 715                 720

CCC CCT GCC CGA CCC CGC GGT CTG GCC CCA GCC CAT GCC TGC CCA CCC                 2208
Pro Pro Ala Arg Pro Arg Gly Leu Ala Pro Ala His Ala Cys Pro Pro
                725                 730                 735

CCG ACC CGC CCC CAG AGC CGA GCC CCA CGG GCT GGG GAC CGC CAG ACG                 2256
Pro Thr Arg Pro Gln Ser Arg Ala Pro Arg Ala Gly Asp Arg Gln Thr
            740                 745                 750

GGG GTC GCG CGG CGC TTG TGC GCA GGG CTC CGC AGC CCC CGG GCC GCC                 2304
Gly Val Ala Arg Arg Leu Cys Ala Gly Leu Arg Ser Pro Arg Ala Ala
            755                 760                 765

CCC CGA CGC CGG GGC CGC CCC TGT CCG ACG TCT CCC GAG TGT CGC GCC                 2352
Pro Arg Arg Arg Gly Arg Pro Cys Pro Thr Ser Pro Glu Cys Arg Ala
770                 775                 780

GCC CAG CCT GGG AGG CGC GGT GGC CGG TGC GGA CCG GGC ACT GCG GGA                 2400
Ala Gln Pro Gly Arg Arg Gly Arg Cys Gly Pro Gly Thr Ala Gly
785                 790                 795                 800

GGC ACC TCT CGG CCT CCG AGC GGC CCC TGT CGC CCG CGC GCT GTC ACT                 2448
Gly Thr Ser Arg Pro Pro Ser Gly Pro Cys Arg Pro Arg Ala Val Thr
                805                 810                 815

ACA GCT CCT TTC CTC GAG CCG ACC GAT CCG GCC GCC CCT TCC TCC CGC                 2496
Thr Ala Pro Phe Leu Glu Pro Thr Asp Pro Ala Ala Pro Ser Ser Arg
                820                 825                 830

TCT TCC CGG AGC CCC CGG AGC TGG AGG ACC TGC CGC TGC TCG GTC CGG                 2544
Ser Ser Arg Ser Pro Arg Ser Trp Arg Thr Cys Arg Cys Ser Val Arg
            835                 840                 845

AGC AGC TGG CCC GGC GGG AGG CCC TGC TGA ACG CGG CCT GGG CCC GGG                 2592
Ser Ser Trp Pro Gly Gly Arg Pro Cys  *  Thr Arg Pro Gly Pro Gly
850                 855                 860

GCT CGC GCC CGA GTC ACG CTT CCC TGC CCA GCT CCG TGG CCG AGG CCT                 2640
Ala Arg Ala Arg Val Thr Leu Pro Cys Pro Ala Pro Trp Pro Arg Pro
865                 870                 875                 880

TCG CTC GGC CCA GCT CGC TGC CCG CTG GGT GCA CCG GCC CCG CCT GCG                 2688
Ser Leu Gly Pro Ala Arg Cys Pro Leu Gly Ala Pro Ala Pro Pro Ala
                885                 890                 895

CCC GCC CCG ACG GCC ACT CGG CCT GCA GGC GCT TGG CGC AGG CGC AGT                 2736
Pro Ala Pro Thr Ala Thr Arg Pro Ala Gly Ala Trp Arg Arg Arg Ser
            900                 905                 910

CGA TGT GCT TGC CGA TCT ACC GGG AGG CCT GCC AGG AGG GCG AGC AGG                 2784
Arg Cys Ala Cys Arg Ser Thr Gly Arg Pro Ala Arg Arg Ala Ser Arg
            915                 920                 925

CAG GGG CCC CCG CCT GGC AGC ACA GAC AGC ACG TCT GCC TGC ACG CCC                 2832
Gln Gly Pro Pro Pro Gly Ser Thr Asp Ser Thr Ser Ala Cys Thr Pro
        930                 935                 940

ACG CCC ACC TGC CAT TGT GCT GGG GGG CTG TCT GTC CTC ACC TTC CAC                 2880
Thr Pro Thr Cys His Cys Ala Gly Gly Leu Ser Val Leu Thr Phe His
945                 950                 955                 960

CCT GTG ACA GCC ACG GCT CCT GGC TCT CCG GCG CCT GGG GGC CTC TGG                 2928
Pro Val Thr Ala Thr Ala Pro Gly Ser Pro Ala Pro Gly Gly Leu Trp
                965                 970                 975

GGC ACA GCG GCA GGA CTC TGG GGC TGG GCA CAG GCT ACA GAG ACA GTG                 2976
Gly Thr Ala Ala Gly Leu Trp Gly Trp Ala Gln Ala Thr Glu Thr Val
                980                 985                 990
```

```
GGG GAC TGG ACG AGA TCA GCA GTG TAG CCC GTG GGA CGC AAG GCT TCC      3024
Gly Asp Trp Thr Arg Ser Ala Val  *  Pro Val Gly Arg Lys Ala Ser
        995                 1000                1005

CGG GAC CCT GCA CCT GGA GAC GGA TCT CCA GTC TGG AGT CAG AAG TGT      3072
Arg Asp Pro Ala Pro Gly Asp Gly Ser Pro Val Trp Ser Gln Lys Cys
   1010                1015                1020

GAG TTA TCA GCC ACT CAG GCT CCG AGC CAG CTG GAT TCT CTG CCT GCC      3120
Glu Leu Ser Ala Thr Gln Ala Pro Ser Gln Leu Asp Ser Leu Pro Ala
1025                1030                1035                1040

ACT GTC AGG GTT AAG CGG CAG GCA GGA TTG GCC CTT CTC TGG CTT CTA      3168
Thr Val Arg Val Lys Arg Gln Ala Gly Leu Ala Leu Leu Trp Leu Leu
                1045                1050                1055

CCA TGA AAT CCT GGC CAT GGC ACC CCA GTG ACA GAT GAT GTC TTC CAT      3216
Pro  *  Asn Pro Gly His Gly Thr Pro Val Thr Asp Asp Val Phe His
            1060                1065                1070

GGT CAT CAG TGA CCT CAG CTA GCC TCA                                  3243
Gly His Gln  *  Pro Gln Leu Ala Ser
        1075                1080

(2) INFORMATION FOR SEQ ID NO:45:

(i) SEQUENCE CHARACTERISTICS:
        (A) LENGTH: 4092 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 189..3923

(xi) SEQUENCE DESCRIPTION: SEQ ID NO:45:

CCCTTAATAA GATTTGCNAC GTACACTCGA GCCATCGCGA GTGTCCTTGA GCCGCGGGTG        60

ACGGTGGCTC TCGCTGCTCG CGCCCCCTCC TCCCGCGGGG GGAGCCTGAT GCCACGTTCC       120

CTATGAATTA TTTATCGCCG GCCTAAAAAT ACCCCGAACT TCACAGCCCG AGTGACCCTC       180

CGGTGGAC ATG GGT GGG GCC CTG GGG CCG GCC CTG TTG CTC ACC TCG CTC       230
         Met Gly Gly Ala Leu Gly Pro Ala Leu Leu Leu Thr Ser Leu
          1               5                  10

TTC GGT GCC TGG GCA GGG CTG GGT CCG GGG CAG GGC GAG CAG GGC ATG        278
Phe Gly Ala Trp Ala Gly Leu Gly Pro Gly Gln Gly Glu Gln Gly Met
 15              20                  25                  30

ACG GTG GCC GTG GTG TTT AGC AGC TCA GGG CCG CCC CAG GCC CAG TTC        326
Thr Val Ala Val Val Phe Ser Ser Ser Gly Pro Pro Gln Ala Gln Phe
                35                  40                  45

CGT GTC CGC CTC ACC CCC CAG AGC TTC CTG GAC CTA CCC CTG GAG ATC        374
Arg Val Arg Leu Thr Pro Gln Ser Phe Leu Asp Leu Pro Leu Glu Ile
            50                  55                  60

CAG CCG CTC ACA GTT GGG GTC AAC ACC ACC AAC CCC AGC AGC CTC CTC        422
Gln Pro Leu Thr Val Gly Val Asn Thr Thr Asn Pro Ser Ser Leu Leu
        65                  70                  75

ACC CAG ATC TGC GGC CTC CTG GGT GCT GCC CAC GTC CAC GGC ATT GTC        470
Thr Gln Ile Cys Gly Leu Leu Gly Ala Ala His Val His Gly Ile Val
    80                  85                  90

TTT GAG GAC AAC GTG GAC ACC GAG GCG GTG GCC CAG ATC CTT GAC TTC        518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT        566
Ile Ser Ser Gln Thr His Val Pro Ile Leu Ser Ile Ser Gly Gly Ser
                115                 120                 125
```

```
                                                      -continued

GCT GTG GTC CTC ACC CCC AAG GAG CCG GGC TCC GCC TTC CTG CAG CTG        614
Ala Val Val Leu Thr Pro Lys Glu Pro Gly Ser Ala Phe Leu Gln Leu
130             135                 140

GGC GTG TCC CTG GAG CAG CAG CTG CAG GTG CTG TTC AAG GTG CTG GAA        662
Gly Val Ser Leu Glu Gln Gln Leu Gln Val Leu Phe Lys Val Leu Glu
            145                 150                 155

GAG TAC GAC TGG AGC GCC TTC GCC GTC ATC ACC AGC CTG CAC CCG GGC        710
Glu Tyr Asp Trp Ser Ala Phe Ala Val Ile Thr Ser Leu His Pro Gly
        160                 165                 170

CAC GCG CTC TTC CTG GAG GGC GTG CGC GCC GTC GCC GAC GCC AGC CAC        758
His Ala Leu Phe Leu Glu Gly Val Arg Ala Val Ala Asp Ala Ser His
175             180                 185                 190

GTG AGT TGG CGG CTG CTG GAC GTG GTC ACG CTG GAA CTG GAC CCG GGA        806
Val Ser Trp Arg Leu Leu Asp Val Val Thr Leu Glu Leu Asp Pro Gly
            195                 200                 205

GGG CCG CGC GCG CGC ACG CAG CGC CTG CTG CGC CAG CTC GAC GCG CCC        854
Gly Pro Arg Ala Arg Thr Gln Arg Leu Leu Arg Gln Leu Asp Ala Pro
        210                 215                 220

GTG TTT GTG GCC TAC TGC TCG CGC GAG GAG GCC GAG GTG CTC TTC GCC        902
Val Phe Val Ala Tyr Cys Ser Arg Glu Glu Ala Glu Val Leu Phe Ala
225             230                 235

GAG GCG GCG CAG GCC GGT CTG GTG GGG CCC GGC CAC GTG TGG CTG GTG        950
Glu Ala Ala Gln Ala Gly Leu Val Gly Pro Gly His Val Trp Leu Val
            240                 245                 250

CCC AAC CTG GCG CTG GGC AGC ACC GAT GCG CCC CCC GCC ACC TTC CCC        998
Pro Asn Leu Ala Leu Gly Ser Thr Asp Ala Pro Pro Ala Thr Phe Pro
255             260                 265                 270

GTG GGC CTC ATC AGC GTC GTC ACC GAG AGC TGG CGC CTC AGC CTG CGC       1046
Val Gly Leu Ile Ser Val Val Thr Glu Ser Trp Arg Leu Ser Leu Arg
            275                 280                 285

CAG AAG GTG CGC GAC GGC GTG GCC ATT CTG GCC CTG GGC GCC CAC AGC       1094
Gln Lys Val Arg Asp Gly Val Ala Ile Leu Ala Leu Gly Ala His Ser
        290                 295                 300

TAC TGG CGC CAG CAT GGA ACC CTG CCA GCC CCG GCC GGG GAC TGC CGT       1142
Tyr Trp Arg Gln His Gly Thr Leu Pro Ala Pro Ala Gly Asp Cys Arg
            305                 310                 315

GTT CAC CCT GGG CCC GTC AGC CCT GCC CGG GAG GCC TTC TAC AGG CAC       1190
Val His Pro Gly Pro Val Ser Pro Ala Arg Glu Ala Phe Tyr Arg His
320             325                 330

CTA CTG AAT GTC ACC TGG GAG GGC CGA GAC TTC TCC TTC AGC CCT GGT       1238
Leu Leu Asn Val Thr Trp Glu Gly Arg Asp Phe Ser Phe Ser Pro Gly
335             340                 345                 350

GGG TAC CTG GTC CAG CCC ACC ATG GTG GTG ATC GCC CTC AAC CGG CAC       1286
Gly Tyr Leu Val Gln Pro Thr Met Val Val Ile Ala Leu Asn Arg His
            355                 360                 365

CGC CTC TGG GAG ATG GTG GGG CGC TGG GAG CAT GGC GTC CTA TAC ATG       1334
Arg Leu Trp Glu Met Val Gly Arg Trp Glu His Gly Val Leu Tyr Met
        370                 375                 380

AAG TAC CCC GTG TGG CCT CGC TAC AGT GCC TCT CTG CAG CCT GTG GTG       1382
Lys Tyr Pro Val Trp Pro Arg Tyr Ser Ala Ser Leu Gln Pro Val Val
            385                 390                 395

GAC AGT CGG CAC CTG ACG GTG GCC ACG CTG GAA GAG CGG CCC TTT GTC       1430
Asp Ser Arg His Leu Thr Val Ala Thr Leu Glu Glu Arg Pro Phe Val
        400                 405                 410

ATC GTG GAG AGC CCT GAC CCT GGC ACA GGA GGC TGT GTC CCC AAC ACC       1478
Ile Val Glu Ser Pro Asp Pro Gly Thr Gly Gly Cys Val Pro Asn Thr
415             420                 425                 430

GTG CCC TGC CGC AGG CAG AGC AAC CAC ACC TTC AGC AGC GGG GAC GTG       1526
Val Pro Cys Arg Arg Gln Ser Asn His Thr Phe Ser Ser Gly Asp Val
            435                 440                 445
```

```
GCC CCC TAC ACC AAG CTC TGC TGT AAG GGA TTC TGC ATC GAC ATC CTC      1574
Ala Pro Tyr Thr Lys Leu Cys Cys Lys Gly Phe Cys Ile Asp Ile Leu
            450                 455                 460

AAG AAG CTG GCC AGA GTG GTC AAA TTC TCC TAC GAC CTG TAC CTG GTG      1622
Lys Lys Leu Ala Arg Val Val Lys Phe Ser Tyr Asp Leu Tyr Leu Val
            465                 470                 475

ACC AAC GGC AAG CAT GGC AAG CGG GTG CGC GGC GTA TGG AAC GGC ATG      1670
Thr Asn Gly Lys His Gly Lys Arg Val Arg Gly Val Trp Asn Gly Met
            480                 485                 490

ATT GGG GAG GTG TAC TAC AAG CGG GCA GAC ATG GCC ATC GGC TCC CTC      1718
Ile Gly Glu Val Tyr Tyr Lys Arg Ala Asp Met Ala Ile Gly Ser Leu
495                 500                 505                 510

ACC ATC AAT GAG GAA CGC TCC GAG ATC GTA GAC TTC TCT GTA CCC TTT      1766
Thr Ile Asn Glu Glu Arg Ser Glu Ile Val Asp Phe Ser Val Pro Phe
                515                 520                 525

GTG GAG ACG GGC ATC AGT GTG ATG GTG GCT CGC AGC AAT GGC ACC GTC      1814
Val Glu Thr Gly Ile Ser Val Met Val Ala Arg Ser Asn Gly Thr Val
            530                 535                 540

TCC CCC TCG GCC TTC TTG GAG CCA TAT AGC CCT GCA GTG TGG GTG ATG      1862
Ser Pro Ser Ala Phe Leu Glu Pro Tyr Ser Pro Ala Val Trp Val Met
            545                 550                 555

ATG TTT GTC ATG TGC CTC ACT GTG GTG GCC ATC ACC GTC TTC ATG TTC      1910
Met Phe Val Met Cys Leu Thr Val Val Ala Ile Thr Val Phe Met Phe
            560                 565                 570

GAG TAC TTC AGC CCT GTC AGC TAC AAC CAG AAC CTC ACC AGA GGC AAG      1958
Glu Tyr Phe Ser Pro Val Ser Tyr Asn Gln Asn Leu Thr Arg Gly Lys
575                 580                 585                 590

AAG TCC GGG GGC CCA GCT TTC ACT ATC GGC AAG TCC GTG TGG CTG CTG      2006
Lys Ser Gly Gly Pro Ala Phe Thr Ile Gly Lys Ser Val Trp Leu Leu
                595                 600                 605

TGG GCG CTG GTC TTC AAC AAC TCA GTG CCC ATC GAG AAC CCG CGG GGC      2054
Trp Ala Leu Val Phe Asn Asn Ser Val Pro Ile Glu Asn Pro Arg Gly
            610                 615                 620

ACC ACC AGC AAG ATC ATG GTT CTG GTC TGG GCC TTC TTT GCT GTC ATC      2102
Thr Thr Ser Lys Ile Met Val Leu Val Trp Ala Phe Phe Ala Val Ile
            625                 630                 635

TTC CTC GCC AGA TAC ACG GCC AAC CTG GCC GCC TTC ATG ATC CAA GAG      2150
Phe Leu Ala Arg Tyr Thr Ala Asn Leu Ala Ala Phe Met Ile Gln Glu
640                 645                 650

CAA TAC ATC GAC ACT GTG TCG GGC CTC AGT GAC AAG AAG TTT CAG CGG      2198
Gln Tyr Ile Asp Thr Val Ser Gly Leu Ser Asp Lys Lys Phe Gln Arg
655                 660                 665                 670

CCT CAA GAT CAG TAC CCA CCT TTC CGC TTC GGC ACG GTG CCC AAC GGC      2246
Pro Gln Asp Gln Tyr Pro Pro Phe Arg Phe Gly Thr Val Pro Asn Gly
                675                 680                 685

AGC ACG GAG CGG AAC ATC CGC AGT AAC TAC CGT GAC ATG CAC ACC CAC      2294
Ser Thr Glu Arg Asn Ile Arg Ser Asn Tyr Arg Asp Met His Thr His
            690                 695                 700

ATG GTC AAG TTC AAC CAG CGC TCG GTG GAG GAC GCG CTC ACC AGC CTC      2342
Met Val Lys Phe Asn Gln Arg Ser Val Glu Asp Ala Leu Thr Ser Leu
            705                 710                 715

AAG ATG GGC TCT GAG GCT CAG CCT GTC CCC AGG AAG CTG GAT GCC TTC      2390
Lys Met Gly Ser Glu Ala Gln Pro Val Pro Arg Lys Leu Asp Ala Phe
            720                 725                 730

ATC TAT GAT GCT GCT GTC CTC AAC TAC ATG GCA GGC AAG GAC GAG GGC      2438
Ile Tyr Asp Ala Ala Val Leu Asn Tyr Met Ala Gly Lys Asp Glu Gly
735                 740                 745                 750

TGC AAG CTG GTC ACC ATT GGG TCT GGC AAG GTC TTT GCT ACC ACT GGC      2486
Cys Lys Leu Val Thr Ile Gly Ser Gly Lys Val Phe Ala Thr Thr Gly
```

```
                   755                 760                 765
TAC GGC ATC GCC ATG CAG AAG GAC TCC CAC TGG AAG CGG GCC ATA GAC        2534
Tyr Gly Ile Ala Met Gln Lys Asp Ser His Trp Lys Arg Ala Ile Asp
                770                 775                 780

CTG GCG CTC TTG CAG TTC CTG GGG GAC GGA GAG ACA CAG AAA CTG GAG        2582
Leu Ala Leu Leu Gln Phe Leu Gly Asp Gly Glu Thr Gln Lys Leu Glu
                785                 790                 795

ACA GTG TGG CTC TCA GGG ATC TGC CAG AAT GAG AAG AAC GAG GTG ATG        2630
Thr Val Trp Leu Ser Gly Ile Cys Gln Asn Glu Lys Asn Glu Val Met
            800                 805                 810

AGC AGC AAG CTG GAC ATC GAC AAC ATG GGA GGC GTC TTC TAC ATG CTG        2678
Ser Ser Lys Leu Asp Ile Asp Asn Met Gly Gly Val Phe Tyr Met Leu
815                 820                 825                 830

CTG GTG GCC ATG GGG CTG GCC CTG CTG GTC TTC GCC TGG GAG CAC CTG        2726
Leu Val Ala Met Gly Leu Ala Leu Leu Val Phe Ala Trp Glu His Leu
                835                 840                 845

GTC TAC TGG AAG CTG CGC CAC TCG GTG CCC AAC TCA TCC CAG CTG GAC        2774
Val Tyr Trp Lys Leu Arg His Ser Val Pro Asn Ser Ser Gln Leu Asp
                850                 855                 860

TTC CTG CTG GCT TTC AGC AGG GGC ATC TAC AGC TGC TTC AGC GGG GTG        2822
Phe Leu Leu Ala Phe Ser Arg Gly Ile Tyr Ser Cys Phe Ser Gly Val
            865                 870                 875

CAG AGC CTC GCC AGC CCA CCG CGG CAG GCC AGC CCG GAC CTC ACG GCC        2870
Gln Ser Leu Ala Ser Pro Pro Arg Gln Ala Ser Pro Asp Leu Thr Ala
            880                 885                 890

AGC TCG GCC CAG GCC AGC GTG CTC AAG ATT CTG CAG GCA GCC CGC GAC        2918
Ser Ser Ala Gln Ala Ser Val Leu Lys Ile Leu Gln Ala Ala Arg Asp
895                 900                 905                 910

ATG GTG ACC ACG GCG GGC GTA AGC AAC TCC CTG GAC CGC GCC ACT CGC        2966
Met Val Thr Thr Ala Gly Val Ser Asn Ser Leu Asp Arg Ala Thr Arg
                915                 920                 925

ACC ATC GAG AAT TGG GGT GGC GGC CGC CGT GCG CCC CCA CCG TCC CCC        3014
Thr Ile Glu Asn Trp Gly Gly Gly Arg Arg Ala Pro Pro Pro Ser Pro
                930                 935                 940

TGC CCG ACC CCG CGG TCT GGC CCC AGC CCA TGC CTG CCC ACC CCC GAC        3062
Cys Pro Thr Pro Arg Ser Gly Pro Ser Pro Cys Leu Pro Thr Pro Asp
            945                 950                 955

CCG CCC CCA GAG CCG AGC CCC ACG GGC TGG GGA CCG CCA GAC GGG GGT        3110
Pro Pro Pro Glu Pro Ser Pro Thr Gly Trp Gly Pro Pro Asp Gly Gly
            960                 965                 970

CGC GCG GCG CTT GTG CGC AGG GCT CCG CAG CCC CCG GGC CGC CCC CCG        3158
Arg Ala Ala Leu Val Arg Arg Ala Pro Gln Pro Pro Gly Arg Pro Pro
975                 980                 985                 990

ACG CCG GGG CCG CCC CTG TCC GAC GTC TCC CGA GTG TCG CGC CGC CCA        3206
Thr Pro Gly Pro Pro Leu Ser Asp Val Ser Arg Val Ser Arg Arg Pro
                995                 1000                1005

GCC TGG GAG GCG CGG TGG CCG GTG CGG ACC GGG CAC TGC GGG AGG CAC        3254
Ala Trp Glu Ala Arg Trp Pro Val Arg Thr Gly His Cys Gly Arg His
1010                1015                1020

CTC TCG GCC TCC GAG CGG CCC CTG TCG CCC GCG CGC TGT CAC TAC AGC        3302
Leu Ser Ala Ser Glu Arg Pro Leu Ser Pro Ala Arg Cys His Tyr Ser
            1025                1030                1035

TCC TTT CCT CGA GCC GAC CGA TCC GGC CGC CCC TTC CTC CCG CTC TTC        3350
Ser Phe Pro Arg Ala Asp Arg Ser Gly Arg Pro Phe Leu Pro Leu Phe
            1040                1045                1050

CCG GAG CCC CCG GAG CTG GAG GAC CTG CCG CTG CTC GGT CCG GAG CAG        3398
Pro Glu Pro Pro Glu Leu Glu Asp Leu Pro Leu Leu Gly Pro Glu Gln
1055                1060                1065                1070

CTG GCC CGG CGG GAG GCC CTG CTG AAC GCG GCC TGG GCC CGG GGC TCG        3446
```

```
Leu Ala Arg Arg Glu Ala Leu Leu Asn Ala Ala Trp Ala Arg Gly Ser
              1075                1080                1085

CGC CCG AGT CAC GCT TCC CTG CCC AGC TCC GTG GCC GAG GCC TTC GCT     3494
Arg Pro Ser His Ala Ser Leu Pro Ser Ser Val Ala Glu Ala Phe Ala
              1090                1095                1100

CGG CCC AGC TCG CTG CCC GCT GGG TGC ACC GGC CCC GCC TGC GCC CGC     3542
Arg Pro Ser Ser Leu Pro Ala Gly Cys Thr Gly Pro Ala Cys Ala Arg
              1105                1110                1115

CCC GAC GGC CAC TCG GCC TGC AGG CGC TTG GCG CAG GCG CAG TCG ATG     3590
Pro Asp Gly His Ser Ala Cys Arg Arg Leu Ala Gln Ala Gln Ser Met
              1120                1125                1130

TGC TTG CCG ATC TAC CGG GAG GCC TGC CAG GAG GGC GAG CAG GCA GGG     3638
Cys Leu Pro Ile Tyr Arg Glu Ala Cys Gln Glu Gly Glu Gln Ala Gly
1135                1140                1145                1150

GCC CCC GCC TGG CAG CAC AGA CAG CAC GTC TGC CTG CAC GCC CAC GCC     3686
Ala Pro Ala Trp Gln His Arg Gln His Val Cys Leu His Ala His Ala
              1155                1160                1165

CAC CTG CCA TTG TGC TGG GGG GCT GTC TGT CCT CAC CTT CCA CCC TGT     3734
His Leu Pro Leu Cys Trp Gly Ala Val Cys Pro His Leu Pro Pro Cys
              1170                1175                1180

GAC AGC CAC GGC TCC TGG CTC TCC GGC GCC TGG GGG CCT CTG GGG CAC     3782
Asp Ser His Gly Ser Trp Leu Ser Gly Ala Trp Gly Pro Leu Gly His
              1185                1190                1195

AGC GGC AGG ACT CTG GGG CTG GGC ACA GGC TAC AGA GAC AGT GGG GGA     3830
Ser Gly Arg Thr Leu Gly Leu Gly Thr Gly Tyr Arg Asp Ser Gly Gly
              1200                1205                1210

CTG GAC GAG ATC AGC AGT GTA GCC CGT GGG ACG CAA GGC TTC CCG GGA     3878
Leu Asp Glu Ile Ser Ser Val Ala Arg Gly Thr Gln Gly Phe Pro Gly
1215                1220                1225                1230

CCC TGC ACC TGG AGA CGG ATC TCC AGT CTG GAG TCA GAA GTG TGAGTTATCA 3930
Pro Cys Thr Trp Arg Arg Ile Ser Ser Leu Glu Ser Glu Val
              1235                1240                124

GCCACTCAGG CTCCGAGCCA GCTGGATTCT CTGCCTGCCA CTGTCAGGGT TAAGCGGCAG   3990

GCAGGATTGG CCCTTCTCTG GCTTCTACCA TGAAATCCTG GCCATGGCAC CCCAGTGACA   4050

GATGATGTCT TCCATGGTCA TCAGTGACCT CAGCTAGCCT CA                      4092

(2) INFORMATION FOR SEQ ID NO:46:

(i) SEQUENCE CHARACTERISTICS:
        (A) LENGTH: 1244 amino acids
        (B) TYPE: amino acid
        (D) TOPOLOGY: linear (ii) MOLECULE TYPE: protein (xi) SEQUENCE DESCRIPTION: SEQ ID NO:46:

Met Gly Gly Ala Leu Gly Pro Ala Leu Leu Leu Thr Ser Leu Phe Gly
 1               5                  10                  15

Ala Trp Ala Gly Leu Gly Pro Gly Gln Gly Glu Gln Gly Met Thr Val
              20                  25                  30

Ala Val Val Phe Ser Ser Ser Gly Pro Pro Gln Ala Gln Phe Arg Val
          35                  40                  45

Arg Leu Thr Pro Gln Ser Phe Leu Asp Leu Pro Leu Glu Ile Gln Pro
      50                  55                  60

Leu Thr Val Gly Val Asn Thr Thr Asn Pro Ser Ser Leu Leu Thr Gln
65                  70                  75                  80

Ile Cys Gly Leu Leu Gly Ala Ala His Val His Gly Ile Val Phe Glu
                  85                  90                  95
```

-continued

```
Asp Asn Val Asp Thr Glu Ala Val Ala Gln Ile Leu Asp Phe Ile Ser
            100                 105                 110

Ser Gln Thr His Val Pro Ile Leu Ser Ile Ser Gly Gly Ser Ala Val
            115                 120                 125

Val Leu Thr Pro Lys Glu Pro Gly Ser Ala Phe Leu Gln Leu Gly Val
            130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
            165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
            195                 200                 205

Arg Ala Arg Thr Gln Arg Leu Leu Arg Gln Leu Asp Ala Pro Val Phe
            210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
            245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
            275                 280                 285

Val Arg Asp Gly Val Ala Ile Leu Ala Leu Gly Ala His Ser Tyr Trp
            290                 295                 300

Arg Gln His Gly Thr Leu Pro Ala Pro Ala Gly Asp Cys Arg Val His
305                 310                 315                 320

Pro Gly Pro Val Ser Pro Ala Arg Glu Ala Phe Tyr Arg His Leu Leu
            325                 330                 335

Asn Val Thr Trp Glu Gly Arg Asp Phe Ser Phe Ser Pro Gly Gly Tyr
            340                 345                 350

Leu Val Gln Pro Thr Met Val Val Ile Ala Leu Asn Arg His Arg Leu
            355                 360                 365

Trp Glu Met Val Gly Arg Trp Glu His Gly Val Leu Tyr Met Lys Tyr
            370                 375                 380

Pro Val Trp Pro Arg Tyr Ser Ala Ser Leu Gln Pro Val Val Asp Ser
385                 390                 395                 400

Arg His Leu Thr Val Ala Thr Leu Glu Glu Arg Pro Phe Val Ile Val
            405                 410                 415

Glu Ser Pro Asp Pro Gly Thr Gly Gly Cys Val Pro Asn Thr Val Pro
            420                 425                 430

Cys Arg Arg Gln Ser Asn His Thr Phe Ser Ser Gly Asp Val Ala Pro
            435                 440                 445

Tyr Thr Lys Leu Cys Cys Lys Gly Phe Cys Ile Asp Ile Leu Lys Lys
            450                 455                 460

Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
            485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
```

-continued

```
            515                 520                 525
Thr Gly Ile Ser Val Met Val Ala Arg Ser Asn Gly Thr Val Ser Pro
        530                 535                 540

Ser Ala Phe Leu Glu Pro Tyr Ser Pro Ala Val Trp Val Met Met Phe
545                 550                 555                 560

Val Met Cys Leu Thr Val Ala Ile Thr Val Phe Met Phe Glu Tyr
                565                 570                 575

Phe Ser Pro Val Ser Tyr Asn Gln Asn Leu Thr Arg Gly Lys Lys Ser
                580                 585                 590

Gly Gly Pro Ala Phe Thr Ile Gly Lys Ser Val Trp Leu Leu Trp Ala
                595                 600                 605

Leu Val Phe Asn Asn Ser Val Pro Ile Glu Asn Pro Arg Gly Thr Thr
610                 615                 620

Ser Lys Ile Met Val Leu Val Trp Ala Phe Phe Ala Val Ile Phe Leu
625                 630                 635                 640

Ala Arg Tyr Thr Ala Asn Leu Ala Ala Phe Met Ile Gln Glu Gln Tyr
                645                 650                 655

Ile Asp Thr Val Ser Gly Leu Ser Asp Lys Lys Phe Gln Arg Pro Gln
                660                 665                 670

Asp Gln Tyr Pro Pro Phe Arg Phe Gly Thr Val Pro Asn Gly Ser Thr
                675                 680                 685

Glu Arg Asn Ile Arg Ser Asn Tyr Arg Asp Met His Thr His Met Val
690                 695                 700

Lys Phe Asn Gln Arg Ser Val Glu Asp Ala Leu Thr Ser Leu Lys Met
705                 710                 715                 720

Gly Ser Glu Ala Gln Pro Val Pro Arg Lys Leu Asp Ala Phe Ile Tyr
                725                 730                 735

Asp Ala Ala Val Leu Asn Tyr Met Ala Gly Lys Asp Glu Gly Cys Lys
                740                 745                 750

Leu Val Thr Ile Gly Ser Gly Lys Val Phe Ala Thr Thr Gly Tyr Gly
                755                 760                 765

Ile Ala Met Gln Lys Asp Ser His Trp Lys Arg Ala Ile Asp Leu Ala
                770                 775                 780

Leu Leu Gln Phe Leu Gly Asp Gly Glu Thr Gln Lys Leu Glu Thr Val
785                 790                 795                 800

Trp Leu Ser Gly Ile Cys Gln Asn Glu Lys Asn Glu Val Met Ser Ser
                805                 810                 815

Lys Leu Asp Ile Asp Asn Met Gly Gly Val Phe Tyr Met Leu Leu Val
                820                 825                 830

Ala Met Gly Leu Ala Leu Leu Val Phe Ala Trp Glu His Leu Val Tyr
                835                 840                 845

Trp Lys Leu Arg His Ser Val Pro Asn Ser Ser Gln Leu Asp Phe Leu
850                 855                 860

Leu Ala Phe Ser Arg Gly Ile Tyr Ser Cys Phe Ser Gly Val Gln Ser
865                 870                 875                 880

Leu Ala Ser Pro Pro Arg Gln Ala Ser Pro Asp Leu Thr Ala Ser Ser
                885                 890                 895

Ala Gln Ala Ser Val Leu Lys Ile Leu Gln Ala Ala Arg Asp Met Val
                900                 905                 910

Thr Thr Ala Gly Val Ser Asn Ser Leu Asp Arg Ala Thr Arg Thr Ile
                915                 920                 925

Glu Asn Trp Gly Gly Gly Arg Ala Pro Pro Pro Ser Pro Cys Pro
930                 935                 940
```

Thr Pro Arg Ser Gly Pro Ser Pro Cys Leu Pro Thr Pro Asp Pro Pro
945                 950                 955                 960

Pro Glu Pro Ser Pro Thr Gly Trp Gly Pro Pro Asp Gly Gly Arg Ala
                965                 970                 975

Ala Leu Val Arg Arg Ala Pro Gln Pro Pro Gly Arg Pro Pro Thr Pro
            980                 985                 990

Gly Pro Pro Leu Ser Asp Val Ser Arg Val Ser Arg Arg Pro Ala Trp
        995                 1000                1005

Glu Ala Arg Trp Pro Val Arg Thr Gly His Cys Gly Arg His Leu Ser
    1010                1015                1020

Ala Ser Glu Arg Pro Leu Ser Pro Ala Arg Cys His Tyr Ser Ser Phe
1025                1030                1035                1040

Pro Arg Ala Asp Arg Ser Gly Arg Pro Phe Leu Pro Leu Phe Pro Glu
                1045                1050                1055

Pro Pro Glu Leu Glu Asp Leu Pro Leu Leu Gly Pro Glu Gln Leu Ala
                1060                1065                1070

Arg Arg Glu Ala Leu Leu Asn Ala Ala Trp Ala Arg Gly Ser Arg Pro
            1075                1080                1085

Ser His Ala Ser Leu Pro Ser Ser Val Ala Glu Ala Phe Ala Arg Pro
        1090                1095                1100

Ser Ser Leu Pro Ala Gly Cys Thr Gly Pro Ala Cys Ala Arg Pro Asp
1105                1110                1115                1120

Gly His Ser Ala Cys Arg Arg Leu Ala Gln Ala Gln Ser Met Cys Leu
                1125                1130                1135

Pro Ile Tyr Arg Glu Ala Cys Gln Glu Gly Glu Gln Ala Gly Ala Pro
                1140                1145                1150

Ala Trp Gln His Arg Gln His Val Cys Leu His Ala His Ala His Leu
        1155                1160                1165

Pro Leu Cys Trp Gly Ala Val Cys Pro His Leu Pro Pro Cys Asp Ser
    1170                1175                1180

His Gly Ser Trp Leu Ser Gly Ala Trp Gly Pro Leu Gly His Ser Gly
1185                1190                1195                1200

Arg Thr Leu Gly Leu Gly Thr Gly Tyr Arg Asp Ser Gly Gly Leu Asp
                1205                1210                1215

Glu Ile Ser Ser Val Ala Arg Gly Thr Gln Gly Phe Pro Gly Pro Cys
                1220                1225                1230

Thr Trp Arg Arg Ile Ser Ser Leu Glu Ser Glu Val
            1235                1240

(2) INFORMATION FOR SEQ ID NO:47:

(i) SEQUENCE CHARACTERISTICS:
        (A) LENGTH: 4053 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 189..3884

(xi) SEQUENCE DESCRIPTION: SEQ ID NO:47:

CCCTTAATAA GATTTGCNAC GTACACTCGA GCCATCGCGA GTGTCCTTGA GCCGCGGGTG    60

ACGGTGGCTC TCGCTGCTCG CGCCCCCTCC TCCCGCGGGG GGAGCCTGAT GCCACGTTCC   120

```
CTATGAATTA TTTATCGCCG GCCTAAAAAT ACCCCGAACT TCACAGCCCG AGTGACCCTC        180

CGGTGGAC ATG GGT GGG GCC CTG GGG CCG GCC CTG TTG CTC ACC TCG CTC        230
         Met Gly Gly Ala Leu Gly Pro Ala Leu Leu Leu Thr Ser Leu
          1               5                  10

TTC GGT GCC TGG GCA GGG CTG GGT CCG GGG CAG GGC GAG CAG GGC ATG         278
Phe Gly Ala Trp Ala Gly Leu Gly Pro Gly Gln Gly Glu Gln Gly Met
 15              20                  25                  30

ACG GTG GCC GTG GTG TTT AGC AGC TCA GGG CCG CCC CAG GCC CAG TTC         326
Thr Val Ala Val Val Phe Ser Ser Ser Gly Pro Pro Gln Ala Gln Phe
             35                  40                  45

CGT GTC CGC CTC ACC CCC CAG AGC TTC CTG GAC CTA CCC CTG GAG ATC         374
Arg Val Arg Leu Thr Pro Gln Ser Phe Leu Asp Leu Pro Leu Glu Ile
         50                  55                  60

CAG CCG CTC ACA GTT GGG GTC AAC ACC ACC AAC CCC AGC AGC CTC CTC         422
Gln Pro Leu Thr Val Gly Val Asn Thr Thr Asn Pro Ser Ser Leu Leu
         65                  70                  75

ACC CAG ATC TGC GGC CTC CTG GGT GCT GCC CAC GTC CAC GGC ATT GTC         470
Thr Gln Ile Cys Gly Leu Leu Gly Ala Ala His Val His Gly Ile Val
     80                  85                  90

TTT GAG GAC AAC GTG GAC ACC GAG GCG GTG GCC CAG ATC CTT GAC TTC         518
Phe Glu Asp Asn Val Asp Thr Glu Ala Val Ala Gln Ile Leu Asp Phe
 95              100                 105                 110

ATC TCC TCC CAG ACC CAT GTG CCC ATC CTC AGC ATC AGC GGA GGC TCT         566
Ile Ser Ser Gln Thr His Val Pro Ile Leu Ser Ile Ser Gly Gly Ser
             115                 120                 125

GCT GTG GTC CTC ACC CCC AAG GAG CCG GGC TCC GCC TTC CTG CAG CTG         614
Ala Val Val Leu Thr Pro Lys Glu Pro Gly Ser Ala Phe Leu Gln Leu
         130                 135                 140

GGC GTG TCC CTG GAG CAG CAG CTG CAG GTG CTG TTC AAG GTG CTG GAA         662
Gly Val Ser Leu Glu Gln Gln Leu Gln Val Leu Phe Lys Val Leu Glu
         145                 150                 155

GAG TAC GAC TGG AGC GCC TTC GCC GTC ATC ACC AGC CTG CAC CCG GGC         710
Glu Tyr Asp Trp Ser Ala Phe Ala Val Ile Thr Ser Leu His Pro Gly
 160                 165                 170

CAC GCG CTC TTC CTG GAG GGC GTG CGC GCC GTC GCC GAC GCC AGC CAC         758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA         806
Val Ser Trp Arg Leu Leu Asp Val Val Thr Leu Glu Leu Asp Pro Gly
             195                 200                 205

GGG CCG CGC GCG CGC ACG CAG CGC CTG CTG CGC CAG CTC GAC GCG CCC         854
Gly Pro Arg Ala Arg Thr Gln Arg Leu Leu Arg Gln Leu Asp Ala Pro
         210                 215                 220

GTG TTT GTG GCC TAC TGC TCG CGC GAG GAG GCC GAG GTG CTC TTC GCC         902
Val Phe Val Ala Tyr Cys Ser Arg Glu Glu Ala Glu Val Leu Phe Ala
         225                 230                 235

GAG GCG GCG CAG GCC GGT CTG GTG GGG CCC GGC CAC GTG TGG CTG GTG         950
Glu Ala Ala Gln Ala Gly Leu Val Gly Pro Gly His Val Trp Leu Val
 240                 245                 250

CCC AAC CTG GCG CTG GGC AGC ACC GAT GCG CCC CCC GCC ACC TTC CCC         998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC        1046
Val Gly Leu Ile Ser Val Val Thr Glu Ser Trp Arg Leu Ser Leu Arg
             275                 280                 285

CAG AAG GTG CGC GAC GGC GTG GCC ATT CTG GCC CTG GGC GCC CAC AGC        1094
Gln Lys Val Arg Asp Gly Val Ala Ile Leu Ala Leu Gly Ala His Ser
         290                 295                 300

TAC TGG CGC CAG CAT GGA ACC CTG CCA GCC CCG GCC GGG GAC TGC CGT        1142
```

-continued

```
                Tyr Trp Arg Gln His Gly Thr Leu Pro Ala Pro Ala Gly Asp Cys Arg
                        305                 310                 315

GTT CAC CCT GGG CCC GTC AGC CCT GCC CGG GAG GCC TTC TAC AGG CAC              1190
Val His Pro Gly Pro Val Ser Pro Ala Arg Glu Ala Phe Tyr Arg His
        320                 325                 330

CTA CTG AAT GTC ACC TGG GAG GGC CGA GAC TTC TCC TTC AGC CCT GGT              1238
Leu Leu Asn Val Thr Trp Glu Gly Arg Asp Phe Ser Phe Ser Pro Gly
335                 340                 345                 350

GGG TAC CTG GTC CAG CCC ACC ATG GTG GTG ATC GCC CTC AAC CGG CAC              1286
Gly Tyr Leu Val Gln Pro Thr Met Val Val Ile Ala Leu Asn Arg His
                355                 360                 365

CGC CTC TGG GAG ATG GTG GGG CGC TGG GAG CAT GGC GTC CTA TAC ATG              1334
Arg Leu Trp Glu Met Val Gly Arg Trp Glu His Gly Val Leu Tyr Met
        370                 375                 380

AAG TAC CCC GTG TGG CCT CGC TAC AGT GCC TCT CTG CAG CCT GTG GTG              1382
Lys Tyr Pro Val Trp Pro Arg Tyr Ser Ala Ser Leu Gln Pro Val Val
385                 390                 395

GAC AGT CGG CAC CTG ACG GTG GCC ACG CTG GAA GAG CGG CCC TTT GTC              1430
Asp Ser Arg His Leu Thr Val Ala Thr Leu Glu Glu Arg Pro Phe Val
        400                 405                 410

ATC GTG GAG AGC CCT GAC CCT GGC ACA GGA GGC TGT GTC CCC AAC ACC              1478
Ile Val Glu Ser Pro Asp Pro Gly Thr Gly Gly Cys Val Pro Asn Thr
415                 420                 425                 430

GTG CCC TGC CGC AGG CAG AGC AAC CAC ACC TTC AGC AGC GGG GAC GTG              1526
Val Pro Cys Arg Arg Gln Ser Asn His Thr Phe Ser Ser Gly Asp Val
                435                 440                 445

GCC CCC TAC ACC AAG CTC TGC TGT AAG GGA TTC TGC ATC GAC ATC CTC              1574
Ala Pro Tyr Thr Lys Leu Cys Cys Lys Gly Phe Cys Ile Asp Ile Leu
        450                 455                 460

AAG AAG CTG GCC AGA GTG GTC AAA TTC TCC TAC GAC CTG TAC CTG GTG              1622
Lys Lys Leu Ala Arg Val Val Lys Phe Ser Tyr Asp Leu Tyr Leu Val
465                 470                 475

ACC AAC GGC AAG CAT GGC AAG CGG GTG CGC GGC GTA TGG AAC GGC ATG              1670
Thr Asn Gly Lys His Gly Lys Arg Val Arg Gly Val Trp Asn Gly Met
        480                 485                 490

ATT GGG GAG GTG TAC TAC AAG CGG GCA GAC ATG GCC ATC GGC TCC CTC              1718
Ile Gly Glu Val Tyr Tyr Lys Arg Ala Asp Met Ala Ile Gly Ser Leu
495                 500                 505                 510

ACC ATC AAT GAG GAA CGC TCC GAG ATC GTA GAC TTC TCT GTA CCC TTT              1766
Thr Ile Asn Glu Glu Arg Ser Glu Ile Val Asp Phe Ser Val Pro Phe
                515                 520                 525

GTG GAG ACG GGC ATC AGT GTG ATG GTG GCT CGC AGC AAT GGC ACC GTC              1814
Val Glu Thr Gly Ile Ser Val Met Val Ala Arg Ser Asn Gly Thr Val
        530                 535                 540

TCC CCC TCG GCC TTC TTG GAG CCA TAT AGC CCT GCA GTG TGG GTG ATG              1862
Ser Pro Ser Ala Phe Leu Glu Pro Tyr Ser Pro Ala Val Trp Val Met
545                 550                 555

ATG TTT GTC ATG TGC CTC ACT GTG GTG GCC ATC ACC GTC TTC ATG TTC              1910
Met Phe Val Met Cys Leu Thr Val Val Ala Ile Thr Val Phe Met Phe
        560                 565                 570

GAG TAC TTC AGC CCT GTC AGC TAC AAC CAG AAC CTC ACC AGA GGC AAG              1958
Glu Tyr Phe Ser Pro Val Ser Tyr Asn Gln Asn Leu Thr Arg Gly Lys
575                 580                 585                 590

ACT TTC ACT ATC GGC AAG TCC GTG TGG CTG CTG TGG GCG CTG GTC TTC              2006
Thr Phe Thr Ile Gly Lys Ser Val Trp Leu Leu Trp Ala Leu Val Phe
                595                 600                 605

AAC AAC TCA GTG CCC ATC GAG AAC CCG CGG GGC ACC ACC AGC AAG ATC              2054
Asn Asn Ser Val Pro Ile Glu Asn Pro Arg Gly Thr Thr Ser Lys Ile
        610                 615                 620
```

-continued

```
ATG GTT CTG GTC TGG GCC TTC TTT GCT GTC ATC TTC CTC GCC AGA TAC    2102
Met Val Leu Val Trp Ala Phe Phe Ala Val Ile Phe Leu Ala Arg Tyr
            625                 630                 635

ACG GCC AAC CTG GCC GCC TTC ATG ATC CAA GAG CAA TAC ATC GAC ACT    2150
Thr Ala Asn Leu Ala Ala Phe Met Ile Gln Glu Gln Tyr Ile Asp Thr
    640                 645                 650

GTG TCG GGC CTC AGT GAC AAG AAG TTT CAG CGG CCT CAA GAT CAG TAC    2198
Val Ser Gly Leu Ser Asp Lys Lys Phe Gln Arg Pro Gln Asp Gln Tyr
655                 660                 665                 670

CCA CCT TTC CGC TTC GGC ACG GTG CCC AAC GGC AGC ACG GAG CGG AAC    2246
Pro Pro Phe Arg Phe Gly Thr Val Pro Asn Gly Ser Thr Glu Arg Asn
                675                 680                 685

ATC CGC AGT AAC TAC CGT GAC ATG CAC ACC CAC ATG GTC AAG TTC AAC    2294
Ile Arg Ser Asn Tyr Arg Asp Met His Thr His Met Val Lys Phe Asn
            690                 695                 700

CAG CGC TCG GTG GAG GAC GCG CTC ACC AGC CTC AAG ATG GGG AAG CTG    2342
Gln Arg Ser Val Glu Asp Ala Leu Thr Ser Leu Lys Met Gly Lys Leu
    705                 710                 715

GAT GCC TTC ATC TAT GAT GCT GCT GTC CTC AAC TAC ATG GCA GGC AAG    2390
Asp Ala Phe Ile Tyr Asp Ala Ala Val Leu Asn Tyr Met Ala Gly Lys
720                 725                 730

GAC GAG GGC TGC AAG CTG GTC ACC ATT GGG TCT GGC AAG GTC TTT GCT    2438
Asp Glu Gly Cys Lys Leu Val Thr Ile Gly Ser Gly Lys Val Phe Ala
735                 740                 745                 750

ACC ACT GGC TAC GGC ATC GCC ATG CAG AAG GAC TCC CAC TGG AAG CGG    2486
Thr Thr Gly Tyr Gly Ile Ala Met Gln Lys Asp Ser His Trp Lys Arg
                755                 760                 765

GCC ATA GAC CTG GCG CTC TTG CAG TTC CTG GGG GAC GGA GAG ACA CAG    2534
Ala Ile Asp Leu Ala Leu Leu Gln Phe Leu Gly Asp Gly Glu Thr Gln
            770                 775                 780

AAA CTG GAG ACA GTG TGG CTC TCA GGG ATC TGC CAG AAT GAG AAG AAC    2582
Lys Leu Glu Thr Val Trp Leu Ser Gly Ile Cys Gln Asn Glu Lys Asn
    785                 790                 795

GAG GTG ATG AGC AGC AAG CTG GAC ATC GAC AAC ATG GGA GGC GTC TTC    2630
Glu Val Met Ser Ser Lys Leu Asp Ile Asp Asn Met Gly Gly Val Phe
800                 805                 810

TAC ATG CTG CTG GTG GCC ATG GGG CTG GCC CTG CTG GTC TTC GCC TGG    2678
Tyr Met Leu Leu Val Ala Met Gly Leu Ala Leu Leu Val Phe Ala Trp
815                 820                 825                 830

GAG CAC CTG GTC TAC TGG AAG CTG CGC CAC TCG GTG CCC AAC TCA TCC    2726
Glu His Leu Val Tyr Trp Lys Leu Arg His Ser Val Pro Asn Ser Ser
                835                 840                 845

CAG CTG GAC TTC CTG CTG GCT TTC AGC AGG GGC ATC TAC AGC TGC TTC    2774
Gln Leu Asp Phe Leu Leu Ala Phe Ser Arg Gly Ile Tyr Ser Cys Phe
            850                 855                 860

AGC GGG GTG CAG AGC CTC GCC AGC CCA CCG CGG CAG GCC AGC CCG GAC    2822
Ser Gly Val Gln Ser Leu Ala Ser Pro Pro Arg Gln Ala Ser Pro Asp
    865                 870                 875

CTC ACG GCC AGC TCG GCC CAG GCC AGC GTG CTC AAG ATT CTG CAG GCA    2870
Leu Thr Ala Ser Ser Ala Gln Ala Ser Val Leu Lys Ile Leu Gln Ala
880                 885                 890

GCC CGC GAC ATG GTG ACC ACG GCG GGC GTA AGC AAC TCC CTG GAC CGC    2918
Ala Arg Asp Met Val Thr Thr Ala Gly Val Ser Asn Ser Leu Asp Arg
895                 900                 905                 910

GCC ACT CGC ACC ATC GAG AAT TGG GGT GGC GGC CGT CGT GCG CCC CCA    2966
Ala Thr Arg Thr Ile Glu Asn Trp Gly Gly Gly Arg Arg Ala Pro Pro
                915                 920                 925

CCG TCC CCC TGC CCG ACC CCG CGG TCT GGC CCC AGC CCA TGC CTG CCC    3014
Pro Ser Pro Cys Pro Thr Pro Arg Ser Gly Pro Ser Pro Cys Leu Pro
            930                 935                 940
```

-continued

```
ACC CCC GAC CCG CCC CCA GAG CCG AGC CCC ACG GGC TGG GGA CCG CCA      3062
Thr Pro Asp Pro Pro Pro Glu Pro Ser Pro Thr Gly Trp Gly Pro Pro
        945                 950                 955

GAC GGG GGT CGC GCG GCG CTT GTG CGC AGG GCT CCG CAG CCC CCG GGC      3110
Asp Gly Gly Arg Ala Ala Leu Val Arg Arg Ala Pro Gln Pro Pro Gly
    960                 965                 970

CGC CCC CCG ACG CCG GGG CCG CCC CTG TCC GAC GTC TCC CGA GTG TCG      3158
Arg Pro Pro Thr Pro Gly Pro Pro Leu Ser Asp Val Ser Arg Val Ser
975                 980                 985                 990

CGC CGC CCA GCC TGG GAG GCG CGG TGG CCG GTG CGG ACC GGG CAC TGC      3206
Arg Arg Pro Ala Trp Glu Ala Arg Trp Pro Val Arg Thr Gly His Cys
                995                1000                1005

GGG AGG CAC CTC TCG GCC TCC GAG CGG CCC CTG TCG CCC GCG CGC TGT      3254
Gly Arg His Leu Ser Ala Ser Glu Arg Pro Leu Ser Pro Ala Arg Cys
            1010                1015                1020

CAC TAC AGC TCC TTT CCT CGA GCC GAC CGA TCC GGC CGC CCC TTC CTC      3302
His Tyr Ser Ser Phe Pro Arg Ala Asp Arg Ser Gly Arg Pro Phe Leu
        1025                1030                1035

CCG CTC TTC CCG GAG CCC CCG GAG CTG GAG GAC CTG CCG CTG CTC GGT      3350
Pro Leu Phe Pro Glu Pro Pro Glu Leu Glu Asp Leu Pro Leu Leu Gly
    1040                1045                1050

CCG GAG CAG CTG GCC CGG CGG GAG GCC CTG CTG AAC GCG GCC TGG GCC      3398
Pro Glu Gln Leu Ala Arg Arg Glu Ala Leu Leu Asn Ala Ala Trp Ala
1055                1060                1065                1070

CGG GGC TCG CGC CCG AGT CAC GCT TCC CTG CCC AGC TCC GTG GCC GAG      3446
Arg Gly Ser Arg Pro Ser His Ala Ser Leu Pro Ser Ser Val Ala Glu
                1075                1080                1085

GCC TTC GCT CGG CCC AGC TCG CTG CCC GCT GGG TGC ACC GGC CCC GCC      3494
Ala Phe Ala Arg Pro Ser Ser Leu Pro Ala Gly Cys Thr Gly Pro Ala
            1090                1095                1100

TGC GCC CGC CCC GAC GGC CAC TCG GCC TGC AGG CGC TTG GCG CAG GCG      3542
Cys Ala Arg Pro Asp Gly His Ser Ala Cys Arg Arg Leu Ala Gln Ala
        1105                1110                1115

CAG TCG ATG TGC TTG CCG ATC TAC CGG GAG GCC TGC CAG GAG GGC GAG      3590
Gln Ser Met Cys Leu Pro Ile Tyr Arg Glu Ala Cys Gln Glu Gly Glu
    1120                1125                1130

CAG GCA GGG GCC CCC GCC TGG CAG CAC AGA CAG CAC GTC TGC CTG CAC      3638
Gln Ala Gly Ala Pro Ala Trp Gln His Arg Gln His Val Cys Leu His
1135                1140                1145                1150

GCC CAC GCC CAC CTG CCA TTG TGC TGG GGG GCT GTC TGT CCT CAC CTT      3686
Ala His Ala His Leu Pro Leu Cys Trp Gly Ala Val Cys Pro His Leu
                1155                1160                1165

CCA CCC TGT GAC AGC CAC GGC TCC TGG CTC TCC GGC GCC TGG GGG CCT      3734
Pro Pro Cys Asp Ser His Gly Ser Trp Leu Ser Gly Ala Trp Gly Pro
            1170                1175                1180

CTG GGG CAC AGC GGC AGG ACT CTG GGG CTG GGC ACA GGC TAC AGA GAC      3782
Leu Gly His Ser Gly Arg Thr Leu Gly Leu Gly Thr Gly Tyr Arg Asp
        1185                1190                1195

AGT GGG GGA CTG GAC GAG ATC AGC AGT GTA GCC CGT GGG ACG CAA GGC      3830
Ser Gly Gly Leu Asp Glu Ile Ser Ser Val Ala Arg Gly Thr Gln Gly
    1200                1205                1210

TTC CCG GGA CCC TGC ACC TGG AGA CGG ATC TCC AGT CTG GAG TCA GAA      3878
Phe Pro Gly Pro Cys Thr Trp Arg Arg Ile Ser Ser Leu Glu Ser Glu
1215                1220                1225                1230

GTG TGAGTTATCA GCCACTCAGG CTCCGAGCCA GCTGGATTCT CTGCCTGCCA           3931
Val

CTGTCAGGGT TAAGCGGCAG GCAGGATTGG CCCTTCTCTG GCTTCTACCA TGAAATCCTG    3991

GCCATGGCAC CCCAGTGACA GATGATGTCT TCCATGGTCA TCAGTGACCT CAGCTAGCCT    4051
```

(2) INFORMATION FOR SEQ ID NO:48:

(i) SEQUENCE CHARACTERISTICS:
        (A) LENGTH: 1231 amino acids
        (B) TYPE: amino acid
        (D) TOPOLOGY: linear (ii) MOLECULE TYPE: protein (xi) SEQUENCE DESCRIPTION: SEQ ID NO:48:

```
Met Gly Gly Ala Leu Gly Pro Ala Leu Leu Thr Ser Leu Phe Gly
 1               5                  10                  15

Ala Trp Ala Gly Leu Gly Pro Gly Gln Gly Glu Gln Gly Met Thr Val
            20                  25                  30

Ala Val Val Phe Ser Ser Gly Pro Pro Gln Ala Gln Phe Arg Val
            35                  40                  45

Arg Leu Thr Pro Gln Ser Phe Leu Asp Leu Pro Leu Glu Ile Gln Pro
     50                  55                  60

Leu Thr Val Gly Val Asn Thr Thr Asn Pro Ser Ser Leu Leu Thr Gln
 65                  70                  75                  80

Ile Cys Gly Leu Leu Gly Ala Ala His Val His Gly Ile Val Phe Glu
                85                  90                  95

Asp Asn Val Asp Thr Glu Ala Val Ala Gln Ile Leu Asp Phe Ile Ser
               100                 105                 110

Ser Gln Thr His Val Pro Ile Leu Ser Ile Ser Gly Gly Ser Ala Val
               115                 120                 125

Val Leu Thr Pro Lys Glu Pro Gly Ser Ala Phe Leu Gln Leu Gly Val
               130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
                180                 185                 190

Trp Arg Leu Leu Asp Val Val Thr Leu Glu Leu Asp Pro Gly Gly Pro
                195                 200                 205

Arg Ala Arg Thr Gln Arg Leu Leu Arg Gln Leu Asp Ala Pro Val Phe
                210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
                260                 265                 270

Leu Ile Ser Val Val Thr Glu Ser Trp Arg Leu Ser Leu Arg Gln Lys
                275                 280                 285

Val Arg Asp Gly Val Ala Ile Leu Ala Leu Gly Ala His Ser Tyr Trp
                290                 295                 300

Arg Gln His Gly Thr Leu Pro Ala Pro Ala Gly Asp Cys Arg Val His
305                 310                 315                 320

Pro Gly Pro Val Ser Pro Ala Arg Glu Ala Phe Tyr Arg His Leu Leu
                325                 330                 335

Asn Val Thr Trp Glu Gly Arg Asp Phe Ser Phe Ser Pro Gly Gly Tyr
```

-continued

```
                340                 345                 350
Leu Val Gln Pro Thr Met Val Ile Ala Leu Asn Arg His Arg Leu
            355                 360                 365
Trp Glu Met Val Gly Arg Trp Glu His Gly Val Leu Tyr Met Lys Tyr
370                 375                 380
Pro Val Trp Pro Arg Tyr Ser Ala Ser Leu Gln Pro Val Val Asp Ser
385                 390                 395                 400
Arg His Leu Thr Val Ala Thr Leu Glu Glu Arg Pro Phe Val Ile Val
                405                 410                 415
Glu Ser Pro Asp Pro Gly Thr Gly Gly Cys Val Pro Asn Thr Val Pro
                420                 425                 430
Cys Arg Arg Gln Ser Asn His Thr Phe Ser Ser Gly Asp Val Ala Pro
            435                 440                 445
Tyr Thr Lys Leu Cys Cys Lys Gly Phe Cys Ile Asp Ile Leu Lys Lys
        450                 455                 460
Leu Ala Arg Val Val Lys Phe Ser Tyr Asp Leu Tyr Leu Val Thr Asn
465                 470                 475                 480
Gly Lys His Gly Lys Arg Val Arg Gly Val Trp Asn Gly Met Ile Gly
                485                 490                 495
Glu Val Tyr Tyr Lys Arg Ala Asp Met Ala Ile Gly Ser Leu Thr Ile
            500                 505                 510
Asn Glu Glu Arg Ser Glu Ile Val Asp Phe Ser Val Pro Phe Val Glu
            515                 520                 525
Thr Gly Ile Ser Val Met Val Ala Arg Ser Asn Gly Thr Val Ser Pro
        530                 535                 540
Ser Ala Phe Leu Glu Pro Tyr Ser Pro Ala Val Trp Val Met Met Phe
545                 550                 555                 560
Val Met Cys Leu Thr Val Val Ala Ile Thr Val Phe Met Phe Glu Tyr
                565                 570                 575
Phe Ser Pro Val Ser Tyr Asn Gln Asn Leu Thr Arg Gly Lys Thr Phe
            580                 585                 590
Thr Ile Gly Lys Ser Val Trp Leu Leu Trp Ala Leu Val Phe Asn Asn
        595                 600                 605
Ser Val Pro Ile Glu Asn Pro Arg Gly Thr Thr Ser Lys Ile Met Val
        610                 615                 620
Leu Val Trp Ala Phe Phe Ala Val Ile Phe Leu Ala Arg Tyr Thr Ala
625                 630                 635                 640
Asn Leu Ala Ala Phe Met Ile Gln Glu Gln Tyr Ile Asp Thr Val Ser
            645                 650                 655
Gly Leu Ser Asp Lys Lys Phe Gln Arg Pro Gln Asp Gln Tyr Pro Pro
            660                 665                 670
Phe Arg Phe Gly Thr Val Pro Asn Gly Ser Thr Glu Arg Asn Ile Arg
            675                 680                 685
Ser Asn Tyr Arg Asp Met His Thr His Met Val Lys Phe Asn Gln Arg
        690                 695                 700
Ser Val Glu Asp Ala Leu Thr Ser Leu Lys Met Gly Lys Leu Asp Ala
705                 710                 715                 720
Phe Ile Tyr Asp Ala Ala Val Leu Asn Tyr Met Ala Gly Lys Asp Glu
                725                 730                 735
Gly Cys Lys Leu Val Thr Ile Gly Ser Gly Lys Val Phe Ala Thr Thr
            740                 745                 750
Gly Tyr Gly Ile Ala Met Gln Lys Asp Ser His Trp Lys Arg Ala Ile
        755                 760                 765
```

-continued

```
Asp Leu Ala Leu Leu Gln Phe Leu Gly Asp Gly Glu Thr Gln Lys Leu
    770                 775                 780
Glu Thr Val Trp Leu Ser Gly Ile Cys Gln Asn Glu Lys Asn Glu Val
785                 790                 795                 800
Met Ser Ser Lys Leu Asp Ile Asp Asn Met Gly Gly Val Phe Tyr Met
                805                 810                 815
Leu Leu Val Ala Met Gly Leu Ala Leu Leu Val Phe Ala Trp Glu His
            820                 825                 830
Leu Val Tyr Trp Lys Leu Arg His Ser Val Pro Asn Ser Ser Gln Leu
        835                 840                 845
Asp Phe Leu Leu Ala Phe Ser Arg Gly Ile Tyr Ser Cys Phe Ser Gly
    850                 855                 860
Val Gln Ser Leu Ala Ser Pro Pro Arg Gln Ala Ser Pro Asp Leu Thr
865                 870                 875                 880
Ala Ser Ser Ala Gln Ala Ser Val Leu Lys Ile Leu Gln Ala Ala Arg
                885                 890                 895
Asp Met Val Thr Thr Ala Gly Val Ser Asn Ser Leu Asp Arg Ala Thr
            900                 905                 910
Arg Thr Ile Glu Asn Trp Gly Gly Arg Arg Ala Pro Pro Pro Ser
        915                 920                 925
Pro Cys Pro Thr Pro Arg Ser Gly Pro Ser Pro Cys Leu Pro Thr Pro
    930                 935                 940
Asp Pro Pro Glu Pro Ser Pro Thr Gly Trp Gly Pro Pro Asp Gly
945                 950                 955                 960
Gly Arg Ala Ala Leu Val Arg Arg Ala Pro Gln Pro Pro Gly Arg Pro
                965                 970                 975
Pro Thr Pro Gly Pro Pro Leu Ser Asp Val Ser Arg Val Ser Arg Arg
            980                 985                 990
Pro Ala Trp Glu Ala Arg Trp Pro Val Arg Thr Gly His Cys Gly Arg
        995                 1000                1005
His Leu Ser Ala Ser Glu Arg Pro Leu Ser Pro Ala Arg Cys His Tyr
    1010                1015                1020
Ser Ser Phe Pro Arg Ala Asp Arg Ser Gly Arg Pro Phe Leu Pro Leu
1025                1030                1035                1040
Phe Pro Glu Pro Pro Glu Leu Glu Asp Leu Pro Leu Leu Gly Pro Glu
                1045                1050                1055
Gln Leu Ala Arg Arg Glu Ala Leu Leu Asn Ala Ala Trp Ala Arg Gly
            1060                1065                1070
Ser Arg Pro Ser His Ala Ser Leu Pro Ser Ser Val Ala Glu Ala Phe
        1075                1080                1085
Ala Arg Pro Ser Ser Leu Pro Ala Gly Cys Thr Gly Pro Ala Cys Ala
    1090                1095                1100
Arg Pro Asp Gly His Ser Ala Cys Arg Arg Leu Ala Gln Ala Gln Ser
1105                1110                1115                1120
Met Cys Leu Pro Ile Tyr Arg Glu Ala Cys Gln Glu Gly Glu Gln Ala
                1125                1130                1135
Gly Ala Pro Ala Trp Gln His Arg Gln His Val Cys Leu His Ala His
            1140                1145                1150
Ala His Leu Pro Leu Cys Trp Gly Ala Val Cys Pro His Leu Pro Pro
        1155                1160                1165
Cys Asp Ser His Gly Ser Trp Leu Ser Gly Ala Trp Gly Pro Leu Gly
    1170                1175                1180
```

-continued

```
His Ser Gly Arg Thr Leu Gly Leu Gly Thr Gly Tyr Arg Asp Ser Gly
1185                1190                1195                1200

Gly Leu Asp Glu Ile Ser Ser Val Ala Arg Gly Thr Gln Gly Phe Pro
        1205                1210                1215

Gly Pro Cys Thr Trp Arg Arg Ile Ser Ser Leu Glu Ser Glu Val
            1220                1225                1230
```

(2) INFORMATION FOR SEQ ID NO:49:

(i) SEQUENCE CHARACTERISTICS:
        (A) LENGTH: 4017 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 189..3848

(xi) SEQUENCE DESCRIPTION: SEQ ID NO:49:

```
CCCTTAATAA GATTTGCNAC GTACACTCGA GCCATCGCGA GTGTCCTTGA GCCGCGGGTG        60

ACGGTGGCTC TCGCTGCTCG CGCCCCCTCC TCCCGCGGGG GGAGCCTGAT GCCACGTTCC       120

CTATGAATTA TTTATCGCCG GCCTAAAAAT ACCCCGAACT TCACAGCCCG AGTGACCCTC       180

CGGTGGAC ATG GGT GGG GCC CTG GGG CCG GCC CTG TTG CTC ACC TCG CTC        230
         Met Gly Gly Ala Leu Gly Pro Ala Leu Leu Leu Thr Ser Leu
          1               5                  10

TTC GGT GCC TGG GCA GGG CTG GGT CCG GGG CAG GGC GAG CAG GGC ATG         278
Phe Gly Ala Trp Ala Gly Leu Gly Pro Gly Gln Gly Glu Gln Gly Met
 15              20                  25                  30

ACG GTG GCC GTG GTG TTT AGC AGC TCA GGG CCG CCC CAG GCC CAG TTC         326
Thr Val Ala Val Val Phe Ser Ser Ser Gly Pro Pro Gln Ala Gln Phe
                 35                  40                  45

CGT GTC CGC CTC ACC CCC CAG AGC TTC CTG GAC CTA CCC CTG GAG ATC         374
Arg Val Arg Leu Thr Pro Gln Ser Phe Leu Asp Leu Pro Leu Glu Ile
             50                  55                  60

CAG CCG CTC ACA GTT GGG GTC AAC ACC ACC AAC CCC AGC AGC CTC CTC         422
Gln Pro Leu Thr Val Gly Val Asn Thr Thr Asn Pro Ser Ser Leu Leu
         65                  70                  75

ACC CAG ATC TGC GGC CTC CTG GGT GCT GCC CAC GTC CAC GGG ATT GTC         470
Thr Gln Ile Cys Gly Leu Leu Gly Ala Ala His Val His Gly Ile Val
     80                  85                  90

TTT GAG GAC AAC GTG GAC ACC GAG GCG GTG GCC CAG ATC CTT GAC TTC         518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT         566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG         614
Ala Val Val Leu Thr Pro Lys Glu Pro Gly Ser Ala Phe Leu Gln Leu
            130                 135                 140

GGC GTG TCC CTG GAG CAG CAG CTG CAG GTG CTG TTC AAG GTG CTG GAA         662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC         710
Glu Tyr Asp Trp Ser Ala Phe Ala Val Ile Thr Ser Leu His Pro Gly
    160                 165                 170

CAC GCG CTC TTC CTG GAG GGC GTG CGC GCC GTC GCC GAC GCC AGC CAC         758
His Ala Leu Phe Leu Glu Gly Val Arg Ala Val Ala Asp Ala Ser His
175                 180                 185                 190
```

```
GTG AGT TGG CGG CTG CTG GAC GTG GTC ACG CTG GAA CTG GAC CCG GGA        806
Val Ser Trp Arg Leu Leu Asp Val Val Thr Leu Glu Leu Asp Pro Gly
            195                 200                 205

GGG CCG CGC GCG CGC ACG CAG CGC CTG CTG CGC CAG CTC GAC GCG CCC        854
Gly Pro Arg Ala Arg Thr Gln Arg Leu Leu Arg Gln Leu Asp Ala Pro
        210                 215                 220

GTG TTT GTG GCC TAC TGC TCG CGC GAG GAG GCC GAG GTG CTC TTC GCC        902
Val Phe Val Ala Tyr Cys Ser Arg Glu Glu Ala Glu Val Leu Phe Ala
            225                 230                 235

GAG GCG GCG CAG GCC GGT CTG GTG GGG CCC GGC CAC GTG TGG CTG GTG        950
Glu Ala Ala Gln Ala Gly Leu Val Gly Pro Gly His Val Trp Leu Val
        240                 245                 250

CCC AAC CTG GCG CTG GGC AGC ACC GAT GCG CCC CCC GCC ACC TTC CCC        998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC       1046
Val Gly Leu Ile Ser Val Val Thr Glu Ser Trp Arg Leu Ser Leu Arg
            275                 280                 285

CAG AAG GTG CGC GAC GGC GTG GCC ATT CTG GCC CTG GGC GCC CAC AGC       1094
Gln Lys Val Arg Asp Gly Val Ala Ile Leu Ala Leu Gly Ala His Ser
        290                 295                 300

TAC TGG CGC CAG CAT GGA ACC CTG CCA GCC CCG GCC GGG GAC TGC CGT       1142
Tyr Trp Arg Gln His Gly Thr Leu Pro Ala Pro Ala Gly Asp Cys Arg
            305                 310                 315

GTT CAC CCT GGG CCC GTC AGC CCT GCC CGG GAG GCC TTC TAC AGG CAC       1190
Val His Pro Gly Pro Val Ser Pro Ala Arg Glu Ala Phe Tyr Arg His
        320                 325                 330

CTA CTG AAT GTC ACC TGG GAG GGC CGA GAC TTC TCC TTC AGC CCT GGT       1238
Leu Leu Asn Val Thr Trp Glu Gly Arg Asp Phe Ser Phe Ser Pro Gly
335                 340                 345                 350

GGG TAC CTG GTC CAG CCC ACC ATG GTG GTG ATC GCC CTC AAC CGG CAC       1286
Gly Tyr Leu Val Gln Pro Thr Met Val Val Ile Ala Leu Asn Arg His
            355                 360                 365

CGC CTC TGG GAG ATG GTG GGG CGC TGG GAG CAT GGC GTC CTA TAC ATG       1334
Arg Leu Trp Glu Met Val Gly Arg Trp Glu His Gly Val Leu Tyr Met
        370                 375                 380

AAG TAC CCC GTG TGG CCT CGC TAC AGT GCC TCT CTG CAG CCT GTG GTG       1382
Lys Tyr Pro Val Trp Pro Arg Tyr Ser Ala Ser Leu Gln Pro Val Val
            385                 390                 395

GAC AGT CGG CAC CTG ACG GTG GCC ACG CTG GAA GAG CGG CCC TTT GTC       1430
Asp Ser Arg His Leu Thr Val Ala Thr Leu Glu Glu Arg Pro Phe Val
        400                 405                 410

ATC GTG GAG AGC CCT GAC CCT GGC ACA GGA GGC TGT GTC CCC AAC ACC       1478
Ile Val Glu Ser Pro Asp Pro Gly Thr Gly Gly Cys Val Pro Asn Thr
415                 420                 425                 430

GTG CCC TGC CGC AGG CAG AGC AAC CAC ACC TTC AGC AGC GGG GAC GTG       1526
Val Pro Cys Arg Arg Gln Ser Asn His Thr Phe Ser Ser Gly Asp Val
            435                 440                 445

GCC CCC TAC ACC AAG CTC TGC TGT AAG GGA TTC TGC ATC GAC ATC CTC       1574
Ala Pro Tyr Thr Lys Leu Cys Cys Lys Gly Phe Cys Ile Asp Ile Leu
        450                 455                 460

AAG AAG CTG GCC AGA GTG GTC AAA TTC TCC TAC GAC CTG TAC CTG GTG       1622
Lys Lys Leu Ala Arg Val Val Lys Phe Ser Tyr Asp Leu Tyr Leu Val
            465                 470                 475

ACC AAC GGC AAG CAT GGC AAG CGG GTG CGC GGC GTA TGG AAC GGC ATG       1670
Thr Asn Gly Lys His Gly Lys Arg Val Arg Gly Val Trp Asn Gly Met
        480                 485                 490

ATT GGG GAG GTG TAC TAC AAG CGG GCA GAC ATG GCC ATC GGC TCC CTC       1718
Ile Gly Glu Val Tyr Tyr Lys Arg Ala Asp Met Ala Ile Gly Ser Leu
```

-continued

```
     495                 500                 505                 510
ACC ATC AAT GAG GAA CGC TCC GAG ATC GTA GAC TTC TCT GTA CCC TTT       1766
Thr Ile Asn Glu Glu Arg Ser Glu Ile Val Asp Phe Ser Val Pro Phe
                515                 520                 525

GTG GAG ACG GGC ATC AGT GTG ATG GTG GCT CGC AGC AAT GGC ACC GTC       1814
Val Glu Thr Gly Ile Ser Val Met Val Ala Arg Ser Asn Gly Thr Val
                530                 535                 540

TCC CCC TCG GCC TTC TTG GAG CCA TAT AGC CCT GCA GTG TGG GTG ATG       1862
Ser Pro Ser Ala Phe Leu Glu Pro Tyr Ser Pro Ala Val Trp Val Met
                545                 550                 555

ATG TTT GTC ATG TGC CTC ACT GTG GTG GCC ATC ACC GTC TTC ATG TTC       1910
Met Phe Val Met Cys Leu Thr Val Val Ala Ile Thr Val Phe Met Phe
                560                 565                 570

GAG TAC TTC AGC CCT GTC AGC TAC AAC CAG AAC CTC ACC AGA GGC AAG       1958
Glu Tyr Phe Ser Pro Val Ser Tyr Asn Gln Asn Leu Thr Arg Gly Lys
575                 580                 585                 590

AAG TCC GGG GGC CCA GCT TTC ACT ATC GGC AAG TCC GTG TGG CTG CTG       2006
Lys Ser Gly Gly Pro Ala Phe Thr Ile Gly Lys Ser Val Trp Leu Leu
                595                 600                 605

TGG GCG CTG GTC TTC AAC AAC TCA GTG CCC ATC GAG AAC CCG CGG GGC       2054
Trp Ala Leu Val Phe Asn Asn Ser Val Pro Ile Glu Asn Pro Arg Gly
                610                 615                 620

ACC ACC AGC AAG ATC ATG GTT CTG GTC TGG GCC TTC TTT GCT GTC ATC       2102
Thr Thr Ser Lys Ile Met Val Leu Val Trp Ala Phe Phe Ala Val Ile
                625                 630                 635

TTC CTC GCC AGA TAC ACG GCC AAC CTG GCC GCC TTC ATG ATC CAA GAG       2150
Phe Leu Ala Arg Tyr Thr Ala Asn Leu Ala Ala Phe Met Ile Gln Glu
                640                 645                 650

CAA TAC ATC GAC ACT GTG TCG GGC CTC AGT GAC AAG AAG TTT CAG CGG       2198
Gln Tyr Ile Asp Thr Val Ser Gly Leu Ser Asp Lys Lys Phe Gln Arg
655                 660                 665                 670

CCT CAA GAT CAG TAC CCA CCT TTC CGC TTC GGC ACG GTG CCC AAC GGC       2246
Pro Gln Asp Gln Tyr Pro Pro Phe Arg Phe Gly Thr Val Pro Asn Gly
                675                 680                 685

AGC ACG GAG CGG AAC ATC CGC AGT AAC TAC CGT GAC ATG CAC ACC CAC       2294
Ser Thr Glu Arg Asn Ile Arg Ser Asn Tyr Arg Asp Met His Thr His
                690                 695                 700

ATG GTC AAG TTC AAC CAG CGC TCG GTG GAG GAC GCG CTC ACC AGC CTC       2342
Met Val Lys Phe Asn Gln Arg Ser Val Glu Asp Ala Leu Thr Ser Leu
                705                 710                 715

AAG ATG GGC AAG GAC GAG GGC TGC AAG CTG GTC ACC ATT GGG TCT GGC       2390
Lys Met Gly Lys Asp Glu Gly Cys Lys Leu Val Thr Ile Gly Ser Gly
                720                 725                 730

AAG GTC TTT GCT ACC ACT GGC TAC GGC ATC GCC ATG CAG AAG GAC TCC       2438
Lys Val Phe Ala Thr Thr Gly Tyr Gly Ile Ala Met Gln Lys Asp Ser
735                 740                 745                 750

CAC TGG AAG CGG GCC ATA GAC CTG GCG CTC TTG CAG TTC CTG GGG GAC       2486
His Trp Lys Arg Ala Ile Asp Leu Ala Leu Leu Gln Phe Leu Gly Asp
                755                 760                 765

GGA GAG ACA CAG AAA CTG GAG ACA GTG TGG CTC TCA GGG ATC TGC CAG       2534
Gly Glu Thr Gln Lys Leu Glu Thr Val Trp Leu Ser Gly Ile Cys Gln
                770                 775                 780

AAT GAG AAG AAC GAG GTG ATG AGC AGC AAG CTG GAC ATC GAC AAC ATG       2582
Asn Glu Lys Asn Glu Val Met Ser Ser Lys Leu Asp Ile Asp Asn Met
                785                 790                 795

GGA GGC GTC TTC TAC ATG CTG CTG GTG GCC ATG GGG CTG GCC CTG CTG       2630
Gly Gly Val Phe Tyr Met Leu Leu Val Ala Met Gly Leu Ala Leu Leu
                800                 805                 810

GTC TTC GCC TGG GAG CAC CTG GTC TAC TGG AAG CTG CGC CAC TCG GTG       2678
```

```
                                                                -continued

Val Phe Ala Trp Glu His Leu Val Tyr Trp Lys Leu Arg His Ser Val
815                 820                 825                 830

CCC AAC TCA TCC CAG CTG GAC TTC CTG CTG GCT TTC AGC AGG GGC ATC    2726
Pro Asn Ser Ser Gln Leu Asp Phe Leu Leu Ala Phe Ser Arg Gly Ile
                    835                 840                 845

TAC AGC TGC TTC AGC GGG GTG CAG AGC CTC GCC AGC CCA CCG CGG CAG    2774
Tyr Ser Cys Phe Ser Gly Val Gln Ser Leu Ala Ser Pro Pro Arg Gln
                850                 855                 860

GCC AGC CCG GAC CTC ACG GCC AGC TCG GCC CAG GCC AGC GTG CTC AAG    2822
Ala Ser Pro Asp Leu Thr Ala Ser Ser Ala Gln Ala Ser Val Leu Lys
            865                 870                 875

ATT CTG CAG GCA GCC CGC GAC ATG GTG ACC ACG GCG GGC GTA AGC AAC    2870
Ile Leu Gln Ala Ala Arg Asp Met Val Thr Thr Ala Gly Val Ser Asn
        880                 885                 890

TCC CTG GAC CGC GCC ACT CGC ACC ATC GAG AAT TGG GGT GGC GGC CGC    2918
Ser Leu Asp Arg Ala Thr Arg Thr Ile Glu Asn Trp Gly Gly Gly Arg
895                 900                 905                 910

CGT GCG CCC CCA CCG TCC CCC TGC CCG ACC CCG CGG TCT GGC CCC AGC    2966
Arg Ala Pro Pro Pro Ser Pro Cys Pro Thr Pro Arg Ser Gly Pro Ser
                    915                 920                 925

CCA TGC CTG CCC ACC CCC GAC CCG CCC CCA GAG CCG AGC CCC ACG GGC    3014
Pro Cys Leu Pro Thr Pro Asp Pro Pro Pro Glu Pro Ser Pro Thr Gly
                930                 935                 940

TGG GGA CCG CCA GAC GGG GGT CGC GCG GCG CTT GTG CGC AGG GCT CCG    3062
Trp Gly Pro Pro Asp Gly Gly Arg Ala Ala Leu Val Arg Arg Ala Pro
            945                 950                 955

CAG CCC CCG GGC CGC CCC CCG ACG CCG GGG CCG CCC CTG TCC GAC GTC    3110
Gln Pro Pro Gly Arg Pro Pro Thr Pro Gly Pro Pro Leu Ser Asp Val
        960                 965                 970

TCC CGA GTG TCG CGC CGC CCA GCC TGG GAG GCG CGG TGG CCG GTG CGG    3158
Ser Arg Val Ser Arg Arg Pro Ala Trp Glu Ala Arg Trp Pro Val Arg
975                 980                 985                 990

ACC GGG CAC TGC GGG AGG CAC CTC TCG GCC TCC GAG CGG CCC CTG TCG    3206
Thr Gly His Cys Gly Arg His Leu Ser Ala Ser Glu Arg Pro Leu Ser
                    995                 1000                1005

CCC GCG CGC TGT CAC TAC AGC TCC TTT CCT CGA GCC GAC CGA TCC GGC    3254
Pro Ala Arg Cys His Tyr Ser Ser Phe Pro Arg Ala Asp Arg Ser Gly
                1010                1015                1020

CGC CCC TTC CTC CCG CTC TTC CCG GAG CCC CCG GAG CTG GAG GAC CTG    3302
Arg Pro Phe Leu Pro Leu Phe Pro Glu Pro Pro Glu Leu Glu Asp Leu
            1025                1030                1035

CCG CTG CTC GGT CCG GAG CAG CTG GCC CGG CGG GAG GCC CTG CTG AAC    3350
Pro Leu Leu Gly Pro Glu Gln Leu Ala Arg Arg Glu Ala Leu Leu Asn
        1040                1045                1050

GCG GCC TGG GCC CGG GGC TCG CGC CCG AGT CAC GCT TCC CTG CCC AGC    3398
Ala Ala Trp Ala Arg Gly Ser Arg Pro Ser His Ala Ser Leu Pro Ser
1055                1060                1065                1070

TCC GTG GCC GAG GCC TTC GCT CGG CCC AGC TCG CTG CCC GCT GGG TGC    3446
Ser Val Ala Glu Ala Phe Ala Arg Pro Ser Ser Leu Pro Ala Gly Cys
                    1075                1080                1085

ACC GGC CCC GCC TGC GCC CGC CCC GAC GGC CAC TCG GCC TGC AGG CGC    3494
Thr Gly Pro Ala Cys Ala Arg Pro Asp Gly His Ser Ala Cys Arg Arg
                1090                1095                1100

TTG GCG CAG GCG CAG TCG ATG TGC TTG CCG ATC TAC CGG GAG GCC TGC    3542
Leu Ala Gln Ala Gln Ser Met Cys Leu Pro Ile Tyr Arg Glu Ala Cys
            1105                1110                1115

CAG GAG GGC GAG CAG GCA GGG GCC CCC GCC TGG CAG CAC AGA CAG CAC    3590
Gln Glu Gly Glu Gln Ala Gly Ala Pro Ala Trp Gln His Arg Gln His
        1120                1125                1130
```

```
GTC TGC CTG CAC GCC CAC GCC CAC CTG CCA TTG TGC TGG GGG GCT GTC    3638
Val Cys Leu His Ala His Ala His Leu Pro Leu Cys Trp Gly Ala Val
1135                1140                1145                1150

TGT CCT CAC CTT CCA CCC TGT GAC AGC CAC GGC TCC TGG CTC TCC GGC    3686
Cys Pro His Leu Pro Pro Cys Asp Ser His Gly Ser Trp Leu Ser Gly
                1155                1160                1165

GCC TGG GGG CCT CTG GGG CAC AGC GGC AGG ACT CTG GGG CTG GGC ACA    3734
Ala Trp Gly Pro Leu Gly His Ser Gly Arg Thr Leu Gly Leu Gly Thr
            1170                1175                1180

GGC TAC AGA GAC AGT GGG GGA CTG GAC GAG ATC AGC AGT GTA GCC CGT    3782
Gly Tyr Arg Asp Ser Gly Gly Leu Asp Glu Ile Ser Ser Val Ala Arg
        1185                1190                1195

GGG ACG CAA GGC TTC CCG GGA CCC TGC ACC TGG AGA CGG ATC TCC AGT    3830
Gly Thr Gln Gly Phe Pro Gly Pro Cys Thr Trp Arg Arg Ile Ser Ser
    1200                1205                1210

CTG GAG TCA GAA GTG TGAGTTATCA GCCACTCAGG CTCCGAGCCA GCTGGATTCT    3885
Leu Glu Ser Glu Val
1215                122

CTGCCTGCCA CTGTCAGGGT TAAGCGGCAG GCAGGATTGG CCCTTCTCTG GCTTCTACCA   3945

TGAAATCCTG GCCATGGCAC CCCAGTGACA GATGATGTCT TCCATGGTCA TCAGTGACCT   4005

CAGCTAGCCT CA                                                       4017

(2) INFORMATION FOR SEQ ID NO:50:

(i) SEQUENCE CHARACTERISTICS:
        (A) LENGTH: 1219 amino acids
        (B) TYPE: amino acid
        (D) TOPOLOGY: linear (ii) MOLECULE TYPE: protein (xi) SEQUENCE DESCRIPTION: SEQ ID NO:50:

Met Gly Gly Ala Leu Gly Pro Ala Leu Leu Leu Thr Ser Leu Phe Gly
 1               5                  10                  15

Ala Trp Ala Gly Leu Gly Pro Gly Gln Gly Glu Gln Gly Met Thr Val
                20                  25                  30

Ala Val Val Phe Ser Ser Gly Pro Pro Gln Ala Gln Phe Arg Val
            35                  40                  45

Arg Leu Thr Pro Gln Ser Phe Leu Asp Leu Pro Leu Glu Ile Gln Pro
    50                  55                  60

Leu Thr Val Gly Val Asn Thr Thr Asn Pro Ser Ser Leu Leu Thr Gln
 65                  70                  75                  80

Ile Cys Gly Leu Leu Gly Ala Ala His Val His Gly Ile Val Phe Glu
                85                  90                  95

Asp Asn Val Asp Thr Glu Ala Val Ala Gln Ile Leu Asp Phe Ile Ser
                100                 105                 110

Ser Gln Thr His Val Pro Ile Leu Ser Ile Ser Gly Gly Ser Ala Val
            115                 120                 125

Val Leu Thr Pro Lys Glu Pro Gly Ser Ala Phe Leu Gln Leu Gly Val
    130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
```

-continued

```
            195                 200                 205
Arg Ala Arg Thr Gln Arg Leu Leu Arg Gln Leu Asp Ala Pro Val Phe
            210                 215                 220
Val Ala Tyr Cys Ser Arg Glu Glu Ala Glu Val Leu Phe Ala Glu Ala
225                 230                 235                 240
Ala Gln Ala Gly Leu Val Gly Pro Gly His Val Trp Leu Val Pro Asn
                245                 250                 255
Leu Ala Leu Gly Ser Thr Asp Ala Pro Pro Ala Thr Phe Pro Val Gly
                260                 265                 270
Leu Ile Ser Val Val Thr Glu Ser Trp Arg Leu Ser Leu Arg Gln Lys
            275                 280                 285
Val Arg Asp Gly Val Ala Ile Leu Ala Leu Gly Ala His Ser Tyr Trp
            290                 295                 300
Arg Gln His Gly Thr Leu Pro Ala Pro Ala Gly Asp Cys Arg Val His
305                 310                 315                 320
Pro Gly Pro Val Ser Pro Ala Arg Glu Ala Phe Tyr Arg His Leu Leu
                325                 330                 335
Asn Val Thr Trp Glu Gly Arg Asp Phe Ser Phe Ser Pro Gly Gly Tyr
                340                 345                 350
Leu Val Gln Pro Thr Met Val Val Ile Ala Leu Asn Arg His Arg Leu
            355                 360                 365
Trp Glu Met Val Gly Arg Trp Glu His Gly Val Leu Tyr Met Lys Tyr
        370                 375                 380
Pro Val Trp Pro Arg Tyr Ser Ala Ser Leu Gln Pro Val Val Asp Ser
385                 390                 395                 400
Arg His Leu Thr Val Ala Thr Leu Glu Glu Arg Pro Phe Val Ile Val
                405                 410                 415
Glu Ser Pro Asp Pro Gly Thr Gly Gly Cys Val Pro Asn Thr Val Pro
                420                 425                 430
Cys Arg Arg Gln Ser Asn His Thr Phe Ser Ser Gly Asp Val Ala Pro
            435                 440                 445
Tyr Thr Lys Leu Cys Cys Lys Gly Phe Cys Ile Asp Ile Leu Lys Lys
        450                 455                 460
Leu Ala Arg Val Val Lys Phe Ser Tyr Asp Leu Tyr Leu Val Thr Asn
465                 470                 475                 480
Gly Lys His Gly Lys Arg Val Arg Gly Val Trp Asn Gly Met Ile Gly
                485                 490                 495
Glu Val Tyr Tyr Lys Arg Ala Asp Met Ala Ile Gly Ser Leu Thr Ile
                500                 505                 510
Asn Glu Glu Arg Ser Glu Ile Val Asp Phe Ser Val Pro Phe Val Glu
            515                 520                 525
Thr Gly Ile Ser Val Met Val Ala Arg Ser Asn Gly Thr Val Ser Pro
            530                 535                 540
Ser Ala Phe Leu Glu Pro Tyr Ser Pro Ala Val Trp Val Met Met Phe
545                 550                 555                 560
Val Met Cys Leu Thr Val Val Ala Ile Thr Val Phe Met Phe Glu Tyr
                565                 570                 575
Phe Ser Pro Val Ser Tyr Asn Gln Asn Leu Thr Arg Gly Lys Lys Ser
                580                 585                 590
Gly Gly Pro Ala Phe Thr Ile Gly Lys Ser Val Trp Leu Leu Trp Ala
            595                 600                 605
Leu Val Phe Asn Asn Ser Val Pro Ile Glu Asn Pro Arg Gly Thr Thr
            610                 615                 620
```

-continued

```
Ser Lys Ile Met Val Leu Val Trp Ala Phe Phe Ala Val Ile Phe Leu
625                 630                 635                 640

Ala Arg Tyr Thr Ala Asn Leu Ala Ala Phe Met Ile Gln Glu Gln Tyr
            645                 650                 655

Ile Asp Thr Val Ser Gly Leu Ser Asp Lys Lys Phe Gln Arg Pro Gln
            660                 665                 670

Asp Gln Tyr Pro Pro Phe Arg Phe Gly Thr Val Pro Asn Gly Ser Thr
        675                 680                 685

Glu Arg Asn Ile Arg Ser Asn Tyr Arg Asp Met His Thr His Met Val
    690                 695                 700

Lys Phe Asn Gln Arg Ser Val Glu Asp Ala Leu Thr Ser Leu Lys Met
705                 710                 715                 720

Gly Lys Asp Glu Gly Cys Lys Leu Val Thr Ile Gly Ser Gly Lys Val
                725                 730                 735

Phe Ala Thr Thr Gly Tyr Gly Ile Ala Met Gln Lys Asp Ser His Trp
            740                 745                 750

Lys Arg Ala Ile Asp Leu Ala Leu Leu Gln Phe Leu Gly Asp Gly Glu
        755                 760                 765

Thr Gln Lys Leu Glu Thr Val Trp Leu Ser Gly Ile Cys Gln Asn Glu
    770                 775                 780

Lys Asn Glu Val Met Ser Ser Lys Leu Asp Ile Asp Asn Met Gly Gly
785                 790                 795                 800

Val Phe Tyr Met Leu Leu Val Ala Met Gly Leu Ala Leu Leu Val Phe
                805                 810                 815

Ala Trp Glu His Leu Val Tyr Trp Lys Leu Arg His Ser Val Pro Asn
            820                 825                 830

Ser Ser Gln Leu Asp Phe Leu Leu Ala Phe Ser Arg Gly Ile Tyr Ser
        835                 840                 845

Cys Phe Ser Gly Val Gln Ser Leu Ala Ser Pro Pro Arg Gln Ala Ser
    850                 855                 860

Pro Asp Leu Thr Ala Ser Ser Ala Gln Ala Ser Val Leu Lys Ile Leu
865                 870                 875                 880

Gln Ala Ala Arg Asp Met Val Thr Thr Ala Gly Val Ser Asn Ser Leu
                885                 890                 895

Asp Arg Ala Thr Arg Thr Ile Glu Asn Trp Gly Gly Arg Arg Ala
            900                 905                 910

Pro Pro Pro Ser Pro Cys Pro Thr Pro Arg Ser Gly Pro Ser Pro Cys
        915                 920                 925

Leu Pro Thr Pro Asp Pro Pro Glu Pro Ser Pro Thr Gly Trp Gly
    930                 935                 940

Pro Pro Asp Gly Gly Arg Ala Ala Leu Val Arg Arg Ala Pro Gln Pro
945                 950                 955                 960

Pro Gly Arg Pro Pro Thr Pro Gly Pro Pro Leu Ser Asp Val Ser Arg
                965                 970                 975

Val Ser Arg Arg Pro Ala Trp Glu Ala Arg Trp Pro Val Arg Thr Gly
            980                 985                 990

His Cys Gly Arg His Leu Ser Ala Ser Glu Arg Pro Leu Ser Pro Ala
        995                 1000                1005

Arg Cys His Tyr Ser Ser Phe Pro Arg Ala Asp Arg Ser Gly Arg Pro
    1010                1015                1020

Phe Leu Pro Leu Phe Pro Glu Pro Glu Leu Glu Asp Leu Pro Leu
1025                1030                1035                1040
```

```
Leu Gly Pro Glu Gln Leu Ala Arg Arg Glu Ala Leu Leu Asn Ala Ala
            1045                1050                1055

Trp Ala Arg Gly Ser Arg Pro Ser His Ala Ser Leu Pro Ser Ser Val
            1060                1065                1070

Ala Glu Ala Phe Ala Arg Pro Ser Ser Leu Pro Ala Gly Cys Thr Gly
            1075                1080                1085

Pro Ala Cys Ala Arg Pro Asp Gly His Ser Ala Cys Arg Arg Leu Ala
            1090                1095                1100

Gln Ala Gln Ser Met Cys Leu Pro Ile Tyr Arg Glu Ala Cys Gln Glu
1105                1110                1115                1120

Gly Glu Gln Ala Gly Ala Pro Ala Trp Gln His Arg Gln His Val Cys
            1125                1130                1135

Leu His Ala His Ala His Leu Pro Leu Cys Trp Gly Ala Val Cys Pro
            1140                1145                1150

His Leu Pro Pro Cys Asp Ser His Gly Ser Trp Leu Ser Gly Ala Trp
            1155                1160                1165

Gly Pro Leu Gly His Ser Gly Arg Thr Leu Gly Leu Gly Thr Gly Tyr
            1170                1175                1180

Arg Asp Ser Gly Gly Leu Asp Glu Ile Ser Ser Val Ala Arg Gly Thr
1185                1190                1195                1200

Gln Gly Phe Pro Gly Pro Cys Thr Trp Arg Arg Ile Ser Ser Leu Glu
            1205                1210                1215

Ser Glu Val (2) INFORMATION FOR SEQ ID NO:51:

(i) SEQUENCE CHARACTERISTICS:
        (A) LENGTH: 4077 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 189..3908

(xi) SEQUENCE DESCRIPTION: SEQ ID NO:51:
```

| | |
|---|---|
| CCCTTAATAA GATTTGCNAC GTACACTCGA GCCATCGCGA GTGTCCTTGA GCCGCGGGTG | 60 |
| ACGGTGGCTC TCGCTGCTCG CGCCCCCTCC TCCCGCGGGG GGAGCCTGAT GCCACGTTCC | 120 |
| CTATGAATTA TTTATCGCCG GCCTAAAAAT ACCCCGAACT TCACAGCCCG AGTGACCCTC | 180 |

```
CGGTGGAC ATG GGT GGG GCC CTG GGG CCG GCC CTG TTG CTC ACC TCG CTC        230
         Met Gly Gly Ala Leu Gly Pro Ala Leu Leu Leu Thr Ser Leu
          1               5                  10

TTC GGT GCC TGG GCA GGG CTG GGT CCG GGG CAG GGC GAG CAG GGC ATG         278
Phe Gly Ala Trp Ala Gly Leu Gly Pro Gly Gln Gly Glu Gln Gly Met
 15                  20                  25                  30

ACG GTG GCC GTG GTG TTT AGC AGC TCA GGG CCG CCC CAG GCC CAG TTC         326
Thr Val Ala Val Val Phe Ser Ser Ser Gly Pro Pro Gln Ala Gln Phe
                 35                  40                  45

CGT GTC CGC CTC ACC CCC CAG AGC TTC CTG GAC CTA CCC CTG GAG ATC         374
Arg Val Arg Leu Thr Pro Gln Ser Phe Leu Asp Leu Pro Leu Glu Ile
             50                  55                  60

CAG CCG CTC ACA GTT GGG GTC AAC ACC ACC AAC CCC AGC AGC CTC CTC         422
Gln Pro Leu Thr Val Gly Val Asn Thr Thr Asn Pro Ser Ser Leu Leu
         65                  70                  75

ACC CAG ATC TGC GGC CTC CTG GGT GCT GCC CAC GTC CAC GGC ATT GTC         470
```

-continued

```
Thr Gln Ile Cys Gly Leu Leu Gly Ala Ala His Val His Gly Ile Val
 80                  85                  90

TTT GAG GAC AAC GTG GAC ACC GAG GCG GTG GCC CAG ATC CTT GAC TTC        518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT        566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG        614
Ala Val Val Leu Thr Pro Lys Glu Pro Gly Ser Ala Phe Leu Gln Leu
            130                 135                 140

GGC GTG TCC CTG GAG CAG CAG CTG CAG GTG CTG TTC AAG GTG CTG GAA        662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC        710
Glu Tyr Asp Trp Ser Ala Phe Ala Val Ile Thr Ser Leu His Pro Gly
    160                 165                 170

CAC GCG CTC TTC CTG GAG GGC GTG CGC GCC GTC GCC GAC GCC AGC CAC        758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA        806
Val Ser Trp Arg Leu Leu Asp Val Val Thr Leu Glu Leu Asp Pro Gly
                195                 200                 205

GGG CCG CGC GCG CGC ACG CAG CGC CTG CTG CGC CAG CTC GAC GCG CCC        854
Gly Pro Arg Ala Arg Thr Gln Arg Leu Leu Arg Gln Leu Asp Ala Pro
            210                 215                 220

GTG TTT GTG GCC TAC TGC TCG CGC GAG GAG GCC GAG GTG CTC TTC GCC        902
Val Phe Val Ala Tyr Cys Ser Arg Glu Glu Ala Glu Val Leu Phe Ala
        225                 230                 235

GAG GCG GCG CAG GCC GGT CTG GTG GGG CCC GGC CAC GTG TGG CTG GTG        950
Glu Ala Ala Gln Ala Gly Leu Val Gly Pro Gly His Val Trp Leu Val
    240                 245                 250

CCC AAC CTG GCG CTG GGC AGC ACC GAT GCG CCC CCC GCC ACC TTC CCC        998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC       1046
Val Gly Leu Ile Ser Val Val Thr Glu Ser Trp Arg Leu Ser Leu Arg
                275                 280                 285

CAG AAG GTG CGC GAC GGC GTG GCC ATT CTG GCC CTG GGC GCC CAC AGC       1094
Gln Lys Val Arg Asp Gly Val Ala Ile Leu Ala Leu Gly Ala His Ser
            290                 295                 300

TAC TGG CGC CAG CAT GGA ACC CTG CCA GCC CCG GCC GGG GAC TGC CGT       1142
Tyr Trp Arg Gln His Gly Thr Leu Pro Ala Pro Ala Gly Asp Cys Arg
        305                 310                 315

GTT CAC CCT GGG CCC GTC AGC CCT GCC CGG GAG GCC TTC TAC AGG CAC       1190
Val His Pro Gly Pro Val Ser Pro Ala Arg Glu Ala Phe Tyr Arg His
    320                 325                 330

CTA CTG AAT GTC ACC TGG GAG GGC CGA GAC TTC TCC TTC AGC CCT GGT       1238
Leu Leu Asn Val Thr Trp Glu Gly Arg Asp Phe Ser Phe Ser Pro Gly
335                 340                 345                 350

GGG TAC CTG GTC CAG CCC ACC ATG GTG GTG ATC GCC CTC AAC CGG CAC       1286
Gly Tyr Leu Val Gln Pro Thr Met Val Val Ile Ala Leu Asn Arg His
                355                 360                 365

CGC CTC TGG GAG ATG GTG GGG CGC TGG GAG CAT GGC GTC CTA TAC ATG       1334
Arg Leu Trp Glu Met Val Gly Arg Trp Glu His Gly Val Leu Tyr Met
            370                 375                 380

AAG TAC CCC GTG TGG CCT CGC TAC AGT GCC TCT CTG CAG CCT GTG GTG       1382
Lys Tyr Pro Val Trp Pro Arg Tyr Ser Ala Ser Leu Gln Pro Val Val
        385                 390                 395
```

```
GAC AGT CGG CAC CTG ACG GTG GCC ACG CTG GAA GAG CGG CCC TTT GTC      1430
Asp Ser Arg His Leu Thr Val Ala Thr Leu Glu Glu Arg Pro Phe Val
    400                 405                 410

ATC GTG GAG AGC CCT GAC CCT GGC ACA GGA GGC TGT GTC CCC AAC ACC      1478
Ile Val Glu Ser Pro Asp Pro Gly Thr Gly Gly Cys Val Pro Asn Thr
415                 420                 425                 430

GTG CCC TGC CGC AGG CAG AGC AAC CAC ACC TTC AGC AGC GGG GAC GTG      1526
Val Pro Cys Arg Arg Gln Ser Asn His Thr Phe Ser Ser Gly Asp Val
                435                 440                 445

GCC CCC TAC ACC AAG CTC TGC TGT AAG GGA TTC TGC ATC GAC ATC CTC      1574
Ala Pro Tyr Thr Lys Leu Cys Cys Lys Gly Phe Cys Ile Asp Ile Leu
            450                 455                 460

AAG AAG CTG GCC AGA GTG GTC AAA TTC TCC TAC GAC CTG TAC CTG GTG      1622
Lys Lys Leu Ala Arg Val Val Lys Phe Ser Tyr Asp Leu Tyr Leu Val
                465                 470                 475

ACC AAC GGC AAG CAT GGC AAG CGG GTG CGC GGC GTA TGG AAC GGC ATG      1670
Thr Asn Gly Lys His Gly Lys Arg Val Arg Gly Val Trp Asn Gly Met
480                 485                 490

ATT GGG GAG GTG TAC TAC AAG CGG GCA GAC ATG GCC ATC GGC TCC CTC      1718
Ile Gly Glu Val Tyr Tyr Lys Arg Ala Asp Met Ala Ile Gly Ser Leu
495                 500                 505                 510

ACC ATC AAT GAG GAA CGC TCC GAG ATC GTA GAC TTC TCT GTA CCC TTT      1766
Thr Ile Asn Glu Glu Arg Ser Glu Ile Val Asp Phe Ser Val Pro Phe
                515                 520                 525

GTG GAG ACG GGC ATC AGT GTG ATG GTG GCT CGC AGC AAT GGC ACC GTC      1814
Val Glu Thr Gly Ile Ser Val Met Val Ala Arg Ser Asn Gly Thr Val
            530                 535                 540

TCC CCC TCG GCC TTC TTG GAG CCA TAT AGC CCT GCA GTG TGG GTG ATG      1862
Ser Pro Ser Ala Phe Leu Glu Pro Tyr Ser Pro Ala Val Trp Val Met
                545                 550                 555

ATG TTT GTC ATG TGC CTC ACT GTG GTG GCC ATC ACC GTC TTC ATG TTC      1910
Met Phe Val Met Cys Leu Thr Val Val Ala Ile Thr Val Phe Met Phe
560                 565                 570

GAG TAC TTC AGC CCT GTC AGC TAC AAC CAG AAC CTC ACC AGA GGC AAG      1958
Glu Tyr Phe Ser Pro Val Ser Tyr Asn Gln Asn Leu Thr Arg Gly Lys
575                 580                 585                 590

ACT TTC ACT ATC GGC AAG TCC GTG TGG CTG CTG TGG GCG CTG GTC TTC      2006
Thr Phe Thr Ile Gly Lys Ser Val Trp Leu Leu Trp Ala Leu Val Phe
                595                 600                 605

AAC AAC TCA GTG CCC ATC GAG AAC CCG CGG GGC ACC ACC AGC AAG ATC      2054
Asn Asn Ser Val Pro Ile Glu Asn Pro Arg Gly Thr Thr Ser Lys Ile
            610                 615                 620

ATG GTT CTG GTC TGG GCC TTC TTT GCT GTC ATC TTC CTC GCC AGA TAC      2102
Met Val Leu Val Trp Ala Phe Phe Ala Val Ile Phe Leu Ala Arg Tyr
                625                 630                 635

ACG GCC AAC CTG GCC GCC TTC ATG ATC CAA GAG CAA TAC ATC GAC ACT      2150
Thr Ala Asn Leu Ala Ala Phe Met Ile Gln Glu Gln Tyr Ile Asp Thr
640                 645                 650

GTG TCG GGC CTC AGT GAC AAG AAG TTT CAG CGG CCT CAA GAT CAG TAC      2198
Val Ser Gly Leu Ser Asp Lys Lys Phe Gln Arg Pro Gln Asp Gln Tyr
655                 660                 665                 670

CCA CCT TTC CGC TTC GGC ACG GTG CCC AAC GGC AGC ACG GAG CGG AAC      2246
Pro Pro Phe Arg Phe Gly Thr Val Pro Asn Gly Ser Thr Glu Arg Asn
                675                 680                 685

ATC CGC AGT AAC TAC CGT GAC ATG CAC ACC CAC ATG GTC AAG TTC AAC      2294
Ile Arg Ser Asn Tyr Arg Asp Met His Thr His Met Val Lys Phe Asn
            690                 695                 700

CAG CGC TCG GTG GAG GAC GCG CTC ACC AGC CTC AAG ATG GGC TCT GAG      2342
Gln Arg Ser Val Glu Asp Ala Leu Thr Ser Leu Lys Met Gly Ser Glu
                705                 710                 715
```

```
GCT CAG CCT GTC CCC AGG AAG CTG GAT GCC TTC ATC TAT GAT GCT GCT    2390
Ala Gln Pro Val Pro Arg Lys Leu Asp Ala Phe Ile Tyr Asp Ala Ala
    720             725                 730

GTC CTC AAC TAC ATG GCA GGC AAG GAC GAG GGC TGC AAG CTG GTC ACC    2438
Val Leu Asn Tyr Met Ala Gly Lys Asp Glu Gly Cys Lys Leu Val Thr
735             740                 745                 750

ATT GGG TCT GGC AAG GTC TTT GCT ACC ACT GGC TAC GGC ATC GCC ATG    2486
Ile Gly Ser Gly Lys Val Phe Ala Thr Thr Gly Tyr Gly Ile Ala Met
                755                 760                 765

CAG AAG GAC TCC CAC TGG AAG CGG GCC ATA GAC CTG GCG CTC TTG CAG    2534
Gln Lys Asp Ser His Trp Lys Arg Ala Ile Asp Leu Ala Leu Leu Gln
            770                 775                 780

TTC CTG GGG GAC GGA GAG ACA CAG AAA CTG GAG ACA GTG TGG CTC TCA    2582
Phe Leu Gly Asp Gly Glu Thr Gln Lys Leu Glu Thr Val Trp Leu Ser
        785                 790                 795

GGG ATC TGC CAG AAT GAG AAG AAC GAG GTG ATG AGC AGC AAG CTG GAC    2630
Gly Ile Cys Gln Asn Glu Lys Asn Glu Val Met Ser Ser Lys Leu Asp
    800                 805                 810

ATC GAC AAC ATG GGA GGC GTC TTC TAC ATG CTG CTG GTG GCC ATG GGG    2678
Ile Asp Asn Met Gly Gly Val Phe Tyr Met Leu Leu Val Ala Met Gly
815                 820                 825                 830

CTG GCC CTG CTG GTC TTC GCC TGG GAG CAC CTG GTC TAC TGG AAG CTG    2726
Leu Ala Leu Leu Val Phe Ala Trp Glu His Leu Val Tyr Trp Lys Leu
                835                 840                 845

CGC CAC TCG GTG CCC AAC TCA TCC CAG CTG GAC TTC CTG CTG GCT TTC    2774
Arg His Ser Val Pro Asn Ser Ser Gln Leu Asp Phe Leu Leu Ala Phe
            850                 855                 860

AGC AGG GGC ATC TAC AGC TGC TTC AGC GGG GTG CAG AGC CTC GCC AGC    2822
Ser Arg Gly Ile Tyr Ser Cys Phe Ser Gly Val Gln Ser Leu Ala Ser
        865                 870                 875

CCA CCG CGG CAG GCC AGC CCG GAC CTC ACG GCC AGC TCG GCC CAG GCC    2870
Pro Pro Arg Gln Ala Ser Pro Asp Leu Thr Ala Ser Ser Ala Gln Ala
    880                 885                 890

AGC GTG CTC AAG ATT CTG CAG GCA GCC CGC GAC ATG GTG ACC ACG GCG    2918
Ser Val Leu Lys Ile Leu Gln Ala Ala Arg Asp Met Val Thr Thr Ala
895                 900                 905                 910

GGC GTA AGC AAC TCC CTG GAC CGC GCC ACT CGC ACC ATC GAG AAT TGG    2966
Gly Val Ser Asn Ser Leu Asp Arg Ala Thr Arg Thr Ile Glu Asn Trp
                915                 920                 925

GGT GGC GGC CGC CGT GCG CCC CCA CCG TCC CCC TGC CCG ACC CCG CGG    3014
Gly Gly Gly Arg Arg Ala Pro Pro Pro Ser Pro Cys Pro Thr Pro Arg
            930                 935                 940

TCT GGC CCC AGC CCA TGC CTG CCC ACC CCC GAC CCG CCC CCA GAG CCG    3062
Ser Gly Pro Ser Pro Cys Leu Pro Thr Pro Asp Pro Pro Pro Glu Pro
        945                 950                 955

AGC CCC ACG GGC TGG GGA CCG CCA GAC GGG GGT CGC GCG GCG CTT GTG    3110
Ser Pro Thr Gly Trp Gly Pro Pro Asp Gly Gly Arg Ala Ala Leu Val
    960                 965                 970

CGC AGG GCT CCG CAG CCC CCG GGC CGC CCC CCG ACG CCG GGG CCG CCC    3158
Arg Arg Ala Pro Gln Pro Pro Gly Arg Pro Pro Thr Pro Gly Pro Pro
975                 980                 985                 990

CTG TCC GAC GTC TCC CGA GTG TCG CGC CGC CCA GCC TGG GAG GCG CGG    3206
Leu Ser Asp Val Ser Arg Val Ser Arg Arg Pro Ala Trp Glu Ala Arg
                995                 1000                1005

TGG CCG GTG CGG ACC GGG CAC TGC GGG AGG CAC CTC TCG GCC TCC GAG    3254
Trp Pro Val Arg Thr Gly His Cys Gly Arg His Leu Ser Ala Ser Glu
            1010                1015                1020

CGG CCC CTG TCG CCC GCG CGC TGT CAC TAC AGC TCC TTT CCT CGA GCC    3302
Arg Pro Leu Ser Pro Ala Arg Cys His Tyr Ser Ser Phe Pro Arg Ala
```

```
          1025                 1030                 1035
GAC CGA TCC GGC CGC CCC TTC CTC CCG CTC TTC CCG GAG CCC CCG GAG        3350
Asp Arg Ser Gly Arg Pro Phe Leu Pro Leu Phe Pro Glu Pro Pro Glu
        1040                 1045                 1050

CTG GAG GAC CTG CCG CTG CTC GGT CCG GAG CAG CTG GCC CGG CGG GAG        3398
Leu Glu Asp Leu Pro Leu Leu Gly Pro Glu Gln Leu Ala Arg Arg Glu
1055                 1060                 1065                 1070

GCC CTG CTG AAC GCG GCC TGG GCC CGG GGC TCG CGC CCG AGT CAC GCT        3446
Ala Leu Leu Asn Ala Ala Trp Ala Arg Gly Ser Arg Pro Ser His Ala
            1075                 1080                 1085

TCC CTG CCC AGC TCC GTG GCC GAG GCC TTC GCT CGG CCC AGC TCG CTG        3494
Ser Leu Pro Ser Ser Val Ala Glu Ala Phe Ala Arg Pro Ser Ser Leu
                1090                 1095                 1100

CCC GCT GGG TGC ACC GGC CCC GCC TGC GCC CGC CCC GAC GGC CAC TCG        3542
Pro Ala Gly Cys Thr Gly Pro Ala Cys Ala Arg Pro Asp Gly His Ser
            1105                 1110                 1115

GCC TGC AGG CGC TTG GCG CAG GCG CAG TCG ATG TGC TTG CCG ATC TAC        3590
Ala Cys Arg Arg Leu Ala Gln Ala Gln Ser Met Cys Leu Pro Ile Tyr
        1120                 1125                 1130

CGG GAG GCC TGC CAG GAG GGC GAG CAG GCA GGG GCC CCC GCC TGG CAG        3638
Arg Glu Ala Cys Gln Glu Gly Glu Gln Ala Gly Ala Pro Ala Trp Gln
1135                 1140                 1145                 1150

CAC AGA CAG CAC GTC TGC CTG CAC GCC CAC GCC CAC CTG CCA TTG TGC        3686
His Arg Gln His Val Cys Leu His Ala His Ala His Leu Pro Leu Cys
                1155                 1160                 1165

TGG GGG GCT GTC TGT CCT CAC CTT CCA CCC TGT GAC AGC CAC GGC TCC        3734
Trp Gly Ala Val Cys Pro His Leu Pro Pro Cys Asp Ser His Gly Ser
            1170                 1175                 1180

TGG CTC TCC GGC GCC TGG GGG CCT CTG GGG CAC AGC GGC AGG ACT CTG        3782
Trp Leu Ser Gly Ala Trp Gly Pro Leu Gly His Ser Gly Arg Thr Leu
        1185                 1190                 1195

GGG CTG GGC ACA GGC TAC AGA GAC AGT GGG GGA CTG GAC GAG ATC AGC        3830
Gly Leu Gly Thr Gly Tyr Arg Asp Ser Gly Gly Leu Asp Glu Ile Ser
        1200                 1205                 1210

AGT GTA GCC CGT GGG ACG CAA GGC TTC CCG GGA CCC TGC ACC TGG AGA        3878
Ser Val Ala Arg Gly Thr Gln Gly Phe Pro Gly Pro Cys Thr Trp Arg
1215                 1220                 1225                 1230

CGG ATC TCC AGT CTG GAG TCA GAA GTG TGAGTTATCA GCCACTCAGG             3925
Arg Ile Ser Ser Leu Glu Ser Glu Val
                1235                 124

CTCCGAGCCA GCTGGATTCT CTGCCTGCCA CTGTCAGGGT TAAGCGGCAG GCAGGATTGG      3985

CCCTTCTCTG GCTTCTACCA TGAAATCCTG GCCATGGCAC CCCAGTGACA GATGATGTCT      4045

TCCATGGTCA TCAGTGACCT CAGCTAGCCT CA                                    4077

(2) INFORMATION FOR SEQ ID NO:52:

(i) SEQUENCE CHARACTERISTICS:
        (A) LENGTH: 1239 amino acids
        (B) TYPE: amino acid
        (D) TOPOLOGY: linear (ii) MOLECULE TYPE: protein (xi) SEQUENCE DESCRIPTION: SEQ ID NO:52:

Met Gly Gly Ala Leu Gly Pro Ala Leu Leu Leu Thr Ser Leu Phe Gly
  1               5                  10                  15

Ala Trp Ala Gly Leu Gly Pro Gly Gln Gly Glu Gln Gly Met Thr Val
             20                  25                  30

Ala Val Val Phe Ser Ser Ser Gly Pro Pro Gln Ala Gln Phe Arg Val
```

-continued

```
                35                  40                  45
Arg Leu Thr Pro Gln Ser Phe Leu Asp Leu Pro Leu Glu Ile Gln Pro
     50                  55                  60
Leu Thr Val Gly Val Asn Thr Asn Pro Ser Ser Leu Leu Thr Gln
 65                  70                  75                  80
Ile Cys Gly Leu Leu Gly Ala Ala His Val His Gly Ile Val Phe Glu
                 85                  90                  95
Asp Asn Val Asp Thr Glu Ala Val Ala Gln Ile Leu Asp Phe Ile Ser
             100                 105                 110
Ser Gln Thr His Val Pro Ile Leu Ser Ile Ser Gly Ser Ala Val
             115                 120                 125
Val Leu Thr Pro Lys Glu Pro Gly Ser Ala Phe Leu Gln Leu Gly Val
     130                 135                 140
Ser Leu Glu Gln Gln Leu Gln Val Leu Phe Lys Val Leu Glu Glu Tyr
145                 150                 155                 160
Asp Trp Ser Ala Phe Ala Val Ile Thr Ser Leu His Pro Gly His Ala
                 165                 170                 175
Leu Phe Leu Glu Gly Val Arg Ala Val Ala Asp Ala Ser His Val Ser
             180                 185                 190
Trp Arg Leu Leu Asp Val Val Thr Leu Glu Leu Asp Pro Gly Gly Pro
     195                 200                 205
Arg Ala Arg Thr Gln Arg Leu Leu Arg Gln Leu Asp Ala Pro Val Phe
     210                 215                 220
Val Ala Tyr Cys Ser Arg Glu Glu Ala Glu Val Leu Phe Ala Glu Ala
225                 230                 235                 240
Ala Gln Ala Gly Leu Val Gly Pro Gly His Val Trp Leu Val Pro Asn
                 245                 250                 255
Leu Ala Leu Gly Ser Thr Asp Ala Pro Pro Ala Thr Phe Pro Val Gly
             260                 265                 270
Leu Ile Ser Val Val Thr Glu Ser Trp Arg Leu Ser Leu Arg Gln Lys
             275                 280                 285
Val Arg Asp Gly Val Ala Ile Leu Ala Leu Gly Ala His Ser Tyr Trp
     290                 295                 300
Arg Gln His Gly Thr Leu Pro Ala Pro Ala Gly Asp Cys Arg Val His
305                 310                 315                 320
Pro Gly Pro Val Ser Pro Ala Arg Glu Ala Phe Tyr Arg His Leu Leu
                 325                 330                 335
Asn Val Thr Trp Glu Gly Arg Asp Phe Ser Phe Ser Pro Gly Gly Tyr
             340                 345                 350
Leu Val Gln Pro Thr Met Val Val Ile Ala Leu Asn Arg His Arg Leu
             355                 360                 365
Trp Glu Met Val Gly Arg Trp Glu His Gly Val Leu Tyr Met Lys Tyr
     370                 375                 380
Pro Val Trp Pro Arg Tyr Ser Ala Ser Leu Gln Pro Val Val Asp Ser
385                 390                 395                 400
Arg His Leu Thr Val Ala Thr Leu Glu Glu Arg Pro Phe Val Ile Val
                 405                 410                 415
Glu Ser Pro Asp Pro Gly Thr Gly Gly Cys Val Pro Asn Thr Val Pro
             420                 425                 430
Cys Arg Arg Gln Ser Asn His Thr Phe Ser Ser Gly Asp Val Ala Pro
             435                 440                 445
Tyr Thr Lys Leu Cys Cys Lys Gly Phe Cys Ile Asp Ile Leu Lys Lys
     450                 455                 460
```

-continued

```
Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
                485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
        515                 520                 525

Thr Gly Ile Ser Val Met Val Ala Arg Ser Asn Gly Thr Val Ser Pro
    530                 535                 540

Ser Ala Phe Leu Glu Pro Tyr Ser Pro Ala Val Trp Val Met Met Phe
545                 550                 555                 560

Val Met Cys Leu Thr Val Val Ala Ile Thr Val Phe Met Phe Glu Tyr
                565                 570                 575

Phe Ser Pro Val Ser Tyr Asn Gln Asn Leu Thr Arg Gly Lys Thr Phe
            580                 585                 590

Thr Ile Gly Lys Ser Val Trp Leu Leu Trp Ala Leu Val Phe Asn Asn
        595                 600                 605

Ser Val Pro Ile Glu Asn Pro Arg Gly Thr Thr Ser Lys Ile Met Val
    610                 615                 620

Leu Val Trp Ala Phe Phe Ala Val Ile Phe Leu Ala Arg Tyr Thr Ala
625                 630                 635                 640

Asn Leu Ala Ala Phe Met Ile Gln Glu Gln Tyr Ile Asp Thr Val Ser
                645                 650                 655

Gly Leu Ser Asp Lys Lys Phe Gln Arg Pro Gln Asp Gln Tyr Pro Pro
            660                 665                 670

Phe Arg Phe Gly Thr Val Pro Asn Gly Ser Thr Glu Arg Asn Ile Arg
        675                 680                 685

Ser Asn Tyr Arg Asp Met His Thr His Met Val Lys Phe Asn Gln Arg
    690                 695                 700

Ser Val Glu Asp Ala Leu Thr Ser Leu Lys Met Gly Ser Glu Ala Gln
705                 710                 715                 720

Pro Val Pro Arg Lys Leu Asp Ala Phe Ile Tyr Asp Ala Ala Val Leu
                725                 730                 735

Asn Tyr Met Ala Gly Lys Asp Glu Gly Cys Lys Leu Val Thr Ile Gly
            740                 745                 750

Ser Gly Lys Val Phe Ala Thr Thr Gly Tyr Gly Ile Ala Met Gln Lys
        755                 760                 765

Asp Ser His Trp Lys Arg Ala Ile Asp Leu Ala Leu Leu Gln Phe Leu
    770                 775                 780

Gly Asp Gly Glu Thr Gln Lys Leu Glu Thr Val Trp Leu Ser Gly Ile
785                 790                 795                 800

Cys Gln Asn Glu Lys Asn Glu Val Met Ser Ser Lys Leu Asp Ile Asp
                805                 810                 815

Asn Met Gly Gly Val Phe Tyr Met Leu Leu Val Ala Met Gly Leu Ala
            820                 825                 830

Leu Leu Val Phe Ala Trp Glu His Leu Val Tyr Trp Lys Leu Arg His
        835                 840                 845

Ser Val Pro Asn Ser Ser Gln Leu Asp Phe Leu Leu Ala Phe Ser Arg
    850                 855                 860

Gly Ile Tyr Ser Cys Phe Ser Gly Val Gln Ser Leu Ala Ser Pro Pro
865                 870                 875                 880
```

```
Arg Gln Ala Ser Pro Asp Leu Thr Ala Ser Ala Gln Ala Ser Val
                885                 890                 895

Leu Lys Ile Leu Gln Ala Ala Arg Asp Met Val Thr Thr Ala Gly Val
                900                 905                 910

Ser Asn Ser Leu Asp Arg Ala Thr Arg Thr Ile Glu Asn Trp Gly Gly
                915                 920                 925

Gly Arg Arg Ala Pro Pro Ser Pro Cys Pro Thr Pro Arg Ser Gly
        930                 935                 940

Pro Ser Pro Cys Leu Pro Thr Pro Asp Pro Pro Glu Pro Ser Pro
945                 950                 955                 960

Thr Gly Trp Gly Pro Pro Asp Gly Gly Arg Ala Ala Leu Val Arg Arg
                965                 970                 975

Ala Pro Gln Pro Pro Gly Arg Pro Pro Thr Pro Gly Pro Pro Leu Ser
                980                 985                 990

Asp Val Ser Arg Val Ser Arg Arg Pro Ala Trp Glu Ala Arg Trp Pro
                995                 1000                1005

Val Arg Thr Gly His Cys Gly Arg His Leu Ser Ala Ser Glu Arg Pro
                1010                1015                1020

Leu Ser Pro Ala Arg Cys His Tyr Ser Ser Phe Pro Arg Ala Asp Arg
1025                1030                1035                1040

Ser Gly Arg Pro Phe Leu Pro Leu Phe Pro Glu Pro Pro Glu Leu Glu
                1045                1050                1055

Asp Leu Pro Leu Leu Gly Pro Glu Gln Leu Ala Arg Arg Glu Ala Leu
                1060                1065                1070

Leu Asn Ala Ala Trp Ala Arg Gly Ser Arg Pro Ser His Ala Ser Leu
                1075                1080                1085

Pro Ser Ser Val Ala Glu Ala Phe Ala Arg Pro Ser Ser Leu Pro Ala
                1090                1095                1100

Gly Cys Thr Gly Pro Ala Cys Ala Arg Pro Asp Gly His Ser Ala Cys
1105                1110                1115                1120

Arg Arg Leu Ala Gln Ala Gln Ser Met Cys Leu Pro Ile Tyr Arg Glu
                1125                1130                1135

Ala Cys Gln Glu Gly Glu Gln Ala Gly Ala Pro Ala Trp Gln His Arg
                1140                1145                1150

Gln His Val Cys Leu His Ala His Ala His Leu Pro Leu Cys Trp Gly
                1155                1160                1165

Ala Val Cys Pro His Leu Pro Pro Cys Asp Ser His Gly Ser Trp Leu
                1170                1175                1180

Ser Gly Ala Trp Gly Pro Leu Gly His Ser Gly Arg Thr Leu Gly Leu
1185                1190                1195                1200

Gly Thr Gly Tyr Arg Asp Ser Gly Gly Leu Asp Glu Ile Ser Ser Val
                1205                1210                1215

Ala Arg Gly Thr Gln Gly Phe Pro Gly Pro Cys Thr Trp Arg Arg Ile
                1220                1225                1230

Ser Ser Leu Glu Ser Glu Val
        1235

(2) INFORMATION FOR SEQ ID NO:53:

(i) SEQUENCE CHARACTERISTICS:
        (A) LENGTH: 4002 base pairs
        (B) TYPE: nucleic acid
        (C) STRANDEDNESS: both
        (D) TOPOLOGY: both (ii) MOLECULE TYPE: cDNA
```

(ix) FEATURE:
    (A) NAME/KEY: CDS
    (B) LOCATION: 189..3833

(xi) SEQUENCE DESCRIPTION: SEQ ID NO:53:

```
CCCTTAATAA GATTTGCNAC GTACACTCGA GCCATCGCGA GTGTCCTTGA GCCGCGGGTG      60

ACGGTGGCTC TCGCTGCTCG CGCCCCCTCC TCCCGCGGGG GGAGCCTGAT GCCACGTTCC     120

CTATGAATTA TTTATCGCCG GCCTAAAAAT ACCCCGAACT TCACAGCCCG AGTGACCCTC     180

CGGTGGAC ATG GGT GGG GCC CTG GGG CCG GCC CTG TTG CTC ACC TCG CTC      230
         Met Gly Gly Ala Leu Gly Pro Ala Leu Leu Leu Thr Ser Leu
           1               5                  10

TTC GGT GCC TGG GCA GGG CTG GGT CCG GGG CAG GGC GAG CAG GGC ATG       278
Phe Gly Ala Trp Ala Gly Leu Gly Pro Gly Gln Gly Glu Gln Gly Met
 15                  20                  25                  30

ACG GTG GCC GTG GTG TTT AGC AGC TCA GGG CCG CCC CAG GCC CAG TTC       326
Thr Val Ala Val Val Phe Ser Ser Ser Gly Pro Pro Gln Ala Gln Phe
                 35                  40                  45

CGT GTC CGC CTC ACC CCC CAG AGC TTC CTG GAC CTA CCC CTG GAG ATC       374
Arg Val Arg Leu Thr Pro Gln Ser Phe Leu Asp Leu Pro Leu Glu Ile
                 50                  55                  60

CAG CCG CTC ACA GTT GGG GTC AAC ACC ACC AAC CCC AGC AGC CTC CTC       422
Gln Pro Leu Thr Val Gly Val Asn Thr Thr Asn Pro Ser Ser Leu Leu
             65                  70                  75

ACC CAG ATC TGC GGC CTC CTG GGT GCT GCC CAC GTC CAC GGC ATT GTC       470
Thr Gln Ile Cys Gly Leu Leu Gly Ala Ala His Val His Gly Ile Val
         80                  85                  90

TTT GAG GAC AAC GTG GAC ACC GAG GCG GTG GCC CAG ATC CTT GAC TTC       518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT       566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG       614
Ala Val Val Leu Thr Pro Lys Glu Pro Gly Ser Ala Phe Leu Gln Leu
                130                 135                 140

GGC GTG TCC CTG GAG CAG CAG CTG CAG GTG CTG TTC AAG GTG CTG GAA       662
Gly Val Ser Leu Glu Gln Gln Leu Gln Val Leu Phe Lys Val Leu Glu
            145                 150                 155

GAG TAC GAC TGG AGC GCC TTC GCC GTC ATC ACC AGC CTG CAC CCG GGC       710
Glu Tyr Asp Trp Ser Ala Phe Ala Val Ile Thr Ser Leu His Pro Gly
160                 165                 170

CAC GCG CTC TTC CTG GAG GGC GTG CGC GCC GTC GCC GAC GCC AGC CAC       758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA       806
Val Ser Trp Arg Leu Leu Asp Val Val Thr Leu Glu Leu Asp Pro Gly
                195                 200                 205

GGG CCG CGC GCG CGC ACG CAG CGC CTG CTG CGC CAG CTC GAC GCG CCC       854
Gly Pro Arg Ala Arg Thr Gln Arg Leu Leu Arg Gln Leu Asp Ala Pro
                210                 215                 220

GTG TTT GTG GCC TAC TGC TCG CGC GAG GAG GCC GAG GTG CTC TTC GCC       902
Val Phe Val Ala Tyr Cys Ser Arg Glu Glu Ala Glu Val Leu Phe Ala
                225                 230                 235

GAG GCG GCG CAG GCC GGT CTG GTG GGG CCC GGC CAC GTG TGG CTG GTG       950
Glu Ala Ala Gln Ala Gly Leu Val Gly Pro Gly His Val Trp Leu Val
            240                 245                 250

CCC AAC CTG GCG CTG GGC AGC ACC GAT GCG CCC CCC GCC ACC TTC CCC       998
Pro Asn Leu Ala Leu Gly Ser Thr Asp Ala Pro Pro Ala Thr Phe Pro
```

```
                    255                    260                    265                    270
GTG GGC CTC ATC AGC GTC GTC ACC GAG AGC TGG CGC CTC AGC CTG CGC                    1046
Val Gly Leu Ile Ser Val Val Thr Glu Ser Trp Arg Leu Ser Leu Arg
                    275                    280                    285

CAG AAG GTG CGC GAC GGC GTG GCC ATT CTG GCC CTG GGC GCC CAC AGC                    1094
Gln Lys Val Arg Asp Gly Val Ala Ile Leu Ala Leu Gly Ala His Ser
                290                    295                    300

TAC TGG CGC CAG CAT GGA ACC CTG CCA GCC CCG GCC GGG GAC TGC CGT                    1142
Tyr Trp Arg Gln His Gly Thr Leu Pro Ala Pro Ala Gly Asp Cys Arg
            305                    310                    315

GTT CAC CCT GGG CCC GTC AGC CCT GCC CGG GAG GCC TTC TAC AGG CAC                    1190
Val His Pro Gly Pro Val Ser Pro Ala Arg Glu Ala Phe Tyr Arg His
        320                    325                    330

CTA CTG AAT GTC ACC TGG GAG GGC CGA GAC TTC TCC TTC AGC CCT GGT                    1238
Leu Leu Asn Val Thr Trp Glu Gly Arg Asp Phe Ser Phe Ser Pro Gly
335                    340                    345                    350

GGG TAC CTG GTC CAG CCC ACC ATG GTG GTG ATC GCC CTC AAC CGG CAC                    1286
Gly Tyr Leu Val Gln Pro Thr Met Val Val Ile Ala Leu Asn Arg His
                355                    360                    365

CGC CTC TGG GAG ATG GTG GGG CGC TGG GAG CAT GGC GTC CTA TAC ATG                    1334
Arg Leu Trp Glu Met Val Gly Arg Trp Glu His Gly Val Leu Tyr Met
            370                    375                    380

AAG TAC CCC GTG TGG CCT CGC TAC AGT GCC TCT CTG CAG CCT GTG GTG                    1382
Lys Tyr Pro Val Trp Pro Arg Tyr Ser Ala Ser Leu Gln Pro Val Val
        385                    390                    395

GAC AGT CGG CAC CTG ACG GTG GCC ACG CTG GAA GAG CGG CCC TTT GTC                    1430
Asp Ser Arg His Leu Thr Val Ala Thr Leu Glu Glu Arg Pro Phe Val
    400                    405                    410

ATC GTG GAG AGC CCT GAC CCT GGC ACA GGA GGC TGT GTC CCC AAC ACC                    1478
Ile Val Glu Ser Pro Asp Pro Gly Thr Gly Gly Cys Val Pro Asn Thr
415                    420                    425                    430

GTG CCC TGC CGC AGG CAG AGC AAC CAC ACC TTC AGC AGC GGG GAC GTG                    1526
Val Pro Cys Arg Arg Gln Ser Asn His Thr Phe Ser Ser Gly Asp Val
                435                    440                    445

GCC CCC TAC ACC AAG CTC TGC TGT AAG GGA TTC TGC ATC GAC ATC CTC                    1574
Ala Pro Tyr Thr Lys Leu Cys Cys Lys Gly Phe Cys Ile Asp Ile Leu
            450                    455                    460

AAG AAG CTG GCC AGA GTG GTC AAA TTC TCC TAC GAC CTG TAC CTG GTG                    1622
Lys Lys Leu Ala Arg Val Val Lys Phe Ser Tyr Asp Leu Tyr Leu Val
        465                    470                    475

ACC AAC GGC AAG CAT GGC AAG CGG GTG CGC GGC GTA TGG AAC GGC ATG                    1670
Thr Asn Gly Lys His Gly Lys Arg Val Arg Gly Val Trp Asn Gly Met
    480                    485                    490

ATT GGG GAG GTG TAC TAC AAG CGG GCA GAC ATG GCC ATC GGC TCC CTC                    1718
Ile Gly Glu Val Tyr Tyr Lys Arg Ala Asp Met Ala Ile Gly Ser Leu
495                    500                    505                    510

ACC ATC AAT GAG GAA CGC TCC GAG ATC GTA GAC TTC TCT GTA CCC TTT                    1766
Thr Ile Asn Glu Glu Arg Ser Glu Ile Val Asp Phe Ser Val Pro Phe
                515                    520                    525

GTG GAG ACG GGC ATC AGT GTG ATG GTG GCT CGC AGC AAT GGC ACC GTC                    1814
Val Glu Thr Gly Ile Ser Val Met Val Ala Arg Ser Asn Gly Thr Val
            530                    535                    540

TCC CCC TCG GCC TTC TTG GAG CCA TAT AGC CCT GCA GTG TGG GTG ATG                    1862
Ser Pro Ser Ala Phe Leu Glu Pro Tyr Ser Pro Ala Val Trp Val Met
        545                    550                    555

ATG TTT GTC ATG TGC CTC ACT GTG GTG GCC ATC ACC GTC TTC ATG TTC                    1910
Met Phe Val Met Cys Leu Thr Val Val Ala Ile Thr Val Phe Met Phe
    560                    565                    570

GAG TAC TTC AGC CCT GTC AGC TAC AAC CAG AAC CTC ACC AGA GGC AAG                    1958
```

-continued

```
Glu Tyr Phe Ser Pro Val Ser Tyr Asn Gln Asn Leu Thr Arg Gly Lys
575                 580                 585                 590

ACT TTC ACT ATC GGC AAG TCC GTG TGG CTG CTG TGG GCG CTG GTC TTC    2006
Thr Phe Thr Ile Gly Lys Ser Val Trp Leu Leu Trp Ala Leu Val Phe
                595                 600                 605

AAC AAC TCA GTG CCC ATC GAG AAC CCG CGG GGC ACC ACC AGC AAG ATC    2054
Asn Asn Ser Val Pro Ile Glu Asn Pro Arg Gly Thr Thr Ser Lys Ile
            610                 615                 620

ATG GTT CTG GTC TGG GCC TTC TTT GCT GTC ATC TTC CTC GCC AGA TAC    2102
Met Val Leu Val Trp Ala Phe Phe Ala Val Ile Phe Leu Ala Arg Tyr
        625                 630                 635

ACG GCC AAC CTG GCC GCC TTC ATG ATC CAA GAG CAA TAC ATC GAC ACT    2150
Thr Ala Asn Leu Ala Ala Phe Met Ile Gln Glu Gln Tyr Ile Asp Thr
640                 645                 650

GTG TCG GGC CTC AGT GAC AAG AAG TTT CAG CGG CCT CAA GAT CAG TAC    2198
Val Ser Gly Leu Ser Asp Lys Lys Phe Gln Arg Pro Gln Asp Gln Tyr
655                 660                 665                 670

CCA CCT TTC CGC TTC GGC ACG GTG CCC AAC GGC AGC ACG GAG CGG AAC    2246
Pro Pro Phe Arg Phe Gly Thr Val Pro Asn Gly Ser Thr Glu Arg Asn
                675                 680                 685

ATC CGC AGT AAC TAC CGT GAC ATG CAC ACC CAC ATG GTC AAG TTC AAC    2294
Ile Arg Ser Asn Tyr Arg Asp Met His Thr His Met Val Lys Phe Asn
            690                 695                 700

CAG CGC TCG GTG GAG GAC GCG CTC ACC AGC CTC AAG ATG GGC AAG GAC    2342
Gln Arg Ser Val Glu Asp Ala Leu Thr Ser Leu Lys Met Gly Lys Asp
        705                 710                 715

GAG GGC TGC AAG CTG GTC ACC ATT GGG TCT GGC AAG GTC TTT GCT ACC    2390
Glu Gly Cys Lys Leu Val Thr Ile Gly Ser Gly Lys Val Phe Ala Thr
720                 725                 730

ACT GGC TAC GGC ATC GCC ATG CAG AAG GAC TCC CAC TGG AAG CGG GCC    2438
Thr Gly Tyr Gly Ile Ala Met Gln Lys Asp Ser His Trp Lys Arg Ala
735                 740                 745                 750

ATA GAC CTG GCG CTC TTG CAG TTC CTG GGG GAC GGA GAG ACA CAG AAA    2486
Ile Asp Leu Ala Leu Leu Gln Phe Leu Gly Asp Gly Glu Thr Gln Lys
                755                 760                 765

CTG GAG ACA GTG TGG CTC TCA GGG ATC TGC CAG AAT GAG AAG AAC GAG    2534
Leu Glu Thr Val Trp Leu Ser Gly Ile Cys Gln Asn Glu Lys Asn Glu
            770                 775                 780

GTG ATG AGC AGC AAG CTG GAC ATC GAC AAC ATG GGA GGC GTC TTC TAC    2582
Val Met Ser Ser Lys Leu Asp Ile Asp Asn Met Gly Gly Val Phe Tyr
        785                 790                 795

ATG CTG CTG GTG GCC ATG GGG CTG GCC CTG CTG GTC TTC GCC TGG GAG    2630
Met Leu Leu Val Ala Met Gly Leu Ala Leu Leu Val Phe Ala Trp Glu
800                 805                 810

CAC CTG GTC TAC TGG AAG CTG CGC CAC TCG GTG CCC AAC TCA TCC CAG    2678
His Leu Val Tyr Trp Lys Leu Arg His Ser Val Pro Asn Ser Ser Gln
815                 820                 825                 830

CTG GAC TTC CTG CTG GCT TTC AGC AGG GGC ATC TAC AGC TGC TTC AGC    2726
Leu Asp Phe Leu Leu Ala Phe Ser Arg Gly Ile Tyr Ser Cys Phe Ser
                835                 840                 845

GGG GTG CAG AGC CTC GCC AGC CCA CCG CGG CAG GCC AGC CCG GAC CTC    2774
Gly Val Gln Ser Leu Ala Ser Pro Pro Arg Gln Ala Ser Pro Asp Leu
            850                 855                 860

ACG GCC AGC TCG GCC CAG GCC AGC GTG CTC AAG ATT CTG CAG GCA GCC    2822
Thr Ala Ser Ser Ala Gln Ala Ser Val Leu Lys Ile Leu Gln Ala Ala
        865                 870                 875

CGC GAC ATG GTG ACC ACG GCG GGC GTA AGC AAC TCC CTG GAC CGC GCC    2870
Arg Asp Met Val Thr Thr Ala Gly Val Ser Asn Ser Leu Asp Arg Ala
880                 885                 890
```

```
ACT CGC ACC ATC GAG AAT TGG GGT GGC GGC CGC CGT GCG CCC CCA CCG    2918
Thr Arg Thr Ile Glu Asn Trp Gly Gly Gly Arg Arg Ala Pro Pro Pro
895                 900                 905                 910

TCC CCC TGC CCG ACC CCG CGG TCT GGC CCC AGC CCA TGC CTG CCC ACC    2966
Ser Pro Cys Pro Thr Pro Arg Ser Gly Pro Ser Pro Cys Leu Pro Thr
                915                 920                 925

CCC GAC CCG CCC CCA GAG CCG AGC CCC ACG GGC TGG GGA CCA GAC        3014
Pro Asp Pro Pro Pro Glu Pro Ser Pro Thr Gly Trp Gly Pro Pro Asp
            930                 935                 940

GGG GGT CGC GCG GCG CTT GTG CGC AGG GCT CCG CAG CCC CCG GGC CGC    3062
Gly Gly Arg Ala Ala Leu Val Arg Arg Ala Pro Gln Pro Pro Gly Arg
            945                 950                 955

CCC CCG ACG CCG GGG CCG CCC CTG TCC GAC GTC TCC CGA GTG TCG CGC    3110
Pro Pro Thr Pro Gly Pro Pro Leu Ser Asp Val Ser Arg Val Ser Arg
960                 965                 970

CGC CCA GCC TGG GAG GCG CGG TGG CCG GTG CGG ACC GGG CAC TGC GGG    3158
Arg Pro Ala Trp Glu Ala Arg Trp Pro Val Arg Thr Gly His Cys Gly
975                 980                 985                 990

AGG CAC CTC TCG GCC TCC GAG CGG CCC CTG TCG CCC GCG CGC TGT CAC    3206
Arg His Leu Ser Ala Ser Glu Arg Pro Leu Ser Pro Ala Arg Cys His
                995                 1000                1005

TAC AGC TCC TTT CCT CGA GCC GAC CGA TCC GGC CGC CCC TTC CTC CCG    3254
Tyr Ser Ser Phe Pro Arg Ala Asp Arg Ser Gly Arg Pro Phe Leu Pro
            1010                1015                1020

CTC TTC CCG GAG CCC CCG GAG CTG GAG GAC CTG CCG CTG CTC GGT CCG    3302
Leu Phe Pro Glu Pro Pro Glu Leu Glu Asp Leu Pro Leu Leu Gly Pro
            1025                1030                1035

GAG CAG CTG GCC CGG CGG GAG GCC CTG CTG AAC GCG GCC TGG GCC CGG    3350
Glu Gln Leu Ala Arg Arg Glu Ala Leu Leu Asn Ala Ala Trp Ala Arg
            1040                1045                1050

GGC TCG CGC CCG AGT CAC GCT TCC CTG CCC AGC TCC GTG GCC GAG GCC    3398
Gly Ser Arg Pro Ser His Ala Ser Leu Pro Ser Ser Val Ala Glu Ala
1055                1060                1065                1070

TTC GCT CGG CCC AGC TCG CTG CCC GCT GGG TGC ACC GGC CCC GCC TGC    3446
Phe Ala Arg Pro Ser Ser Leu Pro Ala Gly Cys Thr Gly Pro Ala Cys
                1075                1080                1085

GCC CGC CCC GAC GGC CAC TCG GCC TGC AGG CGC TTG GCG CAG GCG CAG    3494
Ala Arg Pro Asp Gly His Ser Ala Cys Arg Arg Leu Ala Gln Ala Gln
            1090                1095                1100

TCG ATG TGC TTG CCG ATC TAC CGG GAG GCC TGC CAG GAG GGC GAG CAG    3542
Ser Met Cys Leu Pro Ile Tyr Arg Glu Ala Cys Gln Glu Gly Glu Gln
            1105                1110                1115

GCA GGG GCC CCC GCC TGG CAG CAC AGA CAG CAC GTC TGC CTG CAC GCC    3590
Ala Gly Ala Pro Ala Trp Gln His Arg Gln His Val Cys Leu His Ala
    1120                1125                1130

CAC GCC CAC CTG CCA TTG TGC TGG GGG GCT GTC TGT CCT CAC CTT CCA    3638
His Ala His Leu Pro Leu Cys Trp Gly Ala Val Cys Pro His Leu Pro
1135                1140                1145                1150

CCC TGT GAC AGC CAC GGC TCC TGG CTC TCC GGC GCC TGG GGG CCT CTG    3686
Pro Cys Asp Ser His Gly Ser Trp Leu Ser Gly Ala Trp Gly Pro Leu
                1155                1160                1165

GGG CAC AGC GGC AGG ACT CTG GGG CTG GGC ACA GGC TAC AGA GAC AGT    3734
Gly His Ser Gly Arg Thr Leu Gly Leu Gly Thr Gly Tyr Arg Asp Ser
            1170                1175                1180

GGG GGA CTG GAC GAG ATC AGC AGT GTA GCC CGT GGG ACG CAA GGC TTC    3782
Gly Gly Leu Asp Glu Ile Ser Ser Val Ala Arg Gly Thr Gln Gly Phe
            1185                1190                1195

CCG GGA CCC TGC ACC TGG AGA CGG ATC TCC AGT CTG GAG TCA GAA GTG    3830
Pro Gly Pro Cys Thr Trp Arg Arg Ile Ser Ser Leu Glu Ser Glu Val
            1200                1205                1210
```

```
TGAGTTATCA GCCACTCAGG CTCCGAGCCA GCTGGATTCT CTGCCTGCCA CTGTCAGGGT    3890

TAAGCGGCAG GCAGGATTGG CCCTTCTCTG GCTTCTACCA TGAAATCCTG GCCATGGCAC    3950

CCCAGTGACA GATGATGTCT TCCATGGTCA TCAGTGACCT CAGCTAGCCT CA            4002
```

(2) INFORMATION FOR SEQ ID NO:54:

(i) SEQUENCE CHARACTERISTICS:
        (A) LENGTH: 1214 amino acids
        (B) TYPE: amino acid
        (D) TOPOLOGY: linear (ii) MOLECULE TYPE: protein (xi) SEQUENCE DESCRIPTION: SEQ ID NO:54:

```
Met Gly Gly Ala Leu Gly Pro Ala Leu Leu Thr Ser Leu Phe Gly
  1               5                  10                  15

Ala Trp Ala Gly Leu Gly Pro Gly Gln Gly Glu Gln Gly Met Thr Val
                 20                  25                  30

Ala Val Val Phe Ser Ser Gly Pro Pro Gln Ala Gln Phe Arg Val
             35                  40                  45

Arg Leu Thr Pro Gln Ser Phe Leu Asp Leu Pro Leu Glu Ile Gln Pro
     50                  55                  60

Leu Thr Val Gly Val Asn Thr Thr Asn Pro Ser Ser Leu Leu Thr Gln
 65                  70                  75                  80

Ile Cys Gly Leu Leu Gly Ala Ala His Val His Gly Ile Val Phe Glu
                 85                  90                  95

Asp Asn Val Asp Thr Glu Ala Val Ala Gln Ile Leu Asp Phe Ile Ser
                100                 105                 110

Ser Gln Thr His Val Pro Ile Leu Ser Ile Ser Gly Gly Ser Ala Val
            115                 120                 125

Val Leu Thr Pro Lys Glu Pro Gly Ser Ala Phe Leu Gln Leu Gly Val
        130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
        195                 200                 205

Arg Ala Arg Thr Gln Arg Leu Leu Arg Gln Leu Asp Ala Pro Val Phe
    210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
        275                 280                 285

Val Arg Asp Gly Val Ala Ile Leu Ala Leu Gly Ala His Ser Tyr Trp
    290                 295                 300

Arg Gln His Gly Thr Leu Pro Ala Pro Ala Gly Asp Cys Arg Val His
305                 310                 315                 320
```

-continued

```
Pro Gly Pro Val Ser Pro Ala Arg Glu Ala Phe Tyr Arg His Leu Leu
            325                 330                 335

Asn Val Thr Trp Glu Gly Arg Asp Phe Ser Phe Ser Pro Gly Gly Tyr
            340                 345                 350

Leu Val Gln Pro Thr Met Val Ile Ala Leu Asn Arg His Arg Leu
            355                 360                 365

Trp Glu Met Val Gly Arg Trp Glu His Gly Val Leu Tyr Met Lys Tyr
370                 375                 380

Pro Val Trp Pro Arg Tyr Ser Ala Ser Leu Gln Pro Val Val Asp Ser
385                 390                 395                 400

Arg His Leu Thr Val Ala Thr Leu Glu Glu Arg Pro Phe Val Ile Val
            405                 410                 415

Glu Ser Pro Asp Pro Gly Thr Gly Gly Cys Val Pro Asn Thr Val Pro
            420                 425                 430

Cys Arg Arg Gln Ser Asn His Thr Phe Ser Ser Gly Asp Val Ala Pro
            435                 440                 445

Tyr Thr Lys Leu Cys Cys Lys Gly Phe Cys Ile Asp Ile Leu Lys Lys
            450                 455                 460

Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
            485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
            515                 520                 525

Thr Gly Ile Ser Val Met Val Ala Arg Ser Asn Gly Thr Val Ser Pro
            530                 535                 540

Ser Ala Phe Leu Glu Pro Tyr Ser Pro Ala Val Trp Val Met Met Phe
545                 550                 555                 560

Val Met Cys Leu Thr Val Val Ala Ile Thr Val Phe Met Phe Glu Tyr
            565                 570                 575

Phe Ser Pro Val Ser Tyr Asn Gln Asn Leu Thr Arg Gly Lys Thr Phe
            580                 585                 590

Thr Ile Gly Lys Ser Val Trp Leu Leu Trp Ala Leu Val Phe Asn Asn
            595                 600                 605

Ser Val Pro Ile Glu Asn Pro Arg Gly Thr Thr Ser Lys Ile Met Val
            610                 615                 620

Leu Val Trp Ala Phe Phe Ala Val Ile Phe Leu Ala Arg Tyr Thr Ala
625                 630                 635                 640

Asn Leu Ala Ala Phe Met Ile Gln Glu Gln Tyr Ile Asp Thr Val Ser
            645                 650                 655

Gly Leu Ser Asp Lys Lys Phe Gln Arg Pro Gln Asp Gln Tyr Pro Pro
            660                 665                 670

Phe Arg Phe Gly Thr Val Pro Asn Gly Ser Thr Glu Arg Asn Ile Arg
            675                 680                 685

Ser Asn Tyr Arg Asp Met His Thr His Met Val Lys Phe Asn Gln Arg
            690                 695                 700

Ser Val Glu Asp Ala Leu Thr Ser Leu Lys Met Gly Lys Asp Glu Gly
705                 710                 715                 720

Cys Lys Leu Val Thr Ile Gly Ser Gly Lys Val Phe Ala Thr Thr Gly
            725                 730                 735

Tyr Gly Ile Ala Met Gln Lys Asp Ser His Trp Lys Arg Ala Ile Asp
```

```
                    740              745              750
Leu Ala Leu Leu Gln Phe Leu Gly Asp Gly Glu Thr Gln Lys Leu Glu
                755              760              765

Thr Val Trp Leu Ser Gly Ile Cys Gln Asn Glu Lys Asn Glu Val Met
770              775              780

Ser Ser Lys Leu Asp Ile Asp Asn Met Gly Val Phe Tyr Met Leu
785              790              795              800

Leu Val Ala Met Gly Leu Ala Leu Leu Val Phe Ala Trp Glu His Leu
                805              810              815

Val Tyr Trp Lys Leu Arg His Ser Val Pro Asn Ser Ser Gln Leu Asp
                820              825              830

Phe Leu Leu Ala Phe Ser Arg Gly Ile Tyr Ser Cys Phe Ser Gly Val
                835              840              845

Gln Ser Leu Ala Ser Pro Pro Arg Gln Ala Ser Pro Asp Leu Thr Ala
    850              855              860

Ser Ser Ala Gln Ala Ser Val Leu Lys Ile Leu Gln Ala Ala Arg Asp
865              870              875              880

Met Val Thr Thr Ala Gly Val Ser Asn Ser Leu Asp Arg Ala Thr Arg
                885              890              895

Thr Ile Glu Asn Trp Gly Gly Gly Arg Arg Ala Pro Pro Ser Pro
                900              905              910

Cys Pro Thr Pro Arg Ser Gly Pro Ser Pro Cys Leu Pro Thr Pro Asp
                915              920              925

Pro Pro Pro Glu Pro Ser Pro Thr Gly Trp Gly Pro Pro Asp Gly Gly
    930              935              940

Arg Ala Ala Leu Val Arg Arg Ala Pro Gln Pro Pro Gly Arg Pro Pro
945              950              955              960

Thr Pro Gly Pro Pro Leu Ser Asp Val Ser Arg Val Ser Arg Arg Pro
                965              970              975

Ala Trp Glu Ala Arg Trp Pro Val Arg Thr Gly His Cys Gly Arg His
                980              985              990

Leu Ser Ala Ser Glu Arg Pro Leu Ser Pro Ala Arg Cys His Tyr Ser
                995              1000             1005

Ser Phe Pro Arg Ala Asp Arg Ser Gly Arg Pro Phe Leu Pro Leu Phe
    1010             1015             1020

Pro Glu Pro Pro Glu Leu Glu Asp Leu Pro Leu Leu Gly Pro Glu Gln
1025             1030             1035             1040

Leu Ala Arg Arg Glu Ala Leu Leu Asn Ala Ala Trp Ala Arg Gly Ser
                1045             1050             1055

Arg Pro Ser His Ala Ser Leu Pro Ser Ser Val Ala Glu Ala Phe Ala
                1060             1065             1070

Arg Pro Ser Ser Leu Pro Ala Gly Cys Thr Gly Pro Ala Cys Ala Arg
                1075             1080             1085

Pro Asp Gly His Ser Ala Cys Arg Arg Leu Ala Gln Ala Gln Ser Met
    1090             1095             1100

Cys Leu Pro Ile Tyr Arg Glu Ala Cys Gln Glu Gly Glu Gln Ala Gly
1105             1110             1115             1120

Ala Pro Ala Trp Gln His Arg Gln His Val Cys Leu His Ala His Ala
                1125             1130             1135

His Leu Pro Leu Cys Trp Gly Ala Val Cys Pro His Leu Pro Pro Cys
                1140             1145             1150

Asp Ser His Gly Ser Trp Leu Ser Gly Ala Trp Gly Pro Leu Gly His
    1155             1160             1165
```

```
Ser Gly Arg Thr Leu Gly Leu Gly Thr Gly Tyr Arg Asp Ser Gly Gly
    1170            1175                1180

Leu Asp Glu Ile Ser Ser Val Ala Arg Gly Thr Gln Gly Phe Pro Gly
1185            1190                1195                1200

Pro Cys Thr Trp Arg Arg Ile Ser Ser Leu Glu Ser Glu Val
                1205                1210

(2) INFORMATION FOR SEQ ID NO:55:

(i) SEQUENCE CHARACTERISTICS:
        (A) LENGTH: 5538 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 210..4664

(xi) SEQUENCE DESCRIPTION: SEQ ID NO:55:

TTGAATTTGC ATCTCTTCAA GACACAAGAT TAAAACAAAA TTTACGCTAA ATTGGATTTT     60

AAATTATCTT CCGTTCATTT ATCCTTCGTC TTTCTTATGT GGATATGCAA GCAGAAGAA    120

GGGACTGGAC ATTCCCAACA TGCTCACTCC CTTAATCTGT CCGTCTAGAG GTTTGGCTTC   180

TACAAACCAA GGGAGTCGAC GAGTTGAAG ATG AAG CCC AGA GCG GAG TGC TGT     233
                                Met Lys Pro Arg Ala Glu Cys Cys
                                  1               5

TCT CCC AAG TTC TGG TTG GTG TTG GCC GTC CTG GCC GTG TCA GGC AGC    281
Ser Pro Lys Phe Trp Leu Val Leu Ala Val Leu Ala Val Ser Gly Ser
     10              15                  20

AGA GCT CGT TCT CAG AAG AGC CCC CCC AGC ATT GGC ATT GCT GTC ATC    329
Arg Ala Arg Ser Gln Lys Ser Pro Pro Ser Ile Gly Ile Ala Val Ile
 25              30                  35                  40

CTC GTG GGC ACT TCC GAC GAG GTG GCC ATC AAG GAT GCC CAC GAG AAA    377
Leu Val Gly Thr Ser Asp Glu Val Ala Ile Lys Asp Ala His Glu Lys
             45                  50                  55

GAT GAT TTC CAC CAT CTC TCC GTG GTA CCC CGG GTG GAA CTG GTA GCC    425
Asp Asp Phe His His Leu Ser Val Val Pro Arg Val Glu Leu Val Ala
         60                  65                  70

ATG AAT GAG ACC GAC CCA AAG AGC ATC ATC ACC CGC ATC TGT GAT CTC    473
Met Asn Glu Thr Asp Pro Lys Ser Ile Ile Thr Arg Ile Cys Asp Leu
     75                  80                  85

ATG TCT GAC CGG AAG ATC CAG GGG GTG GTG TTT GCT GAT GAC ACA GAC    521
Met Ser Asp Arg Lys Ile Gln Gly Val Val Phe Ala Asp Asp Thr Asp
 90                  95                  100

CAG GAA GCC ATC GCC CAG ATC CTC GAT TTC ATT TCA GCA CAG ACT CTC    569
Gln Glu Ala Ile Ala Gln Ile Leu Asp Phe Ile Ser Ala Gln Thr Leu
105                 110                 115                 120

ACC CCG ATC CTG GGC ATC CAC GGG GGC TCC TCT ATG ATA ATG GCA GAT    617
Thr Pro Ile Leu Gly Ile His Gly Gly Ser Ser Met Ile Met Ala Asp
             125                 130                 135

AAG GAT GAA TCC TCC ATG TTC TTC CAG TTT GGC CCA TCA ATT GAA CAG    665
Lys Asp Glu Ser Ser Met Phe Phe Gln Phe Gly Pro Ser Ile Glu Gln
         140                 145                 150

CAA GCT TCC GTA ATG CTC AAC ATC ATG GAA GAA TAT GAC TGG TAC ATC    713
Gln Ala Ser Val Met Leu Asn Ile Met Glu Glu Tyr Asp Trp Tyr Ile
     155                 160                 165

TTT TCT ATC GTC ACC ACC TAT TTC CCT GGC TAC CAG GAC TTT GTA AAC    761
Phe Ser Ile Val Thr Thr Tyr Phe Pro Gly Tyr Gln Asp Phe Val Asn
```

```
           170                 175                 180
AAG ATC CGC AGC ACC ATT GAG AAT AGC TTT GTG GGC TGG GAG CTA GAG    809
Lys Ile Arg Ser Thr Ile Glu Asn Ser Phe Val Gly Trp Glu Leu Glu
185                 190                 195                 200

GAG GTC CTC CTA CTG GAC ATG TCC CTG GAC GAT GGA GAT TCT AAG ATC    857
Glu Val Leu Leu Leu Asp Met Ser Leu Asp Asp Gly Asp Ser Lys Ile
                205                 210                 215

CAG AAT CAG CTC AAG AAA CTT CAA AGC CCC ATC ATT CTT CTT TAC TGT    905
Gln Asn Gln Leu Lys Lys Leu Gln Ser Pro Ile Ile Leu Leu Tyr Cys
                220                 225                 230

ACC AAG GAA GAA GCC ACC TAC ATC TTT GAA GTG GCC AAC TCA GTA GGG    953
Thr Lys Glu Glu Ala Thr Tyr Ile Phe Glu Val Ala Asn Ser Val Gly
                235                 240                 245

CTG ACT GGC TAT GGC TAC ACG TGG ATC GTG CCC AGT CTG GTG GCA GGG   1001
Leu Thr Gly Tyr Gly Tyr Thr Trp Ile Val Pro Ser Leu Val Ala Gly
    250                 255                 260

GAT ACA GAC ACA GTG CCT GCG GAG TTC CCC ACT GGG CTC ATC TCT GTA   1049
Asp Thr Asp Thr Val Pro Ala Glu Phe Pro Thr Gly Leu Ile Ser Val
265                 270                 275                 280

TCA TAT GAT GAA TGG GAC TAT GGC CTC CCC CCC AGA GTG AGA GAT GGA   1097
Ser Tyr Asp Glu Trp Asp Tyr Gly Leu Pro Pro Arg Val Arg Asp Gly
                285                 290                 295

ATT GCC ATA ATC ACC ACT GCT GCT TCT GAC ATG CTG TCT GAG CAC AGC   1145
Ile Ala Ile Ile Thr Thr Ala Ala Ser Asp Met Leu Ser Glu His Ser
                300                 305                 310

TTC ATC CCT GAG CCC AAA AGC AGT TGT TAC AAC ACC CAC GAG AAG AGA   1193
Phe Ile Pro Glu Pro Lys Ser Ser Cys Tyr Asn Thr His Glu Lys Arg
                315                 320                 325

ATC TAC CAG TCC AAT ATG CTA AAT AGG TAT CTG ATC AAT GTC ACT TTT   1241
Ile Tyr Gln Ser Asn Met Leu Asn Arg Tyr Leu Ile Asn Val Thr Phe
330                 335                 340

GAG GGG AGG AAT TTG TCC TTC AGT GAA GAT GGC TAC CAG ATG CAC CCG   1289
Glu Gly Arg Asn Leu Ser Phe Ser Glu Asp Gly Tyr Gln Met His Pro
345                 350                 355                 360

AAA CTG GTG ATA ATT CTT CTG AAC AAG GAG AGG AAG TGG GAA AGG GTG   1337
Lys Leu Val Ile Ile Leu Leu Asn Lys Glu Arg Lys Trp Glu Arg Val
                365                 370                 375

GGG AAG TGG AAA GAC AAG TCC CTG CAG ATG AAG TAC TAT GTG TGG CCC   1385
Gly Lys Trp Lys Asp Lys Ser Leu Gln Met Lys Tyr Tyr Val Trp Pro
                380                 385                 390

CGA ATG TGT CCA GAG ACT GAA GAG CAG GAG GAT GAC CAT CTG AGC ATT   1433
Arg Met Cys Pro Glu Thr Glu Glu Gln Glu Asp Asp His Leu Ser Ile
                395                 400                 405

GTG ACC CTG GAG GAG GCA CCA TTT GTC ATT GTG GAA AGT GTG GAC CCT   1481
Val Thr Leu Glu Glu Ala Pro Phe Val Ile Val Glu Ser Val Asp Pro
    410                 415                 420

CTG AGT GGA ACC TGC ATG AGG AAC ACA GTC CCC TGC CAA AAA CGC ATA   1529
Leu Ser Gly Thr Cys Met Arg Asn Thr Val Pro Cys Gln Lys Arg Ile
425                 430                 435                 440

GTC ACT GAG AAT AAA ACA GAC GAG GAG CCG GGT TAC ATC AAA AAA TGC   1577
Val Thr Glu Asn Lys Thr Asp Glu Glu Pro Gly Tyr Ile Lys Lys Cys
                445                 450                 455

TGC AAG GGG TTC TGT ATT GAC ATC CTT AAG AAA ATT TCT AAA TCT GTG   1625
Cys Lys Gly Phe Cys Ile Asp Ile Leu Lys Lys Ile Ser Lys Ser Val
                460                 465                 470

AAG TTC ACC TAT GAC CTT TAC CTG GTT ACC AAT GGC AAG CAT GGG AAG   1673
Lys Phe Thr Tyr Asp Leu Tyr Leu Val Thr Asn Gly Lys His Gly Lys
                475                 480                 485

AAA ATC AAT GGA ACC TGG AAT GGT ATG ATT GGA GAG GTG GTC ATG AAG   1721
```

-continued

```
Lys Ile Asn Gly Thr Trp Asn Gly Met Ile Gly Glu Val Val Met Lys
        490             495             500

AGG GCC TAC ATG GCA GTG GGC TCA CTC ACC ATC AAT GAG GAA CGA TCG      1769
Arg Ala Tyr Met Ala Val Gly Ser Leu Thr Ile Asn Glu Glu Arg Ser
505             510             515             520

GAG GTG GTC GAC TTC TCT GTG CCC TTC ATA GAG ACA GGC ATC AGT GTC      1817
Glu Val Val Asp Phe Ser Val Pro Phe Ile Glu Thr Gly Ile Ser Val
                525             530             535

ATG GTG TCA CGC AGC AAT GGG ACT GTC TCA CCT TCT GCC TTC TTA GAG      1865
Met Val Ser Arg Ser Asn Gly Thr Val Ser Pro Ser Ala Phe Leu Glu
            540             545             550

CCA TTC AGC GCT GAC GTA TGG GTG ATG ATG TTT GTG ATG CTG CTC ATC      1913
Pro Phe Ser Ala Asp Val Trp Val Met Met Phe Val Met Leu Leu Ile
        555             560             565

GTC TCA GCC GTG GCT GTC TTT GTC TTT GAG TAC TTC AGC CCT GTG GGT      1961
Val Ser Ala Val Ala Val Phe Val Phe Glu Tyr Phe Ser Pro Val Gly
570             575             580

TAT AAC AGG TGC CTC GCT GAT GGC AGA GAG CCT GGT GGA CCC TCT TTC      2009
Tyr Asn Arg Cys Leu Ala Asp Gly Arg Glu Pro Gly Gly Pro Ser Phe
585             590             595             600

ACC ATC GGC AAA GCT ATT TGG TTG CTC TGG GGT CTG GTG TTT AAC AAC      2057
Thr Ile Gly Lys Ala Ile Trp Leu Leu Trp Gly Leu Val Phe Asn Asn
                605             610             615

TCC GTA CCT GTG CAG AAC CCA AAG GGG ACC ACC TCC AAG ATC ATG GTG      2105
Ser Val Pro Val Gln Asn Pro Lys Gly Thr Thr Ser Lys Ile Met Val
            620             625             630

TCA GTG TGG GCC TTC TTT GCT GTC ATC TTC CTG GCC AGC TAC ACT GCC      2153
Ser Val Trp Ala Phe Phe Ala Val Ile Phe Leu Ala Ser Tyr Thr Ala
        635             640             645

AAC TTA GCT GCC TTC ATG ATC CAA GAG GAA TAT GTG GAC CAG GTT TCT      2201
Asn Leu Ala Ala Phe Met Ile Gln Glu Glu Tyr Val Asp Gln Val Ser
650             655             660

GGC CTG AGC GAC AAA AAG TTC CAG AGA CCT AAT GAC TTC TCA CCC CCT      2249
Gly Leu Ser Asp Lys Lys Phe Gln Arg Pro Asn Asp Phe Ser Pro Pro
665             670             675             680

TTC CGC TTT GGG ACC GTG CCC AAC GGC AGC ACA GAG AGA AAT ATT CGC      2297
Phe Arg Phe Gly Thr Val Pro Asn Gly Ser Thr Glu Arg Asn Ile Arg
                685             690             695

AAT AAC TAT GCA GAA ATG CAT GCC TAC ATG GGA AAG TTC AAC CAG AGG      2345
Asn Asn Tyr Ala Glu Met His Ala Tyr Met Gly Lys Phe Asn Gln Arg
            700             705             710

GGT GTA GAT GAT GCA TTG CTC TCC CTG AAA ACA GGG AAA CTG GAT GCC      2393
Gly Val Asp Asp Ala Leu Leu Ser Leu Lys Thr Gly Lys Leu Asp Ala
        715             720             725

TTC ATC TAT GAT GCA GCA GTG CTG AAC TAT ATG GCA GGC AGA GAT GAA      2441
Phe Ile Tyr Asp Ala Ala Val Leu Asn Tyr Met Ala Gly Arg Asp Glu
730             735             740

GGC TGC AAG CTG GTG ACC ATT GGC AGT GGG AAG GTC TTT GCT TCC ACT      2489
Gly Cys Lys Leu Val Thr Ile Gly Ser Gly Lys Val Phe Ala Ser Thr
745             750             755             760

GGC TAT GGC ATT GCC ATC CAA AAA GAT TCT GGG TGG AAG CGC CAG GTG      2537
Gly Tyr Gly Ile Ala Ile Gln Lys Asp Ser Gly Trp Lys Arg Gln Val
                765             770             775

GAC CTT GCT ATC CTG CAG CTC TTT GGA GAT GGG GAG ATG GAA GAA CTG      2585
Asp Leu Ala Ile Leu Gln Leu Phe Gly Asp Gly Glu Met Glu Glu Leu
            780             785             790

GAA GCT CTC TGG CTC ACT GGC ATT TGT CAC AAT GAG AAG AAT GAG GTC      2633
Glu Ala Leu Trp Leu Thr Gly Ile Cys His Asn Glu Lys Asn Glu Val
        795             800             805
```

```
ATG AGC AGC CAG CTG GAC ATT GAC AAC ATG GCA GGG GTC TTC TAC ATG     2681
Met Ser Ser Gln Leu Asp Ile Asp Asn Met Ala Gly Val Phe Tyr Met
    810                 815                 820

TTG GGG GCG GCC ATG GCT CTC AGC CTC ATC ACC TTC ATC TGC GAA CAC     2729
Leu Gly Ala Ala Met Ala Leu Ser Leu Ile Thr Phe Ile Cys Glu His
825                 830                 835                 840

CTT TTC TAT TGG CAG TTC CGA CAT TGC TTT ATG GGT GTC TGT TCT GGC     2777
Leu Phe Tyr Trp Gln Phe Arg His Cys Phe Met Gly Val Cys Ser Gly
                845                 850                 855

AAG CCT GGC ATG GTC TTC TCC ATC AGC AGA GGT ATC TAC AGC TGC ATC     2825
Lys Pro Gly Met Val Phe Ser Ile Ser Arg Gly Ile Tyr Ser Cys Ile
            860                 865                 870

CAT GGG GTG GCG ATC GAG GAG CGC CAG TCT GTA ATG AAC TCC CCC ACC     2873
His Gly Val Ala Ile Glu Glu Arg Gln Ser Val Met Asn Ser Pro Thr
        875                 880                 885

GCA ACC ATG AAC AAC ACA CAC TCC AAC ATC CTG CGC CTG CTG CGC ACG     2921
Ala Thr Met Asn Asn Thr His Ser Asn Ile Leu Arg Leu Leu Arg Thr
    890                 895                 900

GCC AAG AAC ATG GCT AAC CTG TCT GGT GTG AAT GGC TCA CCG CAG AGC     2969
Ala Lys Asn Met Ala Asn Leu Ser Gly Val Asn Gly Ser Pro Gln Ser
905                 910                 915                 920

GCC CTG GAC TTC ATC CGA CGG GAG TCA TCC GTC TAT GAC ATC TCA GAG     3017
Ala Leu Asp Phe Ile Arg Arg Glu Ser Ser Val Tyr Asp Ile Ser Glu
                925                 930                 935

CAC CGC CGC AGC TTC ACG CAT TCT GAC TGC AAA TCC TAC AAC AAC CCG     3065
His Arg Arg Ser Phe Thr His Ser Asp Cys Lys Ser Tyr Asn Asn Pro
            940                 945                 950

CCC TGT GAG GAG AAC CTC TTC AGT GAC TAC ATC AGT GAG GTA GAG AGA     3113
Pro Cys Glu Glu Asn Leu Phe Ser Asp Tyr Ile Ser Glu Val Glu Arg
        955                 960                 965

ACG TTC GGG AAC CTG CAG CTG AAG GAC AGC AAC GTG TAC CAA GAT CAC     3161
Thr Phe Gly Asn Leu Gln Leu Lys Asp Ser Asn Val Tyr Gln Asp His
    970                 975                 980

TAC CAC CAT CAC CAC CGG CCC CAT AGT ATT GGC AGT GCC AGC TCC ATC     3209
Tyr His His His His Arg Pro His Ser Ile Gly Ser Ala Ser Ser Ile
985                 990                 995                 1000

GAT GGG CTC TAC GAC TGT GAC AAC CCA CCC TTC ACC ACC CAG TCC AGG     3257
Asp Gly Leu Tyr Asp Cys Asp Asn Pro Pro Phe Thr Thr Gln Ser Arg
                1005                1010                1015

TCC ATC AGC AAG AAG CCC CTG GAC ATC GGC CTC CCC TCC TCC AAG CAC     3305
Ser Ile Ser Lys Lys Pro Leu Asp Ile Gly Leu Pro Ser Ser Lys His
            1020                1025                1030

AGC CAG CTC AGT GAC CTG TAC GGC AAA TTC TCC TTC AAG AGC GAC CGC     3353
Ser Gln Leu Ser Asp Leu Tyr Gly Lys Phe Ser Phe Lys Ser Asp Arg
        1035                1040                1045

TAC AGT GGC CAC GAC GAC TTG ATC CGC TCC GAT GTC TCT GAC ATC TCA     3401
Tyr Ser Gly His Asp Asp Leu Ile Arg Ser Asp Val Ser Asp Ile Ser
    1050                1055                1060

ACC CAC ACC GTC ACC TAT GGG AAC ATC GAG GGC AAT GCC GCC AAG AGG     3449
Thr His Thr Val Thr Tyr Gly Asn Ile Glu Gly Asn Ala Ala Lys Arg
1065                1070                1075                1080

CGT AAG CAG CAA TAT AAG GAC AGC CTG AAG AAG CGG CCT GCC TCG GCC     3497
Arg Lys Gln Gln Tyr Lys Asp Ser Leu Lys Lys Arg Pro Ala Ser Ala
                1085                1090                1095

AAG TCC CGC AGG GAG TTT GAC GAG ATC GAG CTG GCC TAC CGT GCC CGA     3545
Lys Ser Arg Arg Glu Phe Asp Glu Ile Glu Leu Ala Tyr Arg Ala Arg
            1100                1105                1110

CCG CCC CGC TCC CCT GAC CAC AAG CGC TAC TTC AGG GAC AAG GAA GGG     3593
Pro Pro Arg Ser Pro Asp His Lys Arg Tyr Phe Arg Asp Lys Glu Gly
        1115                1120                1125
```

```
CTA CGG GAC TTC TAC CTG GAC CAG TTC CGA ACA AAG GAG AAC TCA CCC      3641
Leu Arg Asp Phe Tyr Leu Asp Gln Phe Arg Thr Lys Glu Asn Ser Pro
    1130                1135                1140

CAC TGG GAG CAC GTA GAC CTG ACC GAC ATC TAC AAG GAG CGG AGT GAT      3689
His Trp Glu His Val Asp Leu Thr Asp Ile Tyr Lys Glu Arg Ser Asp
1145                1150                1155                1160

GAC TTT AAG CGC GAC TCC ATC AGC GGA GGA GGG CCC TGT ACC AAC AGG      3737
Asp Phe Lys Arg Asp Ser Ile Ser Gly Gly Gly Pro Cys Thr Asn Arg
                1165                1170                1175

TCT CAC ATC AAG CAC GGG ACG GGC GAC AAA CAC GGC GTG GTC AGC GGG      3785
Ser His Ile Lys His Gly Thr Gly Asp Lys His Gly Val Val Ser Gly
            1180                1185                1190

GTA CCT GCA CCT TGG GAG AAG AAC CTG ACC AAC GTG GAG TGG GAG GAC      3833
Val Pro Ala Pro Trp Glu Lys Asn Leu Thr Asn Val Glu Trp Glu Asp
        1195                1200                1205

CGG TCC GGG GGC AAC TTC TGC CGC AGC TGT CCC TCC AAG CTG CAC AAC      3881
Arg Ser Gly Gly Asn Phe Cys Arg Ser Cys Pro Ser Lys Leu His Asn
    1210                1215                1220

TAC TCC ACG ACG GTG ACG GGT CAG AAC TCG GGC AGG CAG GCG TGC ATC      3929
Tyr Ser Thr Thr Val Thr Gly Gln Asn Ser Gly Arg Gln Ala Cys Ile
1225                1230                1235                1240

CGG TGT GAG GCT TGC AAG AAA GCA GGC AAC CTG TAT GAC ATC AGT GAG      3977
Arg Cys Glu Ala Cys Lys Lys Ala Gly Asn Leu Tyr Asp Ile Ser Glu
                1245                1250                1255

GAC AAC TCC CTG CAG GAA CTG GAC CAG CCG GCT GCC CCA GTG GCG GTG      4025
Asp Asn Ser Leu Gln Glu Leu Asp Gln Pro Ala Ala Pro Val Ala Val
            1260                1265                1270

ACG TCA AAC GCC TCC ACC ACT AAG TAC CCT CAG AGC CCG ACT AAT TCC      4073
Thr Ser Asn Ala Ser Thr Thr Lys Tyr Pro Gln Ser Pro Thr Asn Ser
        1275                1280                1285

AAG GCC CAG AAG AAG AAC CGG AAC AAA CTG CGC CGG CAG CAC TCC TAC      4121
Lys Ala Gln Lys Lys Asn Arg Asn Lys Leu Arg Arg Gln His Ser Tyr
    1290                1295                1300

GAC ACC TTC GTG GAC CTG CAG AAG GAA GAA GCC GCC CTG GCC CCG CGC      4169
Asp Thr Phe Val Asp Leu Gln Lys Glu Glu Ala Ala Leu Ala Pro Arg
1305                1310                1315                1320

AGC GTA AGC CTG AAA GAC AAG GGC CGA TTC ATG GAT GGG AGC CCC TAC      4217
Ser Val Ser Leu Lys Asp Lys Gly Arg Phe Met Asp Gly Ser Pro Tyr
                1325                1330                1335

GCC CAC ATG TTT GAG ATG TCA GCT GGC GAG AGC ACC TTT GCC AAC AAC      4265
Ala His Met Phe Glu Met Ser Ala Gly Glu Ser Thr Phe Ala Asn Asn
            1340                1345                1350

AAG TCC TCA GTG CCC ACT GCC GGA CAT CAC CAC CAC AAC AAC CCC GGC      4313
Lys Ser Ser Val Pro Thr Ala Gly His His His His Asn Asn Pro Gly
        1355                1360                1365

GGC GGG TAC ATG CTC AGC AAG TCG CTC TAC CCT GAC CGG GTC ACG CAA      4361
Gly Gly Tyr Met Leu Ser Lys Ser Leu Tyr Pro Asp Arg Val Thr Gln
    1370                1375                1380

AAC CCT TTC ATC CCC ACT TTT GGG GAC GAC CAG TGC TTG CTC CAT GGC      4409
Asn Pro Phe Ile Pro Thr Phe Gly Asp Asp Gln Cys Leu Leu His Gly
1385                1390                1395                1400

AGC AAA TCC TAC TTC TTC AGG CAG CCC ACG GTG GCG GGG GCG TCG AAA      4457
Ser Lys Ser Tyr Phe Phe Arg Gln Pro Thr Val Ala Gly Ala Ser Lys
                1405                1410                1415

GCC AGG CCG GAC TTC CGG GCC CTT GTC ACC AAC AAG CCG GTG GTC TCG      4505
Ala Arg Pro Asp Phe Arg Ala Leu Val Thr Asn Lys Pro Val Val Ser
            1420                1425                1430

GCC CTT CAT GGG GCC GTG CCA GCC CGT TTC CAG AAG GAC ATC TGT ATA      4553
Ala Leu His Gly Ala Val Pro Ala Arg Phe Gln Lys Asp Ile Cys Ile
```

```
                    1435                1440                  1445
GGG AAC CAG TCC AAC CCC TGT GTG CCT AAC AAC ACA AAC CCC AGG GCT       4601
Gly Asn Gln Ser Asn Pro Cys Val Pro Asn Asn Thr Asn Pro Arg Ala
            1450                1455                1460

TTC AAT GGC TCC AGC AAT GGG CAT GTT TAT GAG AAA CTT TCT AGT ATT       4649
Phe Asn Gly Ser Ser Asn Gly His Val Tyr Glu Lys Leu Ser Ser Ile
1465                1470                1475                1480

GAG TCT GAT GTC TGAGTGAGGG AACAGAGAGG TTAAGGTGGG TACGGGAGGG           4701
Glu Ser Asp Val
            148

TAAGGCTGTG GGTCGCGTGA TGCGCATGTC ACGGAGGGTG ACGGGGTGA ACTTGGTTCC      4761

CATTTGCTCC TTTCTTGTTT TAATTTATTT ATGGGATCCT GGAGTTCTGG TTCCTACTGG    4821

GGGCAACCCT GGTGACCAGC ACCATCTCTC CTCCTTTTCA CAGTTCTCTC CTTCTTCCCC    4881

CCGCTGTCAG CCATTCCTGT TCCCATGAGA TGATGCCATG GGCCCTCTCA GCAGGGGAGG    4941

GTAGAGCGGA GAAAGGAAGG GCTGCATGCG GGCTTCCTCC TGGTGTGGAA GAGCTCCTTG    5001

ATATCCTCTT TGAGTGAAGC TGGGAGAACC AAAAAGAGGC TATGTGAGCA CAAAGGTAGC    5061

TTTTCCCAAA CTGATCTTTT CATTTAGGTG AGGAAGCAAA AGCATCTATG TGAGACCATT    5121

TAGCACACTG CTTGTGAAAG GAAAGAGGCT CTGGCTAAAT TCATGCTGCT TAGATGACAT    5181

CTGTCTAGGA ATCATGTGCC AAGCAGAGGT TGGGAGGCCA TTTGTGTTTA TATATAAGCC    5241

CAAAAATGCT TGCTTCAACC CCATGAGACT CGATAGTGGT GGTGAACAGA ACCCAAGGTC    5301

ATTGGTGGCA GAGTGGATTC TTGAACAAAC TGGAAAGTAC GTTATGATAG TGTCCCCCGG    5361

TGCCTTGGGG ACAAGAGCAG GTGGATTGTG CGTGCATGTG TGTTCATGCA CACTTGCACC    5421

CATGTGTAGT CAGGTGCCTC AAGAGAAGGC AACCTTGACT CTTTCGTTGA ATTTGCATCT    5481

CTTCAAGACA CAAGATTAAA ACAAAATTTA CGCTAAATTG GATTTTAAAT TATCTTC      5538

(2) INFORMATION FOR SEQ ID NO:56:

(i) SEQUENCE CHARACTERISTICS:
        (A) LENGTH: 1484 amino acids
        (B) TYPE: amino acid
        (D) TOPOLOGY: linear (ii) MOLECULE TYPE: protein (xi) SEQUENCE DESCRIPTION: SEQ ID NO:56:

Met Lys Pro Arg Ala Glu Cys Cys Ser Pro Lys Phe Trp Leu Val Leu
  1               5                  10                  15

Ala Val Leu Ala Val Ser Gly Ser Arg Ala Arg Ser Gln Lys Ser Pro
                 20                  25                  30

Pro Ser Ile Gly Ile Ala Val Ile Leu Val Gly Thr Ser Asp Glu Val
             35                  40                  45

Ala Ile Lys Asp Ala His Glu Lys Asp Phe His His Leu Ser Val
         50                  55                  60

Val Pro Arg Val Glu Leu Val Ala Met Asn Glu Thr Asp Pro Lys Ser
 65                  70                  75                  80

Ile Ile Thr Arg Ile Cys Asp Leu Met Ser Asp Arg Lys Ile Gln Gly
                 85                  90                  95

Val Val Phe Ala Asp Asp Thr Asp Gln Glu Ala Ile Ala Gln Ile Leu
                100                 105                 110

Asp Phe Ile Ser Ala Gln Thr Leu Thr Pro Ile Leu Gly Ile His Gly
            115                 120                 125

Gly Ser Ser Met Ile Met Ala Asp Lys Asp Glu Ser Ser Met Phe Phe
```

-continued

```
            130                 135                 140
Gln Phe Gly Pro Ser Ile Glu Gln Gln Ala Ser Val Met Leu Asn Ile
145                 150                 155                 160

Met Glu Glu Tyr Asp Trp Tyr Ile Phe Ser Ile Val Thr Thr Tyr Phe
                165                 170                 175

Pro Gly Tyr Gln Asp Phe Val Asn Lys Ile Arg Ser Thr Ile Glu Asn
                180                 185                 190

Ser Phe Val Gly Trp Glu Leu Glu Glu Val Leu Leu Leu Asp Met Ser
                195                 200                 205

Leu Asp Asp Gly Asp Ser Lys Ile Gln Asn Gln Leu Lys Lys Leu Gln
                210                 215                 220

Ser Pro Ile Ile Leu Leu Tyr Cys Thr Lys Glu Glu Ala Thr Tyr Ile
225                 230                 235                 240

Phe Glu Val Ala Asn Ser Val Gly Leu Thr Gly Tyr Gly Tyr Thr Trp
                245                 250                 255

Ile Val Pro Ser Leu Val Ala Gly Asp Thr Asp Thr Val Pro Ala Glu
                260                 265                 270

Phe Pro Thr Gly Leu Ile Ser Val Ser Tyr Asp Glu Trp Asp Tyr Gly
                275                 280                 285

Leu Pro Pro Arg Val Arg Asp Gly Ile Ala Ile Thr Thr Ala Ala
                290                 295                 300

Ser Asp Met Leu Ser Glu His Ser Phe Ile Pro Glu Pro Lys Ser Ser
305                 310                 315                 320

Cys Tyr Asn Thr His Glu Lys Arg Ile Tyr Gln Ser Asn Met Leu Asn
                325                 330                 335

Arg Tyr Leu Ile Asn Val Thr Phe Glu Gly Arg Asn Leu Ser Phe Ser
                340                 345                 350

Glu Asp Gly Tyr Gln Met His Pro Lys Leu Val Ile Ile Leu Leu Asn
                355                 360                 365

Lys Glu Arg Lys Trp Glu Arg Val Gly Lys Trp Lys Asp Lys Ser Leu
                370                 375                 380

Gln Met Lys Tyr Tyr Val Trp Pro Arg Met Cys Pro Glu Thr Glu Glu
385                 390                 395                 400

Gln Glu Asp Asp His Leu Ser Ile Val Thr Leu Glu Glu Ala Pro Phe
                405                 410                 415

Val Ile Val Glu Ser Val Asp Pro Leu Ser Gly Thr Cys Met Arg Asn
                420                 425                 430

Thr Val Pro Cys Gln Lys Arg Ile Val Thr Glu Asn Lys Thr Asp Glu
                435                 440                 445

Glu Pro Gly Tyr Ile Lys Lys Cys Cys Lys Gly Phe Cys Ile Asp Ile
                450                 455                 460

Leu Lys Lys Ile Ser Lys Ser Val Lys Phe Thr Tyr Asp Leu Tyr Leu
465                 470                 475                 480

Val Thr Asn Gly Lys His Gly Lys Lys Ile Asn Gly Thr Trp Asn Gly
                485                 490                 495

Met Ile Gly Glu Val Val Met Lys Arg Ala Tyr Met Ala Val Gly Ser
                500                 505                 510

Leu Thr Ile Asn Glu Glu Arg Ser Glu Val Val Asp Phe Ser Val Pro
                515                 520                 525

Phe Ile Glu Thr Gly Ile Ser Val Met Val Ser Arg Ser Asn Gly Thr
                530                 535                 540

Val Ser Pro Ser Ala Phe Leu Glu Pro Phe Ser Ala Asp Val Trp Val
545                 550                 555                 560
```

-continued

```
Met Met Phe Val Met Leu Leu Ile Val Ser Ala Val Ala Val Phe Val
            565                 570                 575

Phe Glu Tyr Phe Ser Pro Val Gly Tyr Asn Arg Cys Leu Ala Asp Gly
            580                 585                 590

Arg Glu Pro Gly Gly Pro Ser Phe Thr Ile Gly Lys Ala Ile Trp Leu
            595                 600                 605

Leu Trp Gly Leu Val Phe Asn Asn Ser Val Pro Val Gln Asn Pro Lys
            610                 615                 620

Gly Thr Thr Ser Lys Ile Met Val Ser Val Trp Ala Phe Phe Ala Val
625                 630                 635                 640

Ile Phe Leu Ala Ser Tyr Thr Ala Asn Leu Ala Ala Phe Met Ile Gln
            645                 650                 655

Glu Glu Tyr Val Asp Gln Val Ser Gly Leu Ser Asp Lys Lys Phe Gln
            660                 665                 670

Arg Pro Asn Asp Phe Ser Pro Pro Phe Arg Phe Gly Thr Val Pro Asn
            675                 680                 685

Gly Ser Thr Glu Arg Asn Ile Arg Asn Asn Tyr Ala Glu Met His Ala
            690                 695                 700

Tyr Met Gly Lys Phe Asn Gln Arg Gly Val Asp Asp Ala Leu Leu Ser
705                 710                 715                 720

Leu Lys Thr Gly Lys Leu Asp Ala Phe Ile Tyr Asp Ala Ala Val Leu
            725                 730                 735

Asn Tyr Met Ala Gly Arg Asp Glu Gly Cys Lys Leu Val Thr Ile Gly
            740                 745                 750

Ser Gly Lys Val Phe Ala Ser Thr Gly Tyr Gly Ile Ala Ile Gln Lys
            755                 760                 765

Asp Ser Gly Trp Lys Arg Gln Val Asp Leu Ala Ile Leu Gln Leu Phe
            770                 775                 780

Gly Asp Gly Glu Met Glu Leu Glu Ala Leu Trp Leu Thr Gly Ile
785                 790                 795                 800

Cys His Asn Glu Lys Asn Glu Val Met Ser Ser Gln Leu Asp Ile Asp
            805                 810                 815

Asn Met Ala Gly Val Phe Tyr Met Leu Gly Ala Ala Met Ala Leu Ser
            820                 825                 830

Leu Ile Thr Phe Ile Cys Glu His Leu Phe Tyr Trp Gln Phe Arg His
            835                 840                 845

Cys Phe Met Gly Val Cys Ser Gly Lys Pro Gly Met Val Phe Ser Ile
            850                 855                 860

Ser Arg Gly Ile Tyr Ser Cys Ile His Gly Val Ala Ile Glu Glu Arg
865                 870                 875                 880

Gln Ser Val Met Asn Ser Pro Thr Ala Thr Met Asn Asn Thr His Ser
            885                 890                 895

Asn Ile Leu Arg Leu Leu Arg Thr Ala Lys Asn Met Ala Asn Leu Ser
            900                 905                 910

Gly Val Asn Gly Ser Pro Gln Ser Ala Leu Asp Phe Ile Arg Arg Glu
            915                 920                 925

Ser Ser Val Tyr Asp Ile Ser Glu His Arg Arg Ser Phe Thr His Ser
            930                 935                 940

Asp Cys Lys Ser Tyr Asn Asn Pro Pro Cys Glu Glu Asn Leu Phe Ser
945                 950                 955                 960

Asp Tyr Ile Ser Glu Val Glu Arg Thr Phe Gly Asn Leu Gln Leu Lys
            965                 970                 975
```

-continued

```
Asp Ser Asn Val Tyr Gln Asp His Tyr His His His Arg Pro His
            980                 985                 990
Ser Ile Gly Ser Ala Ser Ser Ile Asp Gly Leu Tyr Asp Cys Asp Asn
            995                1000                1005
Pro Pro Phe Thr Thr Gln Ser Arg Ser Ile Ser Lys Lys Pro Leu Asp
       1010                1015                1020
Ile Gly Leu Pro Ser Ser Lys His Ser Gln Leu Ser Asp Leu Tyr Gly
1025                1030                1035                1040
Lys Phe Ser Phe Lys Ser Asp Arg Tyr Ser Gly His Asp Asp Leu Ile
                1045                1050                1055
Arg Ser Asp Val Ser Asp Ile Ser Thr His Thr Val Thr Tyr Gly Asn
            1060                1065                1070
Ile Glu Gly Asn Ala Ala Lys Arg Arg Lys Gln Gln Tyr Lys Asp Ser
            1075                1080                1085
Leu Lys Lys Arg Pro Ala Ser Ala Lys Ser Arg Arg Glu Phe Asp Glu
            1090                1095                1100
Ile Glu Leu Ala Tyr Arg Arg Arg Pro Pro Arg Ser Pro Asp His Lys
1105                1110                1115                1120
Arg Tyr Phe Arg Asp Lys Glu Gly Leu Arg Asp Phe Tyr Leu Asp Gln
                1125                1130                1135
Phe Arg Thr Lys Glu Asn Ser Pro His Trp Glu His Val Asp Leu Thr
            1140                1145                1150
Asp Ile Tyr Lys Glu Arg Ser Asp Asp Phe Lys Arg Asp Ser Ile Ser
            1155                1160                1165
Gly Gly Gly Pro Cys Thr Asn Arg Ser His Ile Lys His Gly Thr Gly
            1170                1175                1180
Asp Lys His Gly Val Val Ser Gly Val Pro Ala Pro Trp Glu Lys Asn
1185                1190                1195                1200
Leu Thr Asn Val Glu Trp Glu Asp Arg Ser Gly Gly Asn Phe Cys Arg
                1205                1210                1215
Ser Cys Pro Ser Lys Leu His Asn Tyr Ser Thr Thr Val Thr Gly Gln
            1220                1225                1230
Asn Ser Gly Arg Gln Ala Cys Ile Arg Cys Glu Ala Cys Lys Lys Ala
            1235                1240                1245
Gly Asn Leu Tyr Asp Ile Ser Glu Asp Asn Ser Leu Gln Glu Leu Asp
            1250                1255                1260
Gln Pro Ala Ala Pro Val Ala Val Thr Ser Asn Ala Ser Thr Thr Lys
1265                1270                1275                1280
Tyr Pro Gln Ser Pro Thr Asn Ser Lys Ala Gln Lys Lys Asn Arg Asn
                1285                1290                1295
Lys Leu Arg Arg Gln His Ser Tyr Asp Thr Phe Val Asp Leu Gln Lys
            1300                1305                1310
Glu Glu Ala Ala Leu Ala Pro Arg Ser Val Ser Leu Lys Asp Lys Gly
            1315                1320                1325
Arg Phe Met Asp Gly Ser Pro Tyr Ala His Met Phe Glu Met Ser Ala
            1330                1335                1340
Gly Glu Ser Thr Phe Ala Asn Asn Lys Ser Ser Val Pro Thr Ala Gly
1345                1350                1355                1360
His His His His Asn Asn Pro Gly Gly Gly Tyr Met Leu Ser Lys Ser
                1365                1370                1375
Leu Tyr Pro Asp Arg Val Thr Gln Asn Pro Phe Ile Pro Thr Phe Gly
            1380                1385                1390
Asp Asp Gln Cys Leu Leu His Gly Ser Lys Ser Tyr Phe Phe Arg Gln
```

-continued

```
             1395                1400                  1405
     Pro Thr Val Ala Gly Ala Ser Lys Ala Arg Pro Asp Phe Arg Ala Leu
              1410                1415                1420

Val Thr Asn Lys Pro Val Val Ser Ala Leu His Gly Ala Val Pro Ala
     1425                1430                1435                1440

Arg Phe Gln Lys Asp Ile Cys Ile Gly Asn Gln Ser Asn Pro Cys Val
                   1445                1450                1455

Pro Asn Asn Thr Asn Pro Arg Ala Phe Asn Gly Ser Ser Asn Gly His
                   1460                1465                1470

Val Tyr Glu Lys Leu Ser Ser Ile Glu Ser Asp Val
                   1475                1480
```

(2) INFORMATION FOR SEQ ID NO:57:

- (i) SEQUENCE CHARACTERISTICS:
  - (A) LENGTH: 4695 base pairs
  - (B) TYPE: nucleic acid
  - (C) STRANDEDNESS: both
  - (D) TOPOLOGY: both

- (ii) MOLECULE TYPE: cDNA

- (ix) FEATURE:
  - (A) NAME/KEY: CDS
  - (B) LOCATION: 485..4495

- (xi) SEQUENCE DESCRIPTION: SEQ ID NO:57:

```
CGAGAACACA GCGAGTGTGT GAGTCCCTCC CGCTCCAGCT CCTCCAAGCC GCGGCCGCCG      60

CCGCCACCCT CGCCCGCAGC CTCCCGCAGC CTCCCTCGGC CACCGGTGTC TGGTGGGGGT     120

GTTGCCTGGG TAGGTCGGCC CGGCCCCCAG GGGTCTCTCG AGCGTCTGCC ATCTGCCCGA     180

GAAACATGTG TGGCCACGTC CTCGCCTAGT CCAGGTGGCC GCAACCTTGG GGGAGAGACA     240

GGGCAGGACA GGACCAAGGT AAGAGGTAAG GAGGAGACGG CGCCAGGGAC AGACAGGAGG     300

TCCCGGCTTG CCGTTGTGCG CACCACCACT GCCGCCGCCC CGGGGCCTGC CCCCGACATC     360

GGCTCTCTGA GCCCTCCTCG GAATCTTGGG GTCGCTGGAC GCCGGGTTCC GGTCCTGGCC     420

CCCCCGCCAT CCCCCCAACA GAACAGGGTC ATGAAAAGAG GCCGCCCGGC GGGGCCCGCA     480

GGCG ATG CGC GGC GCC GGT GGC CCC CGC GGC CCT CGG GGC CCC GCT AAG      529
     Met Arg Gly Ala Gly Gly Pro Arg Gly Pro Arg Gly Pro Ala Lys
     1               5                  10                  15

ATG CTG CTG CTG CTG GCG CTG GCC TGC GCC AGC CCG TTC CCG GAG GAG      577
Met Leu Leu Leu Leu Ala Leu Ala Cys Ala Ser Pro Phe Pro Glu Glu
             20                  25                  30

GCG CCG GGG CCG GGC GGG GCC GGT GGG CCC GGC GGC GGC CTC GGC GGG      625
Ala Pro Gly Pro Gly Gly Ala Gly Gly Pro Gly Gly Gly Leu Gly Gly
             35                  40                  45

GCG CGG CCG CTC AAC GTG GCG CTC GTG TTC TCG GGG CCC GCG TAC GCG      673
Ala Arg Pro Leu Asn Val Ala Leu Val Phe Ser Gly Pro Ala Tyr Ala
         50                  55                  60

GCC GAG GCG GCA CGC CTG GGC CCG GCC GTG GCG GCG GCG GTG CGC AGC      721
Ala Glu Ala Ala Arg Leu Gly Pro Ala Val Ala Ala Ala Val Arg Ser
     65                  70                  75

CCG GGC CTA GAC GTG CGG CCC GTG GCG CTG GTG CTC AAC GGC TCG GAC      769
Pro Gly Leu Asp Val Arg Pro Val Ala Leu Val Leu Asn Gly Ser Asp
80                  85                  90                  95

CCG CGC AGC CTC GTG CTG CAG CTC TGC GAC CTG CTG TCG GGG TTG CGC      817
Pro Arg Ser Leu Val Leu Gln Leu Cys Asp Leu Leu Ser Gly Leu Arg
                 100                 105                 110

GTG CAC GGC GTG GTC TTC GAA GAC GAC TCG CGC GCG CCC GCC GTC GCG      865
```

```
                    Val His Gly Val Val Phe Glu Asp Asp Ser Arg Ala Pro Ala Val Ala
                            115                 120                 125

CCC ATC CTC GAC TTC CTG TCG GCG CAG ACC TCG CTC CCC ATC GTG TCC        913
Pro Ile Leu Asp Phe Leu Ser Ala Gln Thr Ser Leu Pro Ile Val Ser
        130                 135                 140

GAG CAC GGC GGC GCC GCG CTC GTG CTC ACG CCC AAG GAG AAG GGC TCC        961
Glu His Gly Gly Ala Ala Leu Val Leu Thr Pro Lys Glu Lys Gly Ser
145                 150                 155

ACC TTC CTC CAC CTG GGC TCT TCC CCC GAG CAA CAG CTT CAG GTC ATC       1009
Thr Phe Leu His Leu Gly Ser Ser Pro Glu Gln Gln Leu Gln Val Ile
160                 165                 170                 175

TTT GAG GTG CTG GAG GAG TAT GAC TGG ACG TCC TTT GTA GCC GTG ACC       1057
Phe Glu Val Leu Glu Glu Tyr Asp Trp Thr Ser Phe Val Ala Val Thr
            180                 185                 190

ACT CGT GCC CCT GGC CAC CGG GCC TTC CTG TCC TAC ATT GAG GTG CTG       1105
Thr Arg Ala Pro Gly His Arg Ala Phe Leu Ser Tyr Ile Glu Val Leu
                195                 200                 205

ACT GAC GGC AGT CTG GTG GGC TGG GAG CAC CGC GGA GCG CTG ACG CTG       1153
Thr Asp Gly Ser Leu Val Gly Trp Glu His Arg Gly Ala Leu Thr Leu
            210                 215                 220

GAC CCT GGG GCG GGC GAG GCC GTG CTC AGT GCC CAG CTC CGC AGT GTC       1201
Asp Pro Gly Ala Gly Glu Ala Val Leu Ser Ala Gln Leu Arg Ser Val
225                 230                 235

AGC GCG CAG ATC CGC CTG CTC TTC TGC GCC CGA GAG GAG GCC GAG CCC       1249
Ser Ala Gln Ile Arg Leu Leu Phe Cys Ala Arg Glu Glu Ala Glu Pro
240                 245                 250                 255

GTG TTC CGC GCA GCT GAG GAG GCT GGC CTC ACT GGA TCT GGC TAC GTC       1297
Val Phe Arg Ala Ala Glu Glu Ala Gly Leu Thr Gly Ser Gly Tyr Val
                260                 265                 270

TGG TTC ATG GTG GGG CCC CAG CTG GCT GGA GGC GGG GGC TCT GGG GCC       1345
Trp Phe Met Val Gly Pro Gln Leu Ala Gly Gly Gly Ser Gly Ala
            275                 280                 285

CCT GGT GAG CCC CCT CTT CTG CCA GGA GGC GCC CCC CTG CCT GCC GGG       1393
Pro Gly Glu Pro Pro Leu Leu Pro Gly Gly Ala Pro Leu Pro Ala Gly
        290                 295                 300

CTG TTT GCA GTG CGC TCG GCT GGC TGG CGG GAT GAC CTG GCT CGG CGA       1441
Leu Phe Ala Val Arg Ser Ala Gly Trp Arg Asp Asp Leu Ala Arg Arg
    305                 310                 315

GTG GCA GCT GGC GTG GCC GTA GTG GCC AGA GGT GCC CAG GCC CTG CTG       1489
Val Ala Ala Gly Val Ala Val Val Ala Arg Gly Ala Gln Ala Leu Leu
320                 325                 330                 335

CGT GAT TAT GGT TTC CTT CCT GAG CTC GGC CAC GAC TGT CGC GCC CAG       1537
Arg Asp Tyr Gly Phe Leu Pro Glu Leu Gly His Asp Cys Arg Ala Gln
                340                 345                 350

AAC CGC ACC CAC CGC GGG GAG AGT CTG CAT AGG TAC TTC ATG AAC ATC       1585
Asn Arg Thr His Arg Gly Glu Ser Leu His Arg Tyr Phe Met Asn Ile
            355                 360                 365

ACG TGG GAT AAC CGG GAT TAC TCC TTC AAT GAG GAC GGC TTC CTA GTG       1633
Thr Trp Asp Asn Arg Asp Tyr Ser Phe Asn Glu Asp Gly Phe Leu Val
        370                 375                 380

AAC CCC TCC CTG GTG GTC ATC TCC CTC ACC AGA GAC AGG ACG TGG GAG       1681
Asn Pro Ser Leu Val Val Ile Ser Leu Thr Arg Asp Arg Thr Trp Glu
385                 390                 395

GTG GTG GGC AGC TGG GAG CAG CAG ACG CTC CGC CTC AAG TAC CCG CTG       1729
Val Val Gly Ser Trp Glu Gln Gln Thr Leu Arg Leu Lys Tyr Pro Leu
400                 405                 410                 415

TGG TCC CGC TAT GGT CGC TTC CTG CAG CCA GTG GAC GAC ACG CAG CAC       1777
Trp Ser Arg Tyr Gly Arg Phe Leu Gln Pro Val Asp Asp Thr Gln His
                420                 425                 430
```

-continued

```
CTC GCG GTG GCC ACG CTG GAG GAA AGG CCG TTT GTC ATC GTG GAG CCT    1825
Leu Ala Val Ala Thr Leu Glu Glu Arg Pro Phe Val Ile Val Glu Pro
            435                 440                 445

GCA GAC CCT ATC AGC GGC ACC TGC ATC CGA GAC TCC GTC CCC TGC CGG    1873
Ala Asp Pro Ile Ser Gly Thr Cys Ile Arg Asp Ser Val Pro Cys Arg
        450                 455                 460

AGC CAG CTC AAC CGA ACC CAC AGC CCT CCA CCG GAT GCC CCC CGC CCG    1921
Ser Gln Leu Asn Arg Thr His Ser Pro Pro Pro Asp Ala Pro Arg Pro
    465                 470                 475

GAA AAG CGC TGC TGC AAG GGT TTC TGC ATC GAC ATT CTG AAG CGG CTG    1969
Glu Lys Arg Cys Cys Lys Gly Phe Cys Ile Asp Ile Leu Lys Arg Leu
480                 485                 490                 495

GCG CAT ACC ATC GGC TTC AGC TAC GAC CTC TAC CTG GTC ACC AAT GGC    2017
Ala His Thr Ile Gly Phe Ser Tyr Asp Leu Tyr Leu Val Thr Asn Gly
                500                 505                 510

AAG CAC GGA AAG AAG ATC GAT GGC GTC TGG AAC GGC ATG ATC GGG GAG    2065
Lys His Gly Lys Lys Ile Asp Gly Val Trp Asn Gly Met Ile Gly Glu
            515                 520                 525

GTG TTC TAC CAG CGC GCA GAC ATG GCC ATC GGC TCC CTC ACC ATC AAC    2113
Val Phe Tyr Gln Arg Ala Asp Met Ala Ile Gly Ser Leu Thr Ile Asn
        530                 535                 540

GAG GAG CGC TCC GAG ATC GTG GAC TTC TCC GTC CCC TTC GTG GAG ACC    2161
Glu Glu Arg Ser Glu Ile Val Asp Phe Ser Val Pro Phe Val Glu Thr
    545                 550                 555

GGC ATC AGC GTC ATG GTG GCG CGC AGC AAT GGC ACG GTG TCC CCC TCG    2209
Gly Ile Ser Val Met Val Ala Arg Ser Asn Gly Thr Val Ser Pro Ser
560                 565                 570                 575

GCC TTC CTC GAG CCC TAC AGC CCC GCC GTG TGG GTG ATG ATG TTC GTC    2257
Ala Phe Leu Glu Pro Tyr Ser Pro Ala Val Trp Val Met Met Phe Val
                580                 585                 590

ATG TGC CTC ACT GTG GTC GCC GTC ACT GTT TTC ATC TTC GAG TAC CTC    2305
Met Cys Leu Thr Val Val Ala Val Thr Val Phe Ile Phe Glu Tyr Leu
            595                 600                 605

AGT CCT GTT GGT TAC AAC CGC AGC CTG GCC ACG GGC AAG CGC CCT GGC    2353
Ser Pro Val Gly Tyr Asn Arg Ser Leu Ala Thr Gly Lys Arg Pro Gly
        610                 615                 620

GGT TCA ACC TTC ACC ATT GGG AAA TCC ATC TGG CTG CTC TGG GCC CTG    2401
Gly Ser Thr Phe Thr Ile Gly Lys Ser Ile Trp Leu Leu Trp Ala Leu
    625                 630                 635

GTG TTC AAT AAT TCG GTG CCC GTG GAG AAC CCC CGG GGA ACC ACC AGC    2449
Val Phe Asn Asn Ser Val Pro Val Glu Asn Pro Arg Gly Thr Thr Ser
640                 645                 650                 655

AAA ATC ATG GTG CTG GTG TGG GCC TTC TTC GCC GTC ATC TTC CTC GCC    2497
Lys Ile Met Val Leu Val Trp Ala Phe Phe Ala Val Ile Phe Leu Ala
                660                 665                 670

AGC TAC ACA GCC AAC CTG GCC GCC TTC ATG ATC CAG GAG GAG TAC GTG    2545
Ser Tyr Thr Ala Asn Leu Ala Ala Phe Met Ile Gln Glu Glu Tyr Val
            675                 680                 685

GAT ACT GTG TCT GGG CTC AGT GAC CGC AAG TTC CAG AGG CCC CAG GAG    2593
Asp Thr Val Ser Gly Leu Ser Asp Arg Lys Phe Gln Arg Pro Gln Glu
        690                 695                 700

CAG TAC CCG CCC CTG AAG TTT GGG ACC GTG CCC AAC GGC TCC ACG GAG    2641
Gln Tyr Pro Pro Leu Lys Phe Gly Thr Val Pro Asn Gly Ser Thr Glu
    705                 710                 715

AAG AAC ATC CGC AGC AAC TAT CCC GAC ATG CAC AGC TAC ATG GTG CGC    2689
Lys Asn Ile Arg Ser Asn Tyr Pro Asp Met His Ser Tyr Met Val Arg
720                 725                 730                 735

TAC AAC CAG CCC CGC GTA GAG GAA GCG CTC ACT CAG CTC AAG GCA GGG    2737
Tyr Asn Gln Pro Arg Val Glu Glu Ala Leu Thr Gln Leu Lys Ala Gly
                740                 745                 750
```

-continued

```
AAG CTG GAC GCC TTC ATC TAC GAT GCT GCA GTG CTC AAT TAC ATG GCC    2785
Lys Leu Asp Ala Phe Ile Tyr Asp Ala Ala Val Leu Asn Tyr Met Ala
            755                 760                 765

CGC AAG GAC GAG GGC TGC AAG CTT GTC ACC ATC GGC TCC GGC AAG GTC    2833
Arg Lys Asp Glu Gly Cys Lys Leu Val Thr Ile Gly Ser Gly Lys Val
            770                 775                 780

TTC GCC ACG ACA GGC TAT GGC ATC GCC CTG CAC AAG GGC TCC CGC TGG    2881
Phe Ala Thr Thr Gly Tyr Gly Ile Ala Leu His Lys Gly Ser Arg Trp
    785                 790                 795

AAG CGG CCC ATC GAC CTG GCG TTG CTG CAG TTC CTG GGG GAT GAT GAG    2929
Lys Arg Pro Ile Asp Leu Ala Leu Leu Gln Phe Leu Gly Asp Asp Glu
800                 805                 810                 815

ATC GAG ATG CTG GAG CGG CTG TGG CTC TCT GGG ATC TGC CAC AAT GAC    2977
Ile Glu Met Leu Glu Arg Leu Trp Leu Ser Gly Ile Cys His Asn Asp
                820                 825                 830

AAA ATC GAG GTG ATG AGC AGC AAG CTG GAC ATC GAC AAC ATG GCG GGC    3025
Lys Ile Glu Val Met Ser Ser Lys Leu Asp Ile Asp Asn Met Ala Gly
            835                 840                 845

GTC TTC TAC ATG CTC CTG GTG GCC ATG GGC CTG TCC CTG CTG GTC TTC    3073
Val Phe Tyr Met Leu Leu Val Ala Met Gly Leu Ser Leu Leu Val Phe
            850                 855                 860

GCC TGG GAG CAC CTG GTG TAC TGG CGC CTG CGG CAC TGC CTG GGG CCC    3121
Ala Trp Glu His Leu Val Tyr Trp Arg Leu Arg His Cys Leu Gly Pro
    865                 870                 875

ACC CAC CGC ATG GAC TTC CTG CTG GCC TTC TCC AGG GGC ATG TAC AGC    3169
Thr His Arg Met Asp Phe Leu Leu Ala Phe Ser Arg Gly Met Tyr Ser
880                 885                 890                 895

TGC TGC AGC GCT GAG GCC GCC CCA CCG CCC GCC AAG CCC CCG CCG CCG    3217
Cys Cys Ser Ala Glu Ala Ala Pro Pro Pro Ala Lys Pro Pro Pro Pro
                900                 905                 910

CCA CAG CCC CTG CCC AGC CCC GCG TAC CCC GCG CCG GGG CCG GCT CCC    3265
Pro Gln Pro Leu Pro Ser Pro Ala Tyr Pro Ala Pro Gly Pro Ala Pro
            915                 920                 925

GGG CCC GCA CCT TTC GTC CCC CGC GAG CGC GCC TCA GTG GCC CGC TGG    3313
Gly Pro Ala Pro Phe Val Pro Arg Glu Arg Ala Ser Val Ala Arg Trp
            930                 935                 940

CGC CGG CCC AAG GGC GCG GGG CCG CCG GGG GGC GCG GGC CTG GCC GAC    3361
Arg Arg Pro Lys Gly Ala Gly Pro Pro Gly Gly Ala Gly Leu Ala Asp
945                 950                 955

GGC TTC CAC CGC TAC TAC GGC CCC ATC GAG CCG CAG GGC CTA GGC CTC    3409
Gly Phe His Arg Tyr Tyr Gly Pro Ile Glu Pro Gln Gly Leu Gly Leu
960                 965                 970                 975

GGC CTG GGC GAA GCG CGC GCG GCA CCG CGG GGC GCA GCC GGG CGC CCG    3457
Gly Leu Gly Glu Ala Arg Ala Ala Pro Arg Gly Ala Ala Gly Arg Pro
                980                 985                 990

CTG TCC CCG CCG GCC GCT CAG CCC CCG CAG AAG CCG CCG GCC TCC TAT    3505
Leu Ser Pro Pro Ala Ala Gln Pro Pro Gln Lys Pro Pro Ala Ser Tyr
            995                 1000                1005

TTC GCC ATC GTA CGC GAC AAG GAG CCA GCC GAG CCC CCC GCC GGC GCC    3553
Phe Ala Ile Val Arg Asp Lys Glu Pro Ala Glu Pro Pro Ala Gly Ala
            1010                1015                1020

TTC CCC GGC TTC CCG TCC CCG CCC GCG CCC CCC GCC GCC GCG GCC ACC    3601
Phe Pro Gly Phe Pro Ser Pro Pro Ala Pro Pro Ala Ala Ala Ala Thr
    1025                1030                1035

GCC GTC GGG CCG CCA CTC TGC CGC TTG GCC TTC GAG GAC GAG AGC CCG    3649
Ala Val Gly Pro Pro Leu Cys Arg Leu Ala Phe Glu Asp Glu Ser Pro
1040                1045                1050                1055

CCG GCG CCC GCG CGG TGG CCG CGC TCG GAC CCC GAG AGC CAA CCC CTG    3697
Pro Ala Pro Ala Arg Trp Pro Arg Ser Asp Pro Glu Ser Gln Pro Leu
```

```
                1060            1065           1070
CTG GGG CCA GGC GCG GGC GGC GCG GGG GGC ACG GGG GGC GCA GGC GGA        3745
Leu Gly Pro Gly Ala Gly Gly Ala Gly Gly Thr Gly Gly Ala Gly Gly
            1075            1080           1085

GGA GCC CCG GCC GCT CCG CCC CCG TGC TTC GCC GCG CCG CCC CCG TGC        3793
Gly Ala Pro Ala Ala Pro Pro Pro Cys Phe Ala Ala Pro Pro Pro Cys
            1090            1095           1100

TTT TAC CTC GAT GTC GAC CAG TCG CCG TCG GAC TCG GAG GAC TCG GAG        3841
Phe Tyr Leu Asp Val Asp Gln Ser Pro Ser Asp Ser Glu Asp Ser Glu
            1105            1110           1115

AGC CTG GCC GGC GCG TCC CTG GCC GGC CTG GAT CCC TGG TGG TTC GCC        3889
Ser Leu Ala Gly Ala Ser Leu Ala Gly Leu Asp Pro Trp Trp Phe Ala
1120            1125            1130           1135

GAC TTC CCT TAC CCG TAT GCC GAT CGC CTC GGG CSG CCC GCG GCA CGC        3937
Asp Phe Pro Tyr Pro Tyr Ala Asp Arg Leu Gly Xaa Pro Ala Ala Arg
            1140            1145           1150

TAC GGA TTG GTC GAC AAA CTA GGG GGC TGG CTC GCC GGG AGC TGG GAC        3985
Tyr Gly Leu Val Asp Lys Leu Gly Gly Trp Leu Ala Gly Ser Trp Asp
            1155            1160           1165

TAC CTG CCT CCS CGC AGC GGT CGG GCC GCC TGG CAC TGT CGG CAC TGC        4033
Tyr Leu Pro Xaa Arg Ser Gly Arg Ala Ala Trp His Cys Arg His Cys
            1170            1175           1180

GCC AGC CTG GAG CTG CTT CCG CCG CCG CGC CAT CTC AGC TGC TCG CAC        4081
Ala Ser Leu Glu Leu Leu Pro Pro Pro Arg His Leu Ser Cys Ser His
            1185            1190           1195

GAT GGC CTG GAC GGC GGC TGG TGG GCG CCA CCG CCT CCA CCC TGG GCC        4129
Asp Gly Leu Asp Gly Gly Trp Trp Ala Pro Pro Pro Pro Pro Trp Ala
1200            1205            1210           1215

GCC GGG CCC CTG CCC CGA CGC CGG GCC CGC TGC GGG TGC CCG CGG TCG        4177
Ala Gly Pro Leu Pro Arg Arg Arg Ala Arg Cys Gly Cys Pro Arg Ser
            1220            1225           1230

CAC CCG CAC CGC CCG CGG GCC TCG CAC CGC ACG CCC GCC GCT GCC GCG        4225
His Pro His Arg Pro Arg Ala Ser His Arg Thr Pro Ala Ala Ala Ala
            1235            1240           1245

CCC CAC CAC CAC AGG CAC CGG CGC GCC GCT GGG GGC TGG GAC CTC CCG        4273
Pro His His His Arg His Arg Arg Ala Ala Gly Gly Trp Asp Leu Pro
            1250            1255           1260

CCG CCC GCG CCC ACC TCG CGC TCG CTC GAG GAC CTC AGC TCG TGC CCT        4321
Pro Pro Ala Pro Thr Ser Arg Ser Leu Glu Asp Leu Ser Ser Cys Pro
            1265            1270           1275

CGC GCC GCC CCT GCG CGC AGG CTT ACC GGG CCC TCC CGC CAC GCT CGC        4369
Arg Ala Ala Pro Ala Arg Arg Leu Thr Gly Pro Ser Arg His Ala Arg
1280            1285            1290           1295

AGG TGT CCG CAC GCC GCG CAC TGG GGG CCG CCG CTG CCT ACA GCT TCC        4417
Arg Cys Pro His Ala Ala His Trp Gly Pro Pro Leu Pro Thr Ala Ser
            1300            1305           1310

CAC CGG AGA CAC CGG GGC GGG GAC CTG GGC ACC CGC AGG GGC TCG GCG        4465
His Arg Arg His Arg Gly Gly Asp Leu Gly Thr Arg Arg Gly Ser Ala
            1315            1320           1325

CAC TTC TCT AGC CTC GAG TCC GAG GTA TGACGCGGCC CCGGGGGCCC            4512
His Phe Ser Ser Leu Glu Ser Glu Val
            1330            1335

CACCGCCCCC TTGGTCAGCG CAGGCCACGG CCCGAGGGGG CGCCCGCAGT GGACAGGACC     4572

CGCGTGGGTT GGGAAGGAAA GCAGTGGAAC TGGCCGGACC CCGCCTGGAG CAGCGTCCTG     4632

CGCCCCCTGG TTCTGGAGGA ACCGCAAGCC GGAGAGGATT TGGTCCCTCA ACTATCACCC     4692

AGG                                                                  4695
```

-continued (2) INFORMATION FOR SEQ ID NO:58:

(i) SEQUENCE CHARACTERISTICS:
        (A) LENGTH: 1336 amino acids
        (B) TYPE: amino acid
        (D) TOPOLOGY: linear (ii) MOLECULE TYPE: protein (xi) SEQUENCE DESCRIPTION: SEQ ID NO:58:

```
Met Arg Gly Ala Gly Gly Pro Arg Gly Pro Arg Gly Pro Ala Lys Met
  1               5                  10                  15

Leu Leu Leu Leu Ala Leu Ala Cys Ala Ser Pro Phe Pro Glu Glu Ala
                 20                  25                  30

Pro Gly Pro Gly Gly Ala Gly Gly Pro Gly Gly Leu Gly Gly Ala
             35                  40                  45

Arg Pro Leu Asn Val Ala Leu Val Phe Ser Gly Pro Ala Tyr Ala Ala
         50                  55                  60

Glu Ala Ala Arg Leu Gly Pro Ala Val Ala Ala Val Arg Ser Pro
 65                  70                  75                  80

Gly Leu Asp Val Arg Pro Val Ala Leu Val Leu Asn Gly Ser Asp Pro
                 85                  90                  95

Arg Ser Leu Val Leu Gln Leu Cys Asp Leu Leu Ser Gly Leu Arg Val
                100                 105                 110

His Gly Val Val Phe Glu Asp Asp Ser Arg Ala Pro Ala Val Ala Pro
            115                 120                 125

Ile Leu Asp Phe Leu Ser Ala Gln Thr Ser Leu Pro Ile Val Ser Glu
130                 135                 140

His Gly Gly Ala Ala Leu Val Leu Thr Pro Lys Glu Lys Gly Ser Thr
145                 150                 155                 160

Phe Leu His Leu Gly Ser Ser Pro Glu Gln Gln Leu Gln Val Ile Phe
                165                 170                 175

Glu Val Leu Glu Glu Tyr Asp Trp Thr Ser Phe Val Ala Val Thr Thr
                180                 185                 190

Arg Ala Pro Gly His Arg Ala Phe Leu Ser Tyr Ile Glu Val Leu Thr
            195                 200                 205

Asp Gly Ser Leu Val Gly Trp Glu His Arg Gly Ala Leu Thr Leu Asp
210                 215                 220

Pro Gly Ala Gly Glu Ala Val Leu Ser Ala Gln Leu Arg Ser Val Ser
225                 230                 235                 240

Ala Gln Ile Arg Leu Leu Phe Cys Ala Arg Glu Glu Ala Glu Pro Val
                245                 250                 255

Phe Arg Ala Ala Glu Glu Ala Gly Leu Thr Gly Ser Gly Tyr Val Trp
            260                 265                 270

Phe Met Val Gly Pro Gln Leu Ala Gly Gly Gly Ser Gly Ala Pro
            275                 280                 285

Gly Glu Pro Pro Leu Leu Pro Gly Gly Ala Pro Leu Pro Ala Gly Leu
290                 295                 300

Phe Ala Val Arg Ser Ala Gly Trp Arg Asp Asp Leu Ala Arg Arg Val
305                 310                 315                 320

Ala Ala Gly Val Ala Val Val Ala Arg Gly Ala Gln Ala Leu Leu Arg
                325                 330                 335

Asp Tyr Gly Phe Leu Pro Glu Leu Gly His Asp Cys Arg Ala Gln Asn
            340                 345                 350

Arg Thr His Arg Gly Glu Ser Leu His Arg Tyr Phe Met Asn Ile Thr
            355                 360                 365
```

-continued

```
Trp Asp Asn Arg Asp Tyr Ser Phe Asn Glu Asp Gly Phe Leu Val Asn
    370                 375                 380
Pro Ser Leu Val Val Ile Ser Leu Thr Arg Asp Arg Thr Trp Glu Val
385                 390                 395                 400
Val Gly Ser Trp Glu Gln Gln Thr Leu Arg Leu Lys Tyr Pro Leu Trp
                405                 410                 415
Ser Arg Tyr Gly Arg Phe Leu Gln Pro Val Asp Asp Thr Gln His Leu
                420                 425                 430
Ala Val Ala Thr Leu Glu Glu Arg Pro Phe Val Ile Val Glu Pro Ala
                435                 440                 445
Asp Pro Ile Ser Gly Thr Cys Ile Arg Asp Ser Val Pro Cys Arg Ser
450                 455                 460
Gln Leu Asn Arg Thr His Ser Pro Pro Asp Ala Pro Arg Pro Glu
465                 470                 475                 480
Lys Arg Cys Cys Lys Gly Phe Cys Ile Asp Ile Leu Lys Arg Leu Ala
                485                 490                 495
His Thr Ile Gly Phe Ser Tyr Asp Leu Tyr Leu Val Thr Asn Gly Lys
                500                 505                 510
His Gly Lys Lys Ile Asp Gly Val Trp Asn Gly Met Ile Gly Glu Val
                515                 520                 525
Phe Tyr Gln Arg Ala Asp Met Ala Ile Gly Ser Leu Thr Ile Asn Glu
                530                 535                 540
Glu Arg Ser Glu Ile Val Asp Phe Ser Val Pro Phe Val Glu Thr Gly
545                 550                 555                 560
Ile Ser Val Met Val Ala Arg Ser Asn Gly Thr Val Ser Pro Ser Ala
                565                 570                 575
Phe Leu Glu Pro Tyr Ser Pro Ala Val Trp Val Met Met Phe Val Met
                580                 585                 590
Cys Leu Thr Val Val Ala Val Thr Val Phe Ile Phe Glu Tyr Leu Ser
                595                 600                 605
Pro Val Gly Tyr Asn Arg Ser Leu Ala Thr Gly Lys Arg Pro Gly Gly
                610                 615                 620
Ser Thr Phe Thr Ile Gly Lys Ser Ile Trp Leu Leu Trp Ala Leu Val
625                 630                 635                 640
Phe Asn Asn Ser Val Pro Val Glu Asn Pro Arg Gly Thr Thr Ser Lys
                645                 650                 655
Ile Met Val Leu Val Trp Ala Phe Phe Ala Val Ile Phe Leu Ala Ser
                660                 665                 670
Tyr Thr Ala Asn Leu Ala Ala Phe Met Ile Gln Glu Glu Tyr Val Asp
                675                 680                 685
Thr Val Ser Gly Leu Ser Asp Arg Lys Phe Gln Arg Pro Gln Glu Gln
                690                 695                 700
Tyr Pro Pro Leu Lys Phe Gly Thr Val Pro Asn Gly Ser Thr Glu Lys
705                 710                 715                 720
Asn Ile Arg Ser Asn Tyr Pro Asp Met His Ser Tyr Met Val Arg Tyr
                725                 730                 735
Asn Gln Pro Arg Val Glu Glu Ala Leu Thr Gln Leu Lys Ala Gly Lys
                740                 745                 750
Leu Asp Ala Phe Ile Tyr Asp Ala Ala Val Leu Asn Tyr Met Ala Arg
                755                 760                 765
Lys Asp Glu Gly Cys Lys Leu Val Thr Ile Gly Ser Gly Lys Val Phe
770                 775                 780
```

```
Ala Thr Thr Gly Tyr Gly Ile Ala Leu His Lys Gly Ser Arg Trp Lys
785                 790                 795                 800

Arg Pro Ile Asp Leu Ala Leu Leu Gln Phe Leu Gly Asp Asp Glu Ile
            805                 810                 815

Glu Met Leu Glu Arg Leu Trp Leu Ser Gly Ile Cys His Asn Asp Lys
            820                 825                 830

Ile Glu Val Met Ser Ser Lys Leu Asp Ile Asp Asn Met Ala Gly Val
            835                 840                 845

Phe Tyr Met Leu Leu Val Ala Met Gly Leu Ser Leu Leu Val Phe Ala
    850                 855                 860

Trp Glu His Leu Val Tyr Trp Arg Leu Arg His Cys Leu Gly Pro Thr
865                 870                 875                 880

His Arg Met Asp Phe Leu Leu Ala Phe Ser Arg Gly Met Tyr Ser Cys
                885                 890                 895

Cys Ser Ala Glu Ala Ala Pro Pro Ala Lys Pro Pro Pro Pro
                900                 905                 910

Gln Pro Leu Pro Ser Pro Ala Tyr Pro Ala Pro Gly Pro Ala Pro Gly
            915                 920                 925

Pro Ala Pro Phe Val Pro Arg Glu Arg Ala Ser Val Ala Arg Trp Arg
930                 935                 940

Arg Pro Lys Gly Ala Gly Pro Gly Gly Ala Gly Leu Ala Asp Gly
945                 950                 955                 960

Phe His Arg Tyr Tyr Gly Pro Ile Glu Pro Gln Gly Leu Gly Leu Gly
                965                 970                 975

Leu Gly Glu Ala Arg Ala Ala Pro Arg Gly Ala Ala Gly Arg Pro Leu
            980                 985                 990

Ser Pro Pro Ala Ala Gln Pro Pro Gln Lys Pro Pro Ala Ser Tyr Phe
    995                 1000                1005

Ala Ile Val Arg Asp Lys Glu Pro Ala Glu Pro Pro Ala Gly Ala Phe
    1010                1015                1020

Pro Gly Phe Pro Ser Pro Pro Ala Pro Ala Ala Ala Ala Thr Ala
1025                1030                1035                1040

Val Gly Pro Pro Leu Cys Arg Leu Ala Phe Glu Asp Glu Ser Pro Pro
                1045                1050                1055

Ala Pro Ala Arg Trp Pro Arg Ser Asp Pro Glu Ser Gln Pro Leu Leu
            1060                1065                1070

Gly Pro Gly Ala Gly Gly Ala Gly Gly Thr Gly Gly Ala Gly Gly Gly
            1075                1080                1085

Ala Pro Ala Ala Pro Pro Cys Phe Ala Ala Pro Pro Cys Phe
            1090                1095                1100

Tyr Leu Asp Val Asp Gln Ser Pro Ser Asp Ser Glu Asp Ser Glu Ser
1105                1110                1115                1120

Leu Ala Gly Ala Ser Leu Ala Gly Leu Asp Pro Trp Trp Phe Ala Asp
                1125                1130                1135

Phe Pro Tyr Pro Tyr Ala Asp Arg Leu Gly Xaa Pro Ala Ala Arg Tyr
            1140                1145                1150

Gly Leu Val Asp Lys Leu Gly Gly Trp Leu Ala Gly Ser Trp Asp Tyr
            1155                1160                1165

Leu Pro Xaa Arg Ser Gly Arg Ala Ala Trp His Cys Arg His Cys Ala
    1170                1175                1180

Ser Leu Glu Leu Leu Pro Pro Arg His Leu Ser Cys Ser His Asp
1185                1190                1195                1200

Gly Leu Asp Gly Gly Trp Trp Ala Pro Pro Pro Pro Trp Ala Ala
```

```
            1205              1210              1215
Gly Pro Leu Pro Arg Arg Ala Arg Cys Gly Cys Pro Arg Ser His
                1220              1225              1230
Pro His Arg Pro Arg Ala Ser His Arg Thr Pro Ala Ala Ala Pro
                1235              1240              1245
His His His Arg His Arg Arg Ala Ala Gly Trp Asp Leu Pro Pro
    1250              1255              1260
Pro Ala Pro Thr Ser Arg Ser Leu Glu Asp Leu Ser Ser Cys Pro Arg
1265              1270              1275              1280
Ala Ala Pro Ala Arg Arg Leu Thr Gly Pro Ser Arg His Ala Arg Arg
                1285              1290              1295
Cys Pro His Ala Ala His Trp Gly Pro Pro Leu Pro Thr Ala Ser His
                1300              1305              1310
Arg Arg His Arg Gly Gly Asp Leu Gly Thr Arg Arg Gly Ser Ala His
            1315              1320              1325
Phe Ser Ser Leu Glu Ser Glu Val
        1330              1335
```

(2) INFORMATION FOR SEQ ID NO:59:

(i) SEQUENCE CHARACTERISTICS:
    (A) LENGTH: 71 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:59:

```
GGGTGGCGGC CGCAGAGCAC CTCCACCATC TCCTTGTCCT ACTCCAAGAT CTGGCCCTAG    60

TCCATGTTTG C                                                        71
```

(2) INFORMATION FOR SEQ ID NO:60:

(i) SEQUENCE CHARACTERISTICS:
    (A) LENGTH: 71 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:60:

```
TGGTGGTCCC CAACCTGTAG GACTTGGTTC TGGAGGAGGA TCTGGTGTAG GCAAACATGG    60

ACTAGGGCCA G                                                        71
```

(2) INFORMATION FOR SEQ ID NO:61:

(i) SEQUENCE CHARACTERISTICS:
    (A) LENGTH: 61 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:61:

```
GTTGGGGACC ACCAGATGGA GGTAGAGCTG CACTTGTACG AAGAGCTCCA CAACCACCTG    60

G                                                                   61
```

(2) INFORMATION FOR SEQ ID NO:62:

(i) SEQUENCE CHARACTERISTICS:
    (A) LENGTH: 62 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:62:

CGTGAGACGT CAGACAAAGG AGGCCCAGGT GTAGGTGGTC TACCAGGTGG TTGTGGAGCT    60

CT    62

(2) INFORMATION FOR SEQ ID NO:63:

(i) SEQUENCE CHARACTERISTICS:
        (A) LENGTH: 195 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:63:

CCGCAGAGCA CCTCCACCAT CTCCTTGTCC TACTCCAAGA TCTGGCCCTA GTCCATGTTT    60

GCCTACACCA GATCCTCCTC CAGAACCAAG TCCTACAGGT TGGGGACCAC CAGATGGAGG    120

TAGAGCTGCA CTTGTACGAA GAGCTCCACA ACCACCTGGT AGACCACCTA CACCTGGGCC    180

TCCTTTGTCT GACGT    195

HUMAN N-METHYL-D-ASPARTATE RECEPTOR SUBUNITS, NUCLEIC ACIDS ENCODING SAME AND USES THEREFOR

This is a divisional of U.S. application Ser. No. 08/231,193, filed Apr. 20, 1994, now U.S. Pat. No. 5,849,895, which is a continuation-in-part of U.S. Ser. No. 08/052,449, filed Apr. 20, 1993, now abandoned.

The present invention relates to nucleic acids and receptor proteins encoded thereby. Invention nucleic acids encode novel human N-methyl-D-aspartate (NMDA) receptor subunits. The invention also relates to methods for making such receptor subunits and for using the receptor proteins in assays designed to identify and characterize compounds which affect the function of such receptors, e.g., agonists and antagonists of NMDA receptors.

BACKGROUND OF THE INVENTION

The amino acid L-glutamate is a major excitatory neurotransmitter in the mammalian central nervous system. Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365–402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria. Glutamate has been observed to mediate its effects through receptors that have been categorized into two main groups: ionotropic and metabotropic. Ionotropic glutamate receptors contain integral cation-specific, ligand-gated ion channels, whereas metabotropic glutamate receptors are G-protein-coupled receptors that transduce extracellular signals via activation of intracellular second messenger systems. Ionotropic receptors are further divided into at least two categories based on the pharmacological and functional properties of the receptors. The two main types of ionotropic receptors are N-methyl-D-aspartic acid (NMDA) and kainic acid (KA)/α-amino-3-hydroxy-5-methyl-isoxazole-4-propionic acid (AMPA), formerly called the quisqualic acid, or QUIS, receptor. While the metabotropic receptors bind to some of the same ligands that bind to ionotropic glutamate receptors, the metabotropic receptors alter synaptic physiology via GTP-binding proteins and second messengers such as cyclic AMP, cyclic GMP, diacylglycerol, inositol 1,4,5-triphosphate and calcium [Gundersen et al., Proc. R. Soc. London Ser. 221:127 (1984); Sladeczek et al., Nature 317:717 (1985); Nicoletti et al., J. Neurosci. 6:1905 (1986); Sugiyama et al., Nature 325:531 (1987)].

The electrophysiological and pharmacological properties of the glutamate receptors have been studied using animal tissues and cell lines, as well as recombinantly produced non-human receptors, as the source of such receptors. The value of such studies for application to the development of human therapeutics has been limited by the availability of only non-human receptor subunits. Moreover, it is only recently that the characteristics and structure of glutamate receptors have been investigated at the molecular level. The majority of such investigation has, however, been carried out in non-human species. Because of the potential physiological and pathological significance of glutamate receptors, it would be desirable (for example, for drug screening assays) to have available human sequences (i.e., DNA, RNA, proteins) which encode representative members of the various glutamate receptor subtypes. The availability of such human sequences will also enable the investigation of receptor distribution in humans, the correlation of specific receptor modification with the occurrence of various disease states, etc.

BRIEF DESCRIPTION OF THE INVENTION

The present invention discloses novel nucleic acids encoding NMDA receptor protein subunits and the proteins encoded thereby. In a particular embodiment the novel nucleic acids encode NMDAR1 and NMDAR2 subunits of human NMDA receptors. More specifically, the invention nucleic acids encode NMDAR1, NMDAR2A, NMDAR2B, NMDAR2C and NMDAR2D subunits that contribute to the formation of NMDA-activated cation-selective ion channels. In addition to being useful for the production of NMDA receptor subunit proteins, these nucleic acids are also useful as probes, thus enabling those skilled in the art, without undue experimentation, to identify and isolate nucleic acids encoding related receptor subunits.

Functional glutamate receptors can be assembled, in accordance with the present invention, from a plurality of NMDA receptor subunit proteins of one type (homomeric) or from combinations of subunit proteins of different types (heteromeric)

In addition to disclosing novel NMDA receptor protein subunits, the present invention also comprises methods for using such receptor subunits to identify and characterize compounds which affect the function of such receptors, e.g., agonists, antagonists, and modulators of glutamate receptor function. The invention also comprises methods for determining whether unknown protein(s) are functional as NMDA receptor subunits.

BRIEF DESCRIPTION OF THE FIGURES

FIG. 3 presents the entire nucleotide sequence of construct NMDAR1A (see Sequence ID No. 1) with the following information added for ease of comparison of the splice variations of the NMDAR1 subunit transcript: lowercase letters indicate 5' untranslated sequence and the 3' untranslated sequence of the NMDAR1 splice variant shown in Sequence ID No. 1 (in some of the other splice variants, this 3' untranslated sequence is actually coding sequence); uppercase letters indicate coding sequence; the translation initiation codon is identified by the word "START" whereas the three different translation termination codons (TGA) used in the different splice variants are identified by small boxes; significant restriction enzyme sites used in preparing full-length variant constructs are identified by name above the sites; the location of a 63-bp insertion (see Sequence ID No. 3) that exists in some of the variants is marked as "63 bp INSERT"; the nucleotide sequences that are deleted from some of the variants are boxed and labeled as "204 bp DELETION," "363 bp DELETION," and "1087 bp DELETION."

FIG. 4 is a schematic representation of various human NMDAR2C clones of the invention, with partial restriction maps of each clone. The clones are aligned and the differences in the DNAs relative to clone NMDA26 are indicated in the same manner as done in FIG. 1.

FIG. 6 presents restriction maps of CMV promoter-based vectors pCMV-T7-2 and pCMV-T7-3.

DETAILED DESCRIPTION OF THE INVENTION

Figure 1:
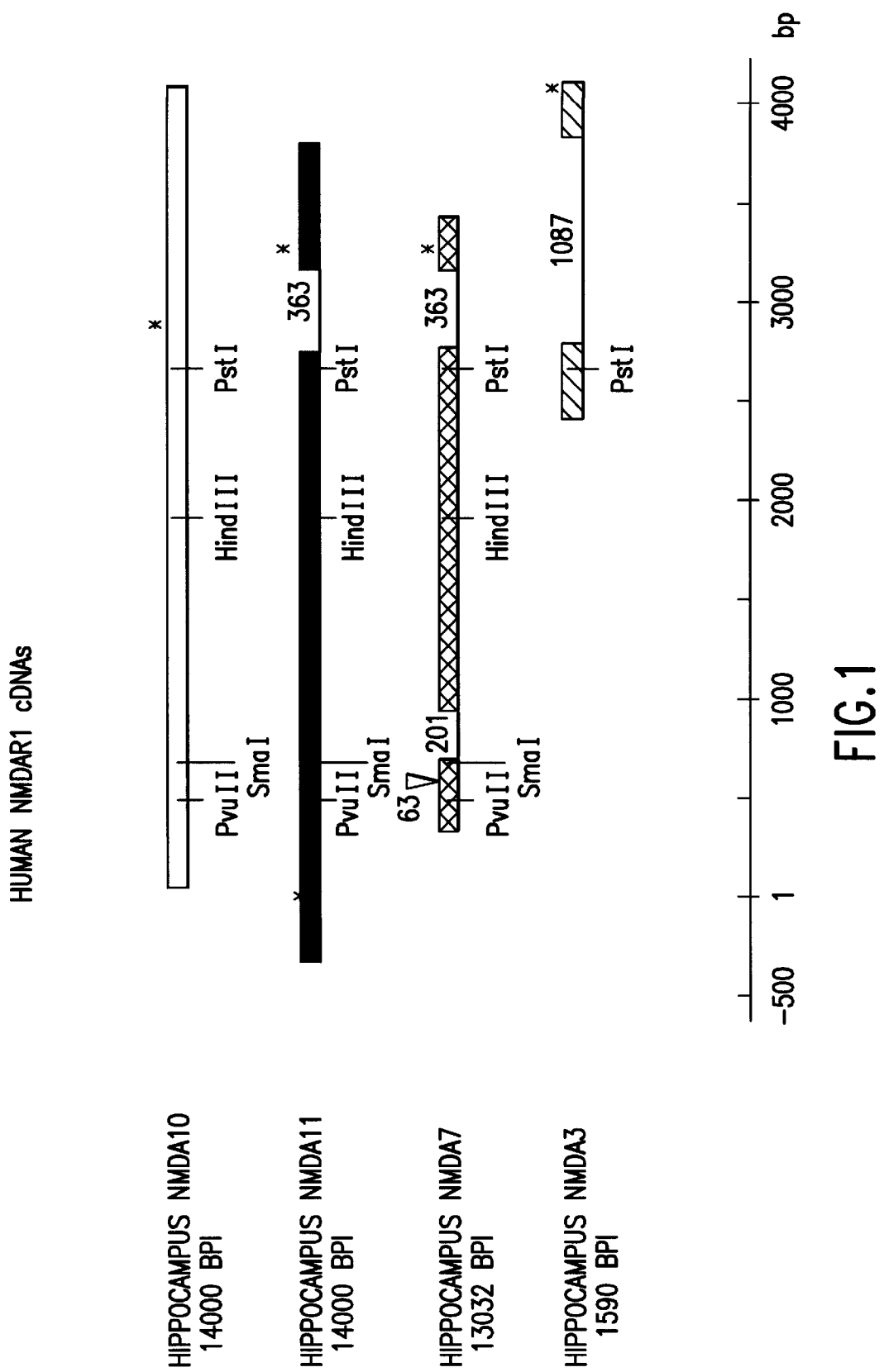
FIG. 1 is a schematic representation of various human. NMDAR1 clones of the invention, with partial restriction maps of each clone. The clones are aligned and the differences in the DNAs (i.e., deletions and insertions), relative to clone NMDA10, are indicated. Translation initiation and termination sites are represented by a "V" and a "*", respectively. Insertions are marked as inverted triangles, deletions are indicated by spaces in the boxes. The numbers above the insertions and deletions refer to the number of nucleotides inserted or deleted relative to NMDA10.

In accordance with the present invention, there are provided isolated nucleic acids encoding human N-methyl-D-aspartate (NMDA) receptor subunit(s). In one aspect of the present invention, nucleic acids encoding NMDA receptor subunit(s) of the NMDAR1 subtype are provided. In another aspect, nucleic acids encoding NMDA receptor subunit(s) of the NMDAR2 subtype are provided. In a further aspect, eukaryotic cells containing such nucleic acids, and eukaryotic cells expressing such nucleic acids are provided.

Also provided are protein(s) encoded by the above-described nucleic acids, as well as antibodies generated against the protein(s). In other aspects of the present invention, there are provided nucleic acid probes comprising at least NMDA receptor subunit-selective portions of the above-described nucleic acids.

As employed herein, the phrase "human N-methyl-D-aspartate (NMDA) receptor subunit(s)" refers to recombinantly produced (i.e., isolated or substantially pure) proteins which participate in the formation of a voltage-sensitive cation-selective channel activated by exposure to NMDA, and having at least one transmembrane domain, a large N-terminal extracellular domain, and the like, including variants thereof encoded by mRNA generated by alternative splicing of a primary transcript, and further including fragments thereof which retain one or more of the above properties.

Use of the phrase "recombinantly produced", "isolated" or "substantially pure" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways that the DNAs, RNAs, polypeptides or proteins as they naturally occur are not, such as identification of selective drugs or compounds.

The term "functional", when used herein as a modifier of receptor protein(s) of the present invention, means that binding of NMDA (or NMDA-like) ligand to receptors comprising the protein(s) causes the receptor "ion channels" to open. This allows cations, particularly $Ca^{2+}$, as well as $Na^+$ and $K^+$, to move across the membrane. Stated another way, "functional" means that a signal is generated as a consequence of agonist activation of receptor protein(s).

As used herein, a splice variant refers to variant NMDA receptor subunit-encoding nucleic acid(s) produced by differential processing of primary transcript(s) of genomic DNA, resulting in the production of more than one type of mRNA. cDNA derived from differentially processed primary transcript will encode NMDA receptor subunits that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Accordingly, also contemplated within the scope of the present invention are DNAs that encode NMDA receptor subunits as defined above, but that by virtue of degeneracy of the genetic code do not necessarily hybridize to the disclosed DNA under specified hybridization conditions. Such subunits also contribute to the formation of functional receptor, as assessed by methods described herein or known to those of skill in the art, with one or more additional NMDA receptor subunits of the same or different type (the presence of additional subunits of a different type is optional when said subunit is an NMDAR1 subunit). Typically, unless an NMDA receptor subunit is encoded by RNA that arises from alternative splicing (i.e., a splice variant), NMDA receptor subunit-encoding DNA and the NMDA receptor subunit encoded thereby share substantial sequence homology with at least one of the NMDA receptor subunit DNAs (and proteins encoded thereby) described herein. It is understood that DNA or RNA encoding a splice variant may share less than 90% overall sequence homology with the DNA or RNA provided herein, but include regions of nearly 100% homology to a DNA fragment described herein, and encode an open reading frame that includes start and stop codons and encodes a functional NMDA receptor subunit.

As employed herein, the phrase "NMDA receptor subunit (s) of the NMDAR1 subtype" refers to proteins which, by hydrophobicity analysis of deduced amino acid sequences, are believed to contain four or more putative transmembrane domains, preceded by a large extracellular N-terminal domain. The amino acid sequence typically contains possible phosphorylation sites for $Ca^{2+}$/calmodulin-dependent protein kinase type II and protein kinase C [see, for example, Kemp et al. (1990) Trends in Biological Science Vol. 15:342–346; Kishimoto et al. (1985) J. Biol. Chem. Vol. 260:12492–12499; Whittemore et al. (1993) Nature 364:70–73]. (These protein kinases reportedly play a crucial role in induction and maintenance of long term potentiation.)

The putative TMII segment (i.e., second transmembrane domain) is typically flanked by a glutamic acid residue at the extracellular side and a stretch of glutamic acid residues at the cytoplasmic side. This segment contains an asparagine residue believed to be responsible for high $Ca^{2+}$ permeability of the NMDAR channel. For a summary of NMDAR properties, see Ben-Ari et al., in TINS 15:333–339 (1992), especially at p. 334.

Exemplary DNA sequences encoding human NMDAR1 subunits are represented by nucleotides which encode substantially the same amino acid sequence as set forth in Sequence ID Nos. 2, 20, 22, 24, 26, 28, 30, 32, 34, 36, 38 or 40. Presently preferred sequences encode substantially the same amino acid sequence as set forth in Sequence ID Nos. 2, 20, 22, 24, 26, 28 or 40.

Exemplary DNA can alternatively be characterized as those nucleotide sequences which encode a human NMDAR1 subunit and hybridize under high stringency conditions to substantially the entire sequence of any one of Sequence ID No. 1, nucleotides 320–3402 of Sequence ID No. 1, or Sequence ID Nos. 13, 15, 17, 19, 21, 23, 25, 27, 29, 31, 33, 35, 37 or 39, or substantial portions thereof (i.e., typically at least 25–30 nucleotides thereof); preferably exemplary DNA will hybridize under high stringency conditions to substantially the entire sequence of any one of Sequence ID Nos. 1, 19, 21, 23, 25, 27 or 39, or substantial portions thereof.

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C.-16.6(\log_{10}[Na^+])+0.41(\% G+C)-600/l,$$

where l is the length of the hybrids in nucleotides. $T_m$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY conditions, with respect to fragment hybridization, refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.;

(2) MODERATE STRINGENCY conditions, with respect to fragment hybridization, refers to conditions equivalent to hybridization in 50% formamide, 5×Denhart's solution, 5×SSPE, 0.2% SDS at 42° C., followed by washing in 0.2×SSPE, 0.2% SDS, at 65° C.;

(3) LOW STRINGENCY conditions, with respect to fragment hybridization, refers to conditions equivalent to hybridization in 10% formamide, 5×Denhart's solution, 6×SSPE, 0.2% SDS at 42° C., followed by washing in 1×SSPE, 0.2% SDS, at 50° C.; and (4) HIGH STRINGENCY conditions, with respect to oligonucleotide (i.e., synthetic DNA≦about 30 nucleotides in length) hybridization, refers to conditions equivalent to hybridization in 10% formamide, 5×Denhart's solution, 6×SSPE, 0.2% SDS at 42° C., followed by washing in 1×SSPE, and 0.2% SDS at 50° C.

It is understood that these conditions may be duplicated using a variety of buffers and temperatures and that they are not necessarily precise.

Denhart's solution and SSPE (see, e.g., Sambrook, Fritsch, and Maniatis, in: *Molecular Cloning, A Laboratory Manual,* Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20×stock solution by dissolving 175.3 g of NaCl, 27.6 g of $NaH_2PO_4$ and 7.4 g EDTA in 800 ml of water, adjusting the pH to 7.4, and then adding water to 1 liter. Denhart's solution (see, Denhart (1966) Biochem. Biophys. Res. Commun. 23:641) can be prepared, for example, as a 50×stock solution by mixing 5 g Ficoll (Type 400, Pharmacia LKB Biotechnology, INC., Piscataway, N.J.), 5 g of polyvinylpyrrolidone, 5 g bovine serum albumin (Fraction V; Sigma, St. Louis, Mo.) water to 500 ml and filtering to remove particulate matter.

Especially preferred sequences are those which have substantially the same nucleotide sequence as the coding sequences in any one of Sequence ID Nos. 1, 19, 21, 23, 25, 27, 29, 31, 33, 35, 37 or 39; with those having substantially the same sequence as the coding sequence in Sequence ID Nos. 1, 19, 21, 23, 25, 27 or 39 being most preferred.

As used herein, the phrase "substantial sequence homology" refers to nucleotide sequences which share at least about 90% identity, and amino acid sequences which typically share more than 95% amino acid identity (>99% amino acid identity when dealing with NMDAR1 subunits). It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

As used herein, the phrase "substantially the same" refers to the nucleotide sequences of DNA, the ribonucleotide sequences of RNA, or the amino acid sequences of protein, that have slight and non-consequential sequence variations from the actual sequences disclosed herein. Species that are "substantially the same" are considered to be equivalent to the disclosed sequences, and as such are within the scope of the appended claims. In this regard, "slight and non-consequential sequence variations" mean that sequences that are substantially the same as the DNA, RNA, or proteins disclosed and claimed herein, are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particular, functionally equivalent DNAs encode human-derived proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

As employed herein, the phrase "NMDA receptor subunit (s) of the NMDAR2 subtype" refers to proteins which have a large putative extracellular domain at the amino-terminal region. Otherwise, the deduced structure of NMDAR2 subunits displays the same general characteristics as the NMDAR1 subunit structure. A notable typical exception is that the negatively charged glutamic acid residues that are generally present in the putative TMII segment of NMDAR1 subunits are generally absent from the TMII segment of NMDAR2. Instead, NMDAR2 subunits may contain a positively charged lysine residue in TMII. Unlike NMDAR1 subunits, NMDAR2 subunits generally do not form homomeric NMDA receptors. Moreover, the amino acid sequences of NMDAR1 and NMDAR2 subunits are generally less than 50% identical, with identities of less than 30% typically observed.

NMDAR2 subunits contemplated by the present invention include NMDAR2A, NMDAR2B, NMDAR2C and NMDAR2D types of subunits. Exemplary DNA sequences encoding human NMDAR2A subunits, or portions thereof, are represented by nucleotides which encode substantially the same amino acid sequence as set forth in Sequence ID No. 11, or substantially the same amino acid sequence as that encoded by the NMDAR2A-encoding portion of clone NMDA57, deposited with the ATCC under accession number 75442.

The deposited clone has been deposited at the American Type Culture Collection (ATCC), 12301 Parklawn Drive, Rockville, Md., U.S.A. 20852, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. patent based on this or any application claiming priority to or incorporating this application by reference thereto, all restriction upon availability of the deposited material will be irrevocably removed.

Exemplary human NMDAR2A subunit-encoding DNAs can alternatively be characterized as those nucleotide sequences which hybridize under high stringency conditions to substantially the entire sequence of Sequence ID No. 10, or substantial portions thereof (i.e., typically at least 25–30 nucleotides thereof), or the NMDAR2A-encoding portion of clone NMDA57 (ATCC accession No. 75442). Especially preferred sequences encoding human NMDAR2A subunits are those which have substantially the same nucleotide sequence as the coding sequence of Sequence ID No. 10, or those which contain substantially the same nucleotide sequence as the coding sequence in the NMDAR2A-encoding portion of clone NMDA57.

Exemplary DNA sequences encoding human NMDAR2B subunits are represented by nucleotides which encode substantially the same amino acid sequence as set forth in Sequence ID No. 56. Exemplary DNAs can alternatively be characterized as those nucleotide sequences which encode a human NMDAR2B subunit and hybridize under high stringency conditions to substantially the entire sequence of Sequence ID No. 55, or substantial portions thereof (i.e., typically at least 25–30 nucleotides thereof). Especially preferred NMDAR2B-encoding sequences are those which have substantially the same nucleotide sequence as the coding sequence in Sequence ID No. 55.

Exemplary DNA sequences encoding human NMDAR2C subunits are represented by nucleotides which encode substantially the sae amino acid sequence as set forth in Sequence ID Nos. 6, 46, 48, 50, 52 or 54.

Exemplary DNAs can alternatively be characterized as those nucleotide sequences which encode a human NMDAR2C subunit and hybridize under high stringency conditions to substantially the entire sequence of any one of Sequence ID Nos. 5, 41, 43 or 44 or nucleotides 1–3025 of Sequence ID No. 5 or Sequence ID Nos. 45, 47, 49, 51 or 53, or substantial portions thereof (i.e., typically at least 25–30 nucleotides thereof); preferably exemplary DNA will hybridize under high stringency conditions to substantially the entire sequence of any one of Sequence ID Nos. 5, 45, 47 or 49, or substantial portions thereof.

Especially preferred NMDAR2C-encoding sequences are those which have substantially the same nucleotide sequence as the coding sequences in any one of Sequence ID Nos. 5, 45, 47, 49, 51 or 53; with those having substantially the same sequence as the coding sequences in Sequence ID Nos. 5, 45, 47, 49 being most preferred.

Exemplary DNA sequences encoding human NMDAR2D subunits are represented by nucleotides which encode substantially the same amino acid sequence as set forth in Sequence ID No. 58. Exemplary DNAs can alternatively be characterized as those nucleotide sequences which encode a human NMDAR2D subunit and hybridize under high stringency conditions to substantially the entire sequence of Sequence ID No. 57, or substantial portions thereof (i.e., typically at least 25–30 nucleotides thereof). Especially preferred NMDAR2D-encoding sequences are those which have substantially the same nucleotide sequence as the coding sequence in Sequence ID No. 57.

DNA encoding human NMDA receptor subunits may be isolated by screening suitable human cDNA or human genomic libraries under suitable hybridization conditions with DNA disclosed herein (including nucleotides derived from any of Sequence ID No. 1, nucleotides 320–3402 of Sequence ID No. 1, Sequence ID Nos. 13, 15, 17, 19, 21, 23, 25, 27, 29, 31, 33, 35, 37, 39, 5, 41, 43 or 44, nucleotides 1–3025 of Sequence ID No. 5 or Sequence ID Nos. 45, 47, 49, 51, 53, 10, 55 or 57). Suitable libraries can be prepared from neuronal tissue samples, e.g., hippocampus and cerebellum tissue, cell lines, and the like. For example, the library can be screened with a portion of DNA including substantially the entire subunit-encoding sequence thereof, or the library may be screened with a suitable probe.

As used herein, a probe is single-stranded DNA or RNA that has a sequence of nucleotides that includes at least 14 contiguous bases that are the same as (or the complement of) any 14 or more contiguous bases set forth in any of Sequence ID No. 1, nucleotides 320–3402 of Sequence ID No. 1, Sequence ID Nos. 13, 15, 17, 19, 21, 23, 25, 27, 29, 31, 33, 35, 37, 39, 5, 41, 43 or 44, nucleotides 1–3025 of Sequence ID No. 5 or Sequence ID Nos. 45, 47, 49, 51, 53, 10, 55 or 57. Preferred regions from which to construct probes include 5' and/or 3' coding sequences, sequences predicted to encode transmembrane domains, sequences predicted to encode cytoplasmic loops, signal sequences, NMDA binding sites, and the like.

Either the full-length cDNA clones or fragments thereof can be used as probes, preferably labeled with suitable label means for ready detection. When fragments are used as probes, preferably the DNA sequences will be from the carboxyl end-encoding portion of the DNA, and most preferably will include predicted transmembrane domain-encoding portions of the DNA sequence (the domains can be predicted based on hydropathy analysis of the deduced amino acid sequence using, for example, the method of Kyte and Doolittle (1982), *J. Mol. Biol.* Vol. 157:105). These probes can be used, for example, for the identification and isolation of additional members of the glutamate receptor family.

As a particular application of the invention sequences, genetic screening can be carried out using the nucleotide sequences of the invention as probes. Thus, nucleic acid samples from patients having neuropathological conditions suspected of involving alteration/modification of any one or more of the glutamate receptors can be screened with appropriate probes to determine if any abnormalities exist with respect to any of the endogenous glutamate receptors. Similarly, patients having a family history of disease states related to glutamate receptor dysfunction can be screened to determine if they are also predisposed to such disease states.

In accordance with another embodiment of the present invention, there is provided a method for identifying DNA encoding human N-methyl-D-aspartate (NMDA) receptor protein subunit(s), said method comprising:

contacting human DNA with a nucleic acid probe as described above, wherein said contacting is carried out under high stringency hybridization conditions, and identifying DNA(s) which hybridize to said probe.

After screening the library, positive clones are identified by detecting a hybridization signal; the identified clones are characterized by restriction enzyme mapping and/or DNA sequence analysis, and then examined, by comparison with the sequences set forth herein to ascertain whether they include DNA encoding a complete NMDA receptor subunit (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNA and encoded proteins provided herein.

Complementary DNA clones encoding various human NMDA receptor subunits (e.g., NMDAR1, NMDAR2A, NMDAR2B, NMDAR2C, NMDAR2D) have been isolated. Each type of subunit appears to be encoded by a different gene. The DNA clones provided herein may be used to isolate genomic clones encoding each type of subunit and to isolate any splice variants by screening libraries prepared from different neural tissues. Nucleic acid amplification techniques, which are well known in the art, can be used to locate DNA encoding splice variants of human NMDA receptor subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human NMDA receptor subunits.

It has been found that not all subunits (and variants thereof) are expressed in all neural tissues or in all portions of the brain. Thus, in order to isolate cDNA encoding a particular subunit or splice variants thereof, it is preferable to screen libraries prepared from different neuronal or neural tissues. Preferred tissues to use as sources of nucleic acids for preparing libraries to obtain DNA encoding each subunit include: hippocampus to isolate human NMDAR1-encoding DNAs; hippocampus, cerebellum and fetal brain to isolate NMDAR2-encoding DNAs; and the like.

Once DNA encoding a subunit has been isolated, ribonuclease (RNase) protection assays can be employed to determine which tissues express mRNA encoding a particular NMDAR subunit subtype or variant. These assays provide a sensitive means for detecting and quantitating an RNA species in a complex mixture of total cellular RNA. The subunit DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualed by gel electrophorsis and autoradiography. In situ hybridization techniques can also be used to determine which tissues express mRNA encoding a particular NMDAR subunit. The labeled subunit DNAs are hybridized to different brain region slices to visualize subunit mRNA expression.

The distribution of expression of some human NMDA receptor subunits may differ from the distribution of such receptors in rat. For example, RNA encoding the rat NMDAR2C subunit is abundant in rat cerebellum, but is not abundant in rat hippocampus [see, e.g., Monyer et al., Science 256:1217–1221 (1992)]. Numerous human NMDAR2C clones were ultimately obtained, however, from a human hippocampus library. Thus, the distribution of some NMDA receptor subunits in humans and rats appears to be different.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the skill of the artisan.

An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention NMDA receptor subunits in eukaryotic host cells, particularly mammalian cells, include cytomegalovirus (CMV) promoter-containing vectors such as pCMV-T7-2 or pCMV-T7-3 (see FIG. 6), pMMTVT7(+) or pMMTVT7(−) (modified versions of pMAMneo (Clontech, Palo Alto, Calif.), prepared as described herein), pcDNA1, and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes and binds to the promoter, and transcribes the DNA. In order to optimize expression and/or in vitro transcription, it may be necessary to remove, add or alter 5' and/or 3' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, for example, Kozak (1991) J. Biol. Chem. 266:19867–19870) can be inserted immediately 5' of the start codon and may enhance expression. Likewise, alternative codons, encoding the same amino acid, can be substituted for coding sequences of the NMDAR subunits in order to enhance transcription (e.g., the codon preference of the host cells can be adopted, the presence of G-C rich domains can be reduced, and the like). Furthermore, for potentially enhanced expression of NMDA receptor subunits in amphibian oocytes, the subunit coding sequence can optionally be incorporated into an expression construct wherein the 5'- and 3'-ends of the coding sequence are contiguous with Xenopus β-globin gene 5' and 3' untranslated sequences, respectively. For example, NMDA receptor subunit coding sequences can be incorporated into vector pSP64T (see Krieg and Melton (1984) in Nucleic Acids Research 12:7057–7070), a modified form of pSP64 (available from Promega, Madison, Wis.). The coding sequence is inserted between the 5' end of the β-globin gene and the 3' untranslated sequences located downstream of the SP6 promoter. In vitro transcripts can then be generated from teh resulting vector. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCMV-T7-2 and pCMV-T7-3 (described herein) or pCDNA1 (Invitrogen, San Diego, Calif.), and MMTV promoter-based vectors such as pMMTVT7(+) or pMMTVT7(−), described herein.

Full-length DNAs encoding human NMDA receptor subunits have been inserted into vectors pcDNA1, pMMTVT7 (+), pCMV-T7-2 and pCMV-T7-3. pCMV-T7-2 is a pUC19-based mammalian cell expression vector containing the CMV promoter/enhancer, SV40 splice/donor sites located immediately downstream of the promoter, a T7 bacteriophage RNA polymerase promoter positioned downstream of the splice sites, followed by an SV40 polyadenylation signal and a polylinker between the T7 promoter and the polyadenylation signal. Placement of NMDA receptor subunit DNA between the CMV promoter and SV40 polyadenylation signal should provide for constitutive expression of the foreign DNA in a mammalian host cell transfected with the construct. Plasmid pCMV-T7-3 is identical to pCMV-T7-2 except that the order of restriction enzyme sites in the polylinker is reversed.

Vectors pMMTVT7(+) and pMMTVT7(−) were prepared by modifying vector pMAMneo (Clontech, Palo Alto, Calif.). pMAMneo is a mammalian expression vector that contains the Rous Sarcoma Virus (RSV) long terminal repeat (LTR) enhancer, linked to the dexamethasone-inducible mouse mammary tumor virus (MMTV)-LTR promoter, followed by SV40 splicing and polyadenylation sites. pMAMneo also contains the E. coli neo gene for selection of transformants, as well as the β-lactamase gene (encoding a protein which imparts ampicillin-resistance) for propagation in E. coli.

Vector pMMTVT7(+) can be generated by modification of pMAMneo to remove the neo gene and insert the multiple cloning site and T7 and T3 promoters from pBluescript (Stratagene, La Jolla, Calif.). Thus, pMMTVT7(+) contains the RSV-LTR enhancer linked to the MMTV-LTR promoter, a T7 bacteriophage RNA polymerase promoter positioned downstream of the MMTV-LTR promoter, a polylinker positioned downstream of the T7 promoter, a T3 bacteriophage RNA polymerase promoter positioned downstream of the T7 promoter, and SV40 splicing and polyadenylation sites positioned downstream of the T3 promoter. The β-lactamase gene (encoding a protein which imparts ampicillin-resistance) from pMAMneo is retained in pMMTVT7(+), although it is incorporated in the reverse orientation relative to the orientation in pMAMneo.

Vector pMMTVT7(−) is identical to pMMTVT7(+) except that the positions of the T7 and T3 promoters are switched, i.e., the T3 promoter in pMMTVT7(−) is located where the T7 promoter is located in pMMTVT7(+), and the T7 promoter in pMMTVT7(−) is located where the T3 promoter is located in pMMTVT7(+). Therefore, vectors pMMTVT7(+) and pMMTVT7(−) contain all of the regulatory elements required for expression of heterologous DNA in a mammalian host cell, wherein the heterologous DNA has been incorporated into the vectors at the polylinker. In addition, because the T7 and T3 promoters are located on either side of the polylinker, these plasmids can be used for synthesis of in vitro transcripts of heterologous DNA that has been subcloned into the vectors at the polylinker.

For inducible expression of human NMDA receptor subunit-encoding DNA in a mammalian cell, the DNA can be inserted into a plasmid such as pMMTVT7(+) or pMMTVT7(−). These plasmids contain the mouse mammary tumor virus (MMTV) promoter for steroid-inducible expression of operatively associated foreign DNA. If the host cell does not express endogenous glucocorticoid receptors required for uptake of glucocorticoids (i.e., inducers of the MMTV promoter) into the cell, it is necessary to additionally transfect the cell with DNA encoding the glucocorticoid receptor (ATCC accession no. 67200). For synthesis of in vitro transcripts, full-length human DNA clones encoding human NMDAR1, NMDAR2A, NMDAR2B, NMDAR2C and NMDAR2D can also be subcloned into pIBI24 (International Biotechnologies, Inc., New Haven, Con.), pCMV-T7-2, pCMV-T7-3, pMMTVT7(+), pMMTVT7(−), pBluescript (Stratagene, La Jolla, Calif.) or pGEM7Z (Promega, Madison, Wis.).

In accordance with another embodiment of the present invention, there are provided cells containing the above-described polynucleic acids (i.e., DNA or mRNA). Such host cells as bacterial, yeast and mammalian cells can be used for replicating DNA and producing NMDA receptor subunit(s). Methods for assessing receptor expression and function are described in PCon. Application Nos. PCT/US91/05625 and PCT/US92/11090, and in co-pending U.S.

application Serial No. 07/563,751 U.S. Pat. No. 5,401,629, and Ser. No. 07/812,254, U.S. Pat. No. 6,127,133. The subject matter of these documents is hereby incorporated by reference herein in their entirety.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual*, Second Edition, Cold Spring Harbor Laboratory Press). Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376) or lipofectamine (GIBCO BRL #18324-012). Recombinant cells can then be cultured under conditions whereby the subunit(s) encoded by the DNA is (are) expressed. Preferred cells include mammalian cells (e.g., HEK293, CHO, BHKBI and Ltk⁻ cells, mouse monocyte macrophage P388D1 and J774A-1 cells (available from ATCC, Rockville, Md.), and the like), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929,555 and 4,855,231), *Saccharomyces cerevisiae, Candida tropicalis, Hansenula polymorpha,* and the like), mammalian expression systems, including commercially available systems and other such systems known to those of skill in the art, for expression of DNA encoding the human NMDA receptor subunits provided herein are presently preferred. Xenopus oocytes are preferred for expression of in vitro RNA transcripts of the DNA.

In preferred embodiments, human NMDAR subunit-encoding DNA is ligated into a vector, and introduced into suitable host cells to produce transformed cell lines that express a specific human NMDA receptor subtype, or specific combinations of subunits. The resulting cell lines can then be produced in quantity for reproducible quantitative analysis of the effects of known or potential drugs on receptor function. In other embodiments, mRNA may be produced by in vitro transcription of DNA encoding each subunit. This mRNA, either from a single subunit clone or from a combination of clones, can then be injected into Xenopus oocytes where the mRNA directs the synthesis of the human receptor subunits, which then form functional receptors. Alternatively, the subunit-encoding DNA can be directly injected into oocytes for expression of functional receptors. The transfected mammalian cells or injected oocytes may then be used in the methods of drug screening provided herein.

Eukaryotic cells in which DNA or RNA may be introduced include any cells that are transfectable by such DNA or RNA or into which such DNA or RNA may be injected. Preferred cells are those that can be transiently or stably transfected and also express the DNA and RNA. Presently most preferred cells are those that can form recombinant or heterologous human NMDA receptors comprising one or more subunits encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney (HEK) cells (particularly HEK293 cells that can be frozen in liquid nitrogen and then thawed and regrown; for example, those described in U.S. Pat. No. 5,024,939 to Gorman (see, also, Stillman et al. (1985) Mol. Cell. Biol. 5:2051–2060)), African green monkey cells and other such cells known to those of skill in the art), amphibian cells (e.g., *Xenopus laevis* oöcytes), yeast cells (e.g., *Saccharomyces cerevisiae, Pichia pastoris*), and the like. Exemplary cells for expressing injected RNA transcripts include *Xenopus laevis* oöcytes. Cells that are preferred for transfection of DNA are known to those of skill in the art or may be empirically identified, and include HEK293 (which are available from ATCC under accession #CRL 1573); Ltk⁻ cells (which are available from ATCC under accession #CCL1.3); COS-7 cells (which are available from ATCC under accession #CRL 1651); and DG44 cells (dhfr⁻ CHO cells; see, e.g., Urlaub et al. (1986) Cell. Molec. Genet. 12: 555). Presently preferred cells include Ltk⁻ cells and DG44 cells.

DNA may be stably incorporated into cells or may be transiently expressed using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the *E. coli* β-galactosidase gene) to monitor transfection efficiency. Selectable marker genes are not included in the transient transfections because the transfectants are typically not grown under selective conditions, and are usually analyzed within a few days after transfection.

To produce such stably or transiently transfected cells, the cells should be transfected with a sufficient concentration of subunit-encoding nucleic acids to form human NMDA receptors that contain the human subunits encoded by heterologous DNA. The precise amounts and ratios of DNA encoding the subunits may be empirically determined and optimized for a particular combination of subunits, cells and assay conditions. Recombinant cells that express NMDA receptors containing subunits encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human NMDA receptor subunits may be purified using protein purification methods known to those of skill in the art. For example, antibodies or other ligands that specifically bind to one or more of the subunits may be used for affinity purification and immunoprecipitation of the subunit or human NMDA receptors containing the subunits.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human NMDA receptor subunit, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Recombinant receptors on recombinant eukaryotic cell surfaces may contain one or more subunits encoded by the DNA or mRNA encoding human NMDA receptor subunits, or may contain a mixture of subunits encoded by the host cell and subunits encoded by heterologous DNA or mRNA. Recombinant receptors may be homomeric or may be a heteromeric combination of multiple subunits. Mixtures of DNA or mRNA encoding receptors from various species, such as rats and humans, may also be introduced into the cells. Thus, a cell can be prepared that expresses recombinant receptors containing only NMDAR1 subunits, or a combination of any one or more NMDAR1 and any one or more NMDAR2 subunits provided herein. For example, NMDAR1 subunits of the present invention can be co-expressed with NMDAR2A, NMDAR2B, NMDAR2C and/or NMDAR2D receptor subunits. Specific examples of heteromeric combinations of recombinant human NMDAR subunits that have been expressed in Xenopus oocytes include NMDAR1+NMDAR2A, NMDAR1+NMDAR2B, and NMDAR1+NMDAR2A+NMDAR2C (see Example 9).

The DNA, mRNA, vectors, receptor subunits, receptor subunit combinations and cells provided herein permit production of selected NMDA receptor subunits and specific combinations thereof, as well as antibodies to said receptor subunits. This provides a means to prepare synthetic or recombinant receptors and receptor subunits that are substantially free of contamination from many other receptor proteins whose presence can interfere with analysis of a single NMDA receptor subtype. The availability of desired receptor subtypes makes it possible to observe the effect of a drug substance on a particular receptor subtype or combination of NMDA receptor subunits, and to thereby perform initial in vitro screening of the drug substance in a test system that is specific for humans and specific for a human NMDA receptor subtype or combination of NMDA receptor subunits. The availability of specific antibodies makes it possible to identify the subunit combinations expressed in vivo. Such specific combinations can then be employed as preferred targets in drug screening.

The ability to screen drug substances in vitro to determine the effect of the drug on specific receptor compositions should permit the development and screening of receptor subtype-specific or disease-specific drugs. Also, testing of single receptor subunits or specific combinations of various types of receptor subunits with a variety of potential agonists or antagonists provides additional information with respect to the function and activity of the individual subunits and should lead to the identification and design of compounds that are capable of very specific interaction with one or more types of receptor subunits or receptor subtypes. The resulting drugs should exhibit fewer unwanted side effects than drugs identified by screening with cells that express a variety of receptor subtypes.

Further in relation to drug development and therapeutic treatment of various disease states, the availability of DNAs encoding human NMDA receptor subunits enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAs. The modified (e.g., deleted or digested) DNAs are expressed, for example, by transcribing the DNA and then introducing the resulting mRNA into Xenopus oocytes, where translation of the mRNAs will occur. Functional analysis of the proteins thus expressed in the oocytes is accomplished by exposing the oocytes to ligands known to bind to and functionally activate glutamate receptors, and then monitoring the oocytes to see if the expressed fragments form ion channel(s). If ion channel(s) are detected, the fragments are functional as glutamate receptors.

The above-described method can be carried out in the presence of NMDAR1-like receptor subunits alone, or in the presence of combinations of NMDAR1-like and NMDAR2-like receptor subunits. Thus, for example, when the protein being tested is an NMDAR2-like receptor subunit, the additional subunit is preferably an NMDAR1-like subunit.

In accordance with still another embodiment of the present invention, there is provided a method for identifying compounds which bind to human N-methyl-D-aspartate (NMDA) receptor subunit(s), said method comprising employing receptor proteins of the invention in a competitive binding assay. Such an assay can accomodate the rapid screening of a large number of compounds to determine which compounds, if any, are capable of binding to NMDA receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamatergic pathway dysfunction can be assayed to determine if the observed symptoms are perhaps caused by over- or under-production of such receptor(s).

The binding assays contemplated by the present invention can be carried out in a variety of ways, as can readily be identified by those of skill in the art. For example, competitive binding assays can be employed, such as radioreceptor assays, and the like.

In accordance with a further embodiment of the present invention, there is provided a bioassay for identifying compounds which modulate the activity of human NMDA receptors of the invention, said bioassay comprising:

(a) exposing cells containing DNA encoding human NMDA receptor subunit (s), wherein said cells express functional NMDA receptors, to at least one compound whose ability to modulate the ion channel activity of said receptors is sought to be determined; and thereafter (b) monitoring said cells for changes in ion channel activity.

The above-described bioassay enables the identification of agonists and antagonists for human NMDA receptors. According to this method, recombinant NMDA receptors are contacted with an "unknown" or test substance (in the further presence of a known NMDA agonist, when antagonist activity is being tested), the ion channel activity of the known glutamate receptor is monitored subsequent to the contact with the "unknown" or test substance, and those substances which increase or decrease the ion channel response of the known glutamate receptor(s) are identified as functional ligands (i.e., modulators, agonists or antagonists) for human NMDA receptors.

In accordance with a particular embodiment of the present invention, recombinant human NMDA receptor-expressing mammalian cells or oocytes can be contacted with a test compound, and the modulating effect(s) thereof can then be evaluated by comparing the NMDA receptor-mediated response in the presence and absence of test compound, or by comparing the response of test cells, or control cells (i.e., cells that do not express NMDA receptors), to the presence of the compound.

As used herein, a compound or signal that "modulates the activity of an NMDA receptor" refers to a compound or signal that alters the activity of NMDA receptors so that activity of the NMDA receptor is different in the presence of the compound or signal than in the absence of the compound or signal. In particular, such compounds or signals include agonists and antagonists. The term agonist refers to a substance or signal, such as NMDA, that activates receptor function; and the term antagonist refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter). A non-competitive antagonist or blocker inactivates the functioning of the receptor by interacting with a site other than the site that interacts with the agonist.

As understood by those of skill in the art, assay methods for identifying compounds that modulate human NMDA receptor activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which is identical to the transfected cells, except the cells employed for the control culture do not express functional human NMDA receptor subunits. In this situation, the response of test cell to test compound is compared to the response (or lack of response) of receptor-negative (control) cell to test compound, when cells or cultures of each type of cell are exposed to substantially the same reaction conditions in the presence of compound being assayed.

In accordance with yet another embodiment of the present invention, the ion channel activity of human N-methyl-D-aspartate (NMDA) receptors can be modulated by contacting such receptors with an effective amount of at least one compound identified by the above-described bioassay.

In accordance with yet another embodiment of the present invention, there are provided antibodies generated against the above-described receptor proteins. Such antibodies can be employed for studying receptor tissue localization, subunit composition, structure of functional domains, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins or portions thereof as antigens for antibody production. Both anti-peptide and anti-fusion protein antibodies can be used [see, for example, Bahouth et al. (1991) *Trends Pharmacol Sci.* vol. 12:338–343; *Current Protocols in Molecular Biology* (Ausubel et al., eds.) John Wiley and Sons, New York (1989)]. Factors to consider in selecting portions of the NMDAR subunits for use as immunogen (as either a synthetic peptide or a recombinantly produced bacterial fusion protein) include antigenicity, accessibility (i.e., extracellular and cytoplasmic domains), uniqueness to the particular subunit, etc.

The availability of subunit-specific antibodies makes possible the application of the technique of immunohistochemistry to monitor the distribution and expression density of various subunits (e.g., in normal vs diseased brain tissue). Such antibodies could also be employed for diagnostic and therapeutic applications.

In accordance with still another embodiment of the present invention, there are provided methods for modulating the ion channel activity of receptor(s) of the invention by contacting said receptors) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

The invention will now be described in greater detail by reference to the following non-limiting examples.

EXAMPLE 1

Isolation of DNA Encoding Human NMDA Receptor NMDAR1 Subunits

A. cDNA Library Screening

RNA isolated from human hippocampus tissue was used as a template for the synthesis of oligo dT-primed and randomly primed, single-stranded cDNA according to standard procedures [see, for example, Maniatis et al. (1982) *Molecular Cloning: A Laboratory Manual,* Cold Spring Harbor Laboratory Press, Cold Spring Harbor, N.Y.]. The single-stranded cDNA was converted to double-stranded cDNA, and EcoRI/SnaBI/XhoI adaptors were added to the ends thereof. The cDNAs were separated by size using agarose gel electrophoresis, and those that were >2.0 kb were ligated into EcoRI-digested λgt10 bacteriophage vectors. The resulting cDNA library was amplified by replication of each clone through limited infection of a bacterial host, and stored at −70° C.

The amplified hippocampus oligo dT-primed cDNA library was later retrieved from storage and $1 \times 10^6$ recombinants were screened for hybridization to oligonucleotides corresponding to nucleotides 96–128 (SE7) and nucleotides 2576–2609 (SE8) of the rat NMDAR1A receptor cDNA (see Moriyoshi et al. (1991) Nature 354:31). Hybridization was performed at 42° C. in 6×SSPE, 5×Denhart's solution, 10% formamide, 0.2% SDS and 200 µg/ml herring sperm DNA. Washes were performed in 1×SSPE and 0.2% SDS at 50° C. Hybridizing clones (e.g. NMDA1–3) were identified. These clones hybridized to SE8 but not to SE7.

A randomly primed primary human hippocampus cDNA library (~$2 \times 10^5$ recombinants prepared by selecting only cDNAs >2.0 kb for inclusion in the library) was screened under the same conditions for hybridization to oligonucleotide SE8 and an oligonucleotide corresponding to nucleotides 129–141 of the rat NMDAR1A receptor cDNA (SE11). Five hybridizing clones, which hybridized to SE8 and not to SE11, were identified: NMDA5–7 and NMDA10–11.

B. Characterization of Clones

The clones were plaque purified and characterized by restriction enzyme mapping and DNA sequence analysis of the inserts. One of the clones, NMDA11 (see description of Sequence ID No. 13 in Summary of Sequences for a description of a portion of NMDA11), is a full-length cDNA (i.e., it contains translation initiation and termination codons) encoding a complete NMDAR1 subunit. The remaining clones are partial cDNAs. Clones NMDA2, NMDA3 (see Sequence ID No. 17), NMDA5, NMDA6, NMDA7 (see Sequence ID No. 15), and NMDA10 (which encodes a 3083 nucleotide sequence comprising nucleotides 320–3402 of Sequence ID No. 1) contain a translation termination codon but lack nucleotides at the 5' end of the coding sequence.

Characterization of the clones revealed that the isolated cDNAs correspond to different alternatively spliced forms of the human NMDAR1 subunit transcript. The four types of alternate splicing represented by the clones are depicted schematically in FIG. 1. Clone NMDA10 (which lacks 5' untranslated sequences as well as 60 nucleotides of the 5' end of the coding sequence) is used as a reference to which the other variants are compared. Clone NMDA11 lacks 363 nucleotides (in the 3' portion of the clone) that are present in NMDA10. This 363-nucleotide deletion does not disrupt the reading frame of the transcript; however, it results in a different termination codon. The last 69 nucleotides of the coding sequence of NMDA11 correspond to 3' untranslated sequence of clone NMDA10 (i.e., nucleotides 3325–3393 of Sequence ID No. 1). Clone NMDA7 lacks the same 363-nucleotide sequence that is deleted from NMDA11 ; however, NMDA7 further lacks 204 nucleotides at the 5' end that are present in NMDA10 and NMDA11. This 204-nucleotide deletion also does not disrupt the reading frame of the transcript. Additionally, NMDA7 contains a 63-nucleotide in-frame insertion at the 5' end relative to NMDA10 and NMDA11. The last 69 base pairs of the coding sequence of NMDA7 correspond to 3' untranslated sequence of NMDA10 i.e., nucleotides 3325–3393 of Sequence ID No. 1). Clone NMDA3 lacks 1087 base pairs at the 3' end that are present in NMDA10. This 1087-base pair deletion does not disrupt the reading frame of the transcript; however it results in a different termination codon. The last 231 base pairs of the coding sequence of NMDA3 correspond to 3' untranslated sequence of clone NMDA10 (i.e., nucleotides 4049–4279 in Sequence ID No. 1).

EXAMPLE 2

Preparation of Full-length NMDAR1 Subunit cDNA Constructs

Portions of clones NMDA10, NMDA11 , NMDA7 and NMDA3 were ligated together to construct full-length cDNAs encoding variants of the NMDA receptor NMDAR1 subunit. The full-length NMDAR1 subunit cDNAs were incorporated into vector pcDNA1 (Invitrogen, San Diego, Calif.) for use in expressing the receptor subunits in mammalian host cells and for use in generating in vitro transcripts of the DNAs to be expressed in Xenopus oocytes.

Vector pcDNA1 is a pUC19-based plasmid that contains the following elements in the 5' -to-3' order: the cytomegalovirus (CMV) immediate early gene promoter/enhancer, the bacteriophage T7 RNA polymerase promoter, a polylinker, the bacteriophage SP6 RNA polymerase promoter, SV40 RNA processing (i.e., splice donor/acceptor) signals, SV40 polyadenylation signal, and the ColE1 origin and supF suppressor tRNA to permit maintenance of the vector in *Escherichia coli* strains with the P3 episome. This vector thus contains all the regulatory elements required for expression of heterologous DNA in a mammalian host cell, wherein the heterologous DNA has been incorporated into the vector at the polylinker. In addition, because the T7 and SP6 promoters are located on either side of the polylinker, this plasmid. can be used for synthesis of in vitro transcripts of heterologous DNA that has been sublconed into the vector at the polylinker.

A. NMDAR1A

Figure 2:
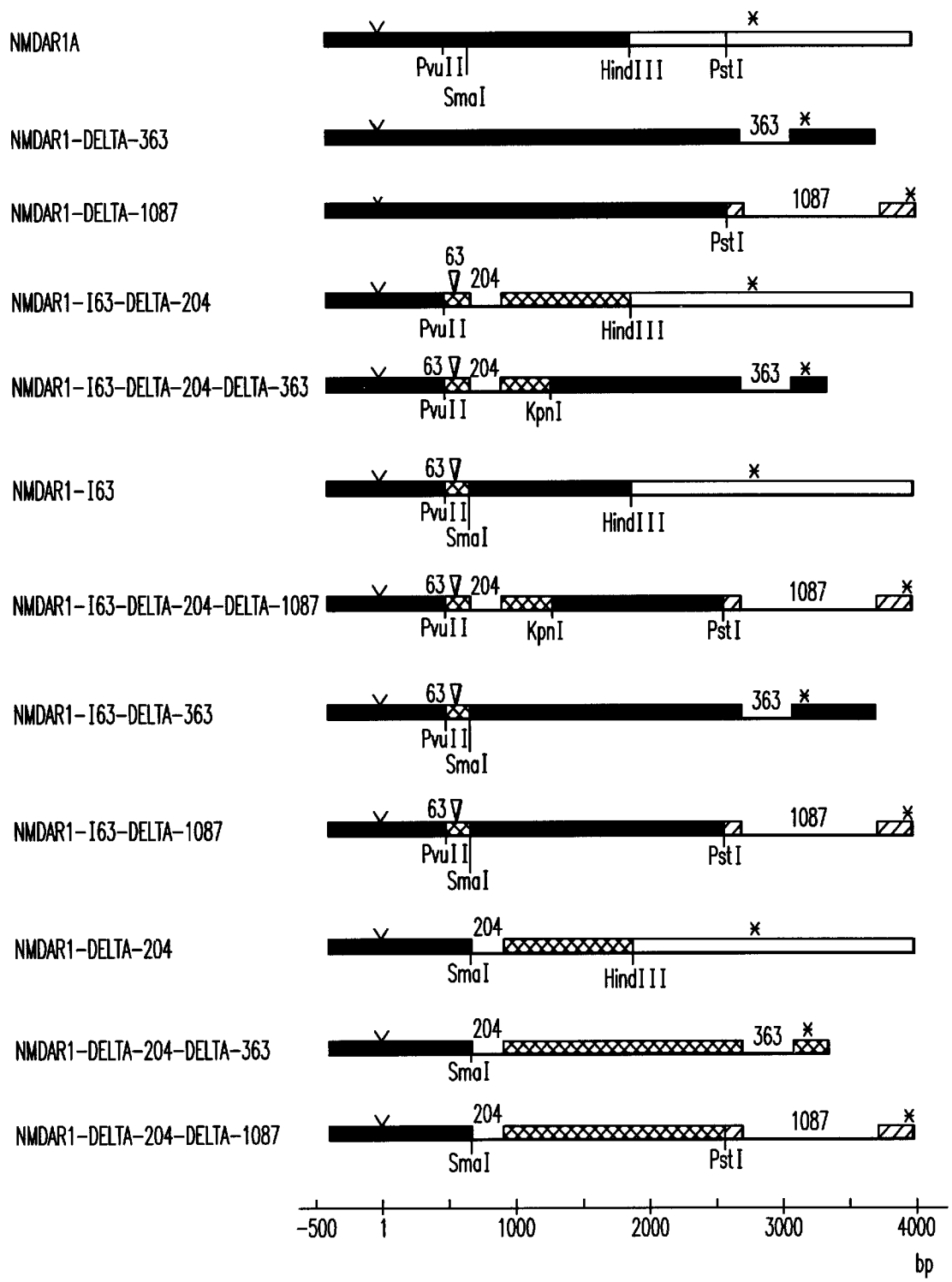
FIG. 2 is a schematic representation of cDNAs encoding full-length human NMDAR1 subunit subtypes of the invention, with partial restriction maps of each DNA. The full-length cDNAs are constructed by ligation of appropriate portions of the clones shown in FIG. 1. Regions of each full-length cDNA composed of nucleotide sequences corresponding to a particular clone are distinguished as solid, striped, cross-hatched or open boxes.

Full-length construct NMDAR1A was prepared by ligation of a 5' portion of NMDA11 (beginning 5' of the translation initiation codon and extending to the HindIII site in the middle of the clone) and a 3' portion of NMDA10 (beginning at the HindIII site in the middle of the clone and extending 3' of the translation termination codon) as depicted in FIG. 2. The two DNA fragments were joined in mammalian expression vector pcDNA1.

Figure 3B:
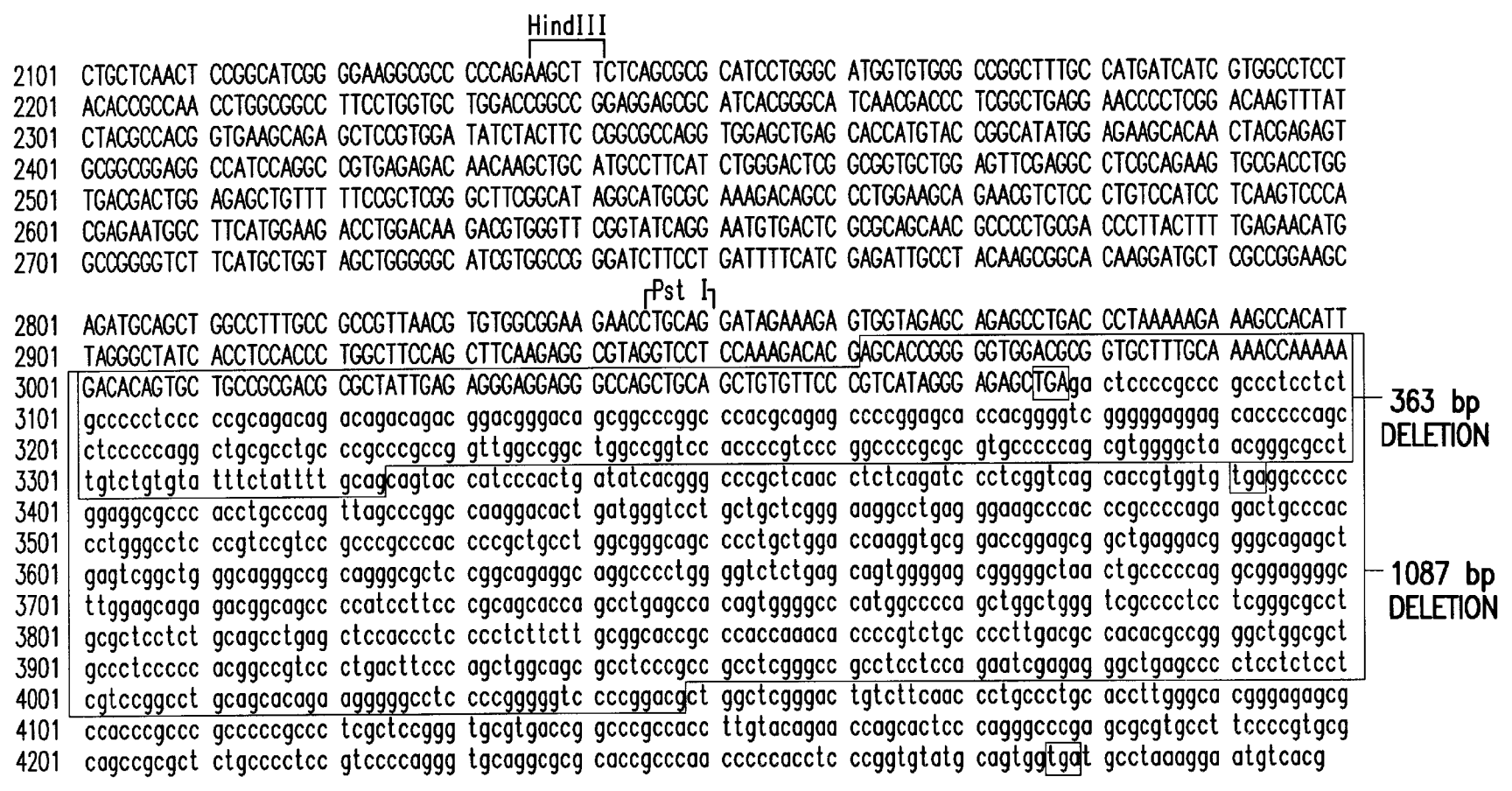

Initially, the strategy for generating the NMDAR1 construct involved a first step of separately subcloning the entire 4.0 kb EcoRI insert fragment of NMDA10 and the entire 4.0 kb SnaBI insert fragment of NMDA11 into pcDNA1; however, two attempts employing this cloning strategy were unsuccessful. It appeared that there may have been selection against *E. coli* hosts retaining the complete insert fragments since the surviving recombinant *E. coli* that were analyzed contained incomplete insert cDNAs from which nucleotides had been deleted. Therefore, it was necessary to prepare the full-length NMDAR1A construct in several steps by subcloning and combining various fragments of NMDA10 and NMDA11 in pcDNA1 as follows (see FIG. 3 for locations of restriction enzyme sites).

Clone NMDA10 as digested with BglII and EcoRI and the ~3.3 kb fragment containing nucleotides 1020–4298 of Sequence ID No. 1 was isolated and subcloned into BamHI/EcoRI-digested pcDNA1. The resulting plasmid was digested with HindIII and NheI and the fragment containing nucleotides 2137–4298 of Sequence ID No. 1 plus a portion of pcDNA1 was isolated.

Clone NMDA11 was digested with EcoRI and HindIII and the ~2.1 kb fragment containing nucleotides 1–2136 of Sequence ID No. 1 was isolated and subcloned into EcoRI/HindIII-digested modified pcDNA1 (modified by deletion of the HindIII site located 5' of the EcoRI site in the polylinker and addition of a HindIII site into the polylinker at a position 3' of the EcoRI site). The resulting plasmid was digested with NheI and HindIII and the fragment containing nucleotides 1–2136 of Sequence ID No. 1 plus a portion of modified pcDNA1 was isolated. This NheI/HindIII fragment was then ligated to the HindIII/NheI fragment containing nucleotides 2137–4298 of Sequence ID No. 1 to generate the full-length construct NMDAR1A (see FIG. 2). The ligation mix was used to transform *E. coli* strain MC1061/P3. Because the NheI site in pcDNA1 occurs within the supF selection gene, only *E. coli* containing the correctly ligated, complete NMDAR1A plasmid (which has the complete, functional selection gene) were able to survive the selection process. This fragment subcloning strategy enabled selection of the desired correct NMDAR1A-containing *E. coli* host cells, even though the total number of such recombinant host cells was small.

In summary, construct NMDAR1A contains 261 base pairs of 5' untranslated sequence from NMDAR11 (nucleotides 1–261 of Sequence ID No. 1) and a complete coding sequence (nucleotides 262–53078 of Sequence ID No.1) for the NMDAR1A variant of the NMDAR1 subunit as well as 1220 base pairs of 3' untranslated sequence (nucleotides 3079–4298 of Sequence ID No. 1). The NMDAR1A-encoding sequence is operatively linked to the regulatory elements in pcDNA1 for expression in mammalian cells.

B. NMDAR1-Δ363

Full-length construct NMDAR1-Δ363 was prepared by ligation of a 5' portion of NMDA11 (beginning 5' of the translation initiation codon and extending to the HindIII site in the middle of the clone, i.e., nucleotides 1–2136 in Sequence ID No. 1) and a 3' portion of NMDA11 (beginning at the HindIII site in the middle of the clone and extending 3' of the translation termination codon, i.e., nucleotides 2137–2961 and 3325–4298 of Sequence ID No. 1). As described above, due to the difficulty in directly subcloning the entire 4.0 kb SnaBI NMDA11 insert into pcDNA1, it was necessary to generate the construct by ligating two fragments of the NMDA11 insert into pcDNA1 as follows (see FIG. 3 for locations of restriction enzyme sites).

To obtain the 5' NMDA11 fragment, clone NMDA11 was digested with EcoRI and HindIII and the ~2.2 kb fragment containing nucleotides 1–2136 of Sequence ID No. 1 was isolated and subcloned into EcoRI/HindIII-digested modified pcDNA1 (modified as described above). The resulting plasmid was digested with NheI and HindIII and the fragment containing nucleotides 1–2136 of Sequence ID No. 1 plus a portion of modified pcDNA1 was isolated.

To obtain the 3' NMDA11 fragment, clone NMDA11 was digested with BglII and EcoRI and the 3.0 kb fragment containing nucleotides 1020–2961 and 3325–4298 of Sequence ID No. 1 was isolated and subcloned into BamHI/EcoRI-digested pcDNA1. The resulting plasmid was digested with HindIII and NheI and the fragment containing nucleotides 2137–2961 and 3325–4298 of Sequence ID No. 1 plus a portion of pcDNA1 was isolated. This HindIII/NheI fragment was then ligated to the NheI/HindIII fragment containing nucleotides 1–2136 of Sequence ID No. 1 to generate NMDAR1-Δ363.

In summary, construct NMDAR1-Δ363 contains 261 base pairs of 5' untranslated sequence (nucleotides 1–261 of Sequence ID No. 1) and a complete coding sequence for the NMDAR1-Δ363 variant NMDAR1 subunit (nucleotides 262–2961 and 3325–3393 of Sequence ID No. 1) as well as 905 base pairs of 3' untranslated sequence (nucleotides 3394–4298 of Sequence ID No. 1). Thus, NMDAR1-Δ363 differs from NMDAR1 in that it lacks 363 nucleotides (nucleotides 2962–3324 of Sequence ID No. 1) that comprise the last 117 nucleotides of the coding sequence and the first 246 nucleotides of the 3' untranslated sequence of NMDAR1. The NMDAR1-Δ363 subunit variant-encoding sequence is operatively linked to the regulatory elements in pcDNA1 for expression in mammalian cells.

C. NMDAR1-Δ1087

Full-length construct NMDAR1-Δ1087 was prepared by replacing the 3' end of the NMDAR1 variant-encoding insert of NMDAR1-Δ363 with a fragment from the 3' end of clone NMDA3 (see FIG. 2). Plasmid NMDAR1-Δ363 was partially digested with PstI and completely digested with XbaI. There is a PstI site ~112 nucleotides upstream of the location of the 363-nucleotide deletion in NMDAR1-Δ363 and an XbaI site in the polylinker located downstream of the 3' untranslated sequence of NMDAR1-Δ363 (see FIG. 3). Thus, PstI/XbaI digestion of NMDAR1-Δ363 results in removal of a fragment containing nucleotides 2850–2961 and 3325–4298 of Sequence ID No. 1 from the vector. The larger fragment was isolated from the digest.

The insert of clone NMDA3 was cloned into the EcoRI restriction site(s) of pGEM (Promega, Madison, Wis.); and the resulting plasmid was digested with PstI and XbaI. The smaller fragment containing nucleotides 2850–2961 and 4049–4298 of Sequence ID No. 1 was isolated and ligated to the larger fragment from the PstI/XbaI digest of NMDAR1-Δ363. The resulting construct was designated NMDAR1-Δ1087.

In summary, NMDAR1-Δ1087 contains 261 base pairs of 5' untranslated sequence (nucleotides 1–261 in Sequence ID No. 1), the complete coding sequence for the NMDAR1-Δ1087 variant NMDAR1 subunit (nucleotides 262–2961 and 4049–4279 of Sequence ID No. 1) and 19 base pairs of 3' untranslated sequence (nucleotides 4280–4298 of Sequence ID No. 1). Thus, NMDAR1-Δ1087 differs from NMDAR1 in that it lacks 1087 nucleotides (nucleotides 2962–4048 of Sequence ID No. 1) that comprise the last 117 nucleotides of the coding sequence and the first 970 nucleotides of the 3' untranslated sequence of NMDAR1. The NMDAR1-Δ1087 subunit variant-encoding sequence is operatively linked to the regulatory elements in pcDNA1 for expression in mammalian cells.

D. NMDAR1-I63-Δ204

Full-length construct NMDAR1-I63-Δ204 was prepared by replacing a 1399-nucleotide fragment of construct NMDAR1A (i.e, nucleotides 738–2136 of Sequence ID No. 1) with the PvuII-HindIII fragment of NMDA7 (i.e., nucleotides 738–831 of sequence ID No. 1, plus nucleotides 1–63 of Sequence ID No. 3 and nucleotides 832–984 and 1189–2136 of Sequence ID No. 1), as depicted in FIG. 2. Because there are multiple PvuII sites in the NMDAR1 construct, a several-step process was required for construction of NMDAR1-I63-Δ204 as follows (see FIG. 3 for the location of restriction enzyme sites).

The ~2.2-kb EcoRI-HindIII fragment isolated from construct NMDAR1A and containing nucleotides 1–2136 of Sequence ID No. 1 was ligated with modified pcDNA1 (modified as described in Example 2A) that had been digested with EcoRI and HindIII. The resulting plasmid was digested with AvrII and self-ligated to remove two PvuII sites from a portion of the plasmid contributed by pcDNA1. The plasmid was then partially digested with PvuII and completely digested with HindIII. The digest was ligated with a 1258-nucleotide PvuII-HindIII fragment isolated from clone NMDA7. The resulting plasmid, designated NMDAR1-I63-Δ204–5', was digested with BamHI and HindIII and the ~2-kb fragment containing nucleotides 1–831 of Sequence ID No. 1, plus nucleotides 1–63 of Sequence ID No. 3 and nucleotides 832–984 and 1189–2136 of Sequence ID No. 1 was isolated and ligated to BamHI/HindIII-digested NMDAR1 to generate NMDAR1-I63-Δ204.

NMDAR1-I63-Δ204 contains 261 base pairs of 5' untranslated sequence (nucleotides 1–261 in Sequence ID No. 1), the complete coding sequence for the NMDAR1-I63-Δ204 variant NMDAR1 subunit (nucleotides 262–831 of Sequence ID No. 1 plus nucleotides 1–63 of Sequence ID No. 3 and nucleotides 832–984 and 1189–3078 of Sequence ID No. 1) and 1220 base pairs of 3' untranslated sequence (nucleotides 3079–4298 of Sequence ID No. 1). Thus NMDAR1-I63-Δ204 differs from NMDAR1 in that it contains 63 nucleotides that are not present in NMDAR1 (nucleotides 1–63 of Sequence ID No. 3) located between nt 831 and 832 of Sequence ID No. 1. Further, NMDAR1-I63-

Δ204 lacks 204 nucleotides that are present in NMDAR1 (nucleotides 985–1188 of Sequence ID No. 1). The NMDAR1-I63-Δ204 subunit variant-encoding sequence is operatively linked to the regulatory elements in pcDNA1 for expression in mammalian cells.

E. NMDAR1-I63

Full-length construct NMDAR1-I63 can be described as NMDAR1 in which a 173-bp fragment (nucleotides 738–910 of Sequence ID No. 1) is replaced with the 236-bp PvuII-SmaI fragment of NMDA7 (nucleotides 738–831, of Sequence ID No. 1, plus nucleotides 1–63 of Sequence ID No. 3 and nucleotides 832–910 of Sequence ID No. 1). Because there are multiple PvuII sites in the NMDAR1 construct, a several-step process was required for construction of NMDAR1-I63 as follows. Plasmid NMDAR1-I63-Δ204-5' was partially digested with SmaI and completely digested with HindIII. The larger vector fragment was ligated with the 1226-bp SmaI/HindIII fragment isolated from NMDA11 (nucleotides 911–2136 of Sequence ID No. 1). The resulting vector was digested with BamHI and HindIII and the ~2.2-kb fragment containing nucleotides 1–831 of Sequence ID No. 1, plus nucleotides 1–63 of Sequence ID No. 3 and nucleotides 832–2136 of Sequence ID No. 1 was isolated and ligated to BamHI/HindIII-digested NMDAR1 to generate NMDAR1-I63.

NMDAR1-I63 contains 261 base pairs of 5' untranslated sequence (nucleotides 1–261 in Sequence ID No. 1), the complete coding sequence for the NMDAR1-I63 variant NMDAR1 subunit (nucleotides 262–831 of Sequence ID No. 1, plus nucleotides 1–63 of Sequence ID No. 3 and nucleotides 832–3078 of Sequence ID No. 1) and 1220 nucleotides of 3' untranslated sequence (nucleotides 3079–4298 of Sequence ID No. 1). Thus, NMDAR1-I63 differs from NMDAR1 in that it contains 63 nucleotides that are not present in NMDAR1 (nucleotides 1–63 of Sequence ID No. 3), located between nucleotides 831 and 832 of Sequence ID No. 1. The NMDAR1-I63 subunit variant-encoding sequence is operatively linked to the regulatory elements in pcDNA1 for expression in mammalian cells.

F. NMDAR1-I63-Δ204-Δ363

Full-length construct NMDAR1-I63-Δ204-Δ363 was prepared by replacing the 2861 nucleotide fragment from construct NMDAR1-I63-Δ204 (ie, nucleotides 1438–4298 Sequence ID No. 1) with the KpnI-XbaI (polylinker site) fragment of NMDAR1-Δ363 (ie, nucleotides 1438–2961 and 3325–4298 of Sequence ID No. 1) as depicted in FIG. 2. The NMDAR1-I63-Δ204 was completely digested with XbaI then partially digested with KpnI due to the presence of two additional KpnI sites in the vector sequence. The resulting 5' NMDAR1-I63-Δ204 fragment, which includes the pcDNAI vector sequences, was ligated with the 3' KpnI-XbaI fragment from NMDAR1-Δ363 to generate NMDAR1-I63-Δ204-Δ363.

In summary, construct NMDAR1-I63-Δ204-Δ363 contains 261 base pairs of 5' untranslated sequence (nucleotides 1–261 in Sequence ID No. 1), the complete coding sequence for the NMDAR1-I63-Δ204-Δ363 variant NMDAR1A subunit (nucleotides 262–831 of Sequence ID No. 1, plus nucleotides 1–63 of Sequence ID No. 3, plus nucleotides 832–984, 1189–2961 and 3325–3393 of Sequence ID No. 1) as well as 905 base pairs of 3' untranslated sequence (nucleotides 3394–4298 of Sequence ID. No. 1). Thus, NMDAR1-I63-Δ204-Δ363 differs from NMDAR1A in that it contains 63 nucleotides that are not present in NMDAR1A (nucleotides 1–63 of Sequence ID No. 3) located between nucleotides 831 and 832 of Sequence ID No. 1. Further, NMDAR1-I63-Δ204-Δ363 lacks 204 nucleotides that are present in NMDAR1A (nucleotides 985–1188 of Sequence ID No. 1) and 363 nucleotides that are present in NMDAR1A (nucleotides 2962–3324 of Sequence ID No. 1) that comprise the last 117 nucleotides of the coding sequence and the first 246 nucleotides of the 3' untranslated sequence of NMDAR1A. The NMDAR1-I63-Δ204-Δ363 subunit variant encoding sequence is operatively linked to the regulatory elements in pcDNAI for expression in mammalian cells.

G. NMDAR1-I63-Δ204-Δ1087

Full-length construct NMDAR1-I63-Δ204-Δ1087 was prepared by replacing the 2861 nucleotide fragment from construct NMDAR1-I63-Δ204 (ie, nucleotides 1438–4298 Sequence ID. No. 1) with the KpnI-XbaI .(polylinker site). fragment of NMDAR1-Δ1087 (ie, nucleotides 1438–2961 and 4049–4298 of Sequence ID No. 1) as depicted in FIG. 2. The NMDAR1-I63-Δ204 was completely digested with XbaI then partially digested with KpnI due to the presence of two additional KpnI sites in the vector sequence. The resulting 5' NMDAR1-I63-Δ204 fragment, which includes the pcDNAI vector sequences, was ligated with the 3' KpnI-XbaI fragment from NMDAR1-Δ1087 to generate NMDAR1-I63-Δ204-Δ1087.

In summary, construct NMDAR1-I63-Δ204-Δ1087 contains 261 base pairs of 5' untranslated sequence (nucleotides 1–261 in Sequence ID No. 1), the complete coding sequence for the NMDAR1-I63-Δ204-Δ363 variant NMDAR1A subunit (nucleotides 262–831 of Sequence ID No. 1, plus nucleotides 1–63 of Sequence ID No. 3, plus nucleotides 832–984, 1189–2961 and 4280–4298 of Sequence ID No. 1) as well as 19 base pairs of 3' untranslated sequence (nucleotides 4280–4298 of Sequence ID. No. 1). Thus, NMDAR1-I63Δ204-Δ1087 differs from NMDAR1A in that it contains 63 nucleotides that are not present in NMDAR1A (nucleotides 1–63 of Sequence ID No. 3) located between nucleotides 831 and 832 of Sequence ID No. 1. Further, NMDAR1-I63-Δ204-Δ1087 lacks 204 nucleotides that are present in NMDAR1A (nucleotides 985–1188 of Sequence ID No. 1) and 1087 nucleotides that are present in NMDAR1A (nucleotides 2962–4048 of Sequence ID No. 1) that comprise the last 117 nucleotides of the coding sequence and the first 970 nucleotides of the 3' untranslated sequence of NMDAR1A. The NMDAR1-I63-Δ204-Δ1087 subunit variant encoding sequence is operatively linked to the regulatory elements in pcDNAI for expression in mammalian cells.

H. Additional Constructs Containing Full-Length cDNAs Encoding Variants of the NMDAR1 Subunit Additional full-length cDNAs encoding further possible NMDAR1 variants can be constructed using methods similar to those described in Examples 2A–G above. Specifically, the following constructs can be prepared by ligating portions of clones NMDA11, NMDA10, NMDA7 and NMDA3 as depicted in FIG. 2:

| | |
|---|---|
| NMDAR1-Δ204 | (Sequence ID No. 29) |
| NMDAR1-Δ204-Δ363 | (Sequence ID No. 31) |
| NMDAR1-I63-Δ363 | (Sequence ID No. 35) |
| NMDAR1-I63-Δ1087 | (Sequence ID No. 37) |
| NMDAR1-Δ204-Δ1087 | (Sequence ID No. 33) |

The full-length cDNAs can also be incorporated into mammalian expression vectors such as pcDNA1, as described in Examples 2A–G.

Several methods can be employed to determine which NMDAR1 subunit variants are actually expressed in various human tissues. For example, oligonucleotides specific for the nucleotide sequences located 5' and 3' of the insertions and deletions of the NMDAR1 transcripts described herein can be used to prime nucleic acid amplifications of RNA isolated from various tissues and/or cDNA libraries prepared from various tissues. The presence or absence of amplification products and the sizes of the products indicate which variants are expressed in the tissues. The products can also be characterized more thoroughly by DNA sequence analysis.

RNase protection assays can also be used to determine which variant transcripts are expressed in various tissues. These assays are a sensitive method for detecting and quantitating an RNA species in a complex mixture of total cellular RNA. A portion of the NMDAR1subunit variant DNA is labeled and hybridized with cellular. RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualed by gel electrophoresis and autoradiography.

Further information on possible splice variants of the NMDAR1 primary transcript can be obtained by isolation of genomic clones containing NMDAR1 subunit-encoding sequences (for example, by hybridization to the human NMDAR1 subunit cDNAs disclosed herein) and subsequent characterization of the resulting clones.

EXAMPLE 3

Isolation of DNA Encoding Human NMDA Receptor NMDAR2C Subunits

Degenerate oligonucleotides were synthesized based on two conserved regions of rat NMDAR2A, NMDAR2B and NMDAR2C DNAs that encode the putative first and fourth transmembrane domains. In rat NMDAR2A DNA, these regions are encoded by nucleotides 1669–1692 (oligo SE74) and 2437–2465 (olig SE75), respectively. [see Monyer et al. (1992) *Science* 256:1217–1221]. These oligonucleotides were used to prime nucleic acid amplification of cDNAs prepared from RNA isolated from human hippocampus, cerebellum, and orbitofrontal tissue. Two products, a 795-bp and a 640-bp fragment, were detected when the reaction mixture was analyzed by gel electrophoresis and ethidium bromide staining. The 795-bp fragment amplified from the cerebellum cDNA was subcloned into PCR1000 (Invitrogen, San Diego, Calif.) and characterized by DNA sequence analysis, which revealed that it is ~86% similar to the rat NMDAR2A DNA sequence, ~78% similar to the rat NMDAR2B DNA sequence, and ~74% similar to the rat NMDAR2C DNA sequence. Thus, this plasmid was named pcrNMDAR2A.

The 795-bp insert from pcrNMDAR2A was used to screen 1×10⁶ recombinants of a human hippocampus cDNA library (prepared by using random primers to synthesize cDNAs from hippocampus tissue and selecting fragments >2.0 kb for insertion into λgt10 vectors) and a human cerebellum cDNA library (random-primed library size-selected for fragments >2.8 kb in λgt10). Hybridization was performed in 5×SSPE, 5×Denhart's solution, 50% deionized formamide, 0.2% SDS, 200 μg/ml sonicated, denatured herring sperm DNA at 42° C. Washes were performed in 1×SSPE, 0.2% SDS at 55° C. The probe hybridized to 11 plaques from the hippocampus library and 8 plaques from the cerebellum library.

DNA sequence analysis and/or restriction enzyme mapping of the hybridizing plaques that were purified surprisingly revealed that they were more similar to rat NMDAR2C DNA than to rat NMDAR2A DNA. All of the clones were partial cDNAs (i.e., they lacked a translation initiation and/or termination codon) and were designated as NMDAR2C cDNAs. Comparison of the clones revealed that the human NMDAR2C subunit transcript is differentially processed.

Clones NMDA26, NMDA24, NMDA22 and NMDA21 (see FIG. 4) represent four basic clones that were identified, all of which are believed to be splice variants. Clone NMDA26 (nucleotides 1–3025 of Sequence ID No. 5) is used as a reference to which the other variants can be compared. Clone NMDA24 (Sequence ID No. 44) contains a 24-bp sequence (see Sequence ID No. 7) that is not present in NMDA26. Clone NMDA22 (Sequence ID No. 43) lacks bp that are present in NMDA26, and clone NMDA21 (Sequence ID No. 41) lacks 51 bp that are present in NMDA26. Clones NMDA22 and NMDA24 both contain an 11-bp sequence (Sequence ID No. 9) that is not present in NMDA26 (between nucleotides 1116–1117 of Sequence ID No. 5). Introduction of this sequence. into these clones (between nucleotides 1116–1117 of Sequence ID No. 5) disrupts the reading frame of the transcript and introduces a premature translation termination (i.e., STOP) codon into the transcript.

Clones NMDA26 and NMDA27 (see FIG. 4) are partial NMDAR2C cDNAs that contain 5' untranslated sequence, a translation initiation codon and some of the coding sequence. Clone NMDA26 contains 188 base pairs of 5' untranslated sequence whereas clone NMDA27 contains ~1.1 kb of 5' untranslated sequence. The sequences of the 5' untranslated regions of these two clones are identical for the first nucleotides proceeding 5' of the translation initiation codon. However, beginning with the 16th nucleotide 5' of the translation initiation codon, the sequences of the two clones diverge (compare nucleotides 116–191 of Sequence ID No. to nucleotides 1–74 of Sequence ID No. 12).

EXAMPLE 4

Preparation of Full-length NMDAR2C Subunit cDNA Constructs

Figure 5:
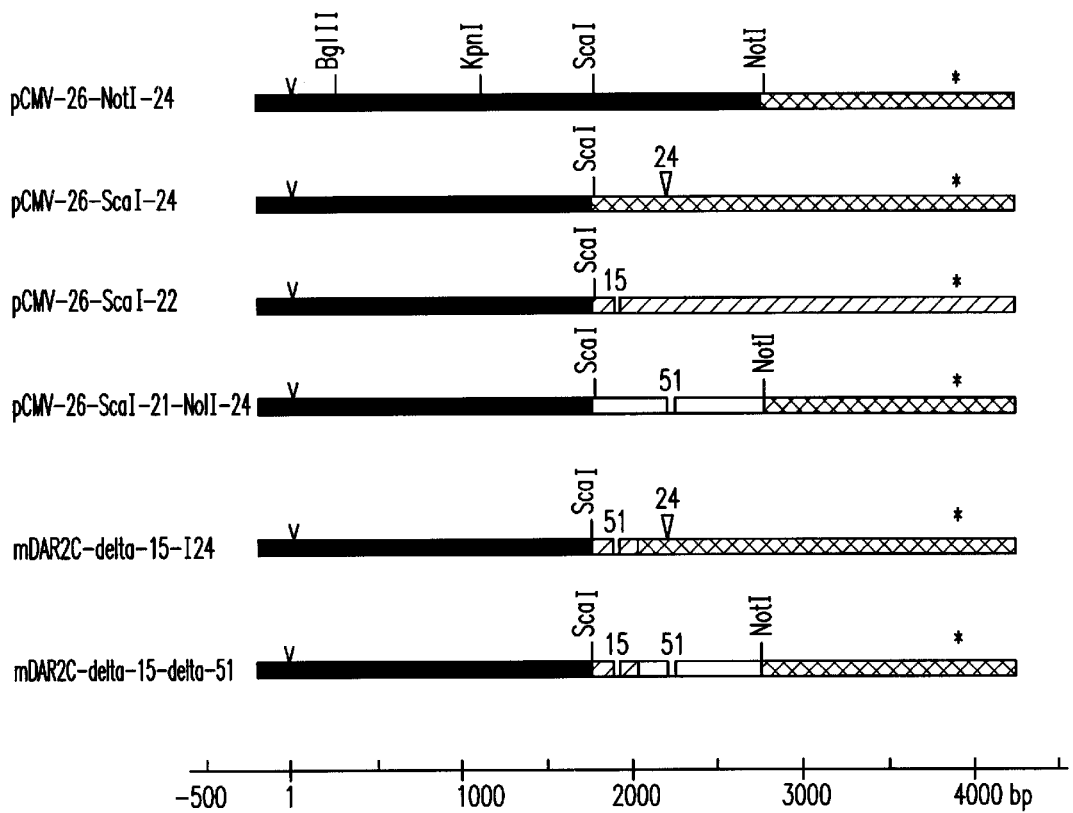
FIG. 5 is a schematic representation of full-length human NMDAR2C subunit subtypes of the invention, with partial restriction maps of each DNA. The full-length cDNAs are constructed by ligation of appropriate portions of the clones shown in FIG. 4. Regions of each full-length cDNA composed of nucleotide sequences corresponding to a particular clone are distinguished as solid, striped, cross-hatched or open boxes.

Portions of the partial NMDAR2C clones can be ligated in a variety of ways to generate constructs encoding full-length NMDAR2C subunit variants. The 5' end of each NMDAR2C cDNA can be contributed by NMDA26, whereas the 3' ends of the constructs are contributed by various combinations of clones NMDA21, NMDA22, and NMDA24. FIG. 5 depicts full-length NMDAR2C constructs and indicates the portions of the different clones that contribute to each construct.

For example, full-length constructs can be prepared using methods such as those described in Example 2 for preparing NMDAR1 constructs. Thus, clone inserts are transferred into a vector (e.g., pcDNA1 ) for ease of manipulation and then desired portions of the cDNAs are isolated by restriction enzyme digestion of the vectors. This can require several steps and/or partial digests if, for example, there are no unique restriction enzyme sites surrounding the desired portions of the cDNAs. The desired cDNA fragments are then ligated and incorporated into an expression plasmid such as pcDNA1 or pCMV-T7-2.

Plasmid pCMV-T7-2 (see FIG. 6) is a pUC19-based vector that contains a cytomegalovirus (CMV) promoter/enhancer, SV40 splice donor/splice acceptor sites located immediately downstream of the promoter, a T7 bacteriophage RNA polymerase promoter positioned downstream of the SV40 splice sites, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. Plasmid pCMV-T7-3, also depicted in FIG. 6, is identical to pCMV-T7-2 except that the order of the restriction enzyme sites in the polylinker is reversed. This plasmid can also be used for heterologous expression of NMDAR subunit DNA.

Construct pcDNA1-26-NotI-24-5' UT contains 188 base pairs of 5' untranslated sequence (nucleotides 1–188 of Sequence ID No. 5), the complete coding sequence of the first variant of the human NMDAR2C subunit (nucleotides 189–3899 of Sequence ID No. 5) and ~440 base pairs of 3' untranslated sequence (nucleotides 3900–4340 of Sequence ID No. 5). The NMDAR2C cDNA is contained within the polylinker of expression vector pcDNA1 for expression.

Construct pCMV-26-NotI-24 (Sequence ID No. 5) contains 49 base pairs of 5' untranslated sequence (nucleotides 140–188 of Sequence ID No. 5), the complete coding sequence of a first variant of the human NMDAR2C subunit (nucleotides 189–3899 of Sequence ID No. 5) and ~440 base pairs of 3' untranslated sequence (nucleotides 3900–4340 of Sequence ID No. 5). The NMDAR2C cDNA is contained within the polylinker of expression vector pCMV-T7-2 for expression.

Construct pCMV-26-ScaI-24 (Sequence ID No. 45) is identical to pCMV-26-NotI-24, except it contains 24-base pairs (Sequence ID No. 7) inserted between nucleotides 2350 and 2351 of Sequence ID No. 5.

Construct pCMV-26-ScaI-22 (Sequence ID No. 47) is identical to pCMV-26-NotI-24, except that it lacks 15-base pairs (nucleotides 1960–1974 of Sequence ID No. 5).

Construct pCMV-26-ScaI-21-NotI-24 (Sequence ID No. 49) is identical to pCMV-26-NotI-24, except that it lacks 51-base pairs (nucleotides 2351–2401 of Sequence ID No. 5).

Construct NMDAR2C-Δ15-I24 (Sequence ID No. 51) is identical to pCMV-26-NotI-24, except that it lacks 15-base pairs (i.e., nucleotides 1960–1974 of Sequence ID No. 5) and includes a 24-base pair sequence (i.e., Sequence ID No. 7; inserted between nucleotides 2350 and 2351 of Sequence ID No. 5).

Construct NMDAR2C-Δ15–Δ51 (Sequence ID No. 53) is identical to pCMV-26-NotI-24, except that it lacks 15-base pairs (i.e., nucleotides 1960–1974 of Sequence ID No. 5) and 51-base pairs (i.e., nucleotides 2351–2401 of Sequence ID No. 5).

Additional full-length NMDAR2C constructs can readily be prepared as described herein. For example, 5' untranslated sequence obtained from NMDA27 (instead of NMDA26) can be employed, and the 3' ends of the constructs can be contributed by various combinations of clones NMDA21, NMDA22, and NMDA24.

Several methods (e.g., nucleic acid amplification, RNase protection assays, etc.), as described in Example 2, can be employed to determine which NMDAR2C subunit variants are actually expressed in various human tissues.

Human NMDAR2C has 83.5% GC nucleotide content between nucleotides 2957 and 3166. To potentially enhance NMDAR2C subunit expression, the GC content in this region can be reduced while maintaining the native amino acid sequence. Synthetic DNAs can be made by oligonucleotide primer extension across this region. Four oligonucleotides, SE343 (Sequence ID No. 59), SE344 (Sequence ID No. 60), SE345 (Sequence ID No. 61), and SE346 (Sequence ID No. 62) were synthesized. These primers maintain the amino acid sequence of the human NMDAR2C receptor and some restriction sites, but lower the overall GC content of this region to 53.4%. The criteria for the modification of bases were: 1) to not have more than 4 guanine nucleotides in a row if at all possible, 2) to maintain the restriction cutting sites for NotI (nucleotides 2962–2969 of Sequence ID No. 5), AvaII (nucleotides 3069–3073 Sequence ID No.5), and AatII (nucleotides 3156–3161 of Sequence ID No. 5), 3) to reduce the secondary structure of the oligonucleotides as much as possible, 4) to not introduce any additional NotI, AvaII or AatII restriction sites into the sequence and 5) to have the basepair overlap between oligonucleotide pairs, {SE343 and SE344} or {SE345 and SE346} have a proposed melting temperature between 62–66° C. The oligonucleotide pair SE343 and SE344 have complementary sequence from nucleotides 51–71 of Sequence ID Nos. 59 and 60. The oligonucleotide pair SE345 and SE346 have complementary sequence from nucleotides 42–61 of Sequence ID No. 61 and nucleotides 43–62 of Sequence ID No. 62, resepectively.

The primer pairs, {SE343 and SE344} and {SE345 and SE346}, are combined in a standard PCR reaction mixture, which contains 50 pmoles of each oligonucleotide, and are amplified according to the following PCR protocol:

Annealing temperature of 55° C. for 1 min, extension temperature of 72° C. for 2 min and melting temperature, 96° C. for seconds for cycles.

The resulting 121 bp PCR product from the primer pair SE343-SE344 is digested with NotI and AvaI, and the resulting 103 bp PCR product from the primer pair SE345-SE346 is digested with AvaI and AatII. These fragments are ligated into pCMV-NMDAR2C-26-NotI-24, which has been partially digested with both NotI and AatII due to the presence of additional NotI and/or AatIII restriction sites in the vector sequence, to form pCMV-26-NotI-24-GCMOD. This construct, pCMV-26-NotI-24-GCMOD, contains nucleotides 140–2965 of Sequence ID No. 5, followed by the 195 nucleotides set forth in Sequence ID No. 63, and then nucleotides 3161 to 4340 of Sequence ID. No. 5.

EXAMPLE 5

Isolation of DNA Encoding Human NMDA Receptor NMDAR2A Subunits

Two human cDNA libraries were prepared using different oligonucleotides (random and specific primers) to prime cDNA synthesis from RNA isolated from cerebellum tissue. The specific primer used for first-strand synthesis was SE162, nucleotides 904 to 929 of Sequence ID No. 10. cDNAs synthesized by random priming that ranged in size from 1.0–2.8 kb, and cDNAs synthesized by specific priming that ranged in size from 0.6–1.1 kb, were isolated and inserted into the λgt10 phage vector to generate the two libraries.

The random-primed library ($3 \times 10^6$ recombinants) was screened for hybridization to the 795-base pair insert from pcrNMDAR2A (see Example 3) in 5×SSPE, 5×Denhart's solution, 50% deionized formamide, 0.2% SDS, 200 μg/ml sonicated, denatured herring sperm DNA at 42° C. Washes were performed in 1×SSPE, 0.2% SDS at 55° C. The probe hybridized to 11 plaques.

The specifically-primed library (6×10⁵ recombinants) was screened for hybridization to oligonucleotide SE177 (nucleotides 859 to 884 of Sequence ID No. 10) in 6×SSPE, 5×Denhart's solution, 10% deionized formamide, 0.2% SDS, 200 µg/ml sonicated, denatured herring sperm DNA at 42° C. Washes were performed in 1×SSPE, 0.2% SDS at 50° C. The probe hybridized to 2 plaques.

Nine of the hybridizing plaques were purified and the inserts were characterized by restriction enzyme mapping and DNA sequence analysis. All clones contained partial cDNAs. Two of the clones, NMDA53 and NMDA54, contain the translation initiation codon and 320 base pairs and 88 base pairs, respectively, of 5' untranslated sequence. The sequences of four other clones, NMDA47, NMDA49, NMDARSO and NMDA51, along with those of NMDA53 and NMDA54, overlap to comprise ~70% of the human NMDAR2A subunit coding sequence (see nucleotides 1–3084 of Sequence ID No. 10).

To obtain clones containing the remaining ~1300 base pairs of 3' sequence needed to complete the NMDAR2A coding sequence, 6.6×10⁶ recombinants of an additional human cDNA library (an amplified randomly primed cerebellum cDNA library with inserts ranging from 1.0–2.8 kb in length) were screened for hybridization to an oligonucleotide corresponding to the 3' end of clone NMDA51 (oligo SE171; nucleotide 3454 to 3479 of Sequence ID No. 10) using the same conditions as used for screening the specifically primed cerebellum cDNA library as described above. Four hybridizing plaques were purified and the inserts were characterized by DNA sequence analysis to determine if they contain the 3' end of the coding sequence and a translation termination codon. Two of the clones (NMDA57 and NMDA58, which were determined to be identical), contain a translation termination codon, as determined by DNA sequence analysis. Phage lysate containing clone NMDA57 were deposited under the provisions of the Budapest Treaty with the American Type Culture Collection (ATCC) on Apr. 13, 1993, and assigned Accession No. 75442.

EXAMPLE 6

Preparation of Full-length NMDAR2A Subunit cDNA Constructs

Two separate constructs encoding a full-length NMDAR2A subunit (pCMV-hNMDAR2A-1(53) and pCMV-hNMDAR2A-2(54) were prepared by ligating portions of the following partial NMDAR2A clones: NMDAR47, NMDAR50, NMDAR58 and either NMDAR53 or NMDAR54 (NMDA53 and NMDA54 differ only in the amount of 5' untranslated sequence contained in the clones. The inserts of clones NMDA47, NMDA50 and NMDA58 were isolated as EcoRI fragments and ligated with EcoRI-digested pCMV-T7-2 to create pNMDA47, pNMDA50 and pNMDA58, respectively. The inserts of clones NMDA53 and NMDA54 were isolated as XhoI fragments and ligated with SalI-digested pCMV-T7-2 to create pNMDA53 and pNMDA54, respectively.

pNMDA47 was digested with ScaI and NsiI to liberate an ~3,350-bp fragment containing a 3' portion of the β-lactamase gene, which encodes a protein which imparts ampicillin-resistance, and nucleotides 824–2415 of Sequence ID No. 10. This fragment was ligated with a ~2890-bp NsiI/ScaI fragment of PNMDA50 (containing a 5' portion of the β-lactamase gene and nucleotides 2416–3346 of Sequence ID No. 10) to generate pNMDA47+50.

The portion of pNMDA58 that encodes the 3' end of NMDAR2A contains two MscI sites. Because the 3' MscI site is cleaved in preference to the 5' MscI site, partial digestion of pNMDA58 was not an option. Thus, pNMDA58 was digested with ScaI/MscI, and the ~2020-bp fragment containing a 5' portion of the β-lactamase gene and a 3' portion of the insert (nucleotides 4751–4808 of Sequence ID No. 10) was isolated. This fragment was ligated to a ~4150-bp ScaI/MscI fragment of pNMDA47+50 (containing a 3' portion of the β-lactamase gene and nucleotides 824–3212 of Sequence ID No. 10) to generate pNMDA47+50+3' END58. This plasmid contained a complete β-lactamase gene and nucleotides 824–3214 and 4751–4808 of Sequence ID No. 10. To add nucleotides 343–4750 of Sequence ID No. to pNMDA47+50+3' END58, pNMDA58 was digested with MscI, and the isolated 1537-bp fragment consisting of nucleotides 3213–4750 of Sequence ID No. 10 was ligated to MscI-digested pNMDA47+50+3' END58. The resulting plasmid, pNMDA47+50+58, contained nucleotides 824–4808 of Sequence ID No. 10.

To generate two constructs containing identical NMDAR2A coding sequences but differing amounts of 5' untranslated sequence, pNMDA53 and pNMDA54 were digested with ScaI/EcoRI to liberate fragments containing a 3' portion of the β-lactamase gene and nucleotides 1–854 and 225–854 of Sequence ID No. 10, respectively. pNMDA47+50+58 was digested with ScaI/EcoRI (partial) and the 3954-bp fragment containing a 5' portion of the β-lactamase gene and nucleotides 855–4808 of Sequence ID No. was separately ligated with the ScaI/EcoRI fragments of pNMDA53 and pNMDA54 to generate pCMV-hNMDAR2A-1(53) and pCMV-hNMDAR2A-2(54), respectively. These two constructs are identical except for the amount of 5' untranslated sequence contained in each. Both contain a full-length NMDAR2A-encoding sequence (nucleotides 311–4705 of Sequence ID No. 10) and 103 nucleotides of 3' untranslated sequence (nucleotides 4706–4808 of Sequence ID No. 10). pCMV-hNMDAR2A-1(53) contains 310 nucleotides of 5' untranslated sequence (nucleotides 1–310 of Sequence ID No. 10), whereas pCMV-hNMDAR2A-2(54) contains 87 nt of 5' untranslated sequence (nucleotides 224–310 of Sequence ID No. 10). The NMDAR2A cDNA is operatively linked to the regulator elements of pCMV-T7-2 for expression in mammalian host cells.

There is no unique restriction site 3' of the NMDAR2A-specific DNA in pCMV-hNMDAR2A-1(53) that can be used to linearize the plasmid in order to prepare in vitro transcripts for injection into Xenopus oocytes. To make a construct that has a unique 3' restriction site (pCMV-hNMDAR2A-3(53)), essentially the entire NMDAR2A-specific DNA of pCMV-hNMDAR2A-1(53) was transferred into vector pCMV-T7-3 as follows. pCMV-NMDAR2A-1 (53) was digested with NotI and the ~4.4-kb fragment was isolated and ligated with NotI-digested pCMV-T7-3 to generate pCMV-hNMDAR2A-3(53).

EXAMPLE 7

Isolation of DNA Encoding Human NMDA Receptor NMDAR2B Subunits

A human fetal brain λZAP cDNA library (1×10⁶ recombinants; Stratagene, La Jolla, Calif.) was screened for hybridization to a DNA fragment containing the entire rat NMDAR2B subunit coding sequence (see Monyer et al. (1992) Science 256:1217–1221). Hybridization was conducted in 50% deionized formamide, 5×Denhart's solution, 5×SSPE, 200 µg/ml sonicated, denatured herring sperm DNA and 0.2% SDS at 42° C. Washes were performed in 0.5×SSPE, 0.2% SDS at 65° C. One of the hybridizing clones excised from the human fetal brain library, NMDA81, containing a 5,435 bp insert and translation initiation and termination codons, encodes a full-length NMDAR2B subunit. This excised plasmid, which is in the pBluescript vector, was called pBS-hNMDAR2B.

NMDA81 was digested with EcoRI/EcoRV and the ~5.5-kbp fragment was isolated and ligated to EcoRI/EcoRV-digested pCMV-T7-3. The resulting construct, pCMVPL3-hNMDAR2B, contains the NMDAR2B coding sequence (nucleotides 210–4664 of Sequence ID No. 55), as well as 209 nucleotides of 5' untranslated sequence (nucleotides 1–209 of Sequence ID No. 55) and 339 nucleotides of 3' untranslated sequence (nucleotides 4665–5003 of Sequence ID No. 55). The NMDAR2B-encoding DNA in this construct is operatively linked to regulatory elements in pCMV-T7-3 for expression in mammalian host cells.

EXAMPLE 8

Isolation of DNA Encoding Human NMDA Receptor NMDAR2D Subunits

A human fetal brain cDNA library ($1\times10^6$ recombinants; Stratagene, La Jolla, Calif.) was screened by subtraction screening methods for DNA encoding a human NMDAR2D receptor subunit. In this method, plaques were selected on the basis of weak or no hybridization to DNAs encoding human NMDAR2A, NMDAR2B and NMDAR2C subunits.

Initially, the library was screened for hybridization to pcrNMDAR2A (see Example 3) under low-stringency conditions (30% deionized formamide, 5×Denhart's solution, 5×SSPE, 200 ng/ml sonicated herring sperm DNA, 0.2% SDS at 42° C.). Washes were also performed using low-stringency conditions (2×SSPE, 0.2% SDS, 50° C.). The filters were stripped, then screened for hybridization to the pcrNMDAR2A fragment and to an ~1200 bp PstI fragment of DNA encoding a human NMDAR2B subunit (see Example 7) and an ~950 bp AccI fragment of DNA encoding a human NMDAR2C subunit (see Example 3). These fragments contain DNA encoding all of the putative transmembrane domains of the subunits. Hybridization was performed under high stringency conditions (50% deionized formamide, 5×Denhart's solution, 5×SSPE, 200 ng/ml sonicated herring sperm DNA, 0.2% SDS at 42° C.) as were washes (0.1×SSPE, 0.1% SDS, 65° C.).

Eighteen of the plaques that hybridized weakly to pcrNMDAR2A in the initial low stringency screening of the library hybridized only weakly or not at all to portions of DNA encoding human NMDAR2A, NMDAR2B and NMDAR2C subunits in the high stringency screening. The plaques were purified, and the insert fragments were characterized by DNA sequence analysis. One of the inserts, NMDA96, corresponds to the 3' half of the human NMDAR2D subunit gene coding sequence. The sequence of this clone is provided in Sequence ID No. 57.

To obtain clones containing the remaining ~2000 bp of 5' sequence needed to complete the NMDAR2D subunit coding sequence, the human fetal brain cDNA library was screened for hybridization to an ~831 bp SmaI fragment of the clone containing the 3' half of the NMDAR2D coding sequence under high stringency hybridization and washing with 0.5×SSPE, 0.2% SDS at 65° C. Nine hybridizing plaques were purified and analyzed by DNA sequencing, which revealed that none of the plaques contain DNA encoding a translation initiation codon and extending 3' to at least the 5' end of the clone containing the 3' half of the NMDAR2D coding sequence.

A human cDNA library was prepared using a specific oligonucleotide, SE296, to prime cDNA synthesis from RNA isolated from human fetal brain. The specific primer used for first-strand synthesis was SE296 (nucleotides 2920–2949 of Sequence ID No. 57). cDNAs synthesized by specific priming that were greater than 2.2 kb in size were isolated and inserted into the λZAPII phage vector to generate the library.

The specifically primed library ($1\times10^6$ recombinants) was screened for hybridization to the 831 bp SmaI fragment from NMDAR2D (nucleotides 2435–3265 of Sequence ID No. 57) in 5×SSPE , 5×Denhart's solution, 50% deionized formamide, 0.2% SDS, 200 µg/ml sonicated, denatured herring sperm DNA at 42° C. Washes were performed in 0.1×SSPE, 0.2% SDS at 65° C. One probe hybridized to 11 plaques.

Eleven of the hybridizing plaques were purified, and the inserts characterized by restriction enzyme mapping and DNA sequence analysis. Six of the clones (NMDA111, NMDA112, NMDA115, NMDA116, NMDA119 and NMDA121) contain the translation initiation codon and varying amounts of 5' untranslated sequence.

The sequences of these clones overlap with NMDA96 to constitute 100% of the human NMDAR2D subunit coding sequence (see nucleotides 485–4495 of Sequence ID No. 57).

The full-length hNMDAR2D construct was prepared using NMDA115 and NMDA96 cDNAs. NMDA115 and NMDA96 cDNAs are already in the pBlueScript vector, however the NMDA115 cDNA is in the sense orientation from the T7 promoter, while the NMDA96 cDNA is in the antisense orientation. For ease of subcloning the full-length construct, the NMDA96 cDNA was cloned into the sense orientation by digesting NMDA96 with EcoRI and screening the resulting clones for orientation (NMDAR96-T7). Within the complete human NMDAR2D sequence, there is a unique HindIII at nucleotides 2804 that was used to clone NMDA115 together with NMDA96. However, there is an additional HindIII site in the pBS polylinker at the 5' end of the NMDA115 cDNA. Therefore NMDA115 was fully digested with SpeI, a 3' polylinker site, and partially digested with HindIII. The resulting ~5.6 kb SpeI-HindIII fragment from pNMDA115 (pBS vector plus nucleotides 397–2804 of Sequence ID No. 57) was ligated with the 1.7 kb HindIII-SpeI fragment (nucleotides 2805–4651 of Sequence ID No. 57) from NMDA96-T7 to form pBS-hNMDAR2D. In vitro transcripts were prepared for co-injection into Xenopus oocytes to test for alteration of NMDAR1A currents.

The complete NMDAR2D insert is then transfered into the pMMTV-T7+mammalian expression vector as a ~4.7 kb EcoRVISpeI fragment. The EcoRV and SpeI restriction sites are in the multiple cloning region of the pBluscript vector.

In summary, construct NMDAR2D contains 88 base pairs of 5' untranslated sequence (nucleotides 397–484 in Sequence ID No. 57), the complete coding sequence for the NMDAR2D subunit (nucleotides 484–4495 of Sequence ID No. 57) as well as 200 base pairs of 3' untranslated sequence (nucleotides 4496–4695 of Sequence ID No. 57). The NMDAR2D subunit encoding sequence is operatively linked to the regulatory elements in pMMTV-T7 for expression in mammalian cells.

EXAMPLE 9

Expression of Recombinant Human NMDA Receptor Subunits on Oocytes

Xenopus oocytes were injected with in vitro transcripts prepared from constructs containing DNA encoding human NMDA receptor NMDAR1 and NMDAR2 subunits. Electrophysiological measurements of the oocyte transmembrane currents were made using the two-electrode voltage clamp technique (see e.g., Stuhmer (1992) Meth. Enzymol. 207:319–339).

A. Preparation of In Vitro Transcripts

Recombinant capped transcripts of NMDA receptor subunit cDNAs contained in constructs NMDAR1A, NMDAR1-I63, NMDAR1-I63-Δ204, NMDAR1-Δ1087, NMDAR1-Δ363, and pCMV-26-NotI-24 were synthesized from linearized plasmids using the mCAP RNA Capping Kit (Cat. #200350, Stratagene, Inc., La Jolla, Calif.). For experiments in which NMDAR2A or NMDAR2B and NMDAR1 or NMDAR1-I63 transcripts were co-injected into Xenopus oocytes, the transcripts were synthesized from linearized constructs NMDAR1A, NMDAR1-I63, pCMv-hNMDAR2A-3(53), pCMV-26-NotI-24 and pBS-hNMDAR2B using mMessage mMachine (Ambion, catalog #1344, Austin, Tex). The mass of each synthesized transcript was determined by UV absorbance and the integrity of each transcript was determined by electrophoresis through an agarose gel.

B. Electrophysiology

Xenopus oocytes were injected with 12.5–50 ng of one or more NMDA receptor subunit transcripts per oocyte. The preparation and injection of oocytes were carried out as described by Dascal [(1987) Crit. Rev. Biochem. 22:317–387]. Two-to-six days following mRNA injection, the oocytes were examined using the two-electrode voltage clamp technique. The cells were bathed in Ringer's solution (115 mM NaCl, 2.5 mM $KC_1$, 1.8 mM $CaCl_2$, 10 mM HEPES, pH 7.3), and the membrane potential was clamped at −80 to −100 mV. Drugs were applied by pipetting 6.0 μl aliquots of drug-containing solution directly into the bath, or by using gravity-feed into a Warner Instruments chamber (volume=110 μl) at a flow rate of 8 ml/min. The data were sampled at 2–5 Hz with a Labmaster data acquisition board in a PC-386 using AXOTAPE version 1.2 (Axon Instruments, Foster City, Calif.) software. The data were exported to a laser printer or plotted using Sigmaplot version 5.0.

NMDA agonists, i.e., 10 . 30 μM glycine (gly) and 10–100 μM glutamate (glu) or 100–1000 μM NMDA, were applied to the bath. If a current response was observed, the agonists were washed from the bath and 0.1–1.0 mM $MgCl_2$ or 1 μM MK801 (Research Biochemicals, Inc., Natick, Mass.) (NMDA receptor antagonists) were applied before a second agonist application in order to determine whether the current was blocked by antagonists. Alternatively, $MgCl_2$ or MK-801 were applied during agonist-induced current flow. The results of multiple recordings are summarized in Table 1.

TABLE 1

Electrophysiological Analysis of Oocytes Injected with NMDA Receptor Subunit Transcripts

| Transcript (ng injected) | No. oocytes Responding | Agonists | Peak Current Amplitude |
|---|---|---|---|
| NMDAR1A (12.5) | 6 of 8[a] | 10 μM gly + 10 μM glu | 3–40 nA* |
| NMDAR1A (12.5) | 2 of 2[a] | 10 μM gly + 100 μM NMDA | 3–8 nA |
| NMDAR1A (12.5) | 0 of 9[a] | 10 μM gly + 10 μM glu | |
| NMDAR1A (50) | 0 of 1[a] | 20 μM gly + 20 μM glu | |
| NMDAR1A (40) | 4 of 10 | 10 μM gly + 10 μM glu | 21.3 ± 20.9 nA* |
| NMDAR1A (40) | 1 of 5 | 10 μM gly + 100 μM NMDA | 24 nA* |
| NMDAR1A (40) | 1 of 1 | 10 μM gly + 100 μM NMDA | 15.4 nA |
| NMDAR1A (30) | 4 of 9 | 10 μM gly + 50 μM glu | 10.6 ± 11.7 nA* |
| NMDAR1A (30) | 0 of 8 | 10–20 μM gly + 10–100 μM glu | |
| NMDAR1A (30) | 1 of 4 | 20 μM gly + 100 μM NMDA | 10.5 nA |
| NMDAR1A (25–50) | 3 of 3 | 30 μM gly + 100 μM glu | 3–10 nA |
| NMDAR1-I63 (12.5) | 1 of 5[a] | 10 μM gly + 10 μM glu | ~30 nA* |
| NMDAR1-I63 (50) | 0 of 4[a] | 10 μM gly + 10 μM glu | |
| NMDAR1-I63 (40) | 4 of 5 | 10 μM gly + 10 μM glu | 13.4 + 7.1 nA* |
| NMDAR1-I63 (40) | 3 of 3 | 10 μM gly + 20 μM glu | 17.4 + 3.7 nA* |
| NMDAR1-I63 (40) | 1 of 1 | 10 μM gly + 100 μM glu | 28 nA |
| NMDAR1-I63 (40) | 1 of 1 | 10 μM gly + 10 μM NMDA | 1.4 nA* |
| NMDAR1-I63 (25–50) | 3 of 3 | 10 μM gly + 100 μM glu | 3–5 nA |
| NMDAR1-I63 (40) | 7 of 10 | 10 μM gly + 100 μM NMDA | 8.1 ± 3.0 nA* |
| NMDAR1-I63 (40) | 1 of 2 | 10 μM gly + 1000 μM NMDA | 16.4 nA[+] |
| NMDAR1-I63-Δ204 (12.5) | 0 of 8[a] | 10 μM gly + 10 μM glu | |
| NMDAR1-I63-Δ204 (50) | 1 of 5[a] | 20 μM gly + 20 μM glu | ~50 nA |
| NMDAR1-Δ1087 (50) | 3 of 13 | 10 μM gly + 10 μM glu | 4–11 nA* |
| NMDAR1A (39) + pCMV-26-NotI-24 (39) | 1 of 5 | 10 μM gly + 50 μM glu | 10 nA |
| NMDAR1A (30) + pCMV-26-NotI-24 (30) | 0 of 7 | 10 μM gly + 20 μM glu | |
| NMDAR1A (32) + pcDNA1-26-NotI-24-5'UT (50) | 4 of 5 | 10 μM gly + 10 μM glu | 15.8 + 2.6 nA |
| NMDAR1A (25-50) + pCMV-hNMDAR2A-3 (53) (25–50) | 16 of 29 | 30 μM gly + 100 μM glu | 40 nA–3.4 μA |

TABLE 1-continued

Electrophysiological Analysis of Oocytes Injected with
NMDA Receptor Subunit Transcripts

| Transcript (ng injected) | No. oocytes Responding | Agonists | Peak Current Amplitude |
|---|---|---|---|
| NMDAR1-I63 (25–50) + pCMV-hNMDAR2A-3 (53) (25–50) | 6 of 11 | 10 $\mu$M gly + 100 $\mu$M glu | 10–100 nA |
| NMDAR1A (25) + pBS-hNMDAR2B (25) | 4 of 5 | 30 $\mu$M gly + 30 $\mu$M glu | >100 nA |
| NMDAR1A (50) + pCMV-hNMDAR2A-3 (50) + pCMV-26-NotI-24 (50) | 15 of 22 | 100 $\mu$M NMDA + 30 $\mu$M gly -or- 100 $\mu$M NMDA + 100 $\mu$M gly | 137.7 nA 1340.1 nA |

<sup>a</sup>Oocytes were unhealthy (i.e., the holding current was large)
*The agonist-induced currents in at least 1 cell were blocked by 100 $\mu$M MgCl$_2$.
<sup>+</sup>The agonist-induced currents in at least 1 cell were blocked by 1.0 $\mu$M MK801.

Analysis of the results shown in Table 1 indicates that, in general, the NMDA agonist-induced currents were blocked by either MgCl$_2$ or MK801.

Oocytes injected with transcripts (12.5 to 65 ng) of the NMDAR-1 subunit-encoding. inserts of constructs NMDAR1A, NMDAR1-I63 or NMDAR1-Δ363 were further analyzed to evaluate human NMDA receptor sensitivity to glutamate and NMDA. The two-electrode voltage clamp methods described above were used to measure current in the cells.

To determine glutamate and NMDA sensitivity of the recombinant human NMDA receptors, various concentrations of glutamate (0.1–100 $\mu$M) or NMDA (3–1000 $\mu$M) were applied to the bath (in the presence of 10–30 $\mu$M glycine) and the current response was recorded. The bath was flushed between agonist applications. Intermediate test applications of 10 $\mu$M glycine plus 10 $\mu$M glutamate were included in the experiments to monitor the receptors for run-down (i.e., inactivation of receptors that have been repeatedly activated during prolonged electrophysiological recording). The data were used to generate dose-response curves from which EC$_{50}$ values for the two agonists were calculated. Glycine sensitivity was determined in the same manner except that various concentrations (0.1–100 $\mu$M) of glycine were co-applied with 100 $\mu$M NMDA.

The EC$_{50}$ values determined for glutamate stimulation of NMDA receptors expressed in oocytes injected with NMDARLA, NMDAR1-I63 or NMDAR1-Δ363 transcripts were 0.4, 0.6 and 0.5 $\mu$M, respectively. The EC$_{50}$ values determined for NMDA stimulation of NMDA receptors expressed in oocytes injected with NMDAR1A, NMDAR1-I63 or NMDARI-Δ363 transcripts were 6.3, 10.9 and 11.9 $\mu$M, respectively.

There was a marked potentiation of the current magnitude in response to glutamate and glycine in oocytes co-injected with in vitro transcripts of pCMV-hNMDAR2A-3(53) and NMDAR1A or NMDAR1-I63 compared to the currents recorded in oocytes injected with transcripts of either NMDAR1A or NMDAR1-I63 alone. Similarly, there was a marked potentiation of the current magnitude in response to glutamate and glycine in oocytes co-injected with in vitro transcripts of NMDAR1A and pBS-hNMDAR2B compared to the currents recorded in oocytes injected with only the NMDAR1A transcript.

To investigate the pharmacological properties of human NMDA receptors generated by coexpression of the human NMDAR1A, NMDAR2A and NMDAR2C subunits, oocytes were co-injected with 50 ng each of in vitro transcripts prepared from the NMDAR1A, pCMV-hNMDAR2A-3, and pCMV-26-NotI-24 (NMDAR2C) constructs. The sensitivity of the recombinant heteromeric receptors to glycine and NMDA was determined as described above. The EC$_{50}$ for glycine activation of inward currents in these recombinant oocytes was calculated from the dose-response curve to be 0.87±0.24 $\mu$M (mean±S.D. of 4 oocytes), which was significantly different than the EC$_{50}$ calculated for glycine sensitivity of oocytes injected with 50 ng each of in vitro transcripts of NMDAR1A and pCMV-hNMDAR2A-3 alone (1.9±0.26 $\mu$M, ; p=0.0002, one-tailed t-test). The sensitivity to NMDA also increased when human NMDAR2C was co-expressed with human NMDAR1A and NMDAR2A subunits. The EC$_{50}$ for NMDA was shifted from 30.2 ±9.4 $\mu$M for oocytes co-injected with 50 ng each of in vitro transcripts of NMDAR1A and pCMV-hNMDAR2A-3 to 11.9±5.2 $\mu$M for oocytes co-injected with 50 ng each of in vitro transcripts of NMDAR1A, pCMV-hNMDAR2A-3 and pCMV-26-NotI-24 (mean±S.D. of 4 oocytes).

EXAMPLE 10

Recombinant Expression of Human NMDA Receptor Subunits in Mammalian Cells

Mammalian cells, such as human embryonic kidney (HEK293) cells can be transiently and/or stably transfected with DNA encoding human NMDA receptor subunits (e.g., DNA encoding an NMDAR1 subunit or DNA encoding an NMDAR1 subunit and DNA encoding an NMDAR2 subunit such as pCMV-26-NotI-24, pCMV-hNMDAR2A-3(53) or pCMVPL3-hNMDAR2B). Transfectants are analyzed for expression of NMDA receptors using various assays, e.g., northern blot hybridization, electrophysiological recording of cell currents, $Ca^{2+}$-sensitive fluorescent indicator-based assays and [$^3$H]-MK801 binding assays.

A. Transient Transfection of HEK Cells

Two transient transfections were performed. In one transfection, HEK 293 cells were transiently transfected with DNA encoding an NMDAR1 (construct NMDAR1A) subunit. In another transfection, HEK 293 cells were transiently co-transfected with DNA encoding NMDAR1 (construct NMDAR1A) and NMDAR2C (pCMV-26-NotI-24) subunits. In both transfections, ~2×10$^6$ HEK cells were transiently transfected with 19 $\mu$g of the indicated plasmid(s) according to standard CaPO$_4$ transfection procedures [Wigler et al. (1979) Proc. Natl. Acad. Sci. USA 76:1373–1376]. In addition, 1 $\mu$g of plasmid pCMVβgal (Clontech Laboratories, Palo Alto, Calif.), which contains the *Escherichia coli* β-galactosidase gene fused to the CMV promoter, were co-transfected as a reporter gene for monitoring the efficiency of transfection. The transfectants were analyzed for β-galactosidase expression by direct staining of the product of a reaction involving β-galactosidase and the x-gal substrate [Jones (1986) *EMBO* 5:3133–3142]. Transfectants can also be analyzed for βgalactosidase expression by measurement of β-galactosidase activity [Miller (1972) in *Experiments in Molecular Genetics*, pp.352–355, Cold Spring Harbor Press].

The efficiency of these transfections of HEK cells was typical of standard efficiencies (i.e., ~50%).

B. Stable Transfection of Mammalian Cells

Mammalian cells, such as HEK 293 cells, can be stably transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing $1-2 \times 10^6$ cells, are transfected with ml of DNA/calcium phosphate precipitate in media containing approximately 19 μg of NMDA receptor subunit-encoding DNA and 1 μg of DNA encoding a selectable marker, for example, neomycin-resistance gene (i.e., pSV2neo). After ~14 days of growth in media containing typically 1 μg/ml G418, colonies form and are individually isolated using cloning cylinders. The isolates are then subjected to limiting dilution and screened to identify those that express NMDA receptors using, for example, methods described below.

C. Analysis of Transfectants

1. Northern Blot Hybridization Analysis

Total RNA was isolated from $\sim 1 \times 10^7$ HEK cells co-transfected with NMDAR1 and pCMV-26-NotI-24, and 5–10 μg of RNA was used for northern hybridization analysis. Fragments from human neuronal NMDAR subunit-encoding plasmids were randomly primed and labeled with $^{32}$P-dCTP Klenow incorporation and used as probes. The northern blot hybridization and wash conditions were as follows:

hybridization in 5×SSPE, 5×Denhart's solution, 50% formamide, at 42° C. followed by washing in 0.2× SSPE, 0.1% SDS, at 65° C.

Results of these studies revealed the transfectants expressed detectable levels of NMDAR1 and NMDAR2C mRNA of the appropriate size (based on the size of the cDNAs).

2. Fluorescent indicator-based assays

Activation of ligand-gated NMDA receptors by agonists leads to an influx of cations (both monovalent and divalent), including $Ca^{2+}$, through the receptor channel. Calcium entry into the cell through the channel can in turn induce release of calcium contained in intracellular stores. Monovalent cation entry into the cell through the channel can also result in an increase in cytoplasmic calcium levels through depolarization of the membrane and subsequent activation of voltage-dependent calcium channels. Therefore, methods of detecting transient increases in intracellular calcium concentration can be applied to the analysis of functional NMDA receptor expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.) are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence. An automated fluorescence detection system for assaying NMDA receptors has been described in commonly assigned pending U.S. patent application No. 07/812,254 and corresponding PCT Patent Application No. US92/11090, incorporated by reference herein in their entirety.

Mammalian cells that have been transfected with DNA encoding NMDAR1 or NMDAR1 and NMDAR2 subunits can be analyzed for expression of functional recombinant NMDA receptors using the automated fluorescent indicator-based assay. The assay procedure is as follows.

Untransfected mammalian host cells (or host cells transiently transfected with pCMV-T7-2) and mammalian cells that have been transfected with NMDAR1±NMDAR2 subunit DNA are plated in the wells of a 96-well microtiter dish (Nunc Catalog No. 1-6708, available through Alameda Industries, Escondido, Calif.) that has been precoated with poly-L-lysine at a density of $2.5 \times 10^5$ cells/well and loaded with fluo-3 by incubation for 2 hours at 20° C. in a medium containing 20 μM fluo-3, 0.2% Pluronic F-127 in HBS (125 mM NaCl, 5 mM KCl, 1.8 mM $CaC_2$, 0.62 mM $MgCl_2$, 20 mM glucose, 20 mM HEPES, pH 7.4). The cells are then washed with assay buffer (i.e. HBS). The microtiter dish is then placed into a fluorescence plate reader (e.g., Fluoroskan II, Lab Products International, Ltd., Raleigh, N.C.) and the basal fluorescence of each well is measured and recorded before addition of 10 μM glycine and 10 μM glutamate to the wells. The fluorescence of the wells is monitored repeatedly (75 readings at 0.63-sec intervals) following addition of agonist.

The fluorescence of the untransfected host cells preferably will not change after addition of glycine and glutamate, i.e., the host cells should not express endogenous excitatory amino acid receptors. The fluorescence of mammalian cells transfected with NMDAR1±NMDAR2 subunit DNA will increase after addition of glycine and glutamate if a sufficient number of functional NMDA receptors are expressed at the cell surface, and fluorescence readings are taken rapidly.

The resting potential of the membrane of some mammalian host cells may be relatively positive (e.g., −35 mV). Because activation of some NMDA receptors may be significantly reduced at relatively positive potentials, it may be necessary to lower the resting potential of the membrane of cells transfected with human NMDA receptor subunit-encoding DNAs prior to assaying the cells for NMDA receptor activity using the fluorescent indicator-based assay. This may be accomplished by adding valinomycin (~10 μM) to the transfected cells prior to adding NMDA receptor agonists to initiate the assay.

3. NMDA Receptor Ligand Binding Assays

Mammalian cells transfected with NMDAR1±NMDAR2 subunit DNAs can be analyzed for [$^3$H]-MK801 binding. An additional ligand-binding assay for NMDA receptors using $^3$H-CGP39653 is also described below. Rat brain membranes are included in the binding assays as a positive control.

a. Preparation of Membranes i. Buffy Coat Homogenate from Rat Cerebral Cortex

Buffy coat membranes are prepared from rat brain cortices as described by Jones et al. [(1989) J. Pharmacol. Meth. 21:161]. Briefly, cortices from ten freshly thawed frozen rat brains are dissected and weighed. The tissue is homogenized in 20 volumes of 0.32 M ice-cold sucrose in a glass homogenizing tube using a Teflon pestle. The suspension is centrifuged at 1,000×g for 10 minutes at 4° C. The supernatant is decanted and centrifuged at 20,000×g for minutes at 4° C. The pellet is resuspended in 20 volumes of ice-cold distilled water with a Polytron for 30 sec at setting 6. The suspension is centrifuged at 8,000×g for minutes at 4° C. The buffy coat pellet is rinsed gently with supernatant and then recentrifuged at 48,000×g for 20 minutes at 4° C. The pellet is resuspended in 20 volumes of ice-cold distilled water with a Polytron and centrifuged again at 48,000×g for minutes. The wash step is repeated once more. The final suspension is divided into aliquots, centrifuged. Each pellet can be stored frozen at −20° C. for 12 hrs or more before use.

ii. Membranes from Transfected and Untransfected Mammalian Cells

In order to prepare membranes from transfected and untransfected mammalian cells, the cells are scraped from the tissue culture plates, and the plates are rinsed with 5 ml of PBS (phosphate-buffered saline: 137 mM NaCl, 2.7 mM KCl, mM $Na_2HPO_4$, 1.7 mM $KH_2PO_4$). The cells are centrifuged at low speed in a table-top centrifuge, and the cell pellet is rinsed with PBS. The cell pellet is resuspended in 20 ml of mM Hepes buffer, pH 7.4, using a Polytron at setting 3–6 for seconds. The cell suspension is centrifuged at 48,000×g for 20 minutes at 4° C. The supernatant is discarded, and the pellet is kept frozen for 12 hrs or more at −20° C.

b. [$^3$H]-MK801 Binding to NMDA Receptors

The binding of [$^3$H]-MK801 to NMDA receptors is carried out as described by Wong et al. [ (1986) *Proc. Natl. Acad. Sci. USA* 83:7104], with a few minor changes. Thus, on the day of the assay, the rat brain and mammalian cell (transfected and untransfected) membrane pellets are resuspended in 50 volumes of 10 mM Hepes buffer, pH 7.4, using a 10-ml syringe and a 21-gauge needle, and incubated for minutes at 37° C. The supernatant is centrifuged at 48,000×g for minutes at 4° C. The pellet is resuspended in 2 ml of 10 mM Hepes, pH 7.4 and centrifuged as described above. The wash step is repeated once more, and the pellet is resuspended in 10 ml of mM Hepes, pH 7.4. The protein concentration is determined using the Biorad Bradford reagent. The pellet is finally resuspended in the assay buffer (10 mM Hepes, pH 7.4) at 1 mg/ml.

For binding studies, the membrane suspension is incubated in duplicate with 2.5 nM [$^3$H]-MK801 (New England Nuclear, Boston, Mass.) in a total volume of 0.5 ml assay buffer (mM Hepes, pH 7.4) in the presence and absence of 10 μM glutamate and 10 μM glycine for 60 or 120 min at 23° C. Bound radioactivity is separated from free radioactivity by rapid filtration through Whatman GF/C filters which are presoaked for 2–3 hrs in 0.05% polyethylenimine. The filters are washed twice with 3 ml ice-cold assay buffer. The filters are dried and transferred to scintillation vials, each containing 10 ml of scintillation fluid. The vials are vortexed, and the radioactivity is measured in a Beckman scintillation counter. The nonspecific binding observed in the presence of 10 μM MK801 is subtracted from the total binding in order to determine the specific binding.

Rat brain cortical buffy coat membranes displayed specific saturable binding of [$^3$H]-MK801. In the presence of glycine and glutamate, the ratio of total-to-nonspecific binding (S:N ratio) was 28:1, whereas in the absence of glutamate and glycine the S:N ratio was 5:1. Thus, the binding of MK801 to rat NMDA receptors is potentiated by glutamatergic agonists. Scatchard analysis of [$^3$H]-MK801 binding to rat brain membranes indicated that the sensitivity of the assay was 90 fmoles of receptor.

C. [$^3$H]-CGP39653 Binding to NMDA ReceDtors

The binding of [$^3$H] -CGP39653 to rat brain membranes is carried out as described by Sills et al. [(1991) *Eur. J. Pharmacol.* 192:19]. The buffy coat membrane pellet is resuspended in 50 volumes of 5 mM Tris-HCl containing 10 mM EDTA, pH 7.7, and incubated for 10 min. at 37° C. The supernatant is centrifuged at 48,00033 g for 10 min. at 4° C. The wash step is repeated once and the pellet is resuspended in ml of mM Tris-HCl containing 10 mM EDTA, pH 7.7. This rat brain membrane suspension is incubated in duplicate or triplicate with 2.0 nM [$^3$H]-CGP39653 (New England Nuclear) in a total volume of 0.5 ml assay buffer (mM Tris-HCl, pH 7.7) for 60 min at 0° C. Nonspecific binding is determined in the presence of 100 μM glutamate. Bound radioactivity is separated from the free by vacuum filtration through GF/C filters which are presoaked for 2–3 hrs in 0.05% polyethylenimine, using the filtration manifold. Unbound radioactivity is removed with two washes of 3 ml each of ice-cold buffer. The filters are dried and transferred to scintillation vials, each containing 10 ml of scintillation fluid. The vials are vortexed, and the radioactivity is measured in a Beckman scintillation counter. The nonspecific binding observed in the presence of 100 μM glutamate is subtracted from the total binding to determine the specific binding.

[$^3$H]-CGP39653 binding was first measured as a function of membrane concentration. Specific binding increased linearly with increasing membrane concentration up to 200 μg of protein in the presence of 2 nM [$^3$H]-CGP39653.

Saturation analysis of [$^3$H]-CGP39653 binding was carried out by incubating 150 μg of rat buffy coat homogenate with increasing concentrations of [$^3$H]-CGP39653 for 60 min at 4° C. Scatchard analysis indicated a single class of binding sites with a $B_{max}$ value of 0.69±0.09 pmoles/mg and a $K_d$ value of 12.3±0.12 nM.

While the invention has been described in detail with reference to certain preferred embodiments thereof, it will be understood that modifications and variations are within the spirit and scope of that which is described and claimed.

Summary of Sequences

Sequence ID No. 1 is a nucleotide sequence encoding a human N-methyl-D-aspartate (NMDA) receptor subunit, NMDAR1A, and the deduced amino acid sequence thereof.

Clone NMDA10 encodes a 3083 nucleotide sequence comprising nucleotides 320–3402 of Sequence ID No. 1. Thus, this sequence encoded by the NMDA10 clone differs from Sequence ID No. 1 in that it does not contain the 319 5' nucleotides, nor the 896 3' nucleotides thereof.

Sequence ID No. 13 is a 3155 nucleotide sequence encoded by clone NMDA11, comprising nucleotides 1–2961, plus nucleotides 3325–3518 of Sequence ID No. 1. Thus, Sequence ID No. 13 differs from Sequence ID No. 1 by the deletion of 363 nucleotides from the 3' portion thereof (i.e., by the deletion of nucleotides 2962–3324 of Sequence ID No. 1), and further by the lack of the 781 terminal 3' nucleotides of Sequence ID No. 1.

Sequence ID No. is a 2542 nucleotide sequence encoded by clone NMDA7, comprising nucleotides 556–831 of Sequence ID No. 1, plus an additional 63 nucleotides (set forth in Sequence ID No. 3) and nucleotides 832–984, 1189–2961 and 3325–3599 of Sequence ID No. 1. Thus, Sequence ID No. 15 differs from Sequence ID No. 1 in that it does not contain the 555 5'-most nucleotides thereof, it does not contain the 204 nucleotides set forth as nucleotides 985–1188 of Sequence ID No. 1, it does not contain the 363 3' nucleotides set forth as nucleotides 2962–3324 of Sequence ID No. 1, and it does not contain the 700 3'-most nucleotides of Sequence ID No. 1, while it does contain an additional 63 nucleotides (Sequence ID No. 3) inserted between nucleotides 831 and 832 of Sequence ID No. 1.

Sequence ID No. 17 is a 593 nucleotide sequence encoded by clone NMDA3, comprising nucleotides 2617–2961, plus nucleotides 4049–4298 of Sequence ID No. 1. Thus, Sequence ID No. 17 differs from Sequence ID No. 1 in that it does not contain the 2616 5' nucleotides thereof, and by the deletion of 1087 nucleotides from the 3' portion thereof (i.e., by the deletion of nucleotides 2962–4048 of Sequence ID No. 1).

Sequence ID No. 19 is a nucleotide sequence encoding human NMDA receptor subunit NMDAR1-Δ363, comprising nucleotides 1–2961, plus nucleotides 3325–4298 of Sequence ID No. 1. Thus, Sequence ID No. 19 differs from Sequence ID No. 1 in that it does not contain the 363 nucleotides set forth as nucleotides 2962–3324 of Sequence ID No. 1.

Sequence ID No. 21 is a nucleotide sequence encoding human NMDA receptor subunit NMDAR1-Δ1087, comprising nucleotides 1–2961, plus nucleotides 4049–4298 of Sequence ID No. 1. Thus, Sequence ID No. 21 differs from Sequence ID No. 1 in that it does not contain the 1087 nucleotides set forth as nucleotides 2962–4048 of Sequence ID No. 1.

Sequence ID No. 23 is a nucleotide sequence encoding human NMDA receptor subunit NMDAR1-I63. Sequence ID No. 23 is the same as Sequence ID No. 1, further comprising an additional 63 nucleotides (set forth in Sequence ID No. 3) inserted between nucleotides 831 and 832 of Sequence ID No. 1.

Sequence ID No. is a nucleotide sequence encoding human NMDA receptor subunit NMDAR1-I63-Δ204. Sequence ID No. 25 is the same as Sequence ID No. 23, except Sequence ID No. 25 does not contain the 204 nucleotides set forth as nucleotides 985–1188 of Sequence ID No. 1.

Sequence ID No. 27 is a nucleotide sequence encoding human NMDA receptor subunit NMDAR1-I63-Δ204-Δ363. Sequence ID No. 27 is the same as Sequence ID No. 25, except Sequence ID No. 27 does not contain the 363 nucleotides set forth as nucleotides 2962–3324 of Sequence ID No. 1.

Sequence ID No. 29 is a nucleotide sequence encoding human NMDA receptor subunit NMDAR1-Δ204. Sequence ID No. 29 is the same as Sequence ID No. 1, except Sequence ID No. 29 does not contain the 204 nucleotides set forth as nucleotides 985–1188 of Sequence ID No. 1.

Sequence ID No. 31 is a nucleotide sequence encoding human NMDA receptor subunit NMDAR1-Δ204-Δ363. Sequence ID No. 31 differs from Sequence ID No. 1 in that Sequence ID No. 31 does not contain the 204 nucleotides set forth as nucleotides 985–1188 of Sequence ID No. 1, nor the 363 nucleotides set forth as nucleotides 2962–3324 of Sequence ID No. 1.

Sequence ID No. 33 is a nucleotide sequence encoding human NMDA receptor subunit NMDAR1-Δ204-Δ1087. Sequence ID No. 33 differs from Sequence ID No. 1 in that Sequence ID No. 33 does not contain the 204 nucleotides set forth as nucleotides 985–1188 of Sequence ID No. 1, nor the 1087 nucleotides set forth as nucleotides 2962–4048 of Sequence ID No. 1.

Sequence ID No. 35 is a nucleotide sequence encoding human NMDA receptor subunit NMDAR1-I63-Δ363. Sequence ID No. 35 is the same as Sequence ID No. 23 except Sequence ID No. 35 does not contain the 363 nucleotides set forth as nucleotides 2962–3324 of Sequence ID No. 1.

Sequence ID No. 37 is a nucleotide sequence encoding human NMDA receptor subunit NMDAR1-I63-Δ1087. Sequence No. 37 is the same as Sequence ID No. 23 except Sequence ID No. 37 does not contain the 1087 nucleotides set forth as nucleotides 2962–4048 of Sequence ID No. 1.

Sequence ID No. 39 is a nucleotide sequence encoding human NMDA receptor subunit NMDAR1-I63-Δ204-Δ1087. Sequence ID No. 39 is the same as Sequence ID No. 25, except Sequence ID No. 39 does not contain the 1087 nucleotides set forth as nucleotides 2962–4048 of Sequence ID No. 1.

Sequence ID No. 2 is the amino acid sequence of the NMDA receptor subunit set forth in Sequence ID No. 1.

Sequence ID No. 14 is the amino acid sequence of an NMDA receptor subunit encoded by the nucleotide sequence of Sequence ID No. 13.

Sequence ID No. 16 is the amino acid sequence of a portion of an NMDA receptor subunit as encoded by the nucleotide sequence of Sequence ID No. 15.

Sequence ID No. 18 is the amino acid sequence of a portion of an NMDA receptor subunit as encoded by the nucleotide sequence of Sequence ID No. 17.

Sequence ID No. 20 is the amino acid sequence of an NMDA receptor subunit encoded by the nucleotide sequence of Sequence ID No. 19.

Sequence ID No. 22 is the amino acid sequence of an NMDA receptor subunit encoded by the nucleotide sequence of Sequence ID No. 21.

Sequence ID No. 24 is the amino acid sequence of an NMDA receptor subunit encoded by the nucleotide sequence of Sequence ID No. 23.

Sequence ID No. 26 is the amino acid sequence of an NMDA receptor subunit encoded by the nucleotide sequence of Sequence ID No. 25.

Sequence ID No. 28 is the amino acid sequence of an NMDA receptor subunit encoded by the nucleotide sequence of Sequence ID No. 27.

Sequence ID No. 30 is the amino acid sequence of an NMDA receptor subunit encoded by the nucleotide sequence of Sequence ID No. 29.

Sequence ID No. 32 is the amino acid sequence of an NMDA receptor subunit encoded by the nucleotide sequence of Sequence ID No. 31.

Sequence ID No. 34 is the amino acid sequence of an NMDA receptor subunit encoded by the nucleotide sequence of Sequence ID No. 33.

Sequence ID No. 36 is the amino acid sequence of an NMDA receptor subunit encoded by the nucleotide sequence of Sequence ID No. 35.

Sequence ID No. 38 is the amino acid sequence of an NMDA receptor subunit encoded by the nucleotide sequence of Sequence ID No. 37.

Sequence ID No. 40 is the amino acid sequence of an NMDA receptor subunit encoded by the nucleotide sequence of Sequence ID No. 39.

Sequence ID No. 3 is a nucleotide sequence encoding the 63 nucleotide insert present in Sequence ID Nos. 15, 23, 25, 27, 35, 37 and 39.

Sequence ID No. 4 is the 21 amino acid sequence encoded by the insert set forth in Sequence ID No. 3.

Sequence ID No. 5 is a nucleotide sequence of a clone (pCMV-26-NotI-24) encoding a human N-methyl-D-aspartate (NMDA) receptor subunit, NMDAR2C, and the deduced amino acid sequence thereof.

Sequence ID No. 41 is a 2026 nucleotide sequence encoded by clone NMDA21, comprising nucleotides 931–2350, and 2402–3307 of Sequence ID No. 5. Thus, Sequence ID No. 41 differs from Sequence ID No. 5 in that it does not contain the 930 5' nucleotides thereof, nor the 51 nucleotides located at position 2351–2401 of Sequence ID No. 5, nor the 1061 3' nucleotides of Sequence ID No. 5.

Sequence ID No. 43 is a 3698 nucleotide sequence encoded by clone NMDA22, comprising nucleotides 367–1300 of Sequence ID No. 5, plus an additional 11 nucleotides (set forth as Sequence ID No. 9), and nucleotides 1301–1959 and 1975–4068 of Sequence ID No. 5. Thus, Sequence ID No. 43 differs from Sequence ID No. 5 by the lack of the 366 5'-most nucleotides, by the insertion of 11 nucleotides between nucleotides 1300 and 1301 of Sequence ID No. 5, and further by the lack of the 15 nucleotides of Sequence ID No. 5 from residue 1960 to residue 1974.

Sequence ID No. 44 is a 3243 nucleotide sequence encoded by clone NMDA24, comprising nucleotides 861–1300 of Sequence ID No. 5, plus an additional 11 nucleotides (Sequence ID No. 9), nucleotides 1301–2350 of Sequence ID No. 5, an additional 24 nucleotides (set forth as Sequence ID No. 7) and nucleotides 2351–4068 of Sequence ID No. 5. Thus, Sequence ID No. 44 differs from Sequence ID No. 5 in that it does not contain the 860 5'-most nucleotides thereof, while it does contain an additional 11 nucleotides (Sequence ID No. 9) inserted between nucleotides 1300 and 1301, plus an additional 24 nucleotides (Sequence ID No. 7) inserted between nucleotides 2350 and 2351 of Sequence ID No. 5.

Nucleotides 1–3025 of Sequence ID No. 5 are a 3025 nucleotide sequence encoded by clone NMDA26. Thus, this sequence differs from Sequence ID No. 5 in that it does not contain the 1043 3'-terminal nucleotides thereof.

Sequence ID No. 45 is a nucleotide sequence encoding human NMDA receptor subunit pCMV-26-ScaI-24, which differs from Sequence ID No. 5 only in the insertion of 24 nucleotides (Sequence ID No. 7) between nucleotides 2350 and 2351 of Sequence ID No. 5.

Sequence ID No. 47 is a nucleotide sequence encoding human NMDA receptor subunit pCMV-26-ScaI-22, which differs from Sequence ID No. 5 only in the deletion of nucleotides 1960–1974 of Sequence ID No. 5.

Sequence ID No. 49 is a nucleotide sequence encoding human NMDA receptor subunit pCMV-26-ScaI-21-NotI-24, which differs from Sequence ID No. 5 only in the deletion of nucleotides 2351–2401 of Sequence ID No. 5.

Sequence ID No. 51 is a nucleotide sequence encoding human NMDA receptor subunit NMDAR2C-Δ15-I24. Sequence ID No. 51 is the same as Sequence ID No. 47, except Sequence ID No. 51 further contains the 24 nucleotide insert set forth in Sequence ID No. 7, positioned between nucleotides 2350 and 2351 of Sequence ID No. 5.

Sequence ID No. 53 is a nucleotide sequence encoding human NMDA receptor subunit NMDAR2C-66 15-Δ51. Sequence ID No. 53 is the same as Sequence ID No. 49, except Sequence ID No. 53 does not contain the 15 nucleotides set forth as nucleotides 1960–1974 of Sequence ID No. 5.

Sequence ID No. 6 is the amino acid sequence of the NMDA receptor subunit set forth in Sequence ID No. 5.

Sequence ID No. 42 is the amino acid sequence of a portion of an NMDA receptor subunit as encoded by the nucleotide sequence of Sequence ID No. 41.

The amino acid sequence of a portion of an NMDA receptor subunit as encoded by the nucleotide sequence of Sequence ID No. 43 is set forth in Sequence ID No. 43.

The amino acid sequence of a portion of an NMDA receptor subunit as encoded by the nucleotide sequence of Sequence ID No. 44 is set forth in Sequence ID No. 44.

Sequence ID No. 46 is the amino acid sequence of an NMDA receptor subunit encoded by the nucleotide sequence of Sequence ID No. 45.

Sequence ID No. 48 is the amino acid sequence of an NMDA receptor subunit encoded by the nucleotide sequence of Sequence ID No. 47.

Sequence ID No. 50 is the amino acid sequence of an NMDA receptor subunit encoded by the nucleotide sequence of Sequence ID No. 49.

Sequence ID No. 52 is the amino acid sequence of an NMDA receptor subunit encoded by the nucleotide sequence of Sequence ID No. 51.

Sequence ID No. 54 is the amino acid sequence of an NMDA receptor subunit encoded by the nucleotide sequence of Sequence ID No. 53.

Sequence ID No. 7 is a nucleotide sequence encoding the 24 nucleotide insert present in Sequence ID Nos. 44, 45 and 51.

Sequence ID No. 8 is the 7 amino acid sequence encoded by nucleotides 2–22 of the insert set forth in Sequence ID No. 7. Because the insert is introduced within a codon, the insert itself only encodes 7 amino acids. The terminal residues of the nucleotide insert participate in forming codons with adjacent sequence at the site of insertion.

Sequence ID No. 9 is a nucleotide sequence encoding the 11 nucleotide insert present in Sequence ID Nos. 43 and 44.

Sequence ID No. 10 is a nucleotide sequence encoding a human N-methyl-D-aspartate (NMDA) receptor subunit, NMDAR2A.

Sequence ID No. 11 is the amino acid sequence of an NMDA receptor subunit as encoded by the nucleotide sequence set forth in Sequence ID No. 10.

Sequence ID No. 12 is the nucleotide sequence of 71 nucleotides of 5' untranslated sequence of clone NMDA27, plus the initiation codon (nucleotides 72–74) of said clone.

Sequence ID No. 55 is a nucleotide sequence of a clone encoding a human N-methyl-D-aspartate (NMDA) receptor subunit, NMDAR2B.

Sequence ID No. 56 is the amino acid sequence of the NMDA receptor subunit set forth in Sequence ID No. 55.

Sequence ID No. 57 is a nucleotide sequence of a clone encoding a human N-methyl-D-aspartate (NMDA) receptor subunit, NMDAR2D.

Sequence ID No. 58 is the amino acid sequence of the NMDA receptor subunit set forth in Sequence ID No. 57.

Sequence ID Nos. 59–62 are four synthetic oligonucleotides used in the preparation of an NMDAR2C clone (pCMV-26-NotI-24-GCMOD) having reduced GC nucleotide content between nucleotides 2957 and 3166.

Sequence id no. 63 is the nucleotide sequence of the 195 basepair insert of NMDAR2Cp clone PCMV-26-NotI-24-GCMOD (replacing nucleotides 2966–3160 of Sequence ID No. 5).

What is claimed is:

1. An isolated nucleic acid molecule comprising a sequence of nucleotides that encode a human N-methyl-D-aspartate (NMDA) receptor subunit selected from the group consisting of:
   (a) a sequence of nucleotides as set forth in SEQ ID NO:55;
   (b) a sequence of nucleotides comprising nucleotides 210–4664 as set forth in SEQ ID NO:55;
   (c) a sequence of nucleotides varying from the nucleotide sequence specified in (a) or (b) as a result of degeneracy of the genetic code;
   (d) a sequence of nucleotides that encode a human N-methyl-D-aspartate receptor type 2B subunit (NMDAR2B) and which hybridizes under conditions of high stringency along its full length to the complement of the NMDAR2B encoding portion of SEQ ID NO:55 and;
   (e) a sequence of nucleotides that encode a human N-methyl-D-aspartate receptor type 2B subunit (NMDAR2B) having an amino acid sequence as set forth in SEQ ID NO:56.

2. The isolated nucleic acid molecule according to claim 1, wherein said nucleic acid molecule encodes a human N-methyl-D-aspartate (NMDA) receptor subunit and comprises the sequence of nucleotides as set forth in SEQ ID NO:55.

3. A host cell transfected or transformed with the isolated nucleic acid molecule of claim 2.

4. The host cell according to claim 3, wherein said host cell is a eukaryotic cell.

5. The host cell according to claim 4, wherein said host cell expresses a functional heterologous NMDA receptor subunit.

6. The isolated nucleic acid molecule according to claim 1, wherein said nucleic acid molecule encodes a human N-methyl-D-aspartate (NMDA) receptor subunit and comprises a sequence of nucleotides comprising nucleotides 210–4664 of SEQ ID NO:55.

7. A host cell transfected or transformed with the isolated nucleic acid molecule of claim 6.

8. The host cell according to claim 7, wherein said host cell is a eukaryotic cell.

9. The isolated nucleic acid molecule according to claim 1, wherein said nucleic acid molecule comprises a sequence of nucleotides that encode a human N-methyl-D-aspartate receptor subtype 2B (NMDAR2B) and which hybridizes along its full length under conditions of high stringency to the complement of the NMDAR2B encoding portion of SEQ ID NO:55.

10. A host cell transfected or transformed with the isolated nucleic acid molecule of claim 9.

11. The host cell according to claim 10, wherein said host cell is a eukaryotic cell.

12. The isolated nucleic acid molecule according to claim 9, wherein said isolated nucleic acid molecule is one of DNA or mRNA.

13. The isolated nucleic acid molecule according to claim 12, wherein said nucleic acid molecule, if DNA, is fully complementary to mRNA native to a human cell and if mRNA, is identical to mRNA native to a human cell.

14. The isolated nucleic acid molecule according to claim 1, wherein said nucleic acid molecule comprises a sequence of nucleotides that encode a human N-methyl-D-aspartate receptor type 2B (NMDAR2B) having a sequence of amino acids as set forth in SEQ ID NO:56.

15. A host cell transfected or transformed with the isolated nucleic acid molecule of claim 14.

16. The host cell according to claim 15, wherein said host cell is a eukaryotic cell.

17. A host cell transfected or transformed with the isolated nucleic acid molecule of claim 1.

18. An amphibian oocyte, comprising the isolated nucleic acid molecule according to claim 1.

19. The nucleic acid molecule according to claim 1, wherein said nucleic acid molecule is mRNA.

20. A plasmid adopted for transformation or transfection of a suitable host cell comprising the nucleic acid molecule of claim 1.

21. A vector comprising the nucleic acid molecule of claim 1.

* * * * *